US010297759B2

(12) United States Patent
Kim et al.

(10) Patent No.: US 10,297,759 B2
(45) Date of Patent: May 21, 2019

(54) COMPOUND AND ORGANIC ELECTROLUMINESCENT DEVICE COMPRISING SAME

(71) Applicant: DOOSAN CORPORATION, Seoul (KR)

(72) Inventors: Tae Hyung Kim, Yongin-si (KR); In Hyuk Lee, Yongin-si (KR); Yong Hwan Lee, Seongnam-si (KR); Jin Yong Shin, Yongin-si (KR); Ho Cheol Park, Suwon-si (KR); Chang Jun Lee, Ansan-si (KR); Eun Jung Lee, Seoul (KR); Young Mi Beak, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 785 days.

(21) Appl. No.: 14/421,488

(22) PCT Filed: Aug. 13, 2013

(86) PCT No.: PCT/KR2013/007265
§ 371 (c)(1),
(2) Date: Feb. 13, 2015

(87) PCT Pub. No.: WO2014/027814
PCT Pub. Date: Feb. 20, 2014

(65) Prior Publication Data
US 2015/0318483 A1 Nov. 5, 2015

(30) Foreign Application Priority Data

Aug. 17, 2012 (KR) ........................ 10-2012-0090295

(51) Int. Cl.
*H01L 51/00* (2006.01)
*C07D 487/04* (2006.01)
*C09K 11/06* (2006.01)
*C07D 403/14* (2006.01)
*H01L 51/50* (2006.01)

(52) U.S. Cl.
CPC ........ *H01L 51/0061* (2013.01); *C07D 403/14* (2013.01); *C07D 487/04* (2013.01); *C09K 11/06* (2013.01); *H01L 51/006* (2013.01); *H01L 51/0059* (2013.01); *H01L 51/0067* (2013.01); *H01L 51/0072* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1059* (2013.01); *H01L 51/0052* (2013.01); *H01L 51/0058* (2013.01); *H01L 51/0081* (2013.01); *H01L 51/0085* (2013.01); *H01L 51/5012* (2013.01); *H01L 51/5056* (2013.01); *H01L 51/5088* (2013.01)

(58) Field of Classification Search
CPC . H01L 51/006; H01L 51/007; H01L 51/0072; H01L 51/0059; H01L 51/0081; H01L 51/0094; H01L 51/505; H01L 51/5012; H01L 51/0052; H01L 51/0058; H01L 51/0061; H01L 51/5056; H01L 51/0067; H01L 51/0085; H01L 51/5088; C07D 487/04; C07D 209/86; C07D 305/14; C07D 407/12; C07D 471/14; C07D 471/22; C07D 487/14; C07D 487/22; C07D 403/14; C07F 7/0812; C07F 7/0816; C09K 11/06; C09K 2211/1011; C09K 2211/1044; C09K 2211/1007; C09K 2211/1022; C09K 2211/1029; C09K 2211/1059
USPC ................ 428/690, 917; 313/504, 505, 506; 257/40, E51.05, E51.032, E51.052; 548/304.1, 418, 440, 444
See application file for complete search history.

(56) References Cited

U.S. PATENT DOCUMENTS

| 9,761,813 | B2* | 9/2017 | Kim ................... H01L 51/0067 |
| 9,837,618 | B2* | 12/2017 | Park .................... C07D 487/04 |
| 10,038,146 | B2* | 7/2018 | Kim ................... H01L 51/0072 |
| 2011/0031483 | A1 | 2/2011 | Kwak et al. |
| 2011/0240979 | A1* | 10/2011 | Kim .................... C07D 487/04 257/40 |
| 2011/0263669 | A1 | 10/2011 | Anizon et al. |

FOREIGN PATENT DOCUMENTS

| CN | 101730681 A | 6/2010 |
| CN | 102017220 A | 4/2011 |
| CN | 102449106 A | 5/2012 |
| JP | 11144867 A | 5/1999 |

(Continued)

OTHER PUBLICATIONS

Isabel C.F.R. Ferreira et al., "Synthesis of New Methylated thieno[2,3-a] and [3,2-b] carbazoles by Reductive Cyclization of 6-(2'-Nitrophenyl)benzo[b]thionphenes Obtained by Palladium-Catalyzed Cross-Coupling", J. Heterocyclic Chem., 2001, pp. 749-754, vol. 38.

(Continued)

*Primary Examiner* — Jennifer A Chriss
*Assistant Examiner* — Elizabeth M. Dahlburg
(74) *Attorney, Agent, or Firm* — Sughrue Mion, PLLC

(57) ABSTRACT

The present disclosure relates to a novel compound having excellent hole injection capabilities and transport capabilities, light-emitting capabilities, and the like, and an organic electroluminescent device which includes the compound in one or more organic material layers thereof so as to improve characteristics such as light-emitting efficiency, driving voltage, and a service life.

8 Claims, No Drawings

(56) References Cited

FOREIGN PATENT DOCUMENTS

| JP | 2011037826 A | 2/2011 |
|---|---|---|
| KR | 10-2010-0131629 A | 12/2010 |
| KR | 10-2011-0105269 A | 9/2011 |
| KR | 10-2011-0117549 A | 10/2011 |
| KR | 10-2012-0009984 A | 2/2012 |
| KR | 10-2012-0034140 A | 4/2012 |
| WO | 2012/011756 A1 | 1/2012 |

OTHER PUBLICATIONS

Vasudevan Dhayalan et al., "A Versatile Synthesis of Annulated Carbazole Analogs Involving a Domino Reaction of Bromomethylindoles with Arenes/Heteroarenes", Eur. J. Org. Chem., 2009, pp. 531-546, vol. 2009.
International Searching Authority International Search Report for PCT/KR2013/007265 dated Nov. 29, 2013.
State Intellectual Property Office of P.R.C., Communication dated Dec. 28, 2015 issued in Corresponding Chinese Application No. 201380053853.5.
Communication dated Jun. 1, 2016, from the Japanese Patent Office in counterpart application No. 2015-527366.

\* cited by examiner

COMPOUND AND ORGANIC ELECTROLUMINESCENT DEVICE COMPRISING SAME

CROSS REFERENCE TO RELATED APPLICATIONS

This application is a National Stage of International Application No. PCT/KR2013/007265 filed Aug. 13, 2013, claiming priority based on Korean Patent Application No. 10-2012-0090295 filed Aug. 17, 2012, the contents of all of which are incorporated herein by reference in their entirety.

TECHNICAL FIELD

The present disclosure relates to a novel compound and an organic electroluminescent device including the same, and more particularly, to a novel compound having excellent hole injection capabilities, hole transport capabilities, light-emitting capabilities, and the like, and an organic electroluminescent device which contains the compound as a material for an organic material layer so as to improve characteristics such as light-emitting efficiency, driving voltage, and a service life.

BACKGROUND ART

A study on an organic electroluminescent (EL) device (hereinafter, simply referred to as 'organic EL device') has continued from the start point of observing an organic thin film light emission by Bernanose in the 1950s to blue electric light emission using an anthracene single crystal in 1965, and an organic EL device having a lamination structure, which is divided into functional layers of a hole layer and a light-emitting layer, was proposed by Tang in 1987. Thereafter, the organic EL device has been developed in the form of introducing a characteristic organic material layer into a device in order to enhance efficiency and a service life of the organic EL device, and the development has also been led to the development of specialized materials used therein.

In the organic electroluminescent device, when voltage is applied between two electrodes, holes are injected into the organic material layer at the anode and electrons are injected into the organic material layer at the cathode. When the injected holes and electrons meet each other, an exciton is formed, and when the exciton falls down to a bottom state, light is emitted. Materials used as the organic material layer may be classified into a light-emitting material, a hole injection material, a hole transporting material, an electron transporting material, an electron injection material, and the like according to the function.

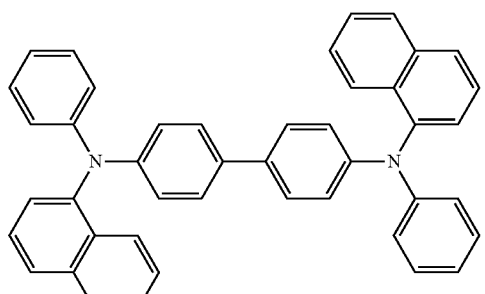

NPB

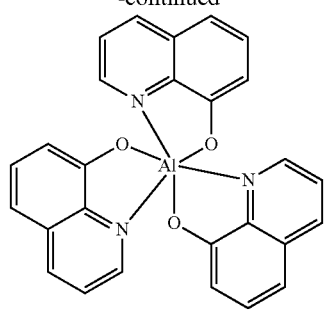

Alq3

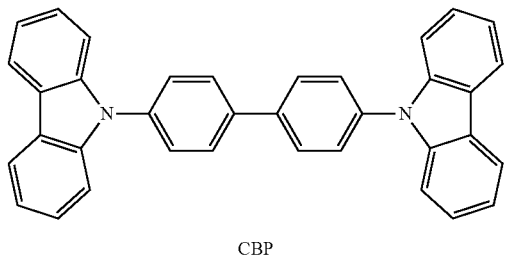

CBP

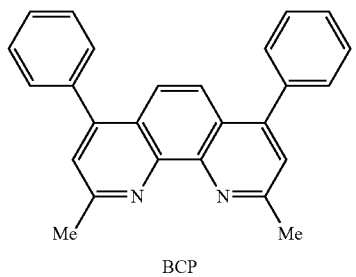

BCP

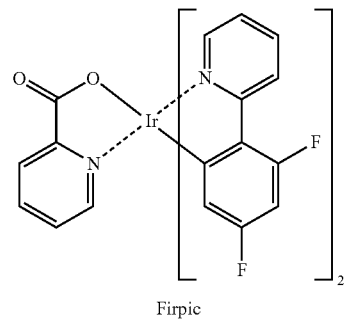

Firpic

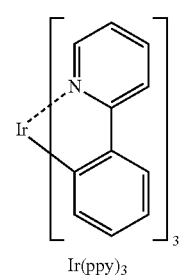

Ir(ppy)$_3$

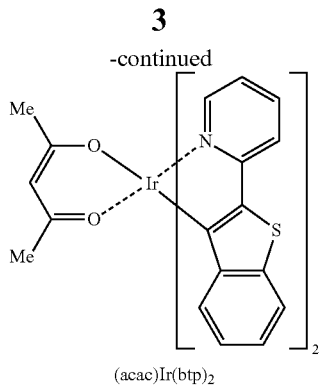

(acac)Ir(btp)₂

Meanwhile, in order to achieve practical application of the organic electroluminescent device and enhance characteristics thereof, the device needs to be formed of an organic material layer having the multi-layered structure as described above, and a material for the device, particularly a hole transporting material, needs to have thermally and electrically stable characteristics. This is because when voltage is applied to an organic electroluminescent device, heat is generated from the device, and molecules having low thermal stability are rearranged due to low crystal stability, and as a result, there occurs a local crystallization, and thus there exists an inhomogeneous portion, and an electric field is concentrated on the inhomogeneous portion, thereby degrading and destroying the device.

In consideration of these points, m-MTDATA [4,4',4"-tris (N-3-methylphenyl-N-phenylamino)-triphenylamine], 2-TNATA [4,4',4"-tris(N-(naphthylen-2-yl)-N-phenylamino)-triphenylamine], TPD [N,N'-diphenyl-N,N'-di(3-methylphenyl)-4,4'-diaminobiphenyl] and NPB [N,N'-di (naphthalene-1-yl)-N,N'-diphenylbenzidine], and the like were used in the related art as a hole transporting material.

However, since m-MTDATA and 2-TNATA have a low glass transition temperature (Tg) of about 78° C. and about 108° C., respectively, and many problems occur in the process of mass production, there has been a problem in implementing a full color. Meanwhile, TPD and NPB also have a low glass transition temperature (Tg) of about 60° C. and about 96° C., respectively, thereby causing deterioration in the service life of the device like m-MTDATA and 2-TNATA.

Therefore, there is a need for the development of a new hole transporting material which may increase thermal stability and has excellent hole transport capabilities, and thus may enhance the light-emitting efficiency and power efficiency of the organic electroluminescent device.

DISCLOSURE

Technical Problem

An object of the present disclosure is to provide a novel compound which has excellent hole injection capabilities, hole transport capabilities, light-emitting capabilities, and the like, and thus may be used as a material for a light-emitting layer, a material for a hole transporting layer, and a material for a hole injection layer.

Further, another object of the present disclosure is to provide an organic electroluminescent device which includes the novel compound, and thus has low driving voltage, high light-emitting efficiency, and enhanced service life.

Technical Solution

In order to achieve the objects, the present disclosure provides a compound represented by the following Formula 1.

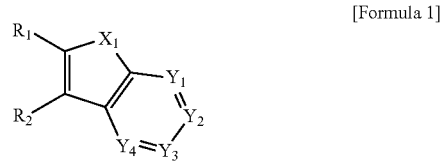

[Formula 1]

In Formula 1, $Y_1$ to $Y_4$ are each independently N or $CR_3$, and in this case, when $CR_3$ is present in a plural number, they are the same as or different from each other, and provided that at least one of $Y_1$ and $Y_2$, $Y_2$ and $Y_3$, and $Y_3$ and $Y_4$ is $CR_3$, and forms a fused ring represented by the following Formula 2;

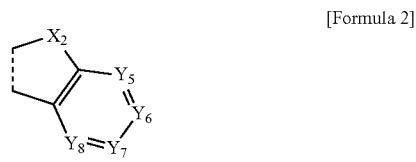

[Formula 2]

in Formula 2, $Y_5$ to $Y_8$ are each independently selected from N or $CR_4$, and in this case, when $CR_4$ is present in a plural number, they are the same as or different from each other, and provided that at least one of $Y_5$ to $Y_8$ is $CR_4$, and in this case, at least one $R_4$ is a substituent represented by the following Formula 3;

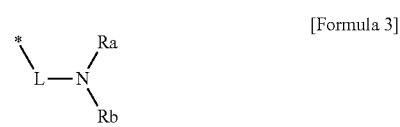

[Formula 3]

in Formula 3,

L is a single bond, or selected from the group consisting of a substituted or unsubstituted $C_6$ to $C_{60}$ arylene group, and a substituted or unsubstituted heteroarylene group having 5 to 60 nuclear atoms, in this case, one or more substituents each introduced into the arylene group and the heteroarylene group of L are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, and a $C_6$ to $C_{60}$ arylamine group, and provided that when the substituent is present in a plural number, these may be the same as or different from each other;

$R_a$ and $R_b$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, and a substituted or unsubstituted heteroaryl group having 5 to 60 nuclear atoms, in this case, one or more substituents each introduced into the alkyl group, the cycloalkyl group, the heterocycloalkyl group, the aryl group, and the heteroaryl group of $R_a$ and $R_b$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, these may be the same as or different from each other;

provided that L, $R_a$, and $R_b$ may combine with an adjacent substituent to form a fused ring;

$X_1$ and $X_2$ are each independently selected from the group consisting of O, S, Se, $N(Ar_1)$, $C(Ar_2)(Ar_3)$, and $Si(Ar_4)(Ar_5)$, and in this case, when $N(Ar_1)$ is present in a plural number, they are the same as or different from each other, when $C(Ar_2)(Ar_3)$ is present in a plural number, they are the same as or different from each other, and when $Si(Ar_4)(Ar_5)$ is present in a plural number, they are the same as or different from each other, and provided that at least one of $X_1$ and $X_2$ is $N(Ar_1)$;

$Ar_1$ to $Ar_5$ are the same as or different from each other, and are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ to $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these form or do not form a fused ring with an adjacent group; and one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ to $Ar_5$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, these may be the same as or different from each other.

Further, the present disclosure provides an organic electroluminescent device including an anode, a cathode, and an organic material layer including one or more layers interposed between the anode and the cathode, in which at least one of the organic material layers including one or more layers includes the compound.

The organic material layer including one or more layers, which includes the compound, is selected from the group consisting of a hole transporting layer, a hole injection layer, and a light-emitting layer, and is preferably a hole transporting layer and/or a light-emitting layer, and is more preferably used as a material for a hole transporting layer.

Advantageous Effects

The compound according to the present disclosure has excellent heat resistance, hole injection capabilities, hole transport capabilities, light-emitting capabilities, and the like, and thus may be used as a material for an organic material layer of an organic electroluminescent device, preferably a material for a hole injection layer, a material for a hole transporting layer, or a material for a light-emitting layer.

In addition, an organic EL device including the compound according to the present disclosure in a hole injection layer, a hole transporting layer and/or a light-emitting layer may be enhanced greatly in terms of light-emitting performance, driving voltage, a service life, efficiency, and the like, and furthermore, the device may be effectively applied to a full-color display panel, and the like.

BEST MODE

Hereinafter, the present disclosure will be described.

A novel compound according to the present disclosure has a basic structure in which an arylamine moiety is bonded directly or through a linking group (for example, an arylene group, and the like) to an end of a moiety in which an indole-based moiety, and the like and an indole-based moiety, and the like are fused, in which various substituents are bonded to the basic structure, and the compound is represented by Formula 1. The compound represented by Formula 1 may enhance phosphorescent characteristics of a device, and simultaneously, may enhance hole injection/transport capabilities, light-emitting efficiency, driving voltage, service life characteristics, durability, and the like, and may also enhance electron transport capabilities, and the like according to the kind of substituent to be introduced. Therefore, the compound of Formula 1 may be used as a material for an organic material layer of an organic electroluminescent device, preferably a material for a light-emitting layer (a phosphorescent host material), a material for a hole transporting layer, and a material for a hole injection layer, and more preferably a material for a hole transporting layer.

Furthermore, the compound of Formula 1 may also be used as a material for an electron transporting layer, and the like by optionally introducing an appropriate substituent.

The compound represented by Formula 1 may include a moiety in which an indole-based moiety, and the like and an indole-based moiety, and the like are fused, thereby having the existing wide singlet energy level and a high triplet energy level. Further, an arylamine moiety is introduced directly or through a linking group (for example, an arylene group, and the like) into a moiety in which the indole-based moieties are fused, so that the energy level is effectively adjusted, thereby maximizing hole blocking capabilities and hole injection/transport capabilities. The compound of Formula 1 may be usefully applied as a material for a hole injection layer and a material for a hole transporting layer of an organic EL device.

In addition, the compound represented by Formula 1 may variously modify the linking group to enhance phosphorescent characteristics, and the compound may be used as a material for a light-emitting layer of a phosphorescent light-emitting organic EL device.

Furthermore, various substitution products, particularly, an aryl group and/or a heteroaryl group, are introduced into the compound represented by Formula 1 to significantly increase the molecular weight of the compound and enhance the glass transition temperature, and accordingly, the compound represented by Formula 1 may have thermal stability higher than that of the existing light-emitting material. Therefore, an organic electroluminescent device including the novel compound represented by Formula 1 according to the present disclosure may greatly enhance durability and service life characteristics.

Furthermore, when the compound represented by Formula 1 is adopted as a hole injection/transporting layer, a blue, green, and/or red phosphorescent host material of an organic electroluminescent device, much better effects may be exhibited in terms of efficiency and a service life compared to the NPB in the related art. Therefore, the compound according to the present disclosure may greatly contribute to the improvement of performance and the enhancement of service life, of the organic electroluminescent device, and furthermore, the enhancement of service life of the organic electroluminescent device may maximize the performance of a full color organic light-emitting panel.

In the compound represented by Formula 1 according to the present disclosure, $Y_1$ to $Y_4$ are each independently N or $CR_3$, and in this case, when $CR_3$ is present in a plural number, they are the same as or different from each other.

Provided that at least one of $Y_1$ and $Y_2$, $Y_2$ and $Y_3$, and $Y_3$ and $Y_4$ is $CR_3$, and forms a fused ring represented by the following Formula 2. For example, when both $Y_1$ and $Y_2$ of $Y_1$ and $Y_2$, $Y_2$ and $Y_3$, and $Y_3$ and $Y_4$ are $CR_3$ and are fused with each other to form the fused ring represented by Formula 2, a compound represented by the following Formula 4 or 9 may be formed.

In Formula 2, the dotted line means a site where condensation with the compound of Formula 1 occurs.

In Formula 2, $Y_5$ to $Y_8$ are each independently N or $CR_4$, and in this case, when $CR_4$ is present in a plural number, they are the same as or different from each other.

Provided that at least one of $Y_5$ to $Y_8$ is $CR_4$, and in this case, at least one $R_4$ is the substituent represented by Formula 3.

According to an example of the present disclosure, all of $Y_1$ to $Y_4$ may be $CR_3$, and all of $Y_5$ to $Y_8$ may be $CR_4$. In this case, a plurality of $R_3$ and a plurality of $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these may or may not form a fused ring with an adjacent group. Provided that at least one of the plurality of $R_4$ is the substituent represented by Formula 3.

In Formula 3, L is a single bond or selected from the group consisting of a substituted or unsubstituted $C_6$ to $C_{60}$ arylene group and a substituted or unsubstituted heteroarylene group having 5 to 60 nuclear atoms, or may form a fused ring with an adjacent group. In this case, one or more substituents each introduced into the arylene group and the heteroarylene group of L are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, and a $C_6$ to $C_{60}$ arylamine group, and provided that when the substituent is present in a plural number, these may be the same as or different from each other.

Preferably, L is a single bond, or may be selected from the group consisting of a phenylene group, a biphenylene group, a fluorenylene group, a naphthylene group, a pyridinylene group, a pyrimidinylene group, a quinolinylene group, and a carbazolylene group.

Further, $R_a$ and $R_b$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, and a substituted or unsubstituted heteroaryl group having 5 to 60 nuclear atoms, or may form a fused ring with an adjacent ring. In this case, one or more substituents each introduced into the alkyl group, the cycloalkyl group, the heterocycloalkyl group, the aryl group, and the heteroaryl group of $R_a$ and $R_b$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, these may be the same as or different from each other.

Preferably, $R_a$ and $R_b$ may be each independently selected from the group consisting of a phenyl group, a biphenyl group, a fluorenyl group, a naphthyl group, a pyridyl group, a pyrimidinyl group, a quinolyl group, and a carbazolyl group.

More preferably, Formula 3 may be selected from the group consisting of the following substituents U1 to U86, and is not limited thereto.
U1
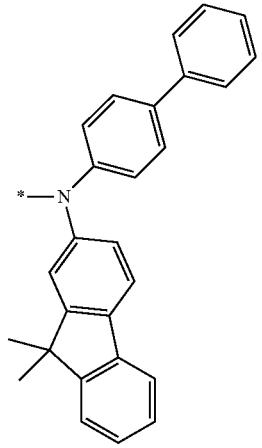
U2
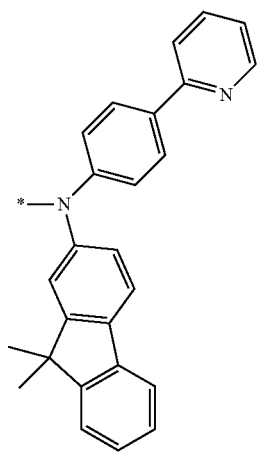
U3
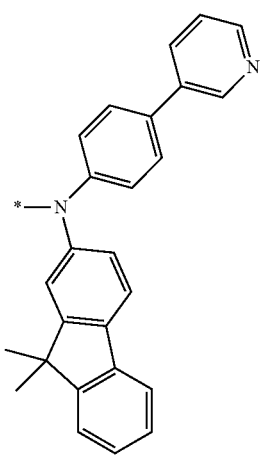
U4
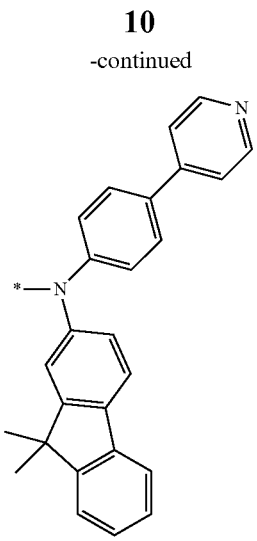
U5
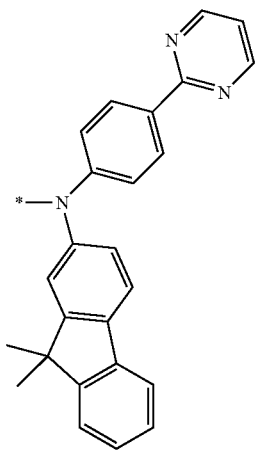
U6
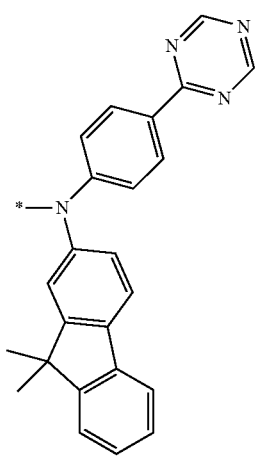

U7
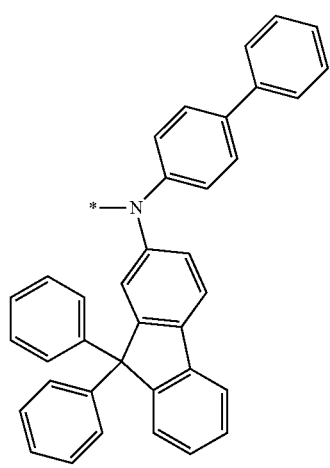
U8
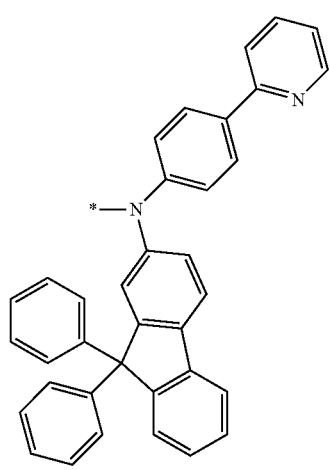
U9
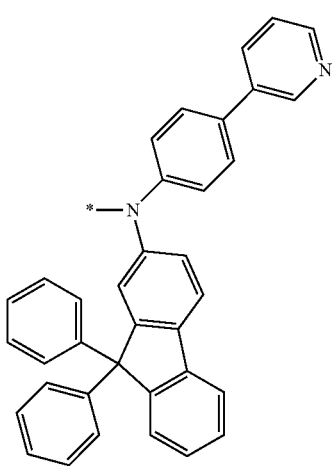
U10
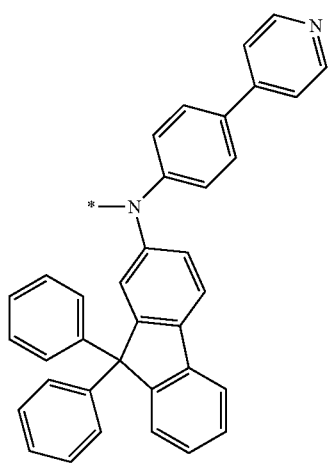
U11
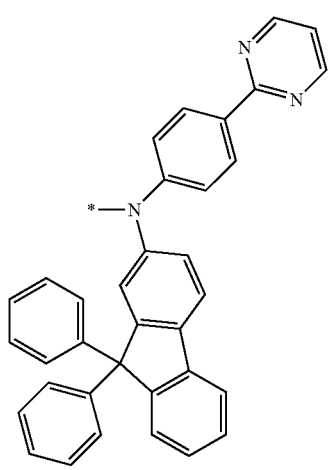
U12
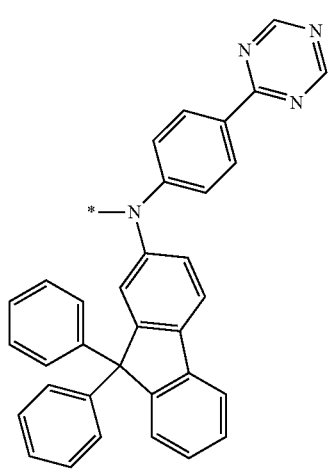

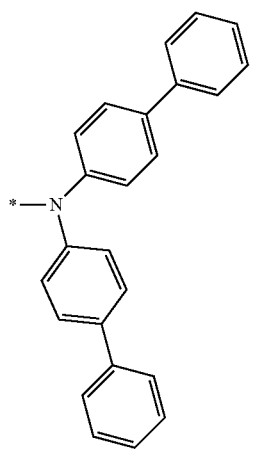 U13
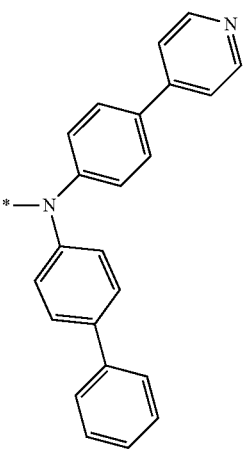 U16
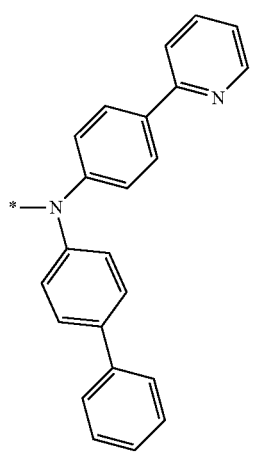 U14
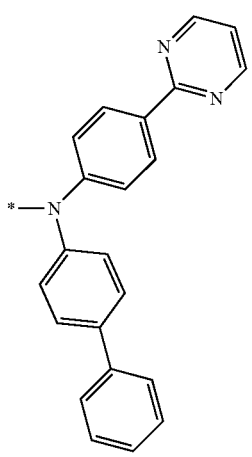 U17
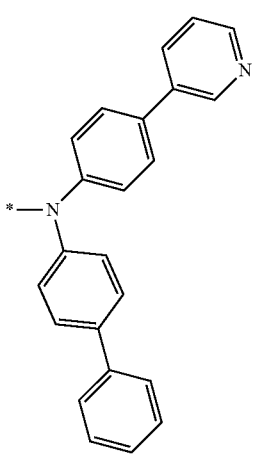 U15
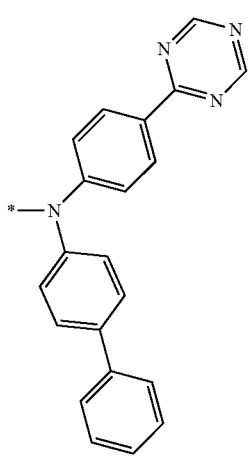 U18

U19
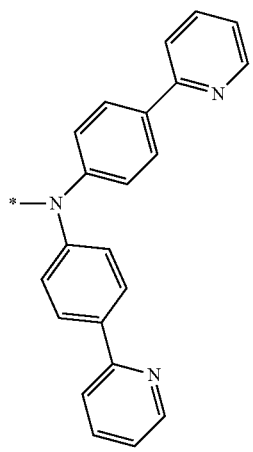
U20
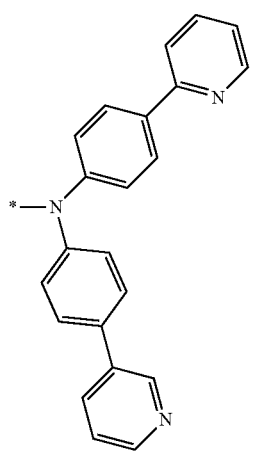
U21
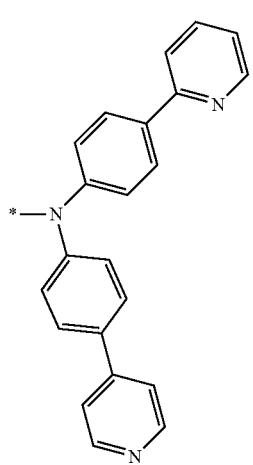
U22
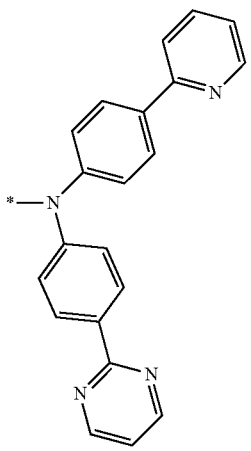
U23
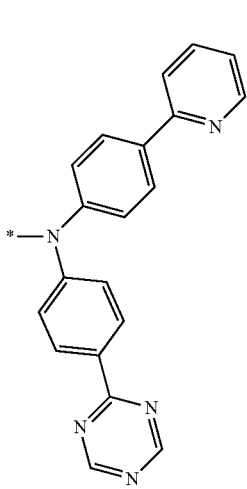
U24
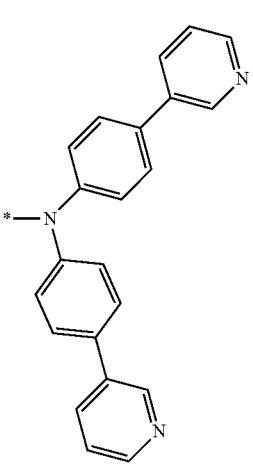

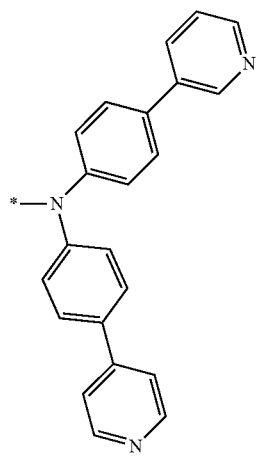 U25
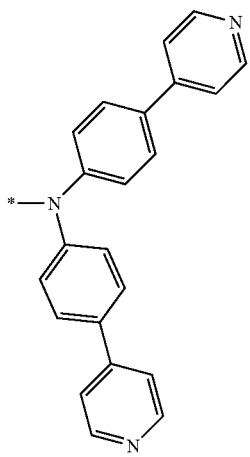 U28
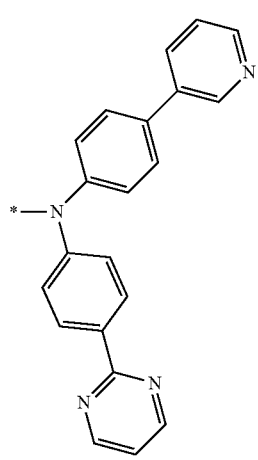 U26
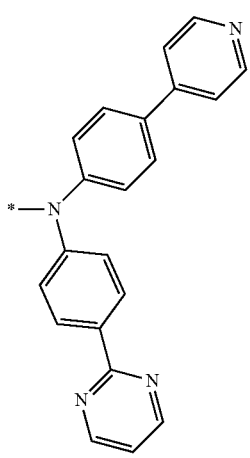 U29
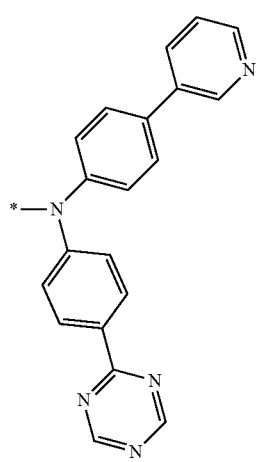 U27
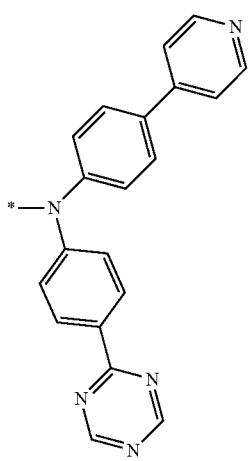 U30

U31 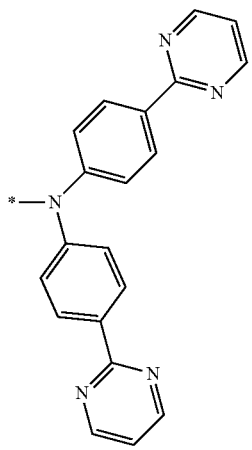
U32 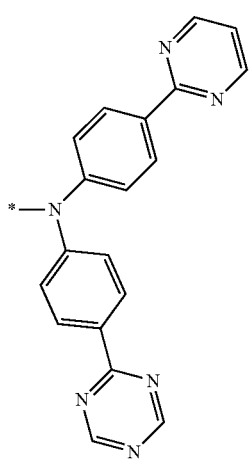
U33 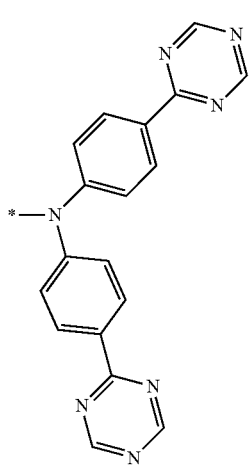
U34 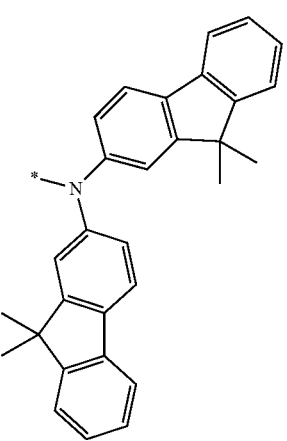
U35 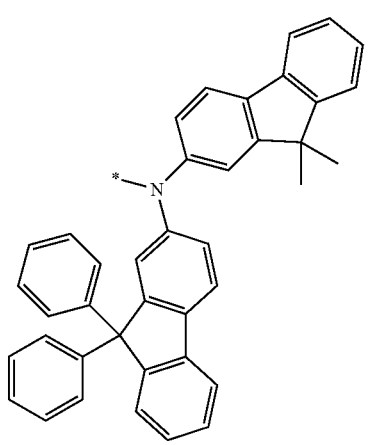
U36 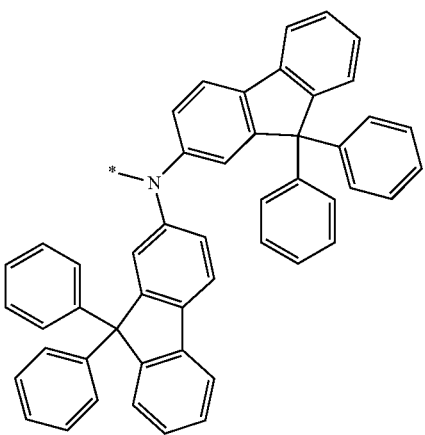

U37 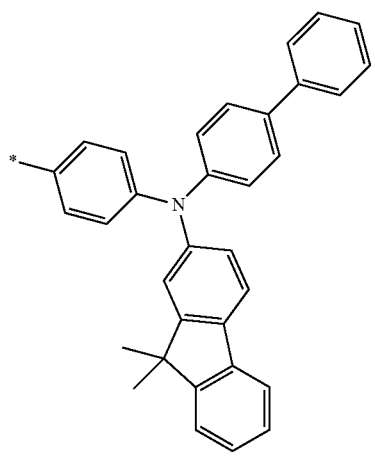
U38 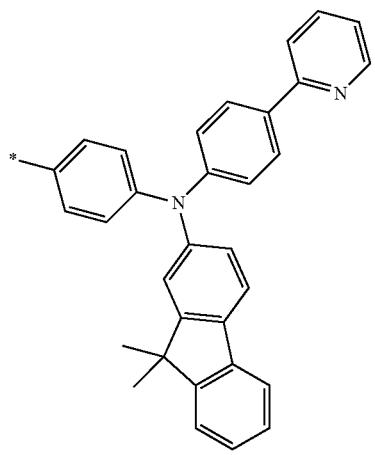
U39 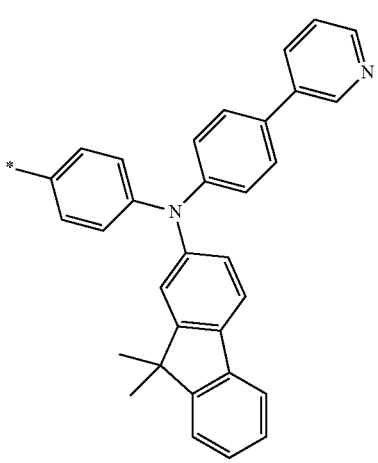
U40 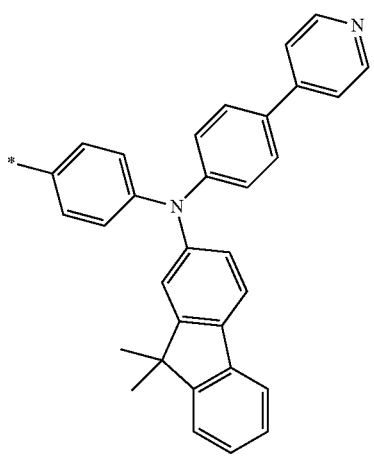
U41 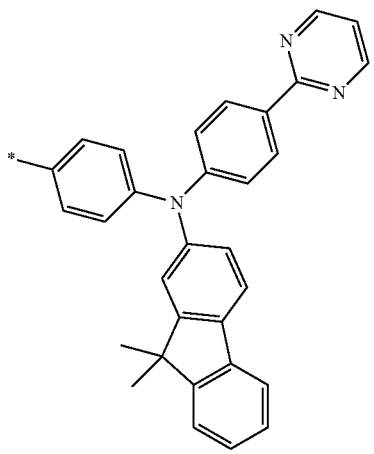
U42 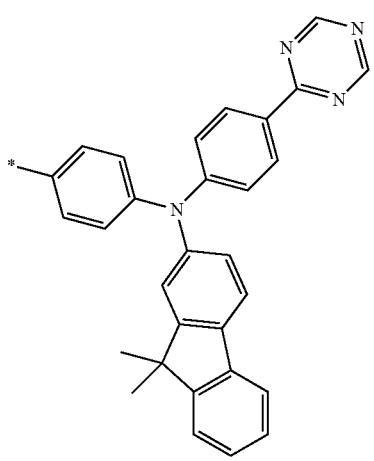

U43
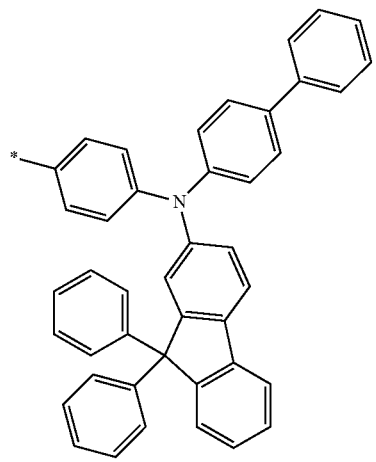
U44
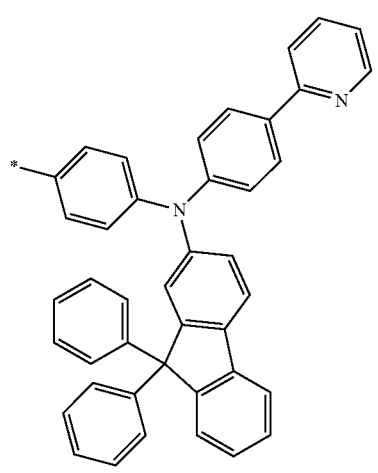
U45
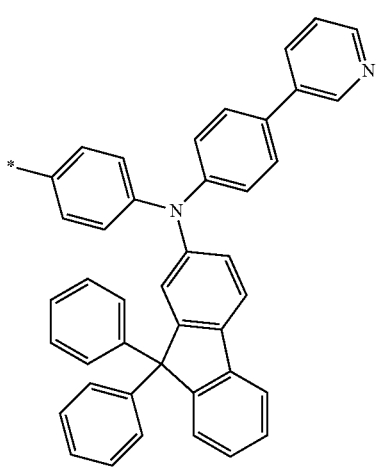
U46
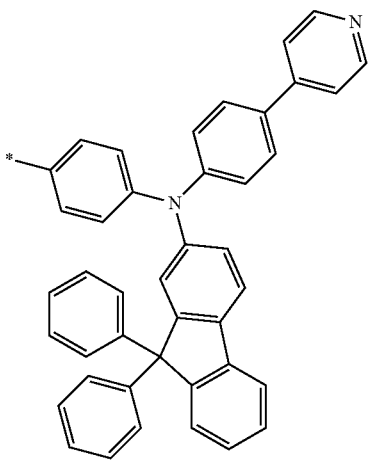
U47
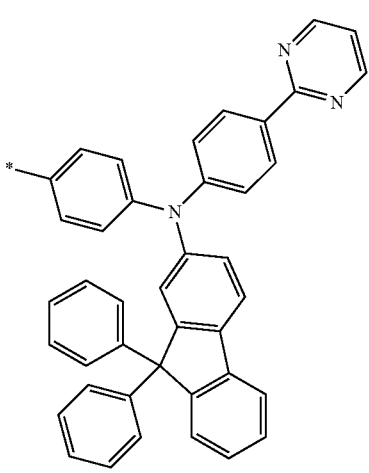
U48
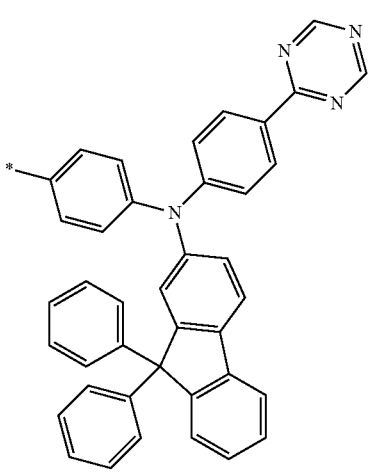

U49
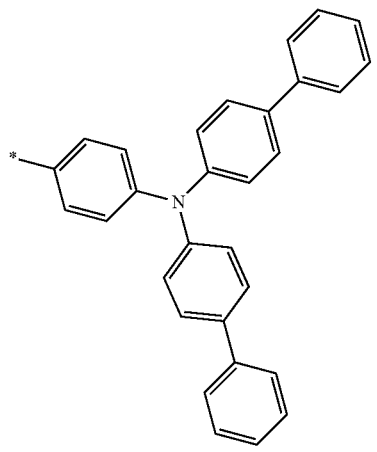
U50
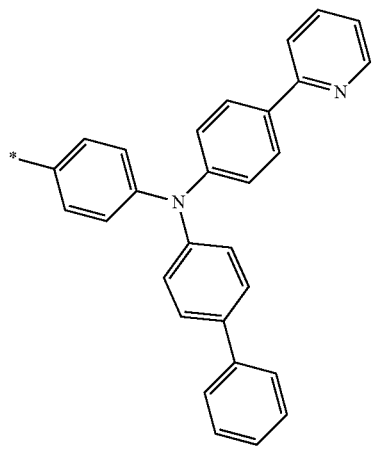
U51
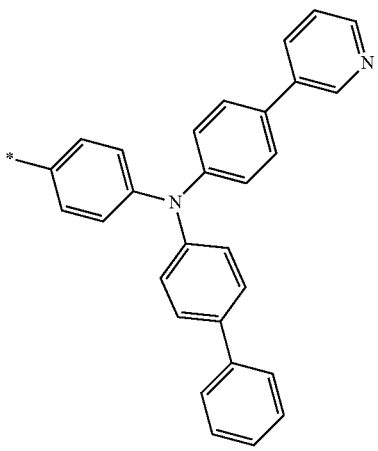
U52
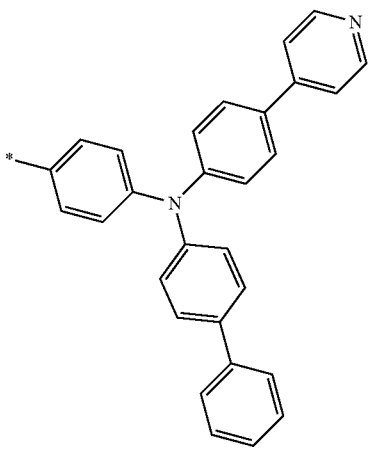
U53
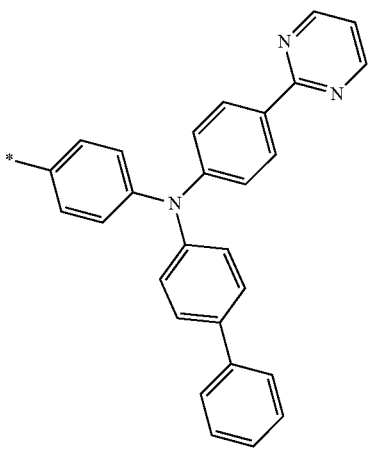
U54
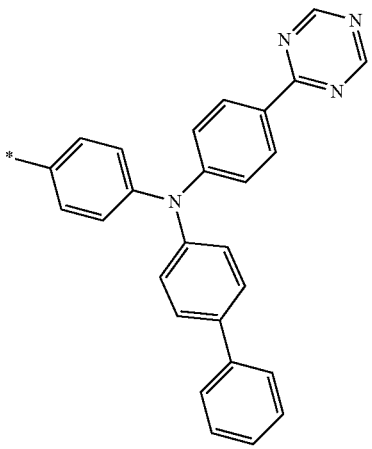

U55 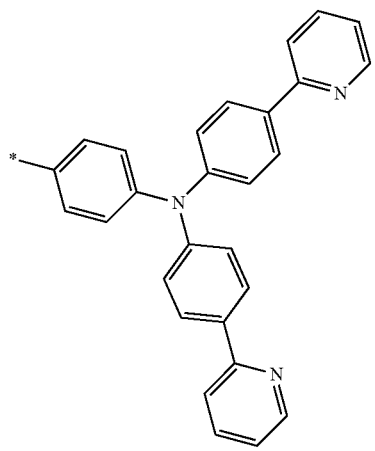
U58 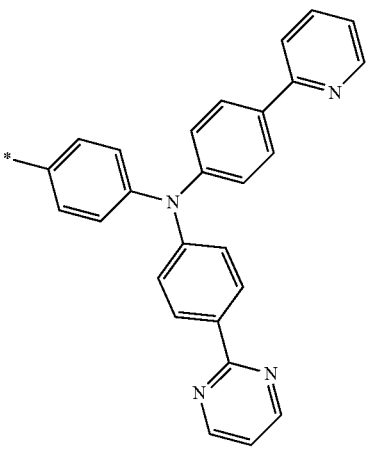
U56 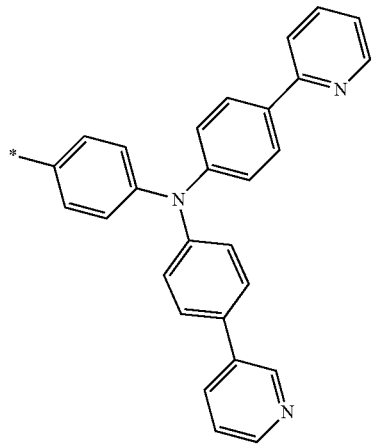
U59 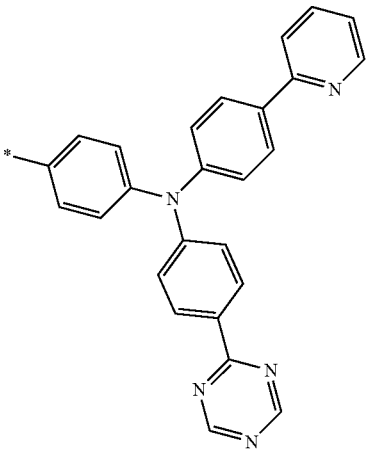
U57 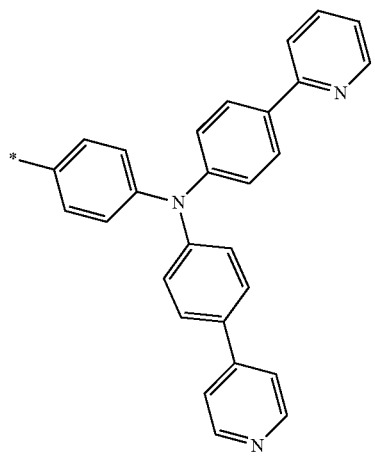
U60 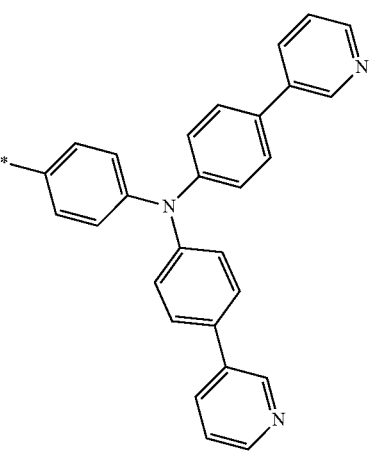

U61
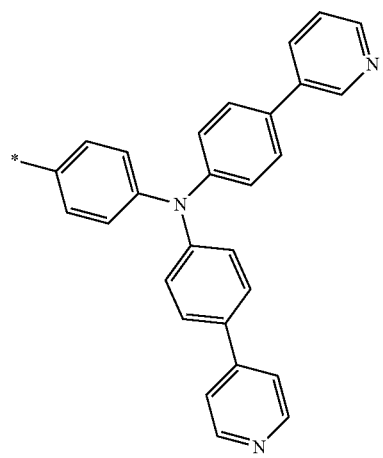
U64
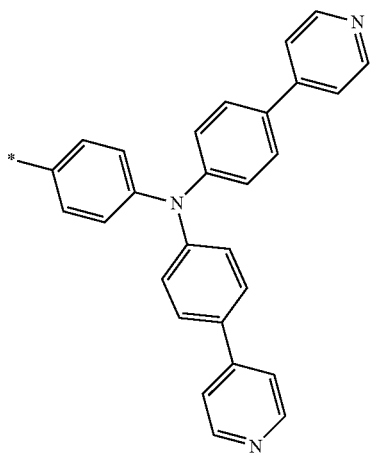
U62
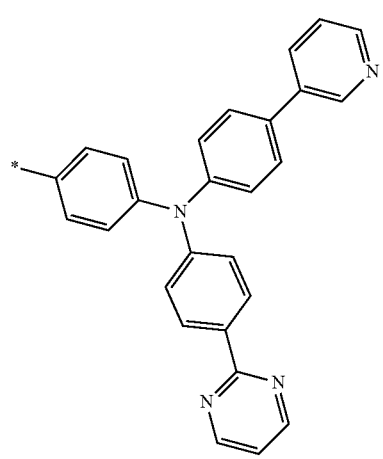
U65
U63
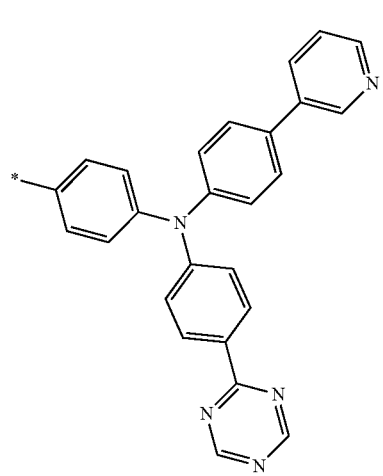
U66
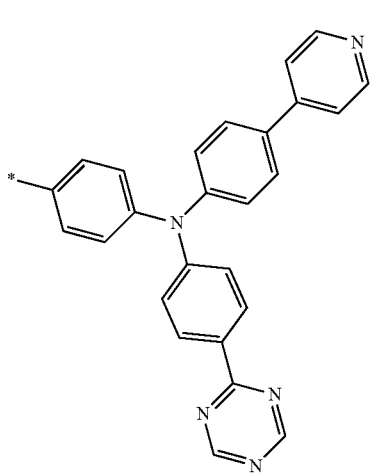

U67
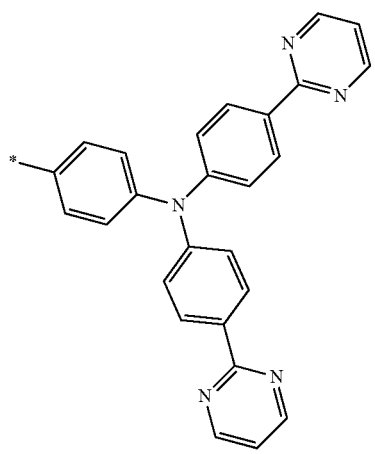
U68
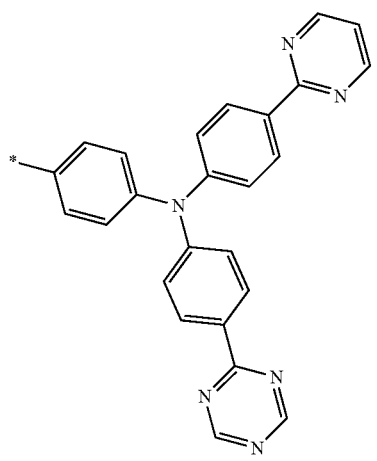
U69
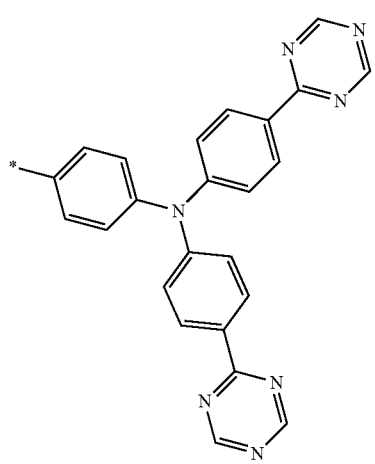
U70
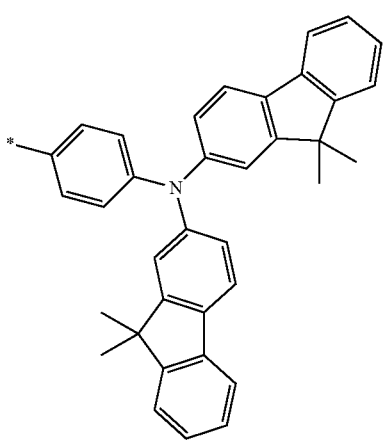
U71
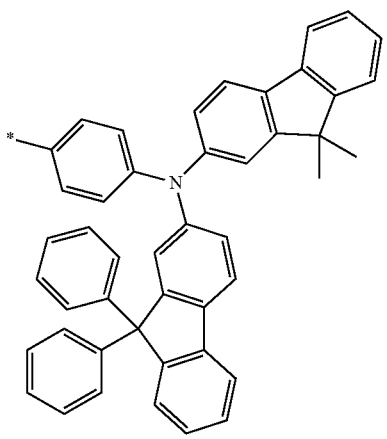
U72
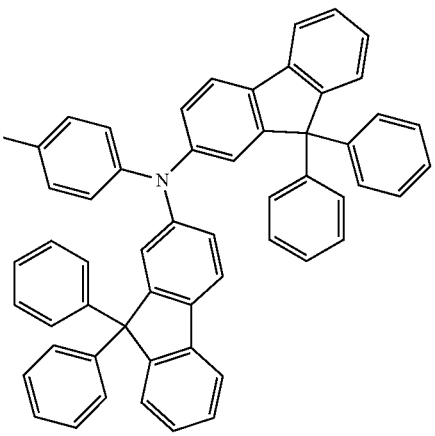

| U73 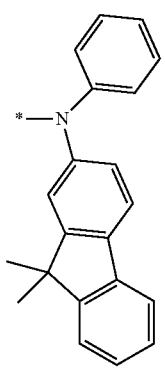 | U77 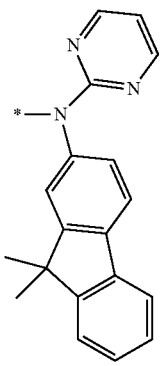 |
| U74 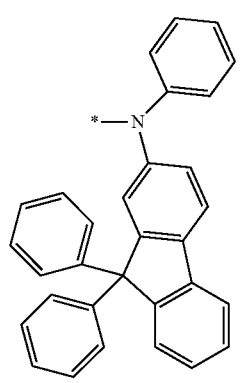 | U78 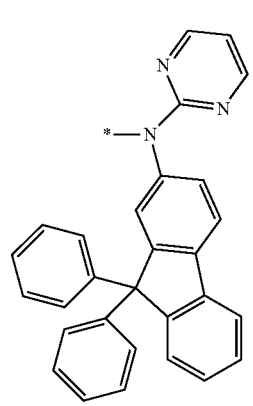 |
| U75 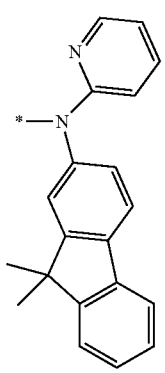 | U79 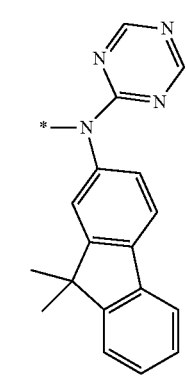 |
| U76 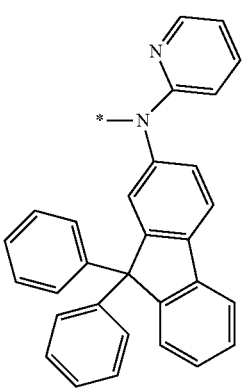 | U80 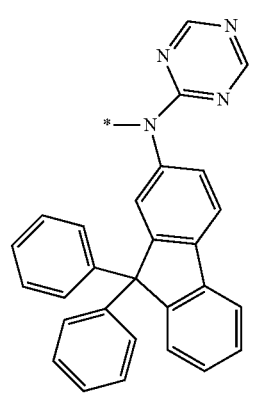 |

U81

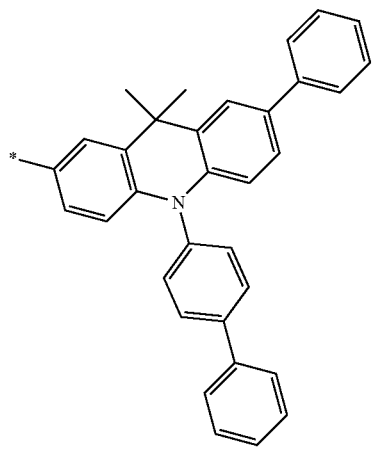

U82

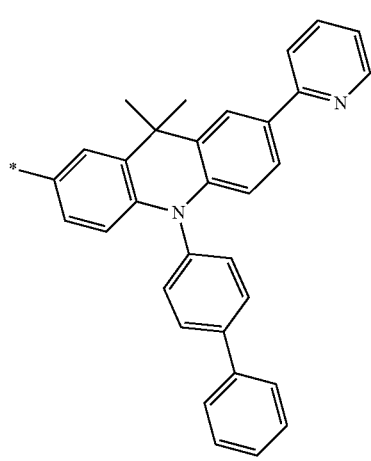

U83

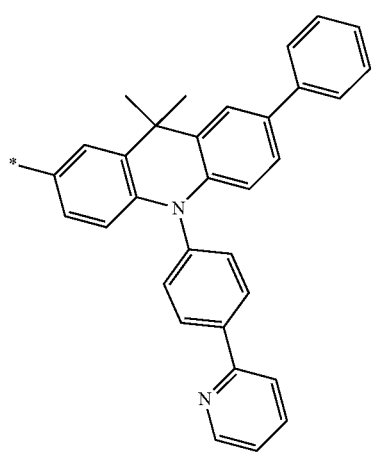

U84

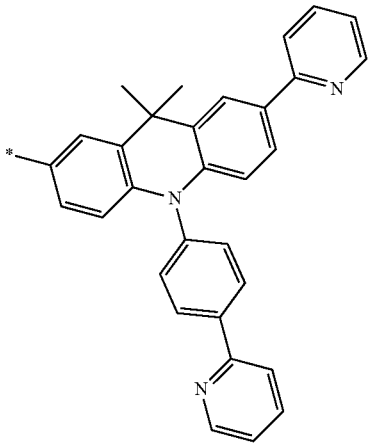

U85

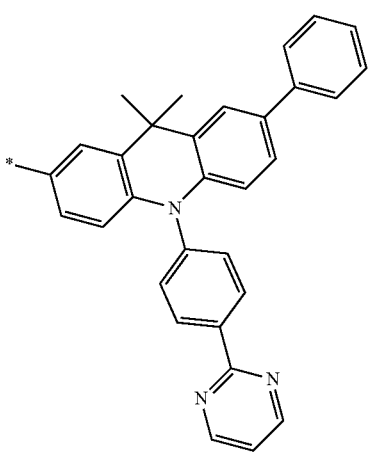

U86

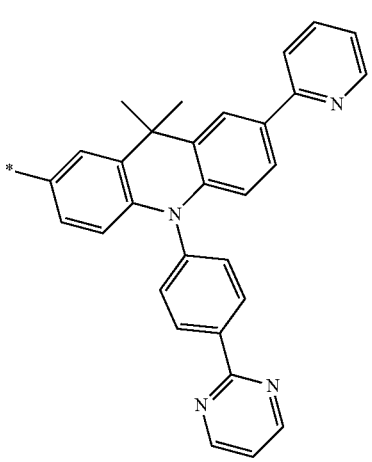

In the compound according to the present disclosure, $X_1$ and $X_2$ are each independently selected from the group consisting of O, S, Se, $N(Ar_1)$, $C(Ar_2)(Ar_3)$, and $Si(Ar_4)(Ar_5)$.

Provided that at least one of $X_1$ and $X_2$ is $N(Ar_1)$, and preferably, both $X_1$ and $X_2$ are $N(Ar_1)$.

In the compound according to the present disclosure, $R_1$ to $R_4$ and $Ar_1$ to $Ar_5$ may be each independently selected from the group consisting of hydrogen and the following S1 to S166, but are not limited thereto. Provided that when at least one of $Y_5$ to $Y_8$ is $CR_4$, at least one $R_4$ is the substituent represented by Formula 3.

-continued
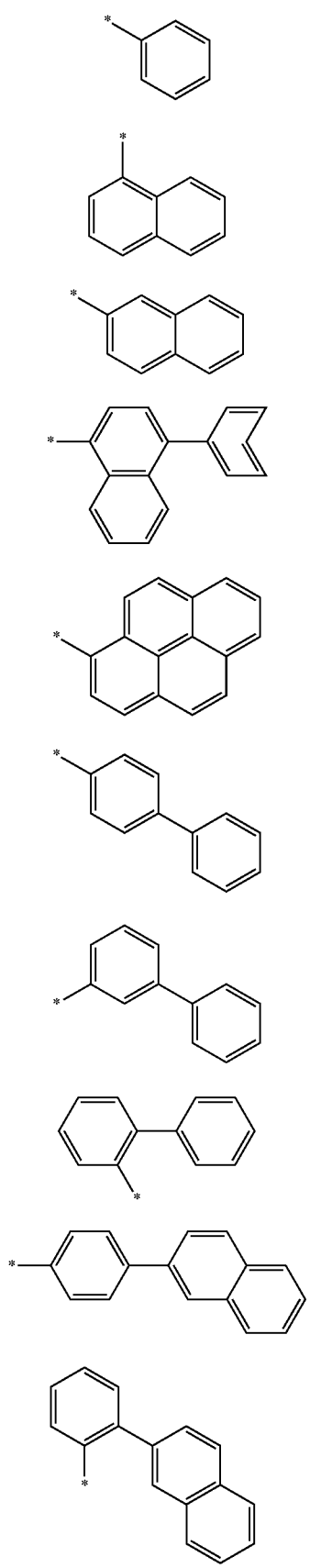
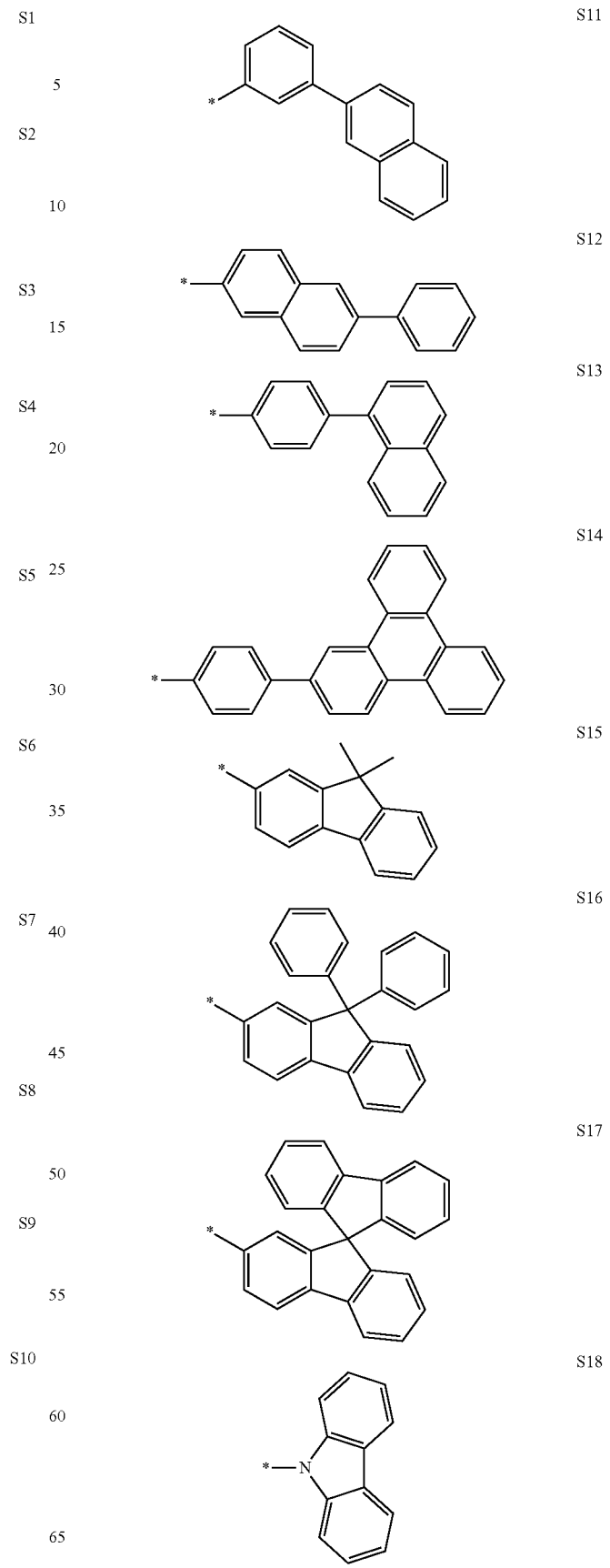

-continued
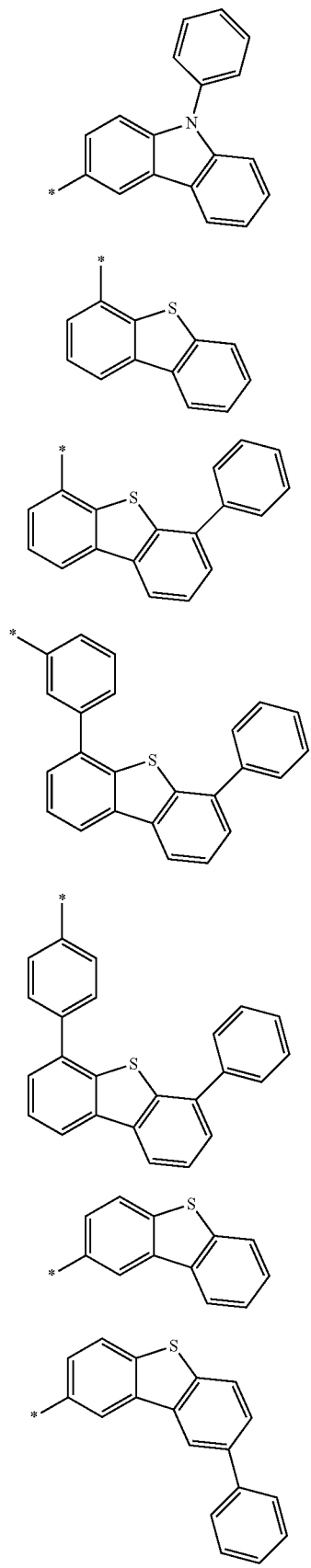
U19
U20
U21
U22
U23
U24
U25
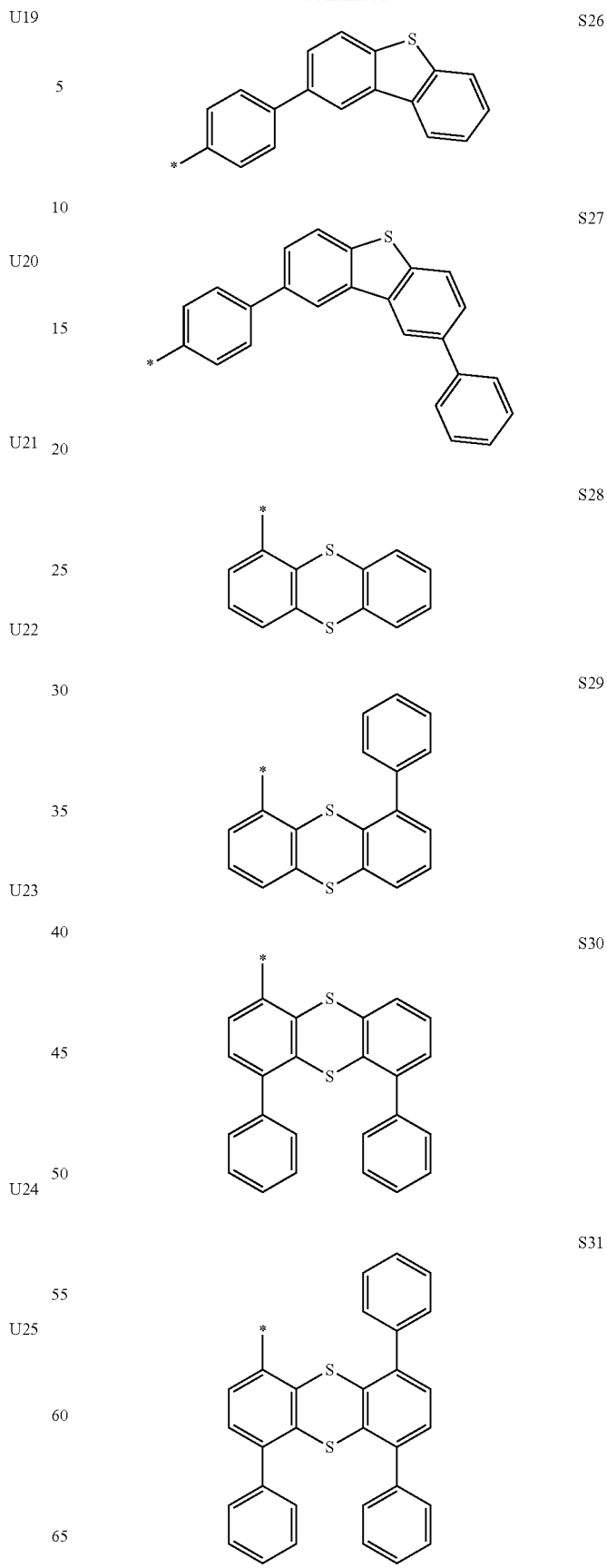
S26
S27
S28
S29
S30
S31

-continued
S32
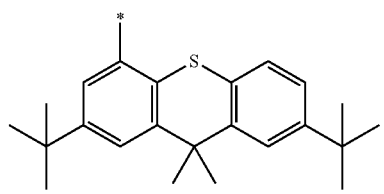
S33
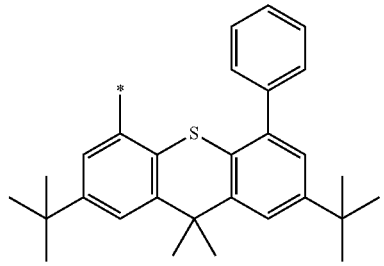
S34
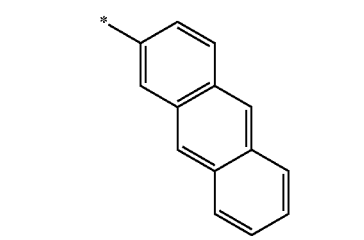
S35
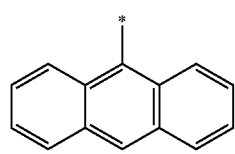
S36
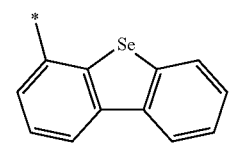
S37
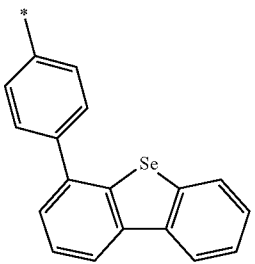
S38
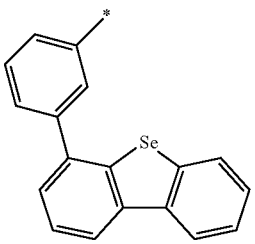
S39
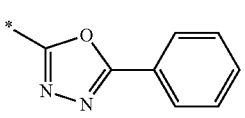
-continued
S40
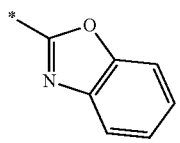
S41
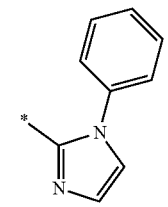
S42
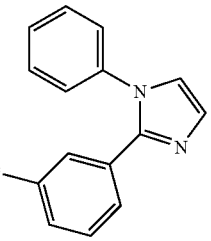
S43
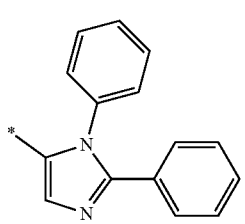
S44
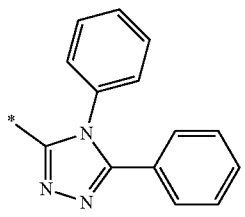
S45
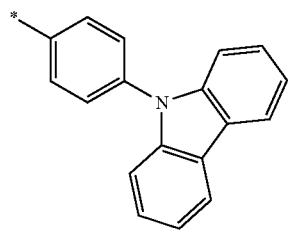
S46
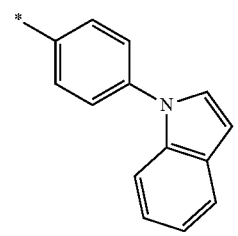

S47 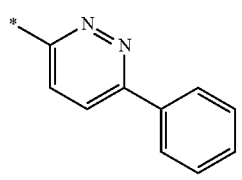
S48 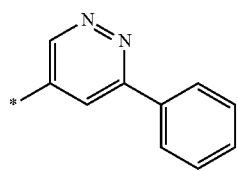
S49 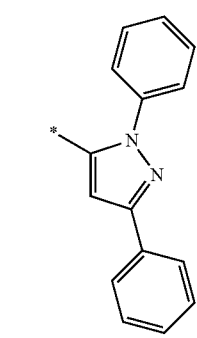
S50 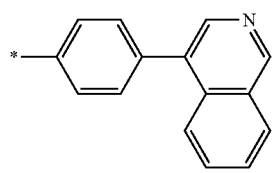
S51 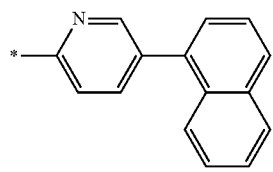
S52 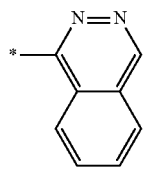
S53 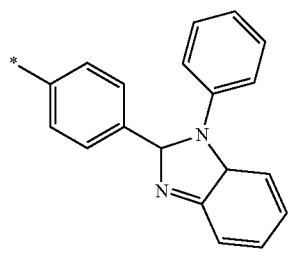
S54 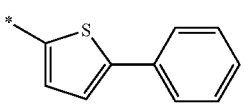
S55 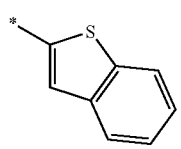
S56 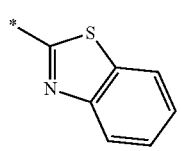
S57 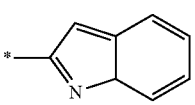
S58 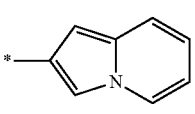
S59 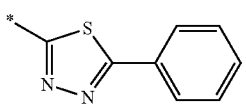
S60 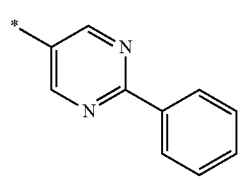
S61 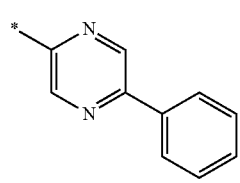
S62 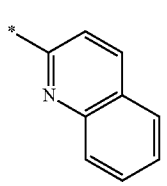
S63 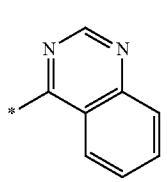
S64 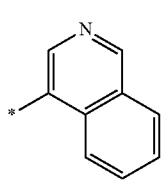

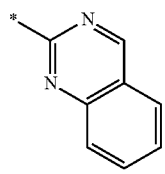 S65
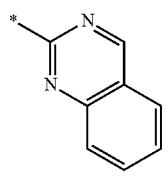 S66
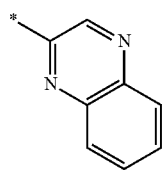 S67
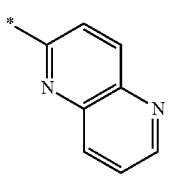 S68
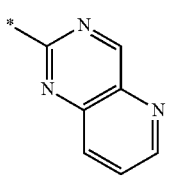 S69
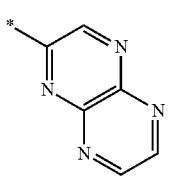 S70
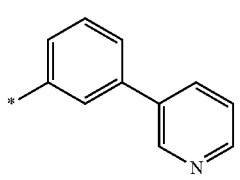 S71
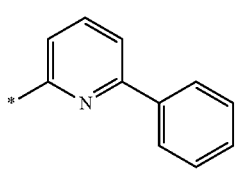 S72
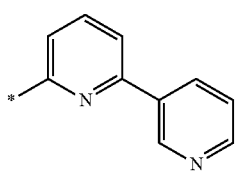 S73
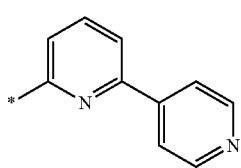 S74
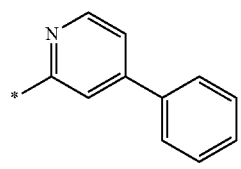 S75
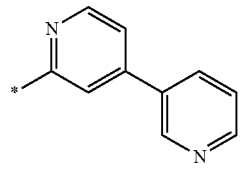 S76
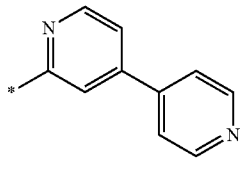 S77
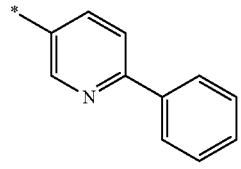 S78
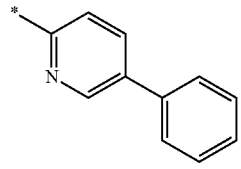 S79
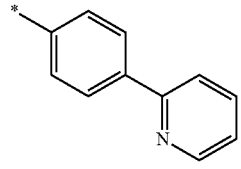 S80
 S81
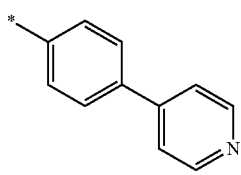 S82

S83 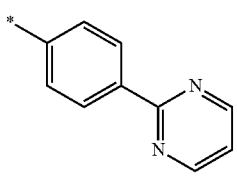
S84 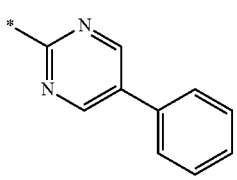
S85 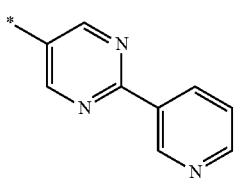
S86 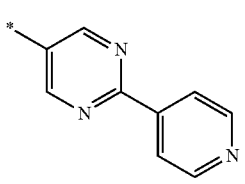
S87 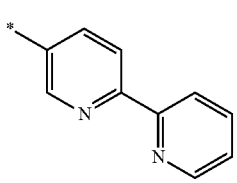
S88 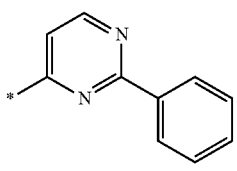
S89 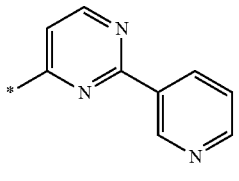
S90 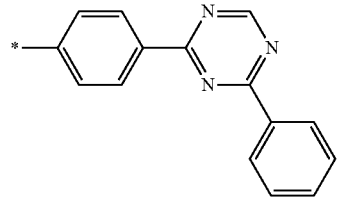
S91 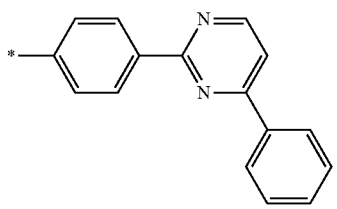
S92 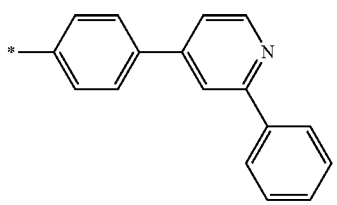
S93 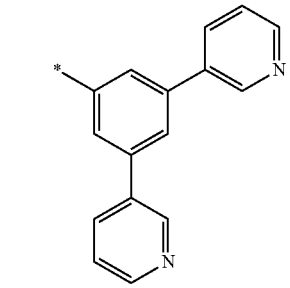
S94 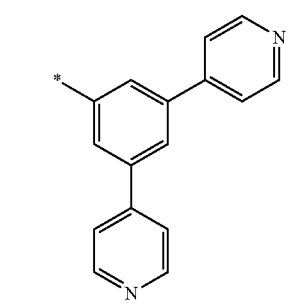
S95 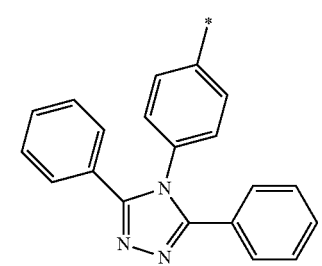
S96 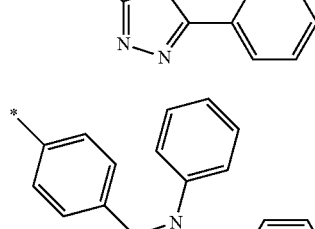

S97, S98, S99, S100, S101, S102, S103, S104, S105, S106

S107
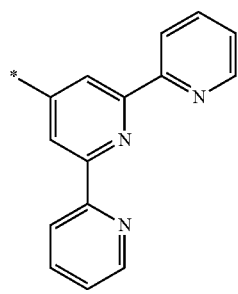
S108
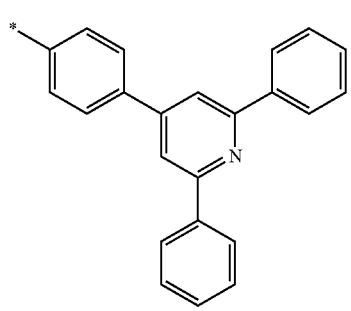
S109
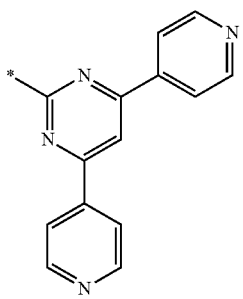
S110
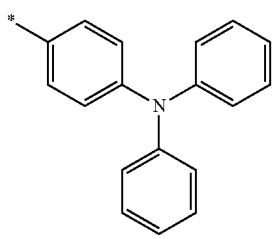
S111
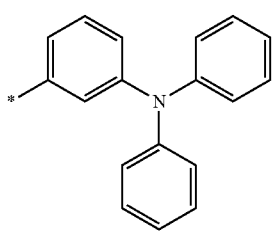
S112
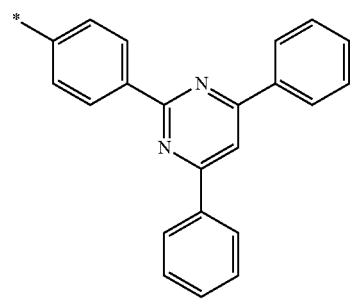
S113
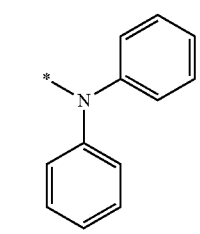
S114
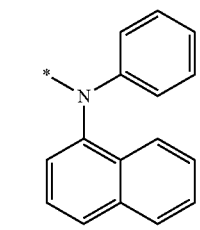
S115
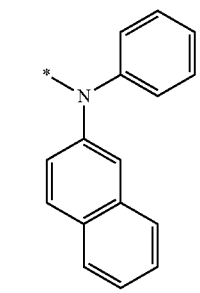
S116
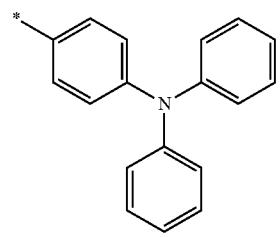
S117
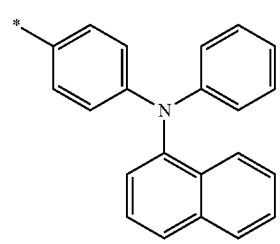

-continued
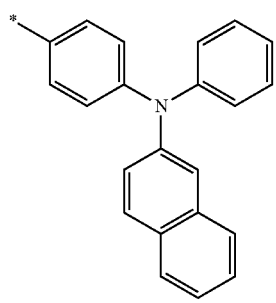
S118
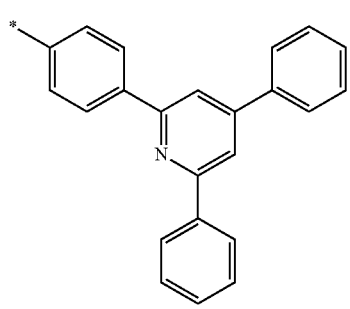
S119
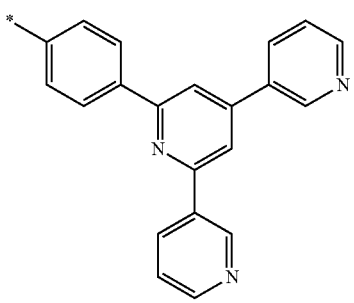
S120
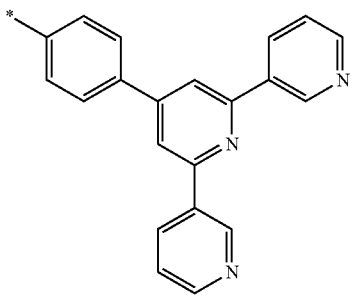
S121
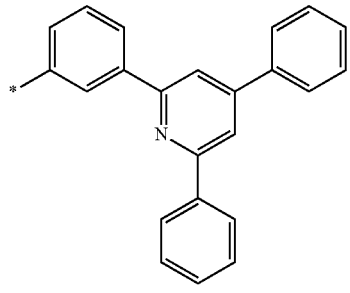
S122
-continued
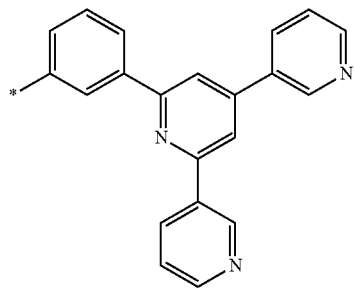
S123
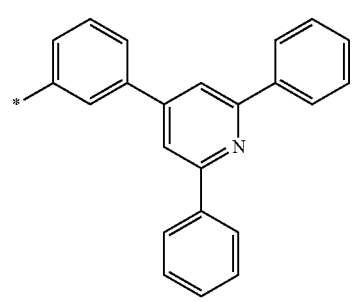
S124
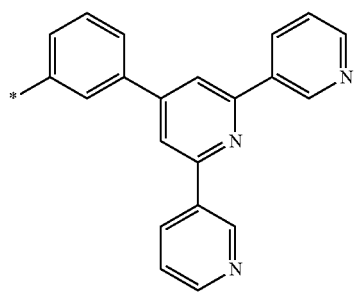
S125
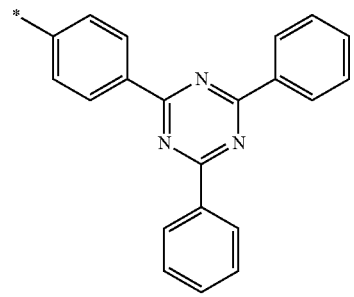
S126
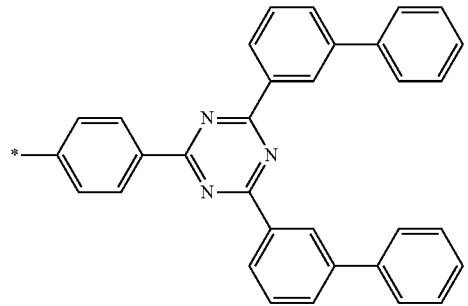
S127

-continued
S128
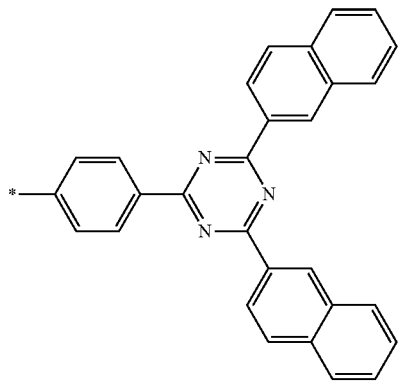
S129
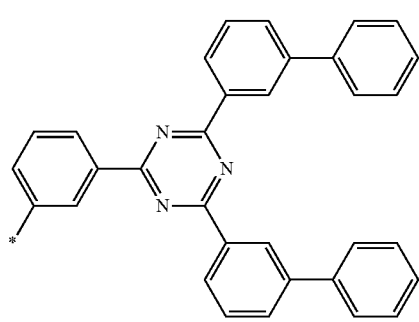
S130
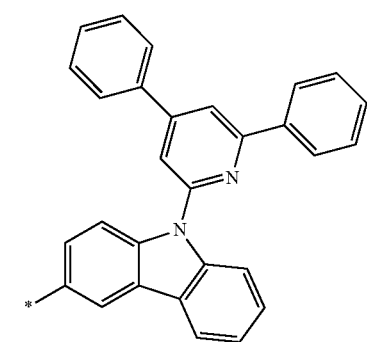
S131
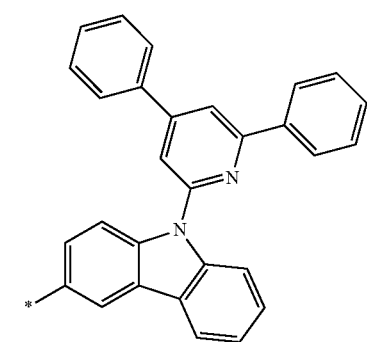
-continued
S132
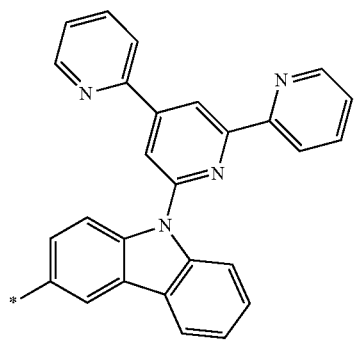
S133
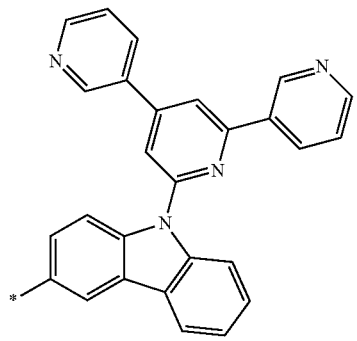
S134
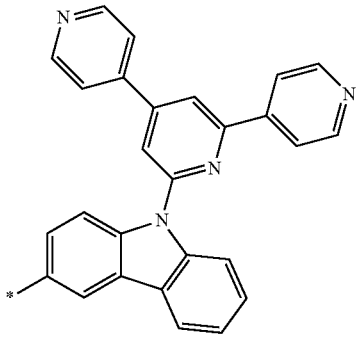
S135
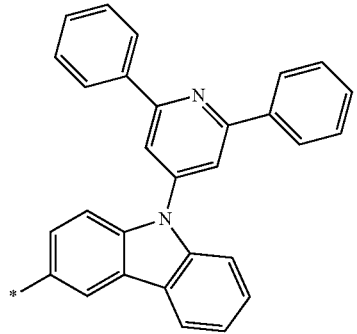

S136 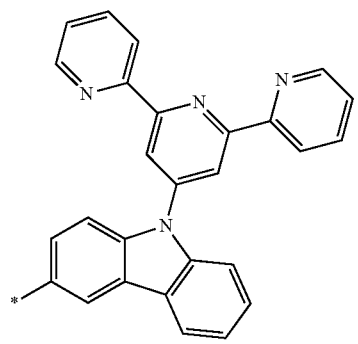
S137 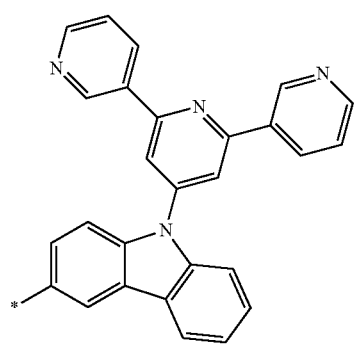
S138 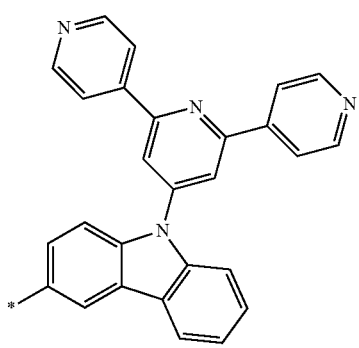
S139 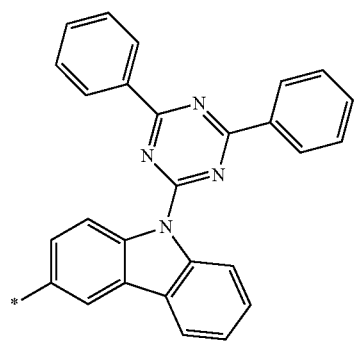
S140 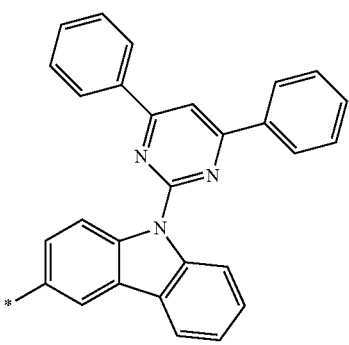
S141 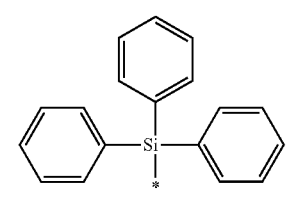
S142 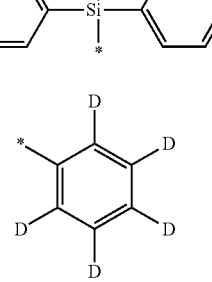
S143 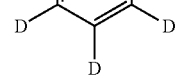
S144 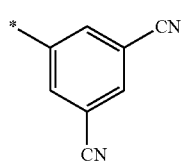
S145 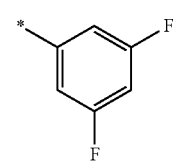
S146 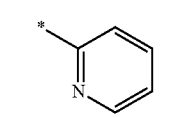
S147 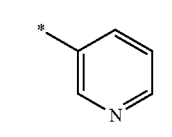
S148 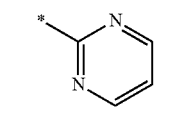

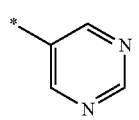 S149
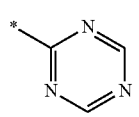 S150
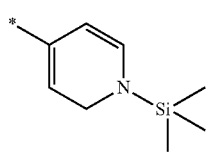 S151
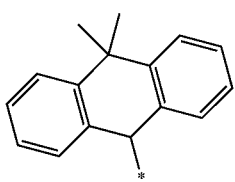 S152
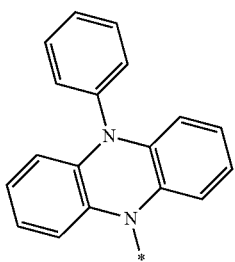 S153
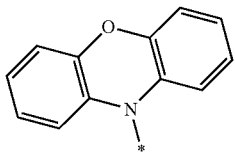 S154
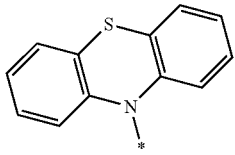 S155
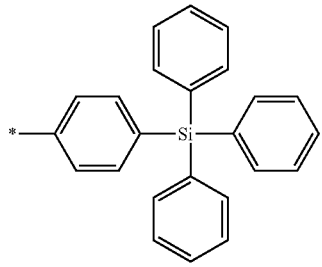 S156
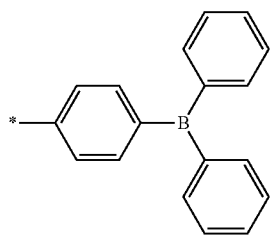 S157
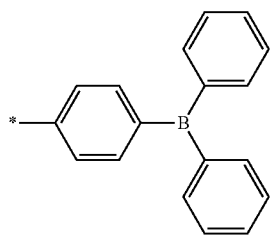 S158
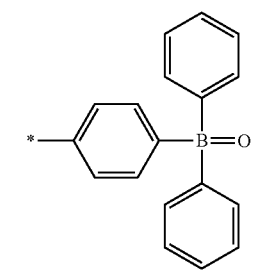 S159
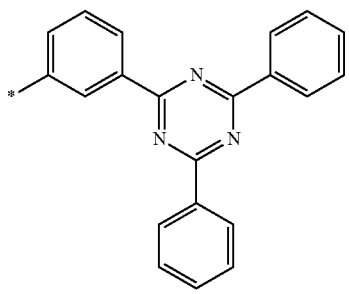 S160
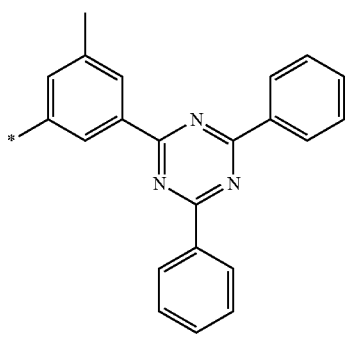 S161

S162 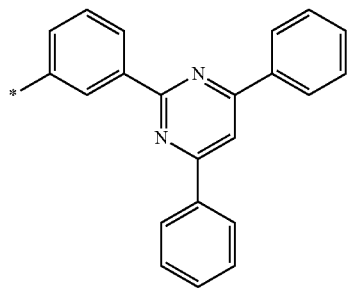
S163 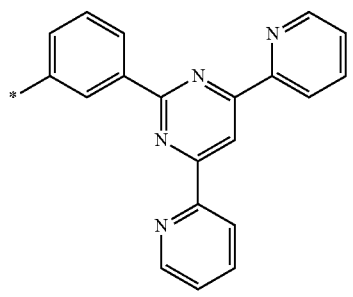
S164 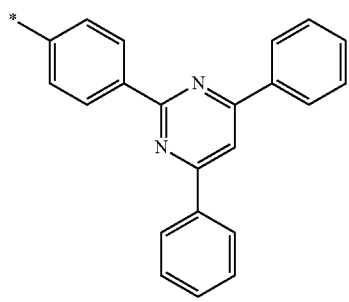
S165 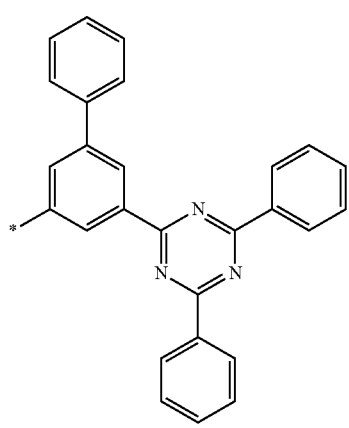
S166 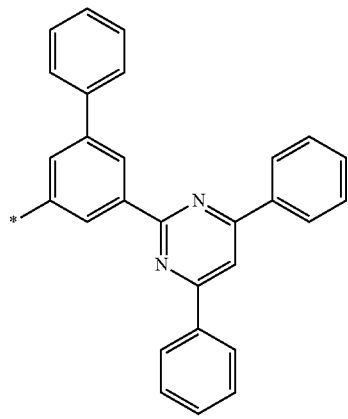
Examples of the compound represented by Formula 1 according to the present disclosure include compounds represented by the following Formulae 4 to 9, but are not limited thereto.
[Formula 4]
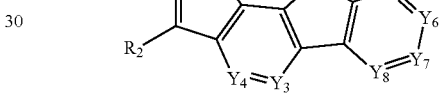
[Formula 5]
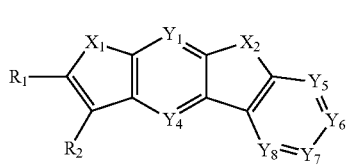
[Formula 6]
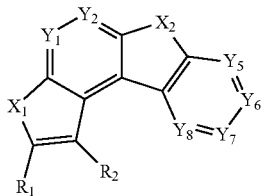
[Formula 7]
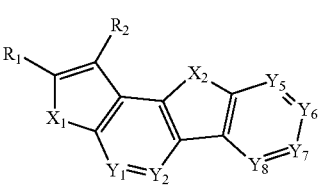
[Formula 8]
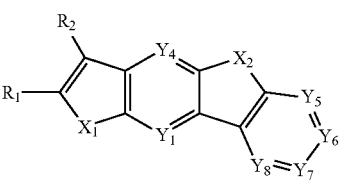

[Formula 9]

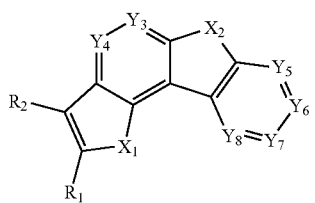

In Formulae 4 to 9, $Y_1$ to $Y_4$ are each independently N or $CR_3$, and in this case, when $CR_3$ is present in a plural number, they are the same as or different from each other; and $X_1$ and $X_2$, $Y_5$ to $Y_8$, $R_1$, $R_2$, and $R_3$ are each the same as those defined in Formula 1.

In addition, examples of the compound represented by Formula 1 according to the present disclosure include compounds represented by the following Formulae 10 to 15, but are not limited thereto.

[Formula 10]

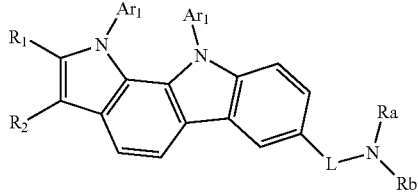

[Formula 11]

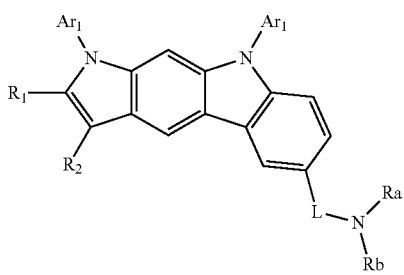

[Formula 12]

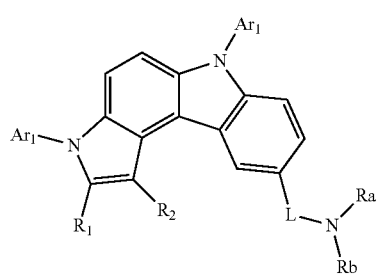

[Formula 13]

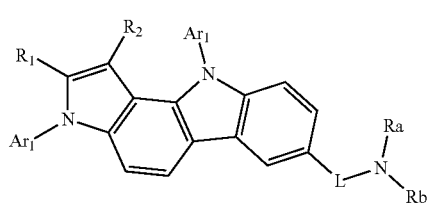

[Formula 14]

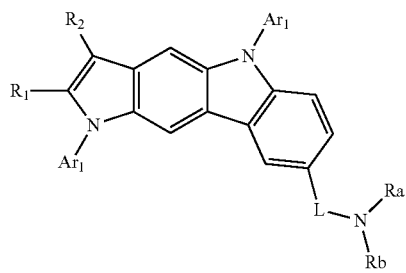

[Formula 15]

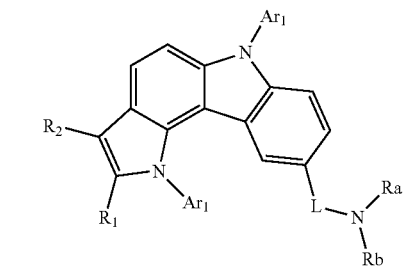

In Formulae 10 to 15, $R_1$, $R_2$, $Ar_1$, $R_a$, $R_b$, and L are each the same as those defined in Formula 1, and in this case, when $Ar_1$ is present in a plural number, they are the same as or different from each other.

Specific examples of the compound represented by Formula 1 include the following Compounds 1 to 489, and the like, but are not limited thereto.

1

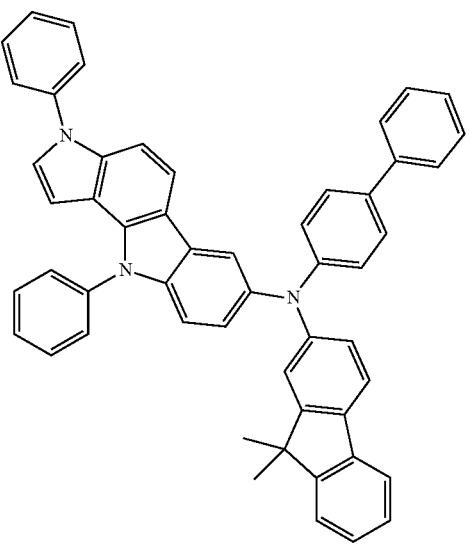

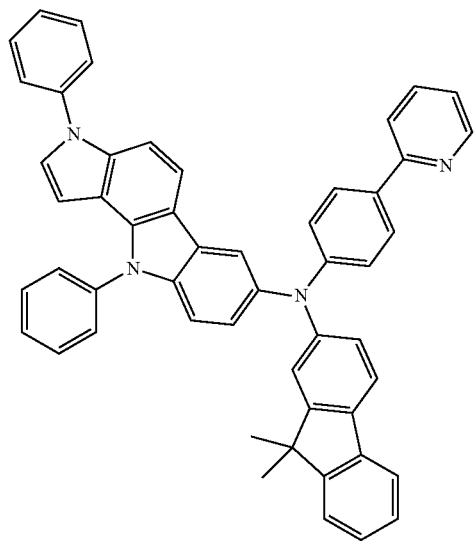
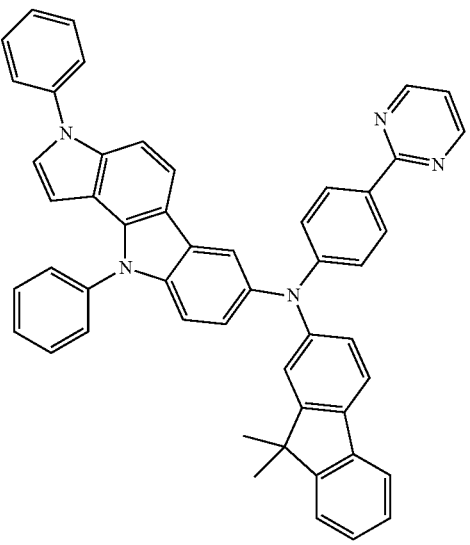
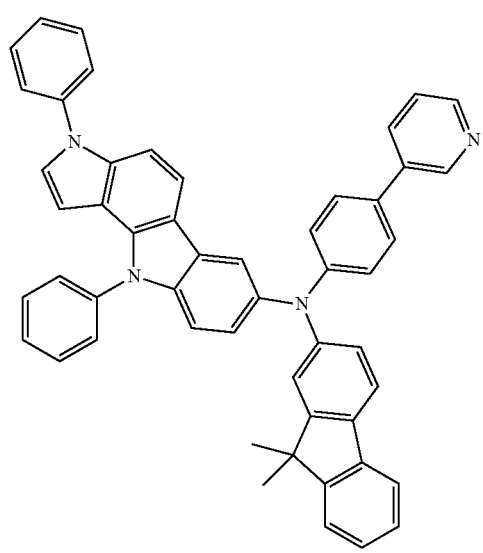
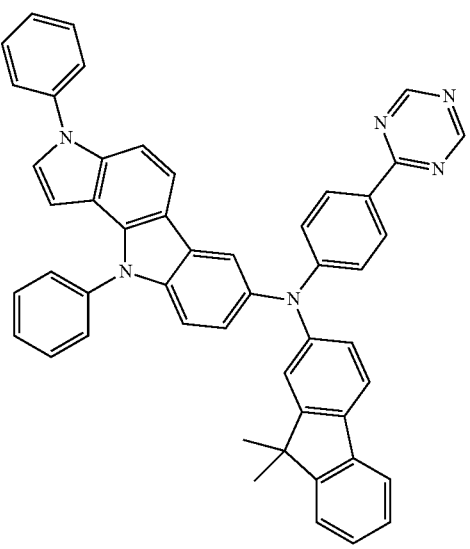
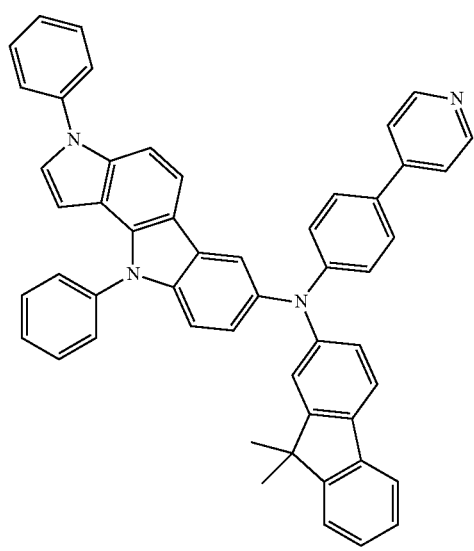
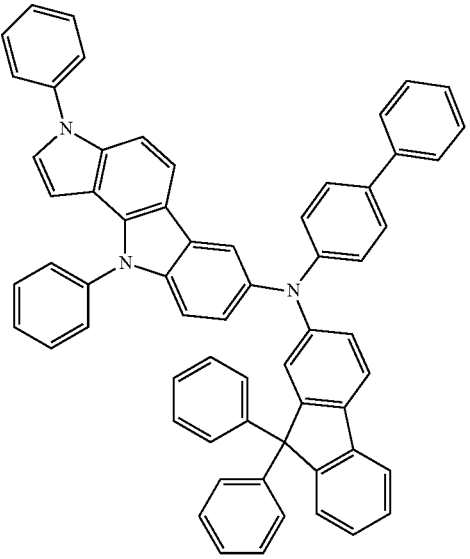

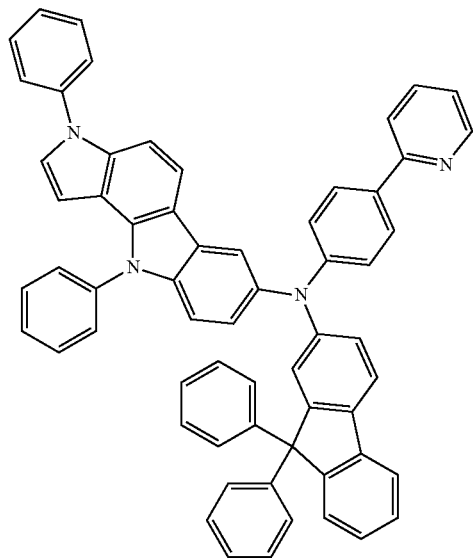
8
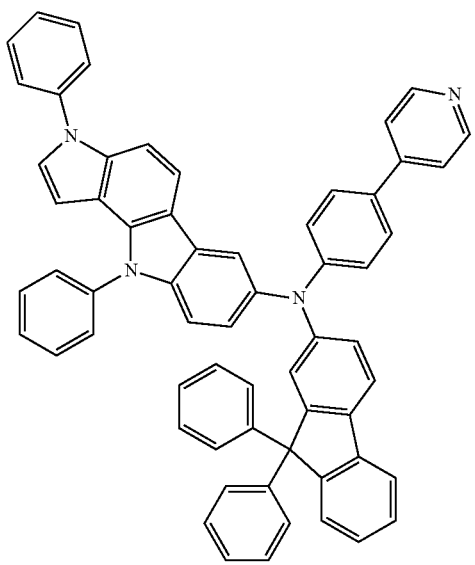
10
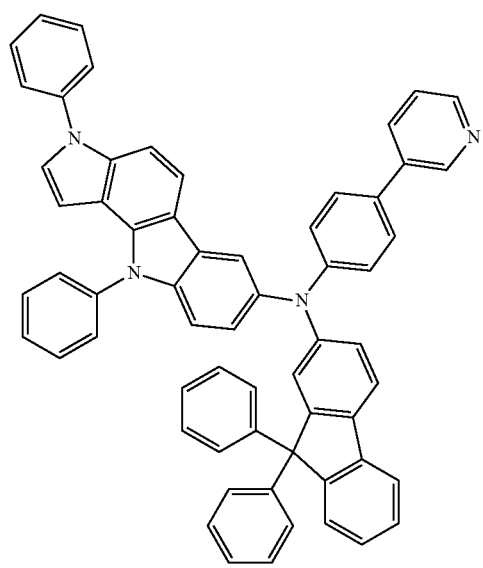
9
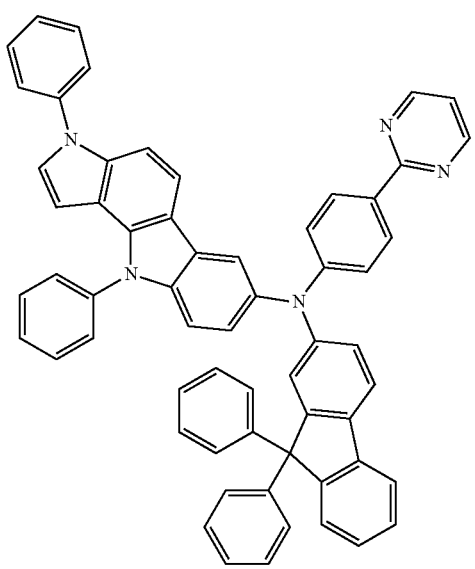
11

12
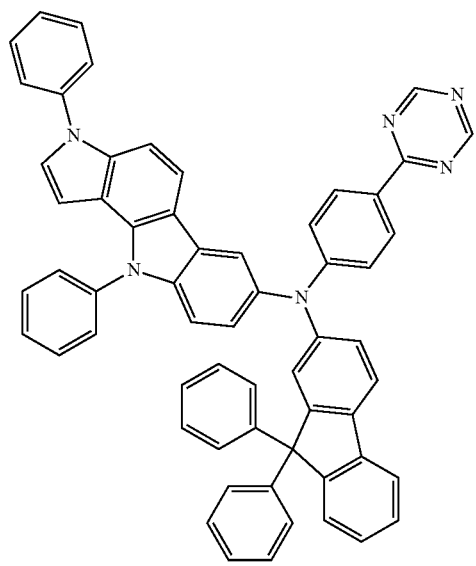
13
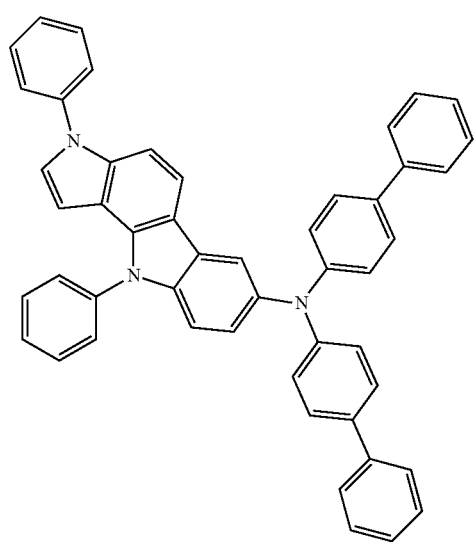
14
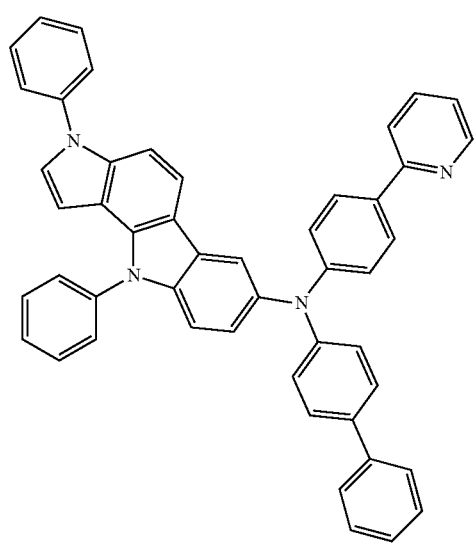
15
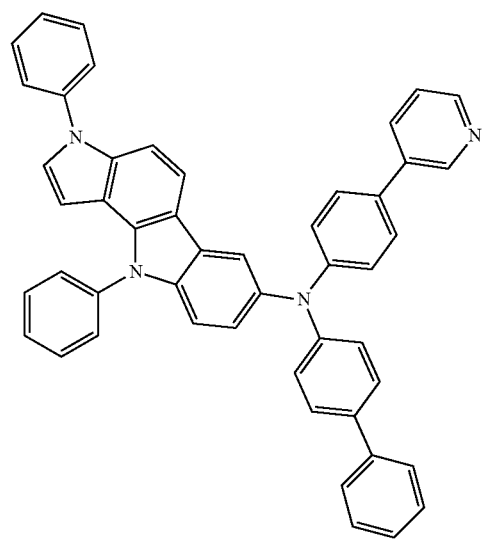
16
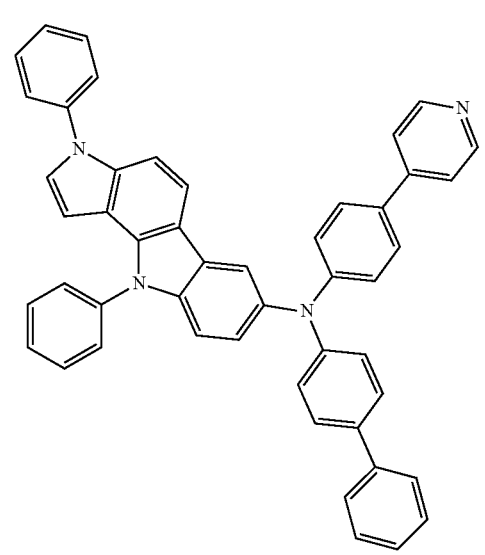
17
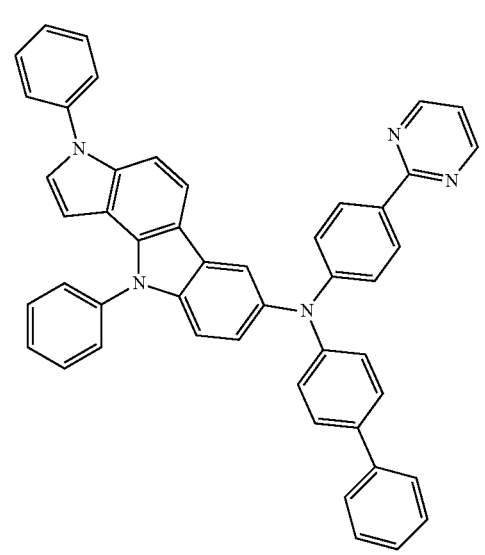

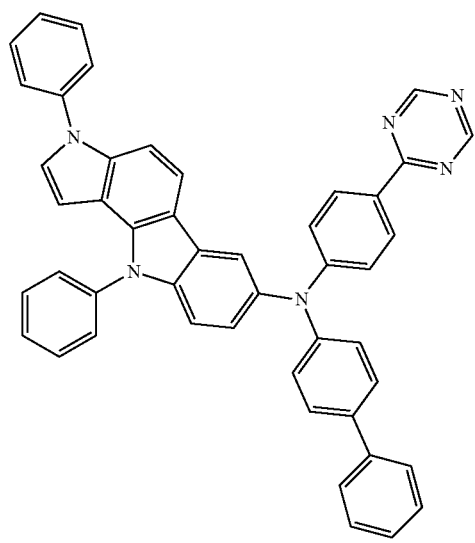
18
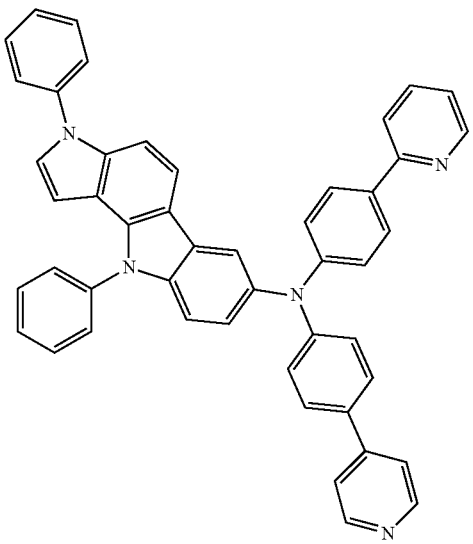
21
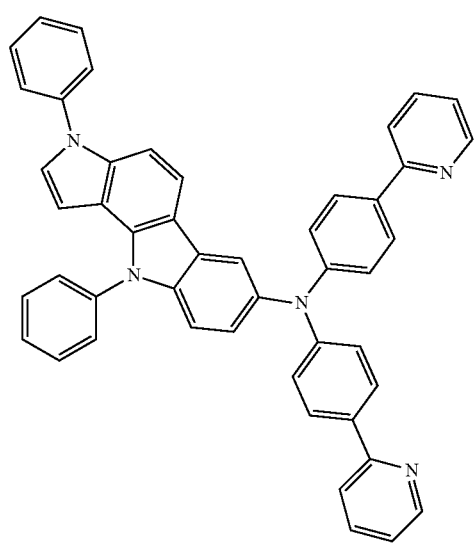
19
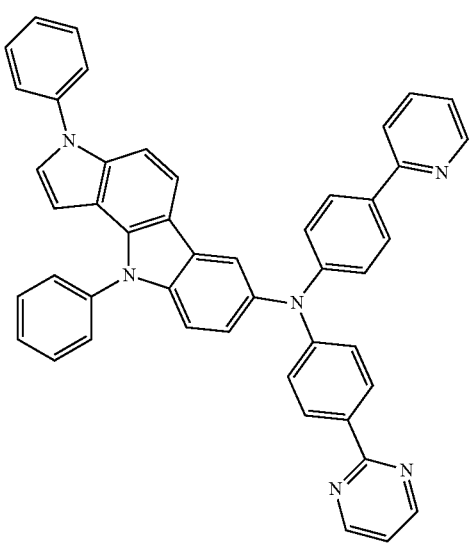
22
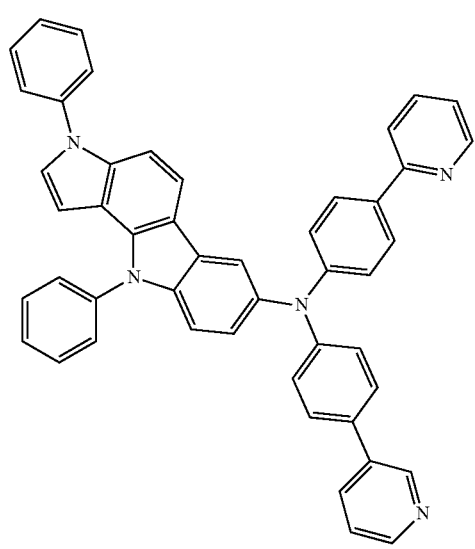
20
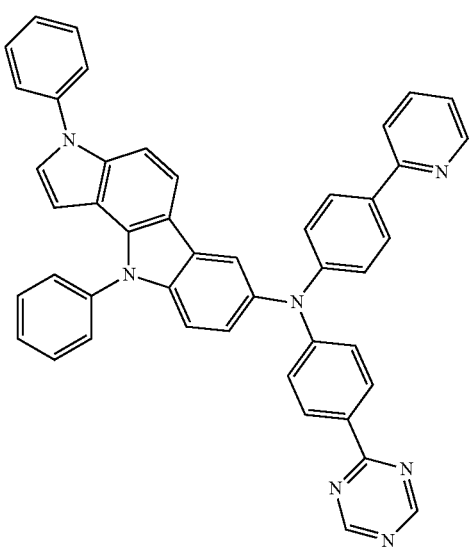
23

24
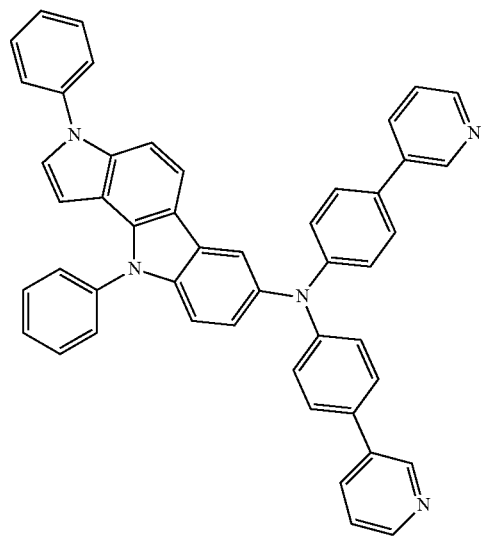
25
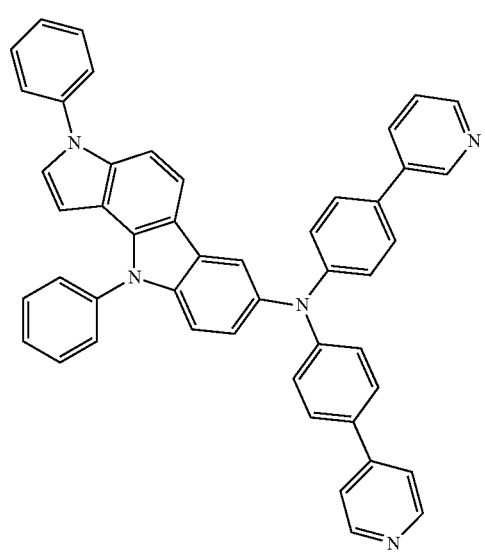
26
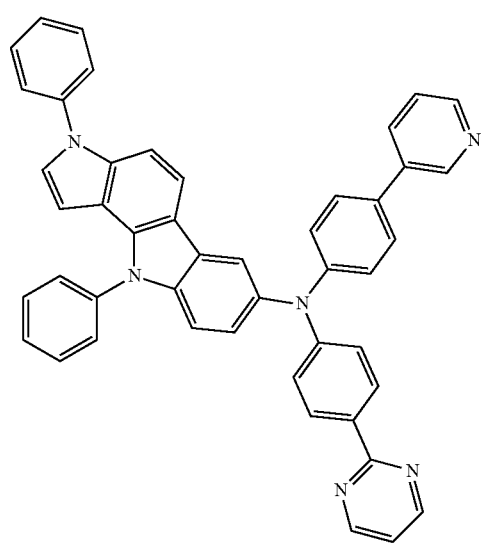
27
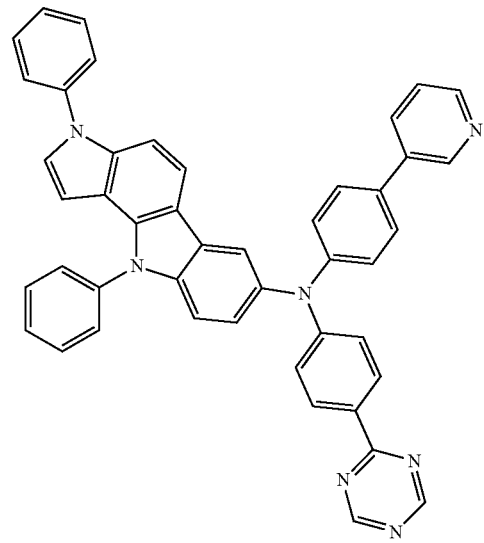
28
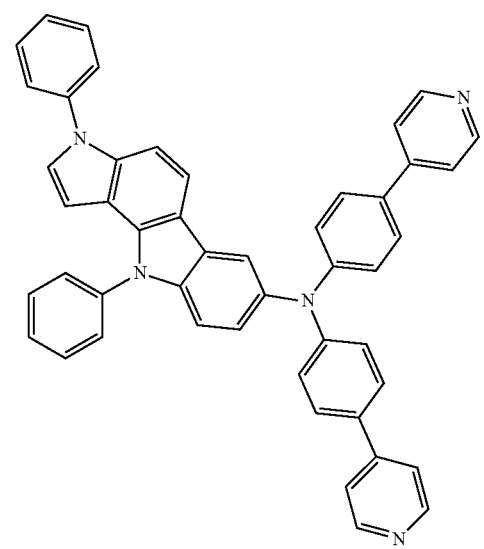
29
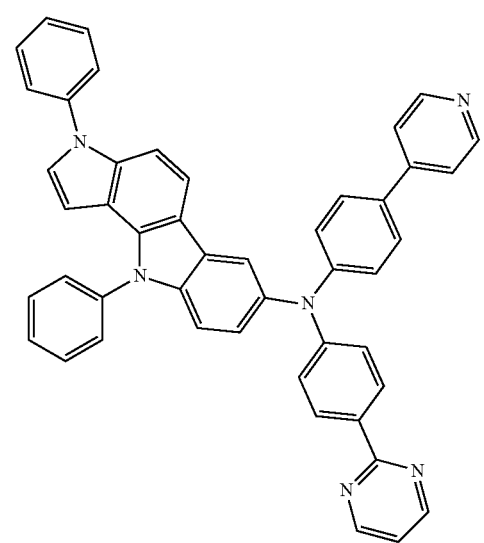

75
-continued
30
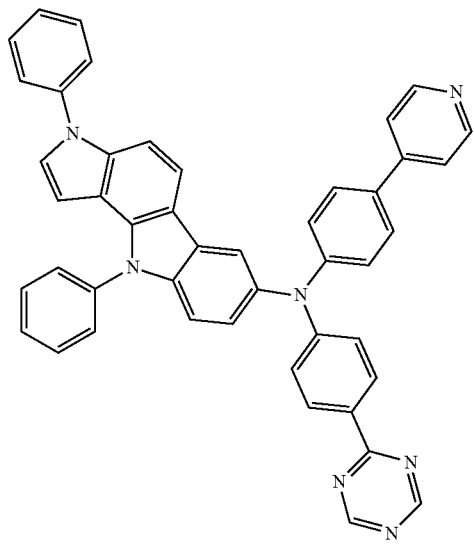
31
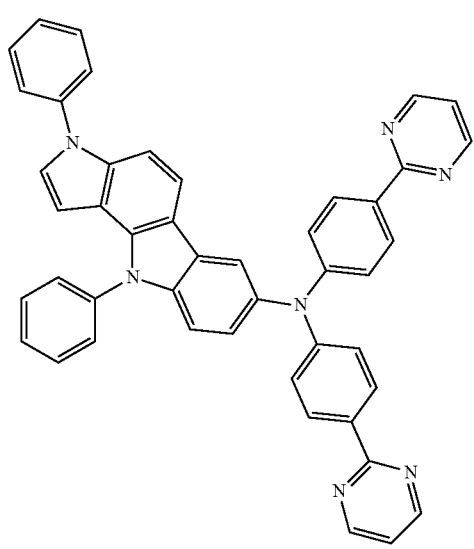
32
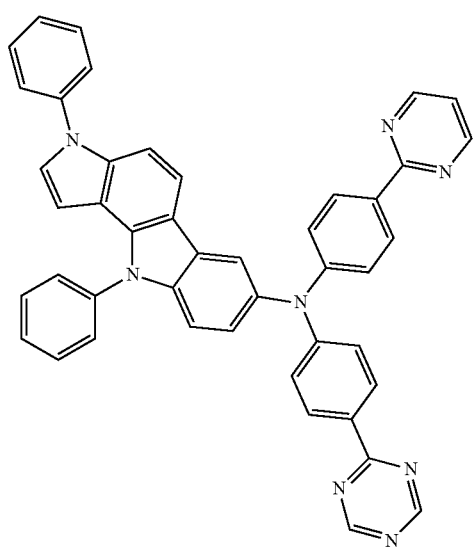
76
-continued
33
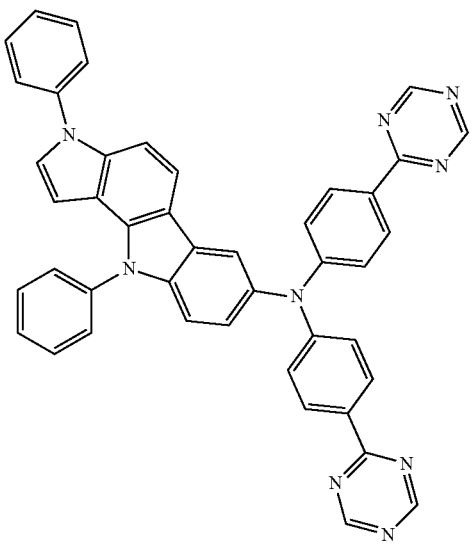
34
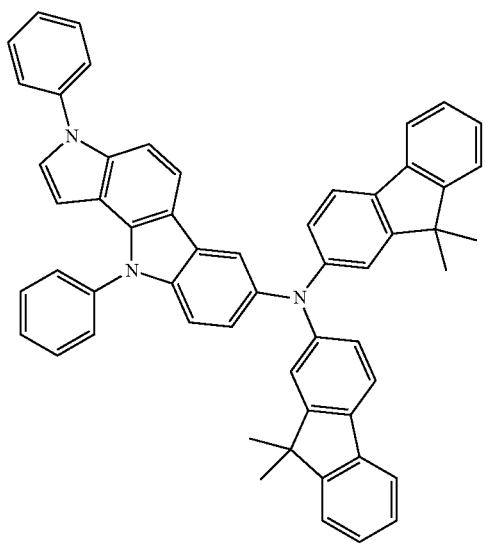
35
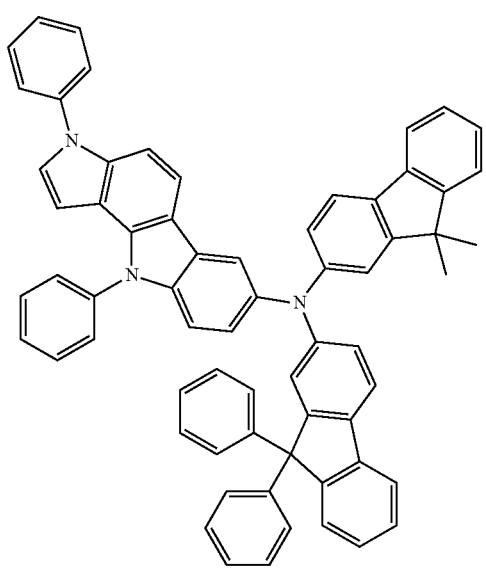

36
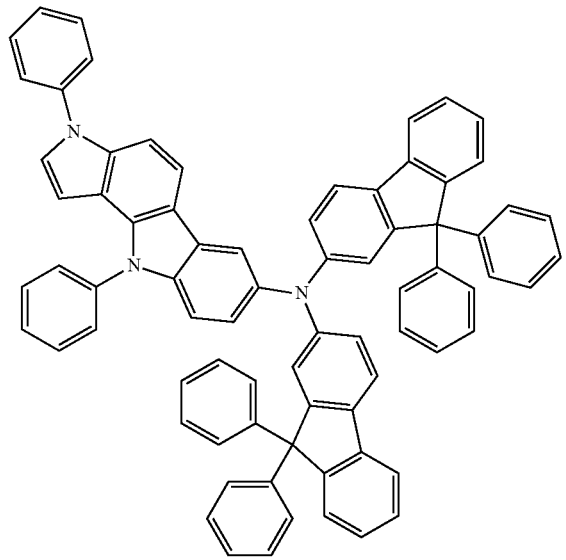
37
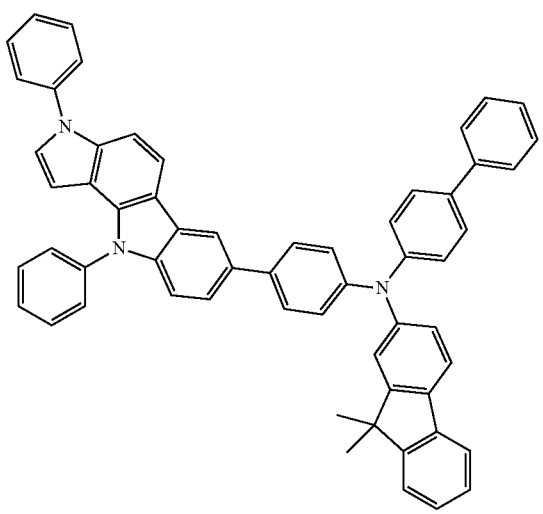
38
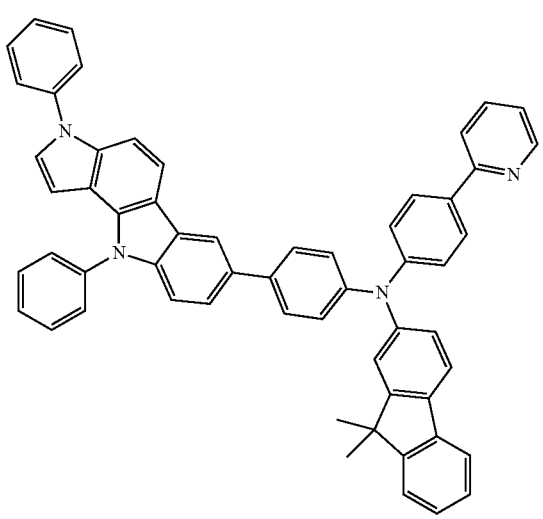
39
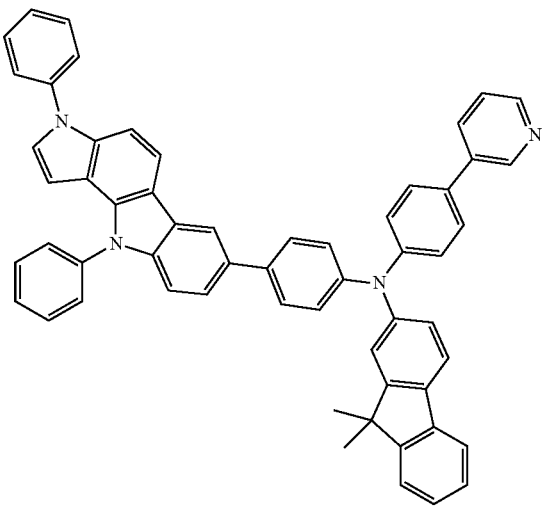
40
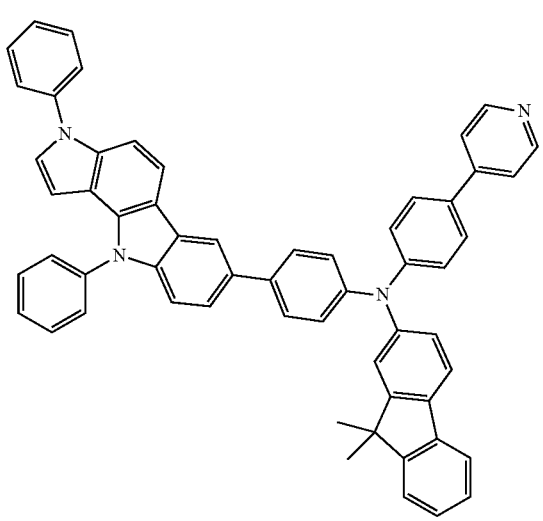
41
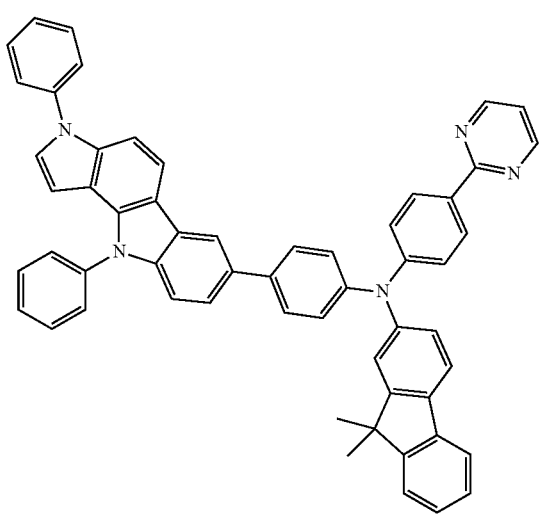

42
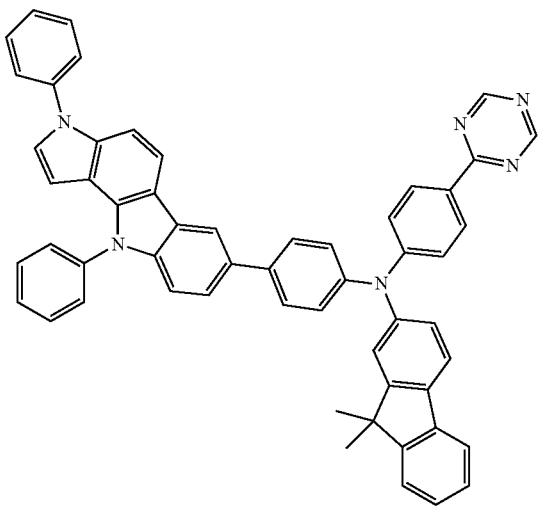
43
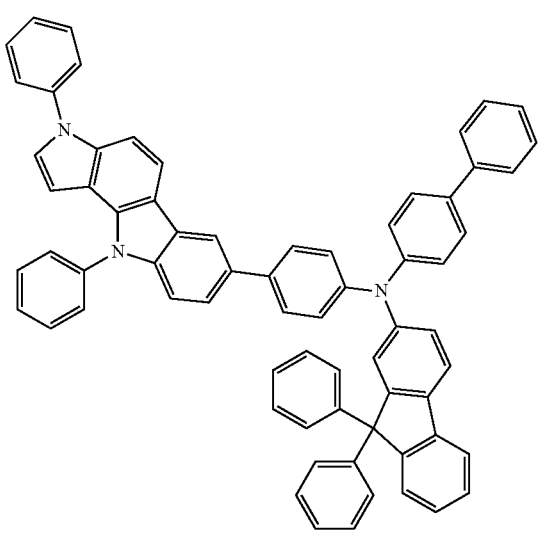
44
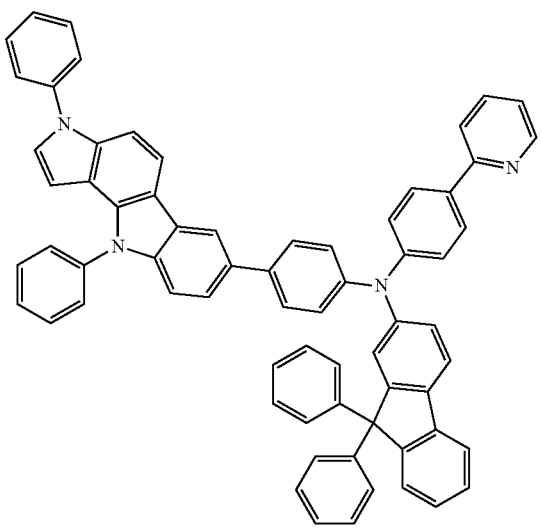
45
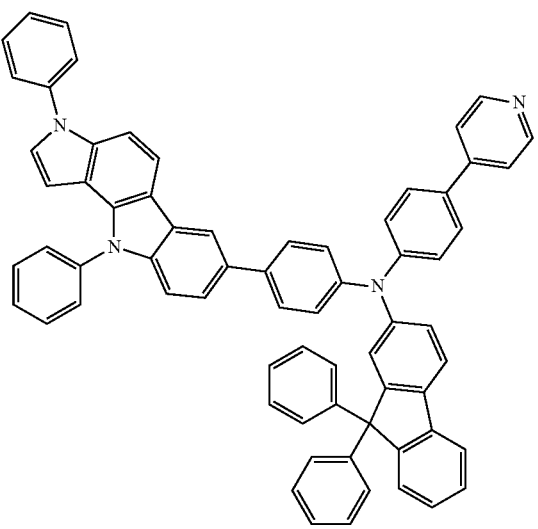
46
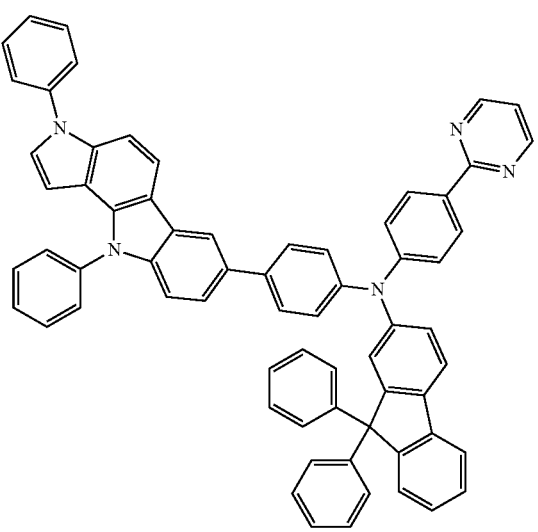
47
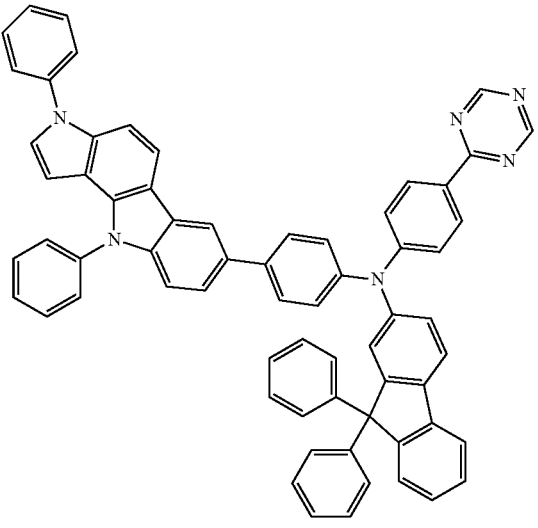

48
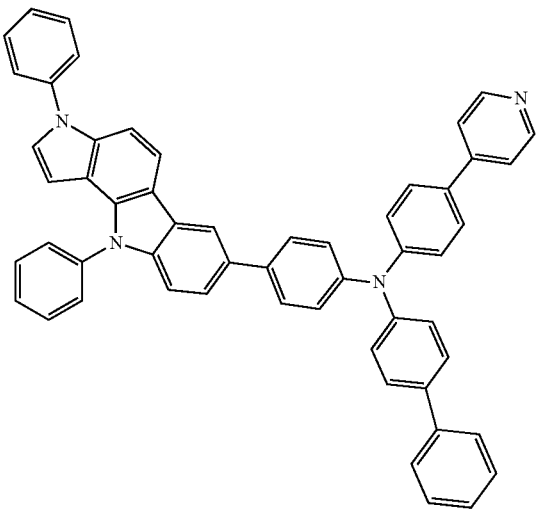
51
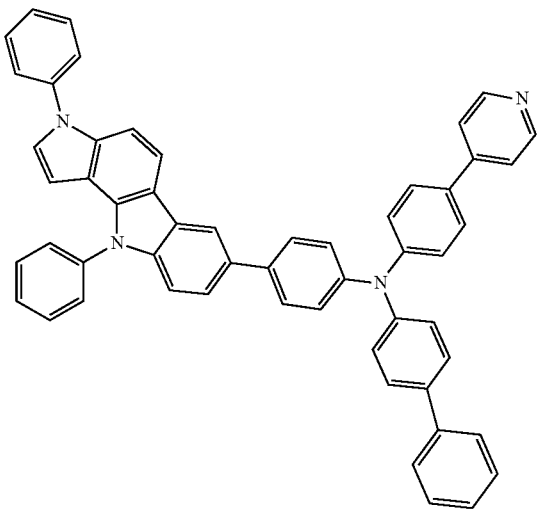
49
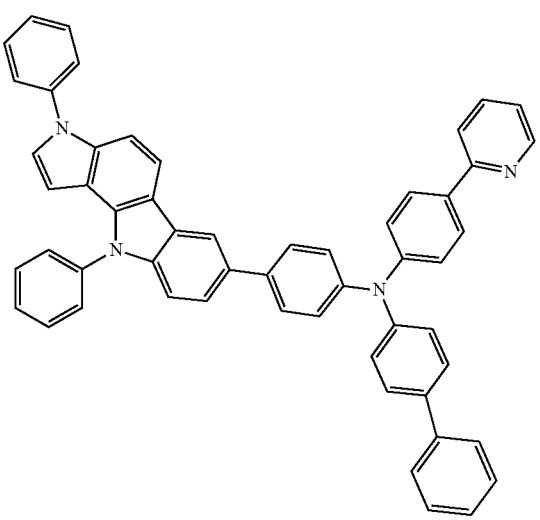
52
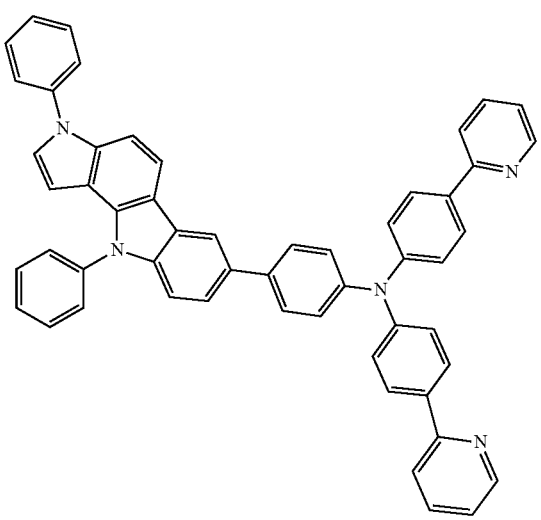
50
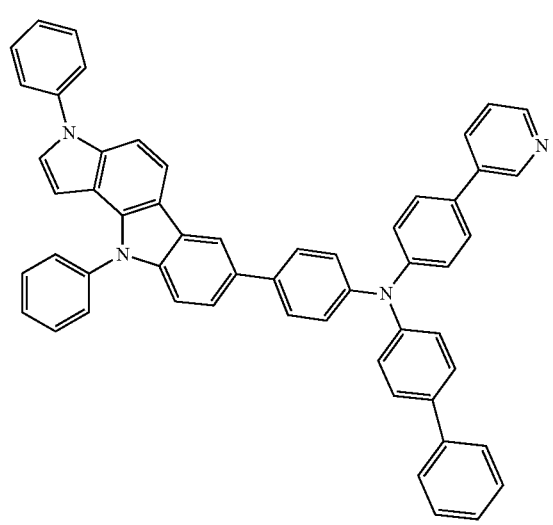
53
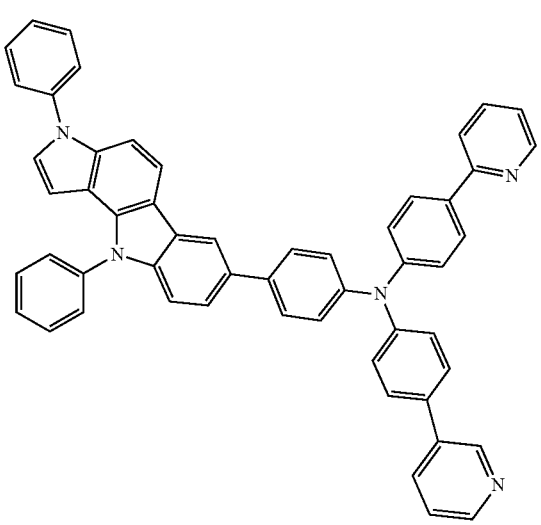

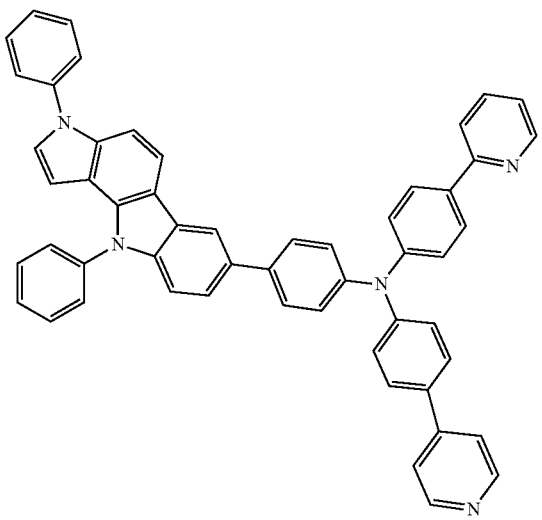
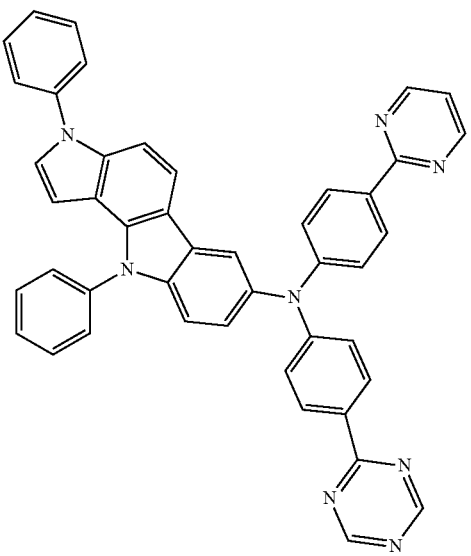

85
-continued
60
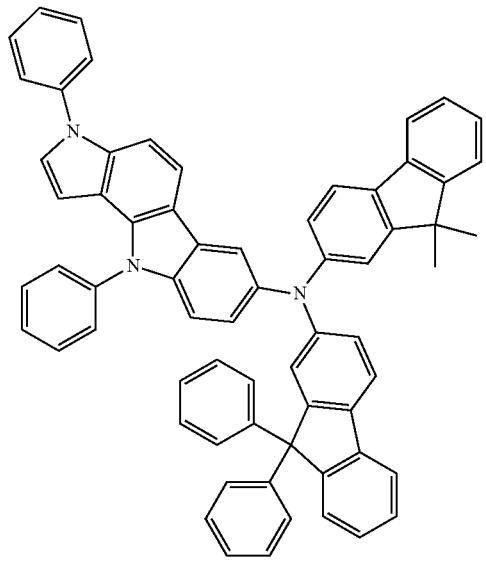
61
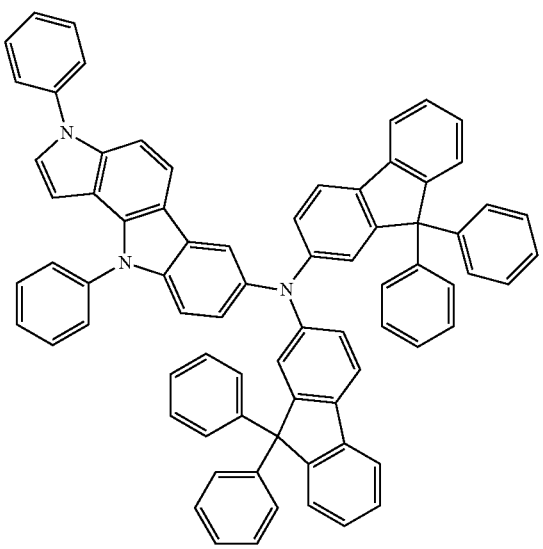
62
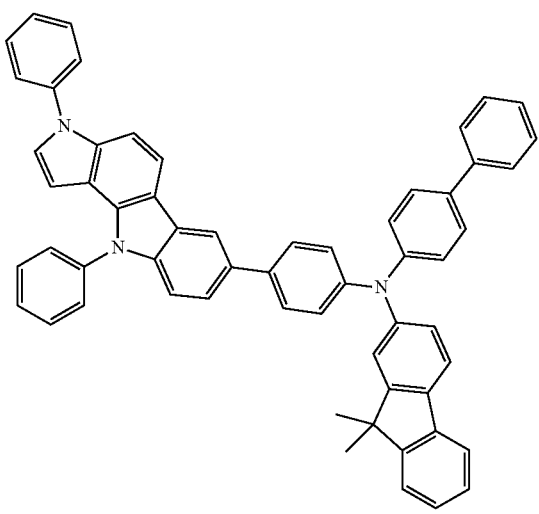
86
-continued
63
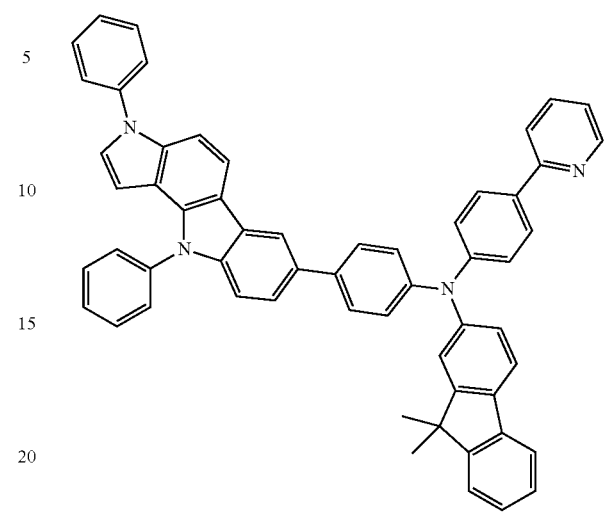
64
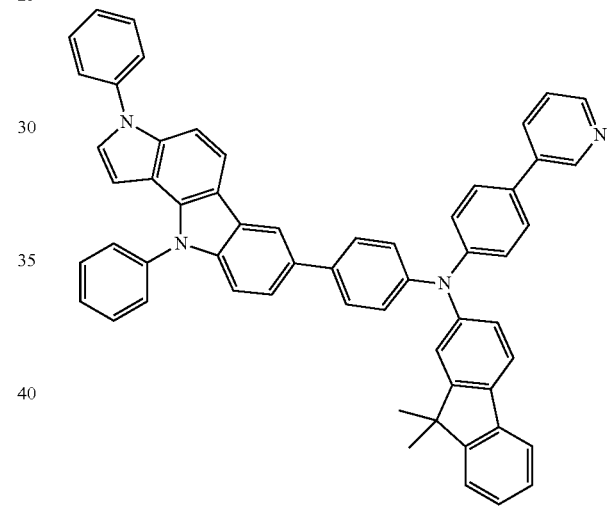
65
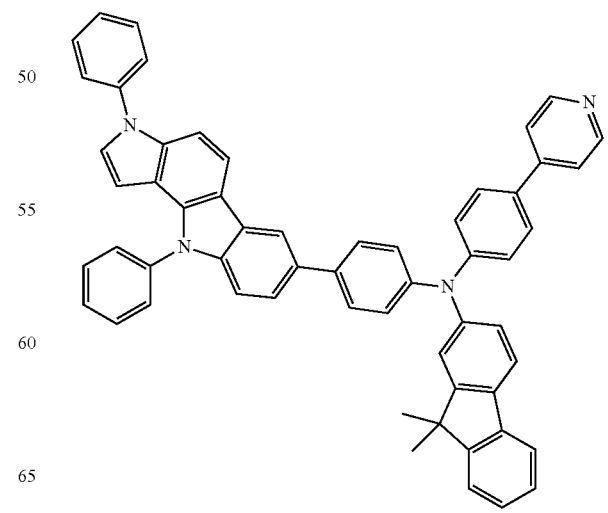

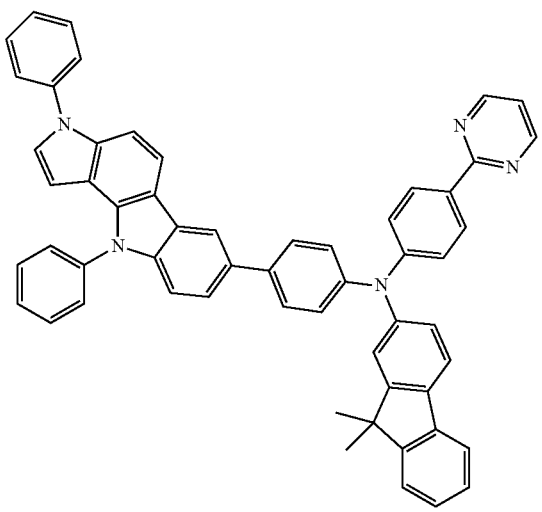
66
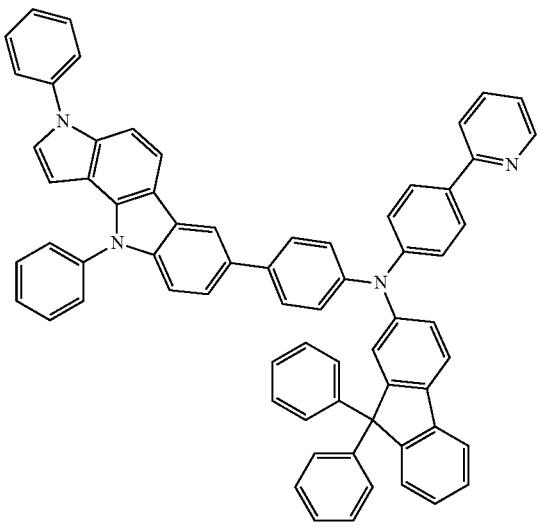
69
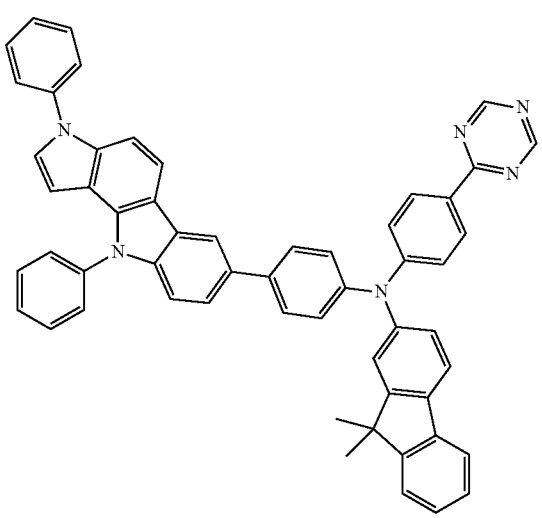
67
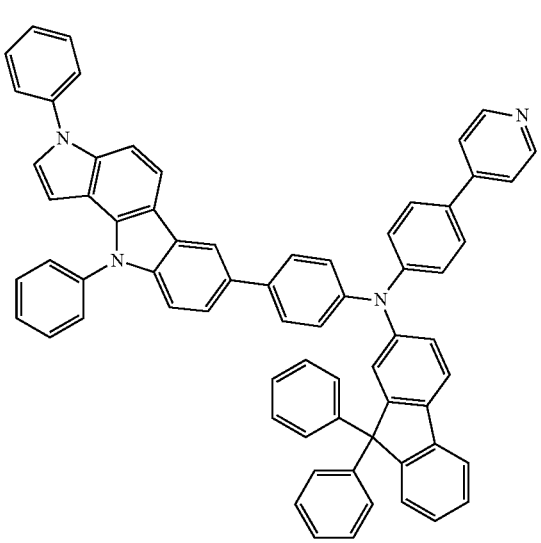
70
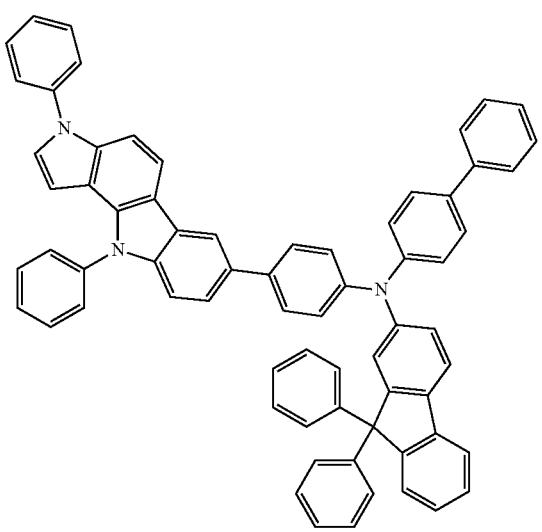
68
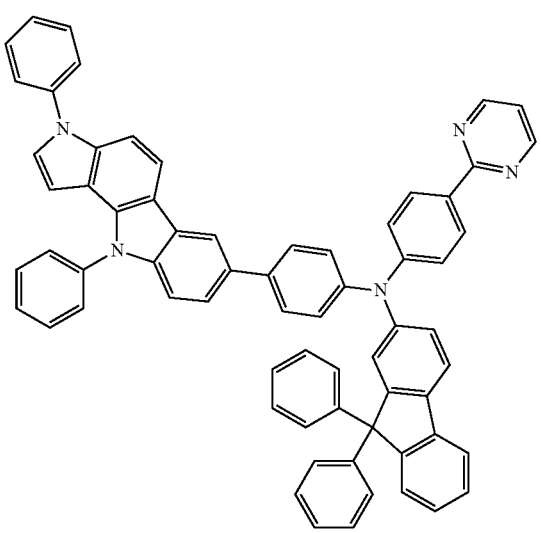
71

72
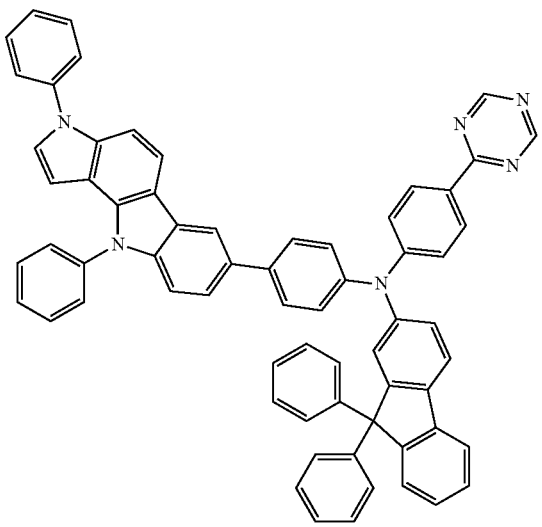
75
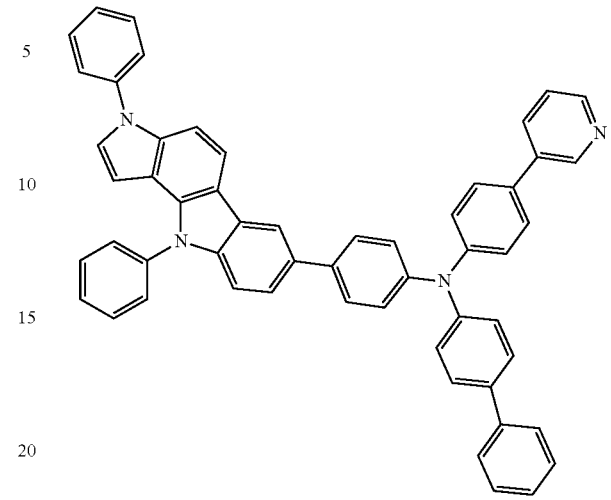
73
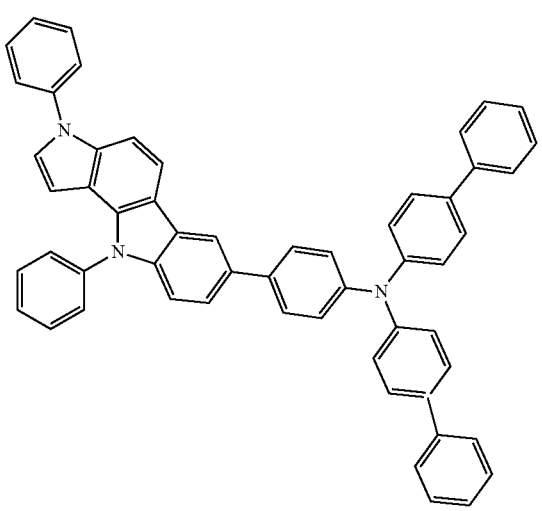
76
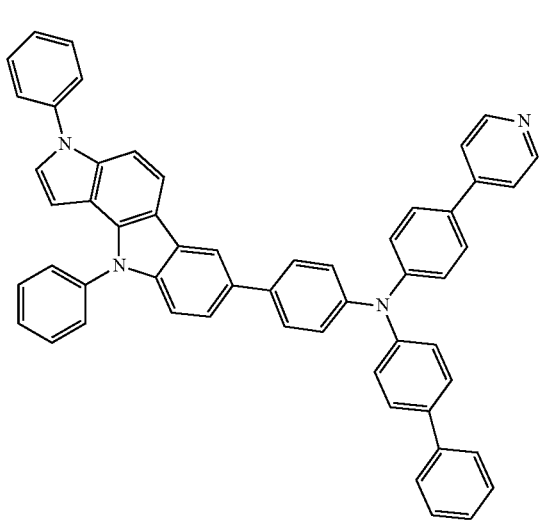
74
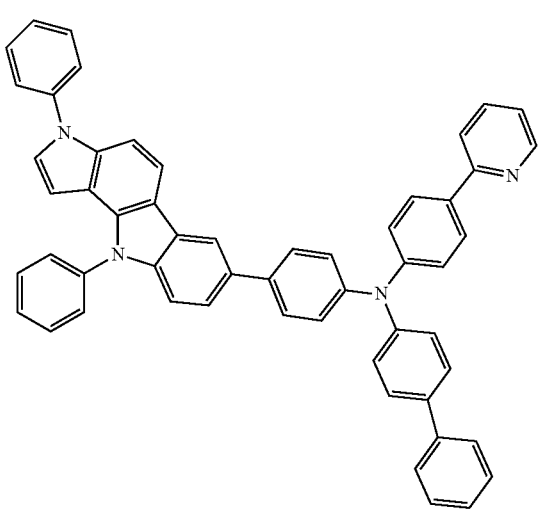
77
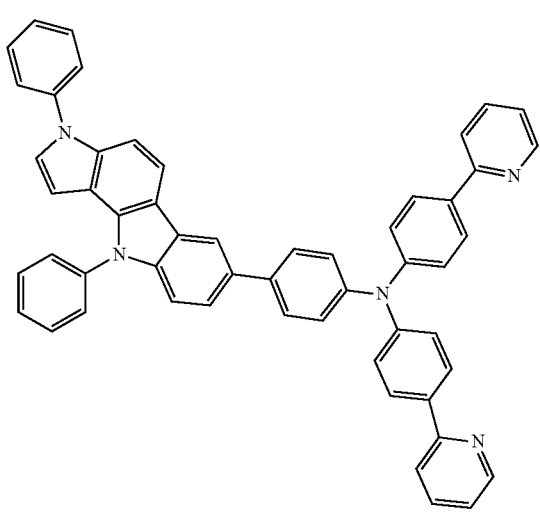

78
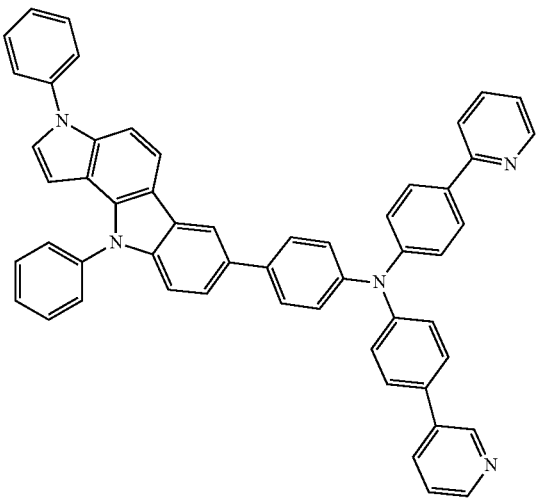
79
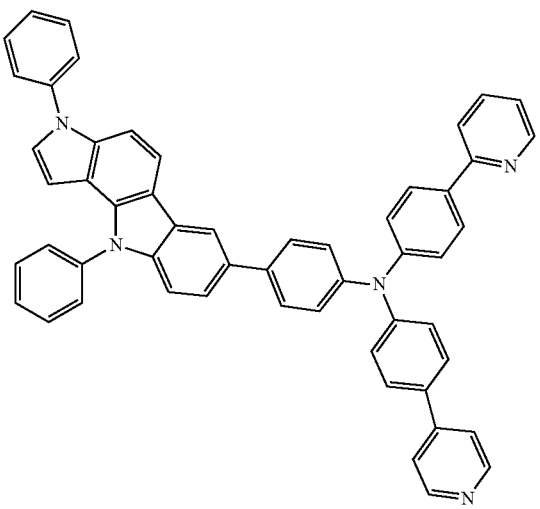
80
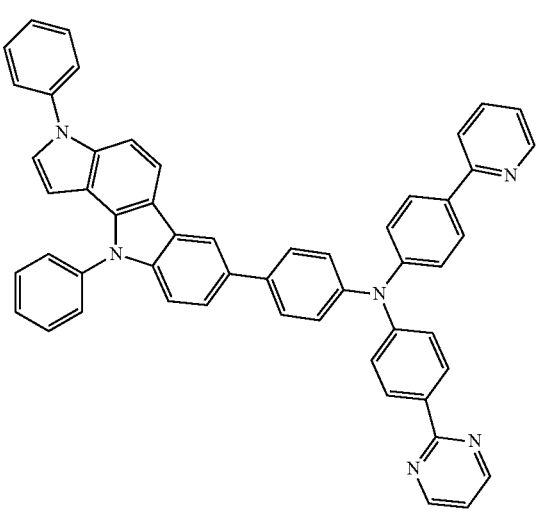
81
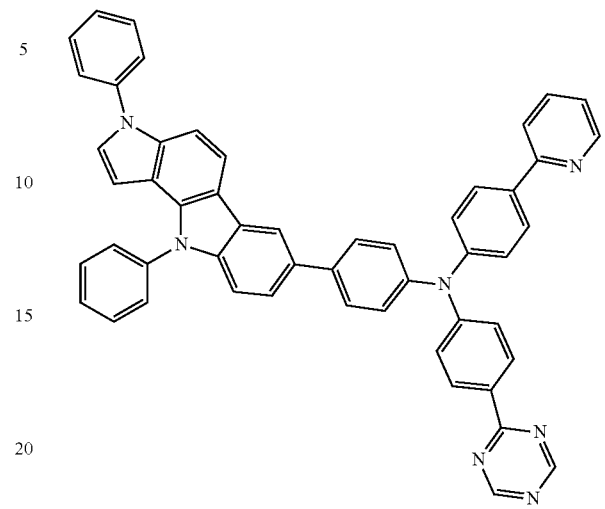
82
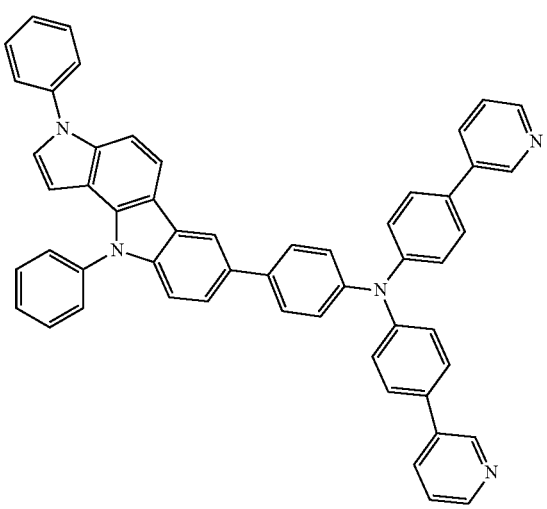
83
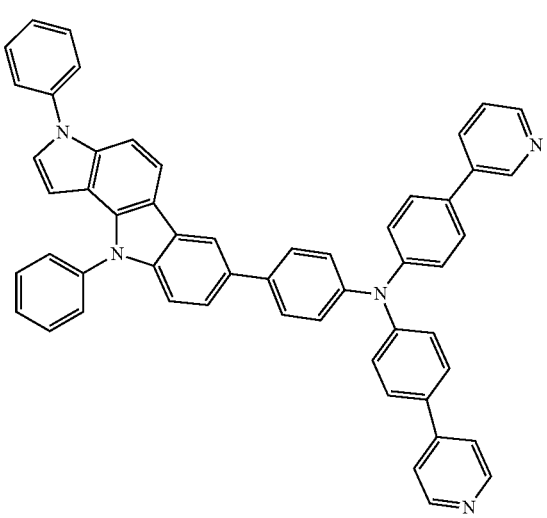

84
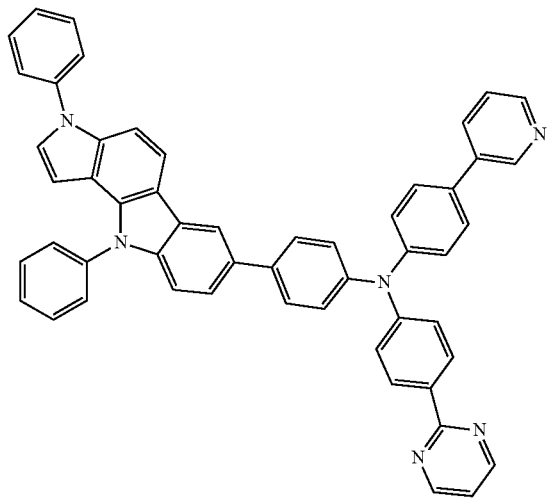
85
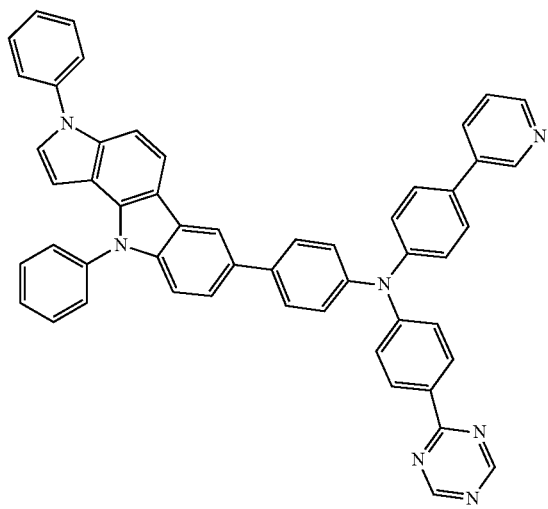
86
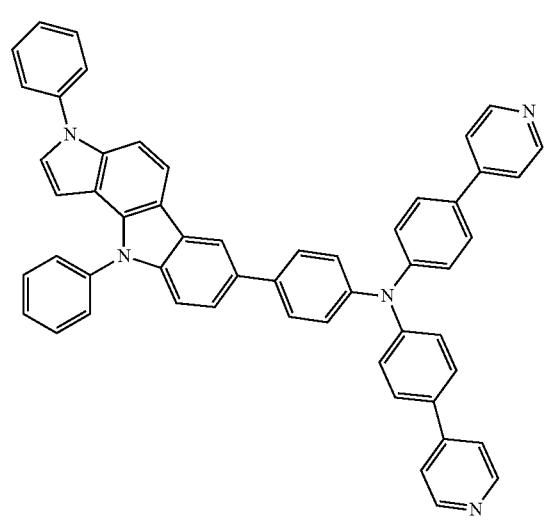
87
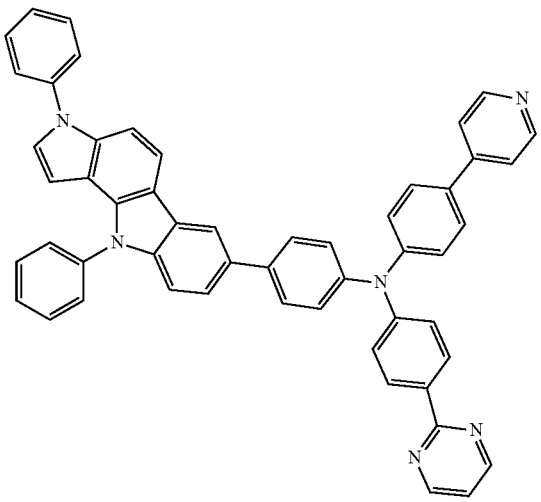
88
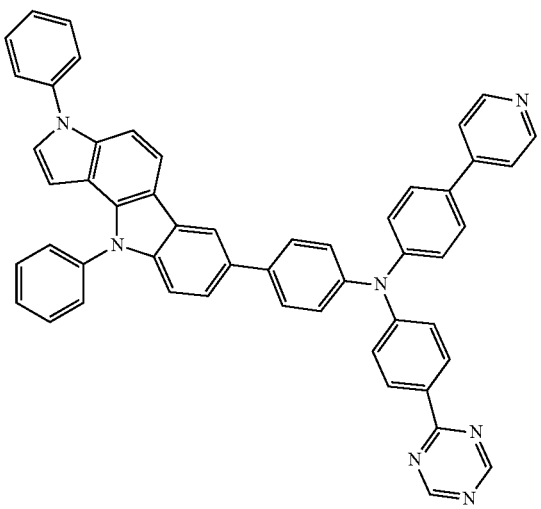
89
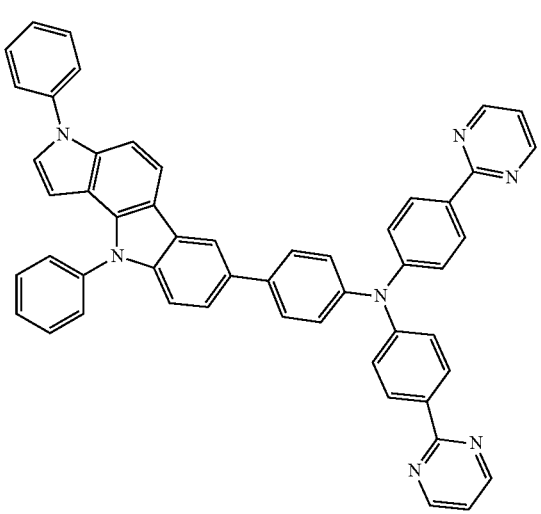

95
-continued
90
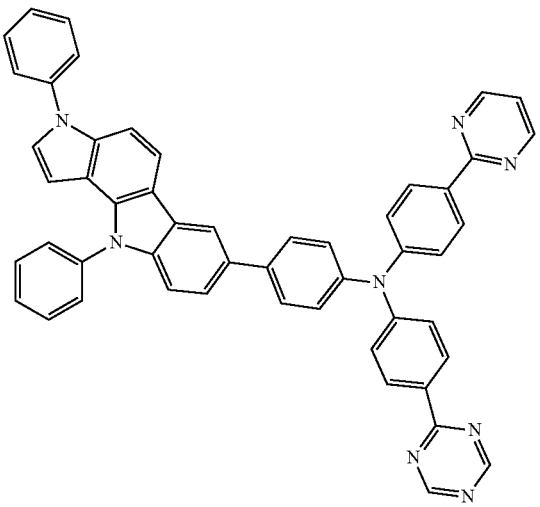
91
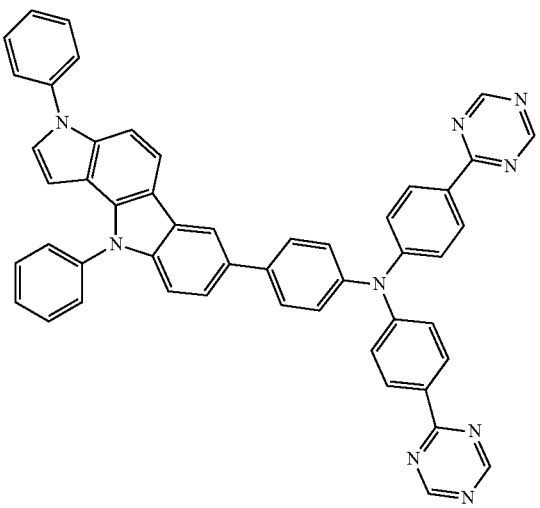
92
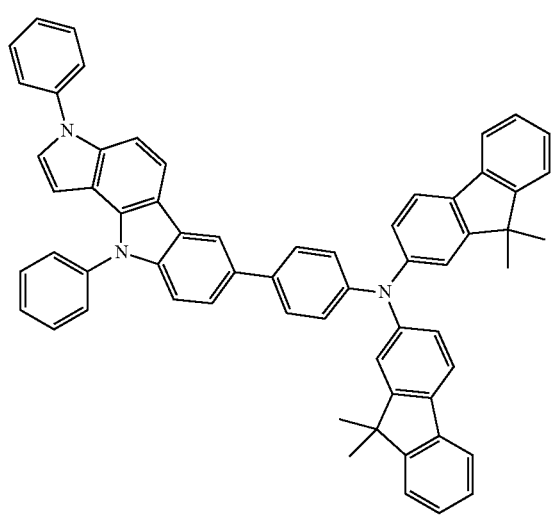
96
-continued
93
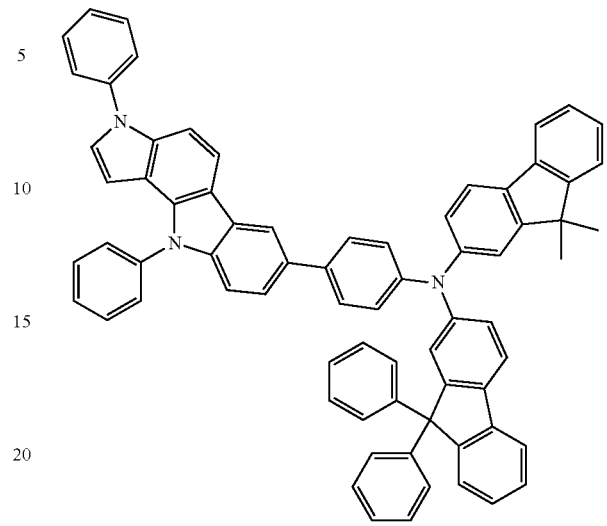
94
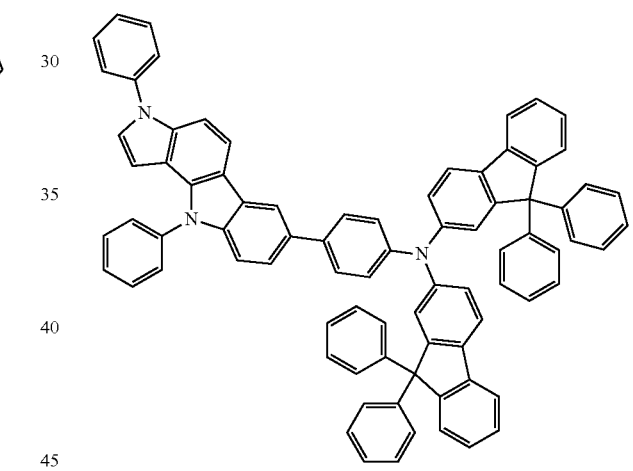
95
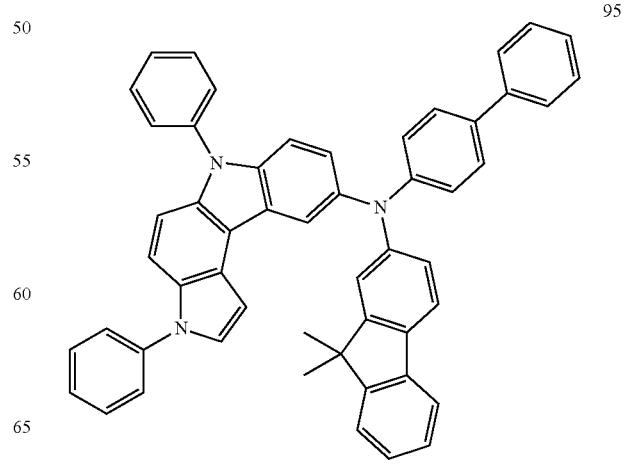

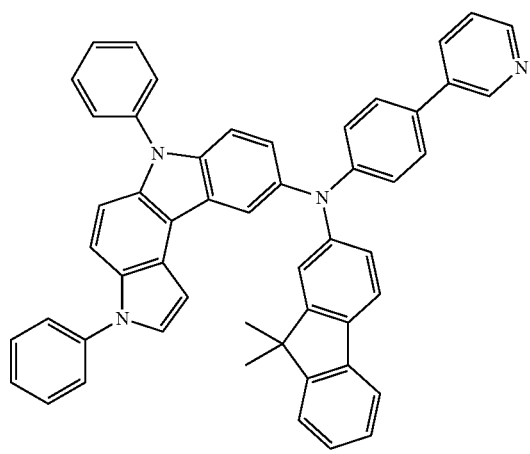
96
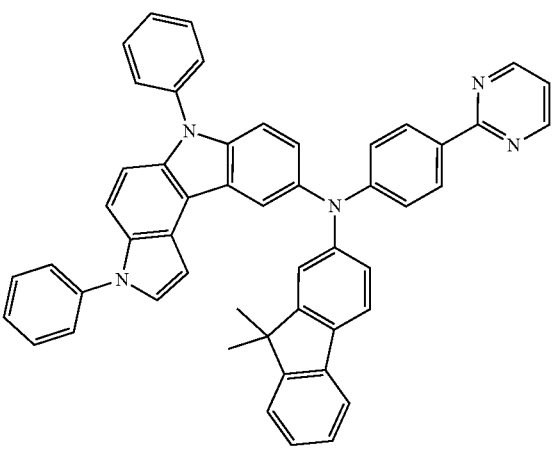
99
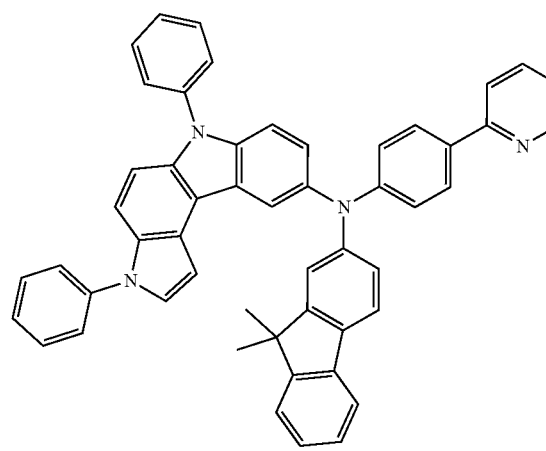
97
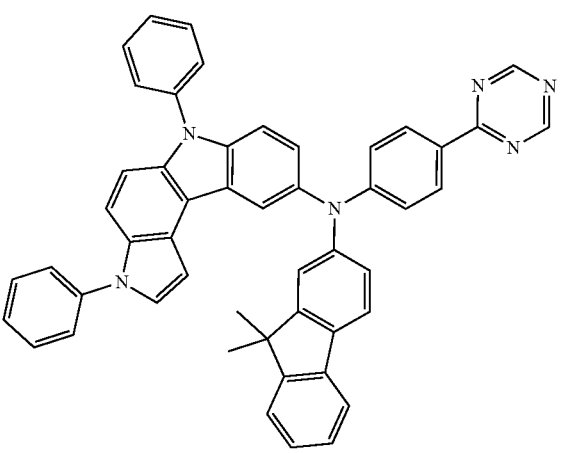
100
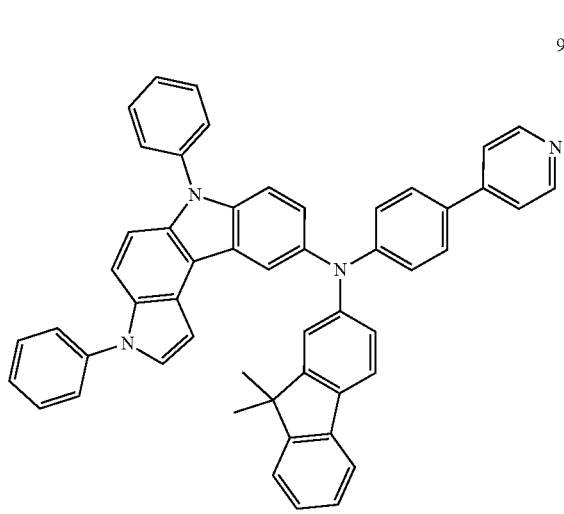
98
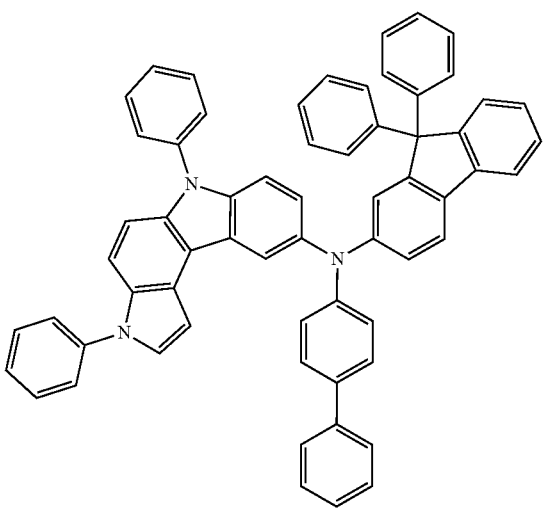
101

99
-continued
102
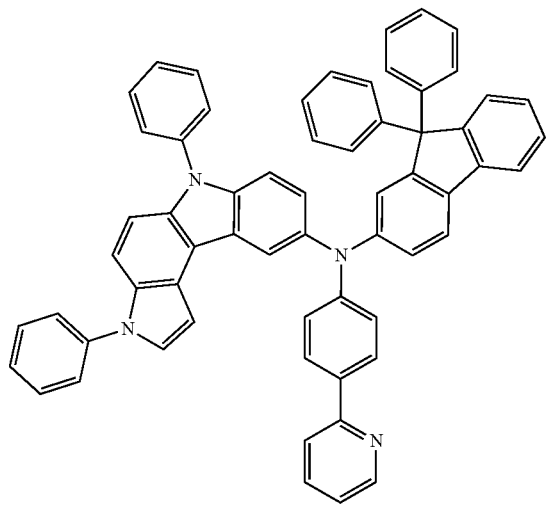
103
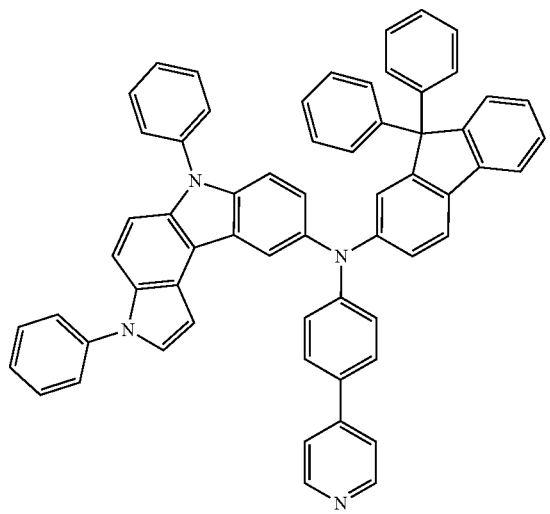
100
-continued
105
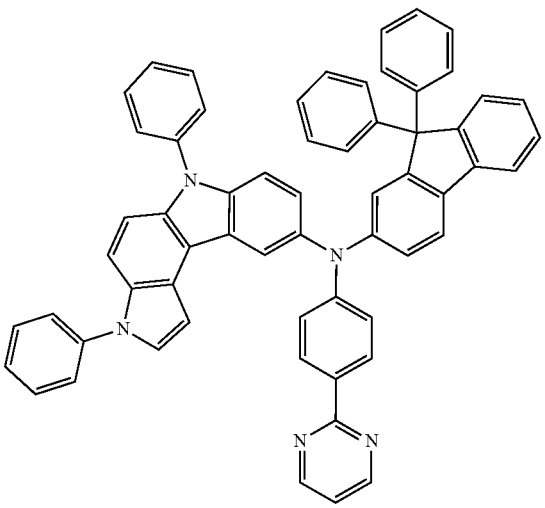
106
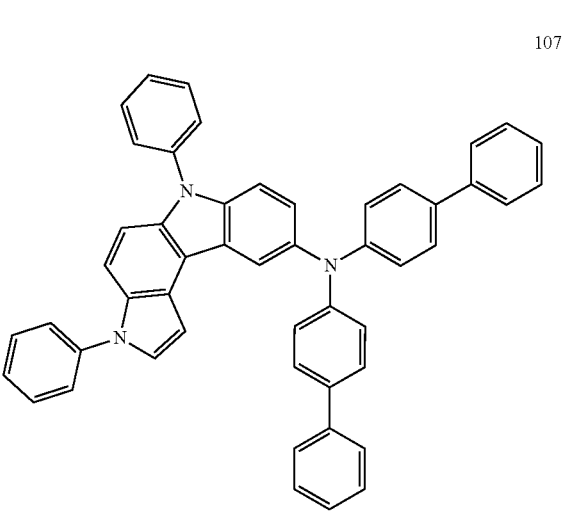
104
107

101
-continued
108
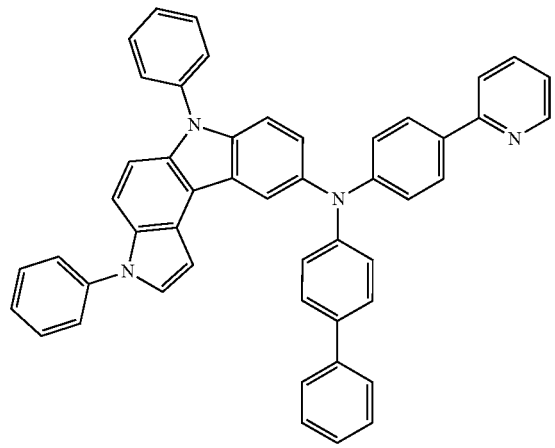
109
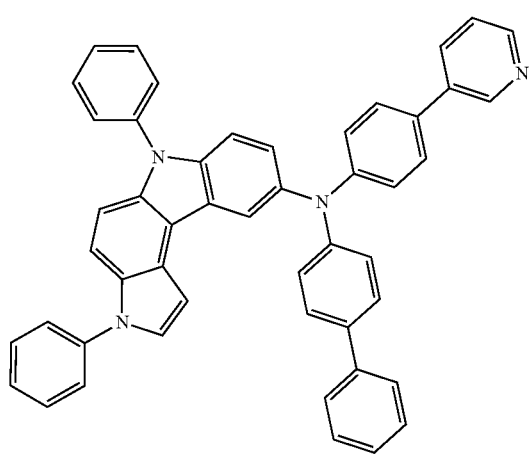
110
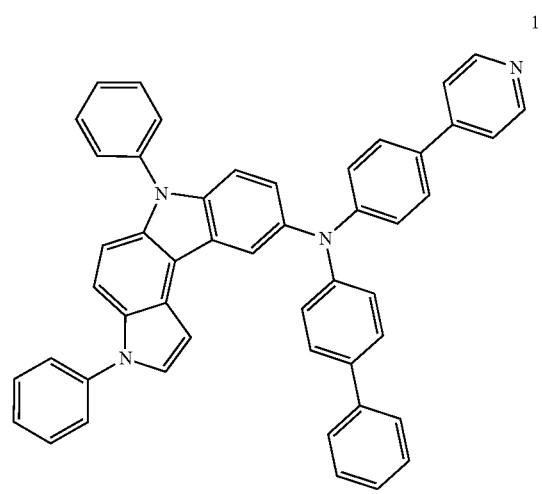
102
-continued
111
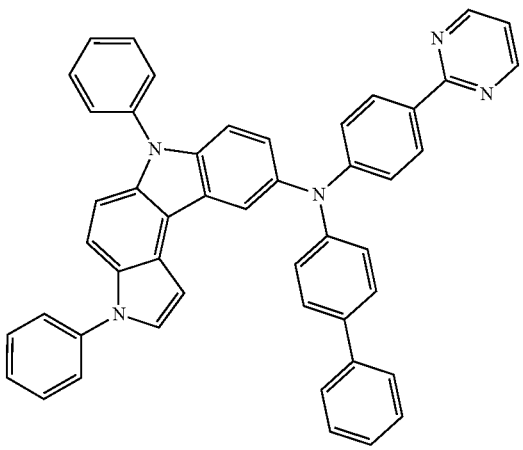
112
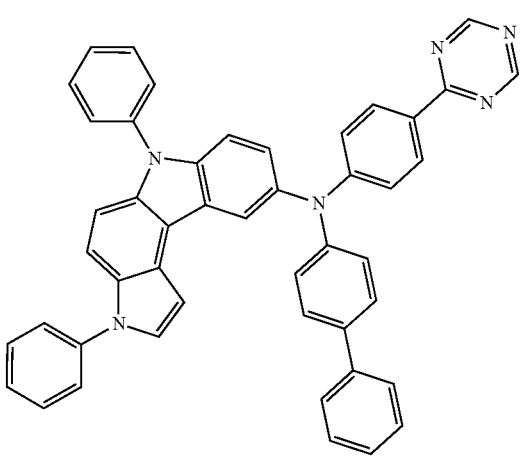
113
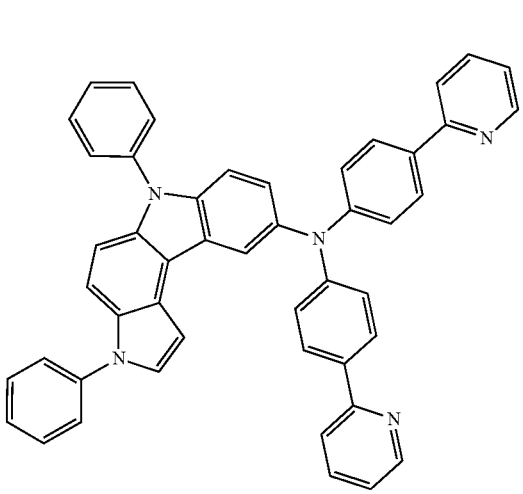

114
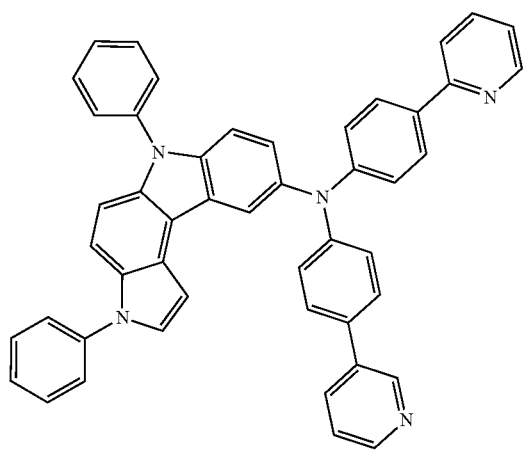
115
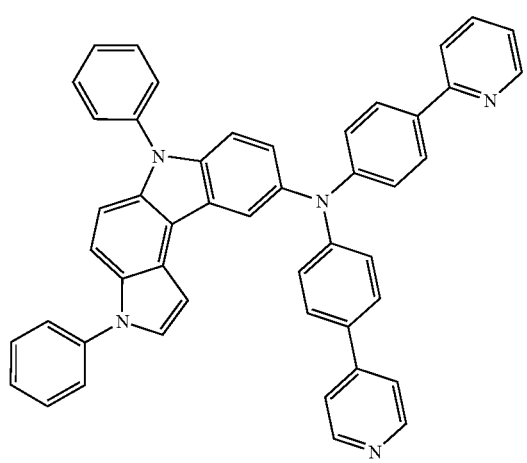
116
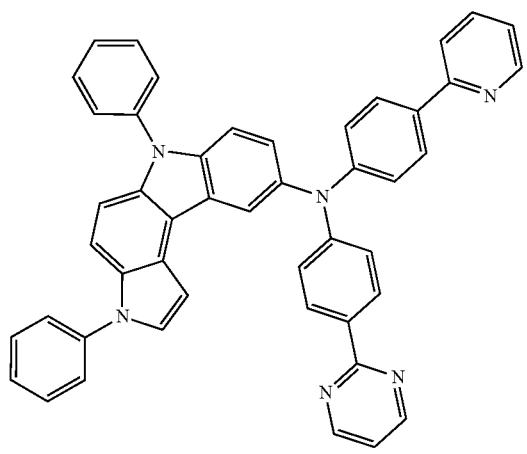
117
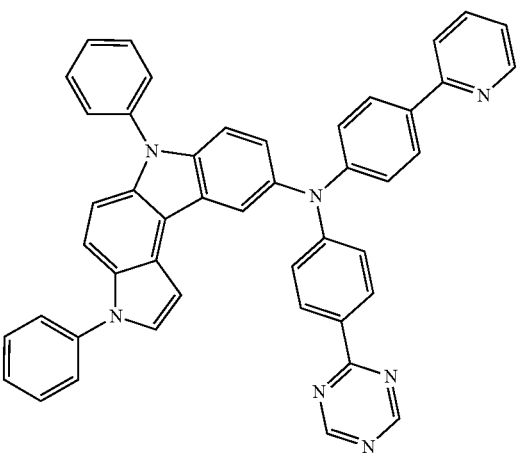
118
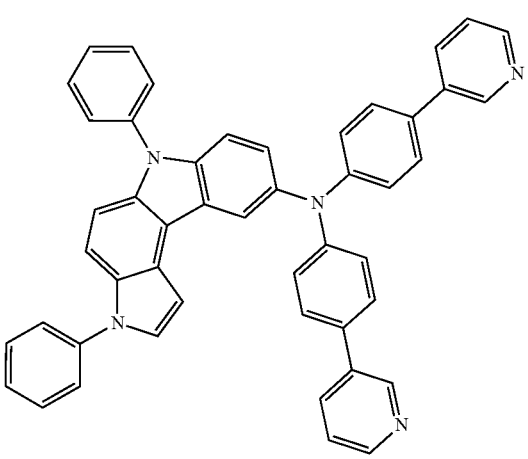
119
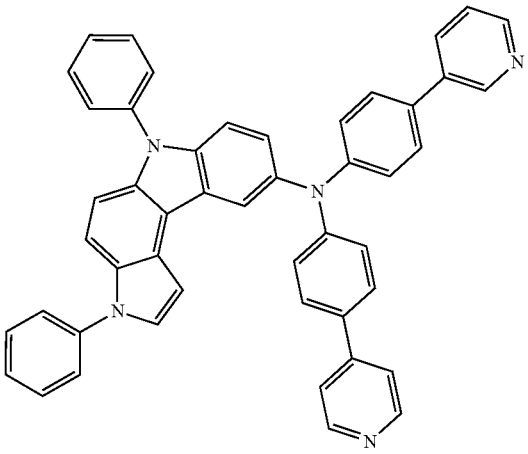

120
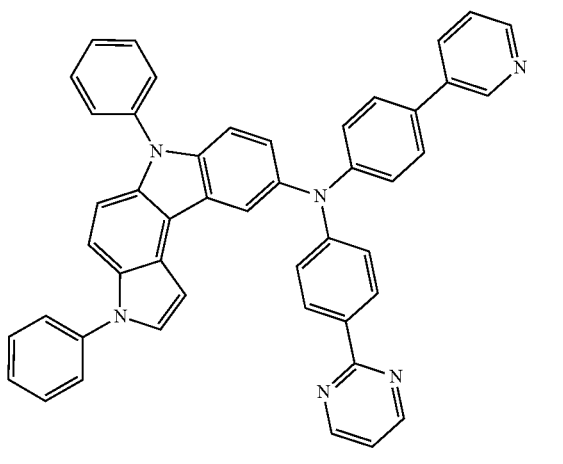
121
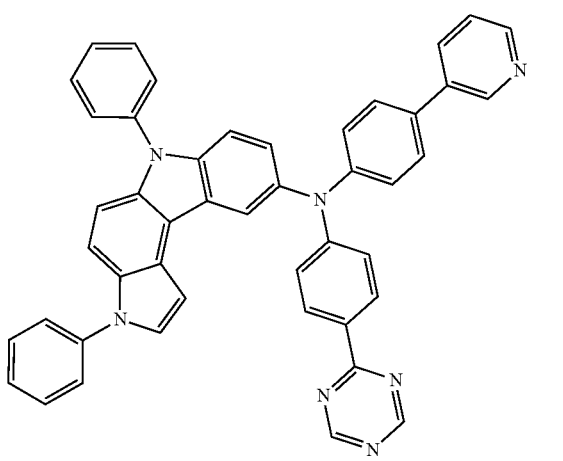
122
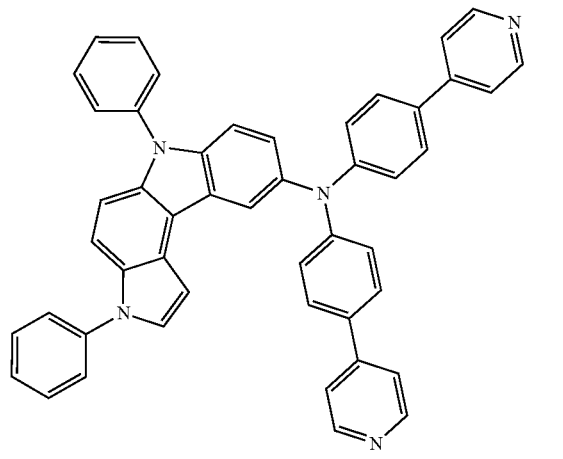
123
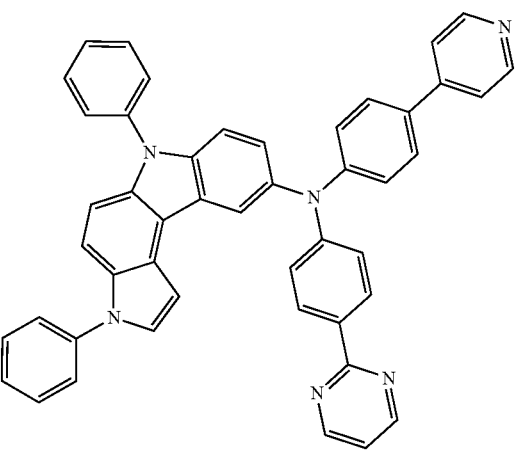
124
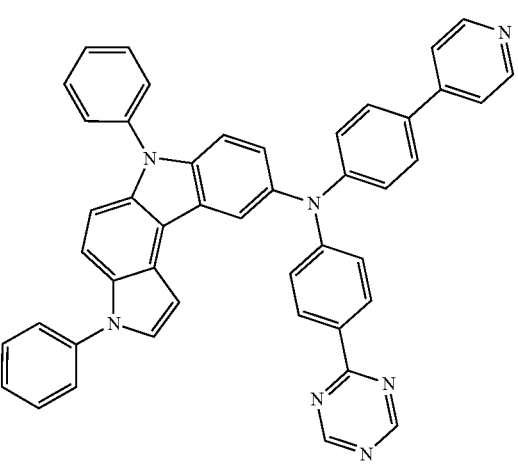
125
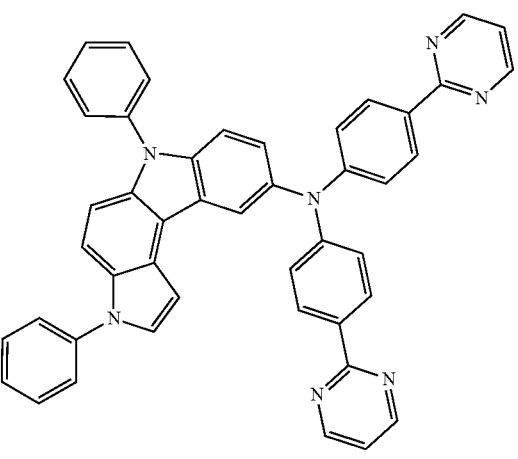

126
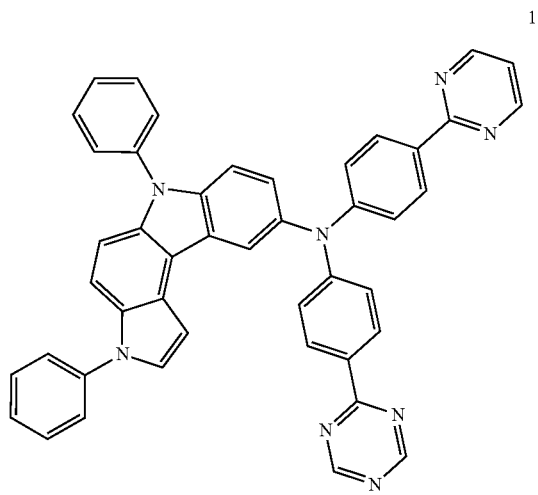
129
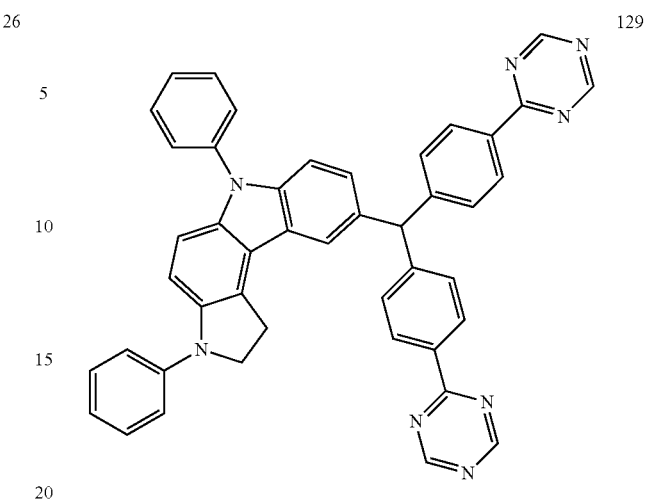
127
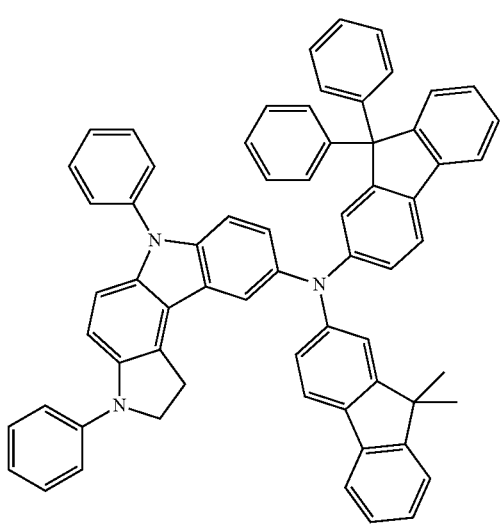
130
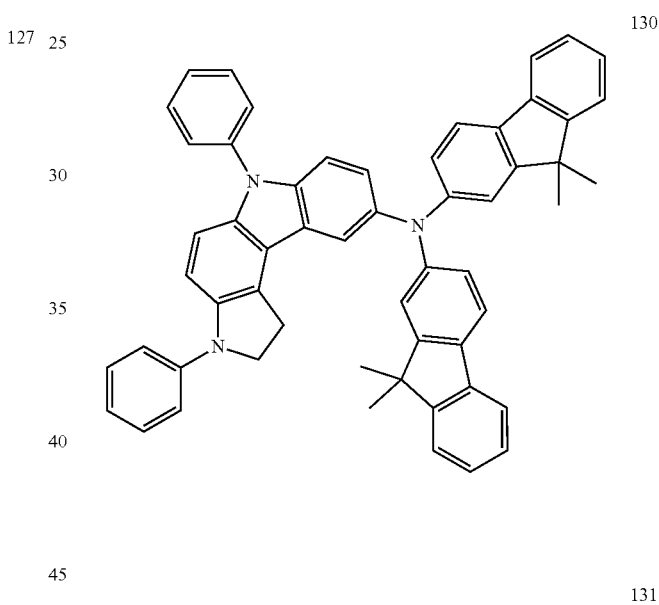
128
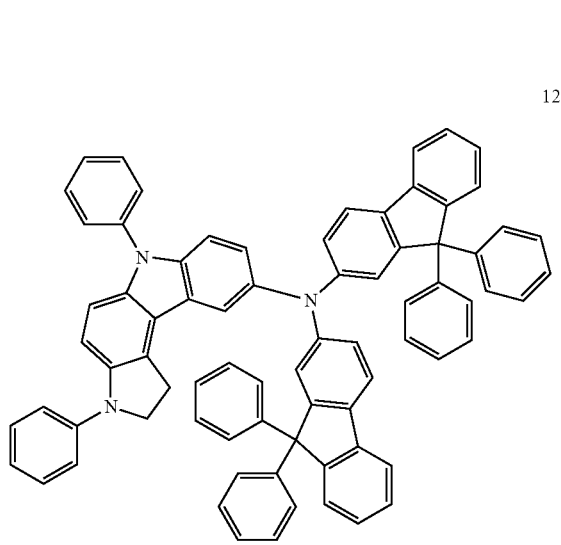
131
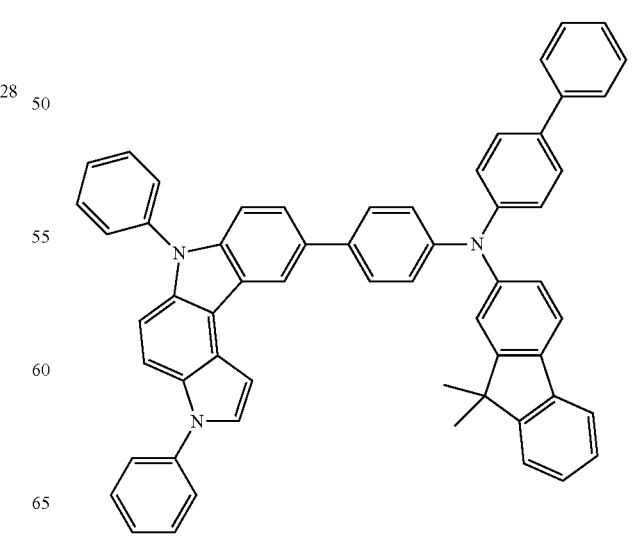

132
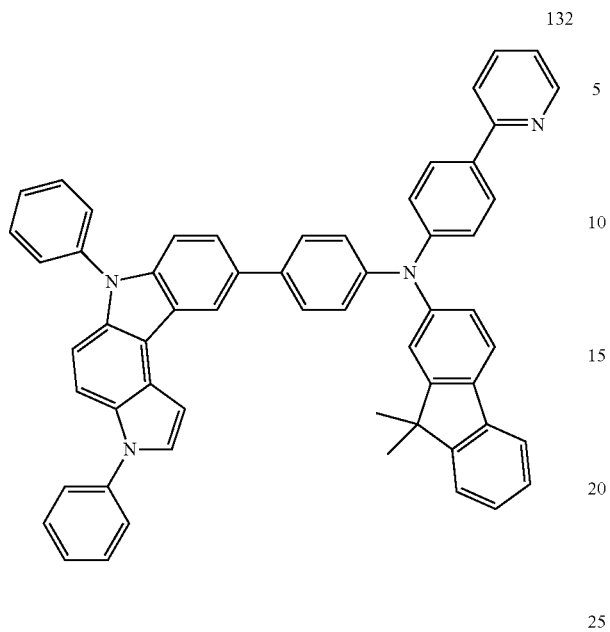
134
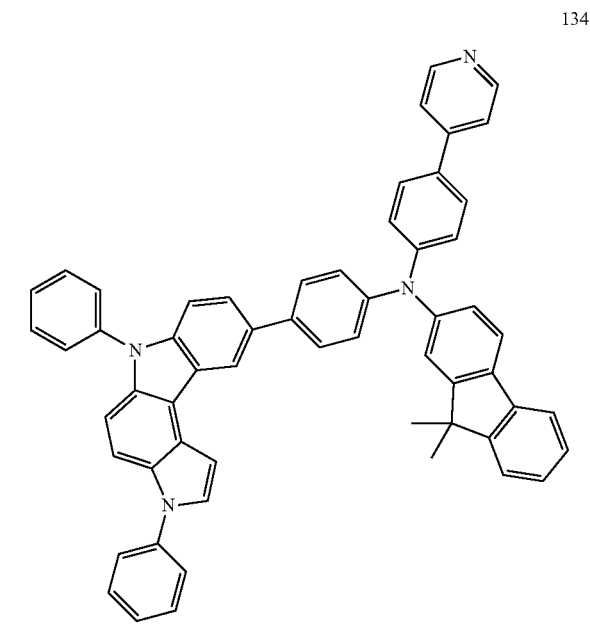
133
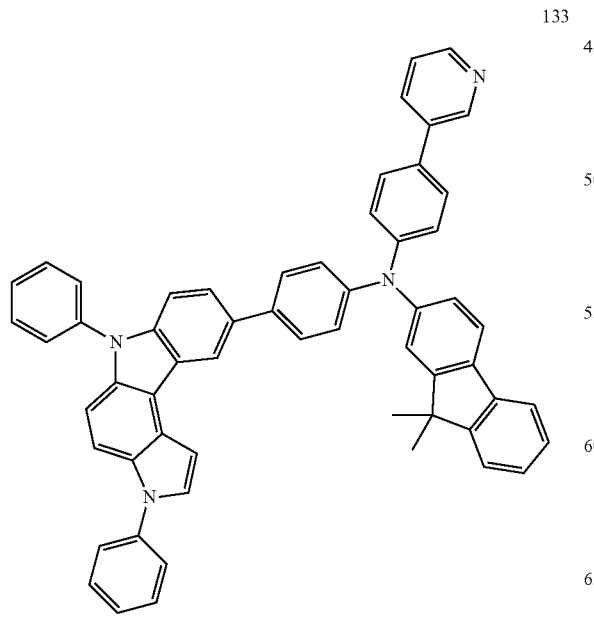
135
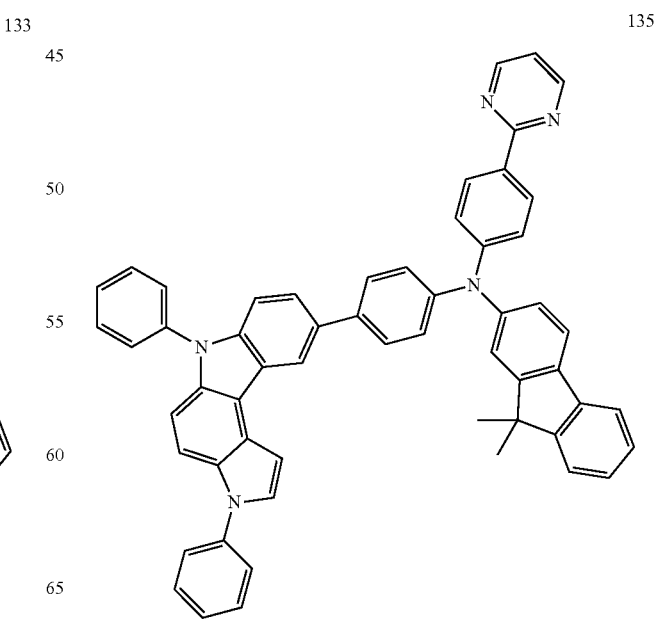

111
-continued
136
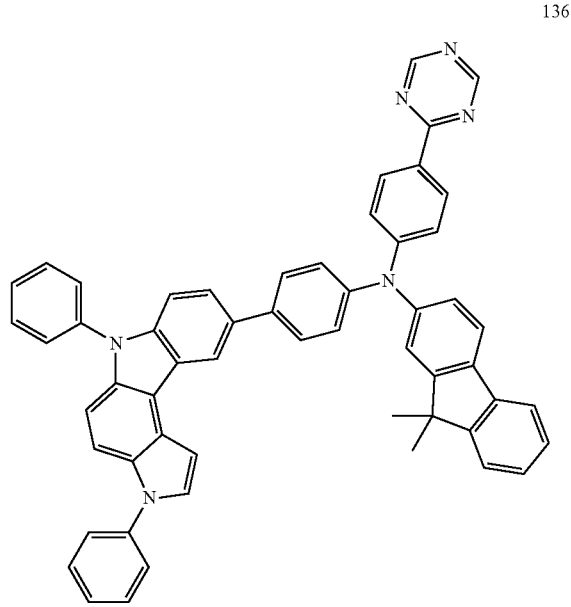
137
138
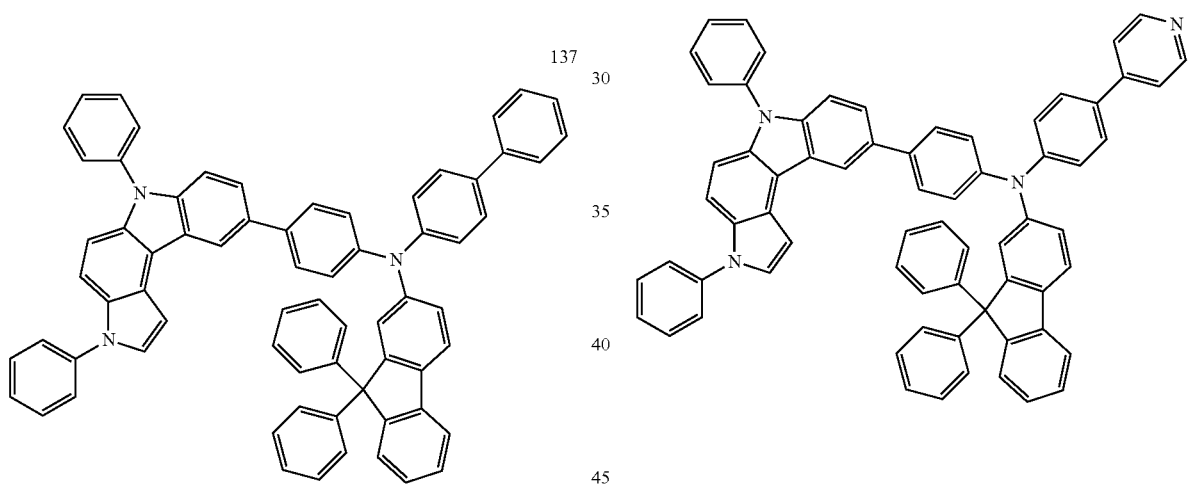
112
-continued
139
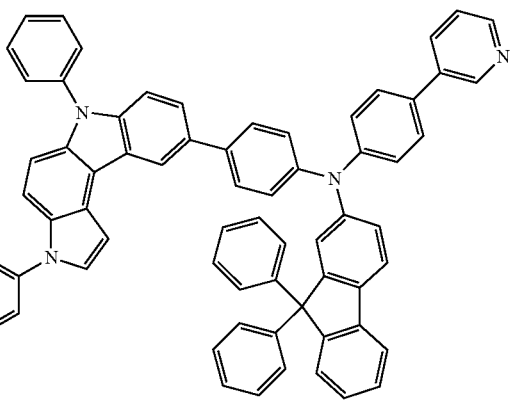
140
141
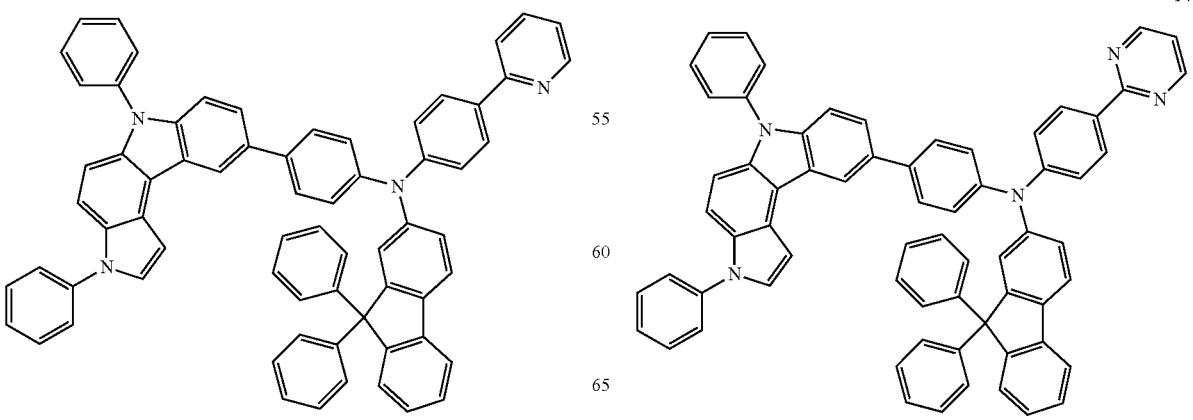

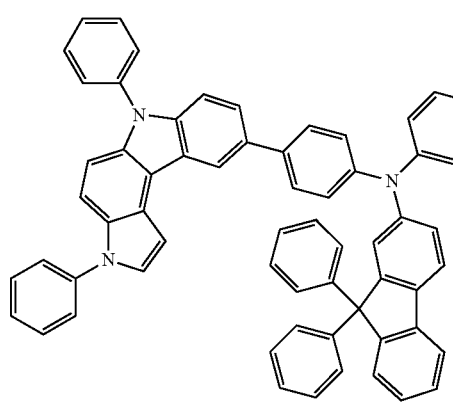
142
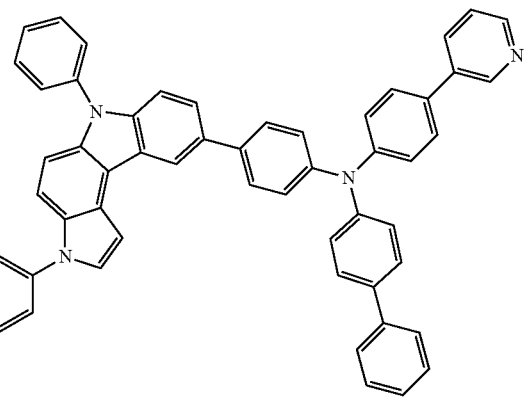
145
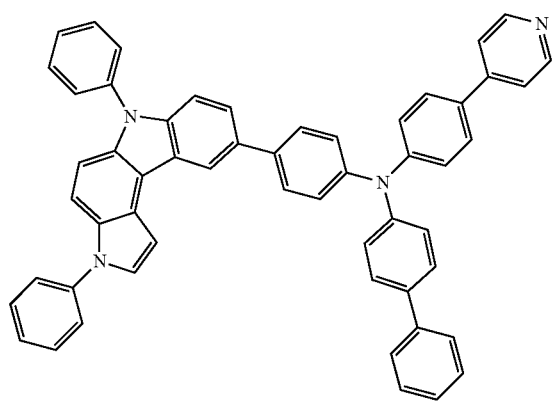
146
143
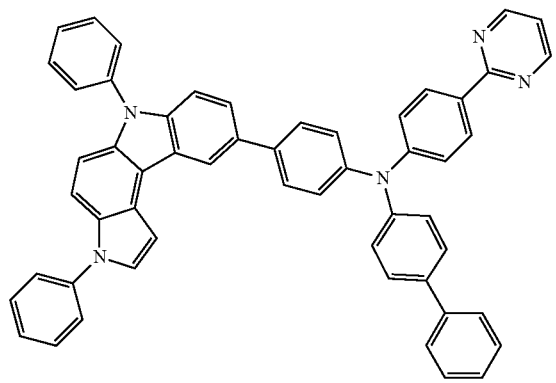
147
144
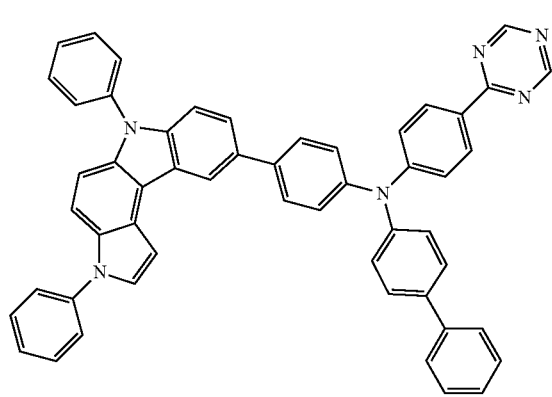
148

149
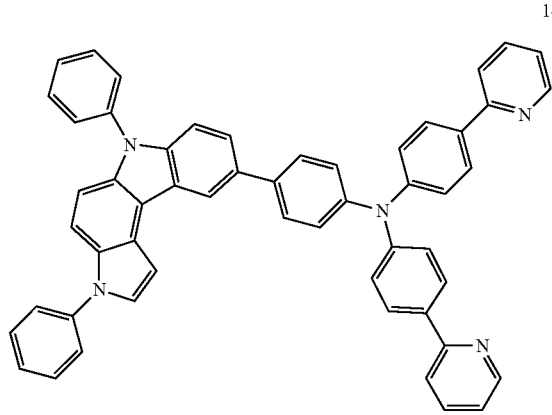
150
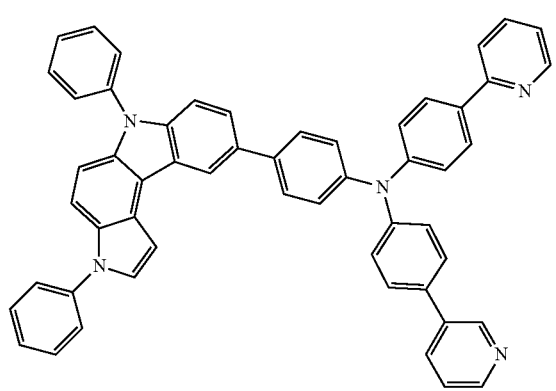
151
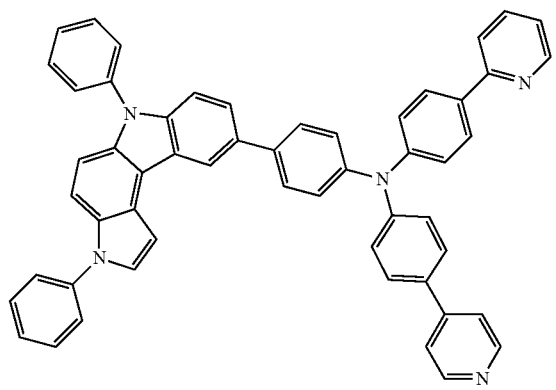
152
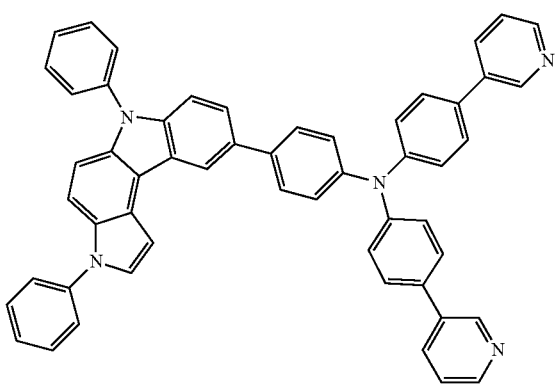
153
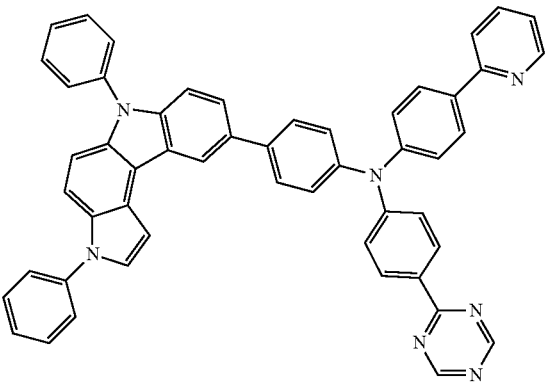
154
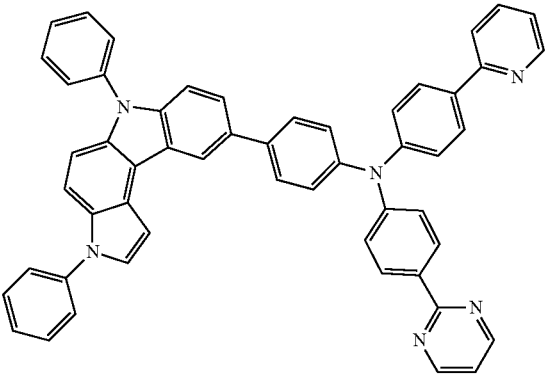
155
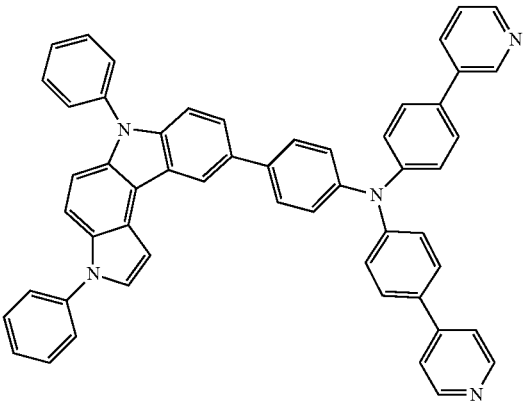
156
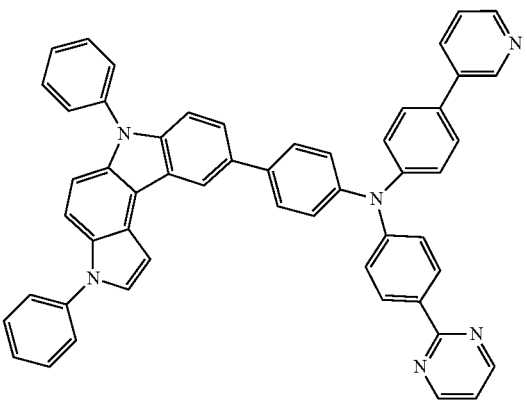

-continued
157
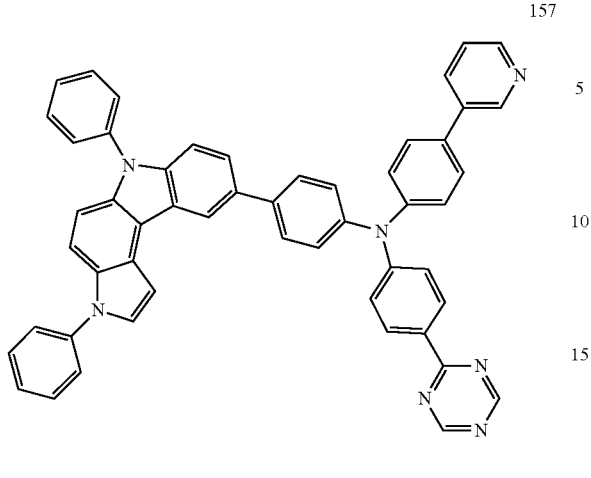
158
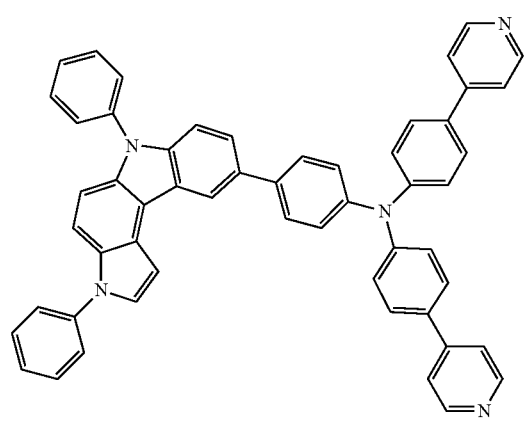
159
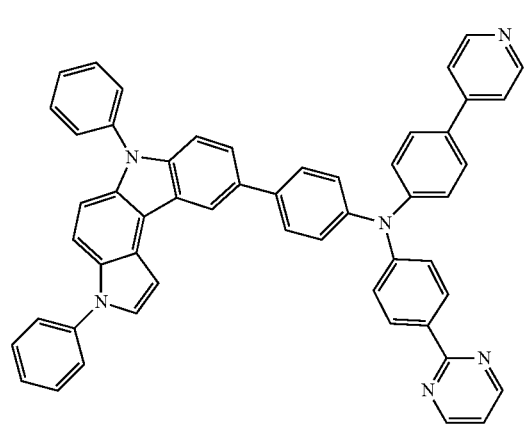
-continued
160
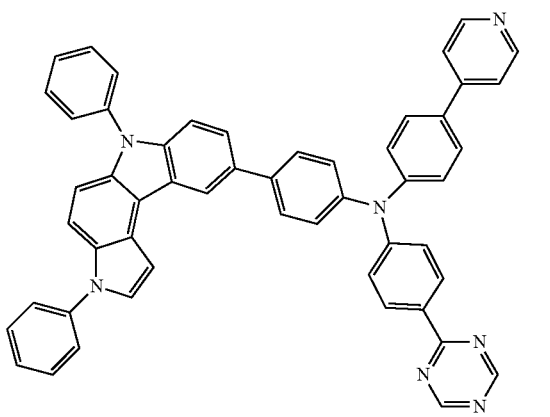
161
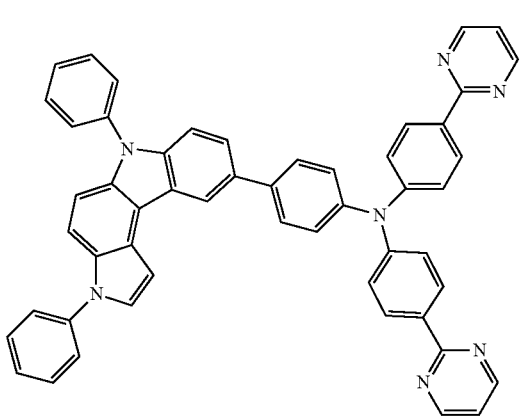
162
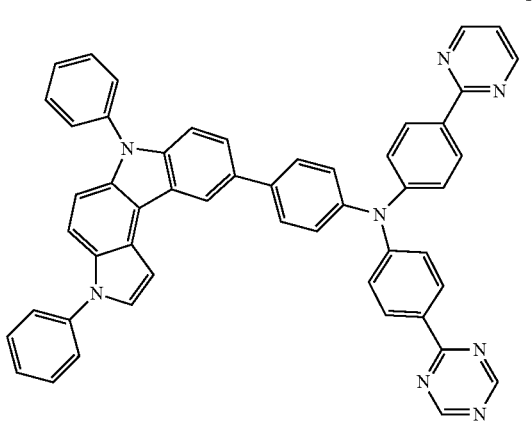

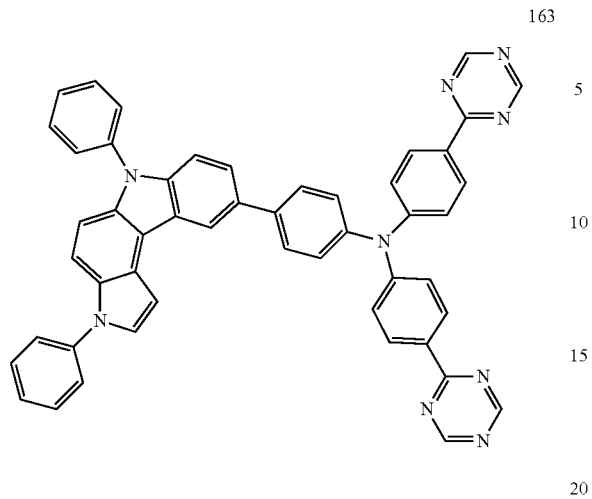
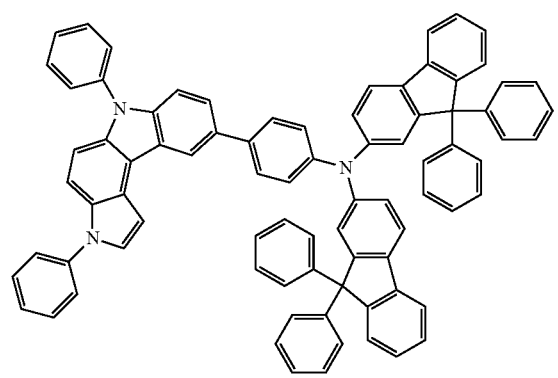
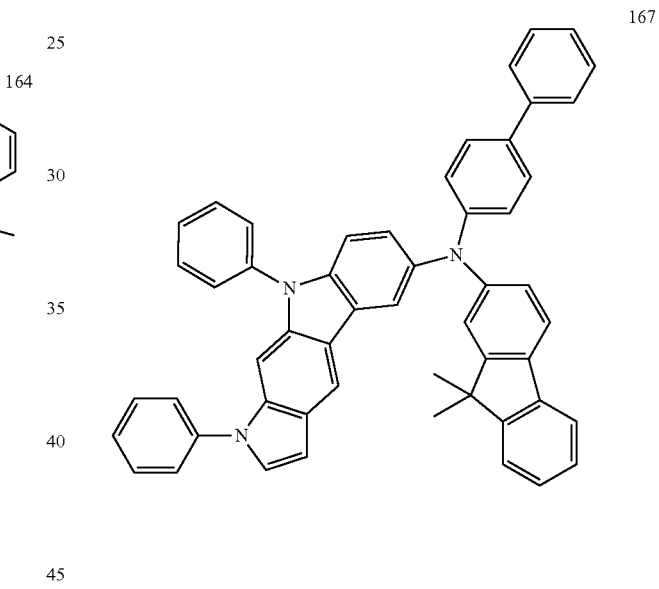
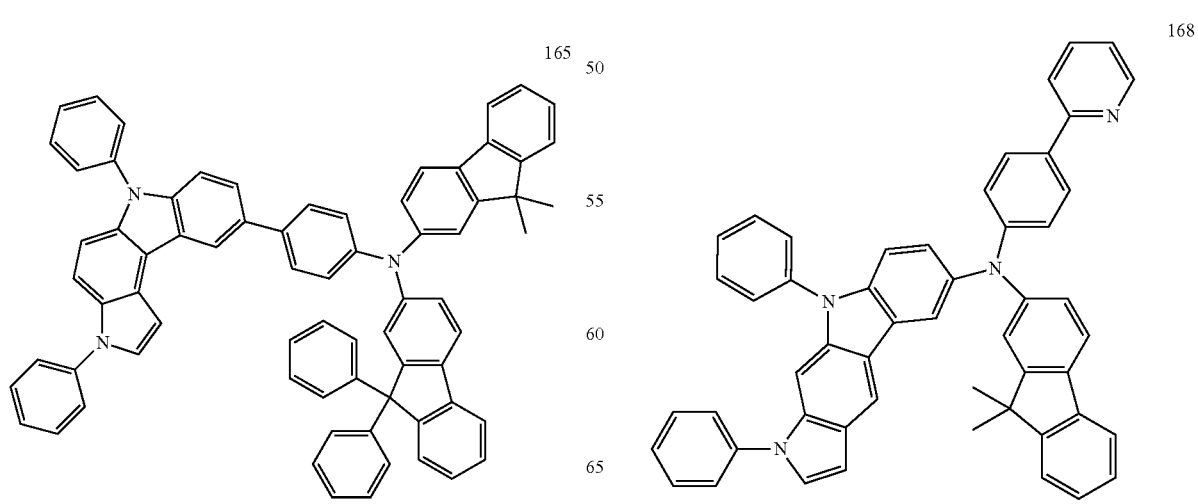

121
-continued
169
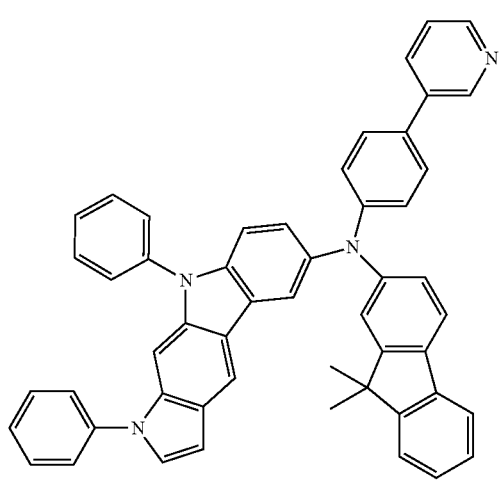
170
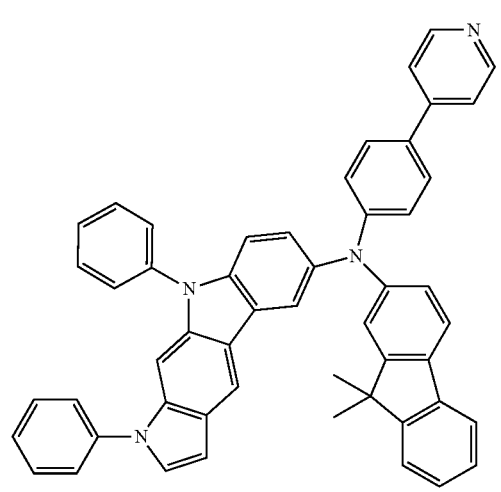
171
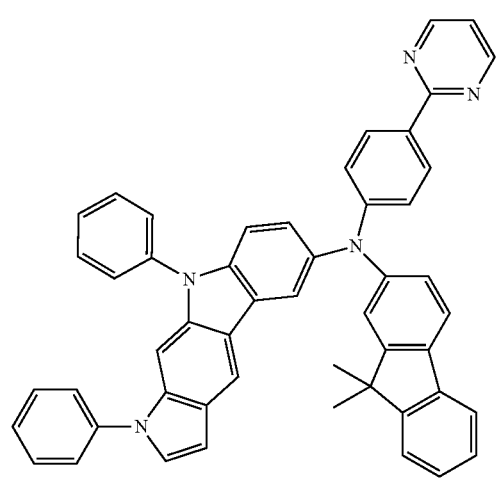
122
-continued
172
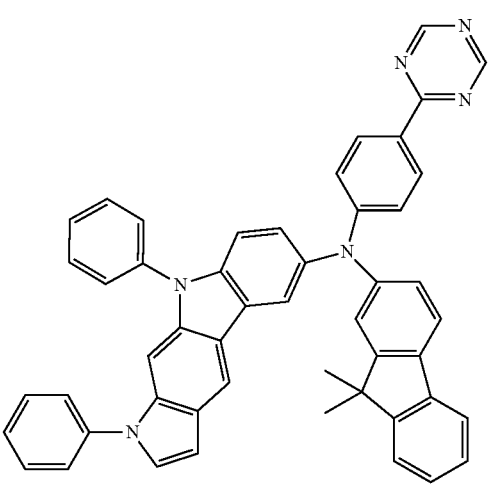
173
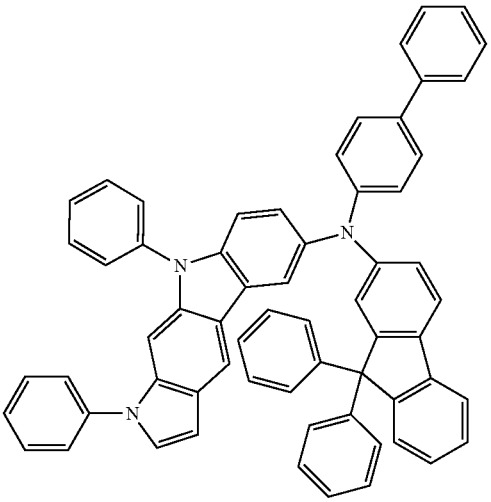
174
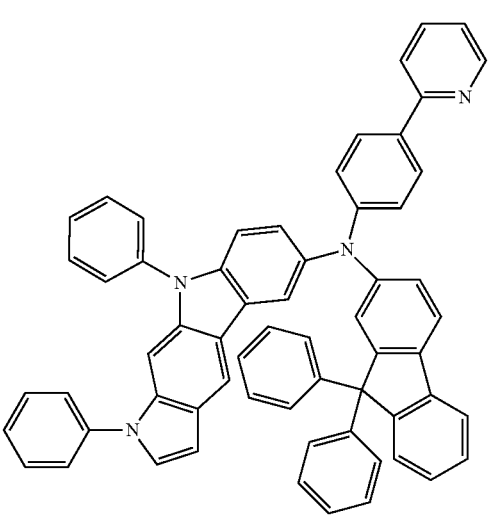

123
-continued
175
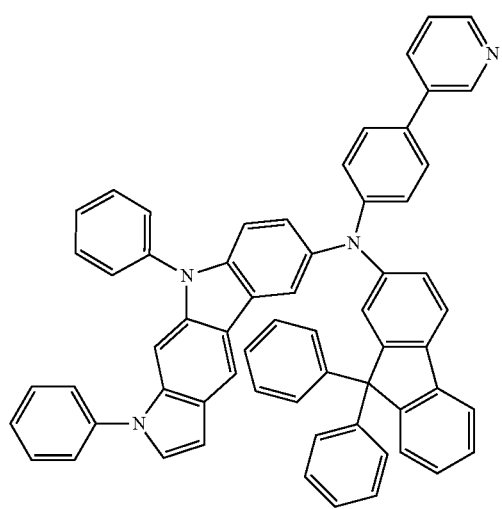
176
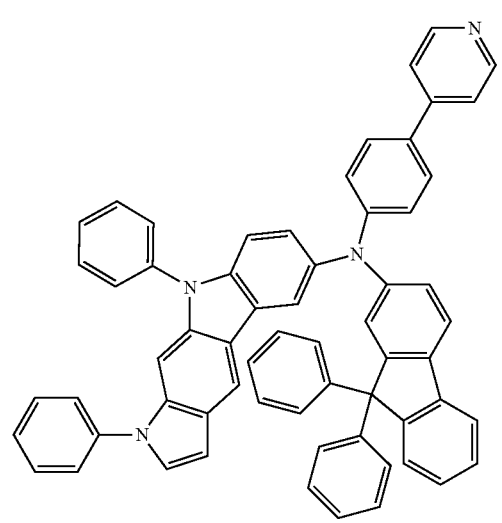
177
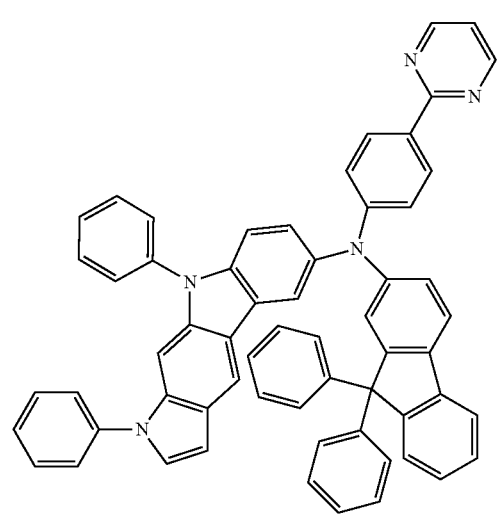
124
-continued
178
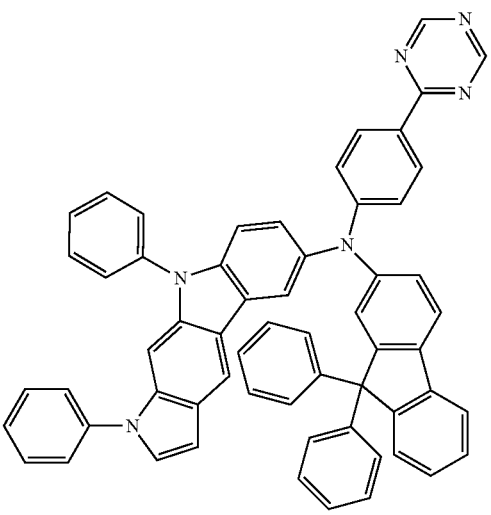
179
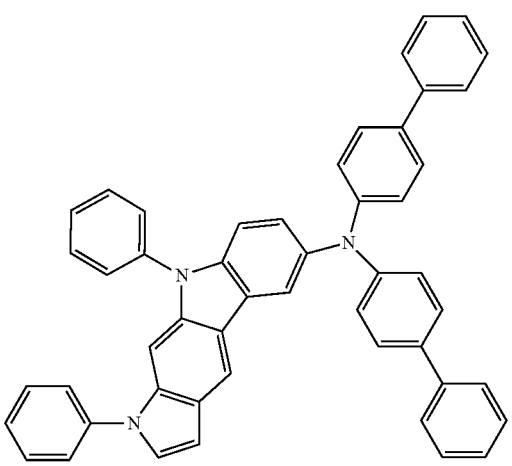
180
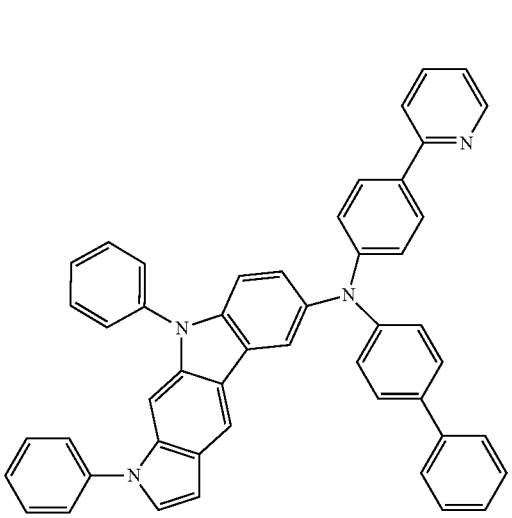

-continued
181
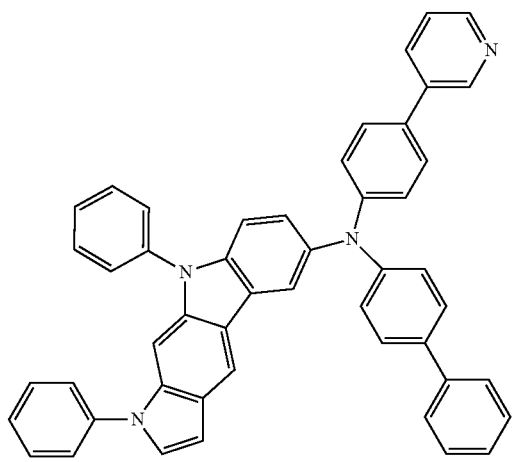
182
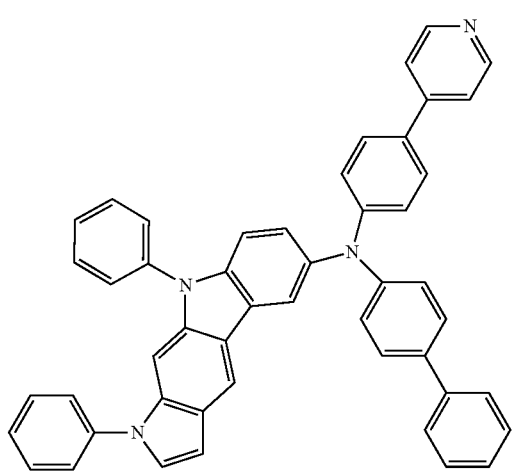
183
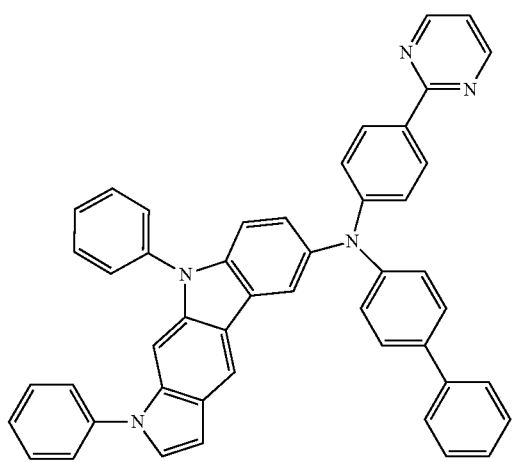
-continued
184
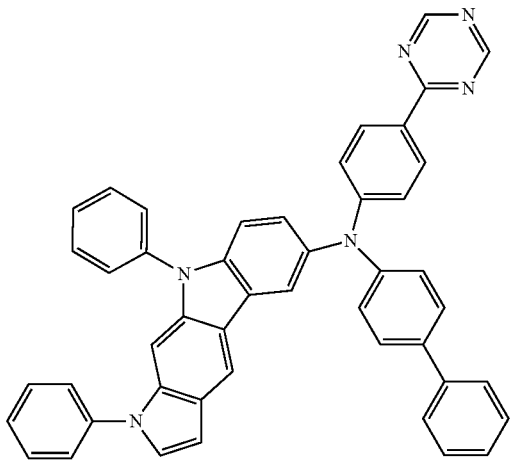
185
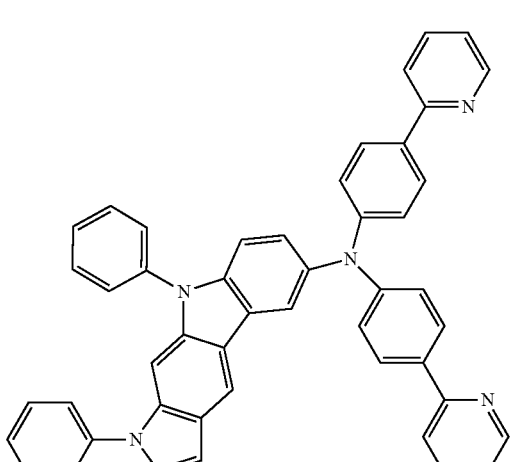
186
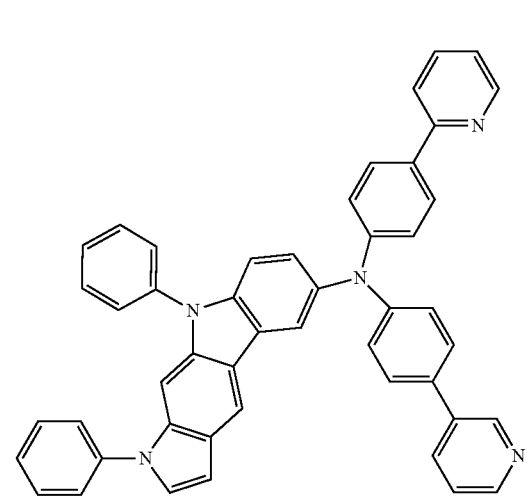

187
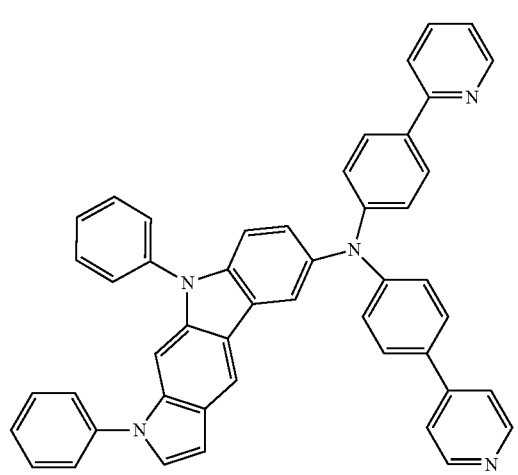
188
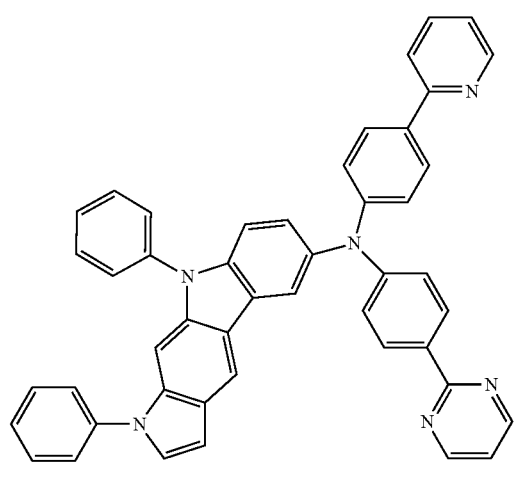
189
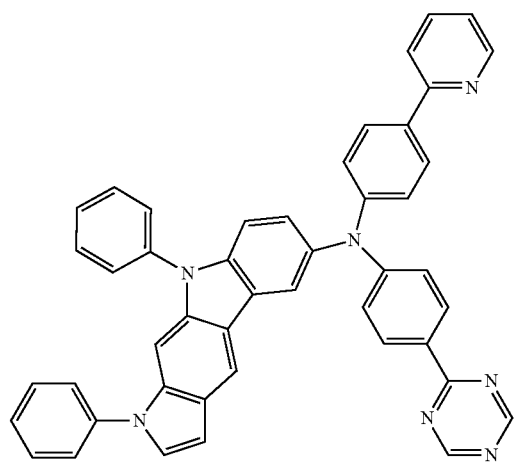
190
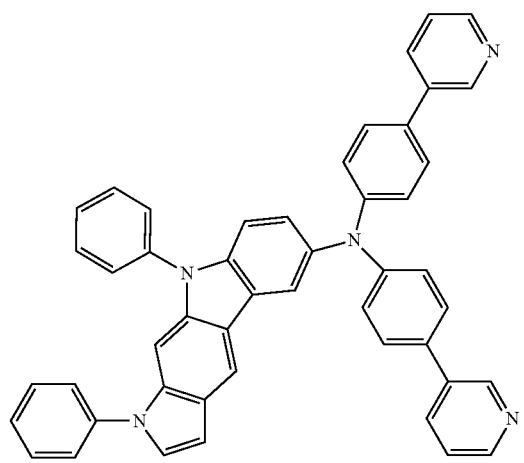
191
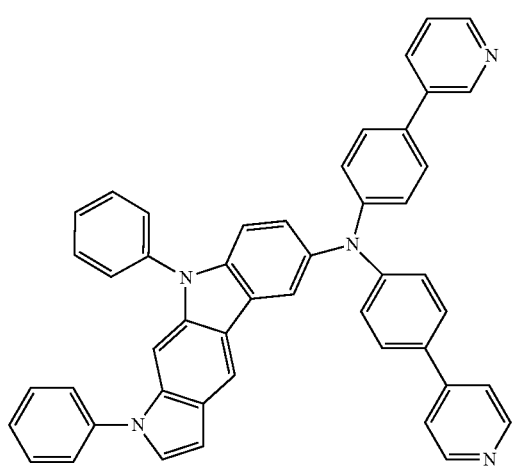
192
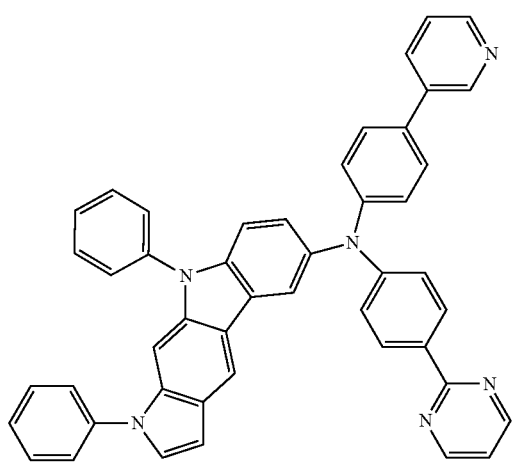

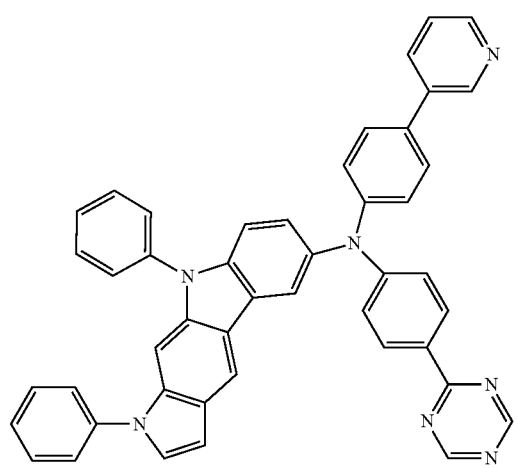
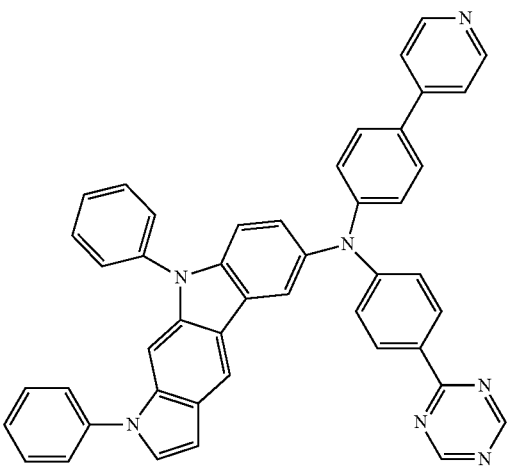

199
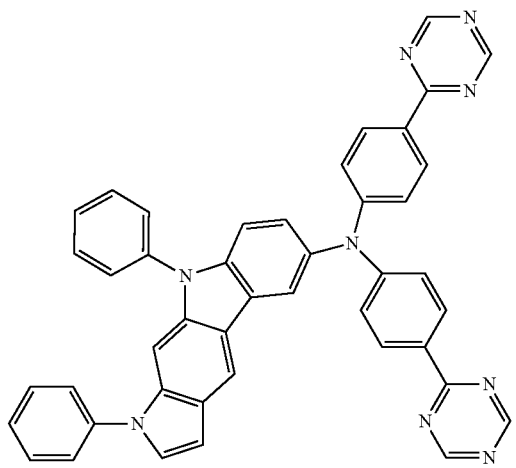
202
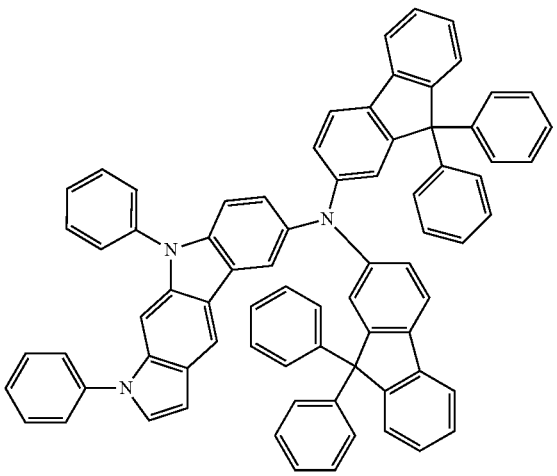
200
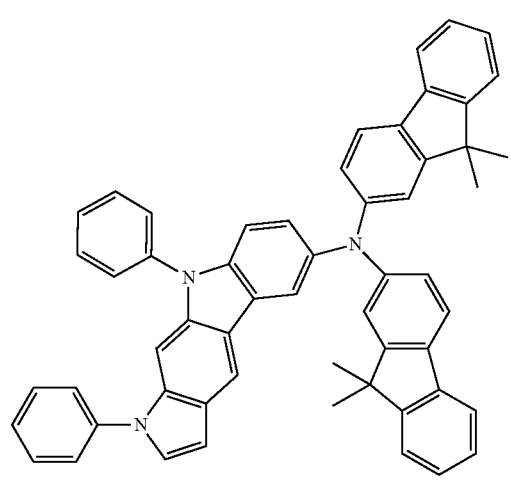
203
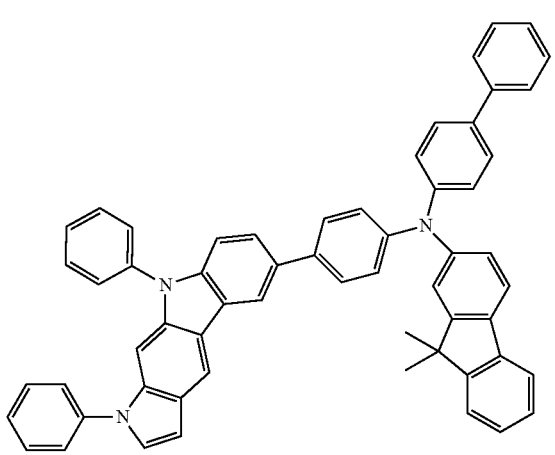
201
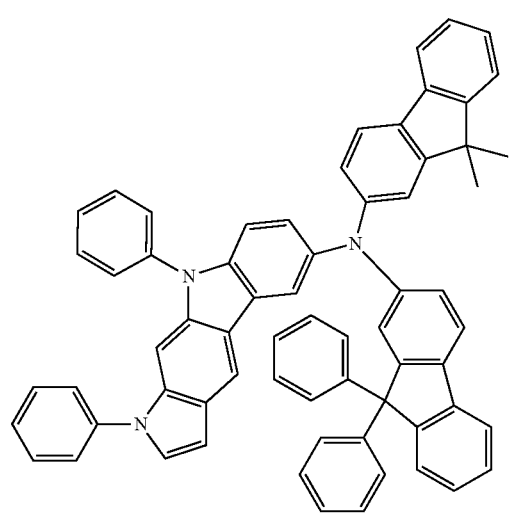
204
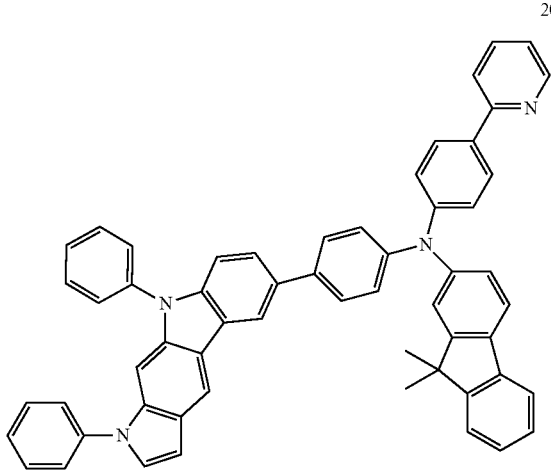

205
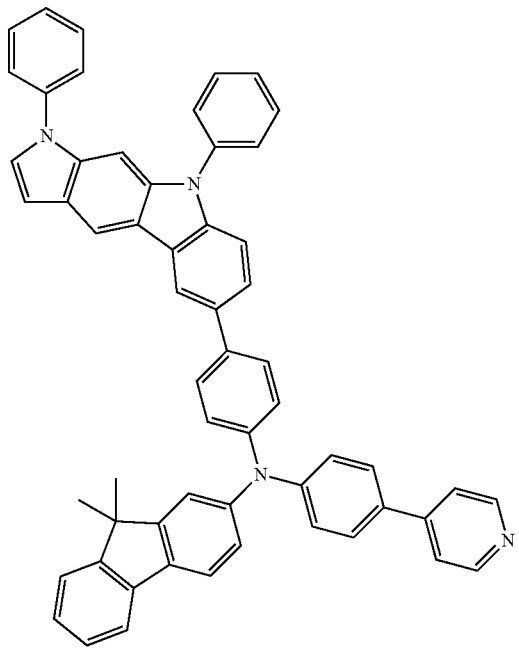
207
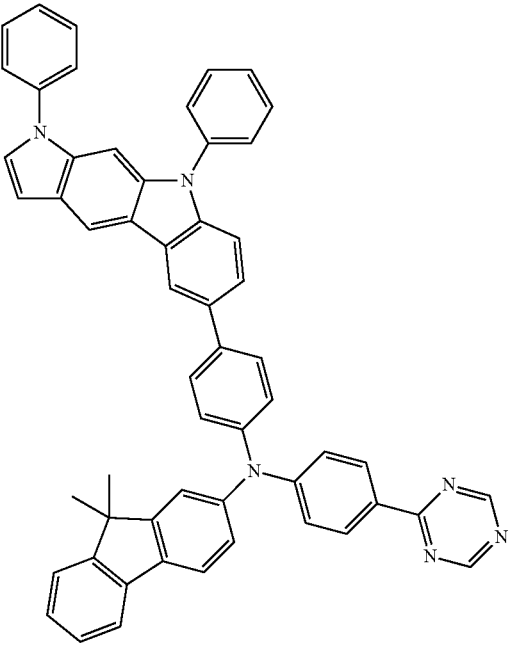
206
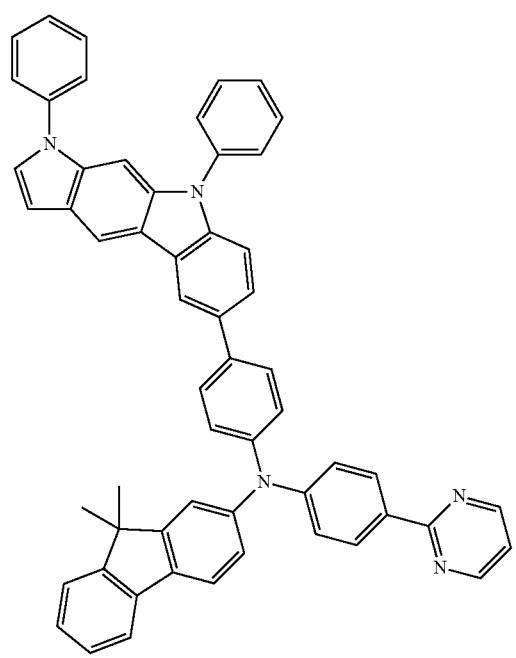
208
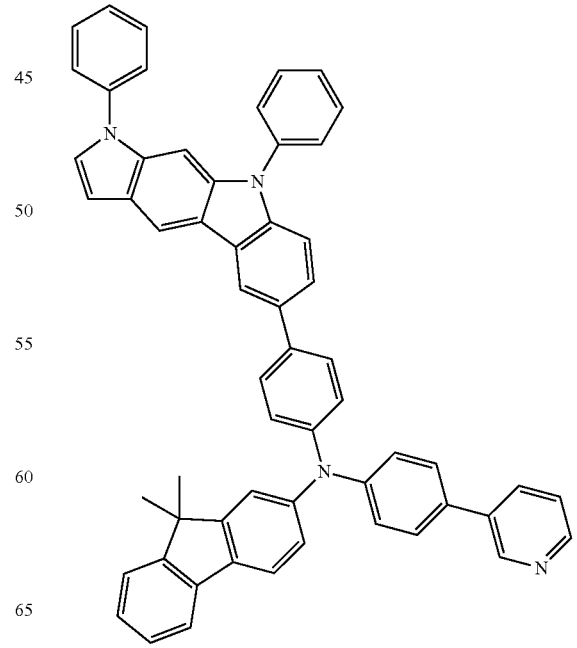

209
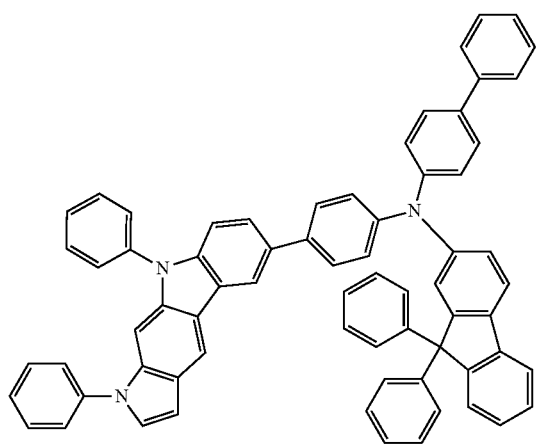
212
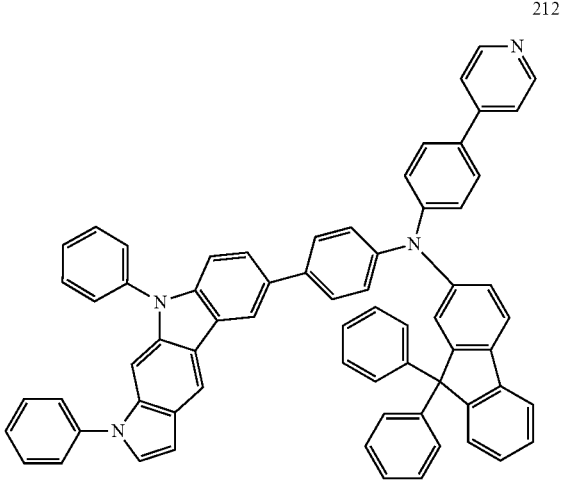
210
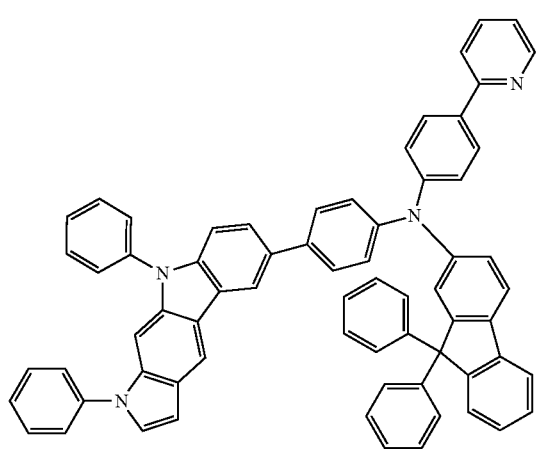
213
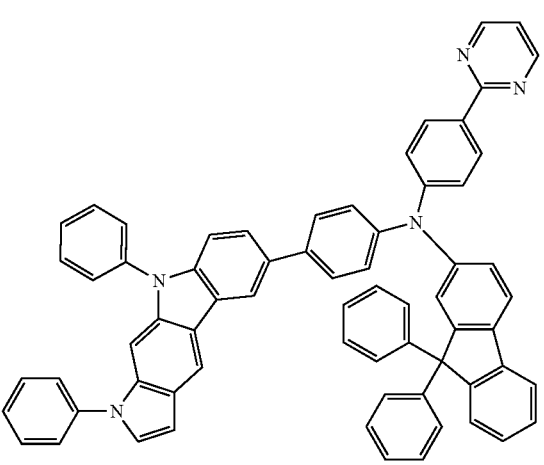
211
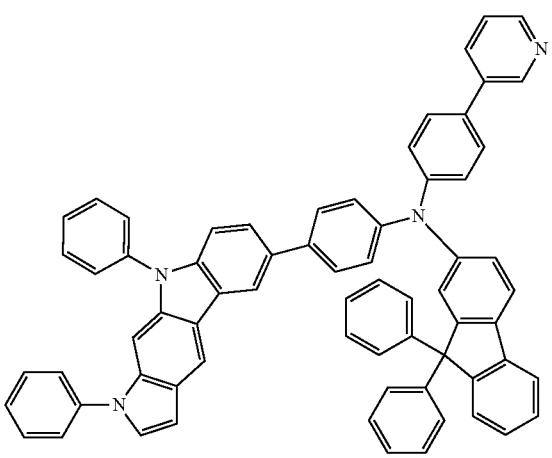
214
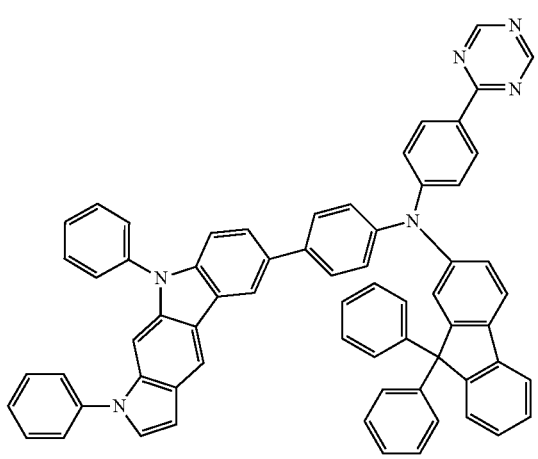

137
-continued
215
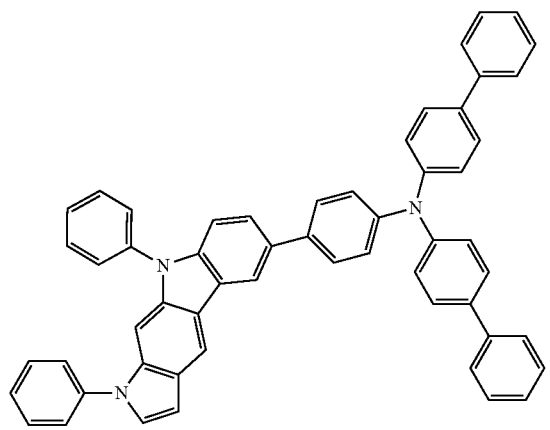
216
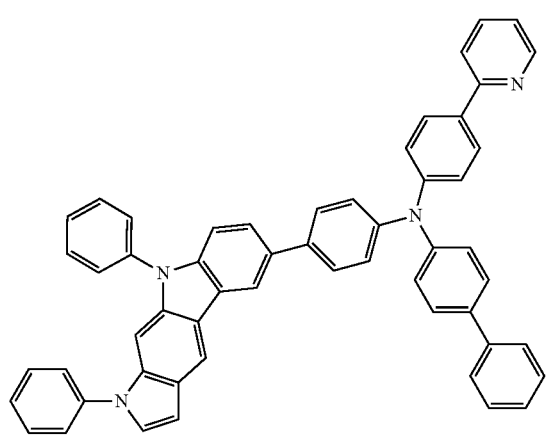
217
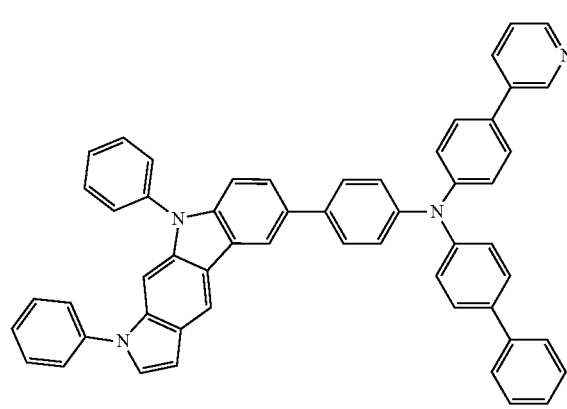
138
-continued
218
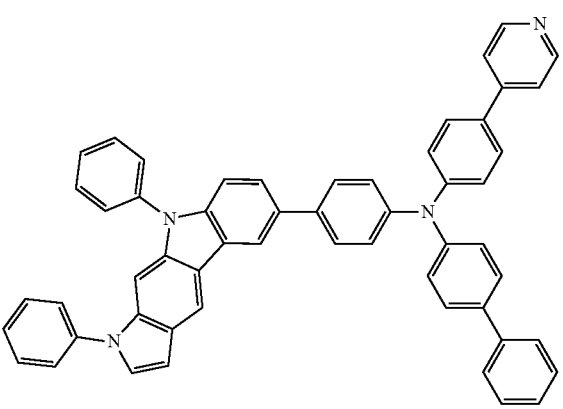
219
220
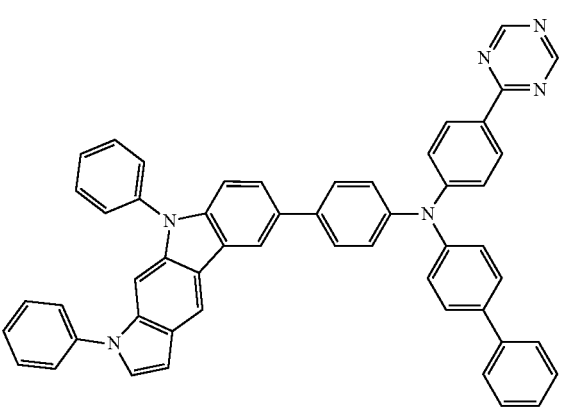

221
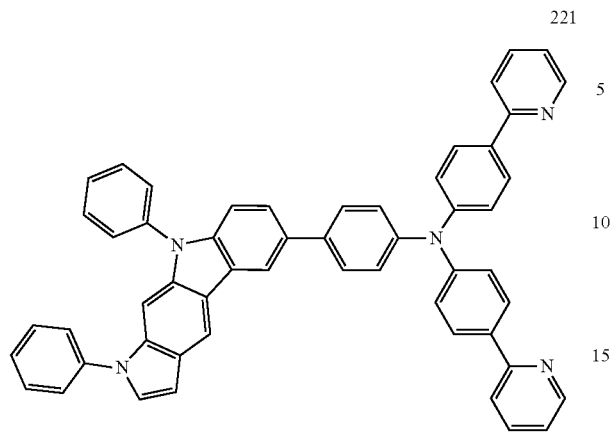
222
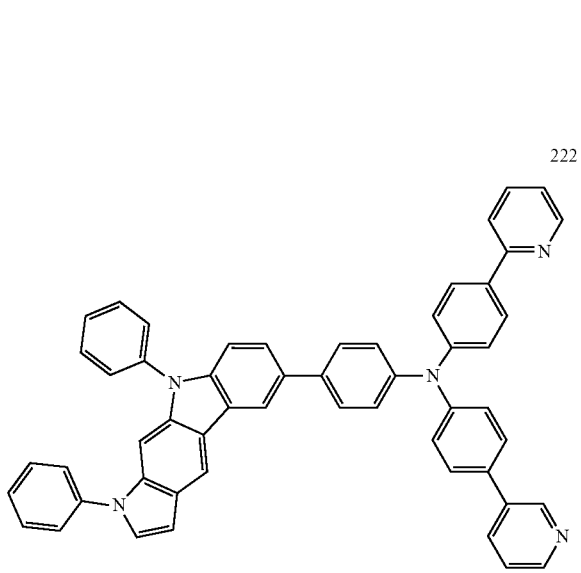
223
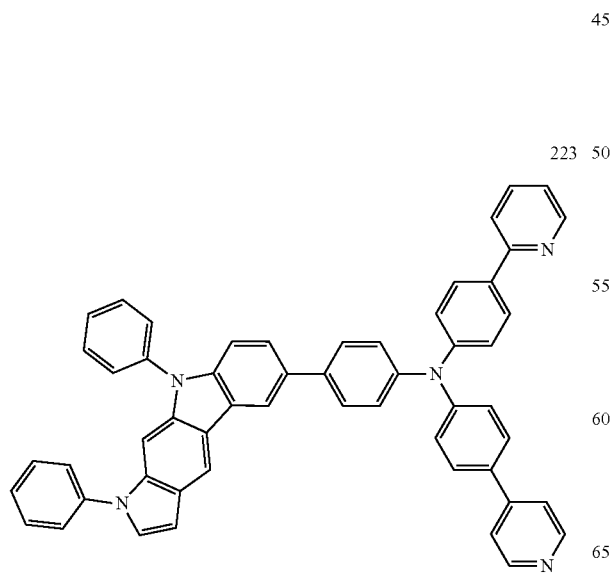
224
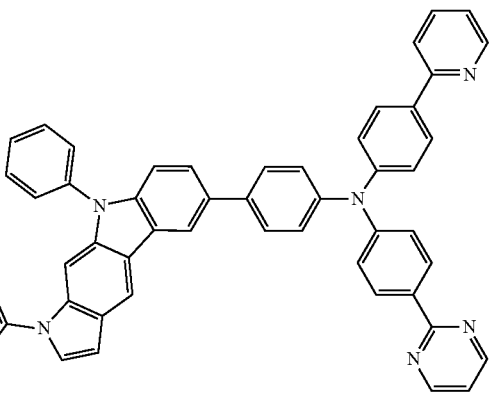
225
226
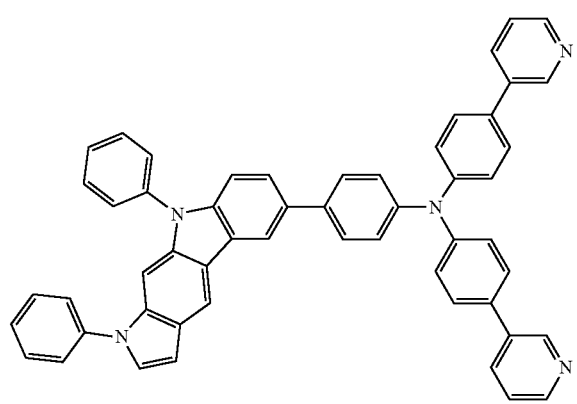

US 10,297,759 B2
141
-continued
142
-continued
227
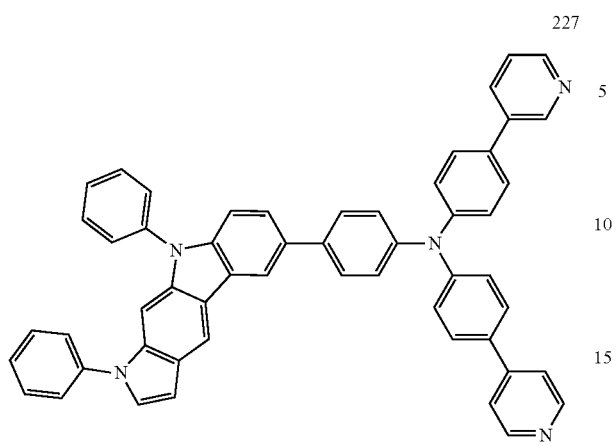
230
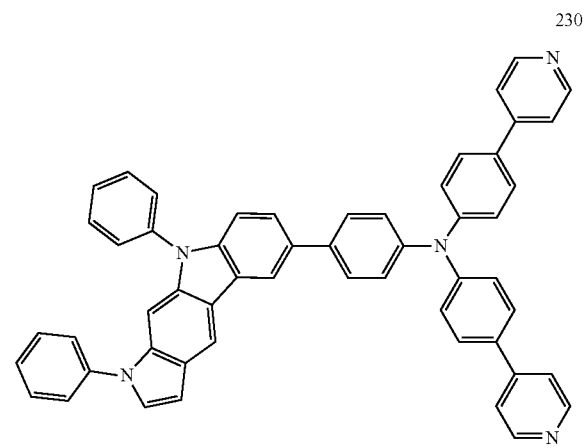
228
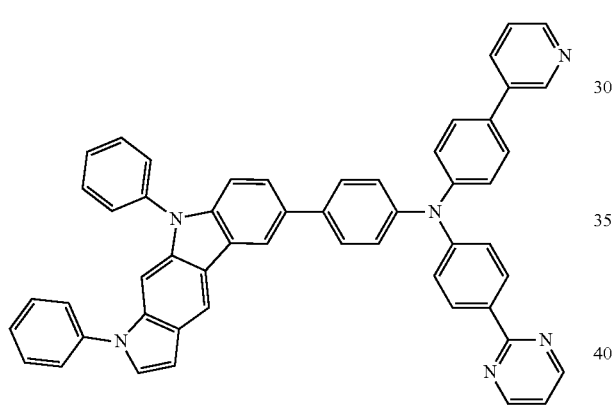
231
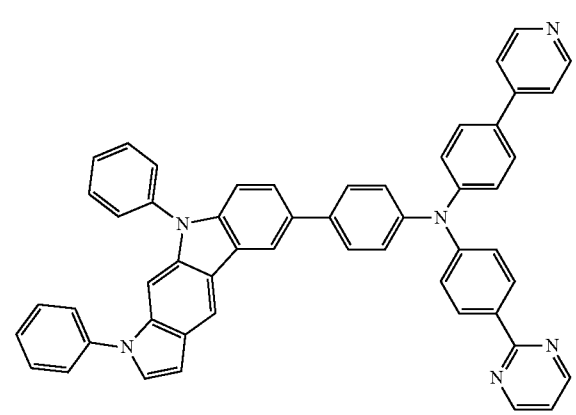
229
232
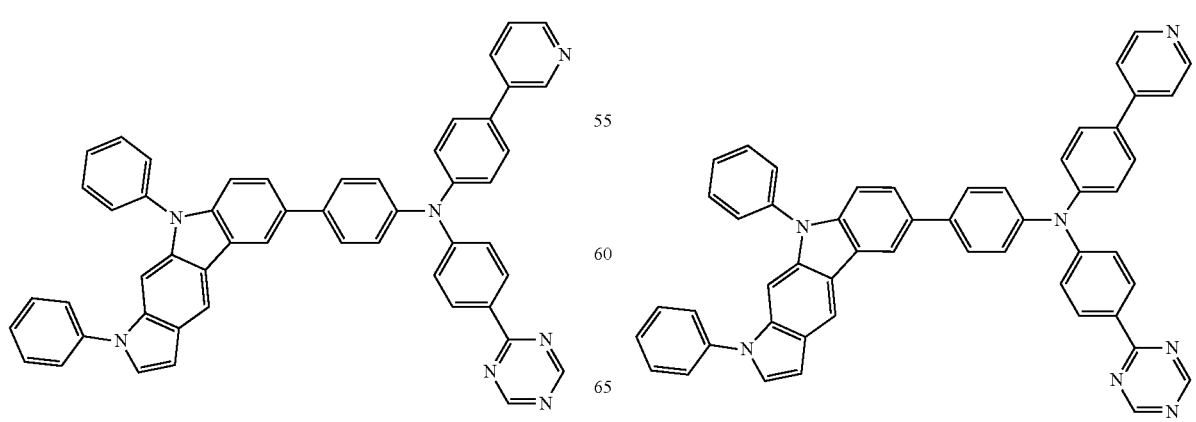

233
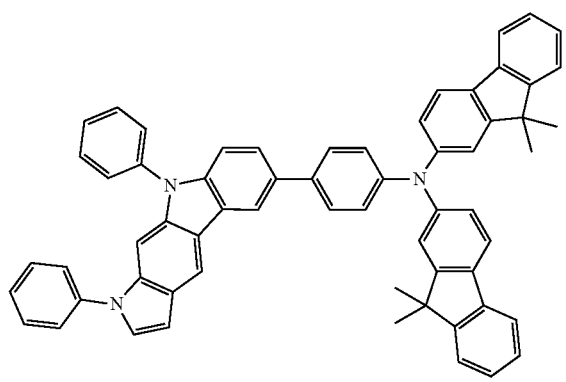
236
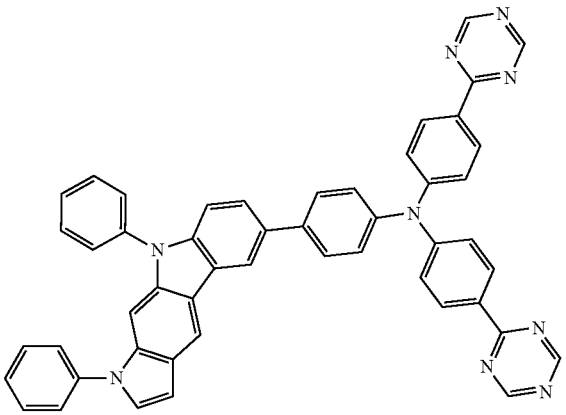
234
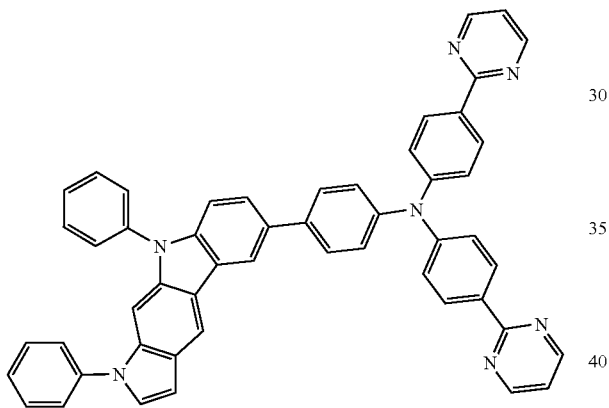
237
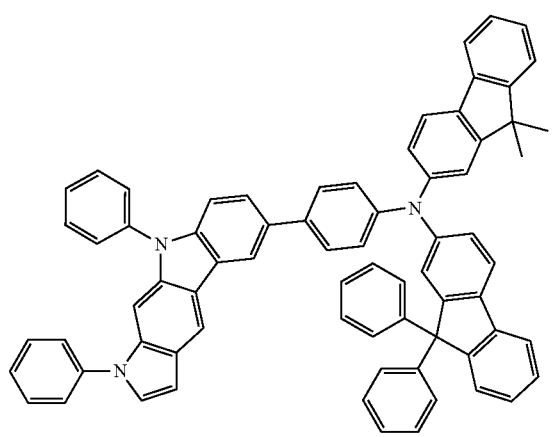
235
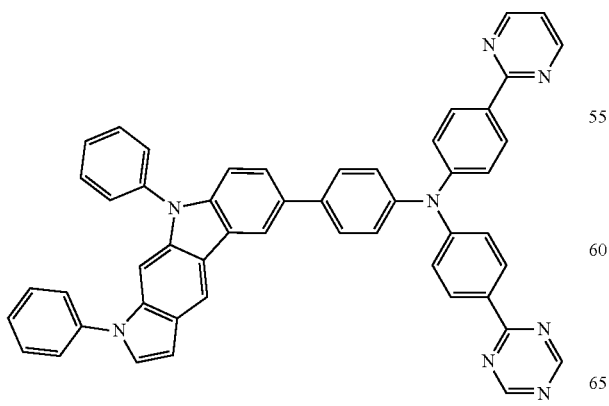
238
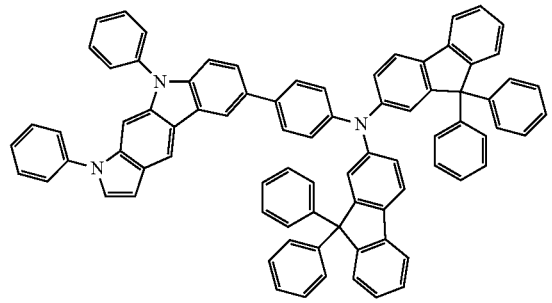

239
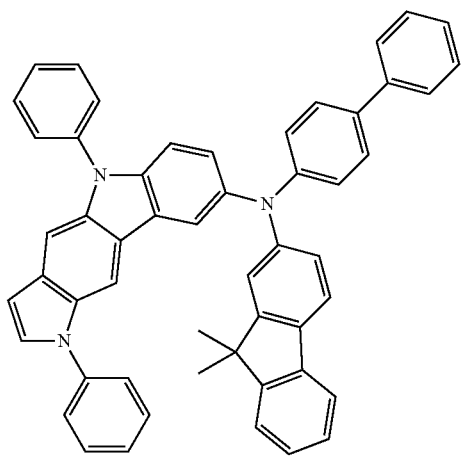
240
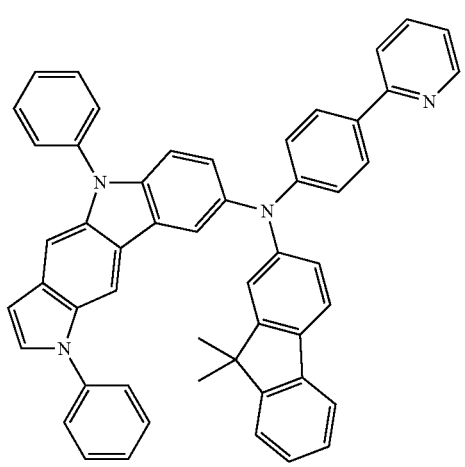
241
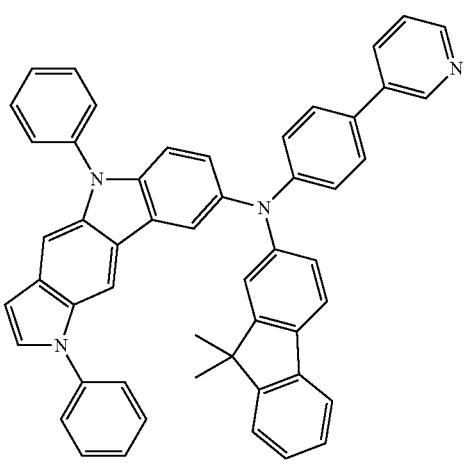
242
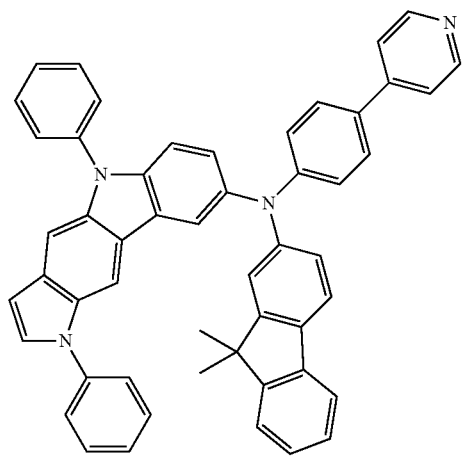
243
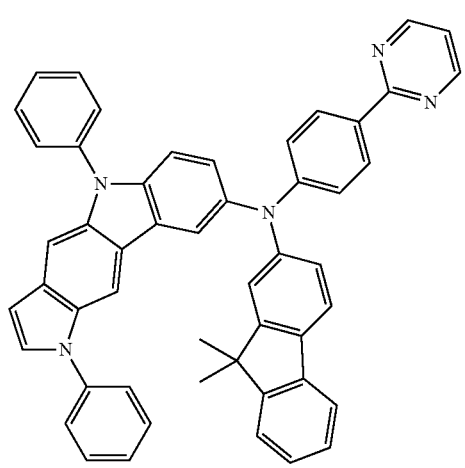
244
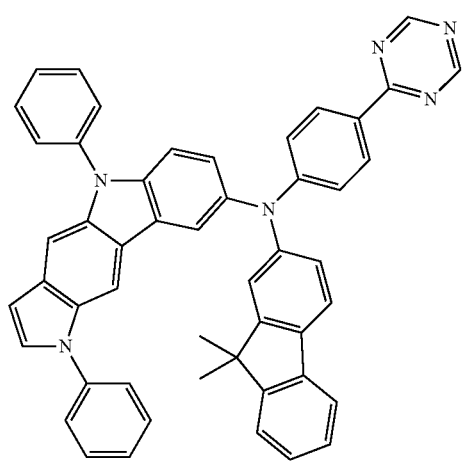

245
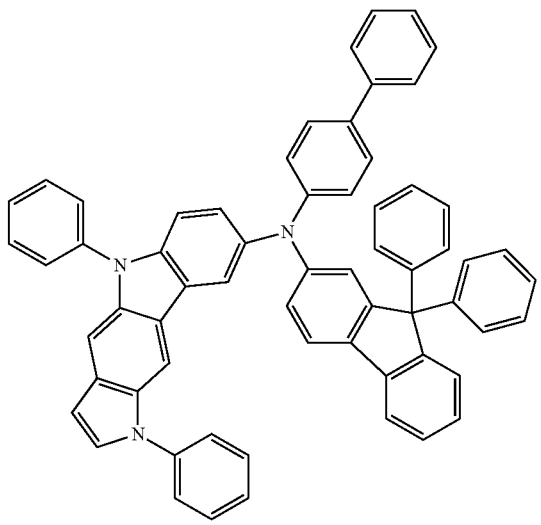
246
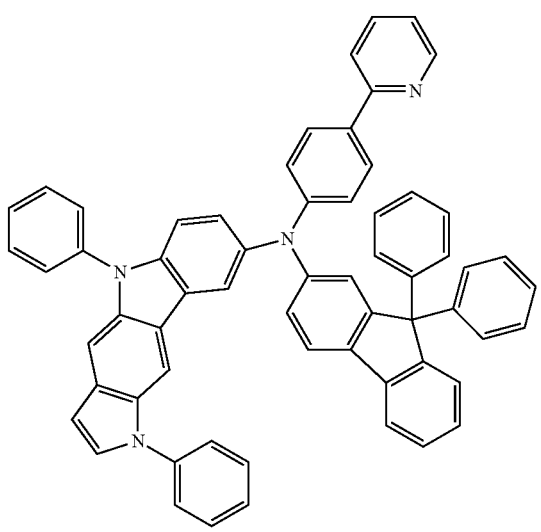
247
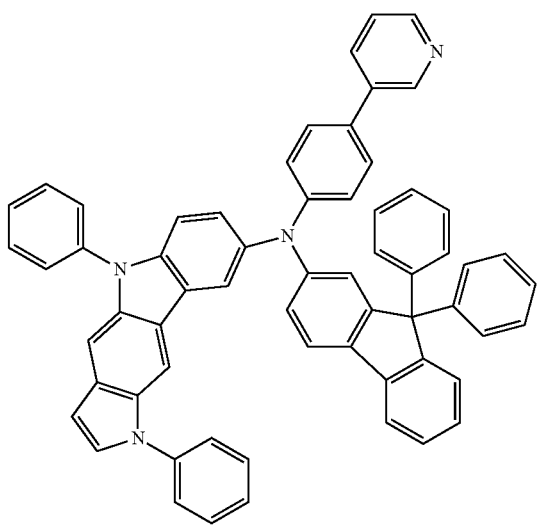
248
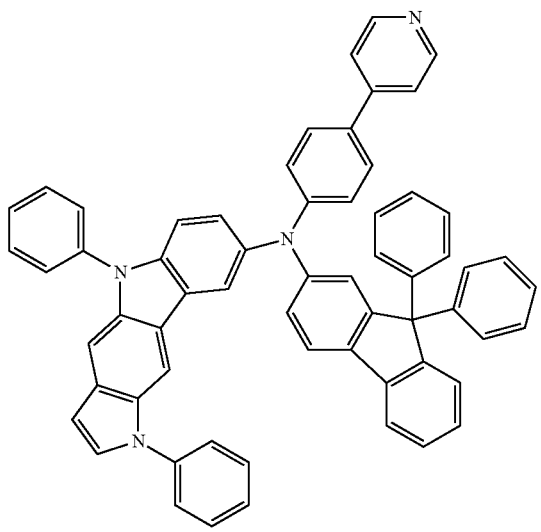
249
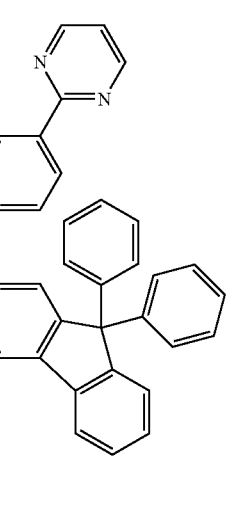
250
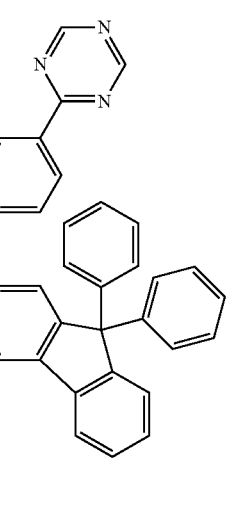

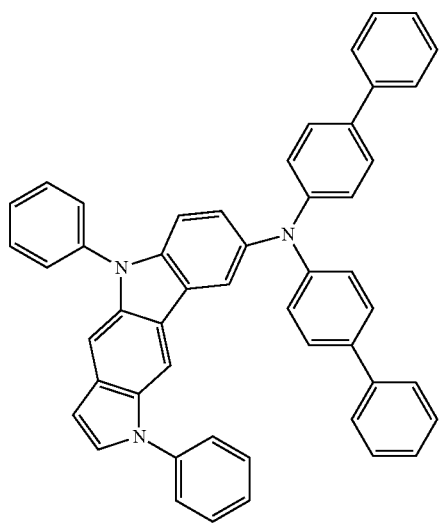
251
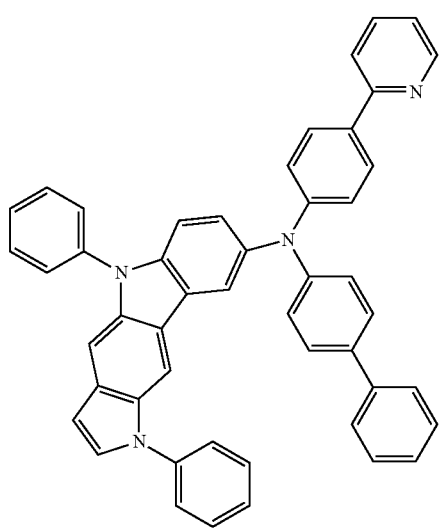
252
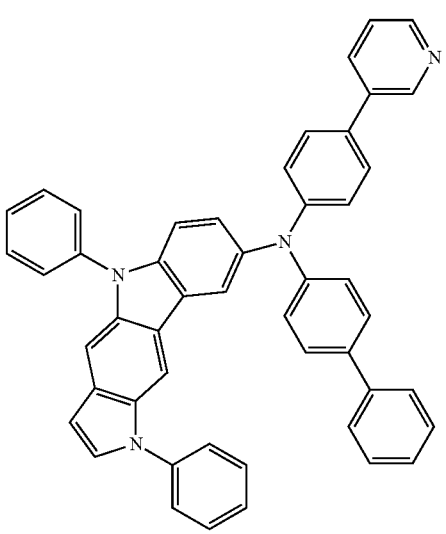
253
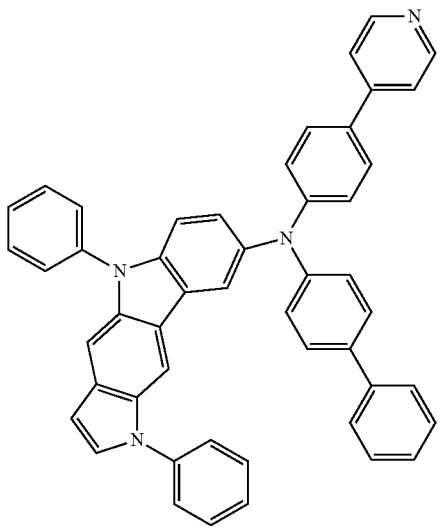
254
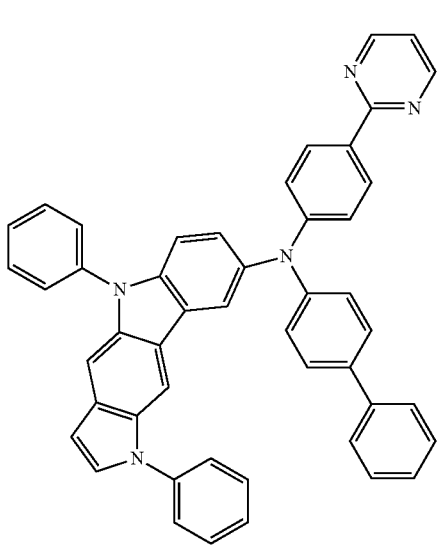
255
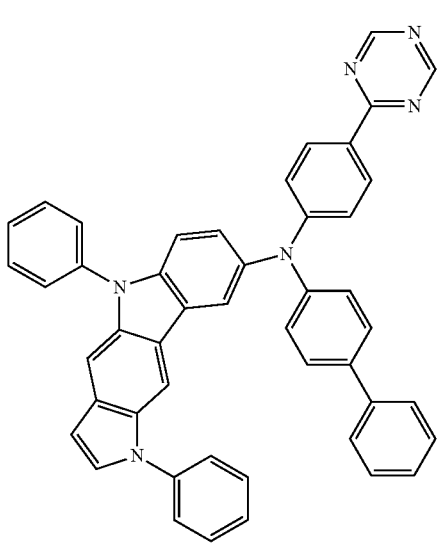
256

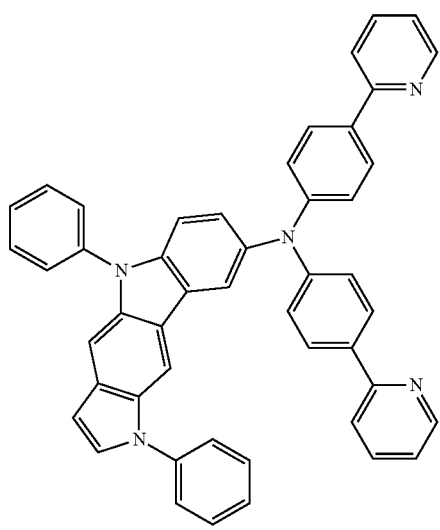
257
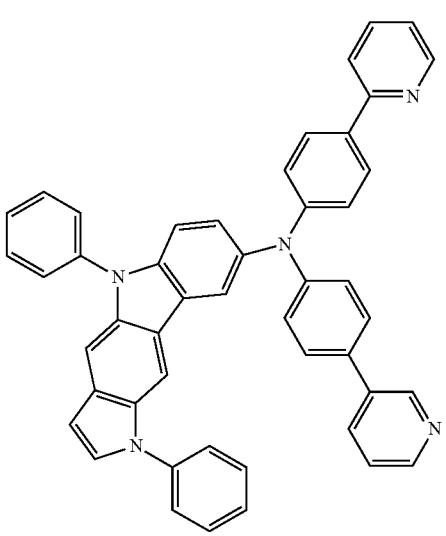
258
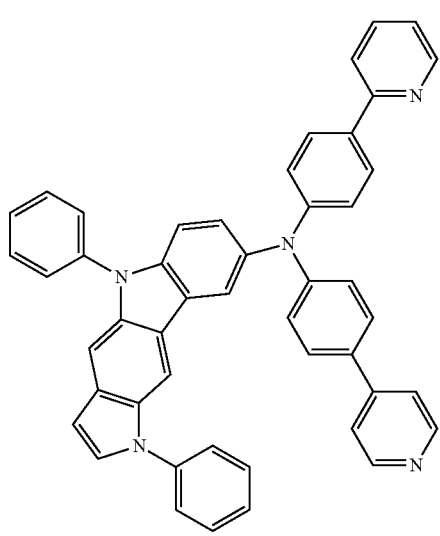
259
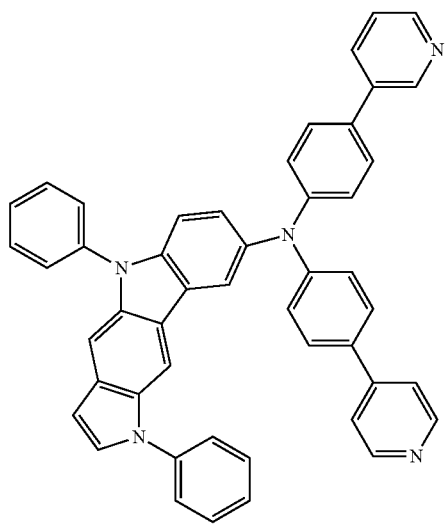
260
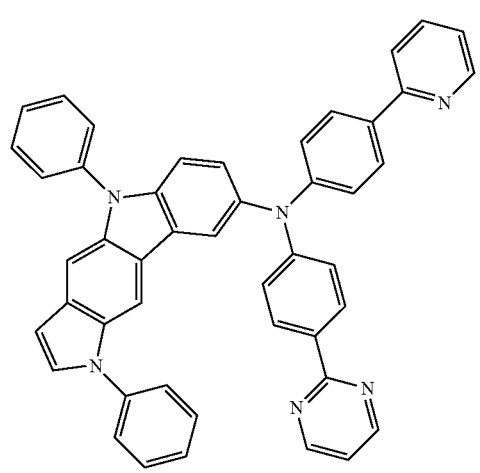
261
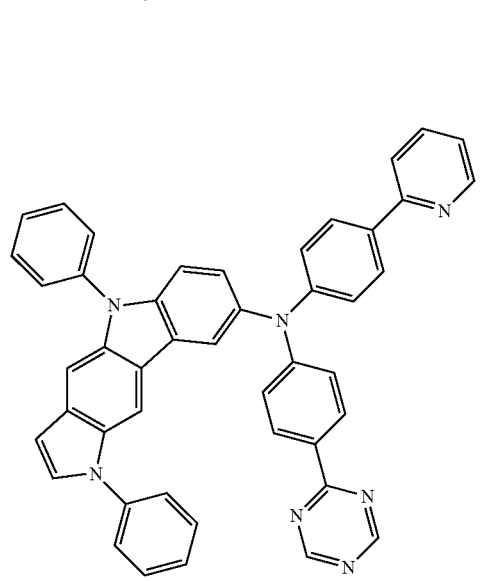
262

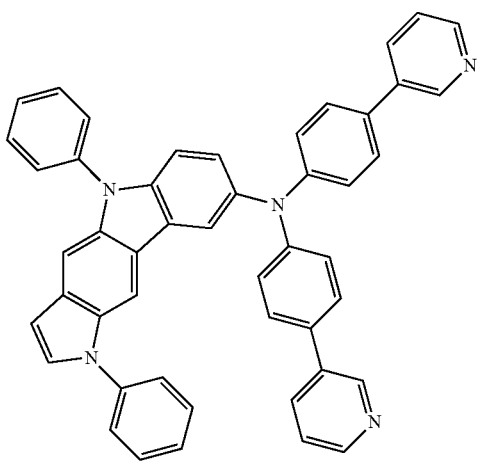
263
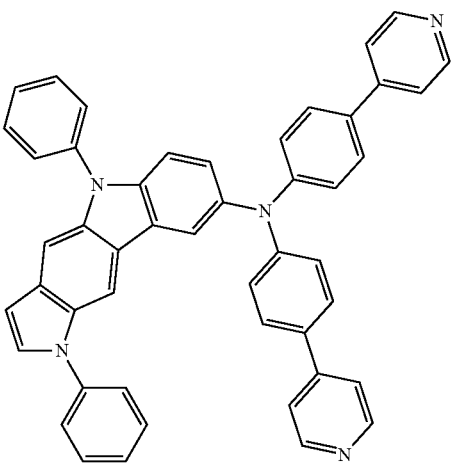
266
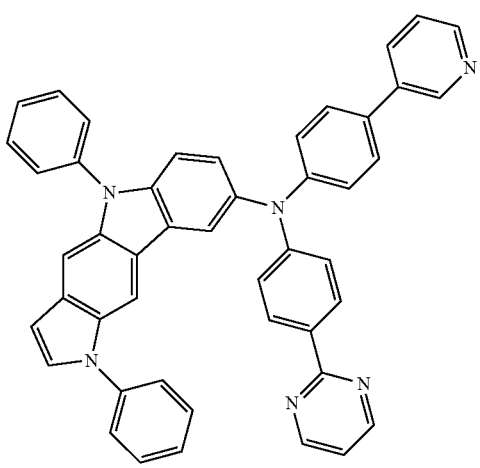
264
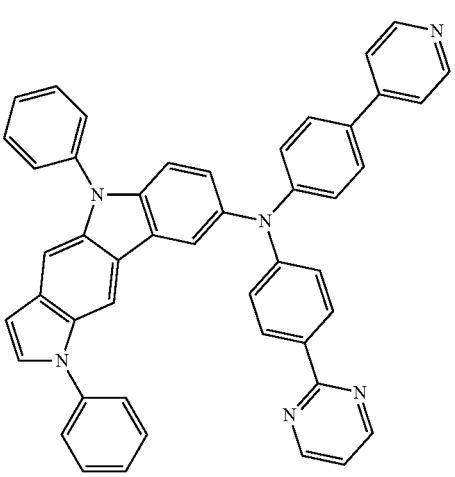
267
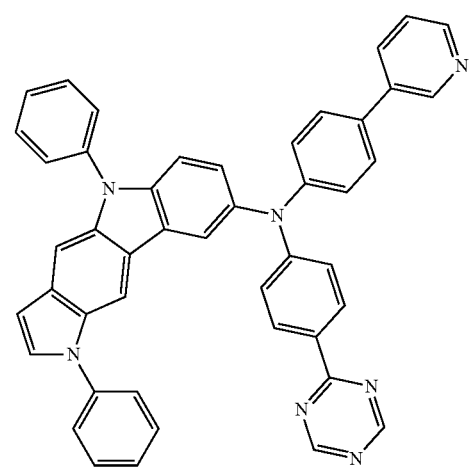
265

269
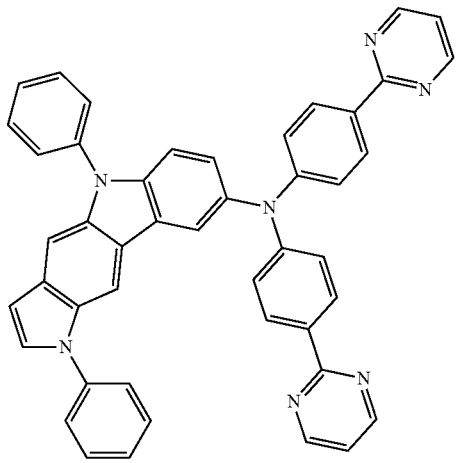
270
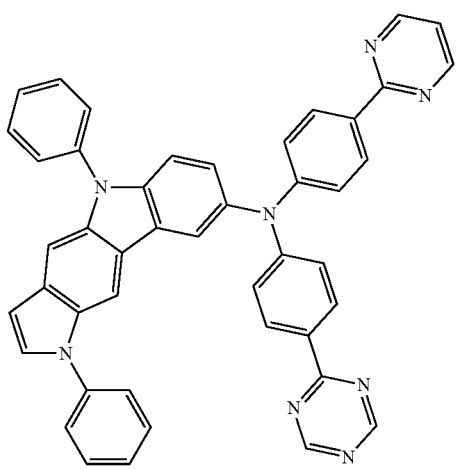
271
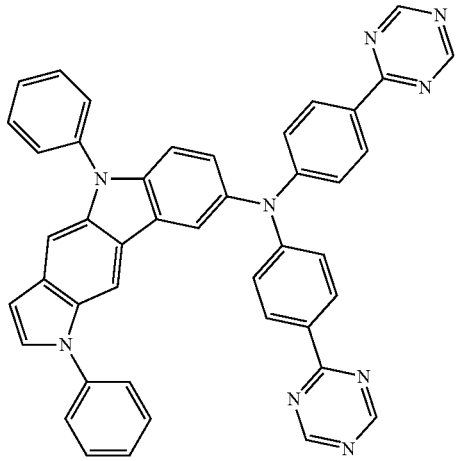
272
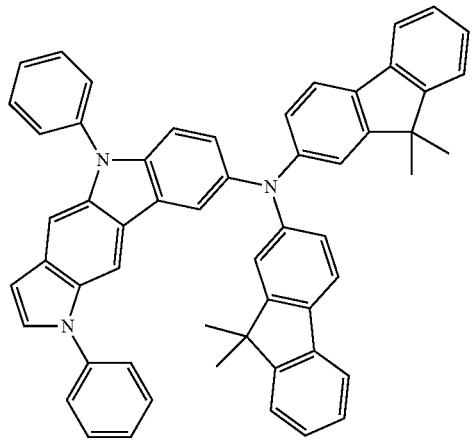
273
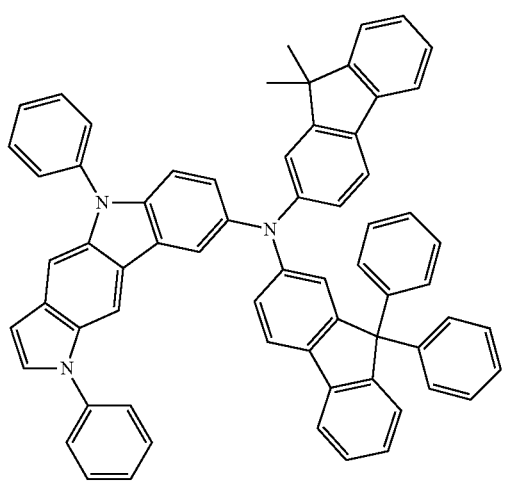
274
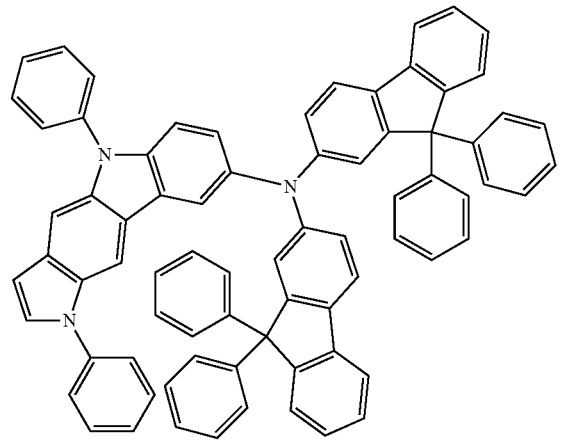

275
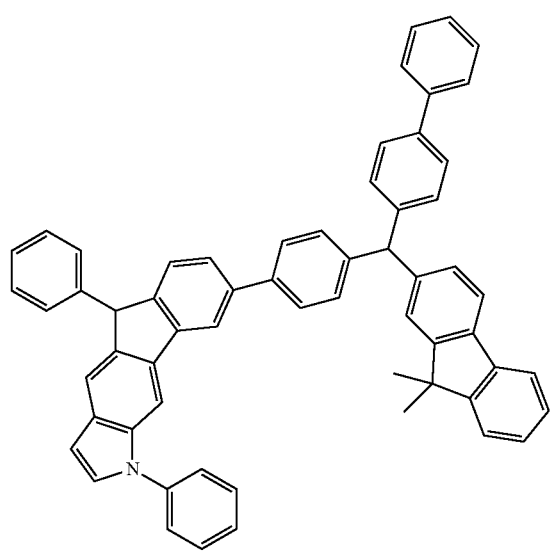
276
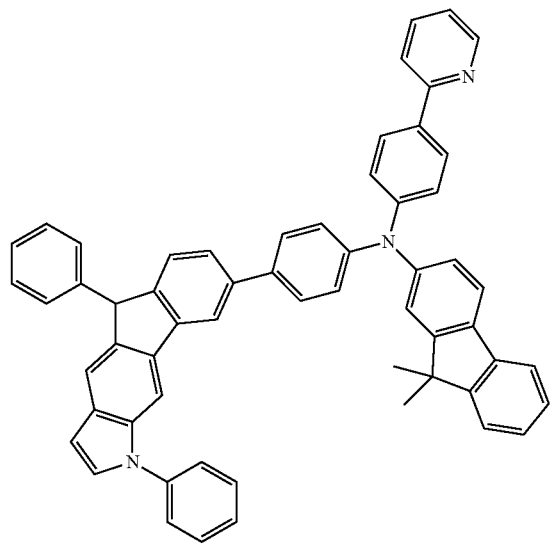
277
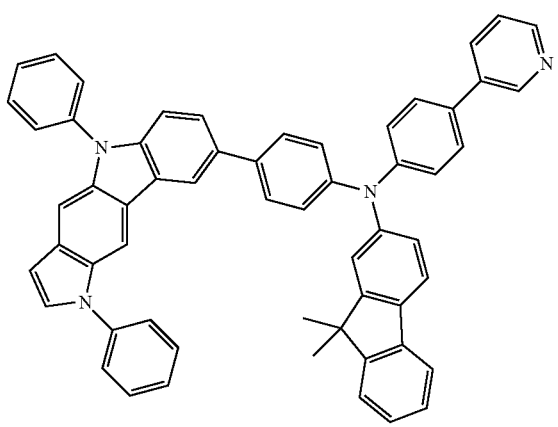
278
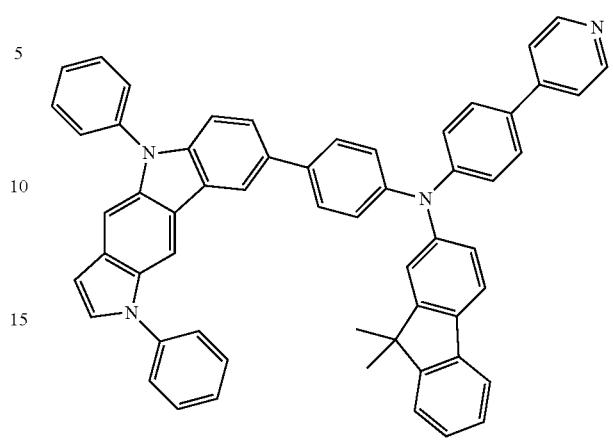
279
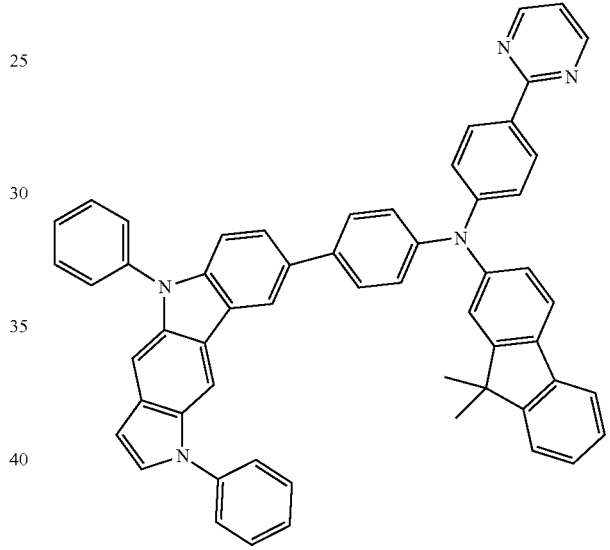
280
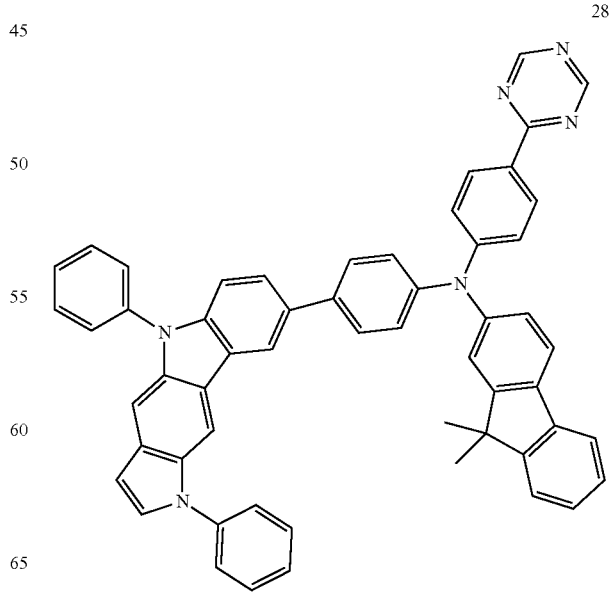

281
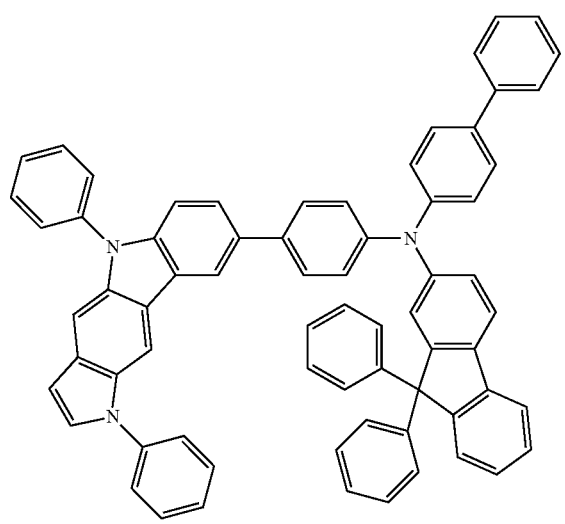
282
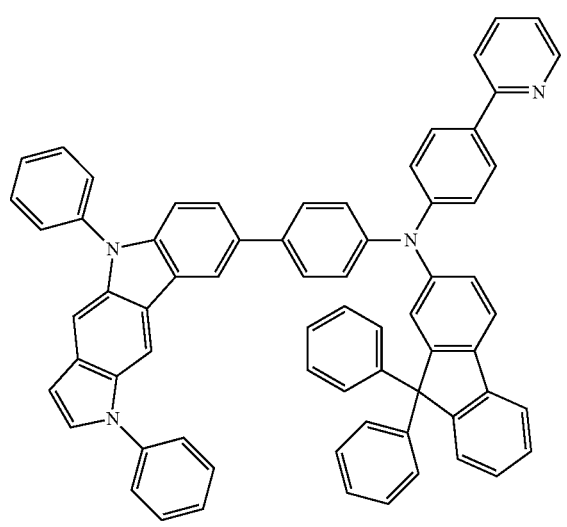
283
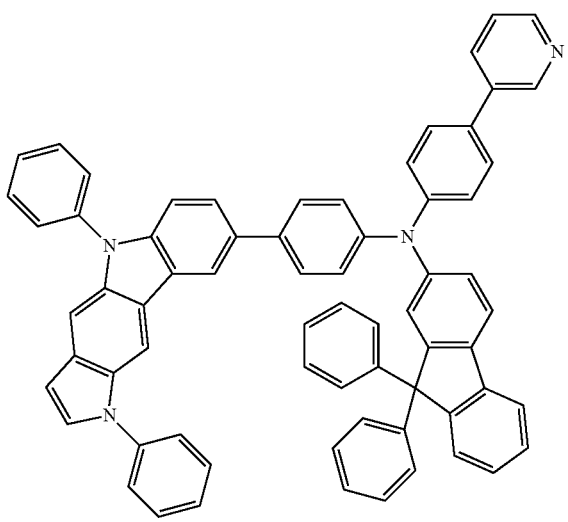
284
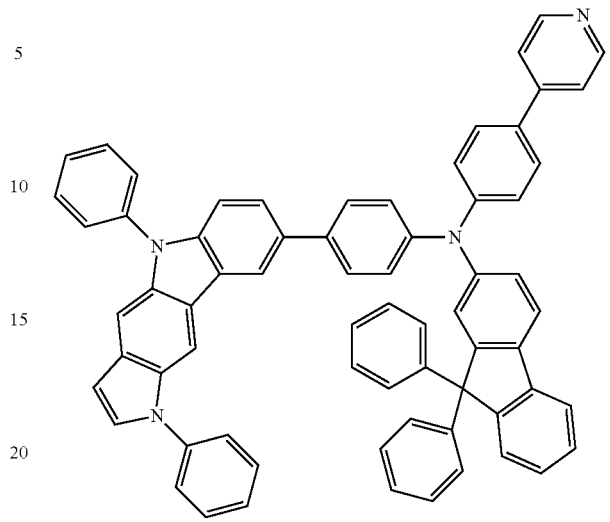
285
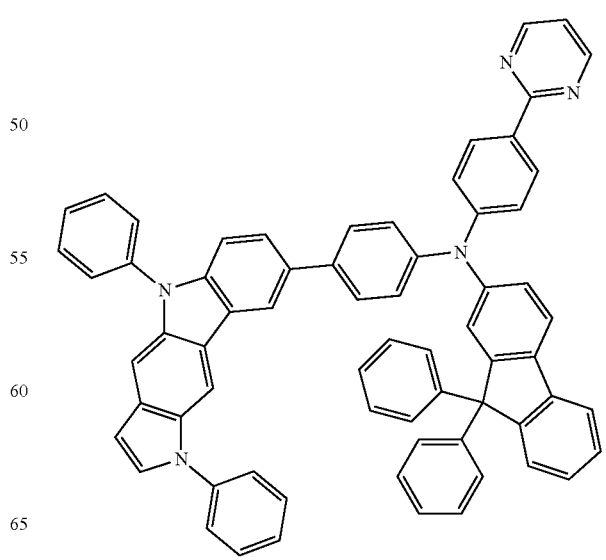

286
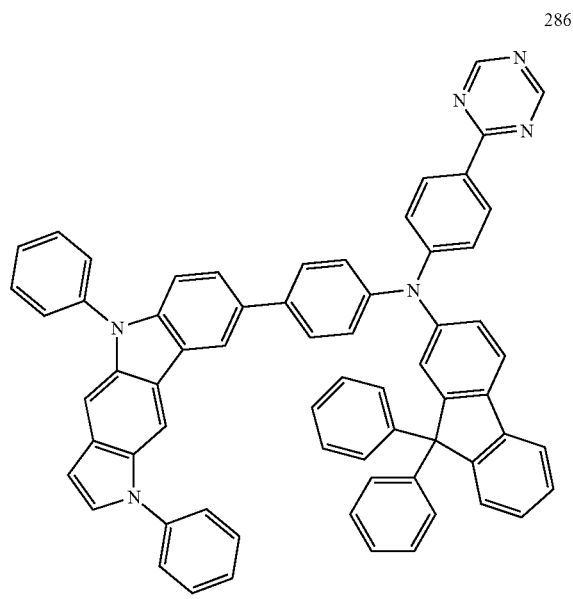
287
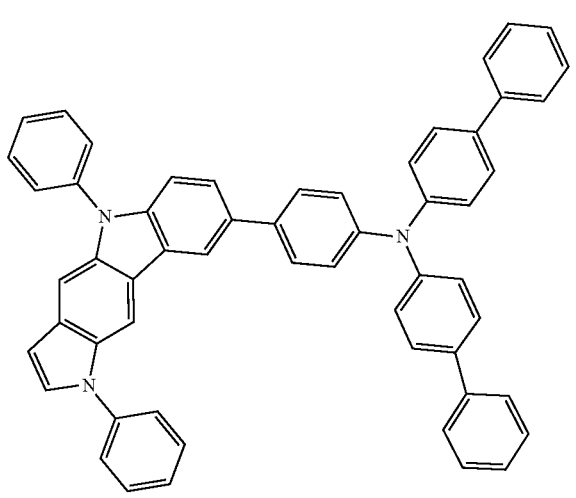
288
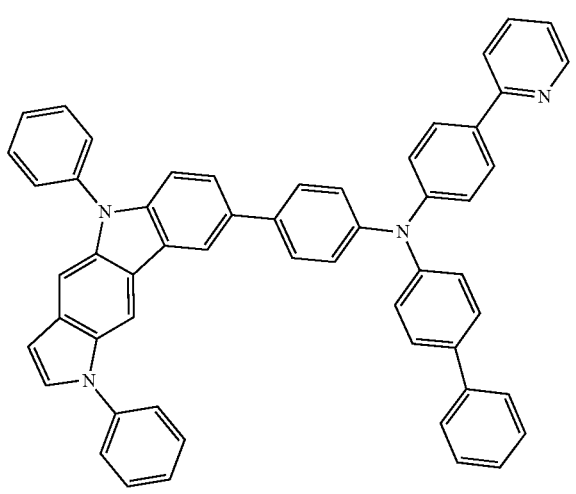
289
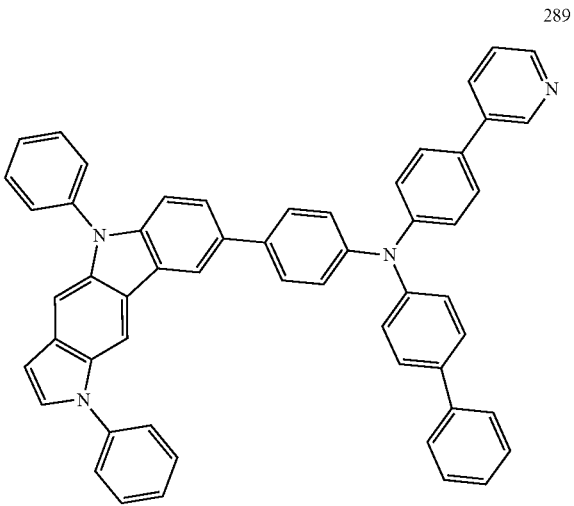
290
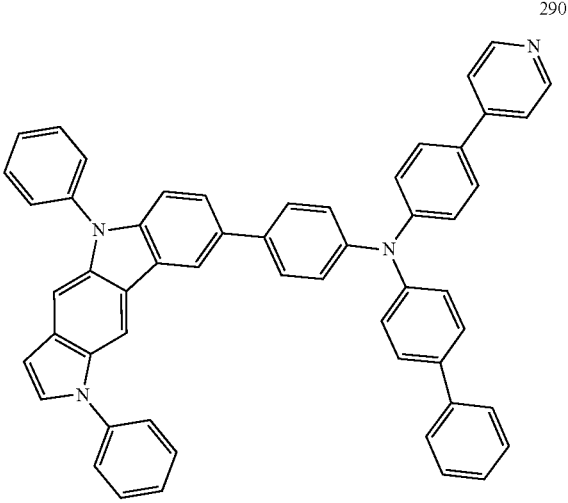
291
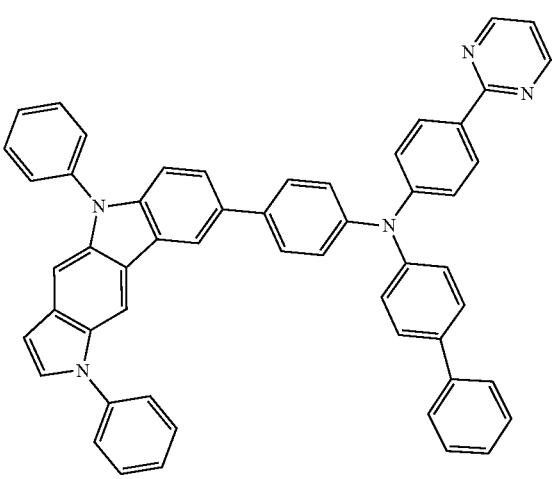

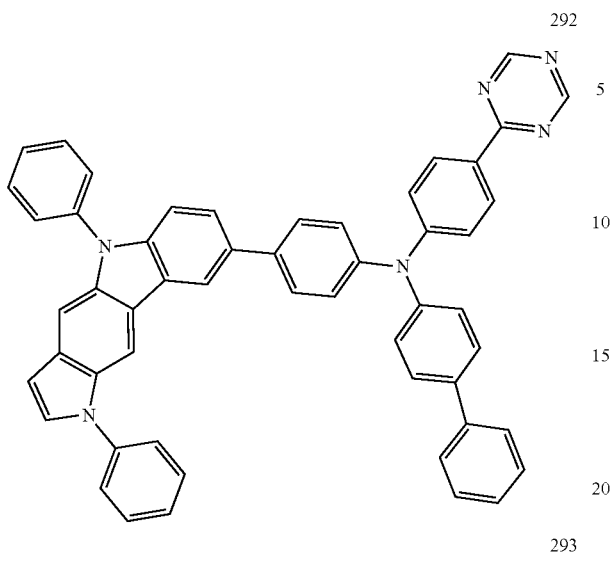
292
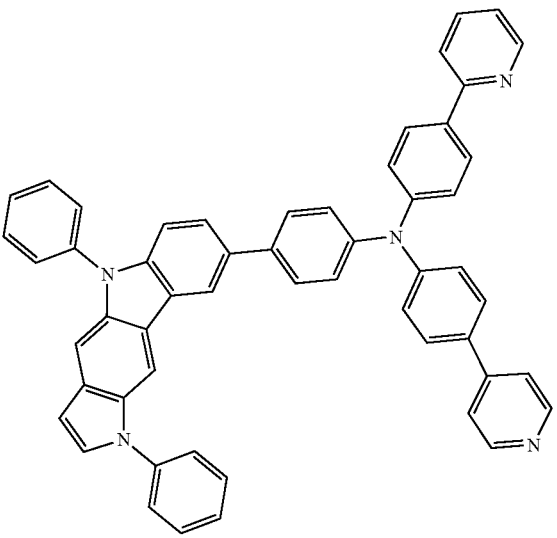
295
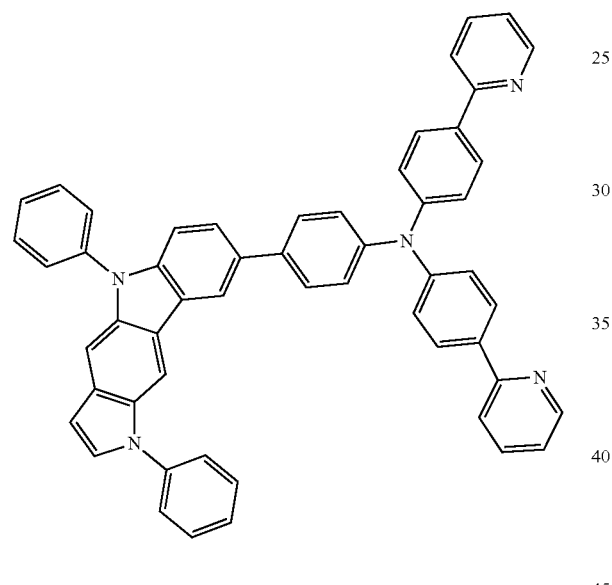
293
296
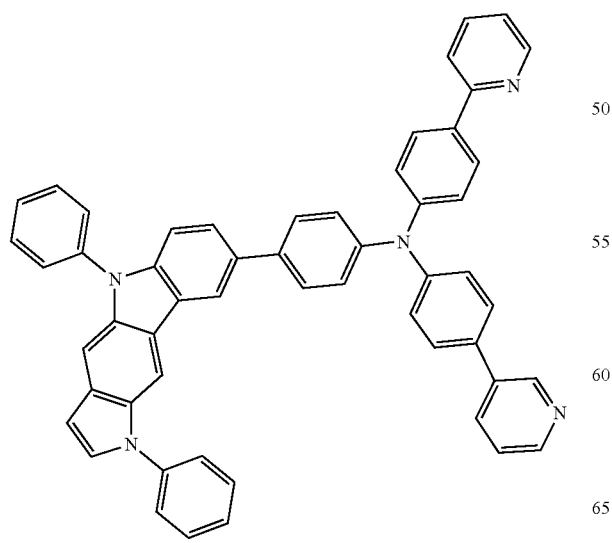
294
297

298
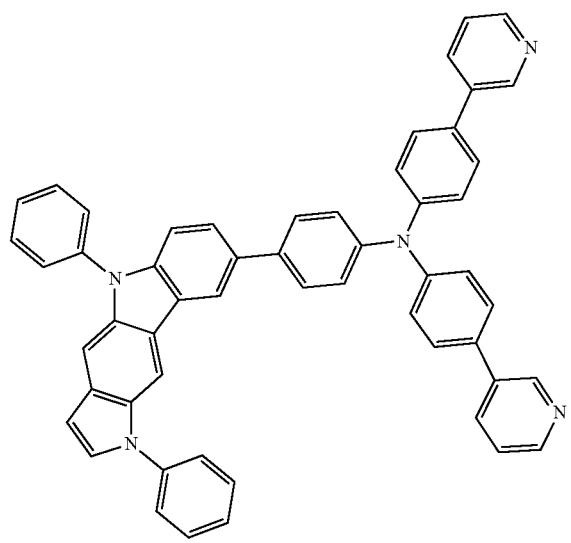
299
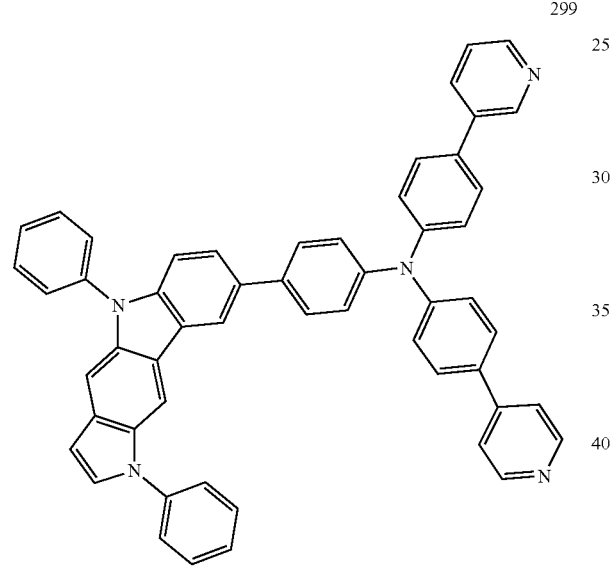
300
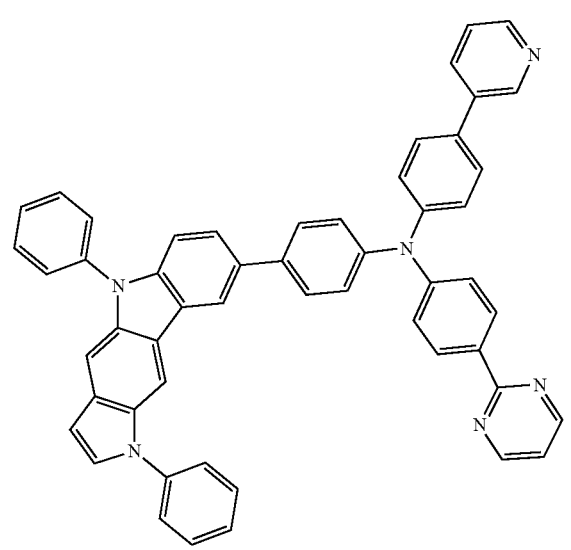
301
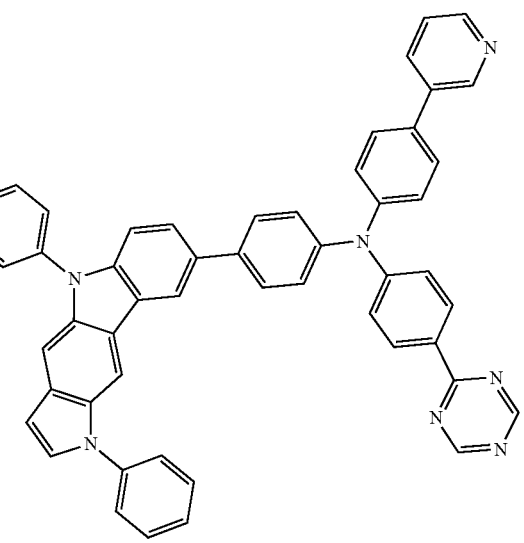
302
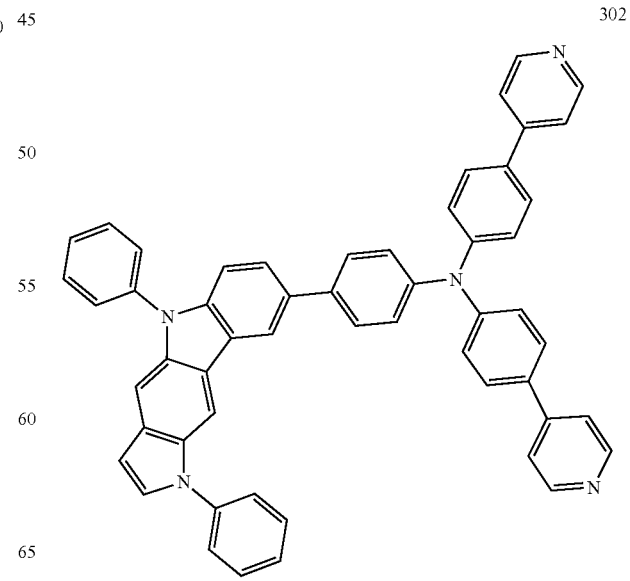

167
-continued
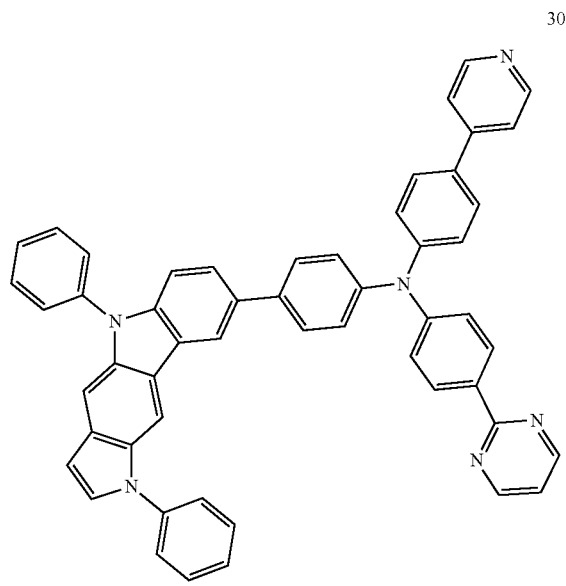
303
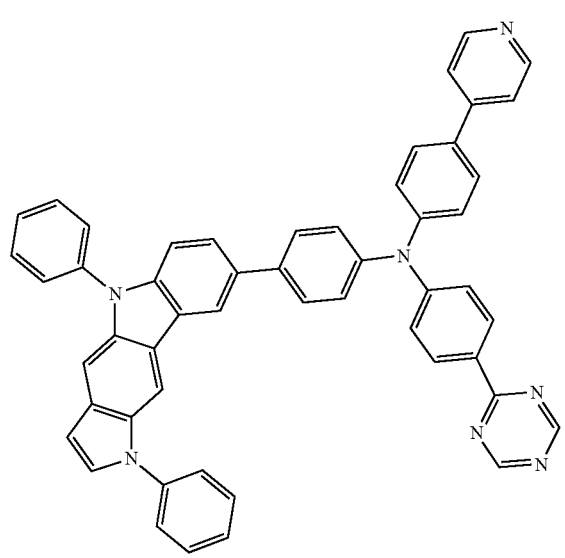
304
168
-continued
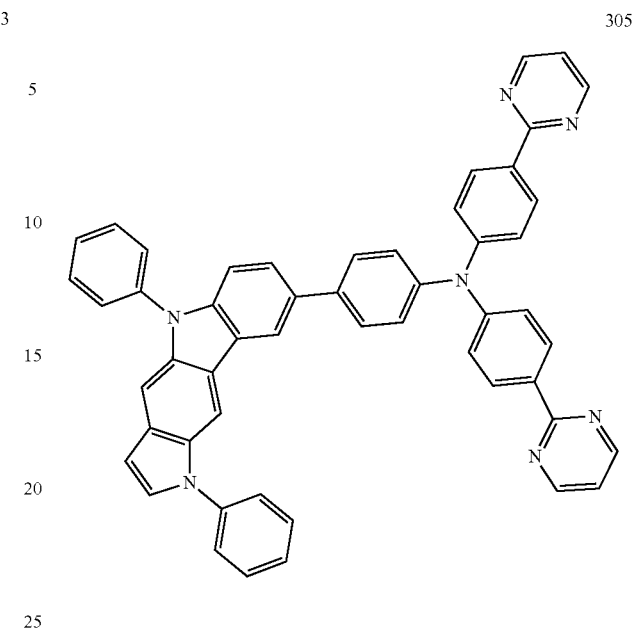
305
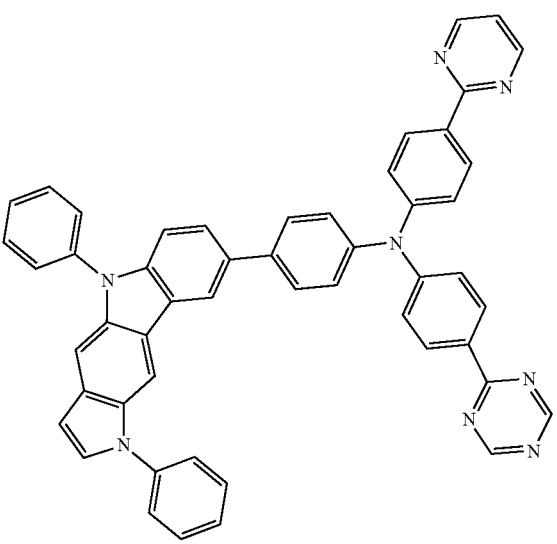
306

307
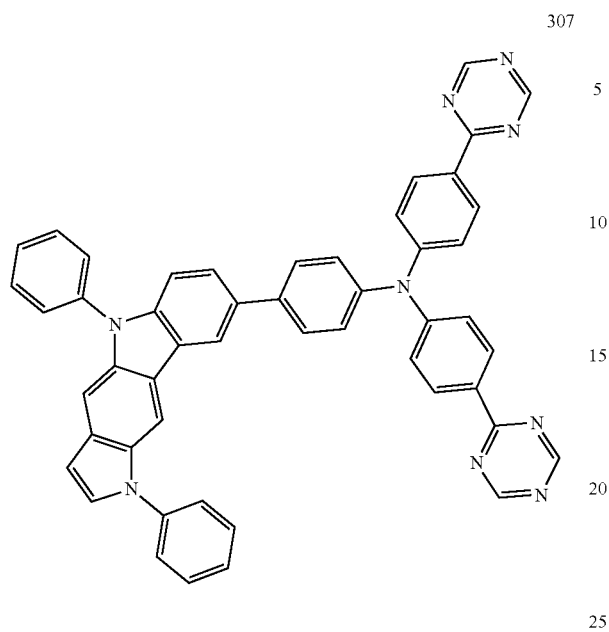
309
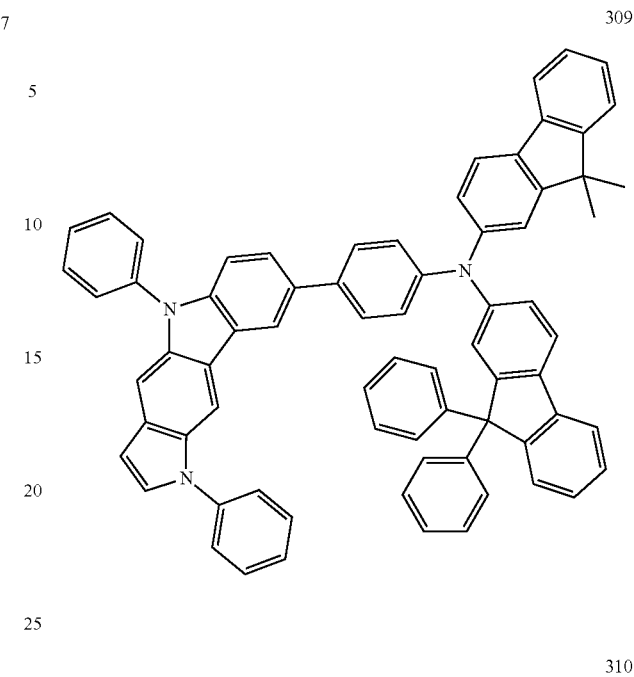
308
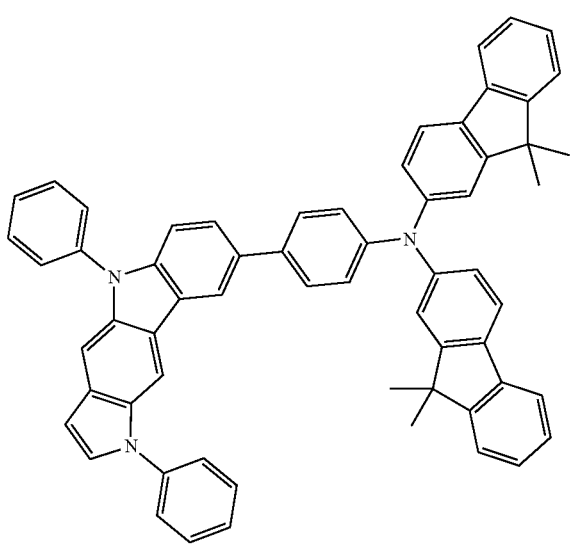
310
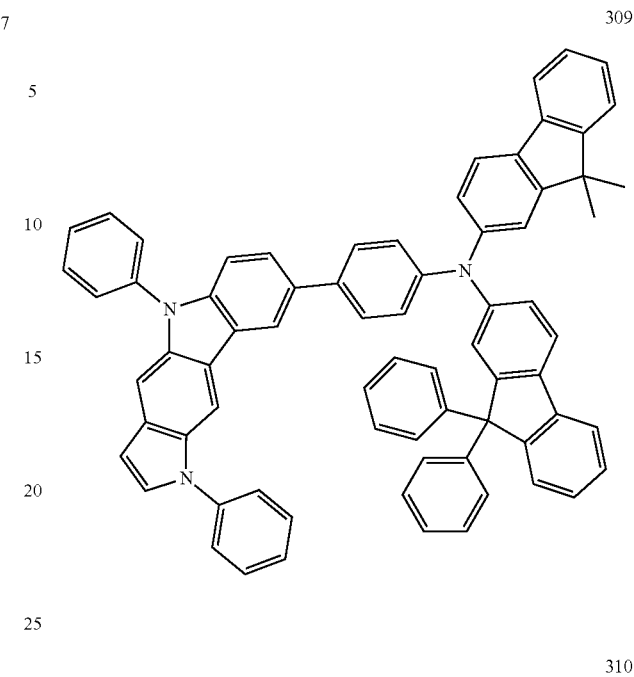
311
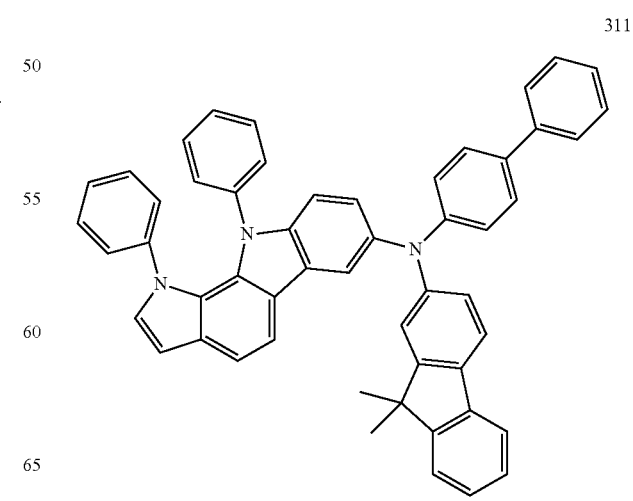

-continued
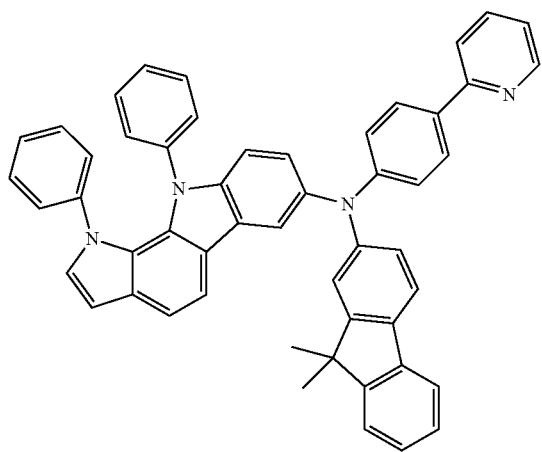
312
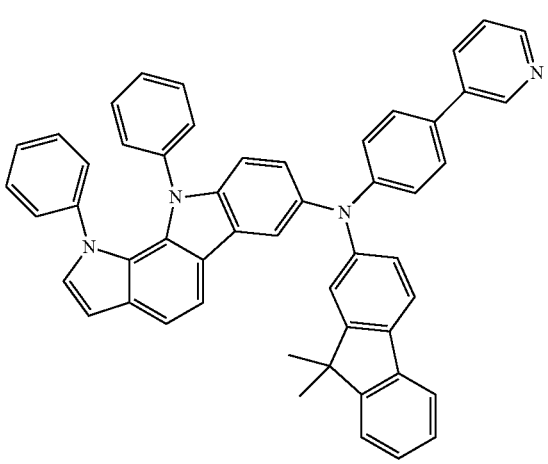
313
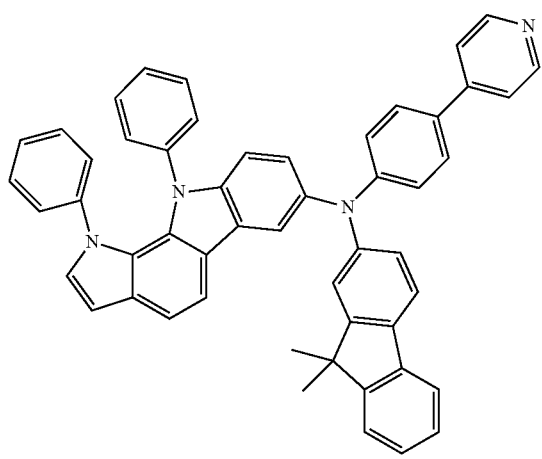
314
-continued
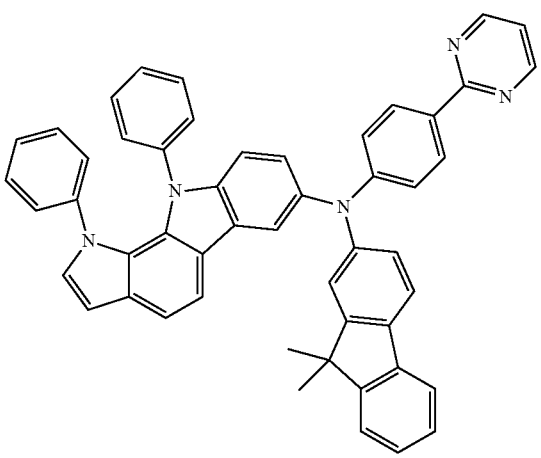
315
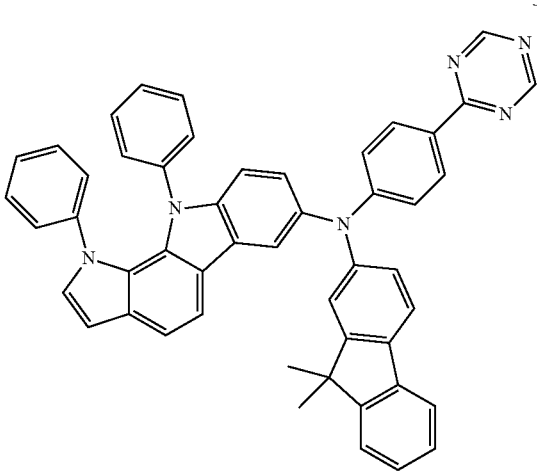
316
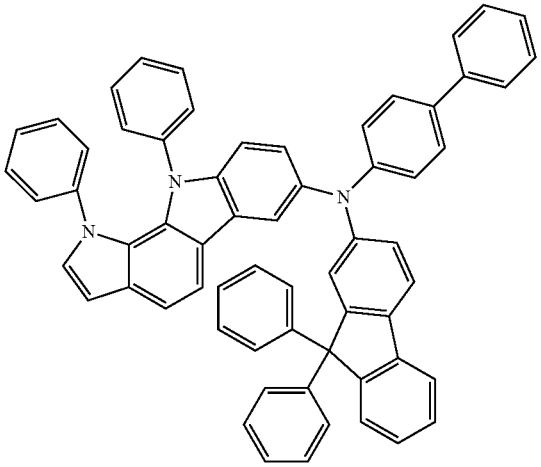
317

318
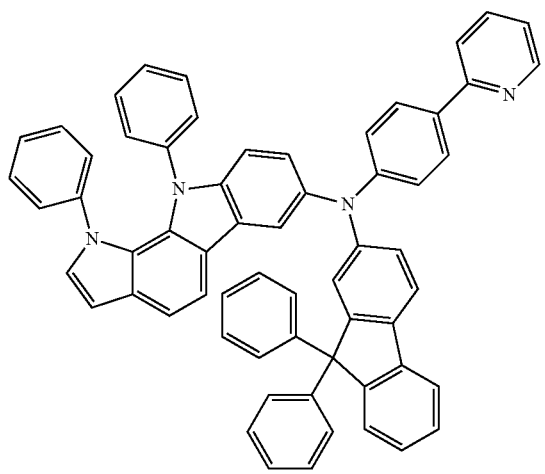
321
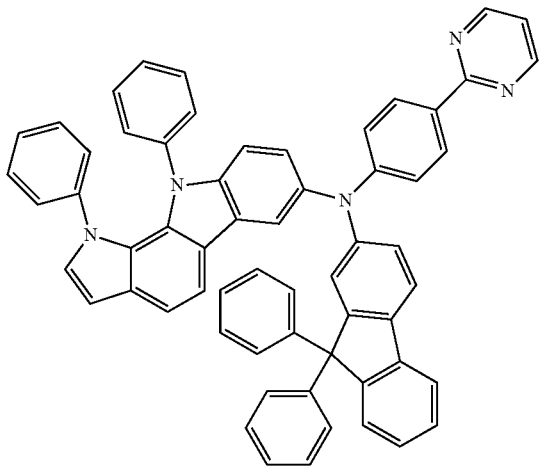
319
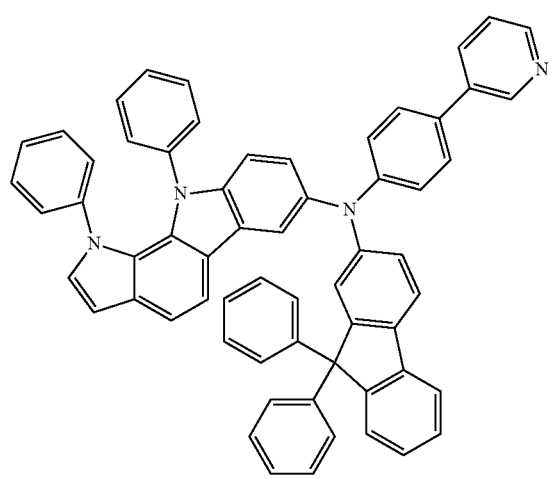
322
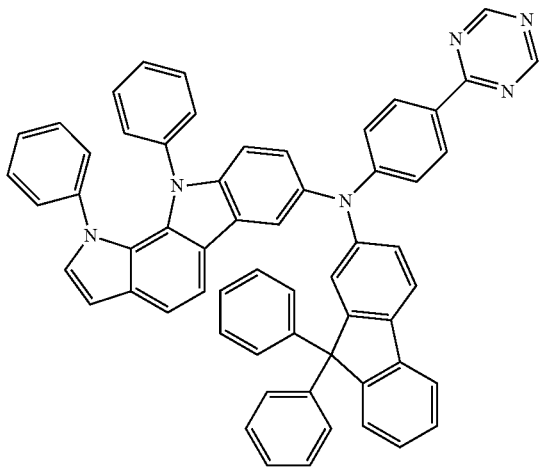
320
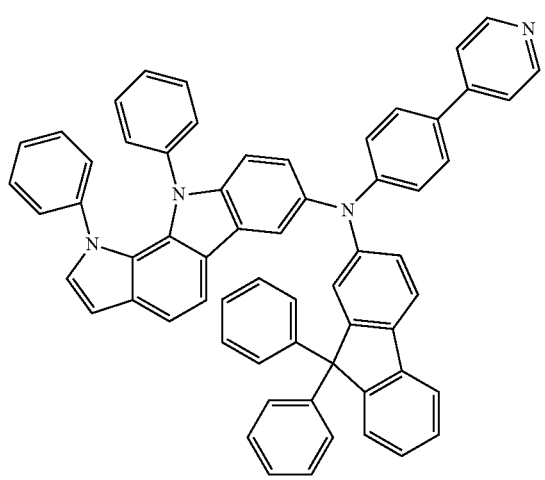
323
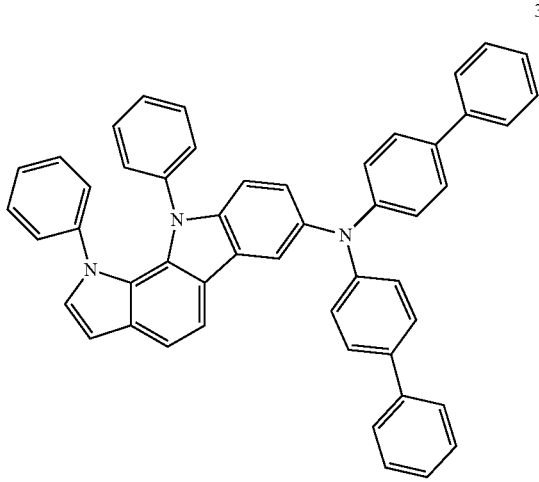

-continued
324
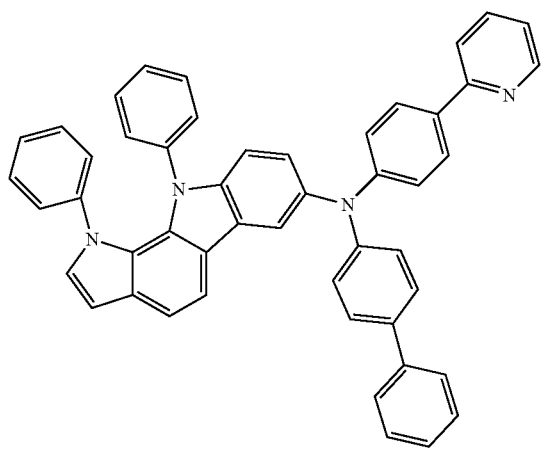
325
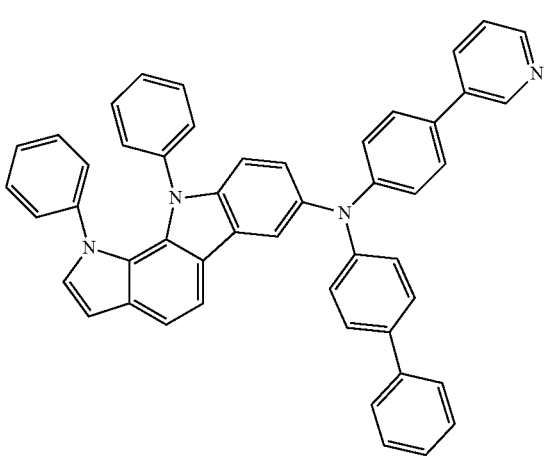
326
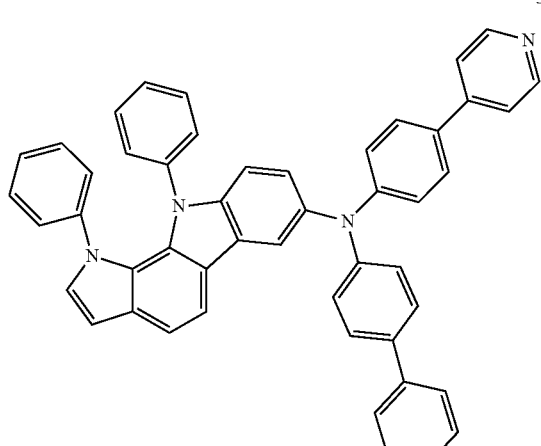
-continued
327
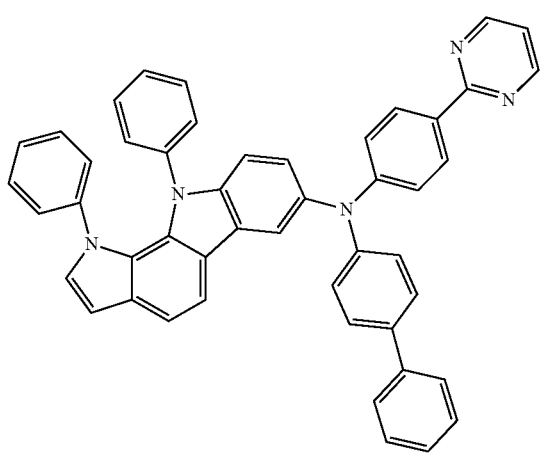
328
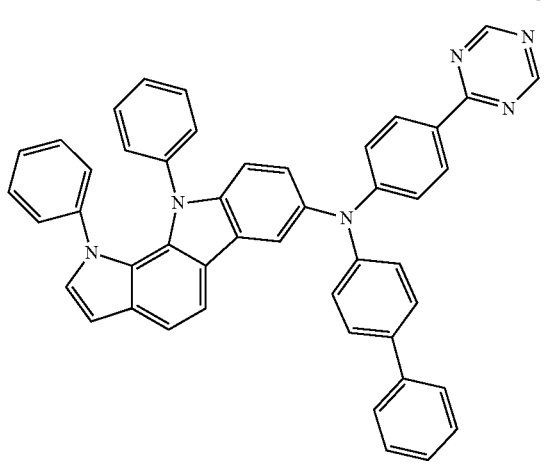
329
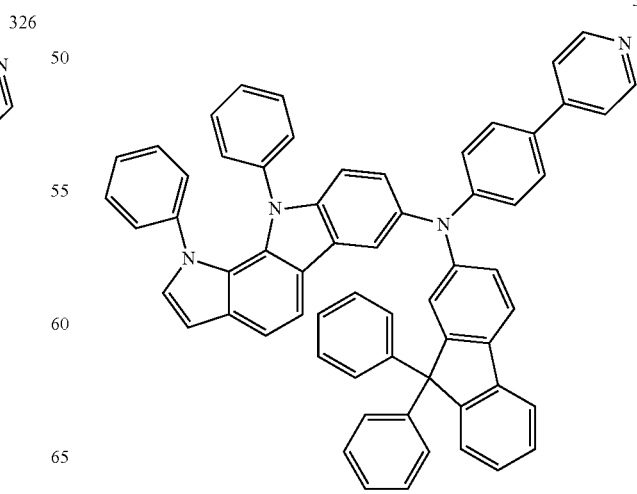

-continued
330
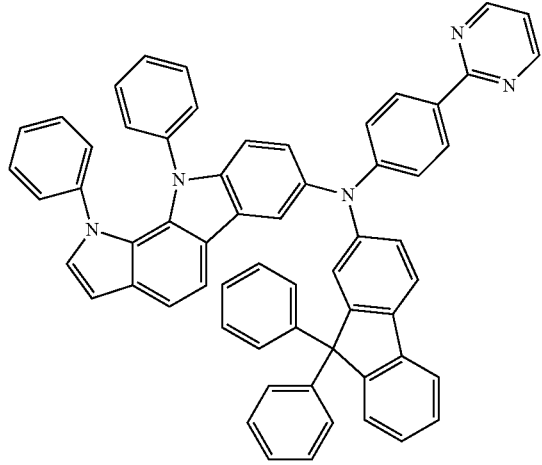
331
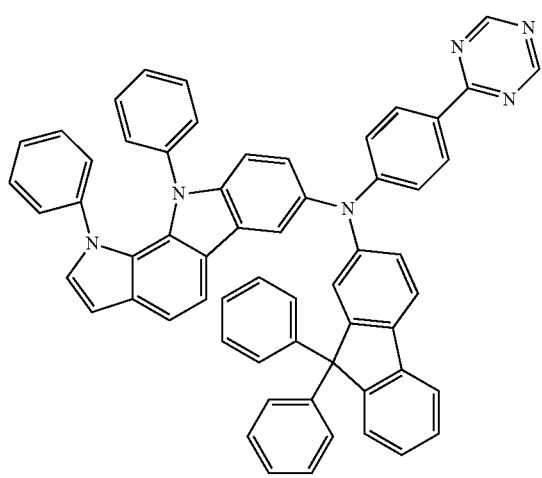
332
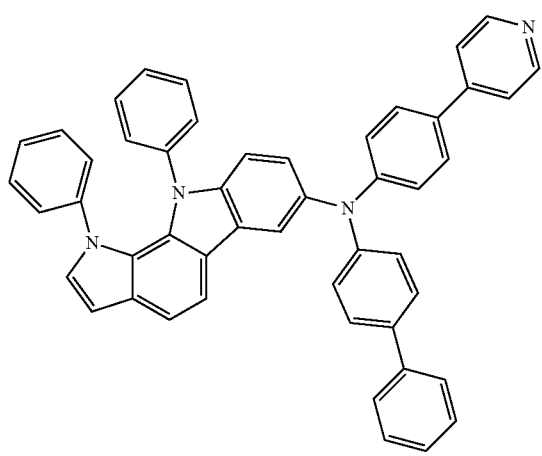
-continued
333
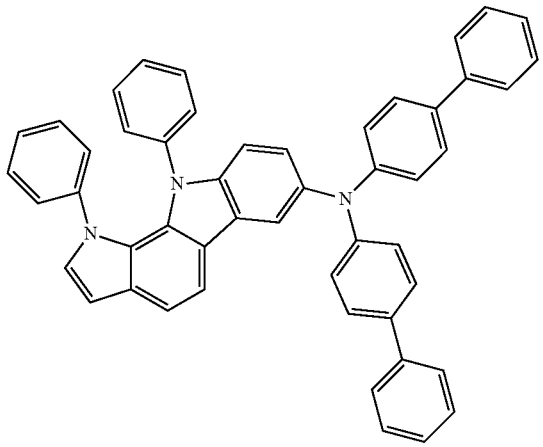
334
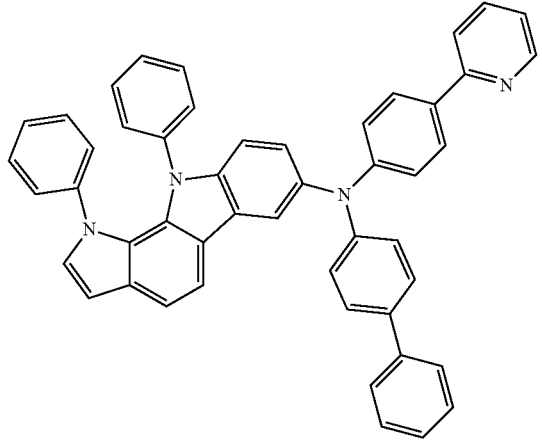
335
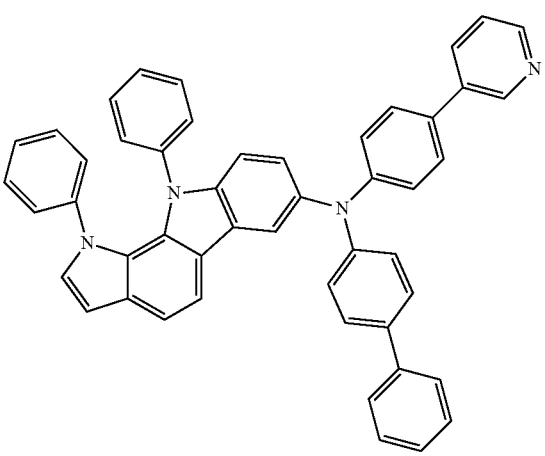

336
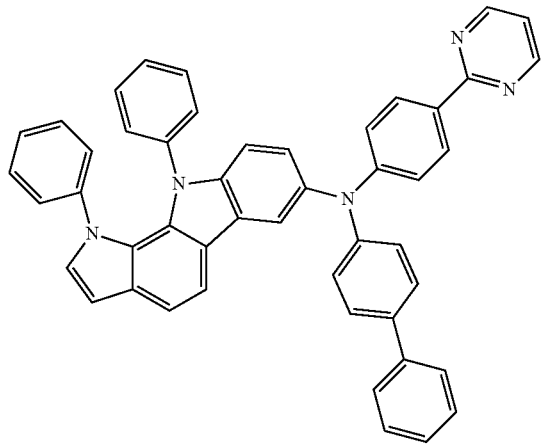
337
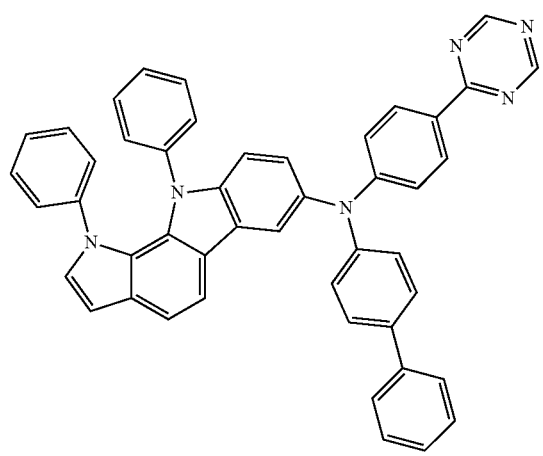
338
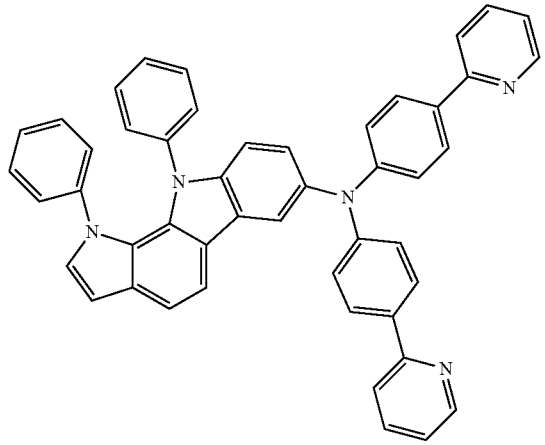
339
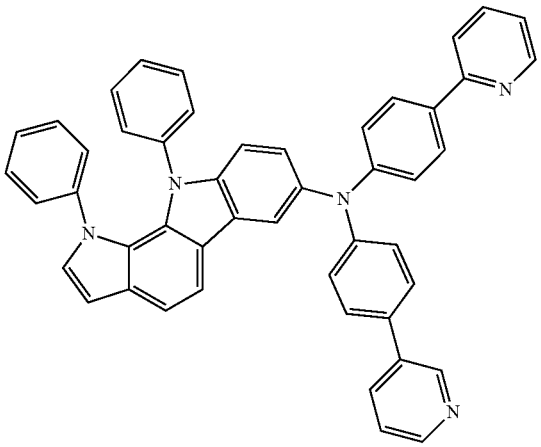
337
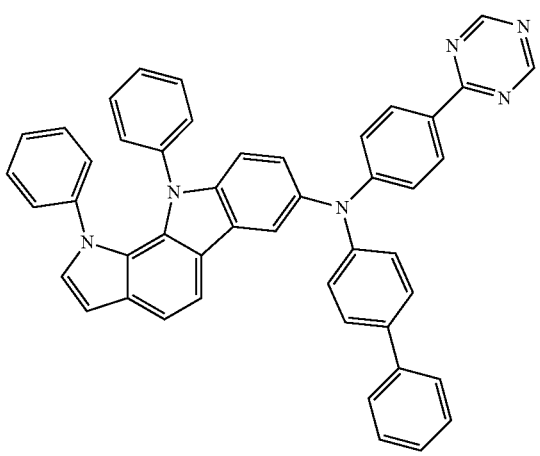
338
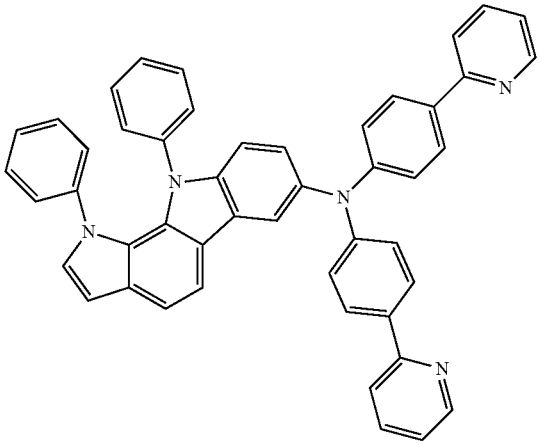

-continued
339
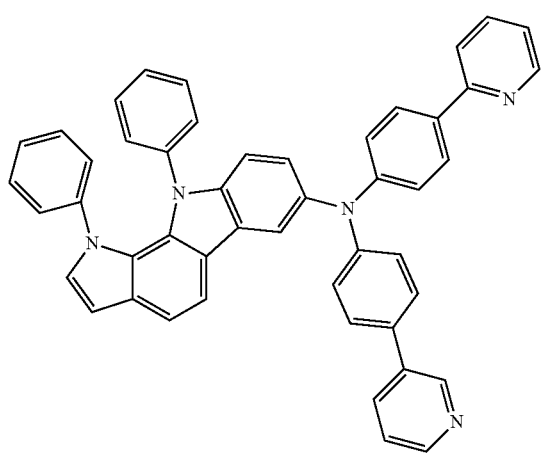
340
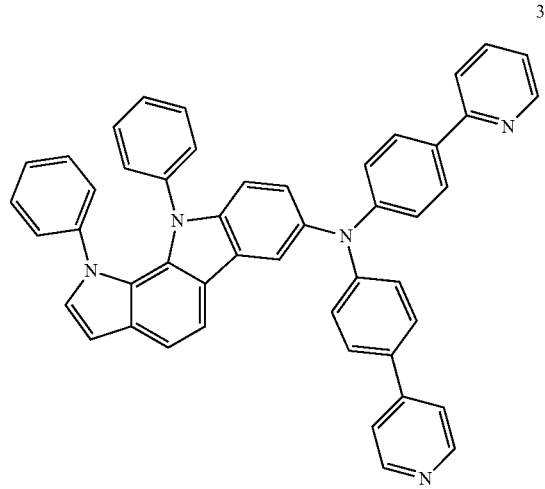
341
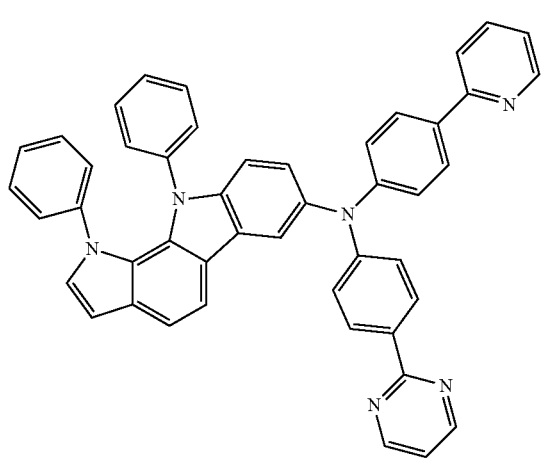
-continued
342
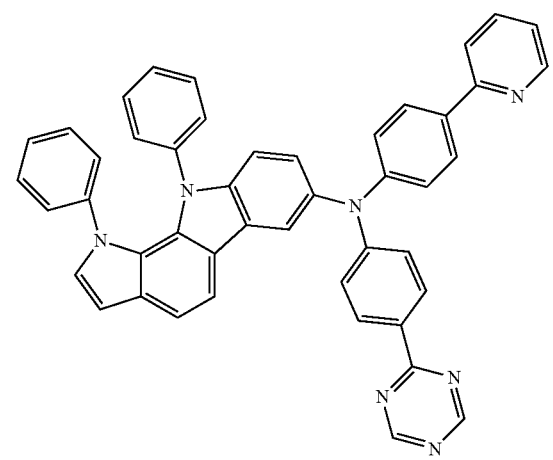
343
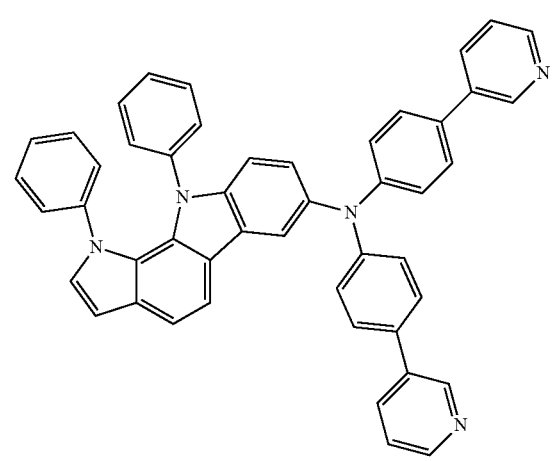
344
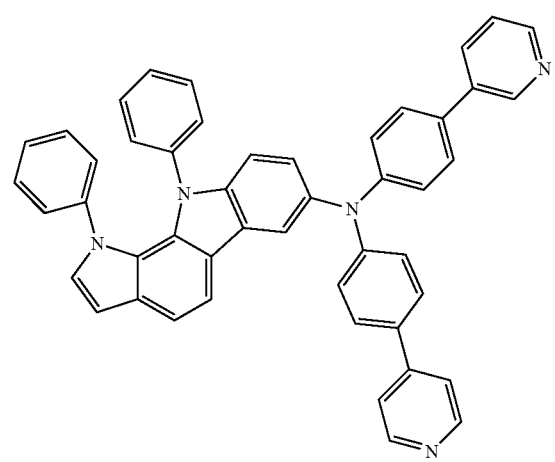

183
-continued
345
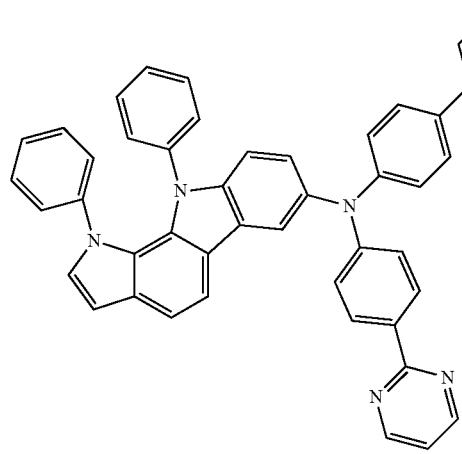
346
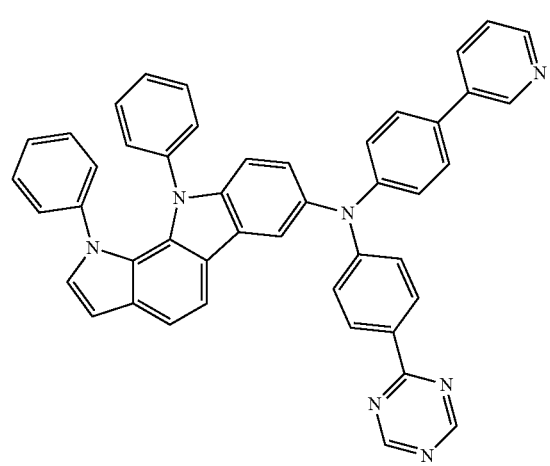
347
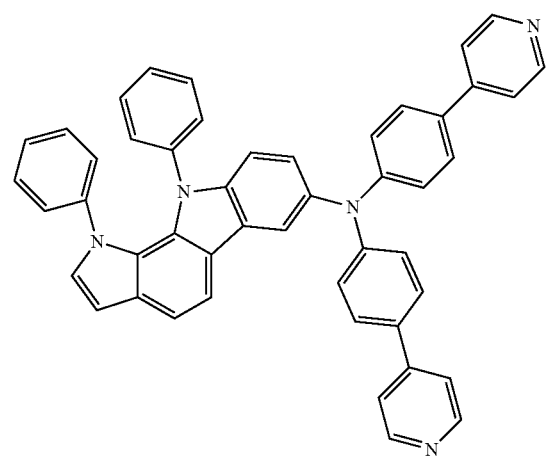
184
-continued
348
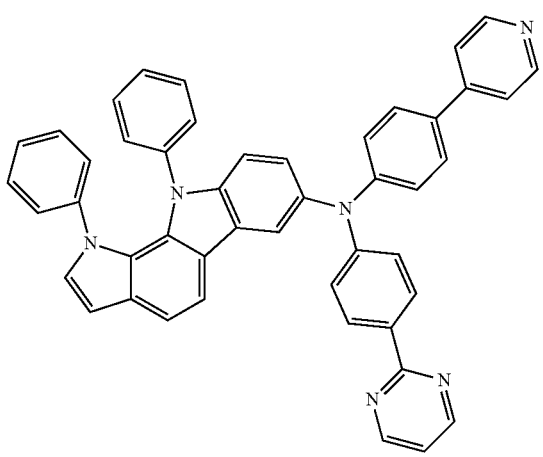
349
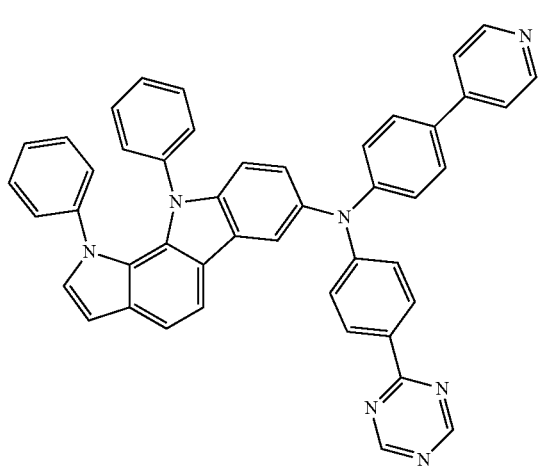
350
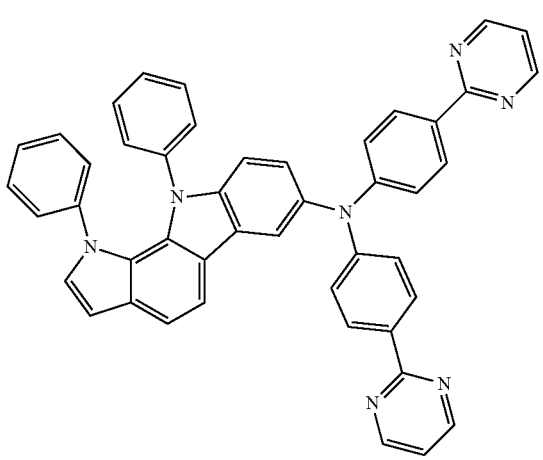

351
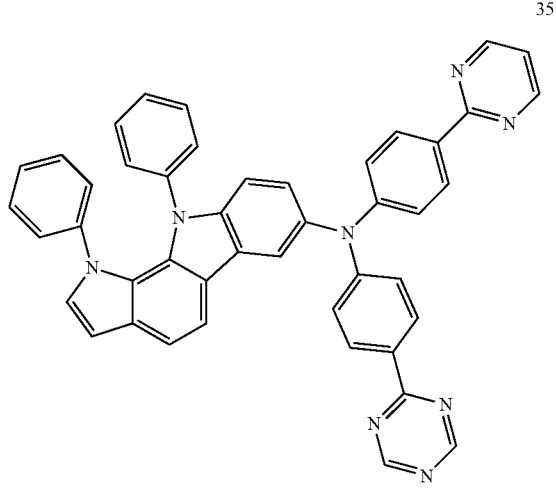
364
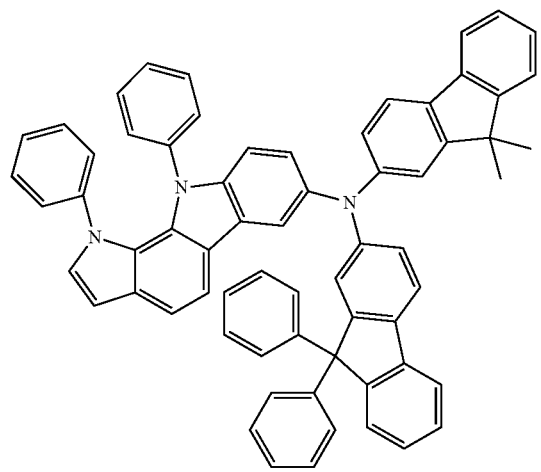
352
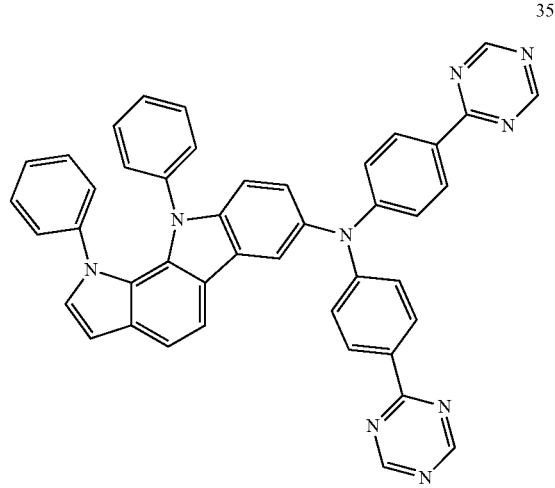
365
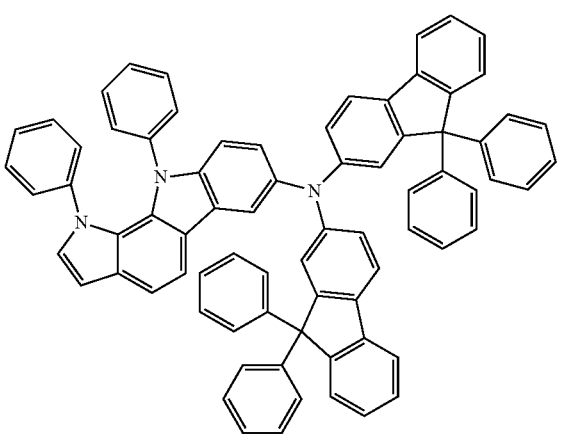
363
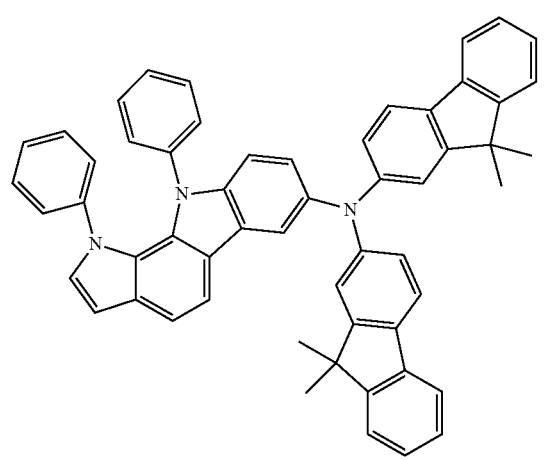
366
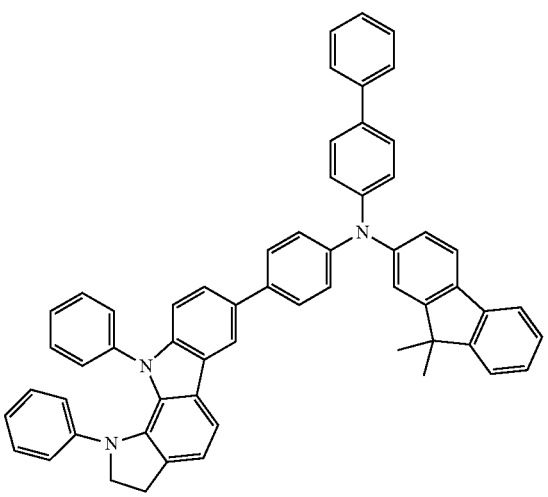

367
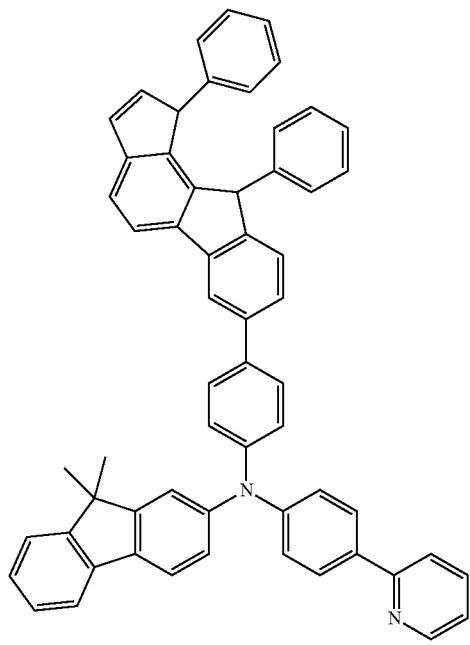
368
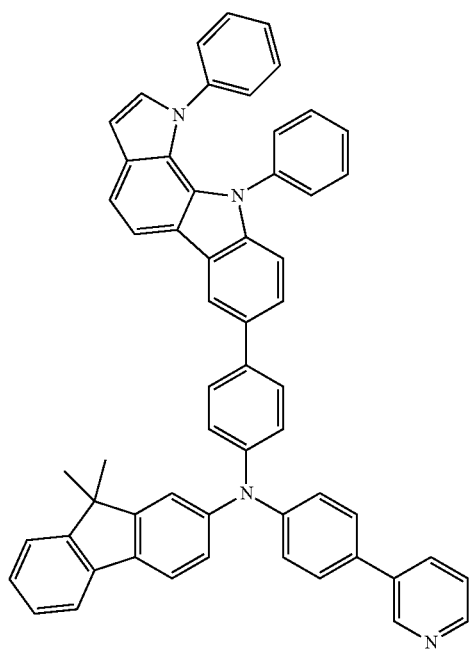
369
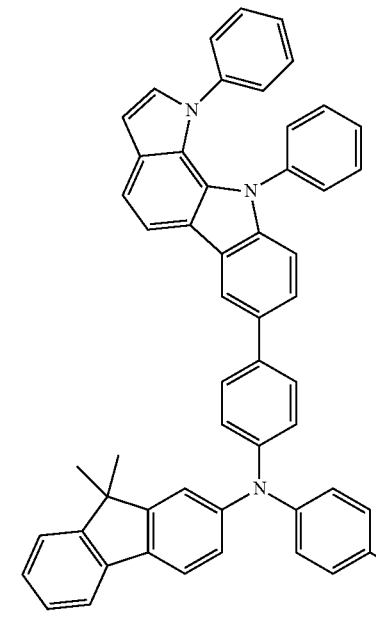
370
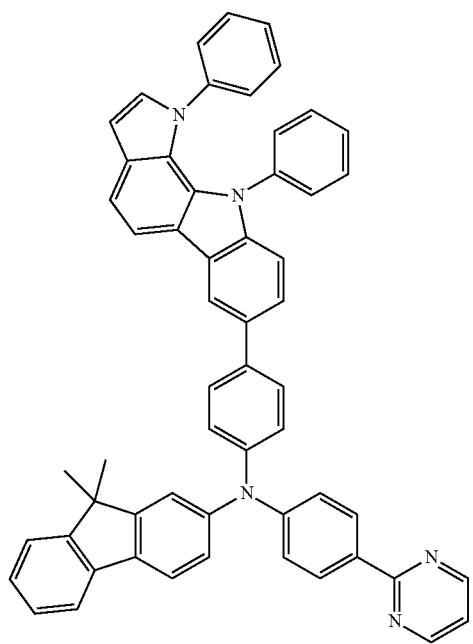

189
-continued
371
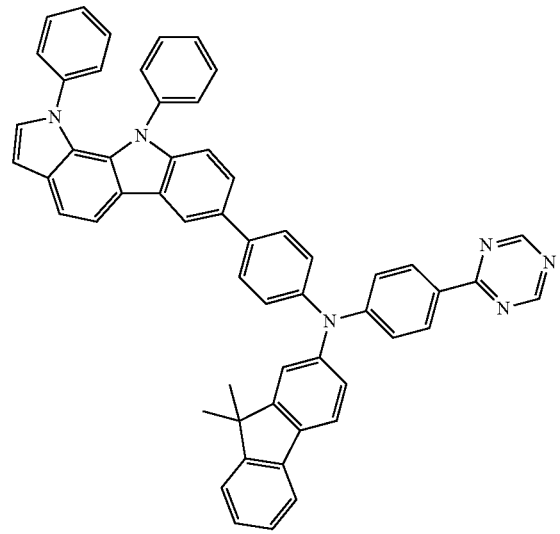
372
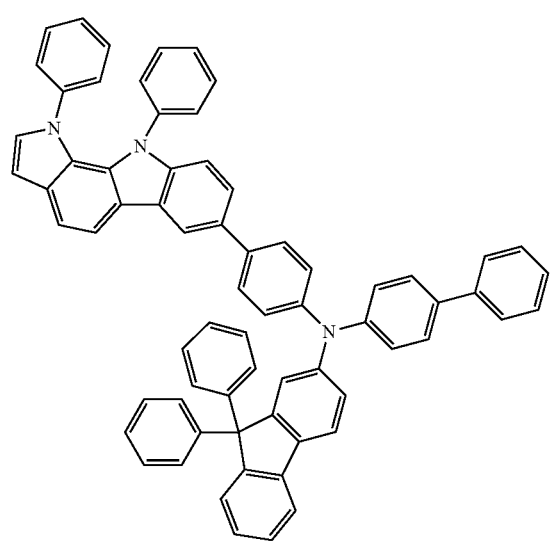
373
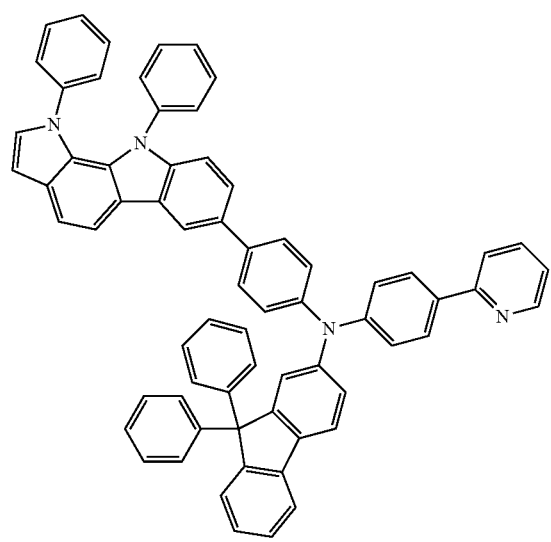
190
-continued
374
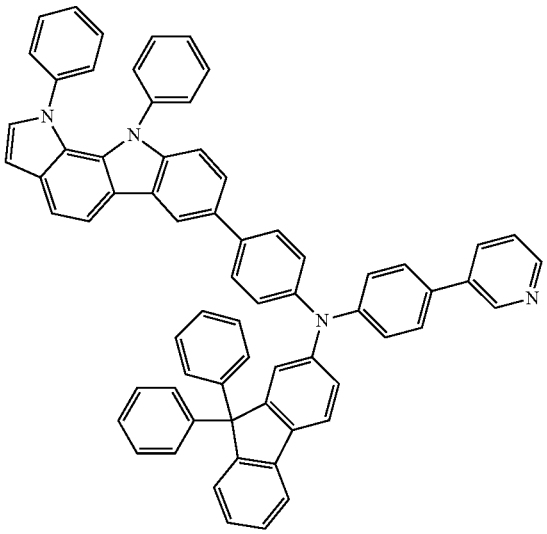
375
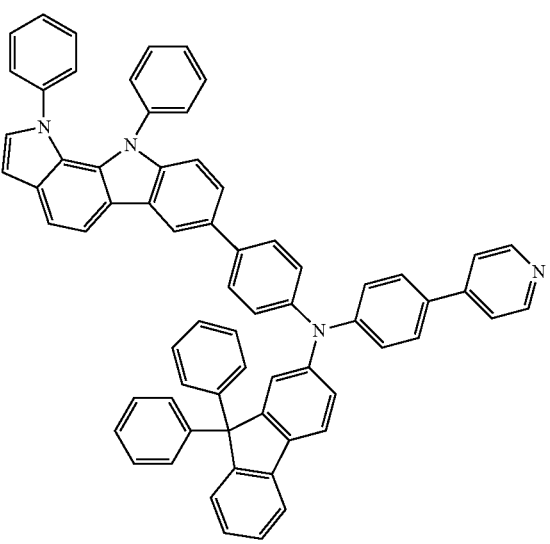
376
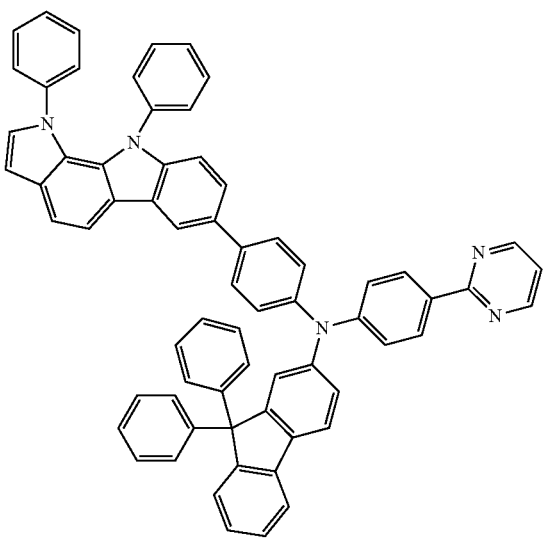

191
-continued
377
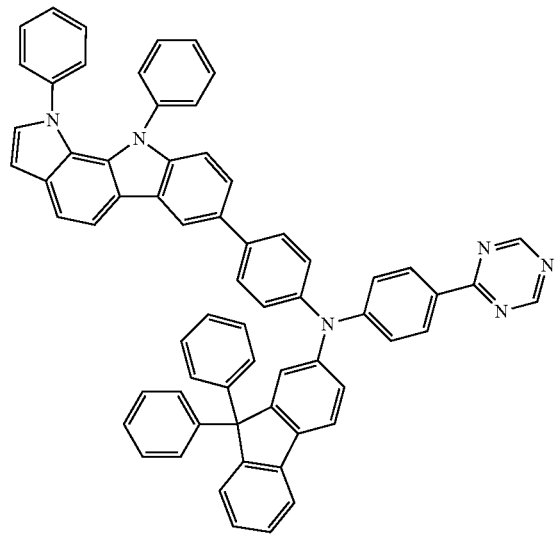
378
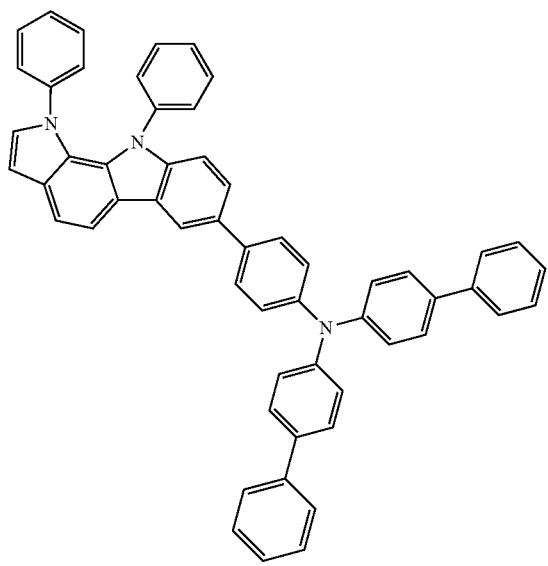
192
-continued
379
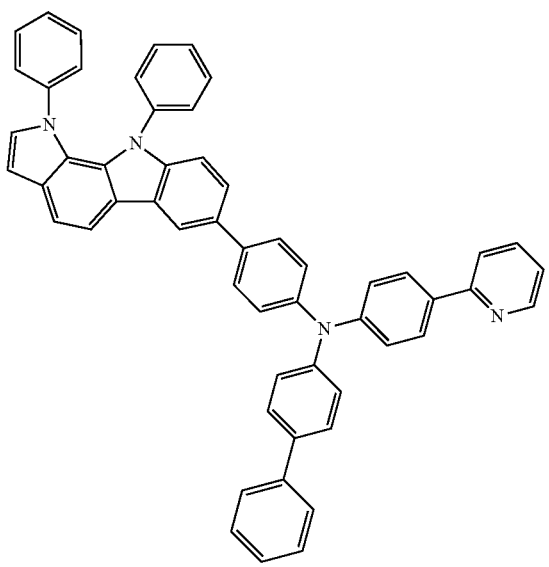
380
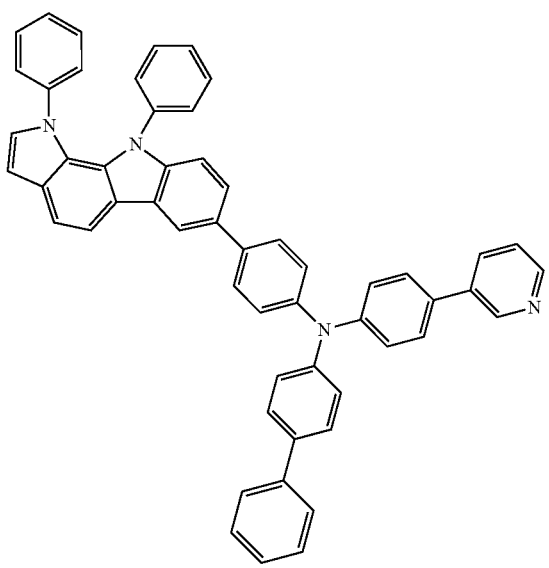

193
-continued
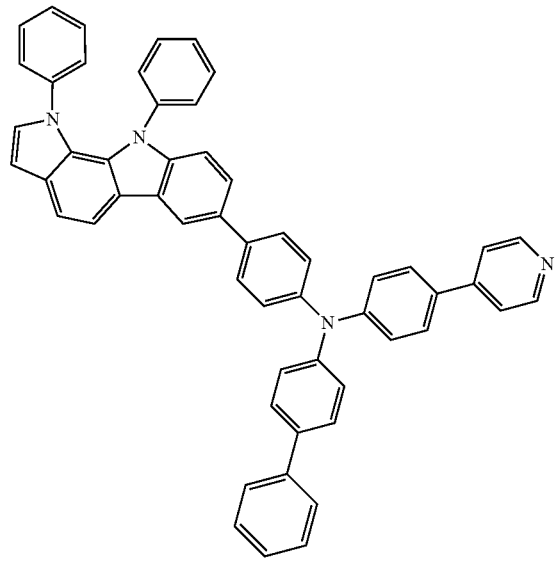
381
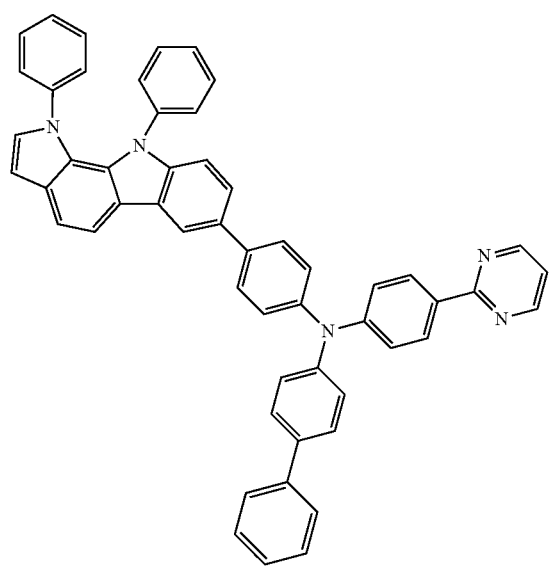
382
194
-continued
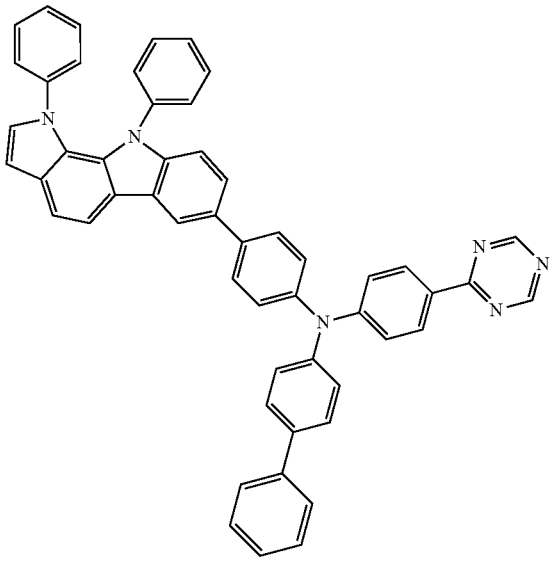
383
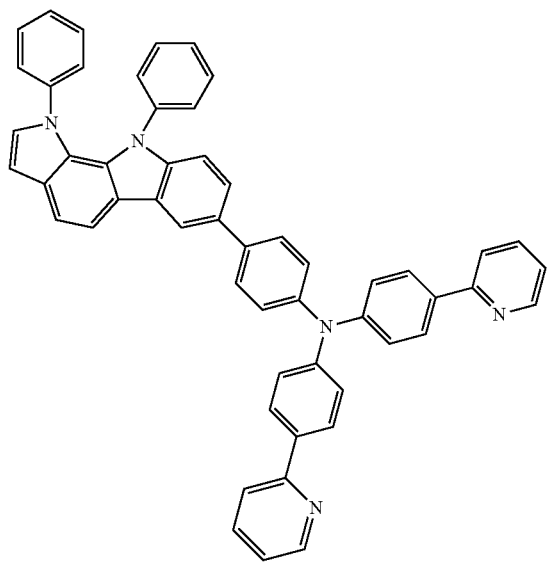
384

385
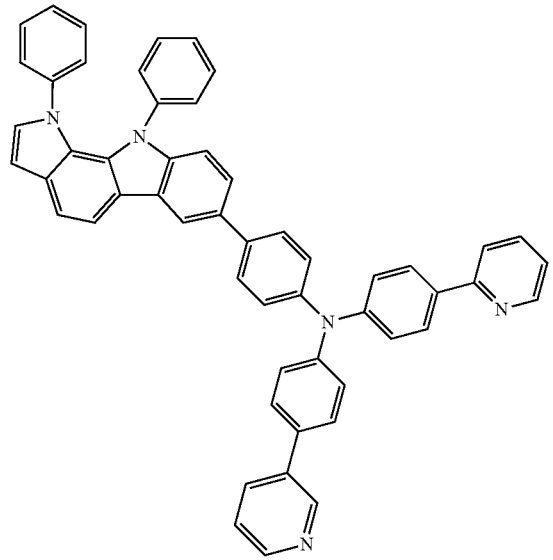
386
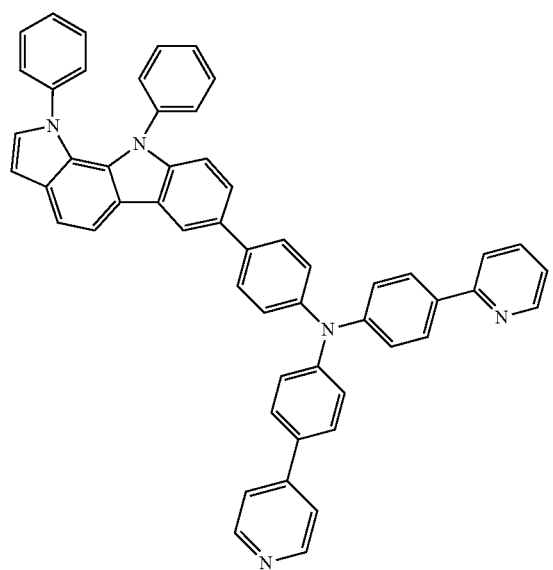
387
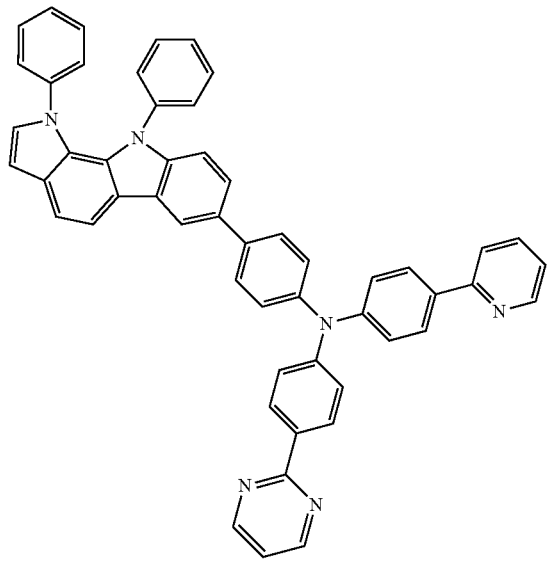
388
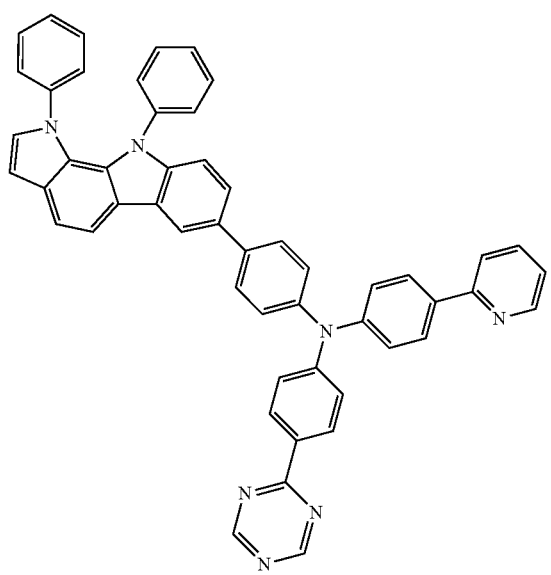

197
-continued
389
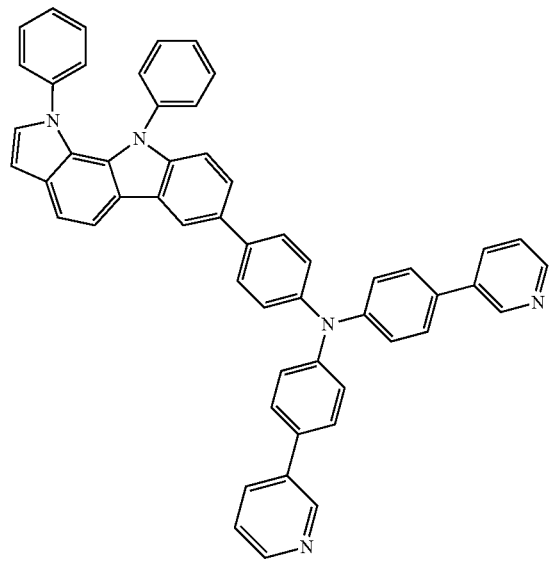
390
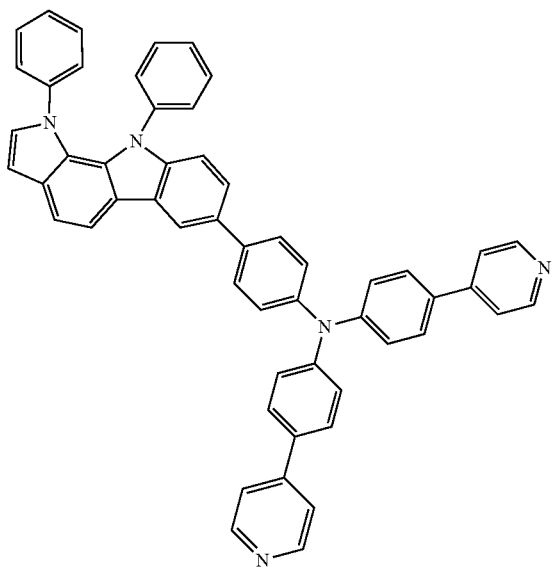
198
-continued
391
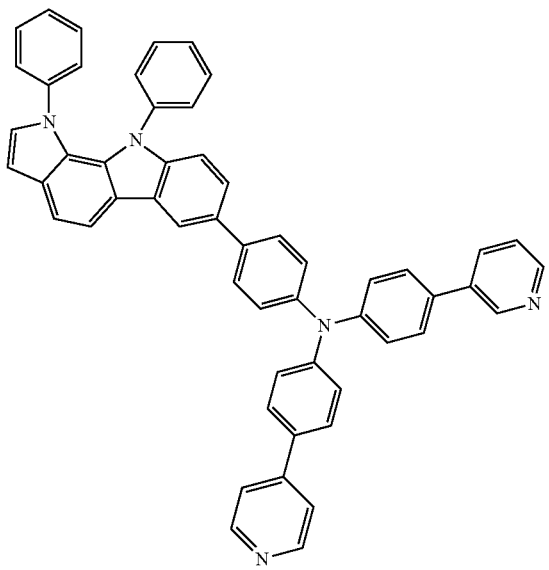
392
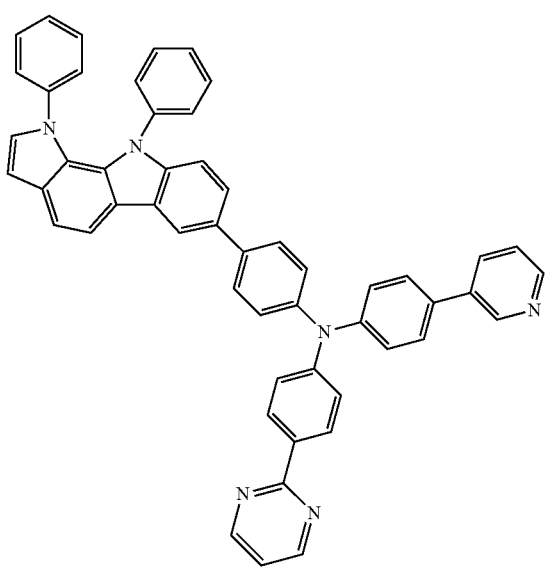

393
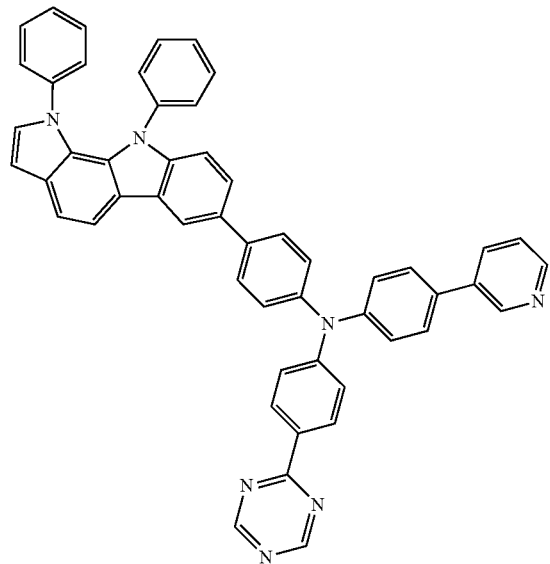
394
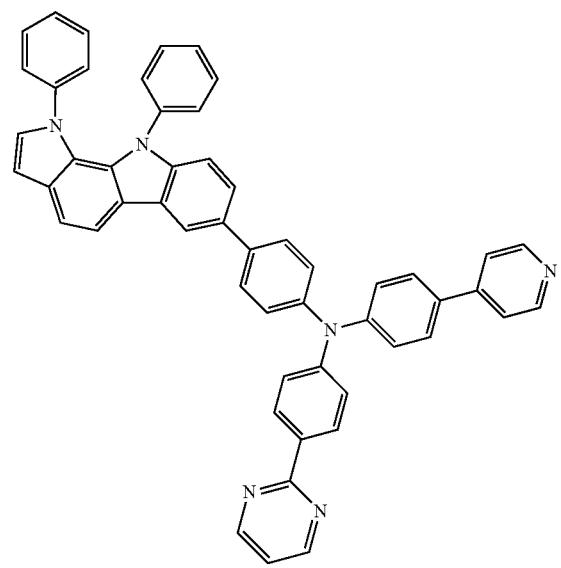
395
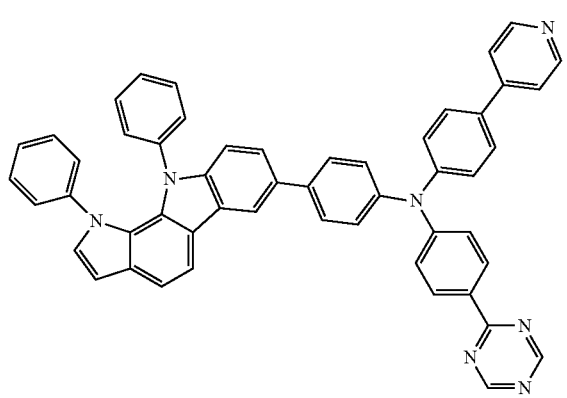
396
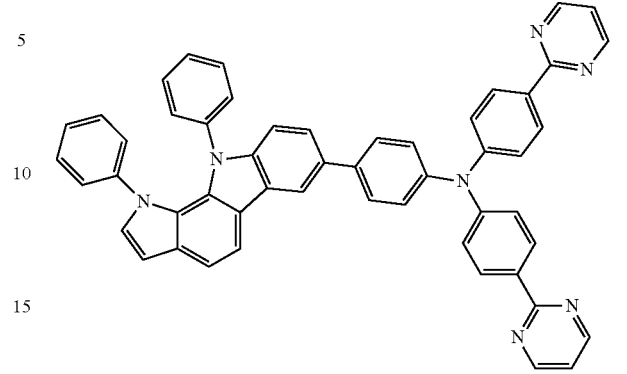
397
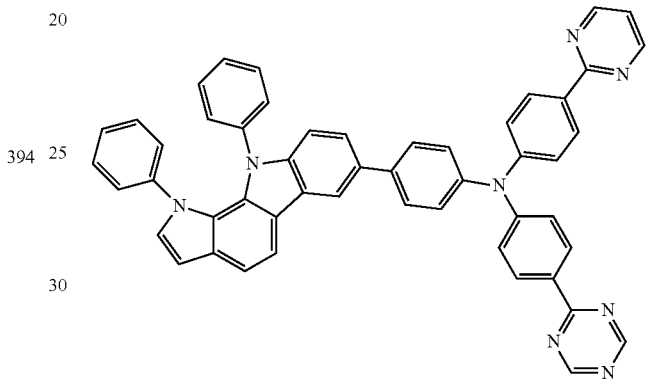
398
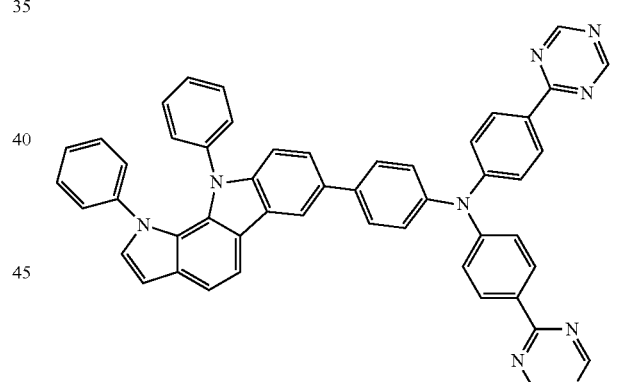
399
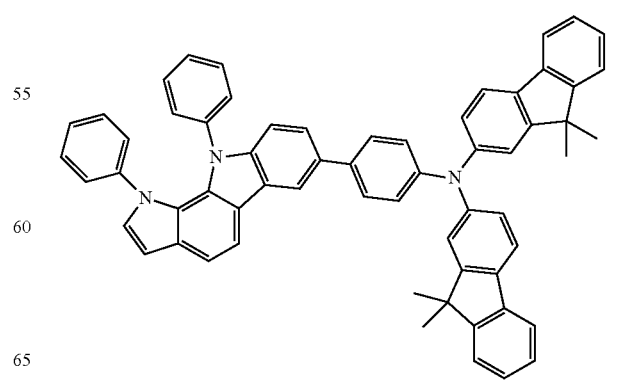

400
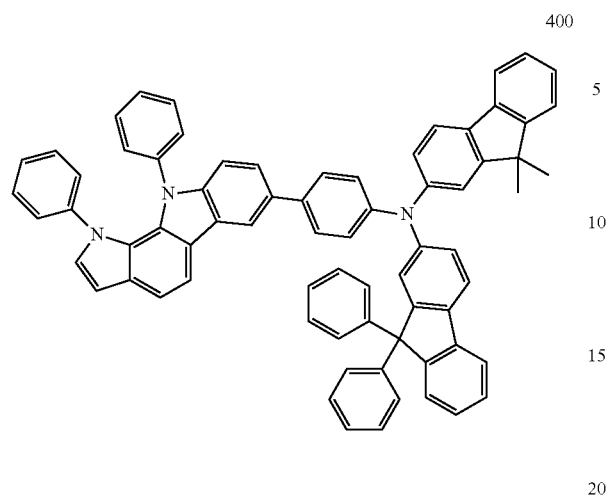
403
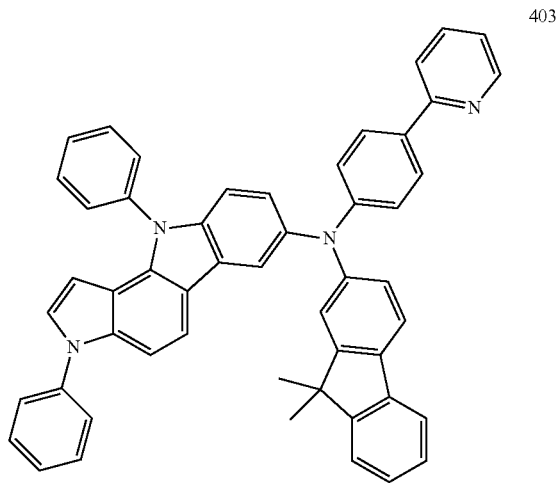
401
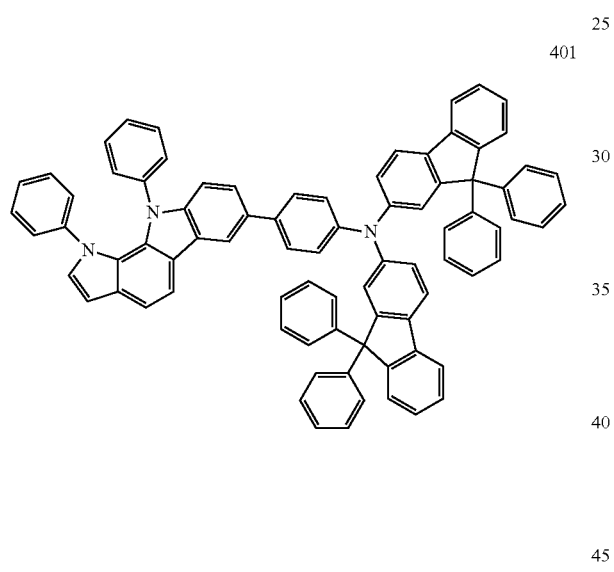
404
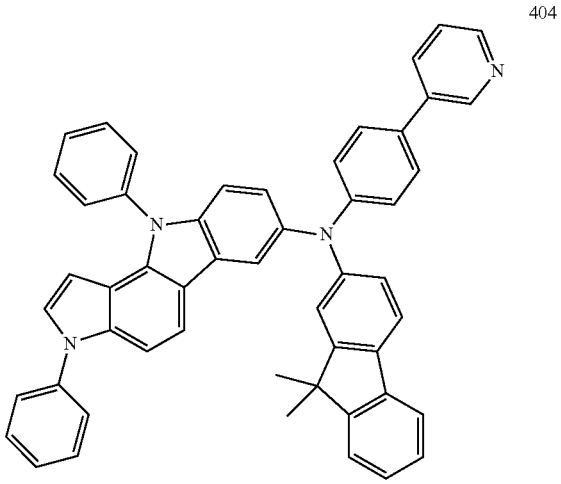
402
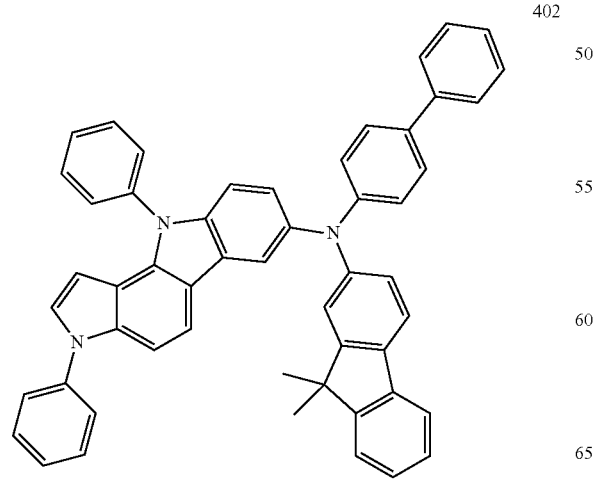
405
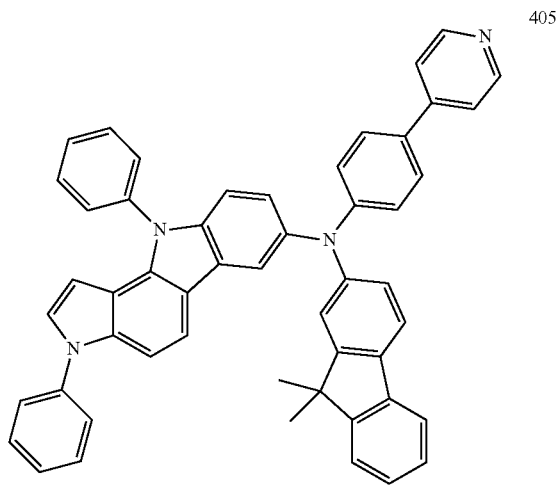

203
-continued
406
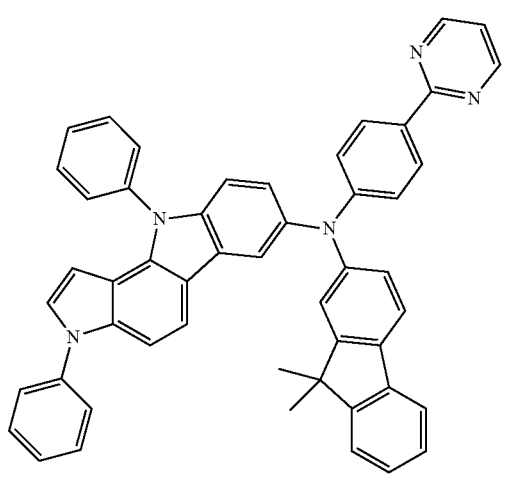
407
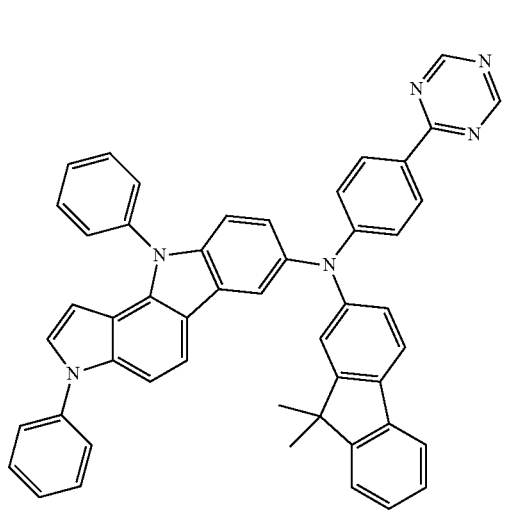
408
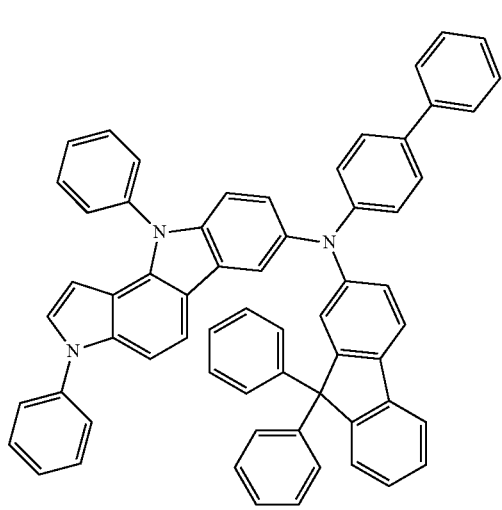
204
-continued
409
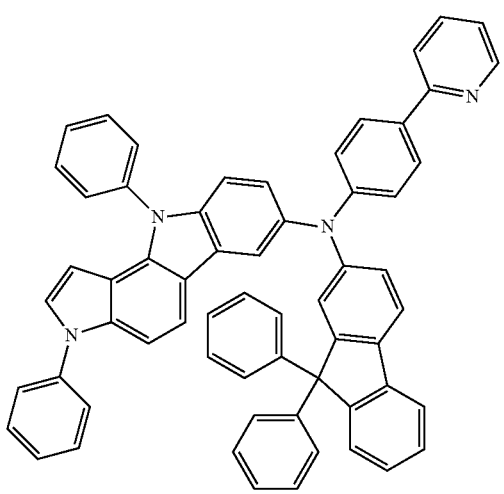
410
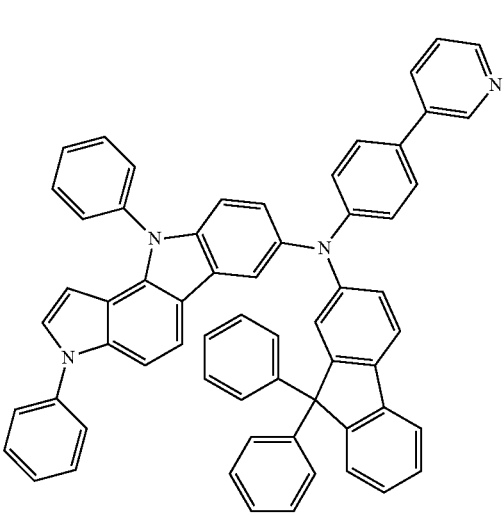
411
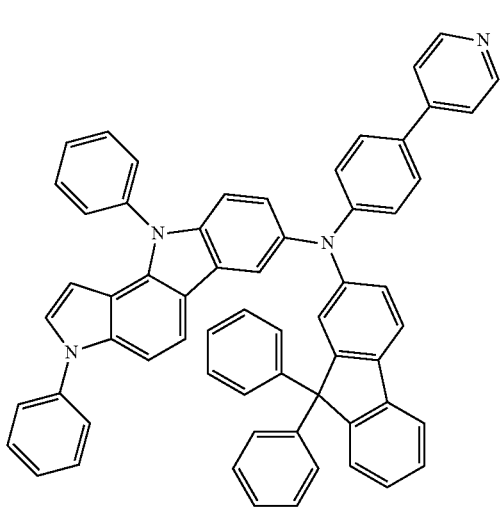

205
-continued
412
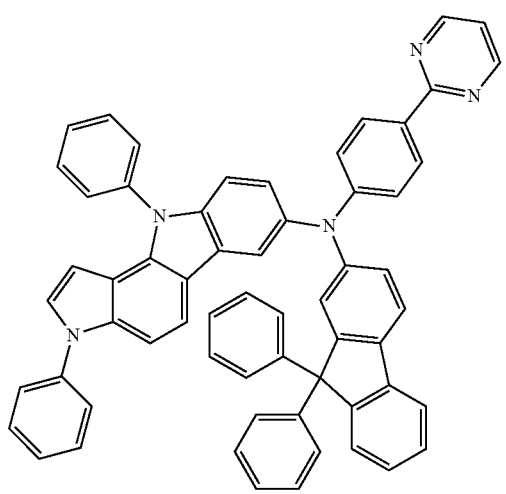
413
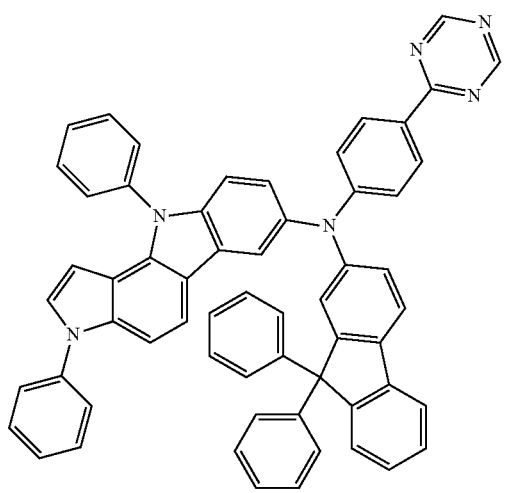
414
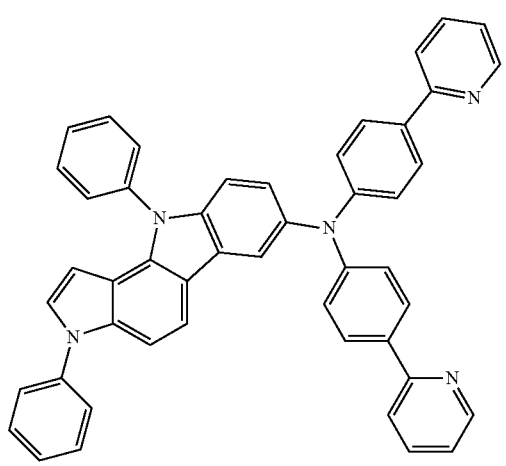
206
-continued
415
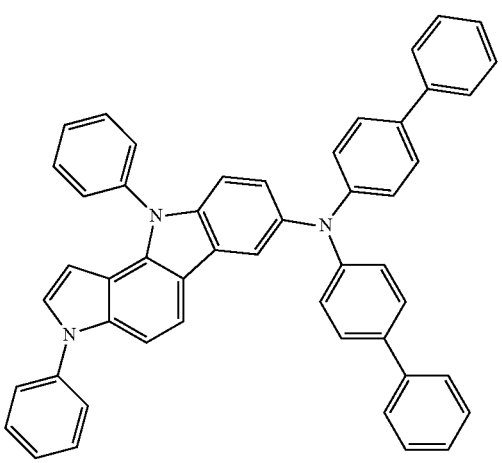
416
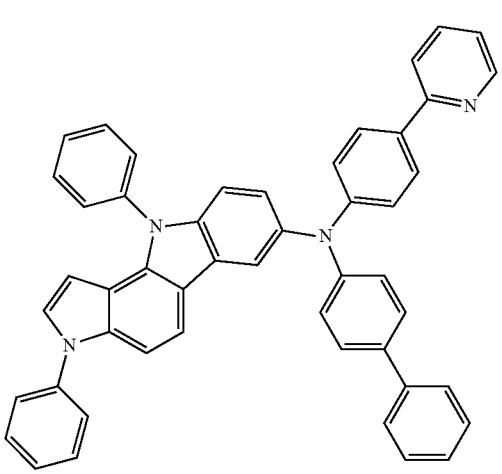
417
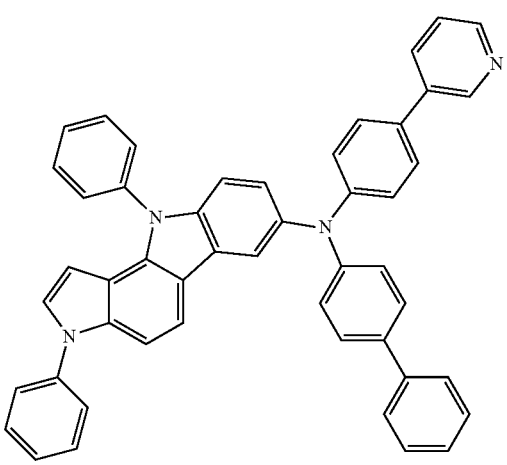

418
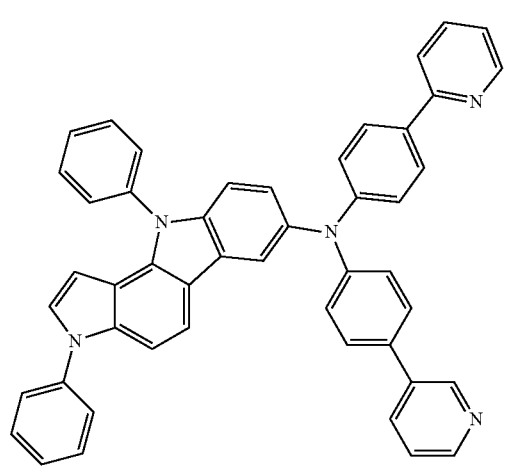
419
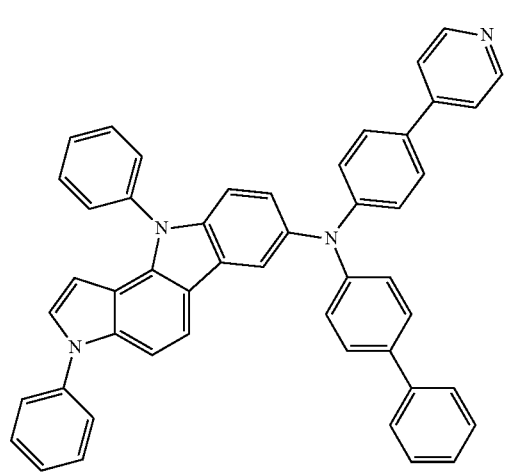
420
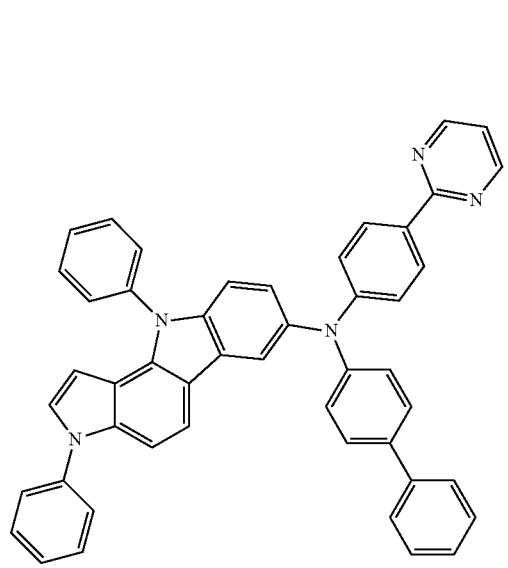
421
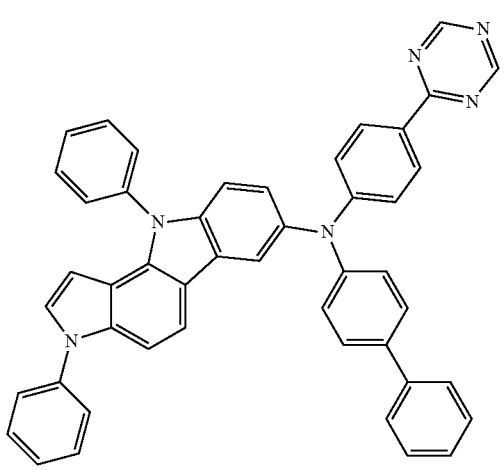
422
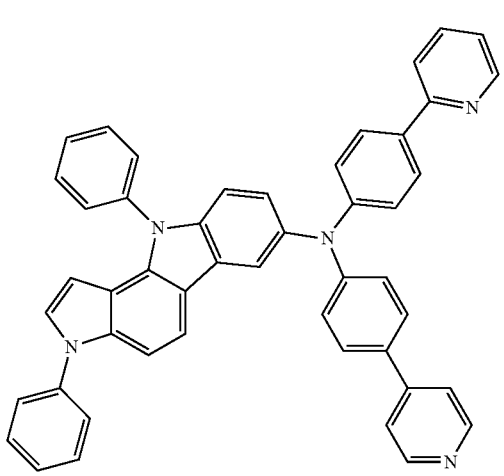
423
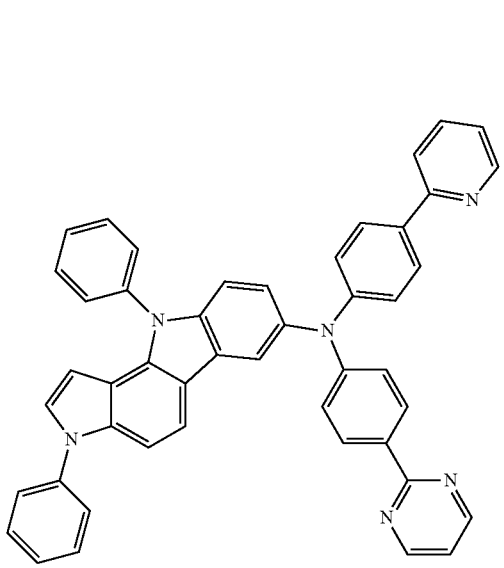

424 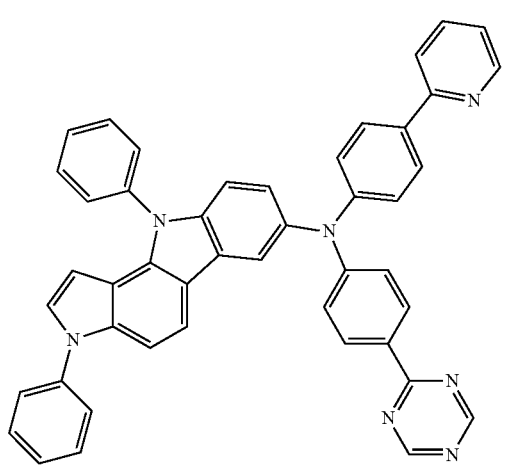
427 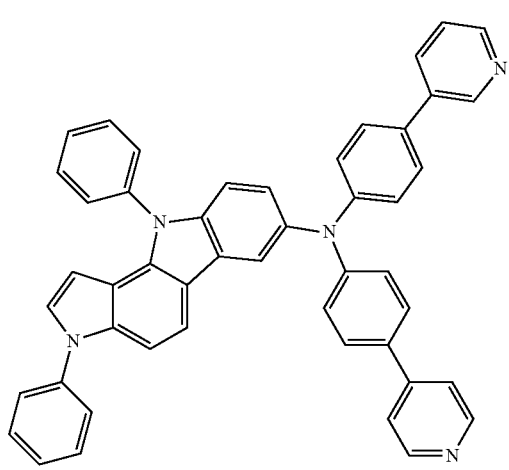
425 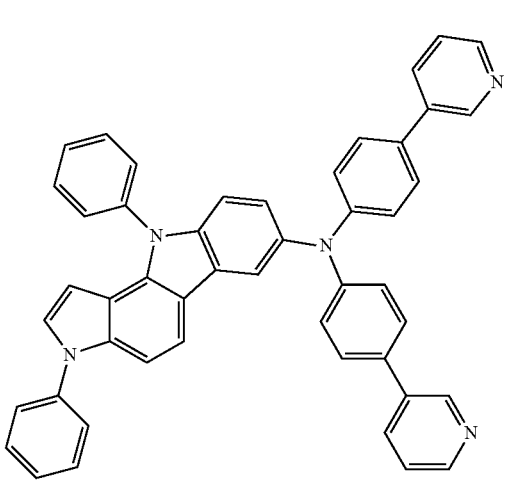
428 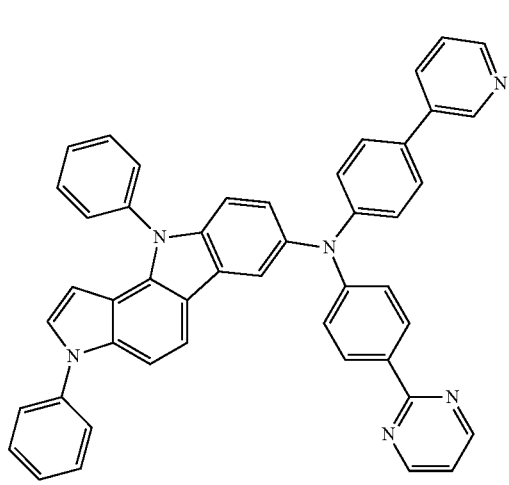
426 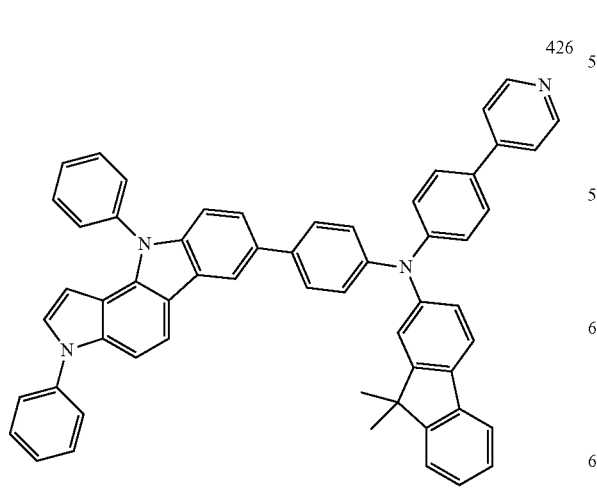
429 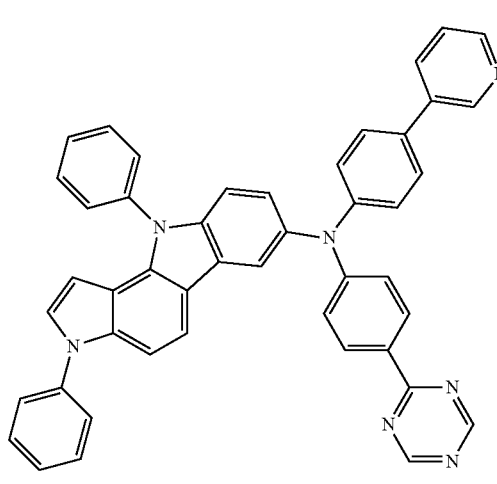

211
-continued
212
-continued
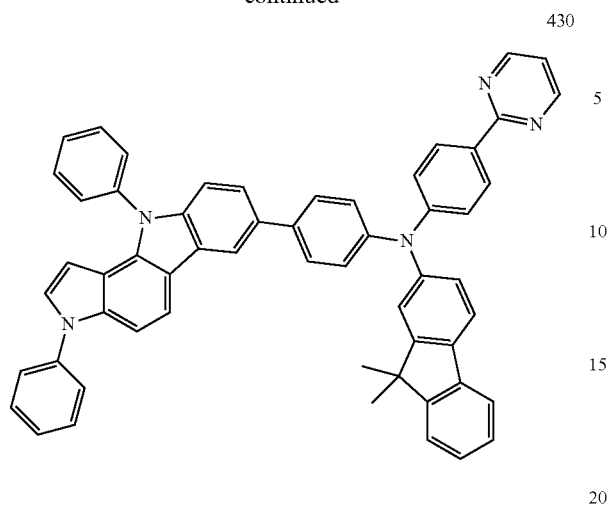
430
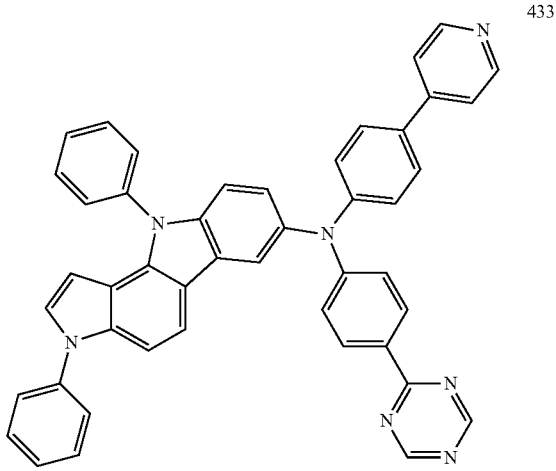
433
431
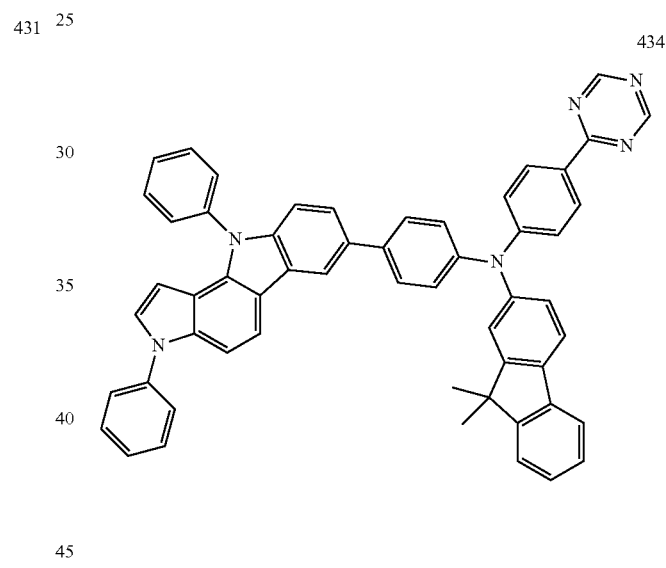
434
432
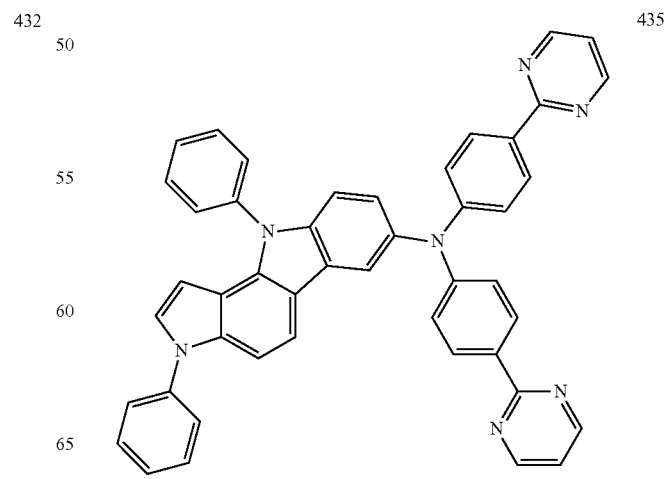
435

| 436 | 439 |
|---|---|
| 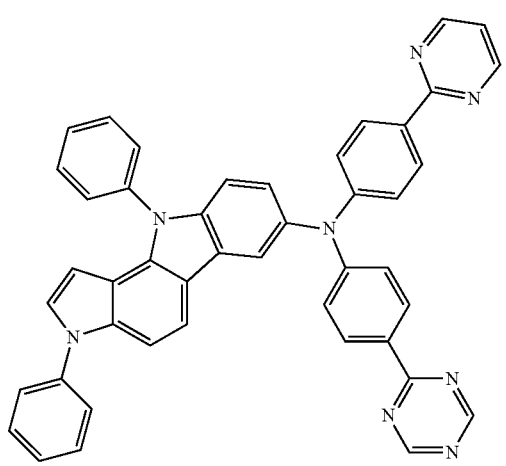 | 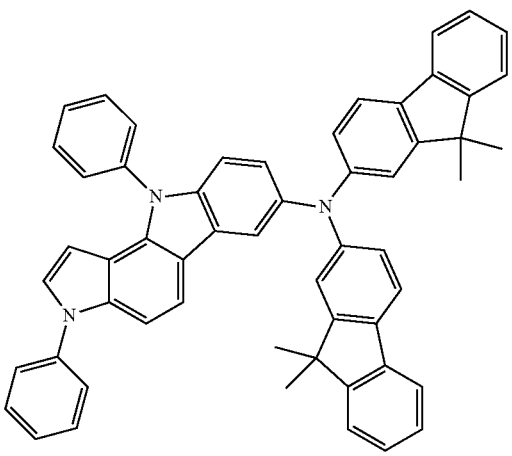 |
| 437 | 440 |
|---|---|
| 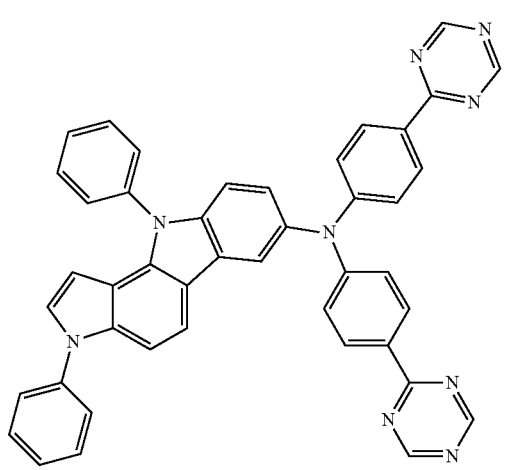 | 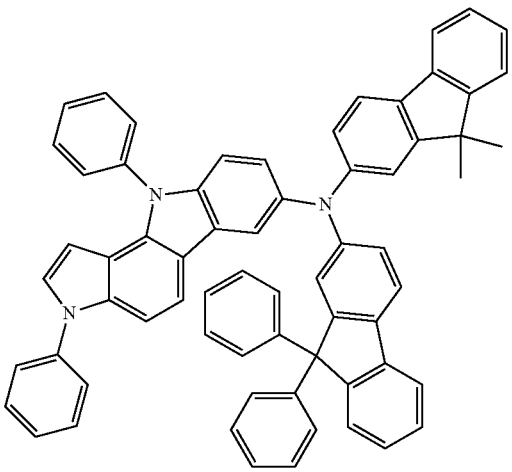 |
| 438 | 441 |
|---|---|
| 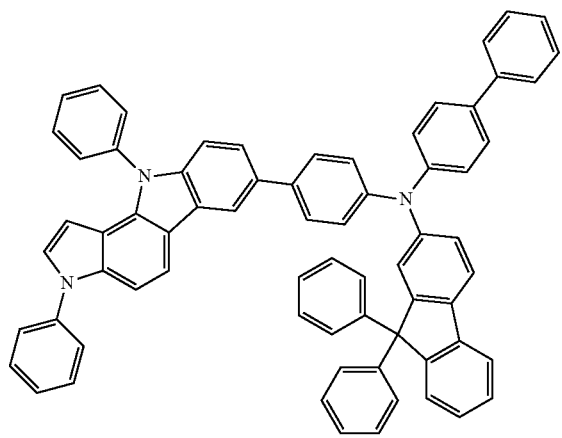 | 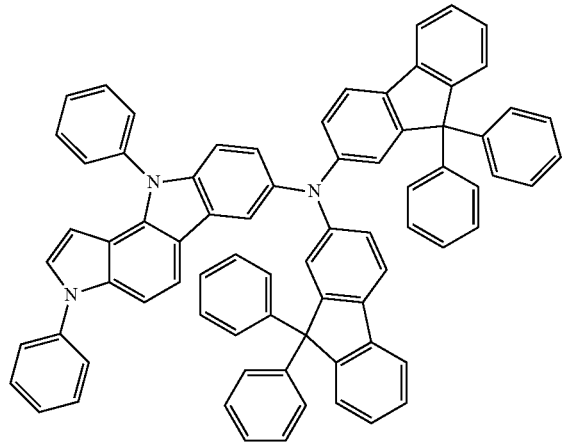 |

215
-continued
442
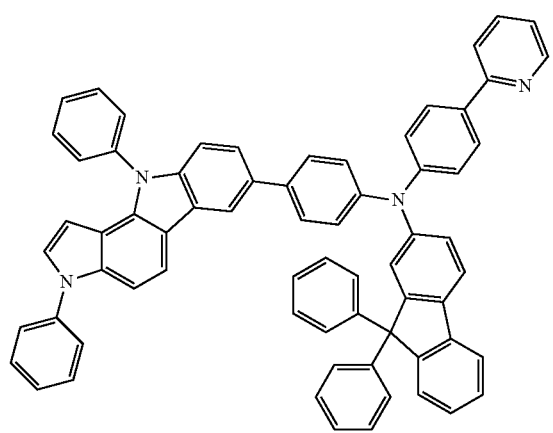
443
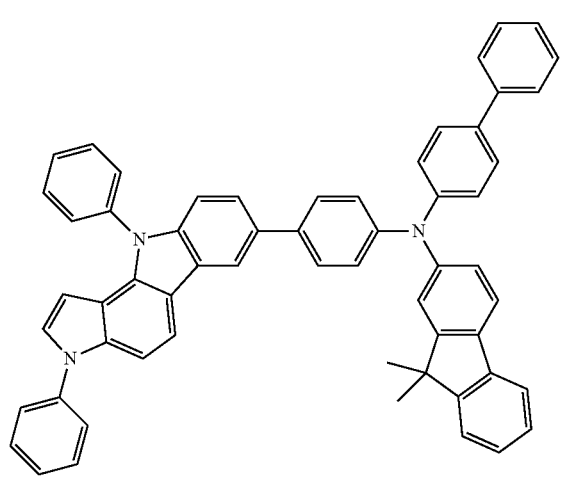
444
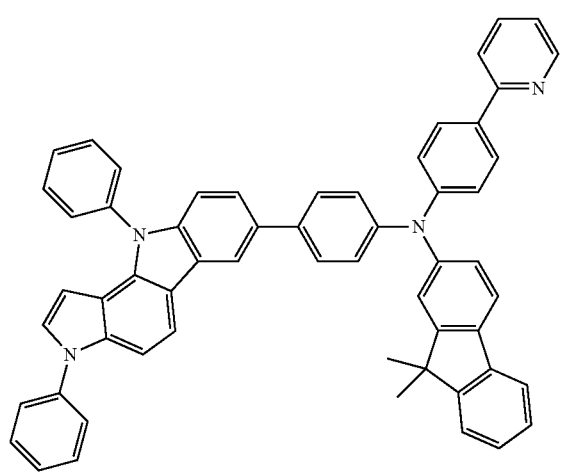
216
-continued
445
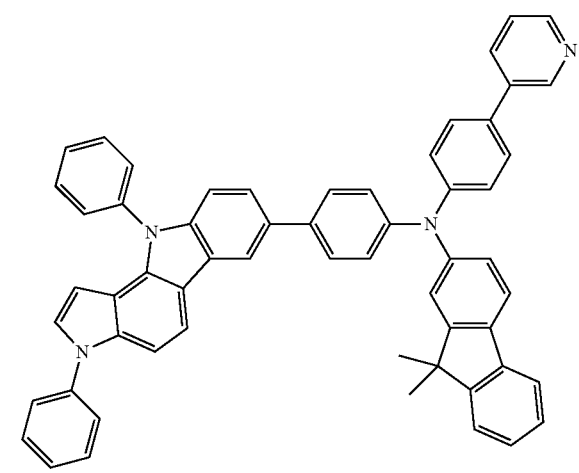
446
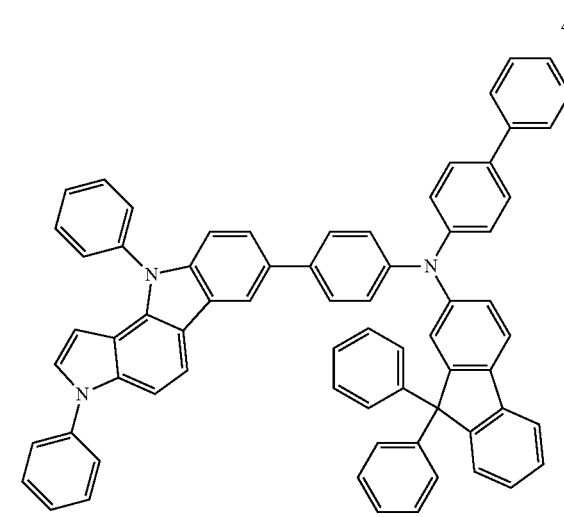
447
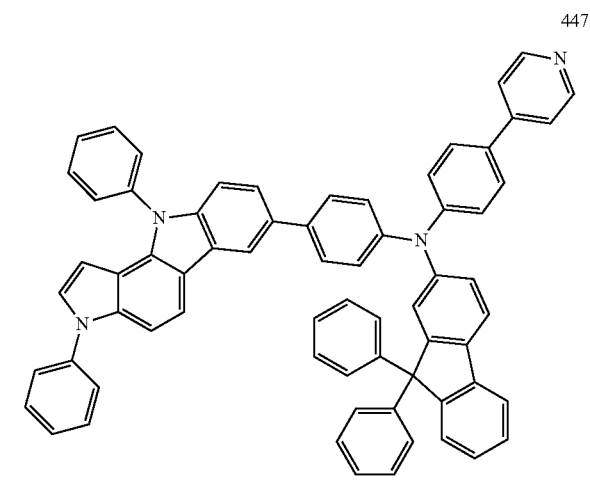

448
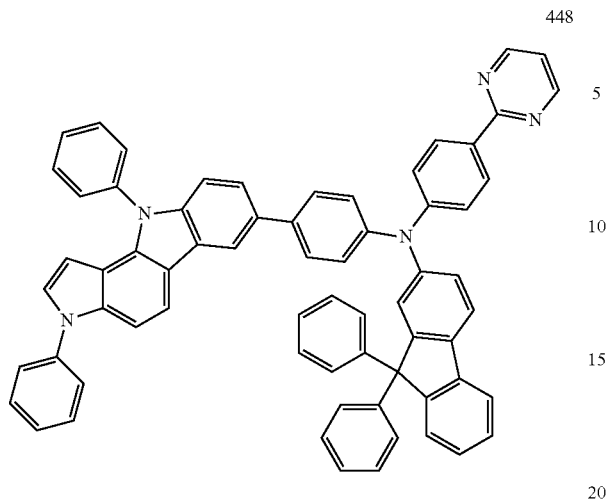
451
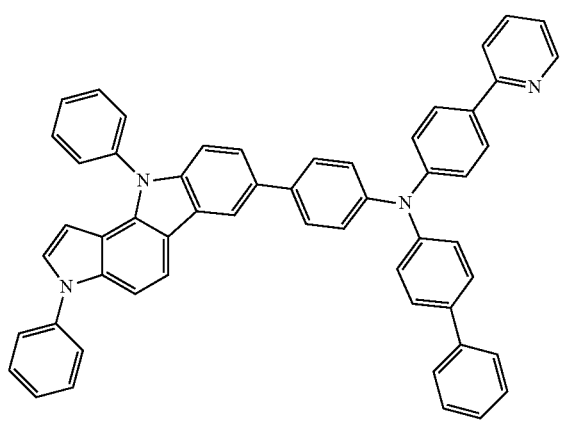
449
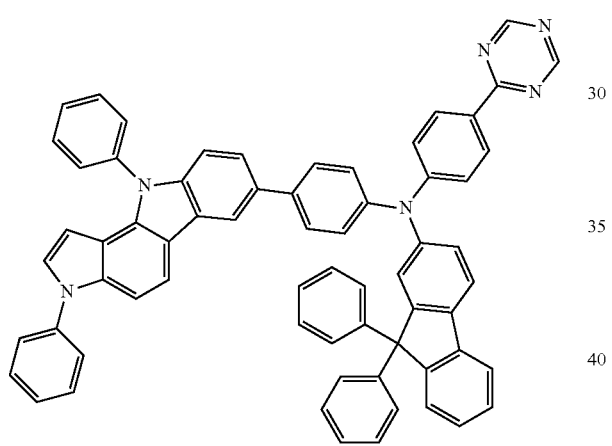
452
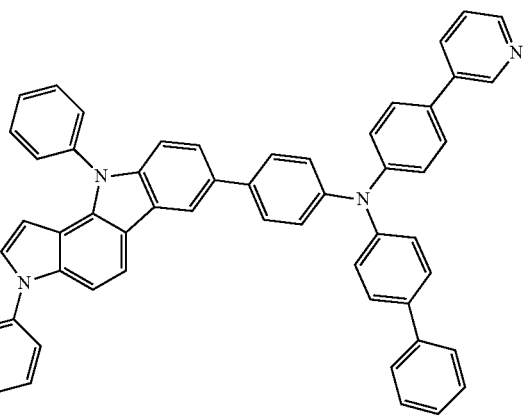
450
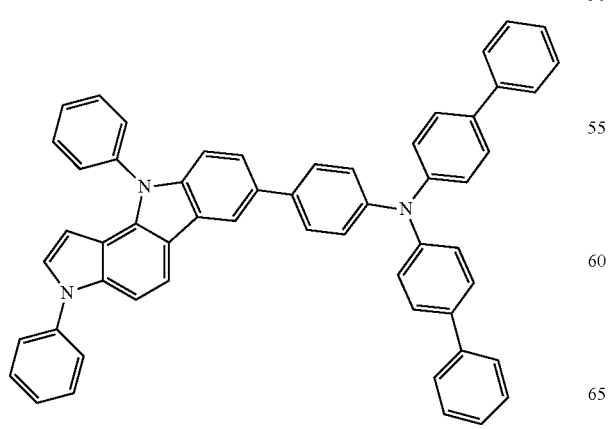
453
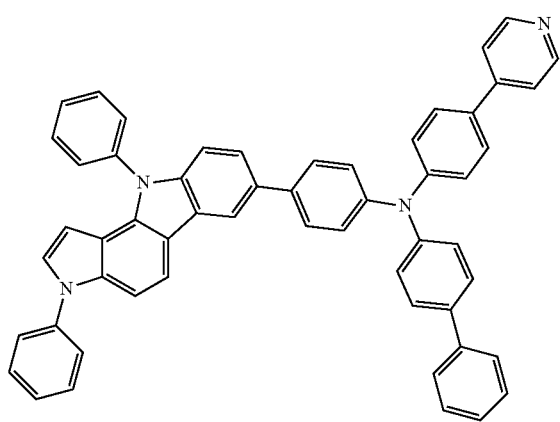

454
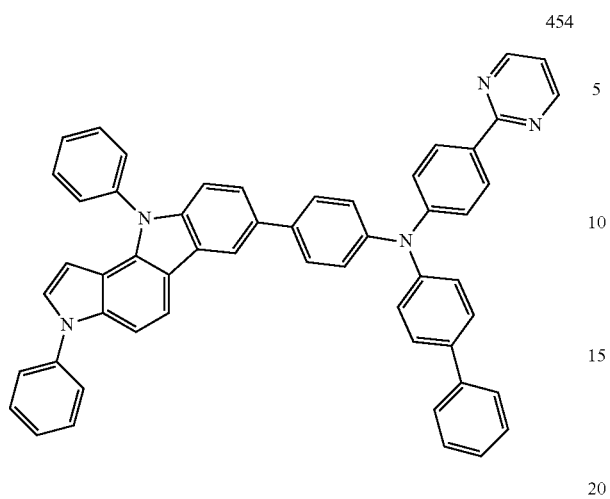
457
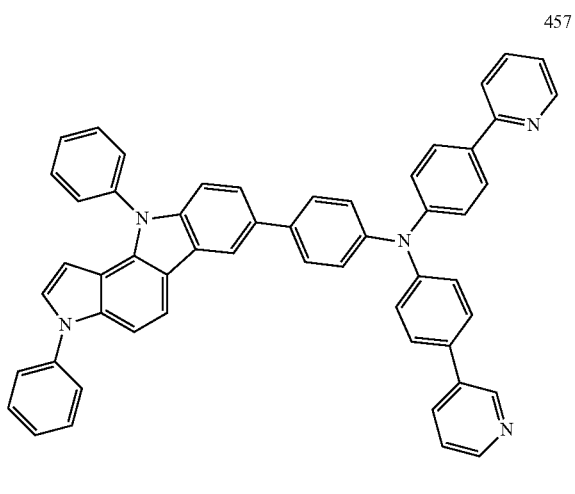
455
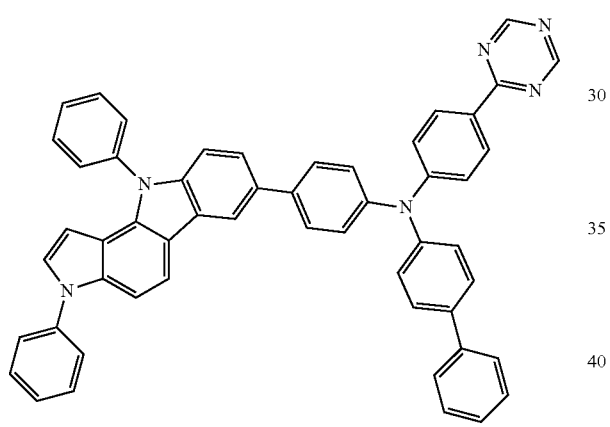
458
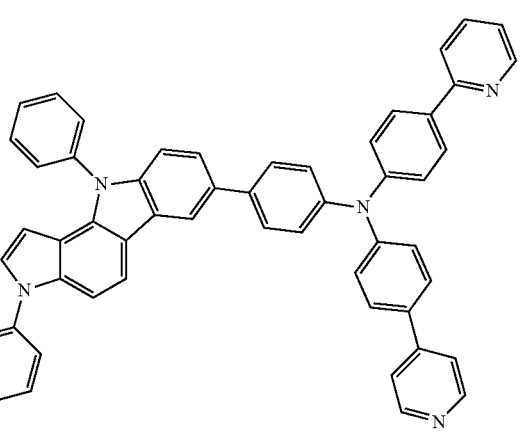
456
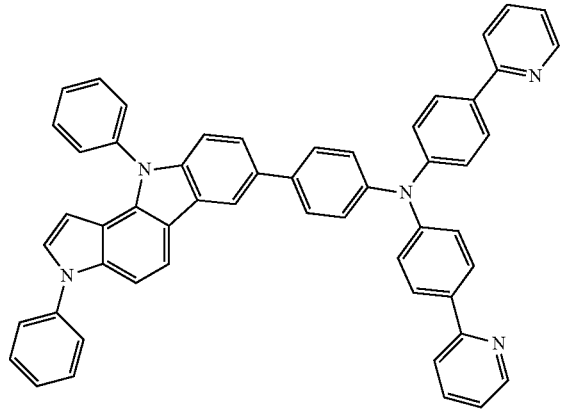
459
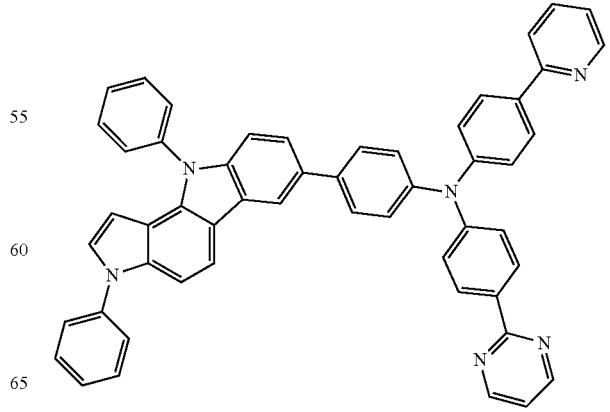

460
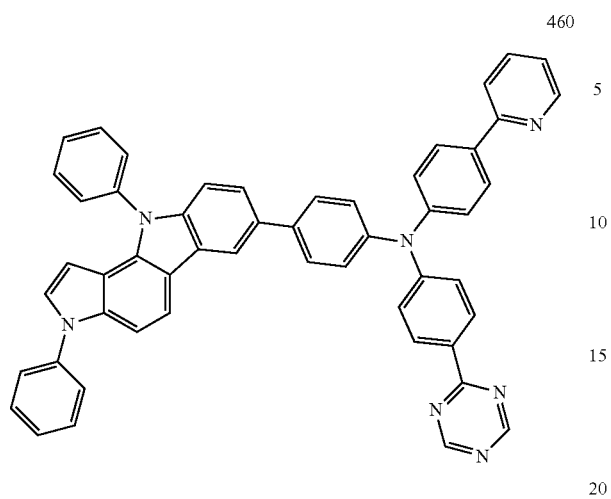
461
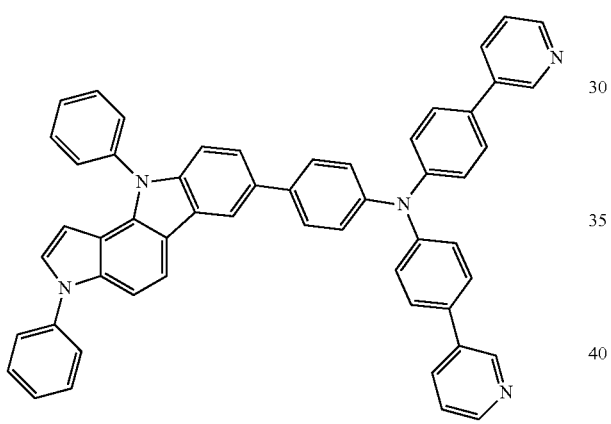
462
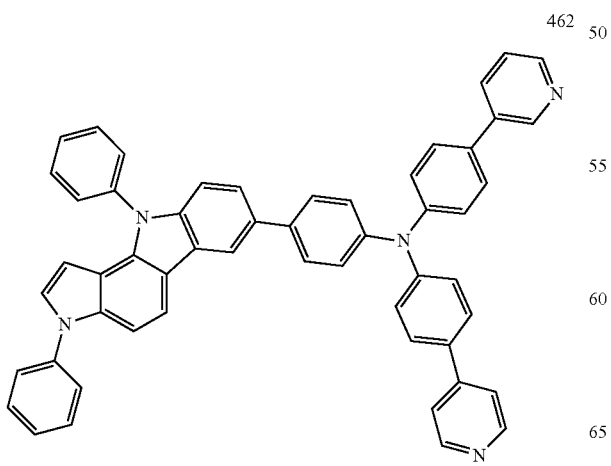
463
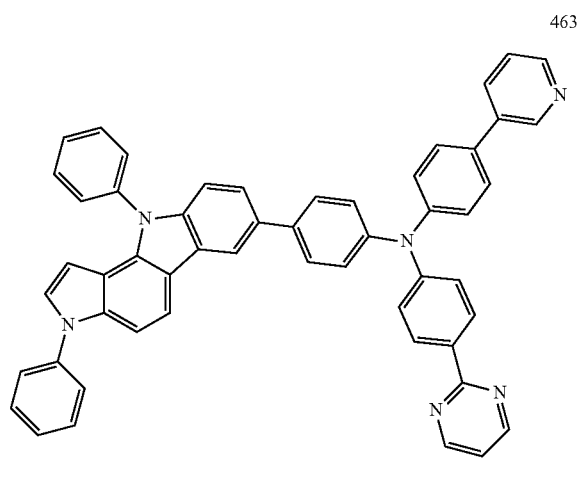
464
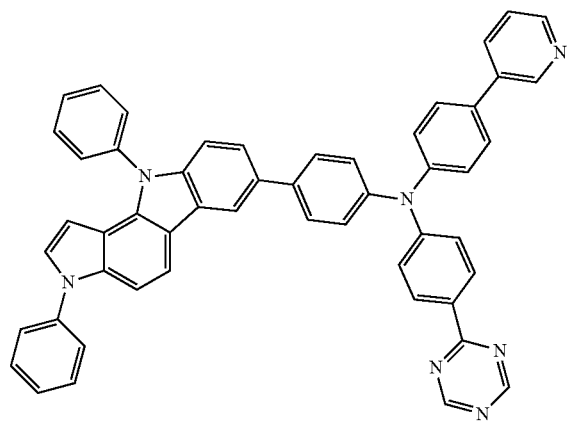
465
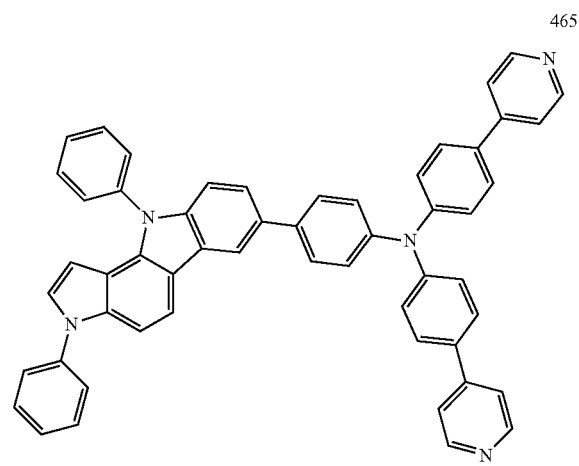

223
-continued
466
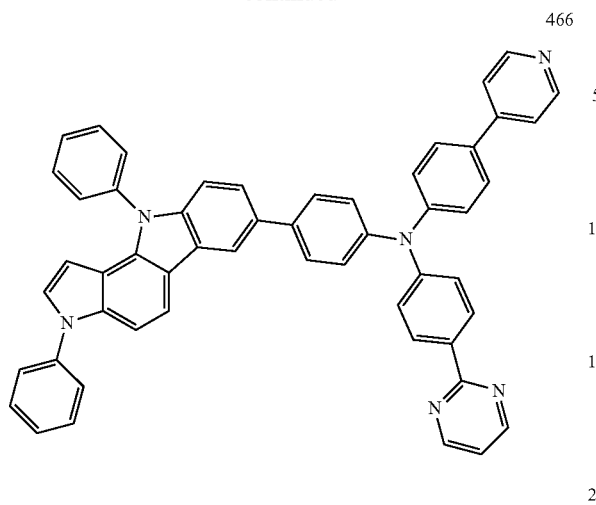
467
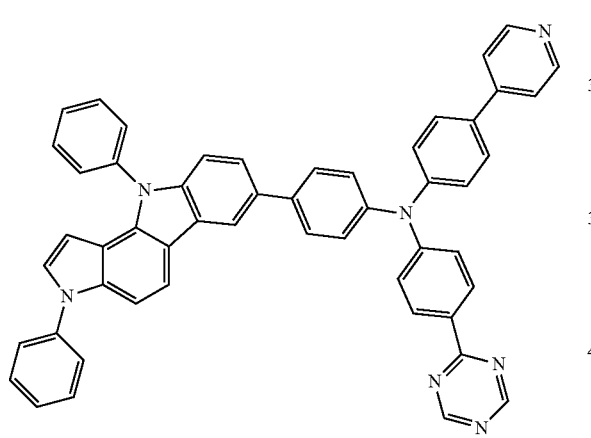
468
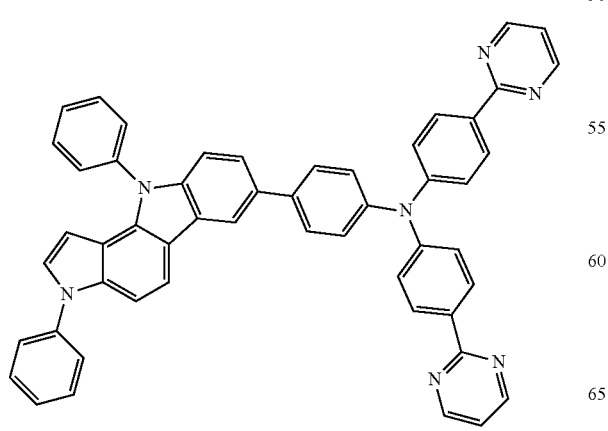
224
-continued
469
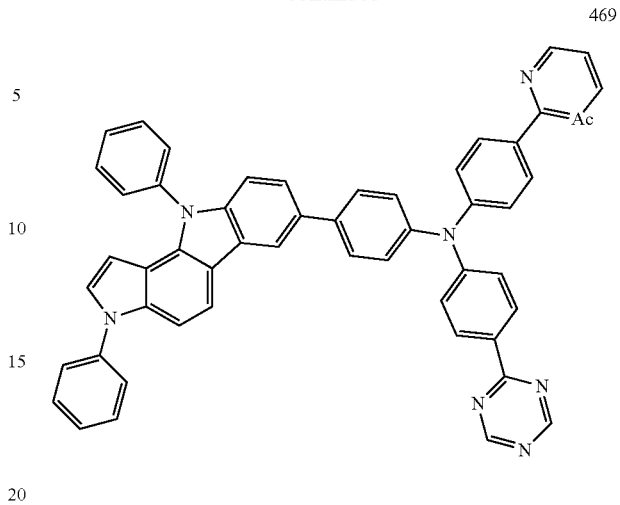
470
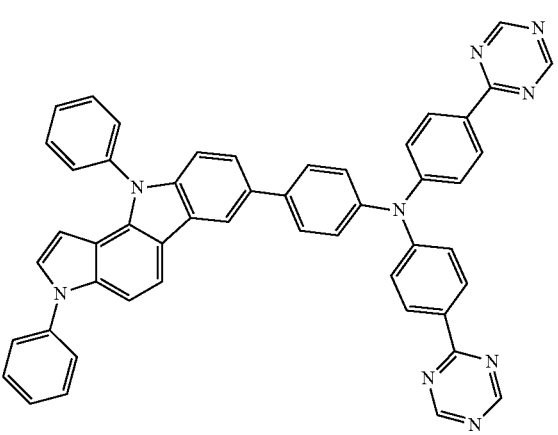
471
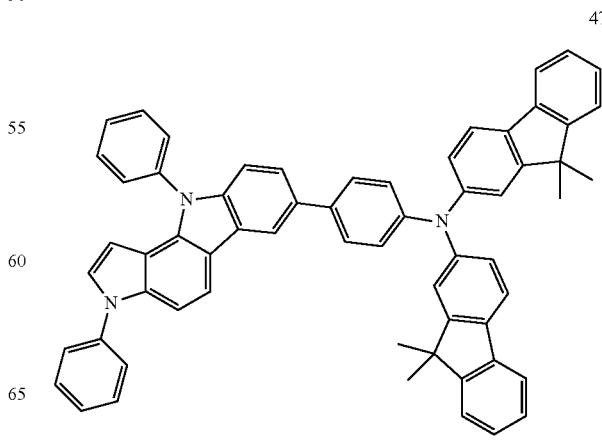

225
-continued
472
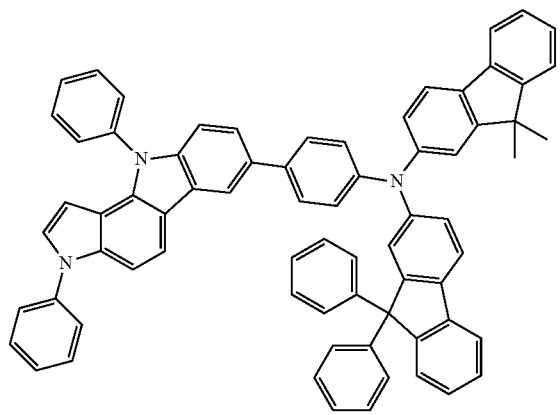
473
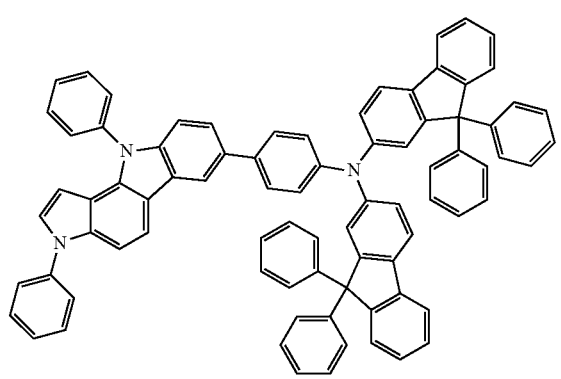
474
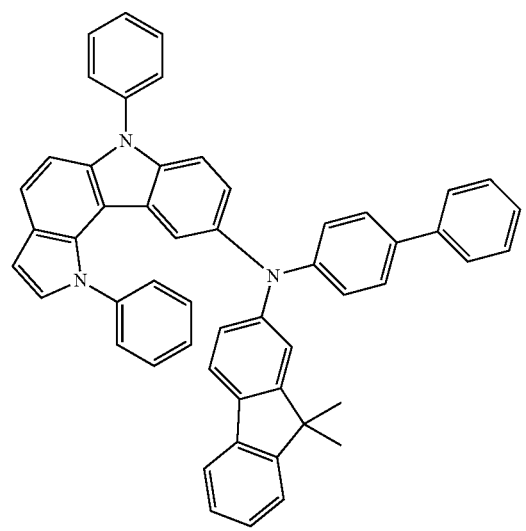
226
-continued
475
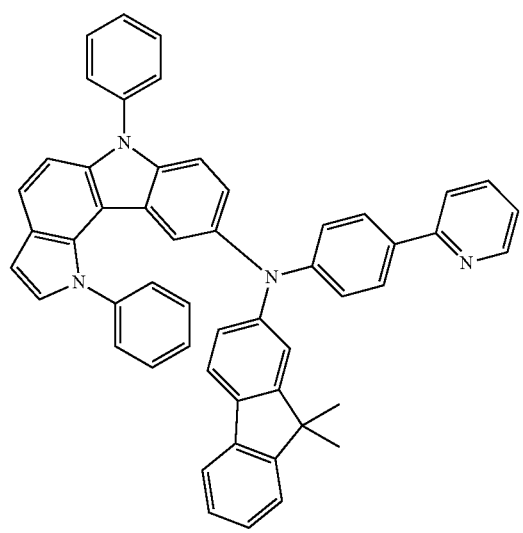
476
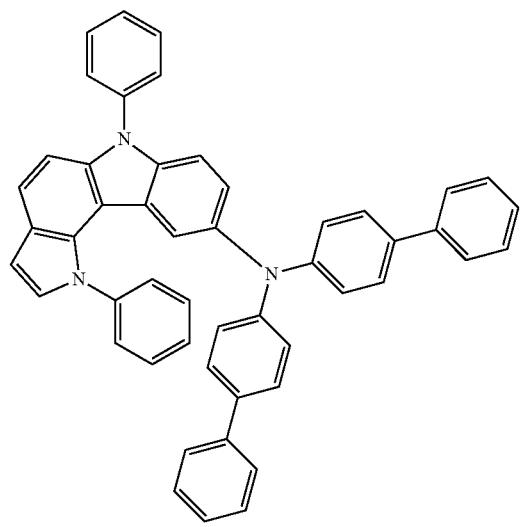

227
-continued
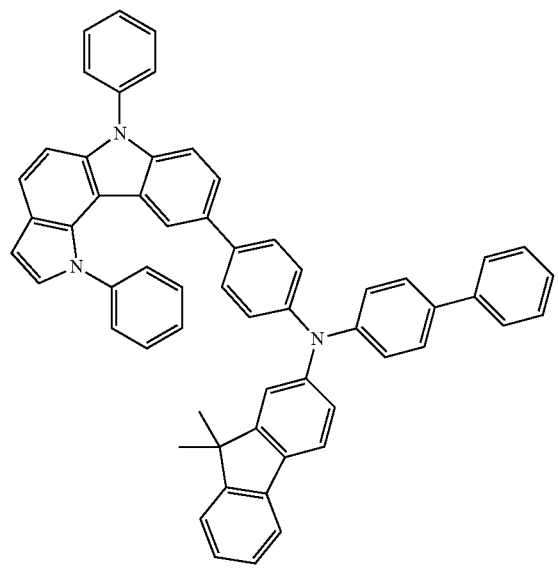
477
228
-continued
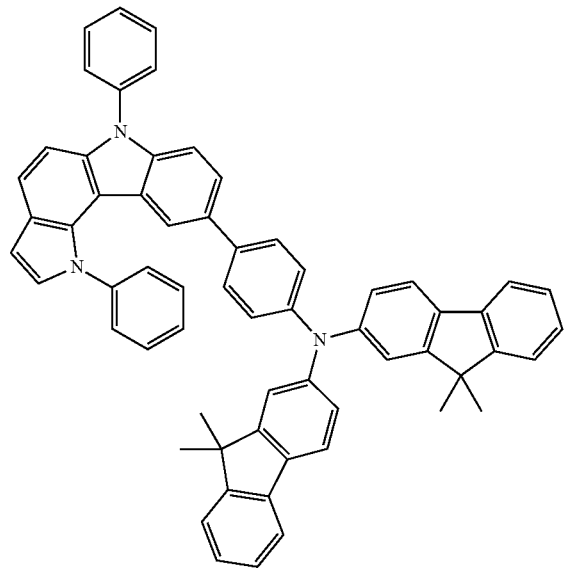
479
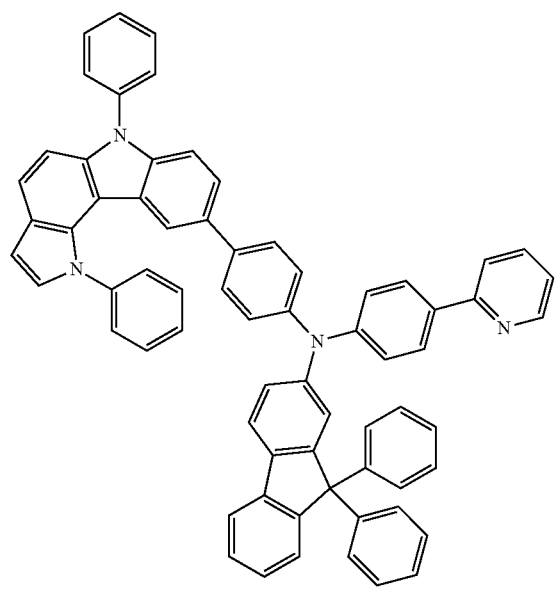
478
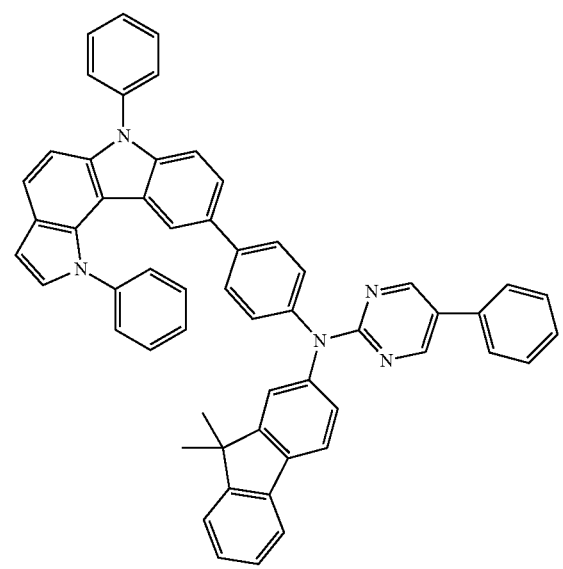
480

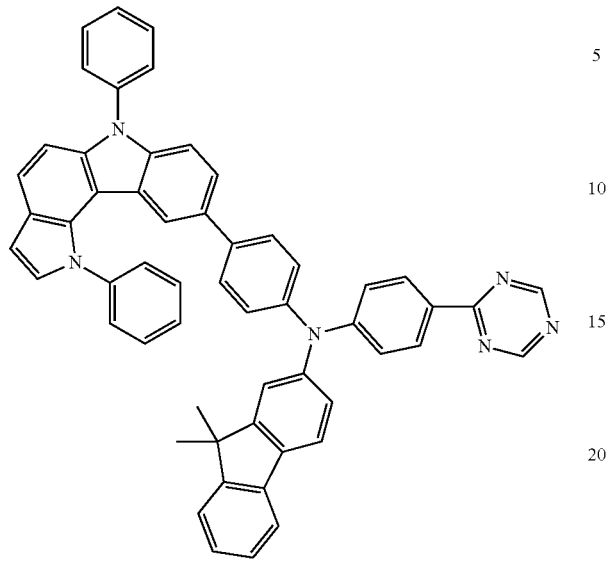
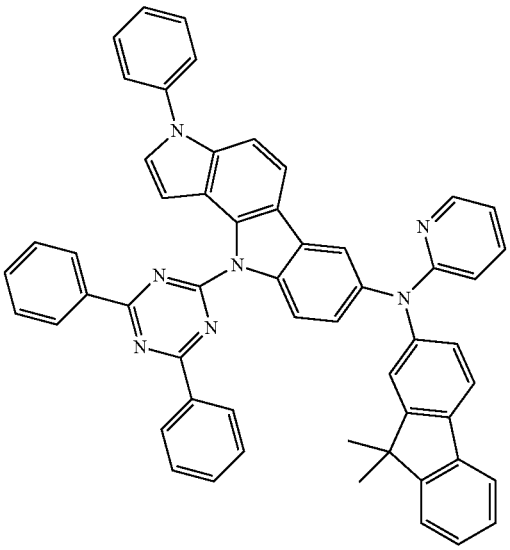
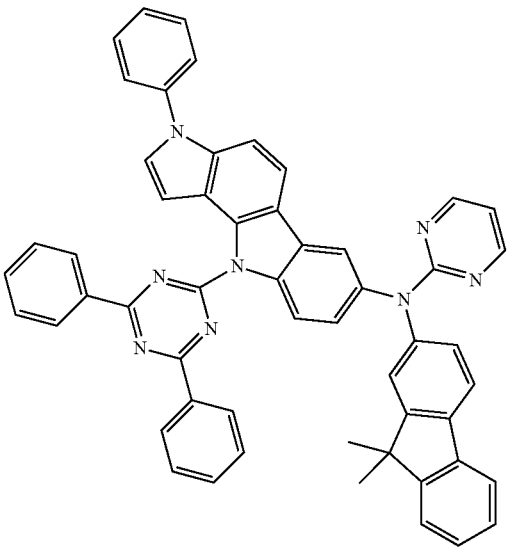

231
-continued

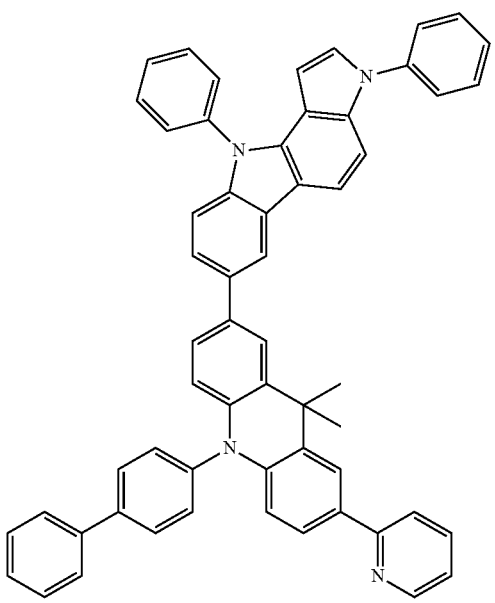
486

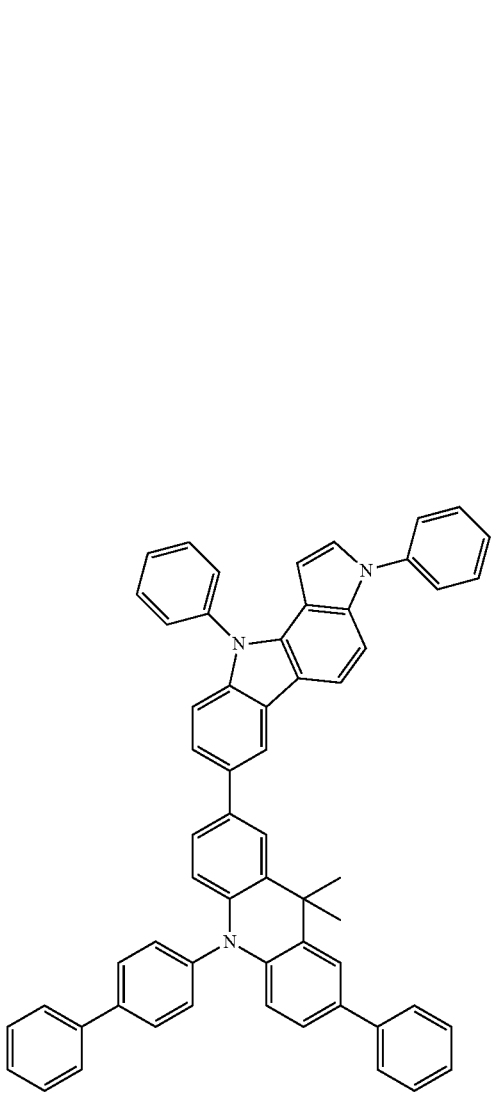
487

232
-continued

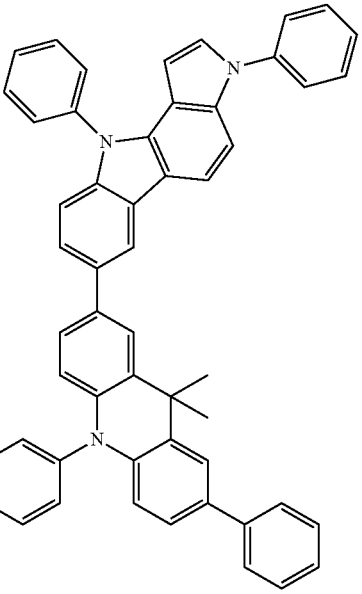
488

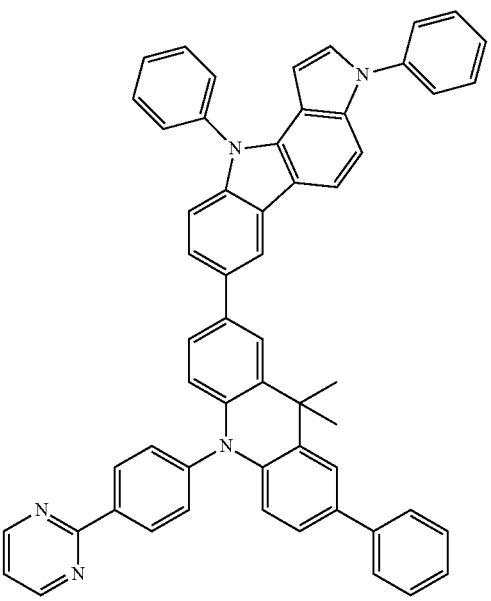
489

The "unsubstituted alkyl" used in the present disclosure means a monovalent functional group obtained by removing a hydrogen atom from a linear or branched, saturated hydrocarbon having 1 to 40 carbon atoms, and non-limiting examples thereof include methyl, ethyl, propyl, isobutyl, sec-butyl, pentyl, iso-amyl, hexyl, and the like.

Furthermore, the "unsaturated cycloalkyl" in the present disclosure means a monovalent functional group obtained by removing a hydrogen atom from a monocyclic or polycyclic non-aromatic hydrocarbon (saturated cyclic hydrocarbon) having 3 to 40 carbon atoms. Examples of the cycloalkyl include cyclopropyl, cyclopentyl, cyclohexyl, norbornyl, adamantine, and the like, but are not limited thereto.

Further, the "unsubstituted heterocycloalkyl" in the present disclosure means a monovalent functional group obtained by removing a hydrogen atom from a non-aromatic hydrocarbon (saturated cyclic hydrocarbon) having 3 to 40 nuclear atoms, and in this case, one or more carbons in the ring, preferably 1 to 3 carbons, are substituted with a heteroatom such as N, O, or S. Non-limiting examples thereof include morpholine, piperazine, and the like.

In addition, the "unsubstituted aryl" in the present disclosure means a monovalent functional group obtained by removing a hydrogen atom from an aromatic hydrocarbon having 6 to 60 carbon atoms of a single ring or a combination of two or more rings. In this case, two or more rings may be simply pendant to each other or pendant to each other in a fused form. Non-limiting examples thereof include phenyl, biphenyl, terphenyl, naphthyl, phenanthryl, anthryl, and the like.

Furthermore, the "unsubstituted heteroaryl" in the present disclosure is a monovalent functional group obtained by removing a hydrogen atom from a monoheterocyclic or polyheterocyclic aromatic hydrocarbon having 5 to 60 nuclear atoms, and one or more carbons in the ring, preferably 1 to 3 carbons, are substituted with a heteroatom such as nitrogen (N), oxygen (O), sulfur (S), or selenium (Se). In this case, in the heteroaryl, two or more rings may be simply pendant to each other or pendant to each other in a fused form, and furthermore, a form that is fused with an aryl group is also included. Non-limiting examples of the heteroaryl include: a six-membered monocyclic ring, such as pyridyl, pyrazinyl, pyrimidinyl, pyridazinyl, and triazinyl; and a polycyclic ring such as phenoxathienyl, indolizinyl, indolyl, purinyl, quinolyl, benzothiazole, and carbazolyl, and it is interpreted that 2-furanyl, N-imidazolyl, 2-isoxazolyl, 2-pyridinyl, 2-pyrimidinyl, and the like are also included.

Further, the "unsubstituted alkyloxy" in the present disclosure means a monovalent functional group represented by RO—, and in this case, it is interpreted that R is an alkyl having 1 to 40 carbon atoms, and includes a linear, branched, or cyclic structure. Non-limiting examples of the alkyloxy include methoxy, ethoxy, n-propoxy, 1-propoxy, t-butoxy, n-butoxy, pentoxy, and the like, and are not limited thereto.

In addition, the "unsubstituted aryloxy" in the present disclosure means a monovalent functional group represented by R'O—, and in this case, R' is an aryl having 6 to 60 carbon atoms. Non-limiting examples of the aryloxy include phenyloxy, naphthyloxy, diphenyloxy, and the like.

Furthermore, the "unsubstituted arylamine" in the present disclosure means an amine substituted with an aryl having 6 to 60 carbon atoms.

Further, the "fused ring" in the present disclosure means a fused aliphatic ring, a fused aromatic ring, a fused heteroaliphatic ring, a fused heteroaromatic ring, or a combined form thereof.

The compound represented by Formula 1 according to the present disclosure may be synthesized according to a general synthesis method [see *Chem. Rev.*, 60:313 (1960); *J. Chem. SOC.* 4482 (1955); Chem. Rev. 95: 2457 (1995), and the like]. The detailed synthesis process on the compound of the present disclosure will be specifically described in the Synthesis Examples to be described below.

Meanwhile, the present disclosure provides an organic electroluminescent device including the aforementioned compound represented by Formula 1 (preferably the compound represented by any one of Formulae 4 to 9, and more preferably the compound represented by any one of Formulae 10 to 15).

Specifically, the organic electroluminescent device according to the present disclosure includes an anode, a cathode, and an organic material layer including one or more layers interposed between the anode and the cathode, in which at least one of the organic material layers including one or more layers includes one or more of the compounds represented by Formula 1 (preferably the compound represented by any one of Formulae 4 to 9, and more preferably the compound represented by any one of Formulae 10 to 15).

Examples of the organic material layer including one or more layers include a hole injection layer, a hole transporting layer, a light-emitting layer, an electron transporting layer, an electron injection layer, and the like, and among them, at least one organic material layer may include the compound represented by Formula 1. Preferably, the organic material layer including one or more layers, which includes the compound of Formula 1, may be a hole transporting layer, a hole injection layer, or a light-emitting layer, more preferably a light-emitting layer or a hole transporting layer, and even more preferably a hole transporting layer. In this case, the light-emitting efficiency, brightness, power efficiency, thermal stability, and service life of the device may be enhanced due to the compound.

The structure of the organic electroluminescent device according to the present disclosure is not particularly limited, but non-limiting examples thereof include a structure in which a substrate, an anode, a hole injection layer, a hole transporting layer, a light-emitting layer, an electron transporting layer, and a cathode are sequentially stacked. Optionally, an electron injection layer may also be additionally stacked on the electron transporting layer. Furthermore, the organic electroluminescent device according to the present disclosure may have a structure in which an anode, an organic material layer including one or more layers, and a cathode are sequentially laminated and may also have a structure in which an insulating layer or an adhesive layer may be inserted into the interface between the electrode and the organic material layer.

The organic electroluminescent device according to the present disclosure may be manufactured by forming another organic material layer and another electrode using materials and methods known in the art, except that one or more layers (for example, a light-emitting layer, a hole transporting layer and/or an electron transporting layer) of the organic material layer are formed so as to include the compound represented by Formula 1.

The organic material layer may be formed by a vacuum deposition method or a solution application method. Examples of the solution application method include spin coating, dip coating, doctor blading, inkjet printing, or a thermal transfer method, but are not limited thereto.

As a substrate which may be used in the present disclosure, a silicon wafer, a quartz or glass plate, a metal plate, a plastic film or sheet, and the like may be used, and examples of the substrate are not limited thereto.

Further, examples of an anode material include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; a conductive polymer, such as polythiophene, poly(3-methylthiophene), poly[3,4-(ethylene-1,2-dioxy)thiophene] (PEDT), polypyrrole, and polyaniline; or carbon black, and the like, but are not limited thereto.

In addition, examples of a cathode material include: a metal, such as magnesium, calcium, sodium, potassium, titanium, indium, yttrium, lithium, gadolinium, aluminum, silver, tin, or lead, or alloys thereof; a multi-layer structured material, such as LiF/Al or $LiO_2$/Al, and the like, but are not limited thereto.

Furthermore, the hole injection layer, the hole transporting layer, the electron injection layer, and the electron transporting layer are not particularly limited, and typical materials known in the art may be used.

Hereinafter, the present disclosure will be described in detail as follows through the Examples. However, the following Examples are only for exemplifying the present disclosure, and the present disclosure is not limited by the following Examples.

[Preparation Example 1] Synthesis of Compound IC-1

<Step 1> Synthesis of 5-(4,4,5,5-tetramethyl-1,3,2-dioxaborolan-2-yl)-1H-indole

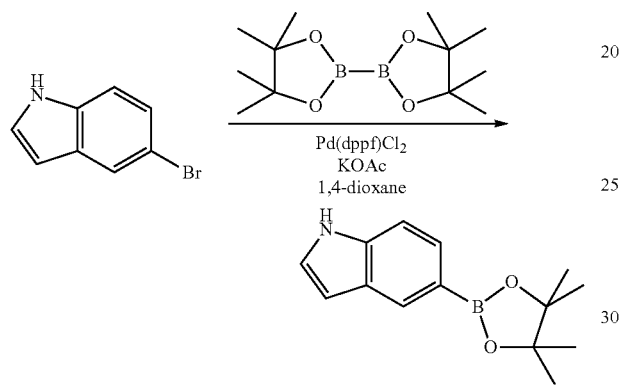

5-bromo-1H-indole (25 g, 0.128 mol), 4,4,4',4',5,5,5',5'-octamethyl-2,2'-bi(1,3,2-dioxaborolane) (48.58 g, 0.191 mol), Pd(dppf)Cl$_2$ (5.2 g, 5 mol), KOAc (37.55 g, 0.383 mol), and 1,4-dioxane (500 ml) were mixed under nitrogen flow, and then the resulting mixture was stirred at 130° C. for 12 hours.

After the reaction was terminated, 5-(4,4,5,5-tetramethyl-1,3,2-dioxaborolan-2-yl)-1H-indole (22.32 g, yield 72%) was obtained by performing extraction with ethyl acetate, removing moisture over MgSO$_4$, and purifying the residue with column chromatography [Hexane:ethyl acetate (EA)=10:1 (v/v)].

$^1$H-NMR: δ 1.24 (s, 12H), 6.45 (d, 1H), 7.27 (d, 1H), 7.42 (d, 1H), 7.52 (d, 1H), 7.95 (s, 1H), 8.21 (s, 1H)

<Step 2> Synthesis of 5-(5-bromo-2-nitrophenyl)-1H-indole

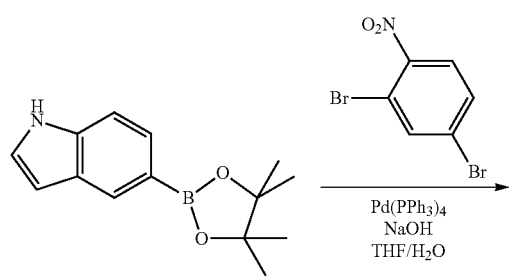

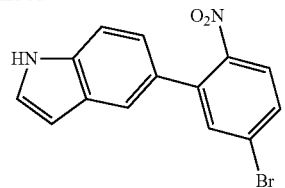

The 5-(4,4,5,5-tetramethyl-1,3,2-dioxaborolan-2-yl)-1H-indole (22 g, 90.49 mmol) synthesized in <Step 1> of Preparation Example 1 was mixed with 2,4-dibromo-1-nitrobenzene (21.18 g, 75.41 mmol), NaOH (9.05 g, 226.24 mmol), and THF/H$_2$O (400 ml/200 ml) under nitrogen flow, Pd(PPh$_3$)$_4$ (4.36 g, 5 mol) was added thereto at 40° C., and then the resulting mixture was stirred at 80° C. for 12 hours.

After the reaction was terminated, an organic layer was obtained by performing extraction with methylene chloride, adding MgSO$_4$ thereto, and filtering the product. 5-(5-bromo-2-nitrophenyl)-1H-indole (9.6 g, yield 40%) was obtained by removing the solvent from the obtained organic layer, and then purifying the residue with column chromatography [Hexane:EA=3:1 (v/v)].

<Step 3> Synthesis of 5-(5-bromo-2-nitrophenyl)-1-phenyl-1H-indole

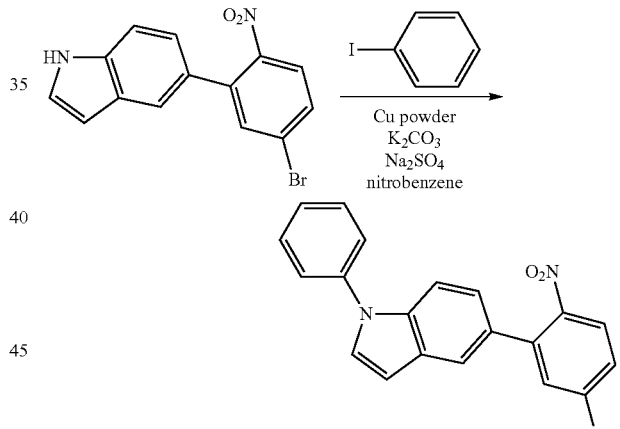

The 5-(5-bromo-2-nitrophenyl)-1H-indole (14.64 g, 46.17 mmol) obtained in <Step 2> of Preparation Example 1, iodobenzene (14.13 g, 69.26 mmol), Cu powder (0.29 g, 4.62 mmol), K$_2$CO$_3$ (6.38 g, 46.17 mmol), Na$_2$SO$_4$ (6.56 g, 46.17 mmol), and nitrobenzene (200 ml) were mixed under nitrogen flow, and then the resulting mixture was stirred at 190° C. for 12 hours.

After the reaction was terminated, nitrobenzene was removed, the organic layer was separated by methylene chloride, and water was removed from the separated organic layer by using MgSO$_4$. 5-(5-bromo-2-nitrophenyl)-1-phenyl-1H-indole (12.89 g, yield 71%) was obtained by removing the solvent from the organic layer from which water had been removed, and then purifying the residue with column chromatography [Hexane:methylene chloride (MC)=3:1 (v/v)].

\<Step 4\> Synthesis of 7-bromo-3-phenyl-3,10-dihydropyrrolo[3,2-a]carbazole

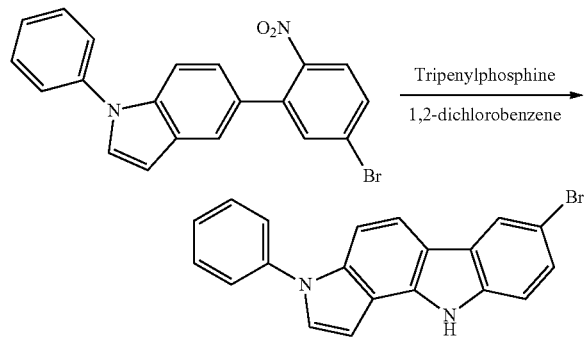

The 5-(5-bromo-2-nitrophenyl)-1-phenyl-1H-indole (6.25 g, 15.91 mmol) obtained in \<Step 3\> of Preparation Example 1, triphenylphosphine (10.43 g, 39.77 mmol), and 1,2-dichlorobenzene (50 ml) were mixed under nitrogen flow, and the resulting mixture was stirred for 12 hours.

After the reaction was terminated, an organic layer was obtained by removing 1,2-dichlorobenzene, and then performing extraction with dichloromethane. 7-bromo-3-phenyl-3,10-dihydropyrrolo[3,2-a]carbazole (3.04 g, yield 53%) was obtained by removing water from the obtained organic layer using MgSO$_4$, and then purifying the residue with column chromatography [Hexane:MC=3:1 (v/v)].

\<Step 5\> Synthesis of Compound IC-1

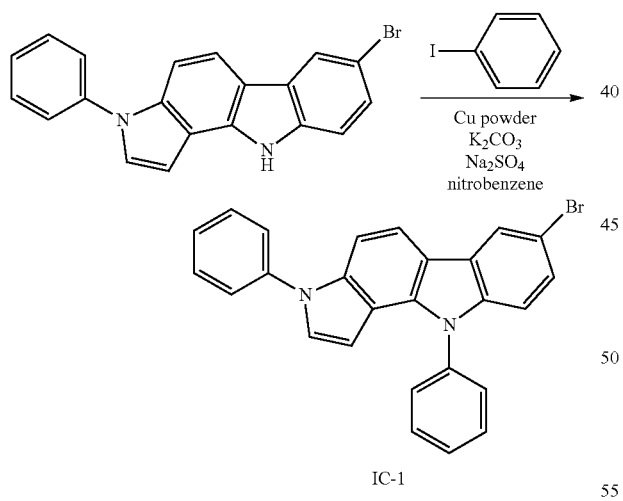

The 7-bromo-3-phenyl-3,10-dihydropyrrolo[3,2-a]carbazole (5 g, 13.84 mmol) obtained in \<Step 4\> of Preparation Example 1, iodobenzene (4.24 g, 20.76 mmol), Cu powder (0.09 g, 1.38 mmol), K$_2$CO$_3$ (1.91 g, 13.84 mmol), Na$_2$SO$_4$ (1.97 g, 13.84 mmol), and nitrobenzene (70 ml) were mixed under nitrogen flow, and then the resulting mixture was stirred at 190° C. for 12 hours.

After the reaction was terminated, nitrobenzene was removed, the organic layer was separated by methylene chloride, and water was removed from the separated organic layer by using MgSO$_4$. Compound IC-1 (3.63 g, yield 60%) was obtained by removing the solvent from the organic layer from which water had been removed, and then purifying the residue with column chromatography [Hexane:MC=3:1 (v:v)].

[Preparation Example 2] Synthesis of Compound IC-2

\<Step 1\> Synthesis of 4-(4,4,5,5-tetramethyl-1,3,2-dioxaborolan-2-yl)-1H-indole

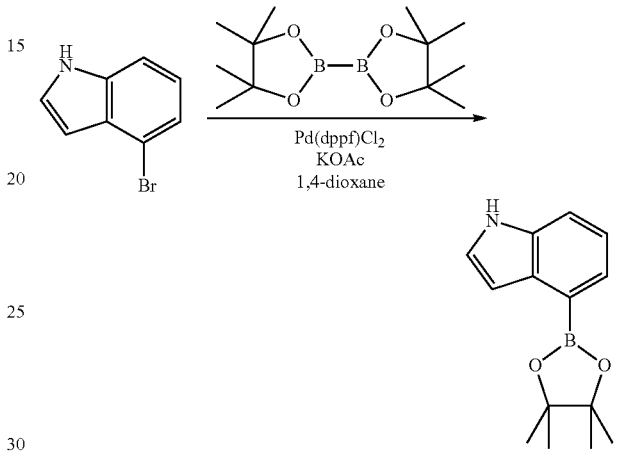

4-(4,4,5,5-tetramethyl-1,3,2-dioxaborolan-2-yl)-1H-indole was obtained by performing the same procedure as in \<Step 1\> of Preparation Example 1, except that 4-bromo-1H-indole (25 g, 0.128 mol) was used instead of the 5-bromo-1H-indole used in \<Step 1\> of Preparation Example 1.

\<Step 2\> Synthesis of 4-(5-bromo-2-nitrophenyl)-1H-indole

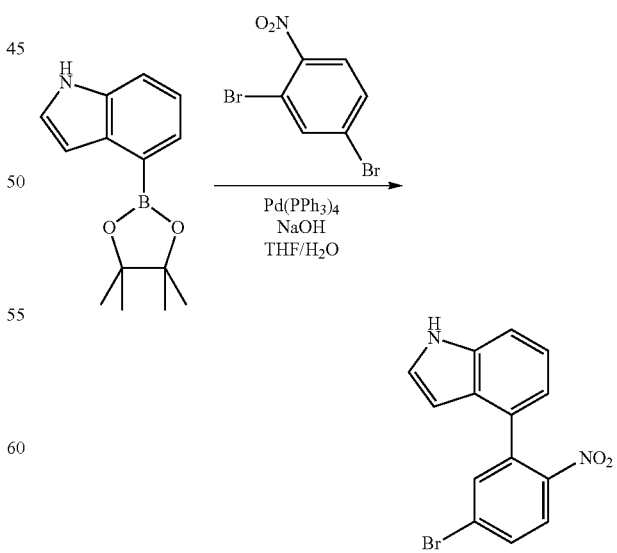

4-(2-nitrophenyl)-1H-indole was obtained by performing the same procedure as in \<Step 2\> of Preparation 1, except that the 4-(4,4,5,5-tetramethyl-1,3,2-dioxaborolan-2-yl)-1H-indole (22 g, 90.49 mmol) synthesized in <Step 1> of Preparation Example 2 was used instead of the 5-(4,4,5,5-tetramethyl-1,3,2-dioxaborolan-2-yl)-1H-indole used in <Step 2> of Preparation Example 1.

<Step 3> Synthesis of 4-(5-bromo-2-nitrophenyl)-1-phenyl-1H-indole

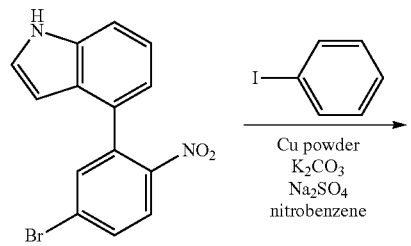

4-(2-nitrophenyl)-1-phenyl-1H-indole was obtained by performing the same procedure as in <Step 3> of Preparation Example 1, except that the 4-(2-nitrophenyl)-1H-indole (14.64 g, 46.17 mmol) synthesized in <Step 2> of Preparation Example 2 was used instead of the 5-(5-bromo-2-nitrophenyl)-1H-indole used in <Step 3> of Preparation Example 1.

<Step 4> Synthesis of 9-bromo-3-phenyl-3,6-dihydropyrrolo[2,3-c]carbazole

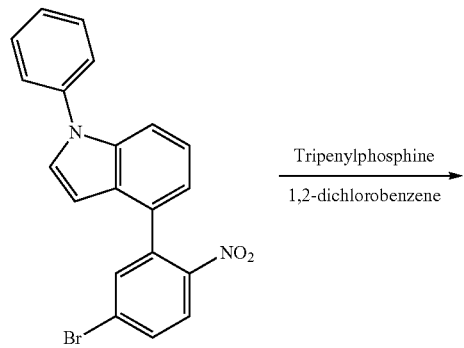

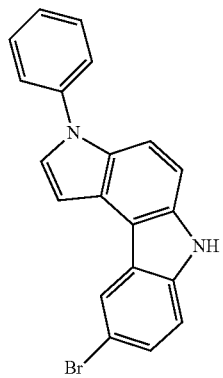

9-bromo-3-phenyl-3,6-dihydropyrrolo[2,3-c]carbazole was obtained by performing the same procedure as in <Step 4> of Preparation Example 1, except that the 4-(2-nitrophenyl)-1-phenyl-1H-indole (6.25 g, 15.91 mmol) synthesized in <Step 3> of Preparation Example 2 was used instead of the 5-(2-nitrophenyl)-1-phenyl-1H-indole used in <Step 4> of Preparation Example 1.

<Step 5> Synthesis of Compound IC-2

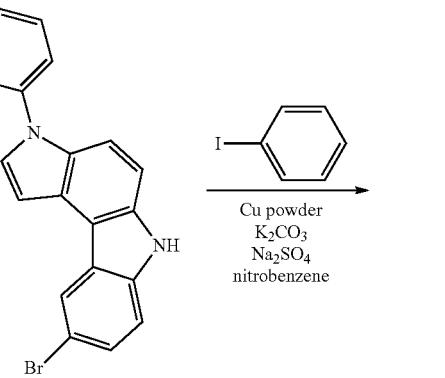

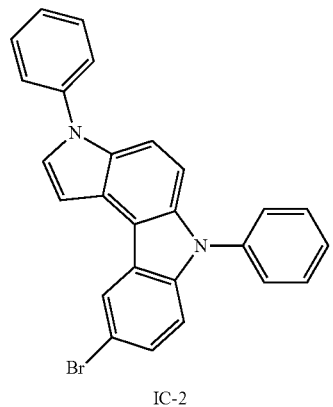

Compound IC-2 was obtained by performing the same procedure as in <Step 5> of Preparation Example 1, except that the 9-bromo-3-phenyl-3,6-dihydropyrrolo[2,3-c]carbazole (5 g, 13.84 mmol) synthesized in <Step 4> of Preparation Example 2 was used instead of the 7-bromo-3-phenyl-3,10-dihydropyrrolo[3,2-a]carbazole used in <Step 5> of Preparation Example 1.

[Preparation Example 3] Synthesis of Compound IC-3

<Step 1> Synthesis of 5-(4,4,5,5-tetramethyl-1,3,2-dioxaborolan-2-yl)-1H-indole

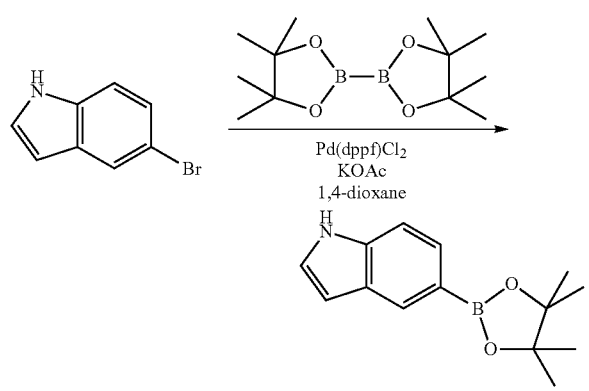

5-(4,4,5,5-tetramethyl-1,3,2-dioxaborolan-2-yl)-1H-indole was obtained by performing the same procedure as in <Step 1> of Preparation Example 1.

<Step 2> Synthesis of 5-(5-bromo-2-nitrophenyl)-1H-indole

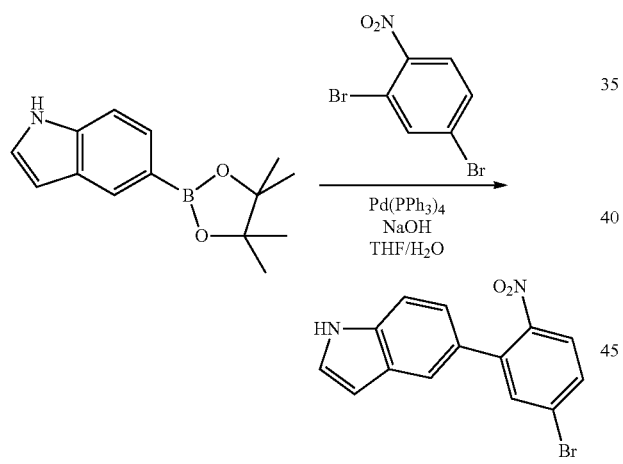

5-(5-bromo-2-nitrophenyl)-1H-indole was obtained by performing the same procedure as in <Step 2> of Preparation Example 1.

<Step 3> Synthesis of 5-(5-bromo-2-nitrophenyl)-1-phenyl-1H-indole

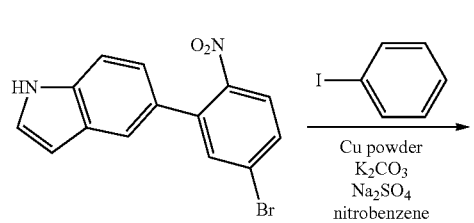

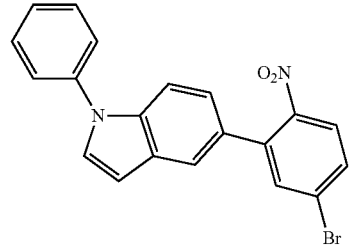

5-(5-bromo-2-nitrophenyl)-1-phenyl-1H-indole was obtained by performing the same procedure as in <Step 3> of Preparation Example 1.

<Step 4> Synthesis of 6-bromo-1-phenyl-1,9-dihydropyrrolo[2,3-b]carbazole

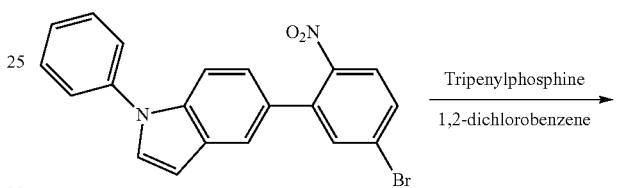

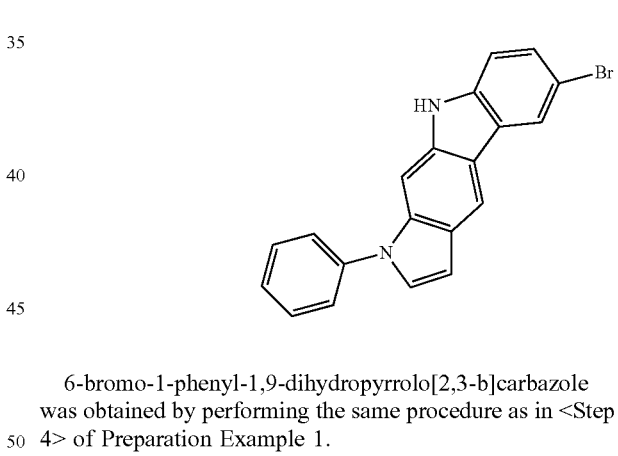

6-bromo-1-phenyl-1,9-dihydropyrrolo[2,3-b]carbazole was obtained by performing the same procedure as in <Step 4> of Preparation Example 1.

<Step 5> Synthesis of Compound IC-3

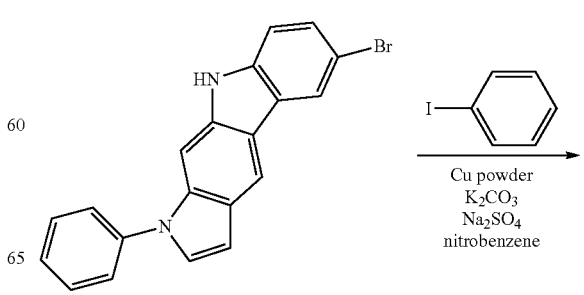

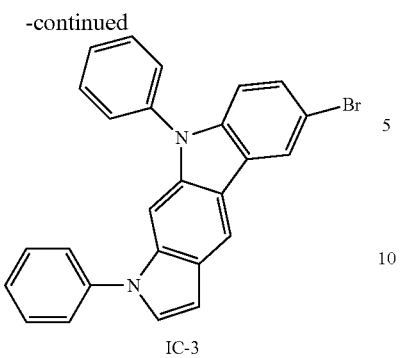

IC-3

Compound IC-3 was obtained by performing the same procedure as in <Step 5> of Preparation Example 1, except that 6-bromo-1-phenyl-1,9-dihydropyrrolo[2,3-b]carbazole (5 g, 13.84 mmol) was used instead of the 7-bromo-3-phenyl-3,10-dihydropyrrolo[3,2-a]carbazole used in <Step 5> of Preparation Example 1.

[Preparation Example 4] Synthesis of Compound IC-4

<Step 1> Synthesis of 6-(4,4,5,5-tetramethyl-1,3,2-dioxaborolan-2-yl)-1H-indole

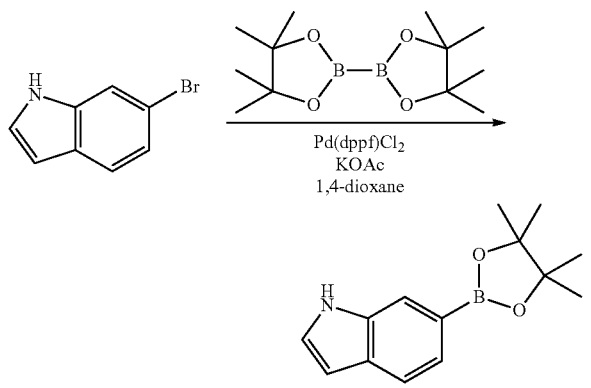

6-(4,4,5,5-tetramethyl-1,3,2-dioxaborolan-2-yl)-1H-indole was obtained by performing the same procedure as in <Step 1> of Preparation Example 1, except that 6-bromo-1H-indole (25 g, 0.128 mol) was used instead of the 5-bromo-1H-indole used in <Step 1> of Preparation Example 1.

<Step 2> Synthesis of 6-(5-bromo-2-nitrophenyl)-1H-indole

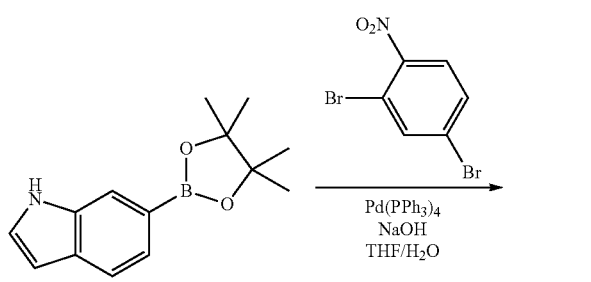

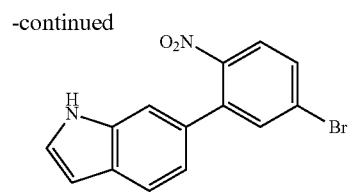

6-(5-bromo-2-nitrophenyl)-1H-indole was obtained by performing the same procedure as in <Step 2> of Preparation Example 1, except that 6-(4,4,5,5-tetramethyl-1,3,2-dioxaborolan-2-yl)-1H-indole (22 g, 90.49 mmol) was used instead of the 5-(4,4,5,5-tetramethyl-1,3,2-dioxaborolan-2-yl)-1H-indole used in <Step 2> of Preparation Example 1.

<Step 3> Synthesis of 6-(5-bromo-2-nitrophenyl)-1-phenyl-1H-indole

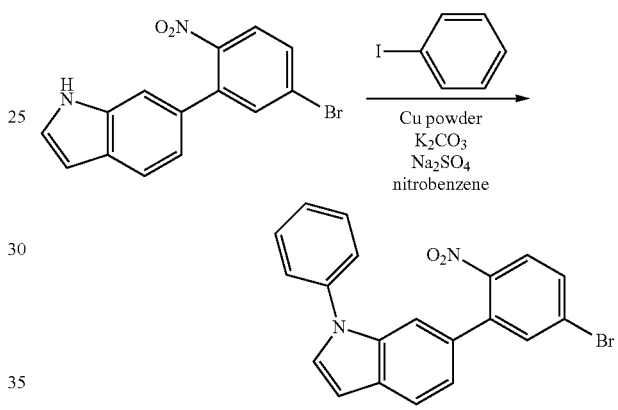

6-(5-bromo-2-nitrophenyl)-1-phenyl-1H-indole was obtained by performing the same procedure as in <Step 3> of Preparation Example 1, except that 6-(5-bromo-2-nitrophenyl)-1H-indole (14.64 g, 46.17 mmol) was used instead of the 5-(5-bromo-2-nitrophenyl)-1H-indole used in <Step 3> of Preparation Example 1.

<Step 4> Synthesis of 8-bromo-1-phenyl-1,5-dihydropyrrolo[3,2-b]carbazole

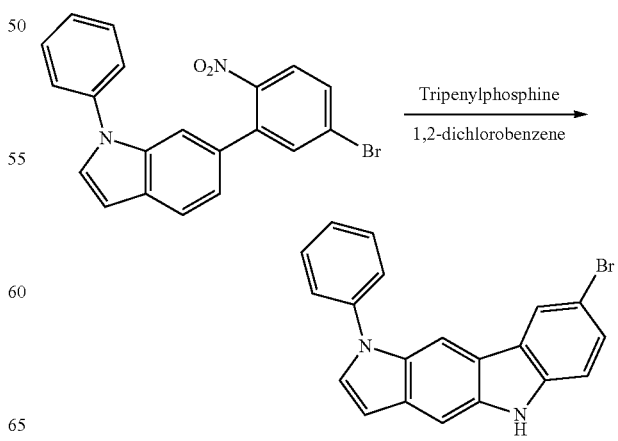

8-bromo-1-phenyl-1,5-dihydropyrrolo[3,2-b]carbazole was obtained by performing the same procedure as in <Step 4> of Preparation Example 1, except that 6-(5-bromo-2-nitrophenyl)-1-phenyl-1H-indole (6.25 g, 15.91 mmol) was used instead of the 5-(5-bromo-2-nitrophenyl)-1-phenyl-1H-indole used in <Step 4> of Preparation Example 1.

<Step 5> Synthesis of Compound IC-4

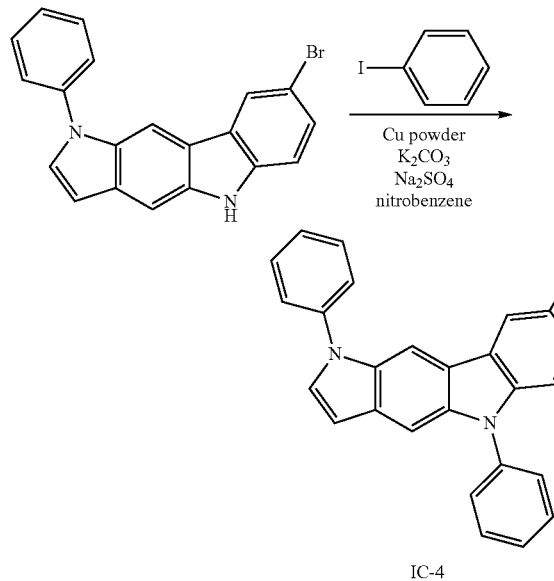

IC-4

Compound IC-4 was obtained by performing the same procedure as in <Step 5> of Preparation Example 1, except that the 8-bromo-1-phenyl-1,5-dihydropyrrolo[3,2-b]carbazole (5 g, 13.84 mmol) synthesized in <Step 4> of Preparation Example 4 was used instead of the 7-bromo-3-phenyl-3,10-dihydropyrrolo[3,2-a]carbazole used in <Step 5> of Preparation Example 1.

[Preparation Example 5] Synthesis of Compound IC-5

<Step 1> Synthesis of 6-(4,4,5,5-tetramethyl-1,3,2-dioxaborolan-2-yl)-1H-indole

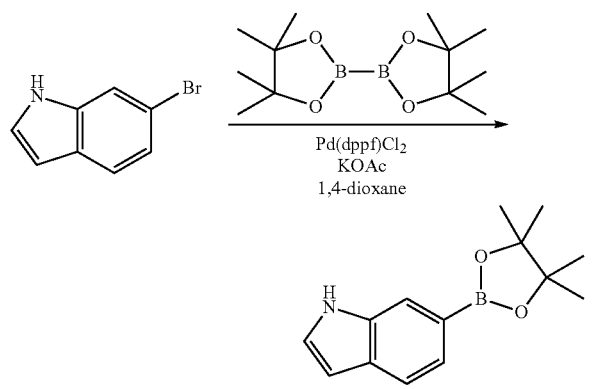

6-(4,4,5,5-tetramethyl-1,3,2-dioxaborolan-2-yl)-1H-indole was obtained by performing the same procedure as in <Step 1> of Preparation Example 1, except that 6-bromo-1H-indole (25 g, 0.128 mol) was used instead of the 5-bromo-1H-indole used in <Step 1> of Preparation Example 1.

<Step 2> Synthesis of 6-(5-bromo-2-nitrophenyl)-1H-indole

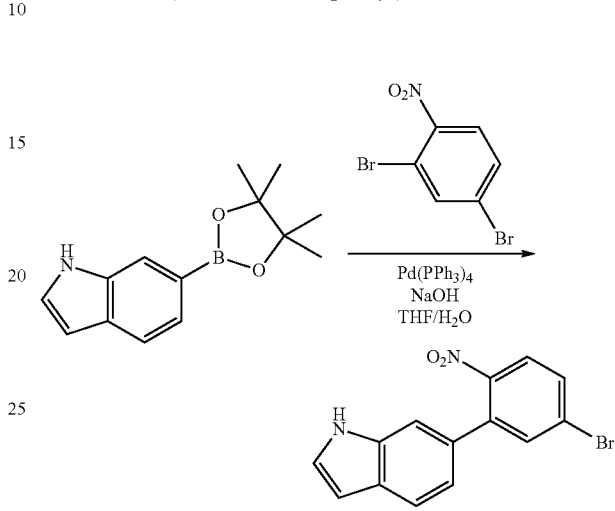

6-(5-bromo-2-nitrophenyl)-1H-indole was obtained by performing the same procedure as in <Step 2> of Preparation Example 1, except that the 6-(4,4,5,5-tetramethyl-1,3,2-dioxaborolan-2-yl)-1H-indole (22 g, 90.49 mmol) synthesized in <Step 1> of Preparation Example 5 was used instead of the 5-(4,4,5,5-tetramethyl-1,3,2-dioxaborolan-2-yl)-1H-indole used in <Step 2> of Preparation Example 1.

<Step 3> Synthesis of 6-(5-bromo-2-nitrophenyl)-1-phenyl-1H-indole

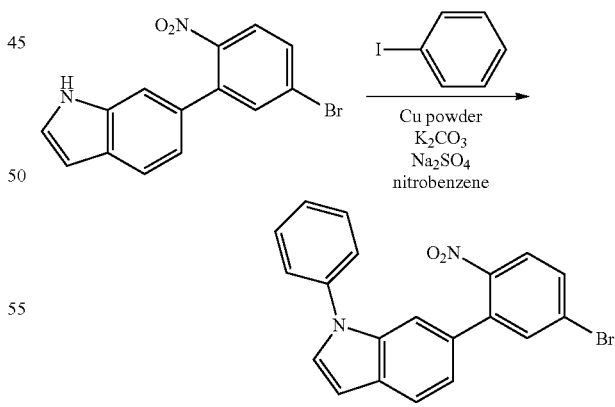

6-(5-bromo-2-nitrophenyl)-1-phenyl-1H-indole was obtained by performing the same procedure as in <Step 3> of Preparation Example 1, except that the 6-(5-bromo-2-nitrophenyl)-1H-indole (14.64 g, 46.17 mmol) synthesized in <Step 2> of Preparation Example 5 was used instead of the 5-(5-bromo-2-nitrophenyl)-1H-indole used in <Step 3> of Preparation Example 1.

\<Step 4\> Synthesis of 7-bromo-1-phenyl-1,10-dihydropyrrolo[2,3-a]carbazole

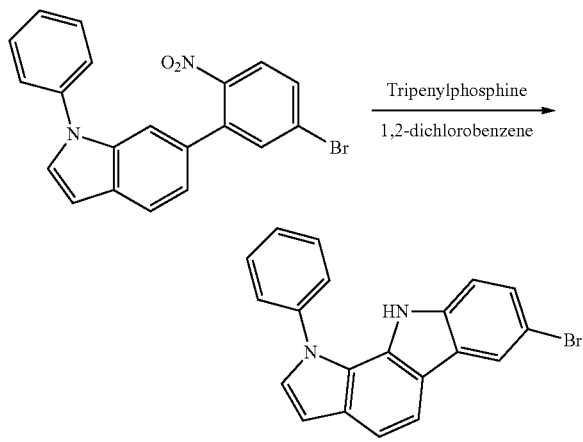

7-bromo-1-phenyl-1,10-dihydropyrrolo[2,3-a]carbazole was obtained by performing the same procedure as in \<Step 4\> of Preparation Example 1, except that the 6-(5-bromo-2-nitrophenyl)-1-phenyl-1H-indole (6.25 g, 15.91 mmol) synthesized in \<Step 3\> of Preparation Example 5 was used instead of the 5-(5-bromo-2-nitrophenyl)-1-phenyl-1H-indole used in \<Step 4\> of Preparation Example 1.

\<Step 5\> Synthesis of Compound IC-5

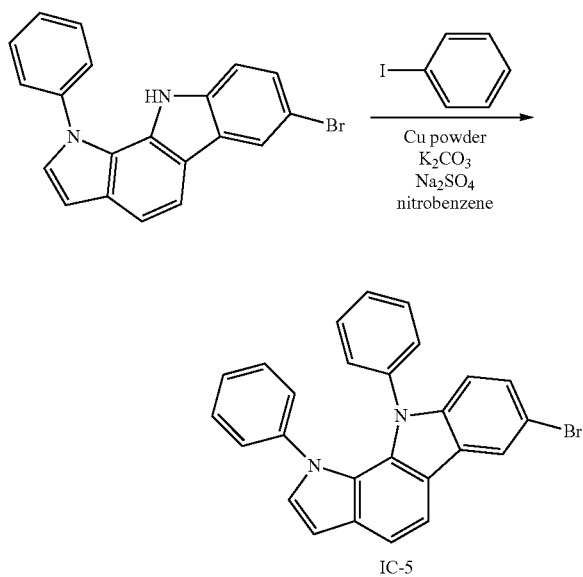

Compound IC-5 was obtained by performing the same procedure as in \<Step 5\> of Preparation Example 1, except that the 7-bromo-1-phenyl-1,10-dihydropyrrolo[2,3-a]carbazole (5 g, 13.84 mmol) synthesized in \<Step 4\> of Preparation Example 5 was used instead of the 7-bromo-3-phenyl-3,10-dihydropyrrolo[3,2-a]carbazole used in \<Step 5\> of Preparation Example 1.

[Preparation Example 6] Synthesis of Compound IC-6

\<Step 1\> Synthesis of 7-(4,4,5,5-tetramethyl-1,3,2-dioxaborolan-2-yl)-1H-indole

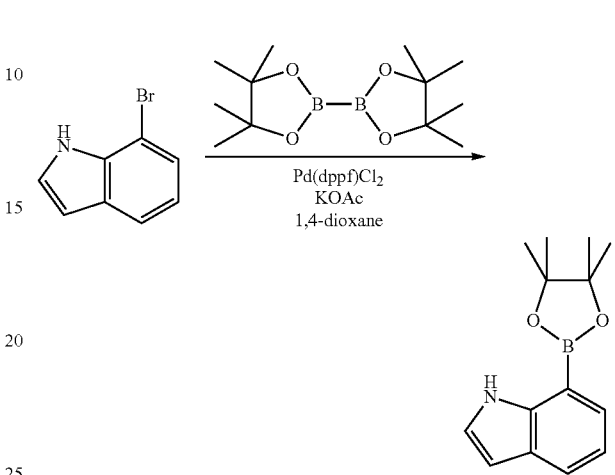

7-(4,4,5,5-tetramethyl-1,3,2-dioxaborolan-2-yl)-1H-indole was obtained by performing the same procedure as in \<Step 1\> of Preparation Example 1, except that 7-bromo-1H-indole (25 g, 0.128 mol) was used instead of the 5-bromo-1H-indole used in \<Step 1\> of Preparation Example 1.

\<Step 2\> Synthesis of 7-(5-bromo-2-nitrophenyl)-1H-indole

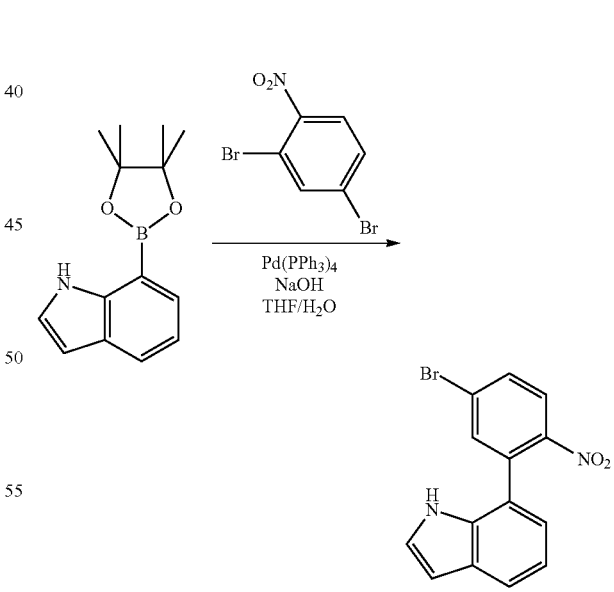

7-(5-bromo-2-nitrophenyl)-1H-indole was obtained by performing the same procedure as in \<Step 2\> of Preparation Example 1, except that the 7-(4,4,5,5-tetramethyl-1,3,2-dioxaborolan-2-yl)-1H-indole (22 g, 90.49 mmol) synthesized in \<Step 1\> of Preparation Example 6 was used instead of the 5-(4,4,5,5-tetramethyl-1,3,2-dioxaborolan-2-yl)-1H-indole used in \<Step 2\> of Preparation Example 1.

\<Step 3\> Synthesis of 7-(5-bromo-2-nitrophenyl)-1-phenyl-1H-indole

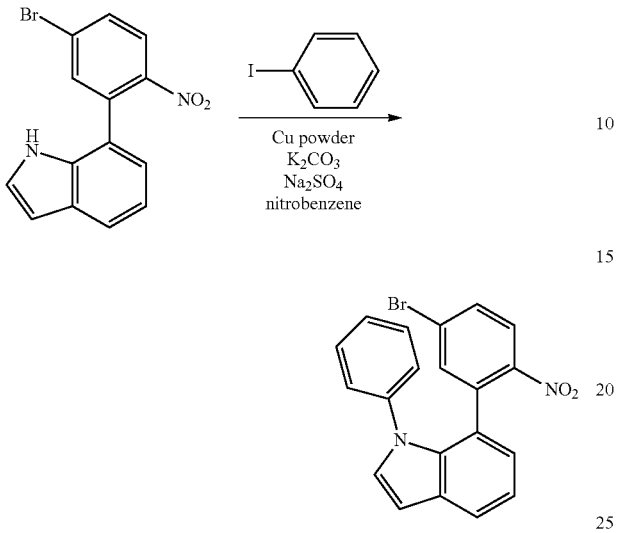

7-(5-bromo-2-nitrophenyl)-1-phenyl-1H-indole was obtained by performing the same procedure as in \<Step 3\> of Preparation Example 1, except that the 7-(5-bromo-2-nitrophenyl)-1H-indole (14.64 g, 46.17 mmol) synthesized in \<Step 2\> of Preparation Example 6 was used instead of the 5-(5-bromo-2-nitrophenyl)-1H-indole used in \<Step 3\> of Preparation Example 1.

\<Step 4\> Synthesis of 9-bromo-1-phenyl-1,6-dihydropyrrolo[3,2-c]carbazole

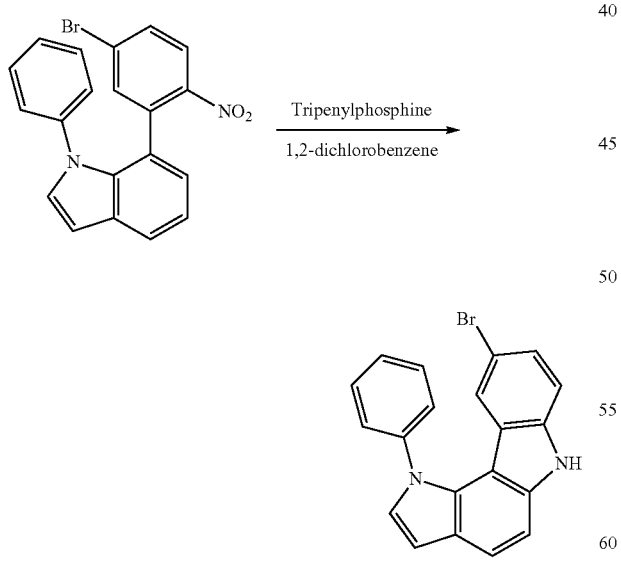

9-bromo-1-phenyl-1,6-dihydropyrrolo[3,2-c]carbazole was obtained by performing the same procedure as in \<Step 4\> of Preparation Example 1, except that the 7-(5-bromo-2-nitrophenyl)-1-phenyl-1H-indole (6.25 g, 15.91 mmol) synthesized in \<Step 4\> of Preparation Example 6 was used instead of the 5-(5-bromo-2-nitrophenyl)-1-phenyl-1H-indole used in \<Step 4\> of Preparation Example 1.

\<Step 5\> Synthesis of Compound IC-6

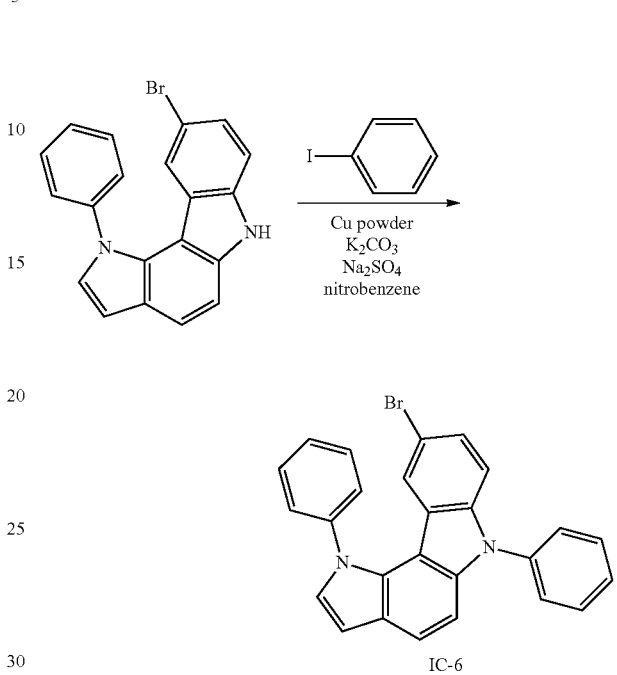

Compound IC-6 was synthesized by performing the same procedure as in \<Step 5\> of Preparation Example 1, except that the 9-bromo-1-phenyl-1,6-dihydropyrrolo[3,2-c]carbazole (5 g, 13.84 mmol) synthesized in \<Step 4\> of Preparation Example 6 was used instead of the 7-bromo-3-phenyl-3,10-dihydropyrrolo[3,2-a]carbazole used in \<Step 5\> of Preparation Example 1.

[Preparation Example 7] Synthesis of IC-7

\<Step 1\> Synthesis of 5-(4,4,5,5-tetramethyl-1,3,2-dioxaborolan-2-yl)-1H-indole

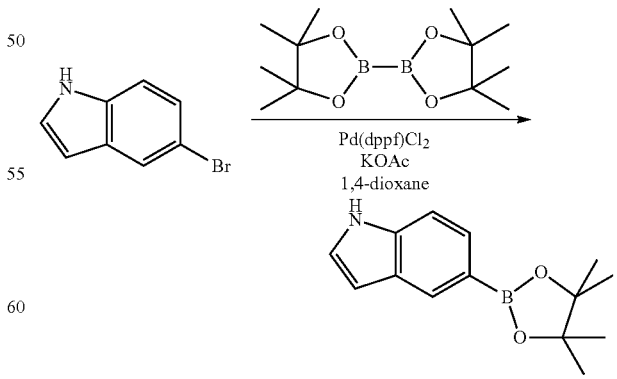

5-(4,4,5,5-tetramethyl-1,3,2-dioxaborolan-2-yl)-1H-indole was obtained by performing the same procedure as in \<Step 1\> of Preparation Example 1.

\<Step 2\> Synthesis of 5-(5-bromo-2-nitrophenyl)-1H-indole

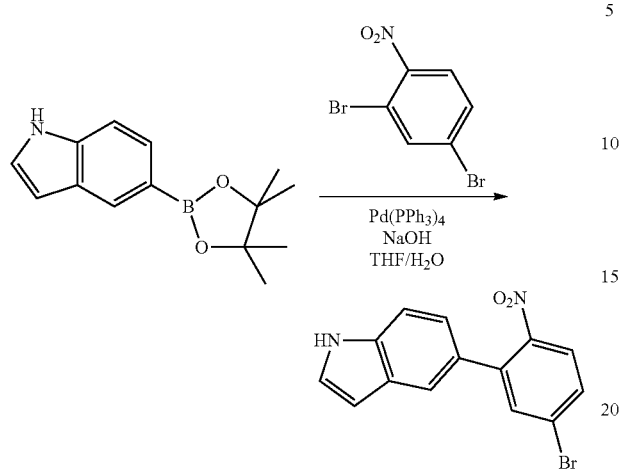

5-(5-bromo-2-nitrophenyl)-1H-indole was obtained by performing the same procedure as in \<Step 2\> of Preparation Example 1.

\<Step 3\> Synthesis of 5-(5-bromo-2-nitrophenyl)-1-phenyl-1H-indole

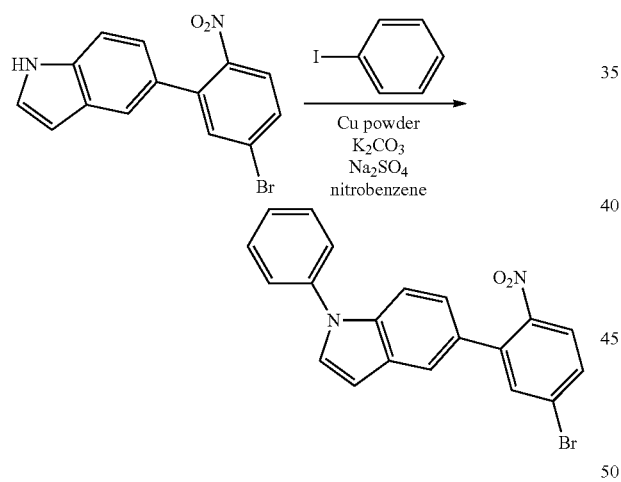

5-(5-bromo-2-nitrophenyl)-1-phenyl-1H-indole was obtained by performing the same procedure as in \<Step 3\> of Preparation Example 1.

\<Step 4\> Synthesis of 7-bromo-3-phenyl-3,10-dihydropyrrolo[3,2-a]carbazole

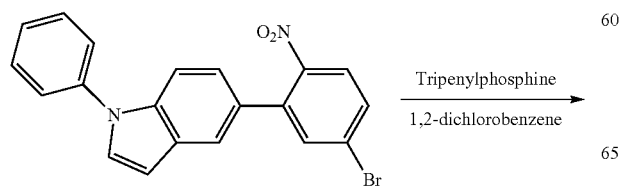

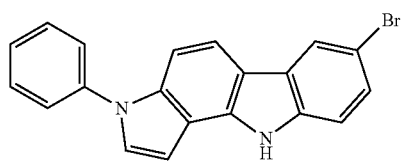

7-bromo-3-phenyl-3,10-dihydropyrrolo[3,2-a]carbazole was obtained by performing the same procedure as in \<Step 4\> of Preparation Example 1.

\<Step 5\> Synthesis of Compound IC-7

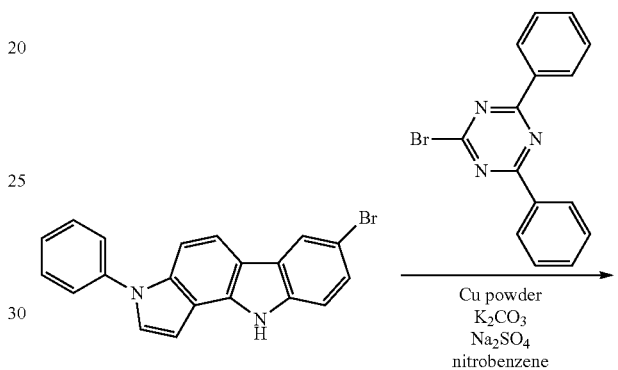

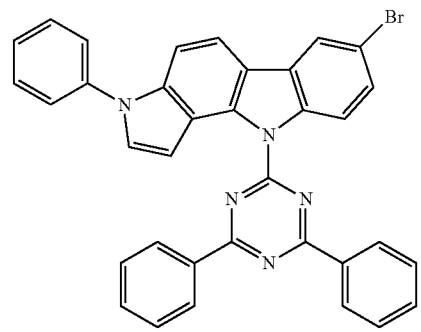

IC-7

Compound IC-7 was obtained by performing the same procedure as in \<Step 5\> of Preparation Example 1, except that 2-bromo-4,6-diphenyl-1,3,5-triazine (6.48 g, 20.76 mmol) was used instead of the iodobenzene used in \<Step 5\> of Preparation Example 1.

[Synthesis Example 1] Synthesis of Compound Mat-1

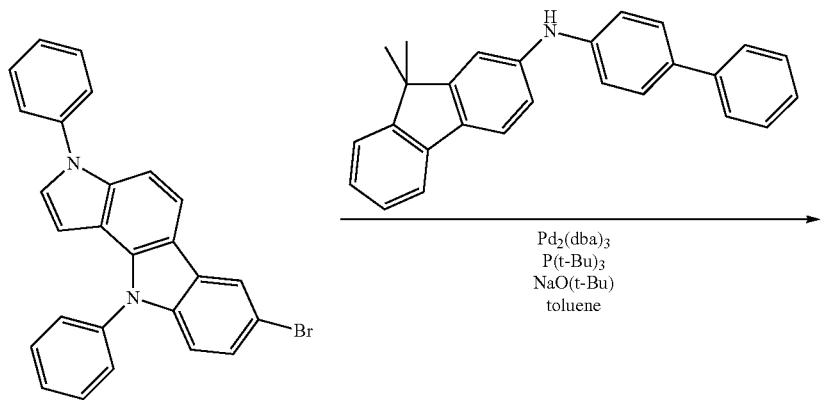

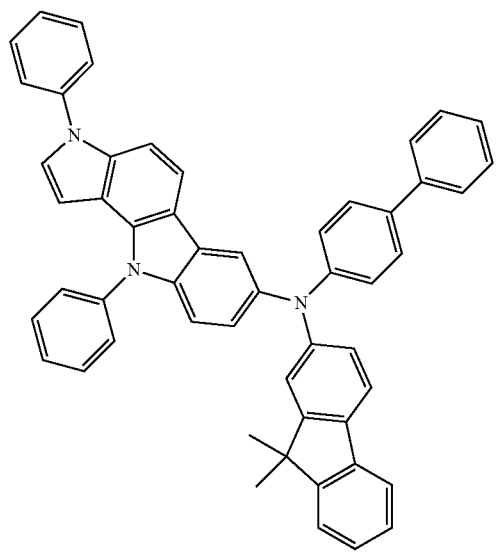

Mat-1

Compound IC-1 (10 g, 22.87 mmol) synthesized in Preparation Example 1, N-(biphenyl-4-yl)-9,9-dimethyl-9H-fluoren-2-amine (9.1 g, 25.16 mmol), sodium tert-butoxide (6.59 g, 68.61 mmol), tris(dibenzylideneacetone)dipalladium(0) (0.65 g, 0.6861 mmol), and tri-tert-butyl phosphine (0.14 g, 0.6861 mmol) were mixed under nitrogen flow, and then the resulting mixture was stirred under reflux in 220 ml of toluene overnight.

After the reaction was terminated, Mat-1 (9.85 g, yield 60%) was obtained by filtering the reaction solution through celite, removing the solvent, and then purifying the residue with column chromatography [Hexane:MC=4:1 (v:v)].

[Synthesis Example 2] Synthesis of Compound Mat-2
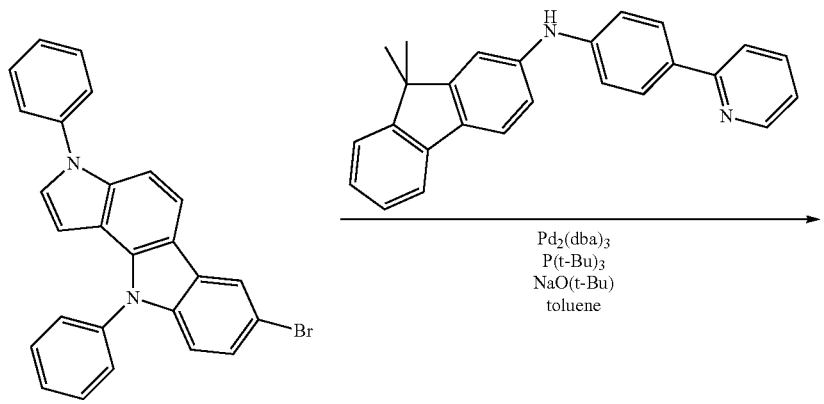
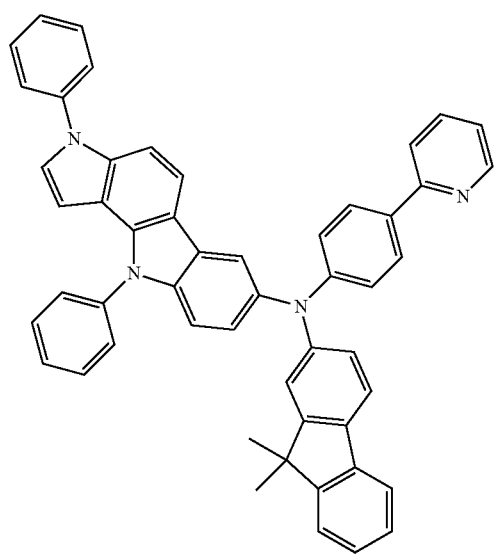
Mat-2
Compound Mat-2 was obtained by performing the same procedure as in Synthesis Example 1, except that 9,9-dimethyl-N-(4-(pyridin-2-yl)phenyl)-9H-fluoren-2-amine (9.1 g, 25.16 mmol) was used instead of the N-(biphenyl-4-yl)-9,9-dimethyl-9H-fluoren-2-amine used in Synthesis Example 1.
[Synthesis Example 3] Synthesis of Compound Mat-3
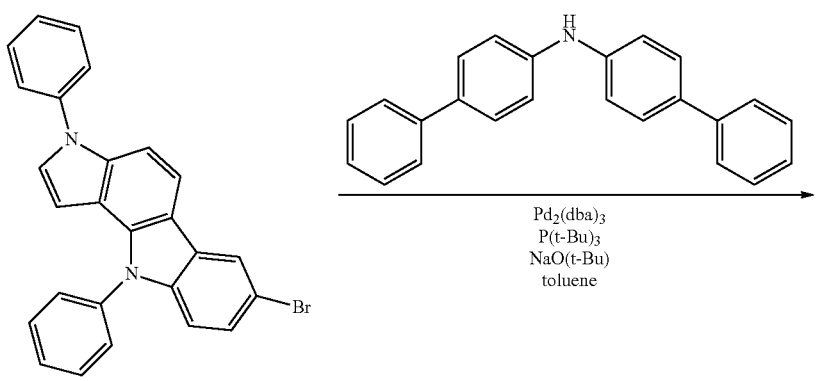

-continued
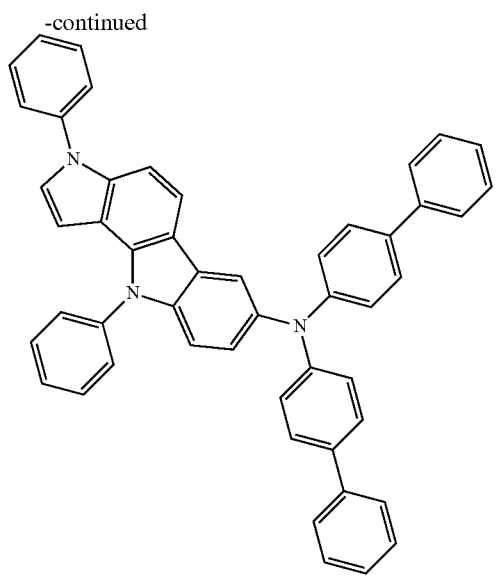
Mat-3
Compound Mat-3 was synthesized by performing the same procedure as in Synthesis Example 1, except that 9,9-dimethyl-N-(4-(pyridin-2-yl)phenyl)-9H-fluoren-2-amine (8.1 g, 25.16 mmol) was used instead of the N-(biphenyl-4-yl)-9,9-dimethyl-9H-fluoren-2-amine used in Synthesis Example 1.
[Synthesis Example 4] Synthesis of Compound Mat-4
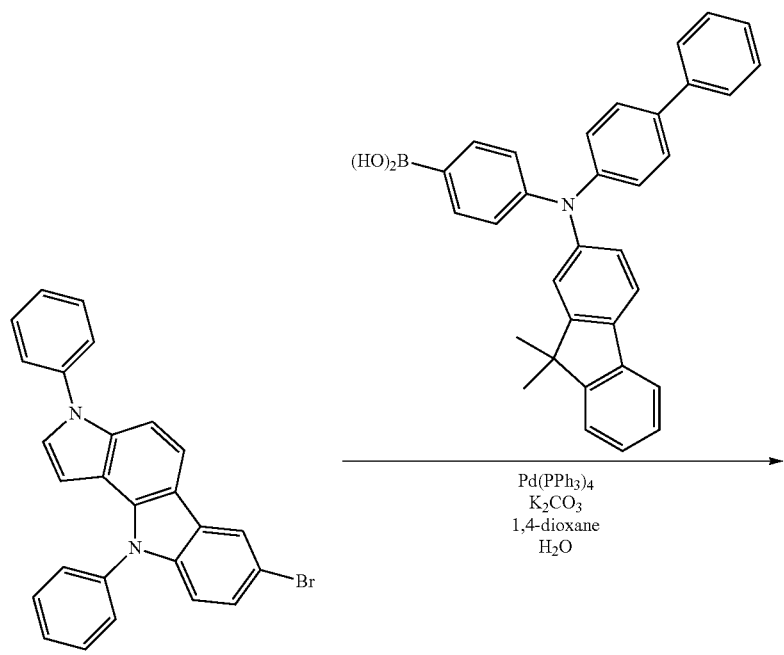

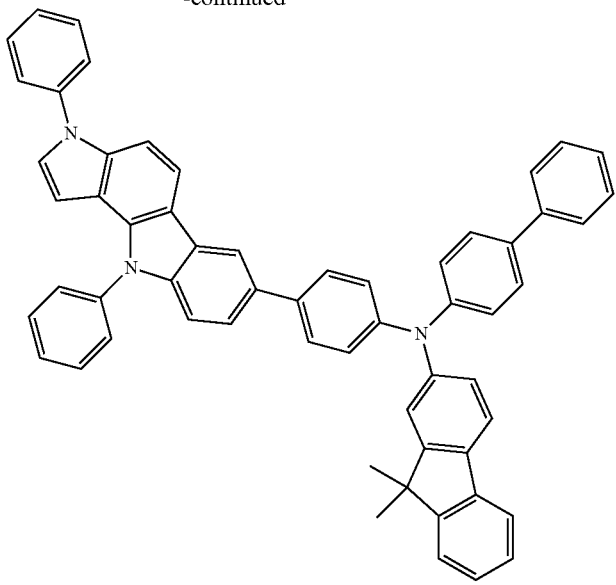

Mat-4

Compound IC-1 (10 g, 22.87 mmol) synthesized in Preparation Example 1, 4-(biphenyl-4-yl(9,9-dimethyl-9H-fluoren-2-yl)amino)phenylboronic acid (12.11 g, 25.16 mmol), tetrakis(triphenylphosphine)palladium(0) (0.79 g, 0.6861 mmol), and potassium carbonate (9.48 g, 68.61 mmol) were mixed under nitrogen flow, and then the resulting mixture was stirred under reflux in 220 ml of 1,4-dioxane and 35 ml of H$_2$O overnight.

After the reaction was terminated, the organic layer was separated with methylene chloride and water was removed from the separated organic layer by using MgSO$_4$. Compound Mat-4 (12.71 g, yield 70%) was obtained by removing the solvent from the organic layer from which water had been removed, and then purifying the residue with column chromatography [Hexane:MC=3:1 (v:v)].

Elemental Analysis: C, 89.25; H, 5.46; N, 5.29/HRMS [M]$^+$: 793

[Synthesis Example 5] Synthesis of Compound Mat-5

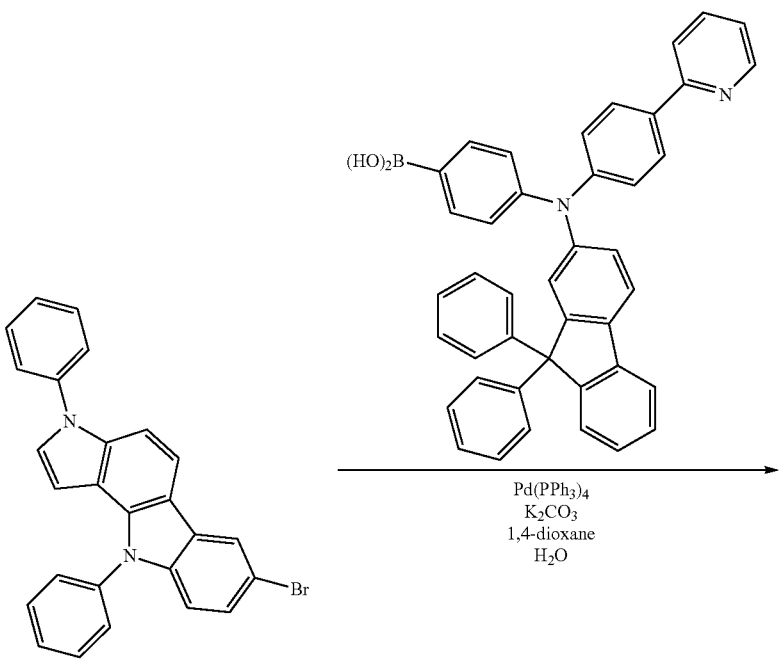

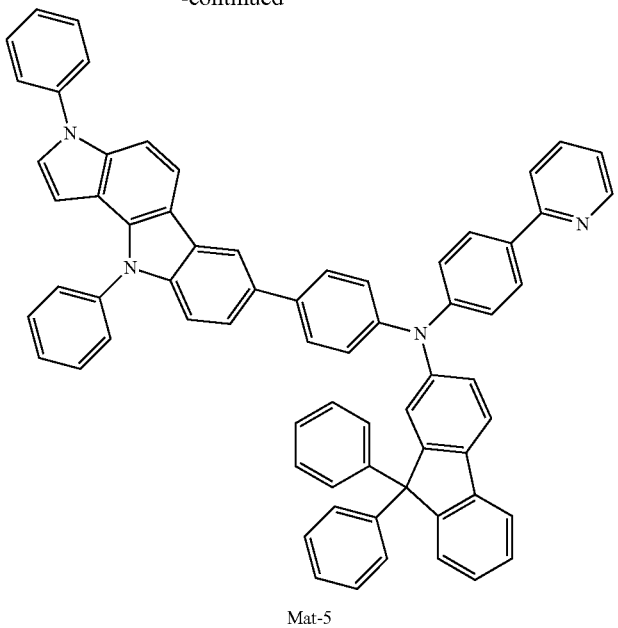

Mat-5

Compound Mat-5 was synthesized by performing the same procedure as in Synthesis Example 4, except that 4-((9,9-diphenyl-9H-fluoren-2-yl)(4-(pyridin-2-yl)phenyl)amino)phenylboronic acid (15.26 g, 25.16 mmol) was used instead of the 4-(biphenyl-4-yl(9,9-dimethyl-9H-fluoren-2yl)amino)phenylboronic acid used in Synthesis Example 4.

Elemental Analysis: C, 88.86; H, 5.04; N, 6.10/HRMS [M]+: 919

[Synthesis Example 6] Synthesis of Compound Mat-6

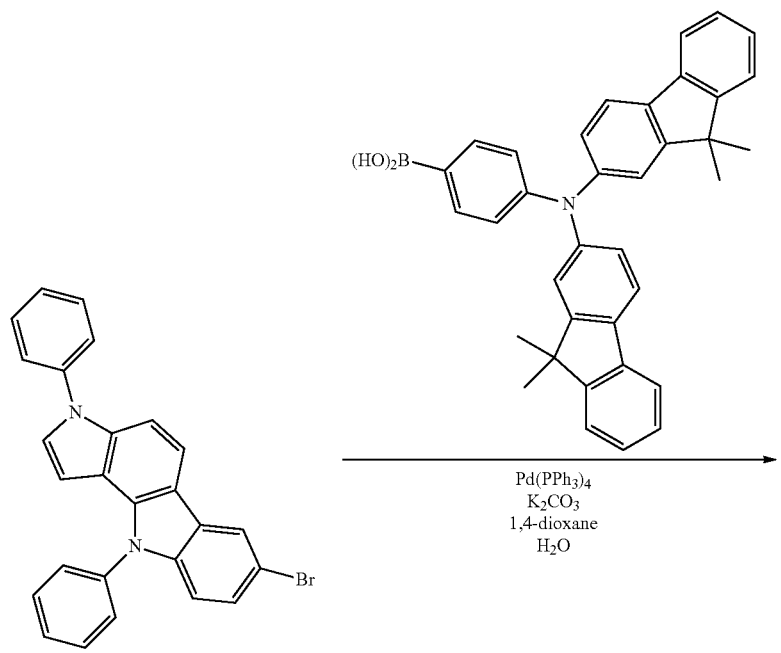

-continued

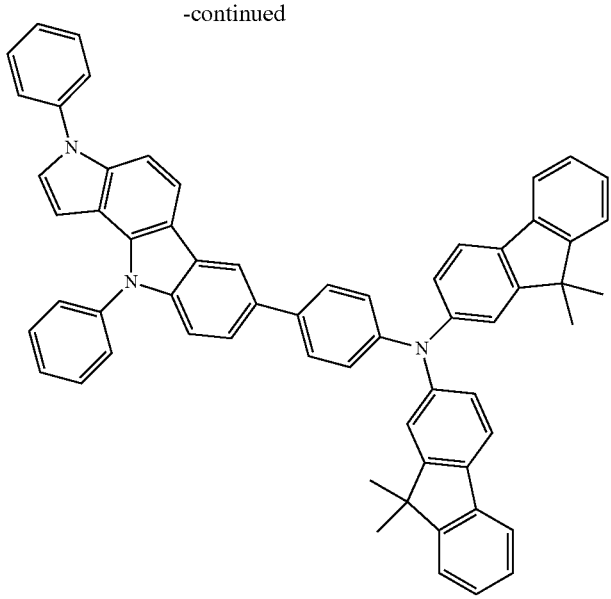

Mat-6

Compound Mat-6 was synthesized by performing the same procedure as in Synthesis Example 4, except that N-(4-bromophenyl)-N-(9,9-dimethyl-9H-fluoren-2-yl)-9,9-dimethyl-9H-fluoren-2-amine (13.1 g, 25.16 mmol) was used instead of the 4-(biphenyl-4-yl(9,9-dimethyl-9H-fluoren-2yl)amino)phenylboronic acid used in Synthesis Example 4.

Elemental Analysis: C, 89.28; H, 5.68; N, 5.04/HRMS [M]+: 834

[Synthesis Example 7] Synthesis of Compound Mat-7

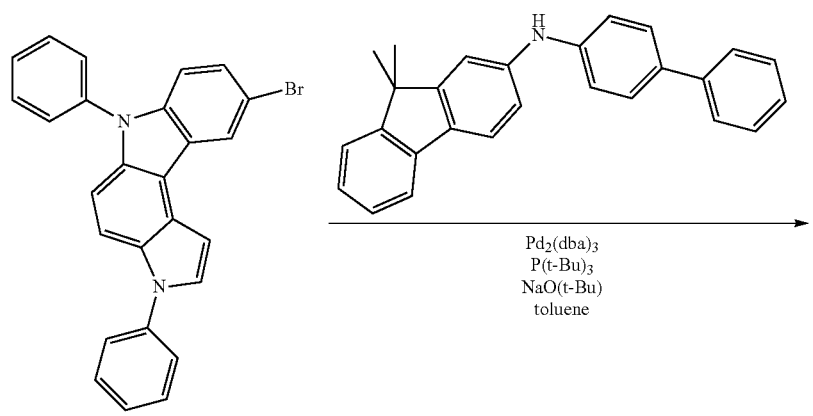

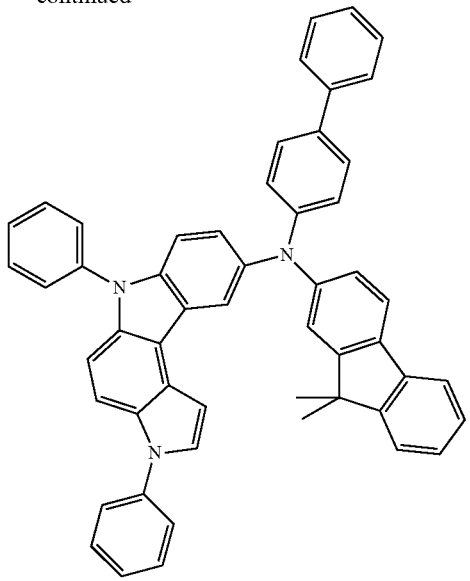
Mat-7
Compound Mat-7 was synthesized by performing the same procedure as in Synthesis Example 1, except that Compound IC-2 (10 g, 22.87 mmol) synthesized in Preparation Example 2 was used instead of Compound IC-1 used in Synthesis Example 1.
Elemental Analysis: C, 88.67; H, 5.48; N, 5.85/HRMS [M]+: 717
[Synthesis Example 8] Synthesis of Compound Mat-8
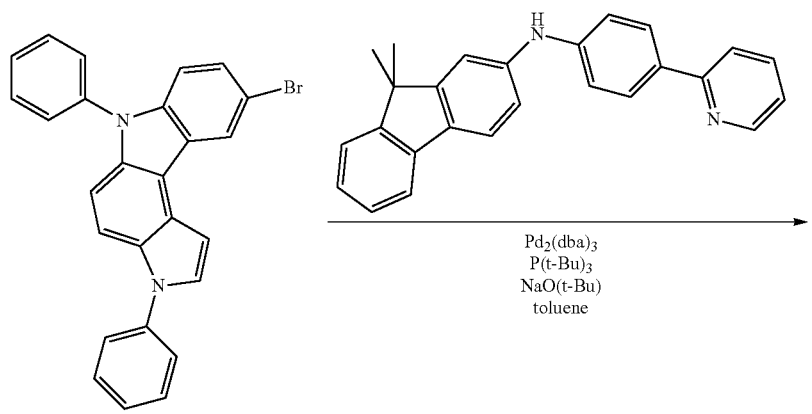

-continued

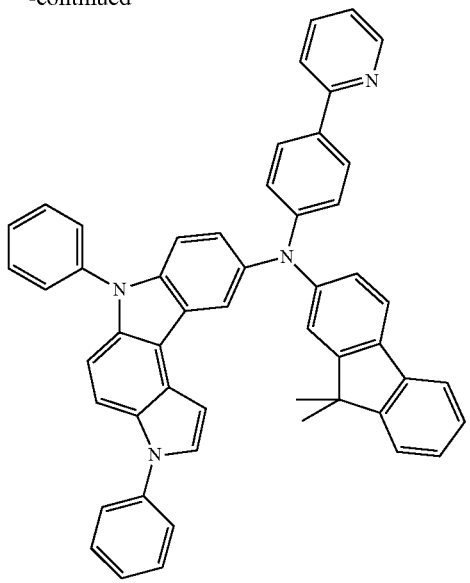

Mat-8

Compound Mat-8 was synthesized by performing the same procedure as in Synthesis Example 1, except that Compound IC-2 (10 g, 22.87 mmol) synthesized in Preparation Example 2 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

[Synthesis Example 9] Synthesis of Compound Mat-9

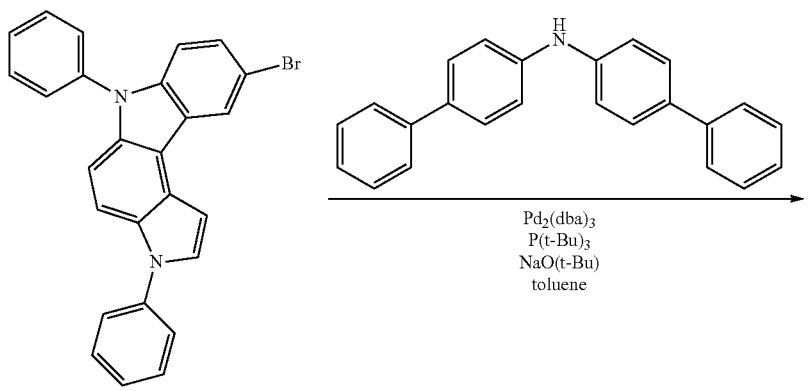

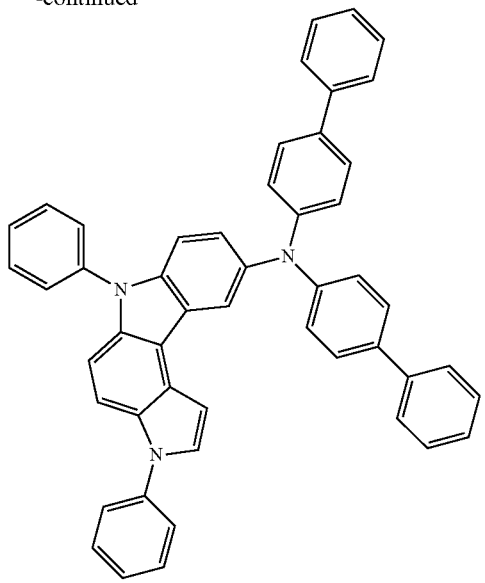

Mat-9

Compound Mat-9 was synthesized by performing the same procedure as in Synthesis Example 1, except that Compound IC-2 (10 g, 22.87 mmol) synthesized in Preparation Example 2 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

[Synthesis Example 10] Synthesis of Compound Mat-10

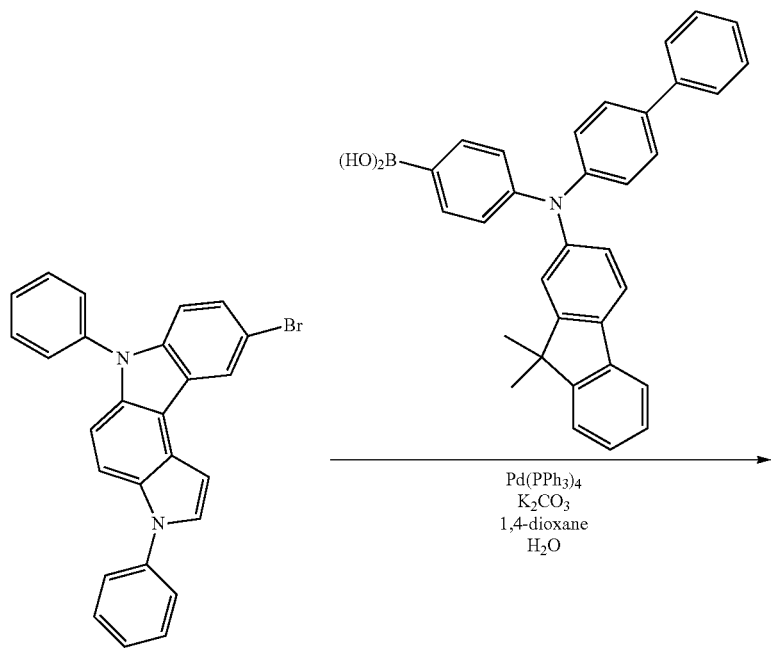

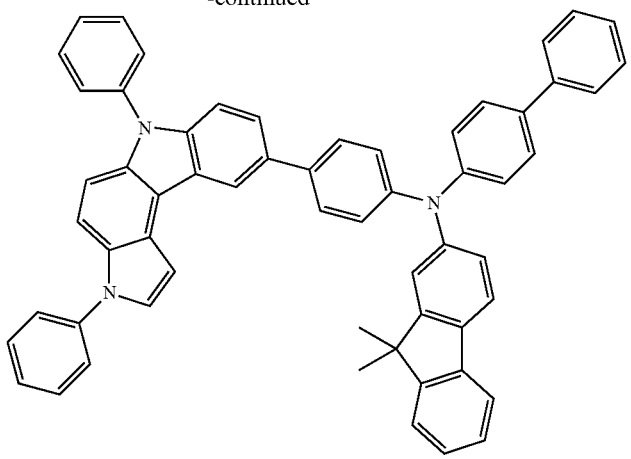
Mat-10
Compound Mat-10 was synthesized by performing the same procedure as in Synthesis Example 4, except that Compound IC-2 (10 g, 22.87 mmol) synthesized in Preparation Example 2 was used instead of Compound IC-1 used in Synthesis Example 4.
Elemental Analysis: C, 89.25; H, 5.46; N, 5.29/HRMS [M]+: 793
[Synthesis Example 11] Synthesis of Compound Mat-11
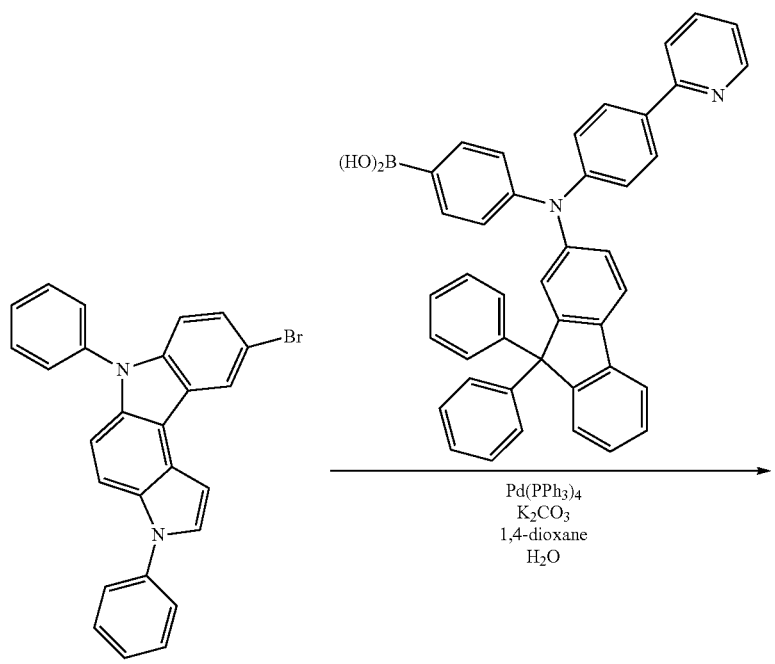

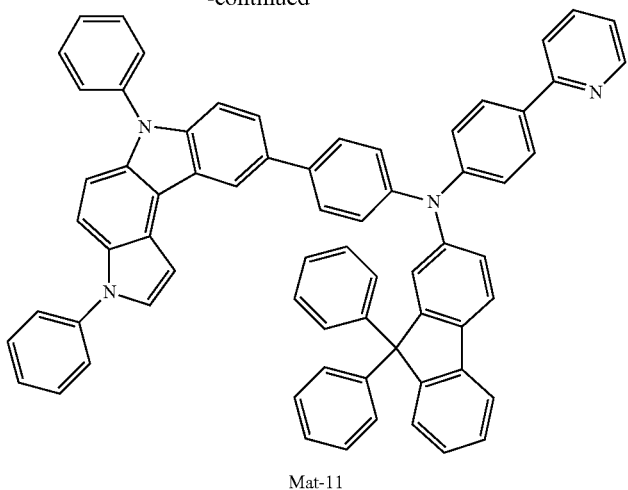

Mat-11

Compound Mat-11 was synthesized by performing the same procedure as in Synthesis Example 4, except that Compound IC-2 (10 g, 22.87 mmol) synthesized in Preparation Example 2 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

[Synthesis Example 12] Synthesis of Compound Mat-12

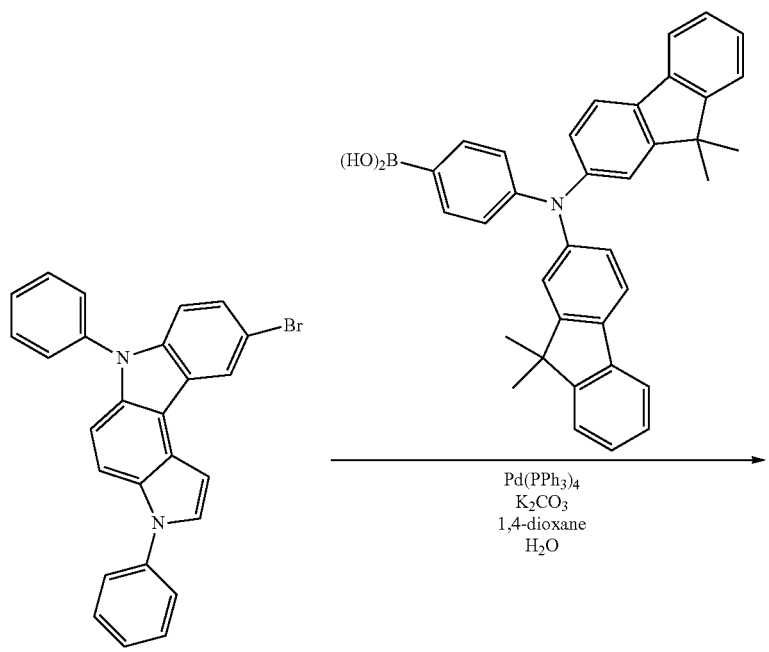

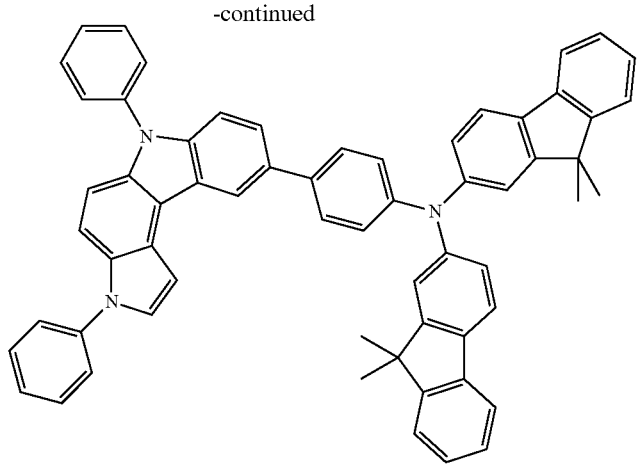

Mat-12

Compound Mat-12 was synthesized by performing the same procedure as in Synthesis Example 4, except that Compound IC-2 (10 g, 22.87 mmol) synthesized in Preparation Example 2 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

[Synthesis Example 13] Synthesis of Compound Mat-13

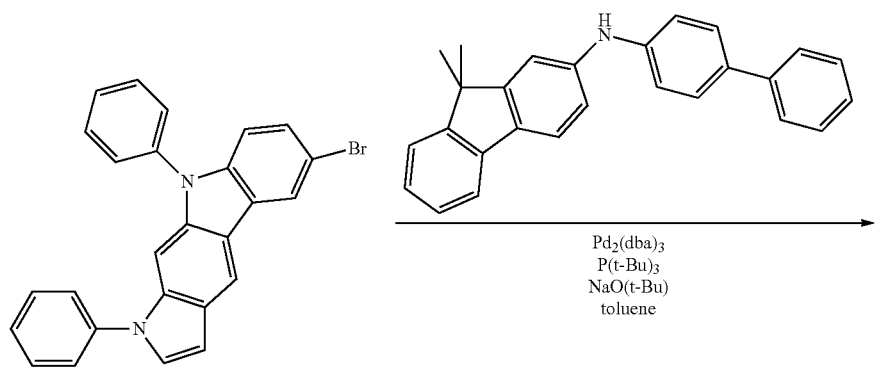

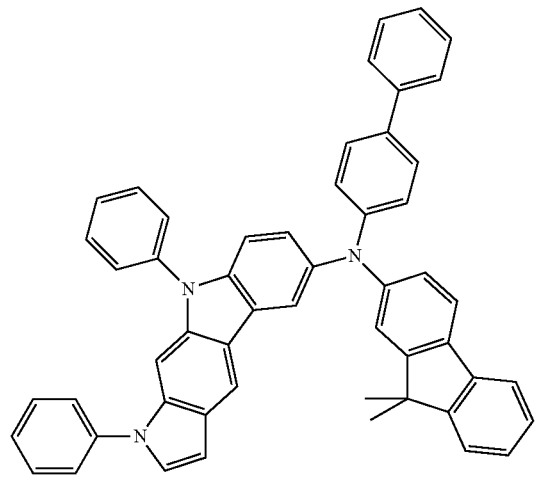

Mat-13

Compound Mat-13 was synthesized by performing the same procedure as in Synthesis Example 1, except that Compound IC-3 (10 g, 22.87 mmol) synthesized in Preparation Example 3 was used instead of Compound IC-1 used in Synthesis Example 1.

Elemental Analysis: C, 88.67; H, 5.48; N, 5.85/HRMS [M]+: 717

[Synthesis Example 14] Synthesis of Compound Mat-14

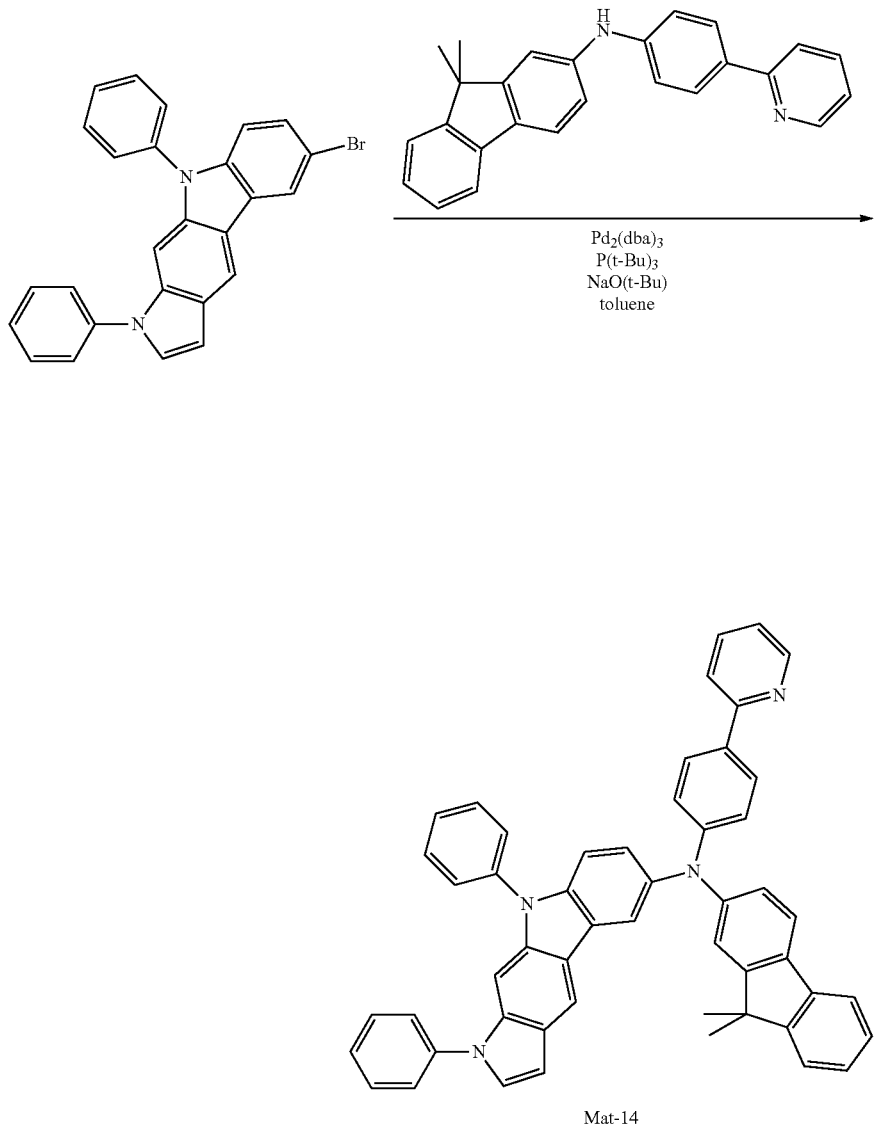

Mat-14

Compound Mat-14 was synthesized by performing the same procedure as in Synthesis Example 1, except that Compound IC-3 (10 g, 22.87 mmol) synthesized in Preparation Example 3 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

[Synthesis Example 15] Synthesis of Compound Mat-15

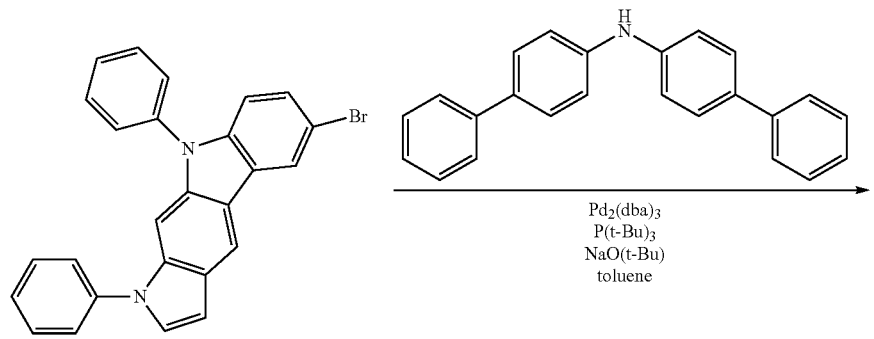

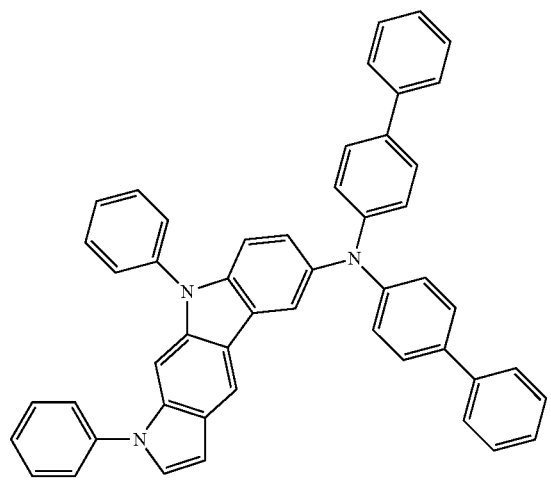

Mat-15

Compound Mat-15 was synthesized by performing the same procedure as in Synthesis Example 3, except that Compound IC-3 (10 g, 22.87 mmol) synthesized in Preparation Example 3 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

[Synthesis Example 16] Synthesis of Mat-16
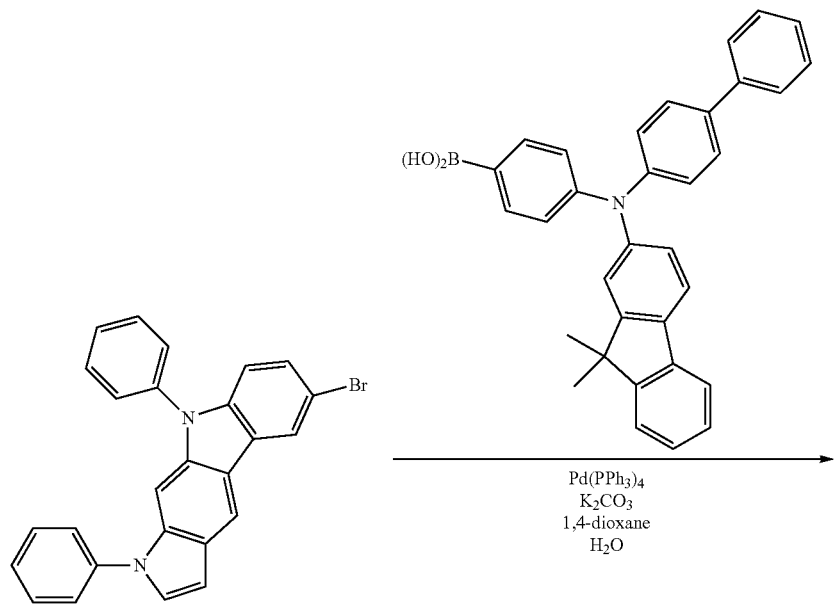
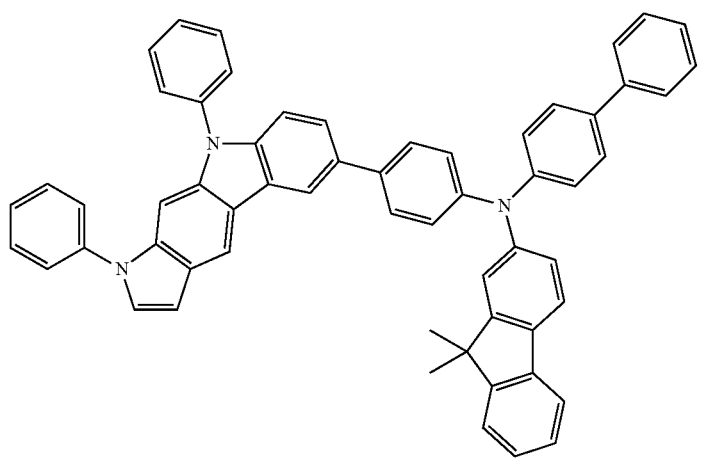
Mat-16
Compound Mat-16 was synthesized by performing the same procedure as in Synthesis Example 4, except that Compound IC-3 (10 g, 22.87 mmol) synthesized in Preparation Example 3 was used instead of Compound IC-1 used in Synthesis Example 1.
Elemental Analysis: C, 89.25; H, 5.46; N, 5.29/HRMS [M]+: 793

[Synthesis Example 17] Synthesis of Compound Mat-17

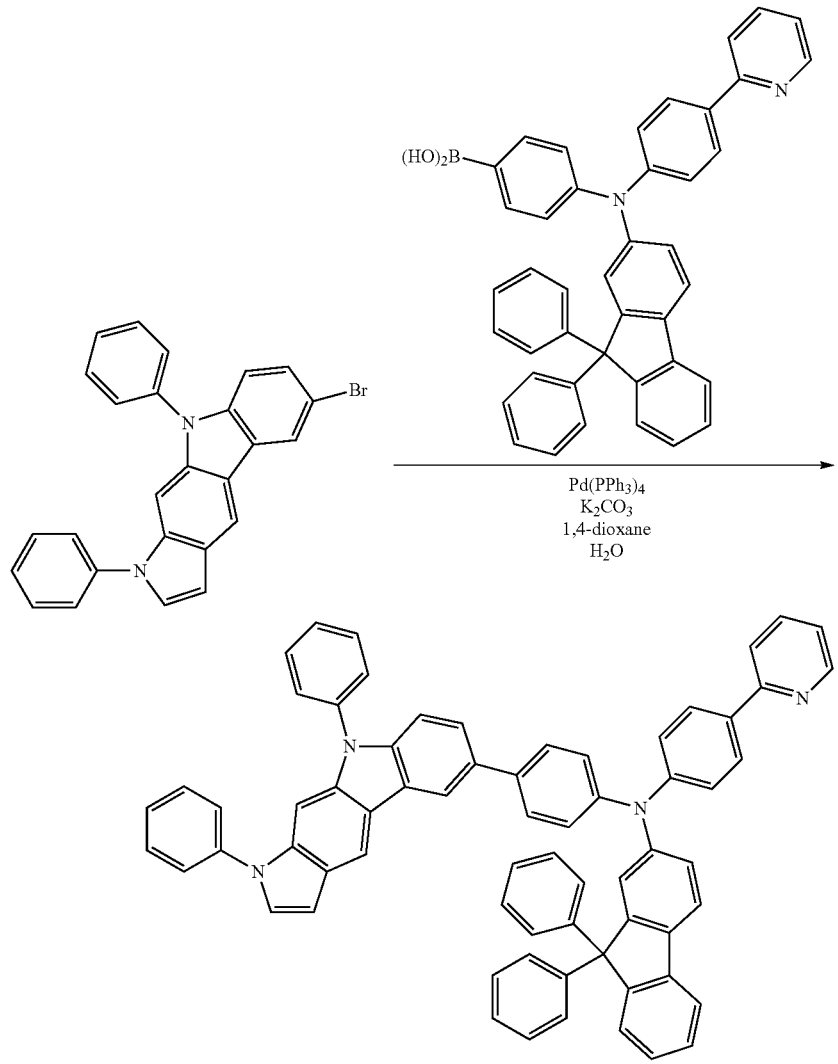

Compound Mat-17 was synthesized by performing the same procedure as in Synthesis Example 4, except that Compound IC-3 (10 g, 22.87 mmol) synthesized in Preparation Example 3 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

[Synthesis Example 18] Synthesis of Compound Mat-18

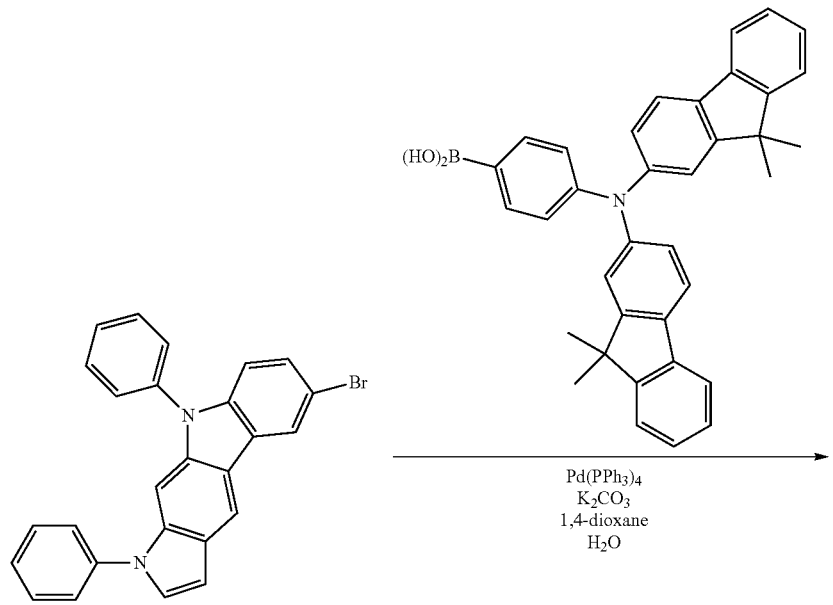

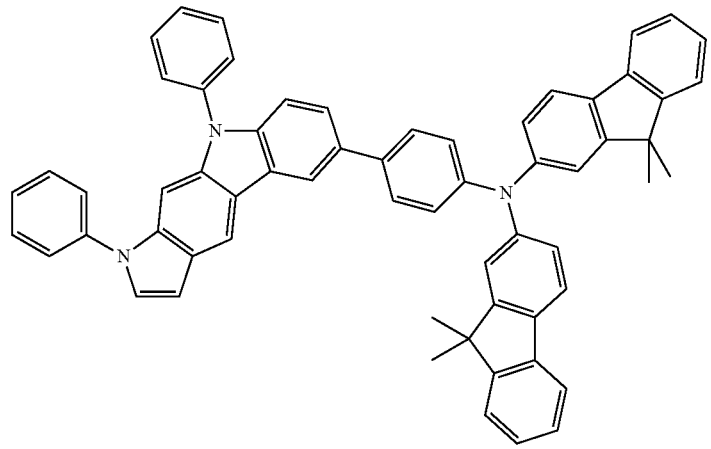

Mat-18

Compound Mat-18 was synthesized by performing the same procedure as in Synthesis Example 4, except that Compound IC-3 (10 g, 22.87 mmol) synthesized in Preparation Example 3 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

[Synthesis Example 19] Synthesis of Compound Mat-19
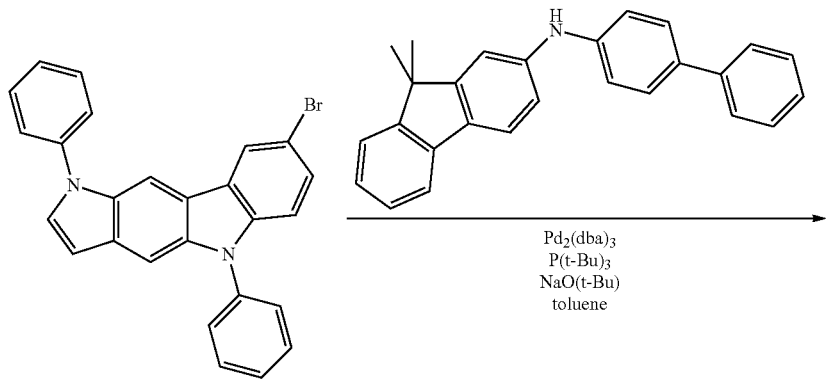
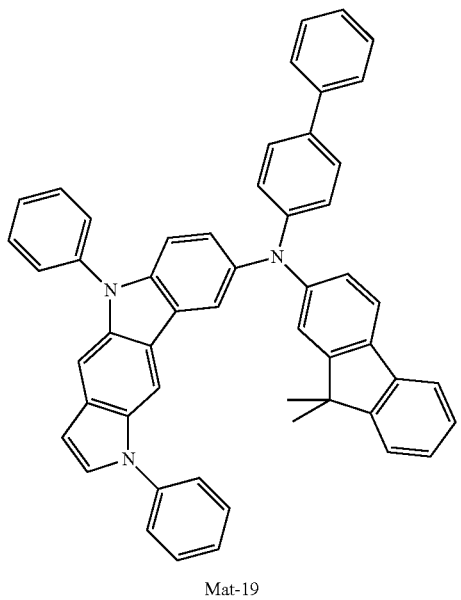
Mat-19
Compound Mat-19 was synthesized by performing the same procedure as in Synthesis Example 1, except that Compound IC-4 (10 g, 22.87 mmol) synthesized in Preparation Example 4 was used instead of Compound IC-1 used in Synthesis Example 1.
Elemental Analysis: C, 88.67; H, 5.48; N, 5.85/HRMS [M]+: 717
[Synthesis Example 20] Synthesis of Compound Mat-20
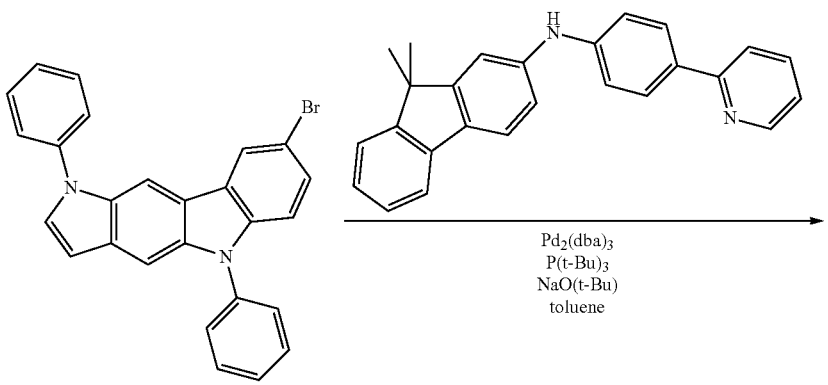

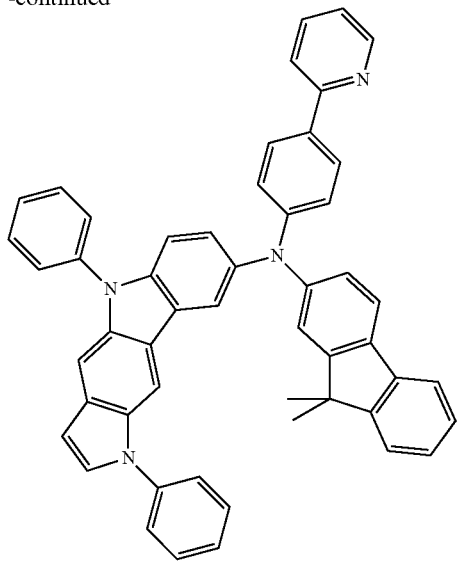

Mat-20

Compound Mat-20 was synthesized by performing the same procedure as in Synthesis Example 1, except that Compound IC-4 (10 g, 22.87 mmol) synthesized in Preparation Example 4 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

[Synthesis Example 21] Synthesis of Compound Mat-21

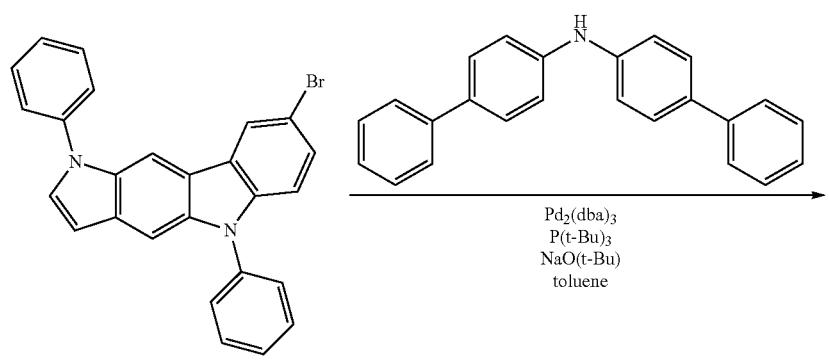

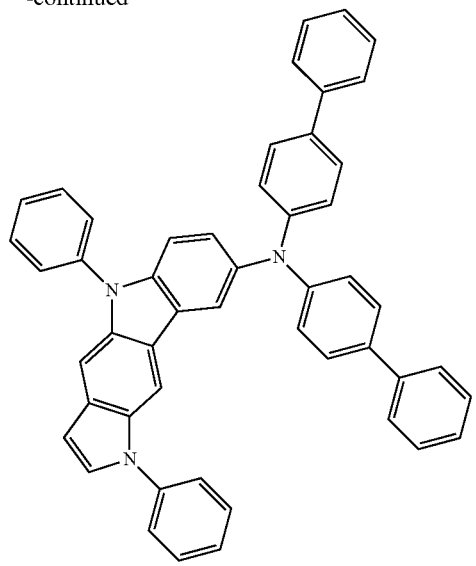

Mat-21

Compound Mat-21 was synthesized by performing the same procedure as in Synthesis Example 1, except that Compound IC-4 (10 g, 22.87 mmol) synthesized in Preparation Example 4 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

[Synthesis Example 22] Synthesis of Compound Mat-22

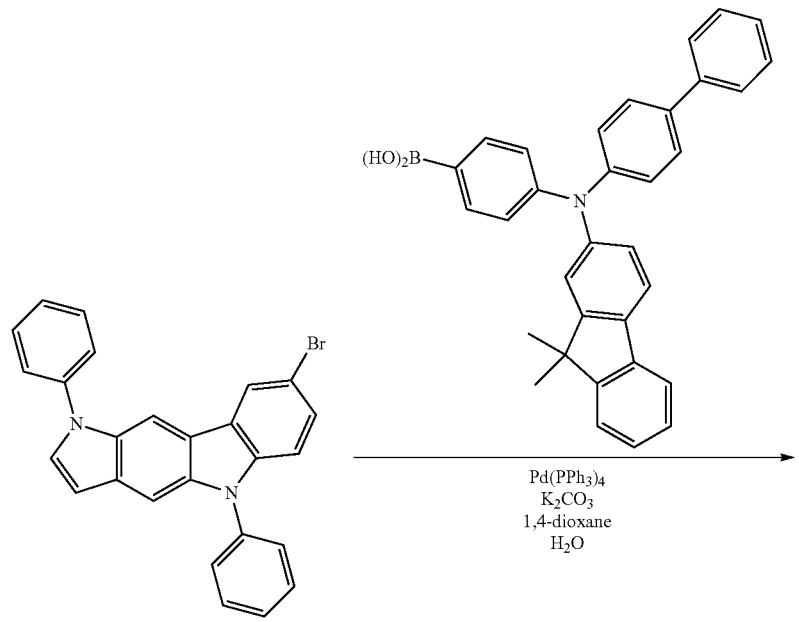

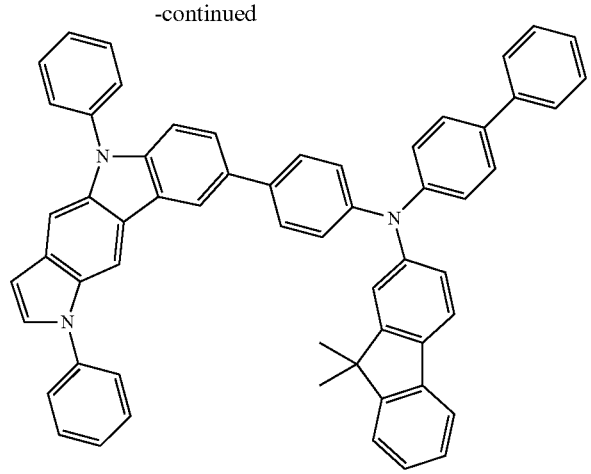
Mat-22
Compound Mat-22 was synthesized by performing the same procedure as in Synthesis Example 4, except that Compound IC-4 (10 g, 22.87 mmol) synthesized in Preparation Example 4 was used instead of Compound IC-1 used in Synthesis Example 4.
Elemental Analysis: C, 89.25; H, 5.46; N, 5.29/HRMS [M]+: 793
[Synthesis Example 23] Synthesis of Compound Mat-23
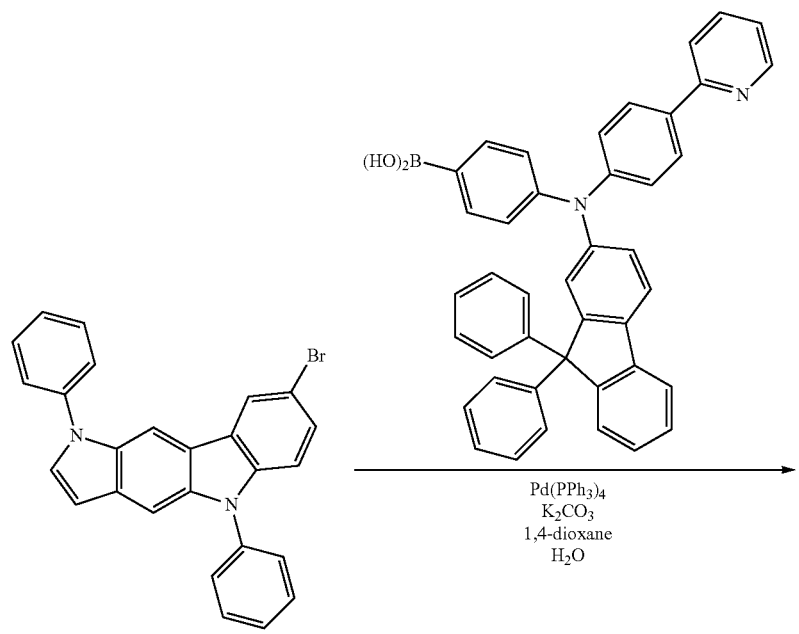

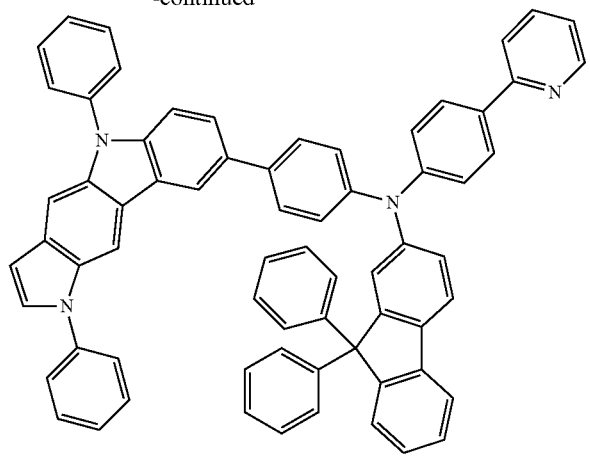

Mat-23

Compound Mat-23 was synthesized by performing the same procedure as in Synthesis Example 4, except that Compound IC-4 (10 g, 22.87 mmol) synthesized in Preparation Example 4 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

[Synthesis Example 24] Synthesis of Compound Mat-24

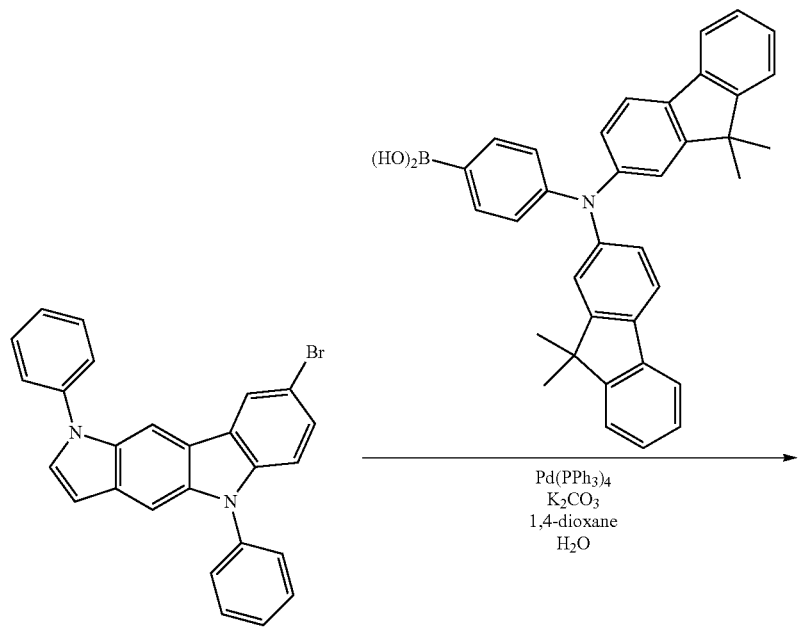

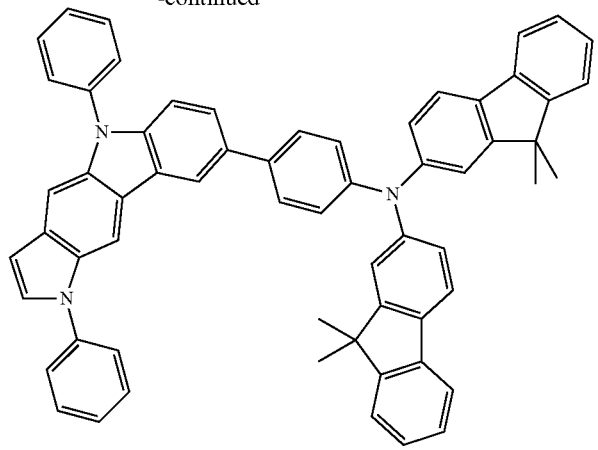

Mat-24

Compound Mat-24 was synthesized by performing the same procedure as in Synthesis Example 4, except that Compound IC-4 (10 g, 22.87 mmol) synthesized in Preparation Example 4 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

[Synthesis Example 25] Synthesis of Compound Mat-25

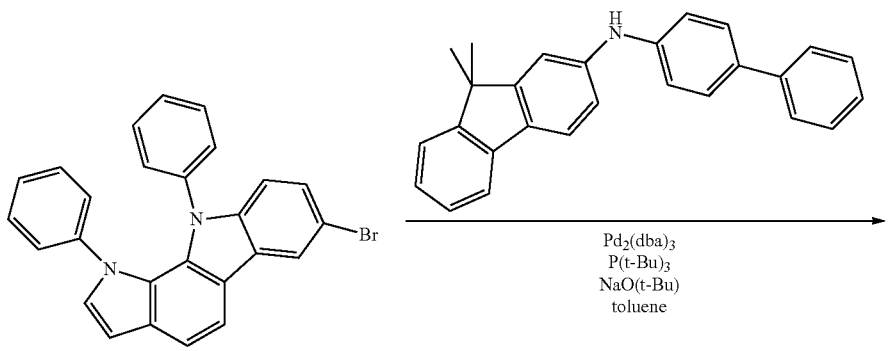

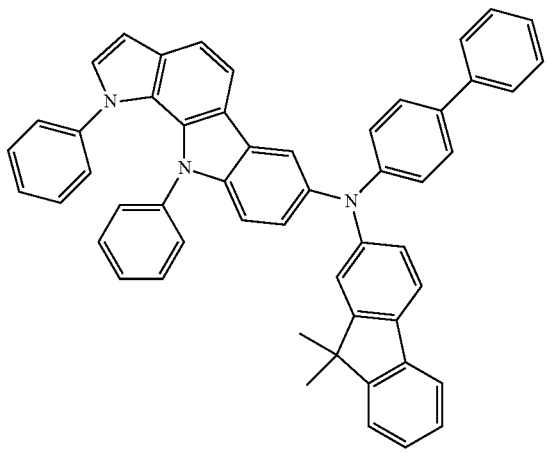

Mat-25

Compound Mat-25 was synthesized by performing the same procedure as in Synthesis Example 1, except that Compound IC-5 (10 g, 22.87 mmol) synthesized in Preparation Example 5 was used instead of Compound IC-1 used in Synthesis Example 1.

Elemental Analysis: C, 88.67; H, 5.48; N, 5.85/HRMS [M]+: 717

[Synthesis Example 26] Synthesis of Compound Mat-26

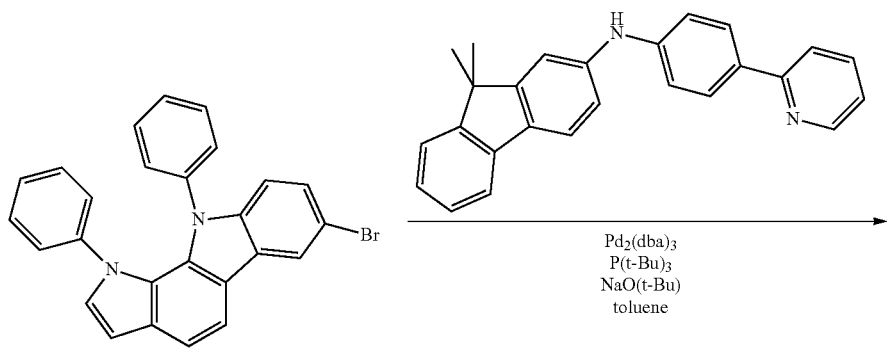

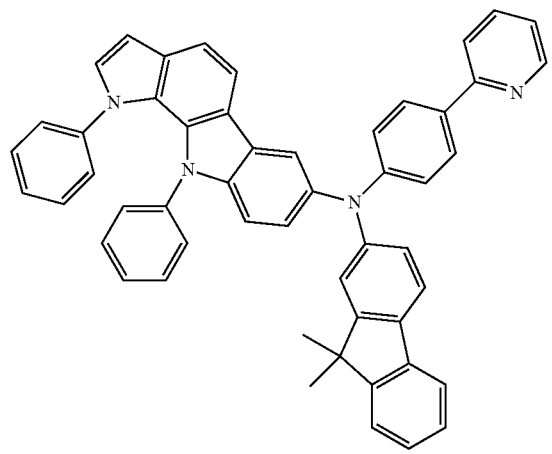

Mat-26

Compound Mat-26 was synthesized by performing the same procedure as in Synthesis Example 1, except that Compound IC-5 (10 g, 22.87 mmol) synthesized in Preparation Example 5 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

[Synthesis Example 27] Synthesis of Compound Mat-27

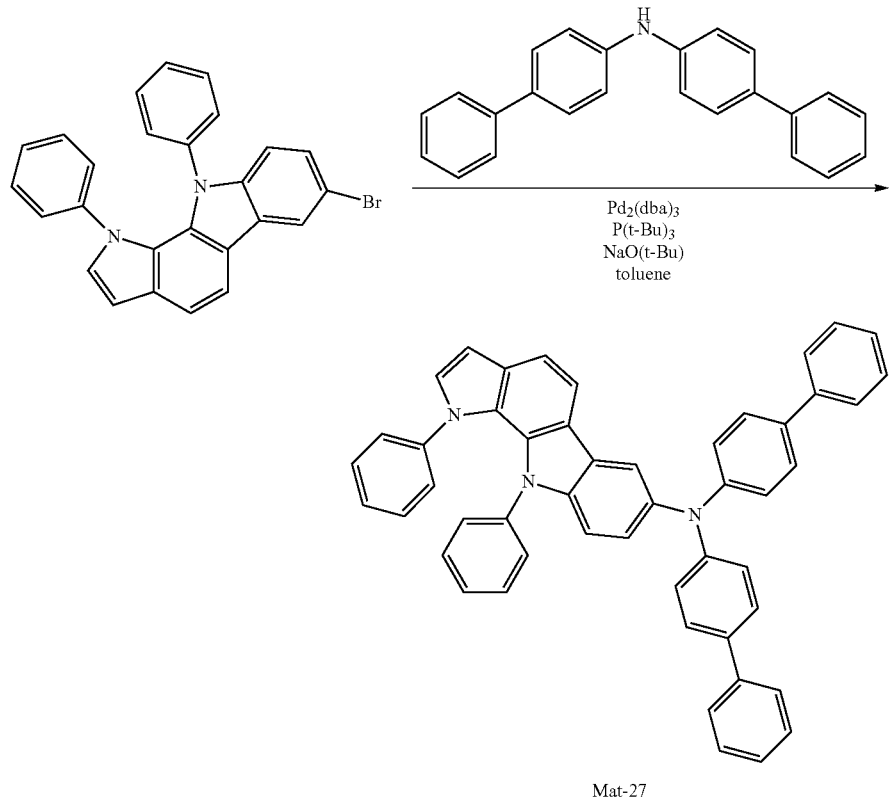

Mat-27

Compound Mat-27 was synthesized by performing the same procedure as in Synthesis Example 1, except that Compound IC-5 (10 g, 22.87 mmol) synthesized in Preparation Example 5 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

[Synthesis Example 28] Synthesis of Compound Mat-28

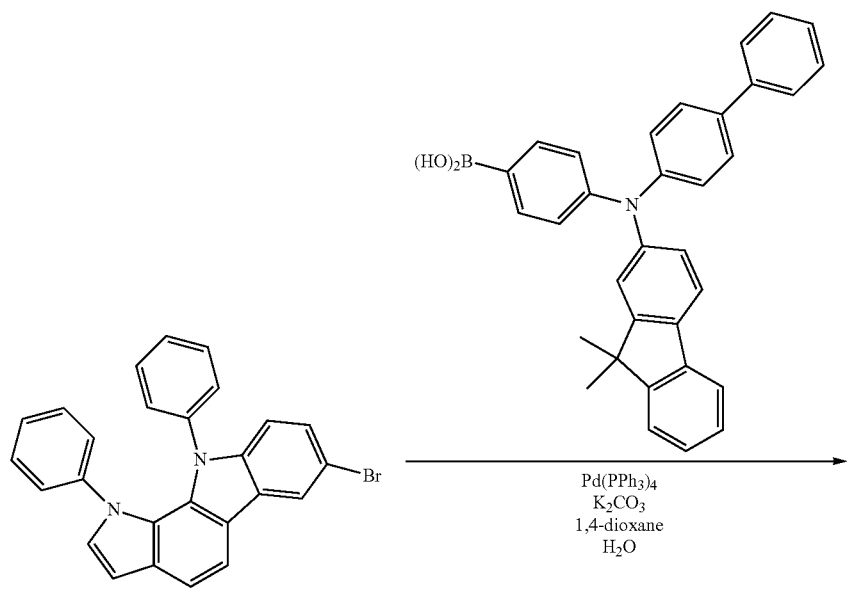

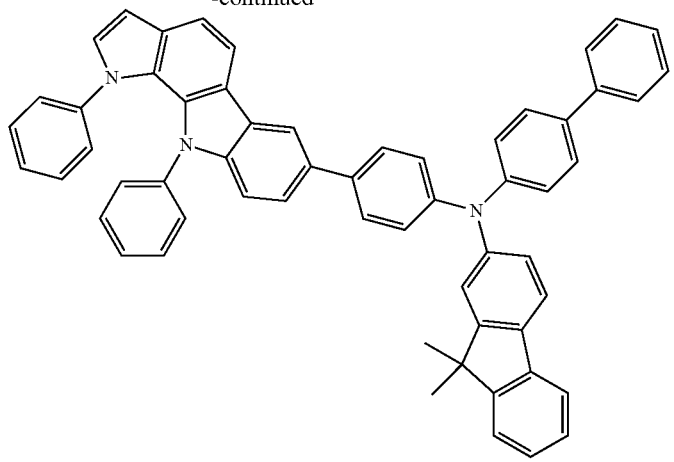
Mat-28
Compound Mat-28 was synthesized by performing the same procedure as in Synthesis Example 4, except that Compound IC-5 (10 g, 22.87 mmol) synthesized in Preparation Example 5 was used instead of Compound IC-1 used in Synthesis Example 4.
Elemental Analysis: C, 89.25; H, 5.46; N, 5.29/HRMS [M]+: 793
[Synthesis Example 29] Synthesis of Compound Mat-29
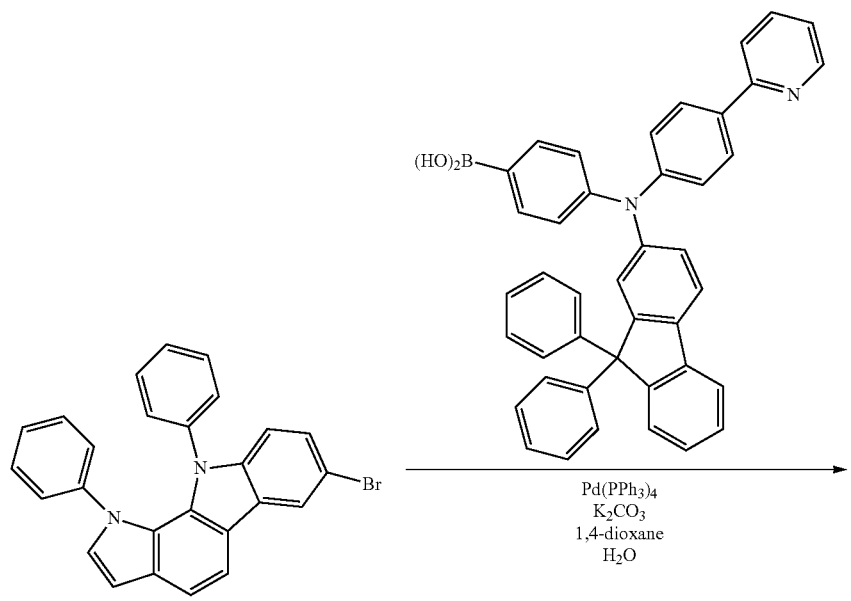

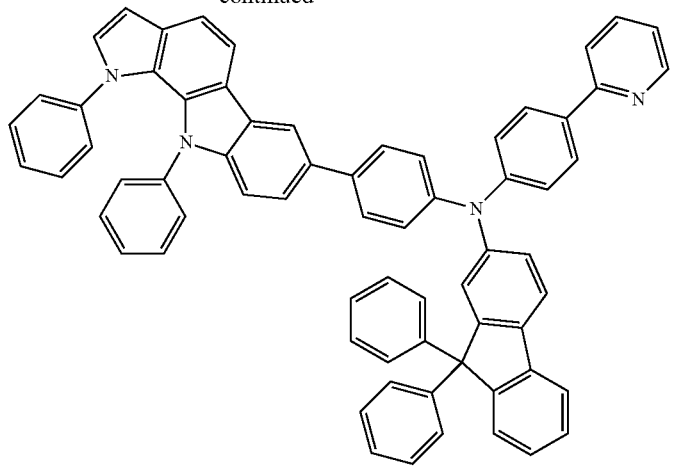

Mat-29

Compound Mat-29 was synthesized by performing the same procedure as in Synthesis Example 4, except that Compound IC-5 (10 g, 22.87 mmol) used in Preparation Example 5 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

[Synthesis Example 30] Synthesis of Compound Mat-30

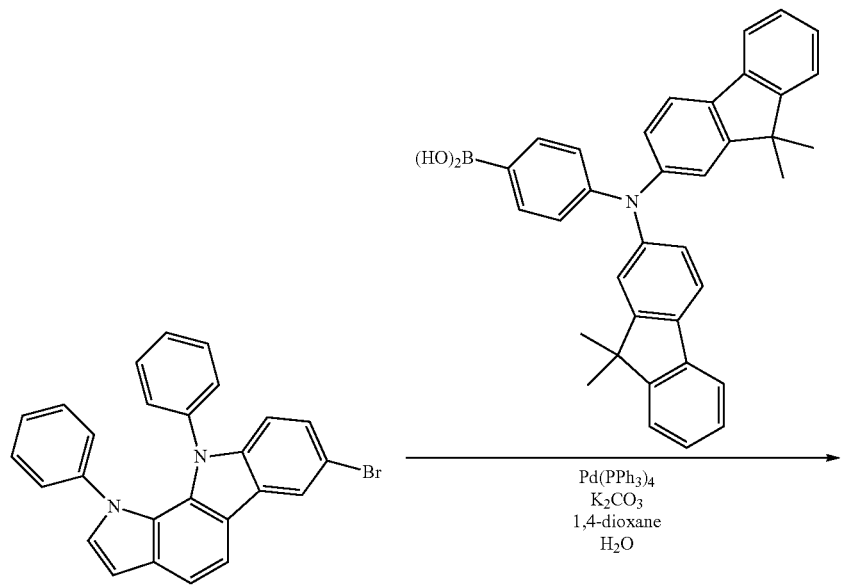

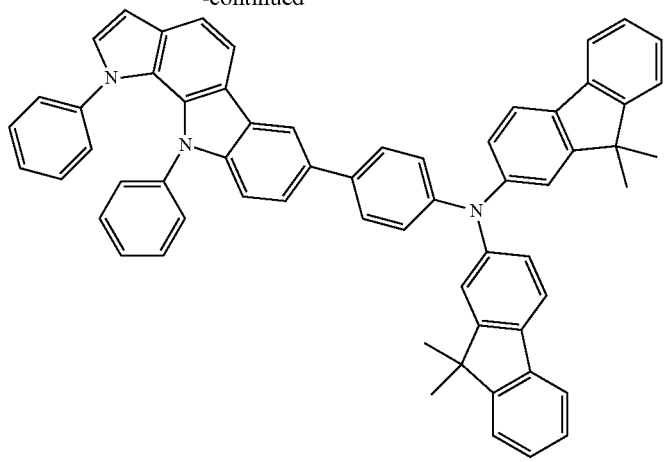

Mat-30

Compound Mat-30 was synthesized by performing the same procedure as in Synthesis Example 4, except that Compound IC-5 (10 g, 22.87 mmol) synthesized in Preparation Example 5 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

[Synthesis Example 31] Synthesis of Compound Mat-31

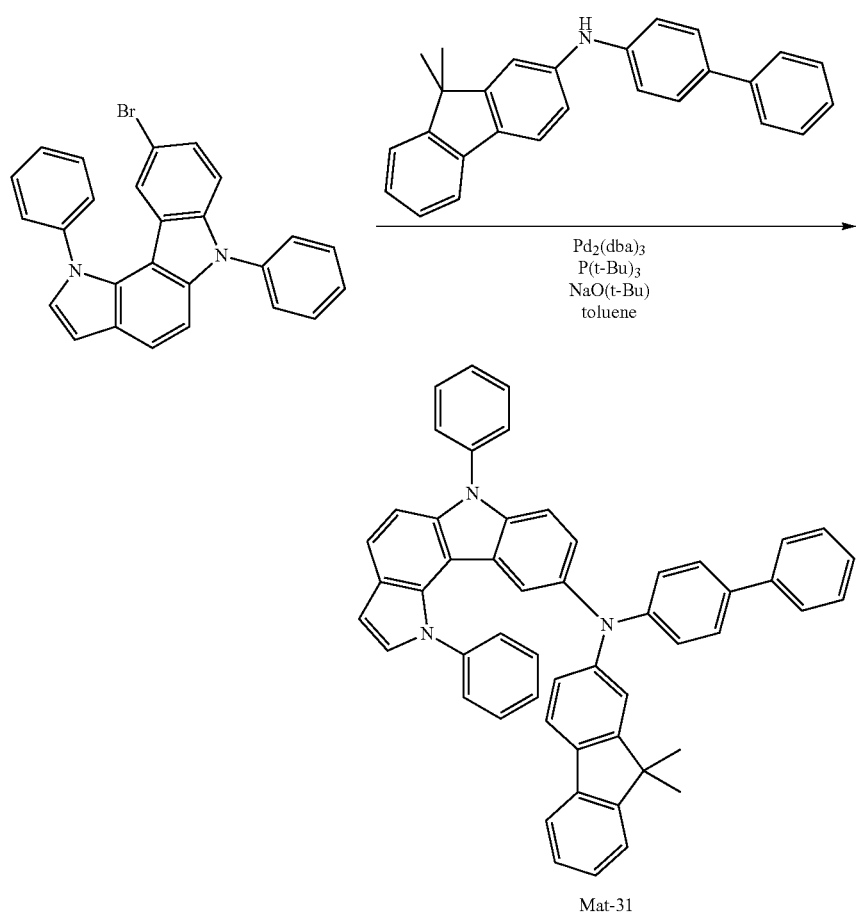

Mat-31

Compound Mat-31 was synthesized by performing the same procedure as in Synthesis Example 1, except that Compound IC-6 (10 g, 22.87 mmol) synthesized in Preparation Example 6 was used instead of Compound IC-1 used in Synthesis Example 1.

Elemental Analysis: C, 88.67; H, 5.48; N, 5.85/HRMS [M]+: 717

[Synthesis Example 32] Synthesis of Compound Mat-32

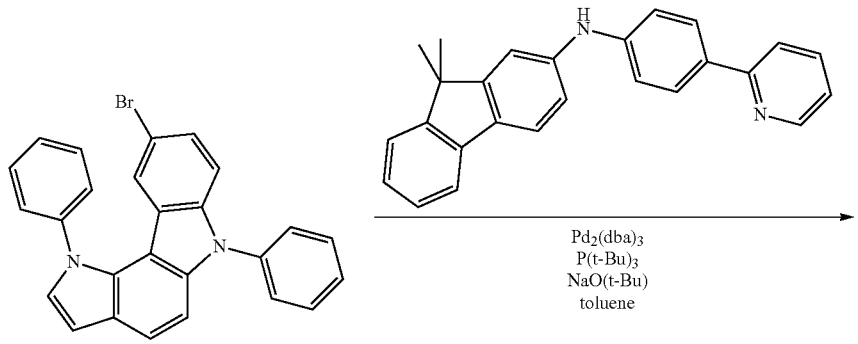

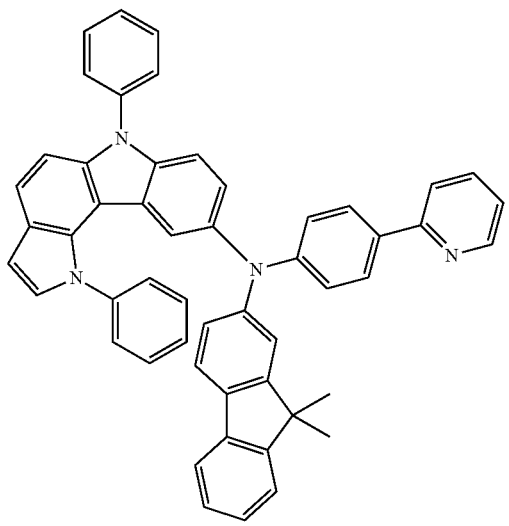

Mat-32

Compound Mat-32 was synthesized by performing the same procedure as in Synthesis Example 1, except that Compound IC-6 (10 g, 22.87 mmol) synthesized in Preparation Example 6 was used instead of Compound IC-1 used in Synthesis Example 1, and 9,9-dimethyl-N-(4-(pyridin-2-yl)phenyl)-9H-fluoren-2-amine (9.12 g, 25.16 mmol) was used instead of N-(biphenyl-4-yl)-9,9-dimethyl-9H-fluoren-2-amine.

Elemental Analysis: C, 86.88; H, 5.33; N, 7.79/HRMS [M]+: 718

[Synthesis Example 33] Synthesis of Compound Mat-33

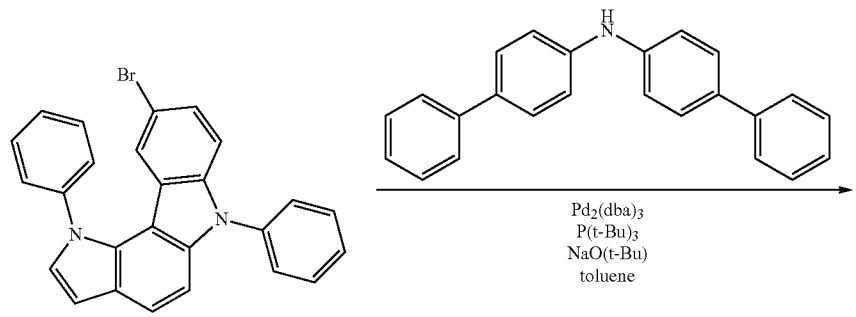

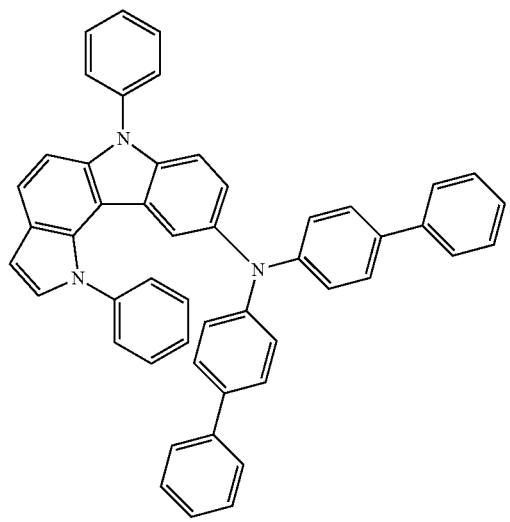

Mat-33

Compound Mat-33 was synthesized by performing the same procedure as in Synthesis Example 1, except that Compound IC-6 (10 g, 22.87 mmol) synthesized in Preparation Example 6 was used instead of Compound IC-1 used in Synthesis Example 1, and 9,9-dimethyl-N-(4-(pyridin-2-yl)phenyl)-9H-fluoren-2-amine (8.1 g, 25.16 mmol) was used instead of N-(biphenyl-4-yl)-9,9-dimethyl-9H-fluoren-2-amine.

Elemental Analysis: C, 88.60; H, 5.20; N, 6.20/HRMS [M]+: 667

[Synthesis Example 34] Synthesis of Compound Mat-34
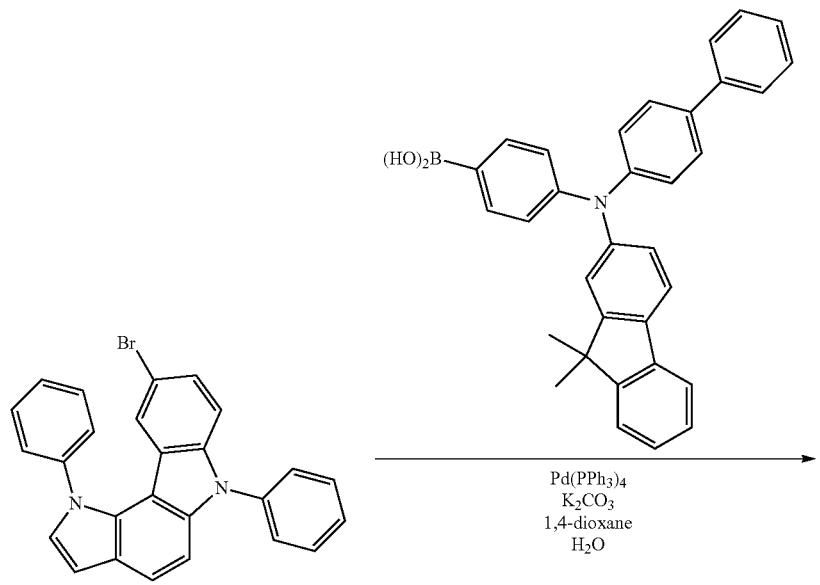
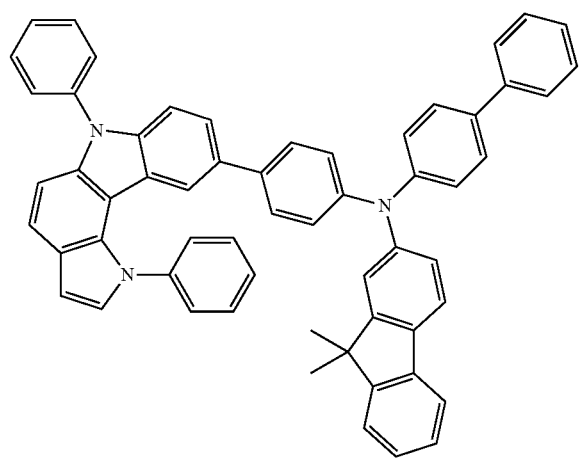
Mat-34
Compound Mat-34 was synthesized by performing the same procedure as in Synthesis Example 4, except that Compound IC-6 (10 g, 22.87 mmol) synthesized in Preparation Example 6 was used instead of Compound IC-1 used in Synthesis Example 4.
Elemental Analysis: C, 89.25; H, 5.46; N, 5.29/HRMS [M]+: 793

[Synthesis Example 35] Synthesis of Compound Mat-35

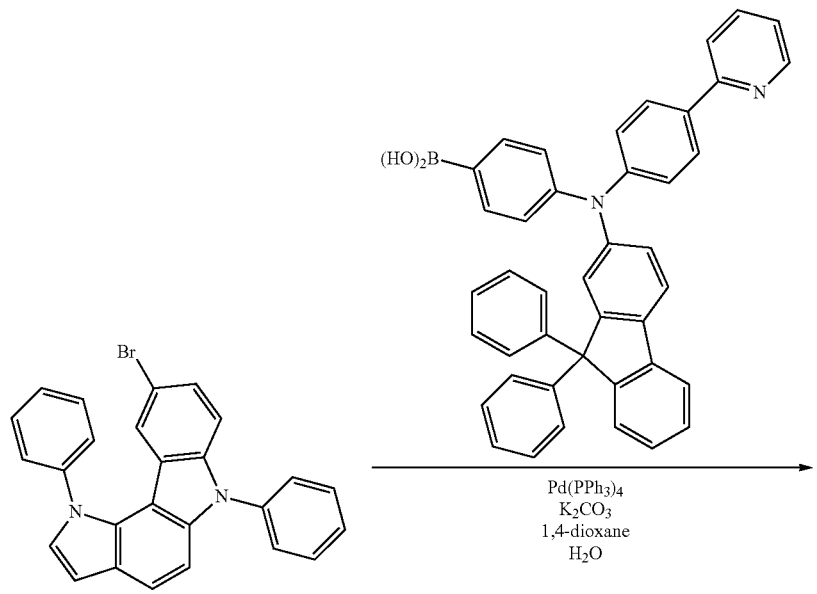

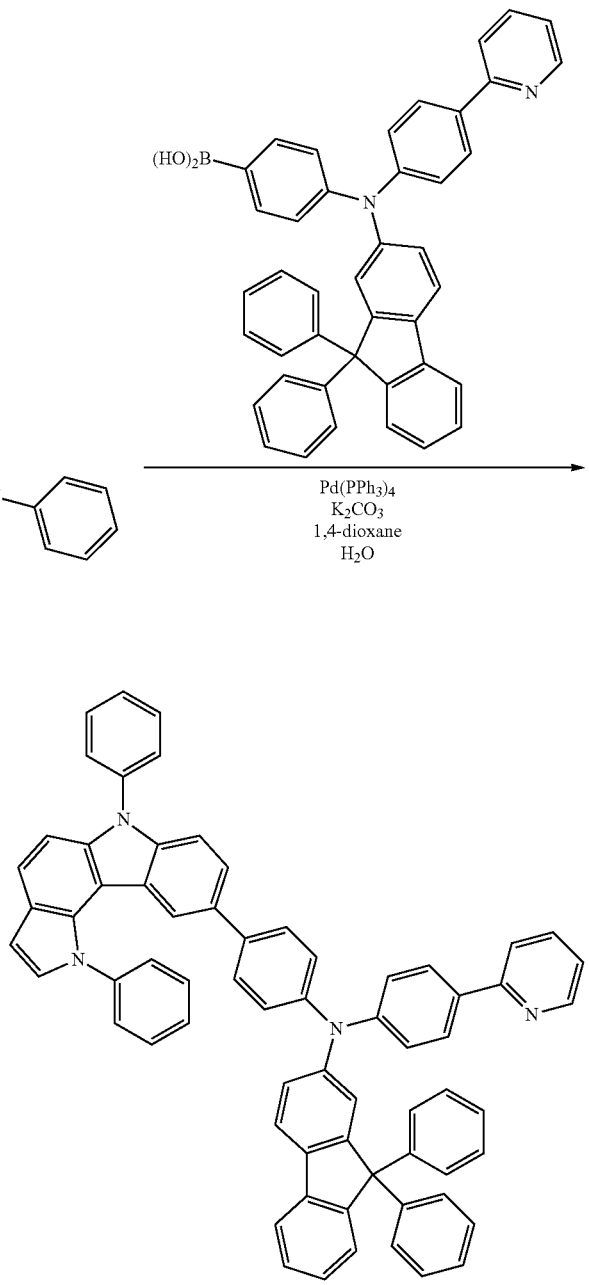

Mat-35

Compound Mat-35 was synthesized by performing the same procedure as in Synthesis Example 4, except that Compound IC-6 (10 g, 22.87 mmol) synthesized in Preparation Example 6 was used instead of Compound IC-1 used in Synthesis Example 4, and 4-((9,9-diphenyl-9H-fluoren-2-yl)(4-(pyridin-2-yl)phenyl)amino)phenylboronic acid (15.26 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 88.86; H, 5.04; N, 6.10/HRMS [M]+: 918

[Synthesis Example 36] Synthesis of Compound Mat-36

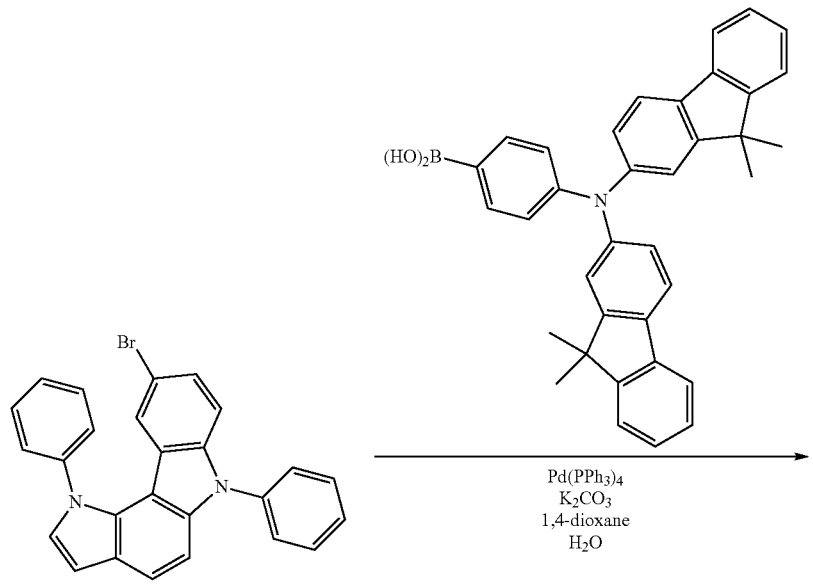

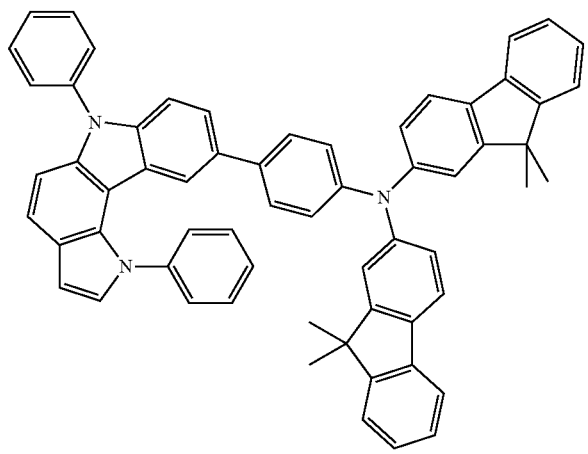

Mat-36

Compound Mat-36 was synthesized by performing the same procedure as in Synthesis Example 4, except that Compound IC-6 (10 g, 22.87 mmol) synthesized in Preparation Example 6 was used instead of Compound IC-1 used in Synthesis Example 4, and N-(4-bromophenyl)-N-(9,9-dimethyl-9H-fluoren-2-yl)-9,9-dimethyl-9H-fluoren-2-amine (13.1 g, 25.16 mmol) was used instead of 4-(biphenyl-4-yl(9,9-dimethyl-9H-fluoren-2yl)amino)phenylboronic acid (12.11 g, 25.16 mmol).

Elemental Analysis: C, 89.28; H, 5.68; N, 5.04/HRMS [M]+: 833

[Synthesis Example 37] Synthesis of Compound Mat-37
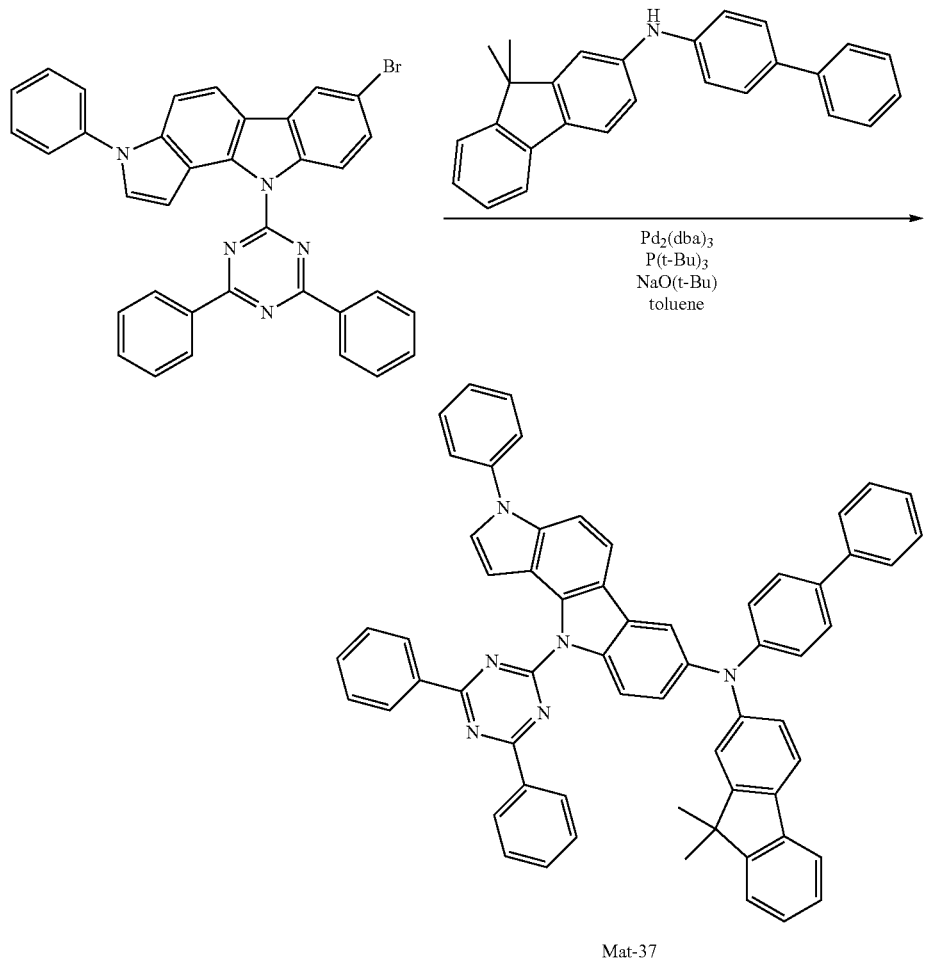
Compound Mat-37 was synthesized by performing the same procedure as in Synthesis Example 1, except that Compound IC-7 (13.55 g, 22.87 mmol) synthesized in Preparation Example 7 was used instead of Compound IC-1 used in Synthesis Example 1.
Elemental Analysis: C, 85.29; H, 5.08; N, 9.63/HRMS [M]+: 872
[Synthesis Example 38] Synthesis of Compound Mat-38
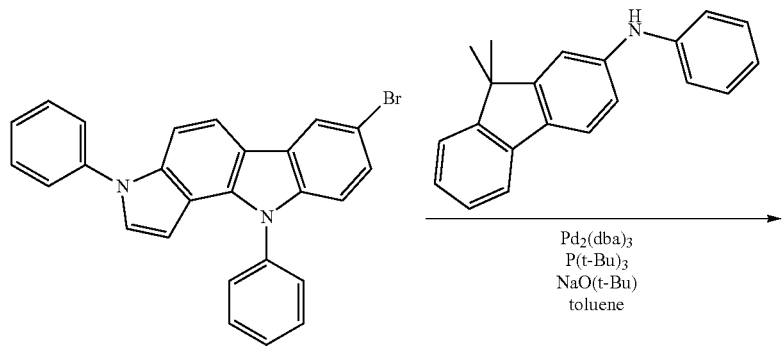

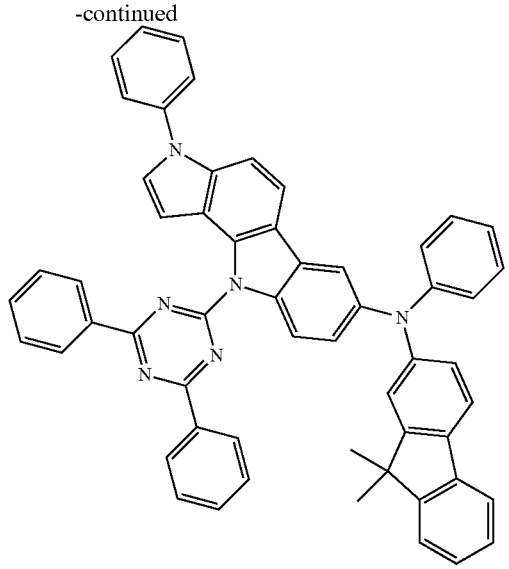
Mat-38
Compound Mat-38 was synthesized by performing the same procedure as in Synthesis Example 1, except that 9,9-dimethyl-N-phenyl-9H-fluoren-2-amine (7.18 g, 25.16 mmol) was used instead of the N-(biphenyl-4-yl)-9,9-dimethyl-9H-fluoren-2-amine used in Synthesis Example 1.
Elemental Analysis: C, 87.96; H, 5.50; N, 6.55/HRMS [M]+: 641
[Synthesis Example 39] Synthesis of Compound Mat-39
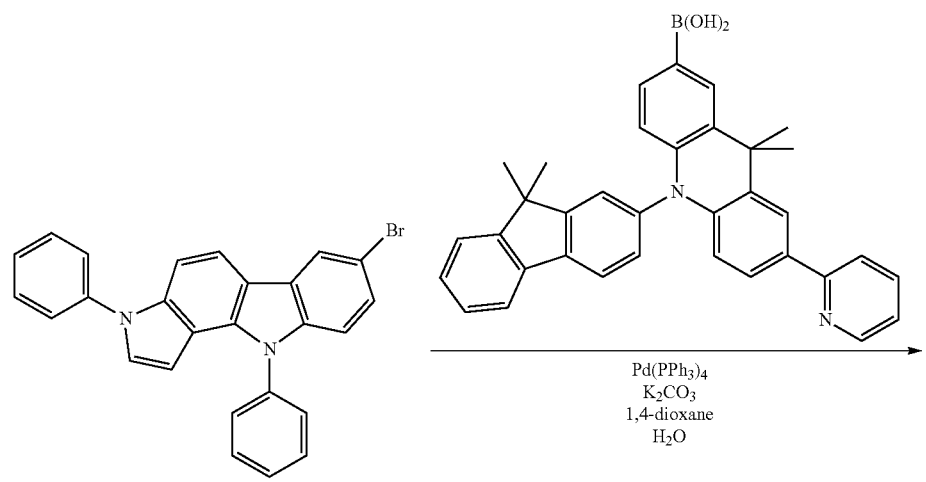

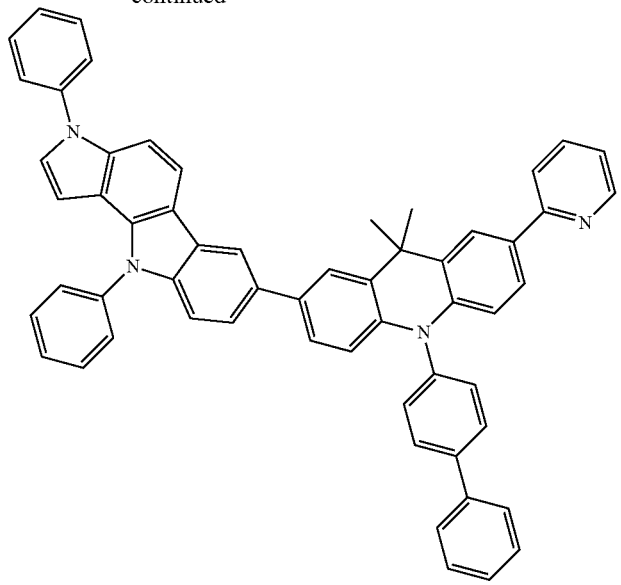

Mat-39

Compound Mat-39 was synthesized by performing the same procedure as in Synthesis Example 1, except that 10-(biphenyl-4-yl)-2-bromo-9,9-dimethyl-7-(pyridin-2-yl)-9,10-dihydroacridine (13.46 g, 25.16 mmol) was used instead of the N-(biphenyl-4-yl)-9,9-dimethyl-9H-fluoren-2-amine used in Synthesis Example 1.

Elemental Analysis: C, 87.63; H, 5.33; N, 7.05/HRMS [M]+: 794

[Example 1] Manufacture of Organic EL Device

A glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic EL device was manufactured by laminating m-MTDATA (60 nm)/Mat-1 (80 nm) which is a compound synthesized in Synthesis Example 1/DS-H522+5% DS-501 (300 nm)/BCP (10 nm)/Alq$_3$ (30 nm)/LiF (1 nm)/Al (200 nm) in this order on the thus prepared ITO transparent electrode.

DS-H522 and DS-501, which were used in the manufacture of the device, were products manufactured by Doosan Corporation Electro-Materials BG, and the structures of m-MTDATA, TCTA, CBP, Ir(ppy)$_3$, and BCP are as follows.

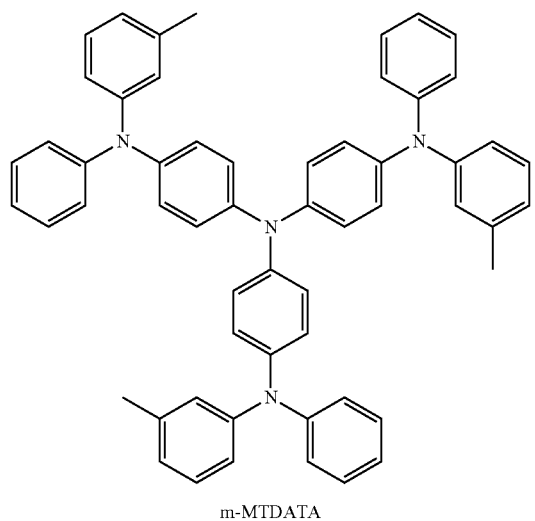

m-MTDATA

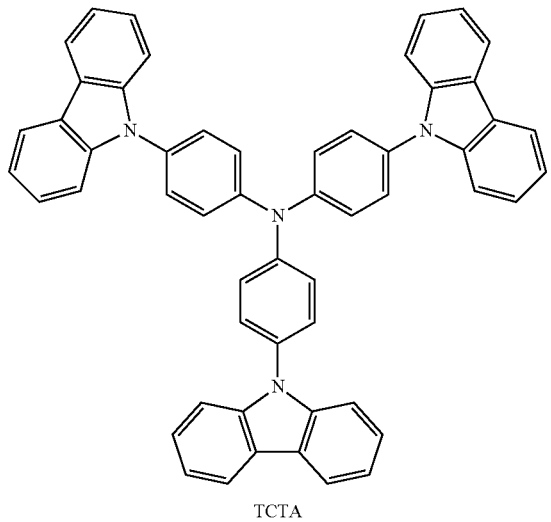

TCTA

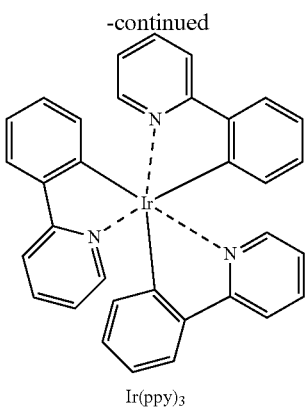

Ir(ppy)₃

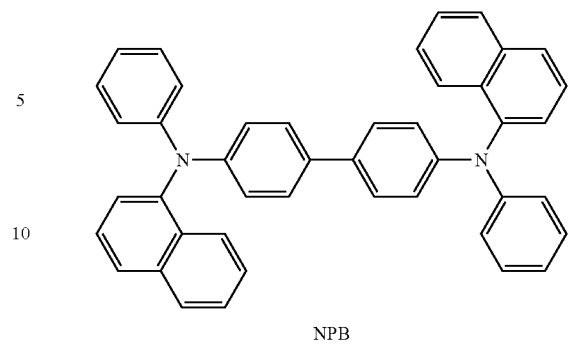

NPB

CPB

BCP

[Examples 2 to 39] Manufacture of Organic EL Device

Organic EL devices were manufactured by performing the same procedure as in Example 1, except that Compounds Mat-2 to Mat-39 each synthesized in Synthesis Examples 2 to 39 were used instead of Compound Mat-1 used as a material for a hole transporting layer when a hole transporting layer is formed in Example 1.

[Comparative Example 1] Manufacture of Organic EL Device

An organic EL device was manufactured in the same manners as in Example 1, except that NPB was used as a material for a hole transporting layer instead of Compound Mat-1 used as a material for a hole transporting layer when a hole transporting layer is formed in Example 1. The structure of the NPB used is as follows.

Experimental Example

For each of the organic EL devices manufactured in Examples 1 to 39 and Comparative Example 1, the driving voltage and current efficiency were measured at a current density of 10 mA/cm$^2$, and the results are shown in the following Table 1.

TABLE 1

| Sample | Hole transporting layer | Driving voltage (V) | Current efficiency (cd/A) |
|---|---|---|---|
| Example 1 | Compound Mat-1 | 4.1 | 22.2 |
| Example 2 | Compound Mat-2 | 4.3 | 20.1 |
| Example 3 | Compound Mat-3 | 4.4 | 21.3 |
| Example 4 | Compound Mat-4 | 4.0 | 22.6 |
| Example 5 | Compound Mat-5 | 4.5 | 19.5 |
| Example 6 | Compound Mat-6 | 4.7 | 20.1 |
| Example 7 | Compound Mat-7 | 4.3 | 21.6 |
| Example 8 | Compound Mat-8 | 4.5 | 20.5 |
| Example 9 | Compound Mat-9 | 4.7 | 20.6 |
| Example 10 | Compound Mat-10 | 4.4 | 21.6 |
| Example 11 | Compound Mat-11 | 5.0 | 20.1 |
| Example 12 | Compound Mat-12 | 5.1 | 18.6 |
| Example 13 | Compound Mat-13 | 4.3 | 22.0 |
| Example 14 | Compound Mat-14 | 4.6 | 21.2 |
| Example 15 | Compound Mat-15 | 4.5 | 21.2 |
| Example 16 | Compound Mat-16 | 4.4 | 22.3 |
| Example 17 | Compound Mat-17 | 5.1 | 18.3 |
| Example 18 | Compound Mat-18 | 5.0 | 18.9 |
| Example 19 | Compound Mat-19 | 4.5 | 21.7 |
| Example 20 | Compound Mat-20 | 4.7 | 21.2 |
| Example 21 | Compound Mat-21 | 4.8 | 20.8 |
| Example 22 | Compound Mat-22 | 4.5 | 21.4 |
| Example 23 | Compound Mat-23 | 5.1 | 18.2 |
| Example 24 | Compound Mat-24 | 5.1 | 18.5 |
| Example 25 | Compound Mat-25 | 4.3 | 22.3 |
| Example 26 | Compound Mat-26 | 4.6 | 21.4 |
| Example 27 | Compound Mat-27 | 4.8 | 21.6 |
| Example 28 | Compound Mat-28 | 4.2 | 22.5 |
| Example 29 | Compound Mat-29 | 4.7 | 20.6 |
| Example 30 | Compound Mat-30 | 4.6 | 20.2 |
| Example 31 | Compound Mat-31 | 4.2 | 22.1 |
| Example 32 | Compound Mat-32 | 4.6 | 21.2 |
| Example 33 | Compound Mat-33 | 4.8 | 20.0 |
| Example 34 | Compound Mat-34 | 4.2 | 22.3 |
| Example 35 | Compound Mat-35 | 4.8 | 21.8 |
| Example 36 | Compound Mat-36 | 5.0 | 19.2 |
| Example 37 | Compound Mat-37 | 4.5 | 20.3 |
| Example 38 | Compound Mat-38 | 5.1 | 18.5 |
| Example 39 | Compound Mat-39 | 4.9 | 20.3 |
| Comparative Example 1 | NPB | 5.2 | 18.1 |

As shown in Table 1, it can be seen that the organic EL device (organic EL device each manufactured in Examples 1 to 39), in which the compounds (Mat 1 to Mat 39) according to the present disclosure are used as a hole transporting layer, exhibits excellent performance in terms of current efficiency and driving voltage as compared to the organic EL device (organic EL device of Comparative Example 1) in which the NPB in the related art is used.

The invention claimed is:

1. A compound of the following Formula 5, 6, 7, or 9:

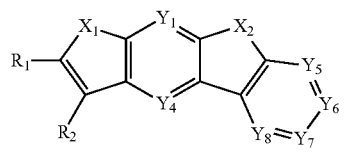

Formula 5

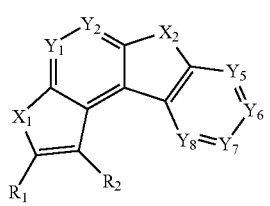

Formula 6

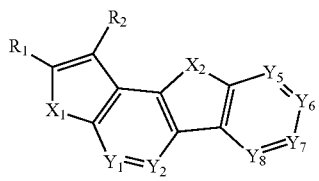

Formula 7

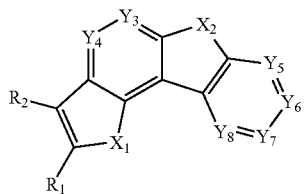

Formula 9 wherein, $Y_1$ to $Y_4$ are each independently N or $CR_3$, and, when $CR_3$ is present in a plural number, they are the same as or different from each other, $Y_5$ to $Y_8$ are each independently N or $CR_4$, and, when $CR_4$ is present in a plural number, they are the same as or different from each other, and provided that at least one of $Y_5$ to $Y_8$ is $CR_4$, and at least one of one or more $R_4$'s is a substituent of the following Formula 3,

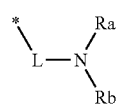

Formula 3 wherein the substituent represented by the Formula 3 is selected from the group consisting of the following substituents U1 to U86:

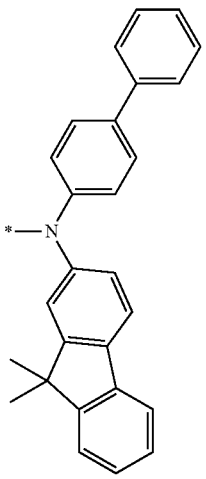

U1

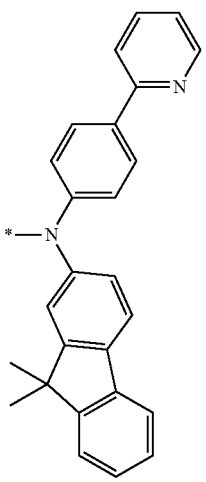

U2

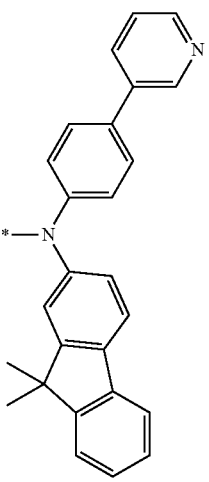

U3

329
-continued
U4
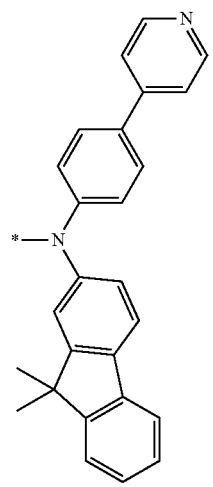
U5
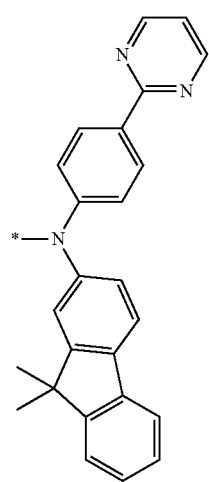
U6
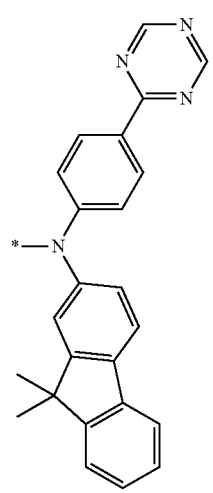
330
-continued
U7
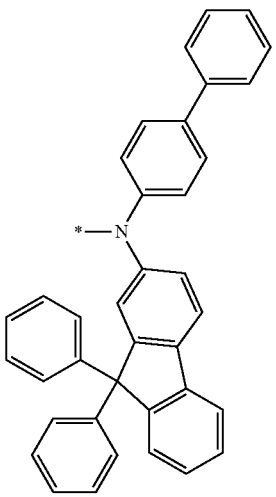
U8
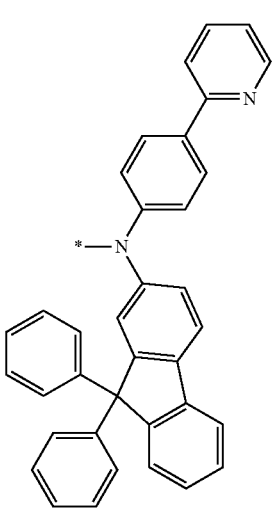
U9
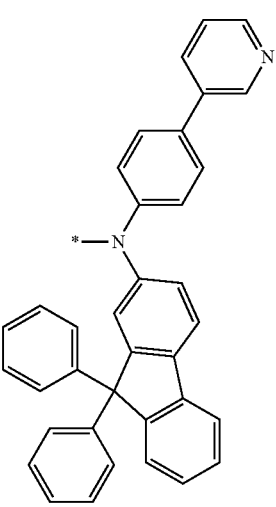

331
-continued
U10
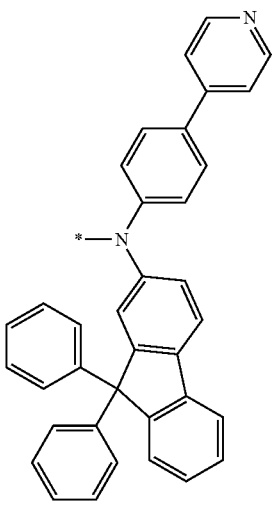
U11
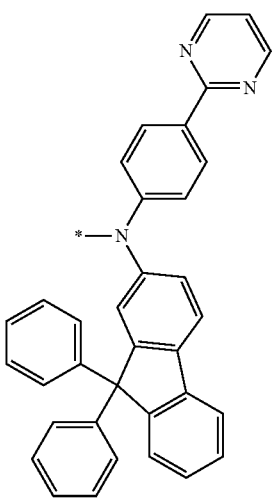
U12
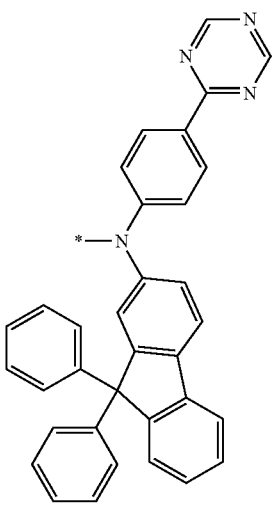
332
-continued
U13
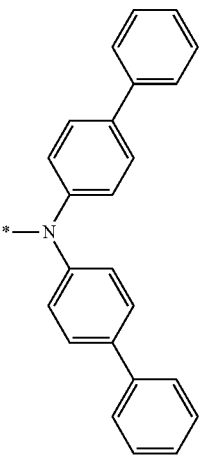
U14
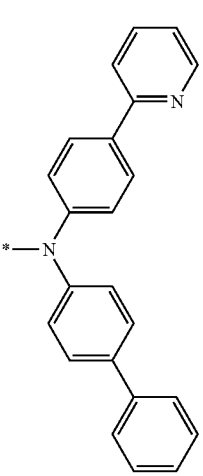
U15
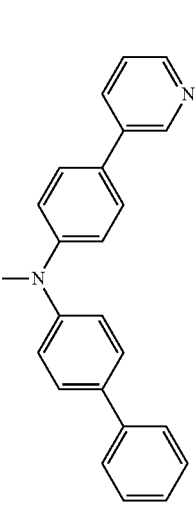

U16 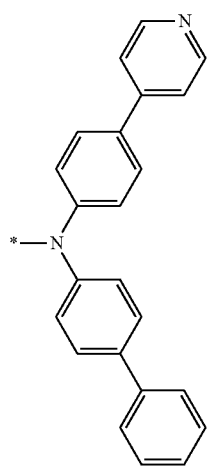
U17 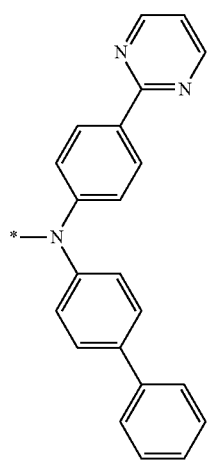
U18 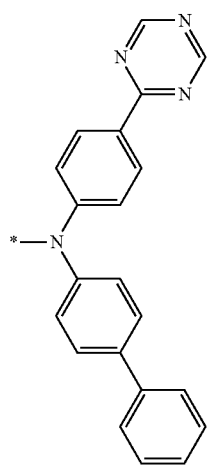
U19 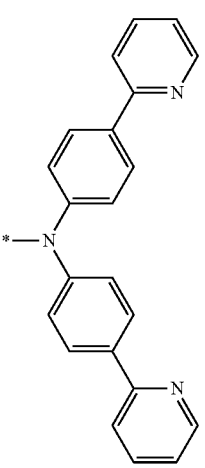
U21 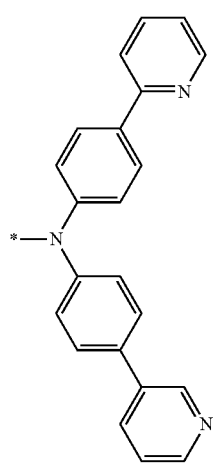
U21 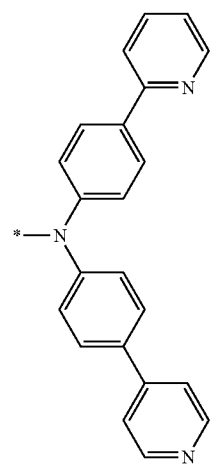

U22 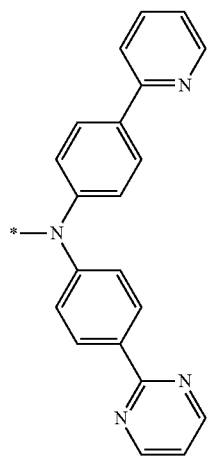
U23 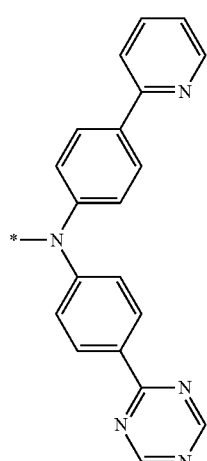
U24 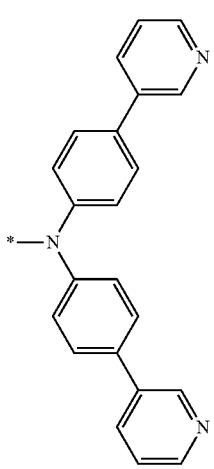
U25 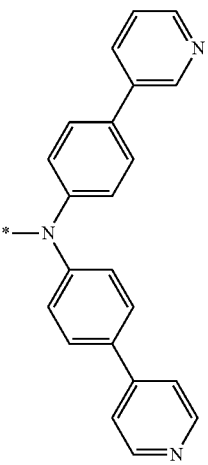
U26 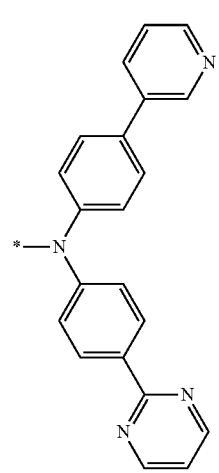
U27 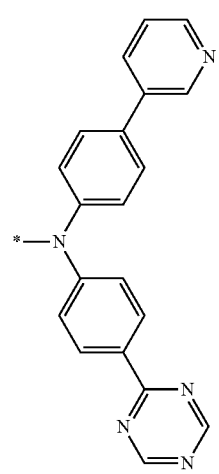

-continued
U28 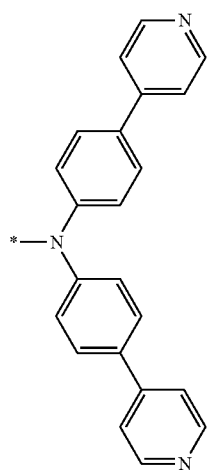
U29 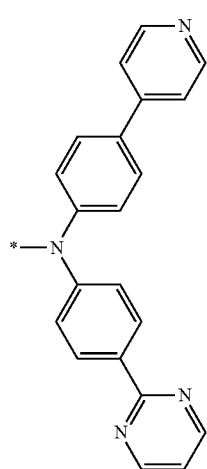
U30 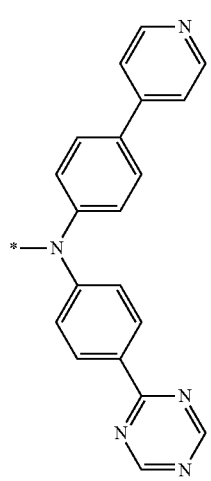
-continued
U31 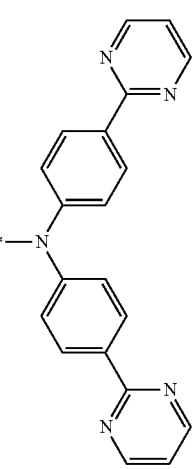
U32 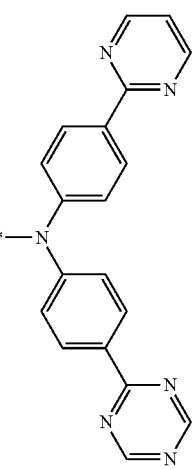
U33 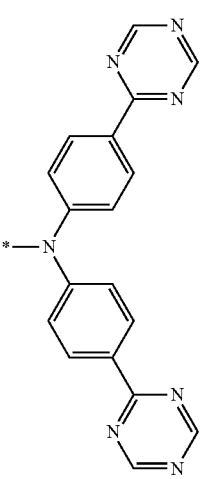

-continued
U34
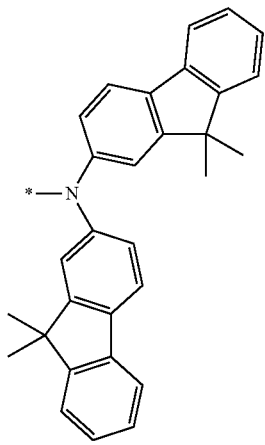
U35
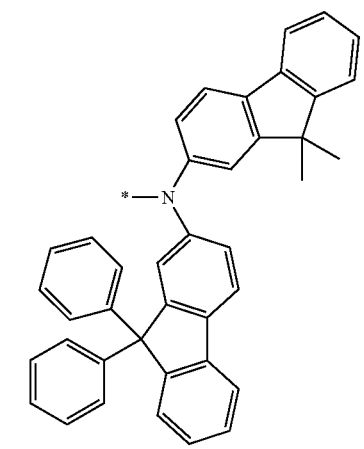
U36
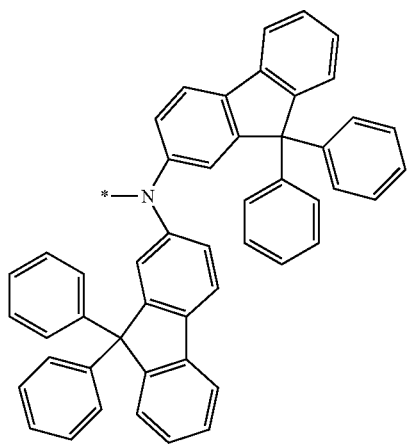
-continued
U37
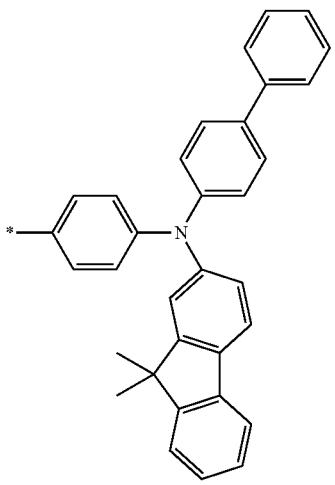
U38
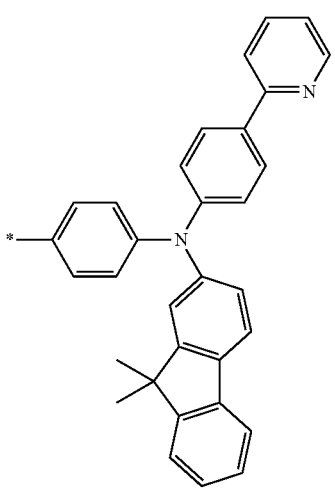
U39
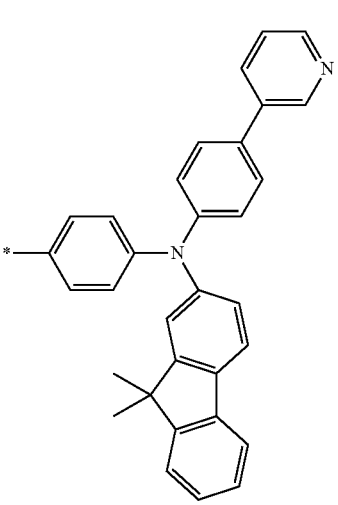

U40
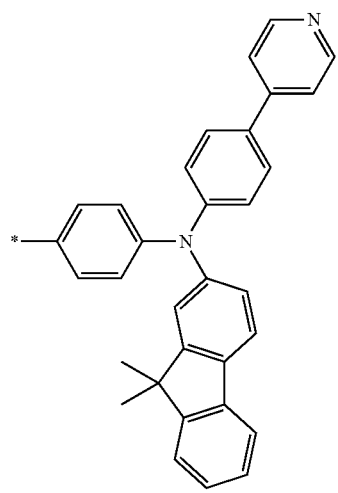
U41
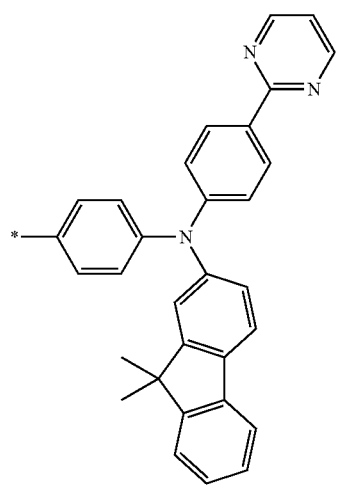
U42
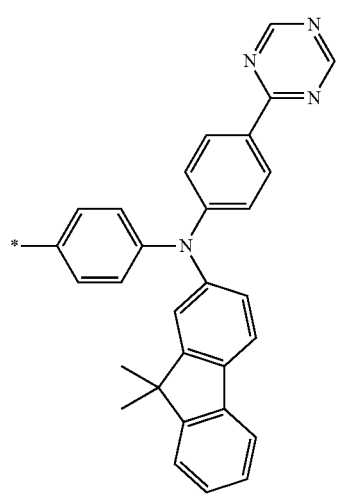
U43
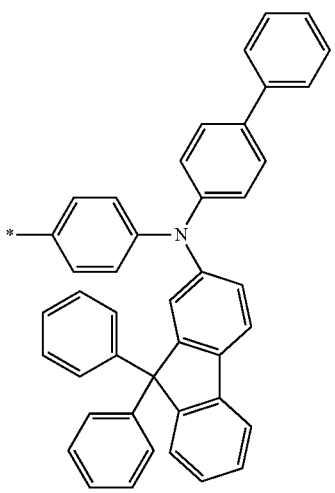
U44
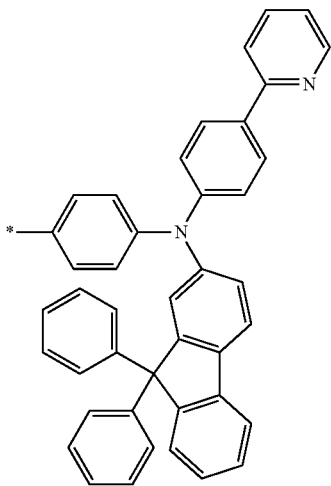
U45
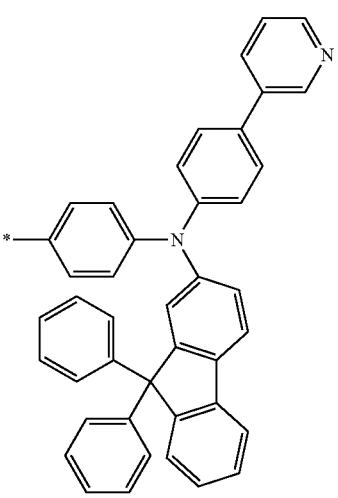

U46
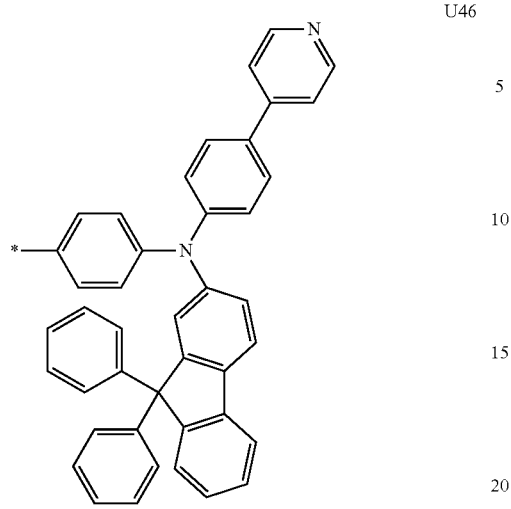
U47
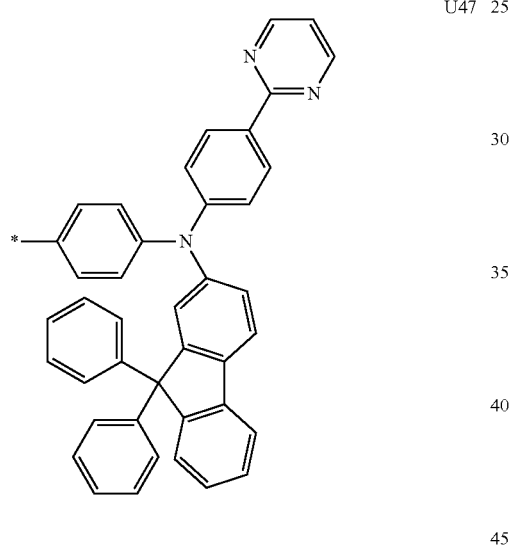
U48
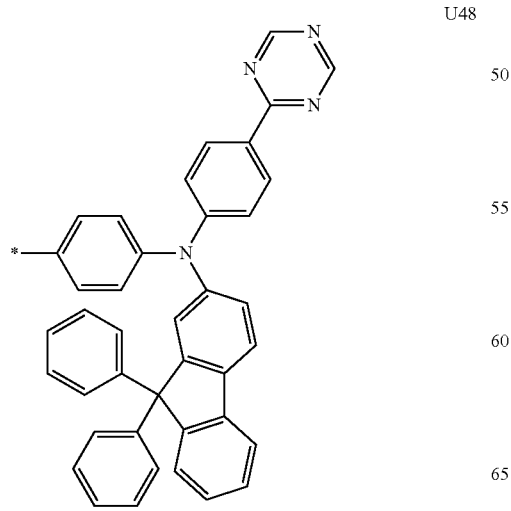
U49
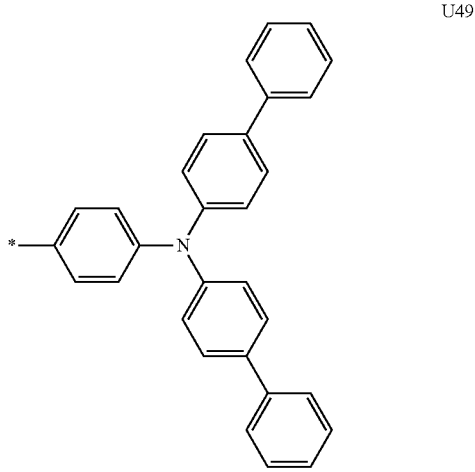
U50
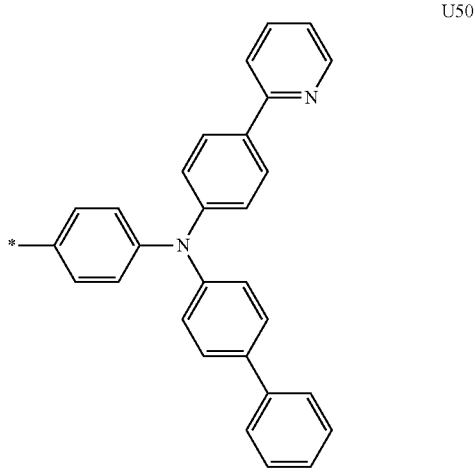
U51
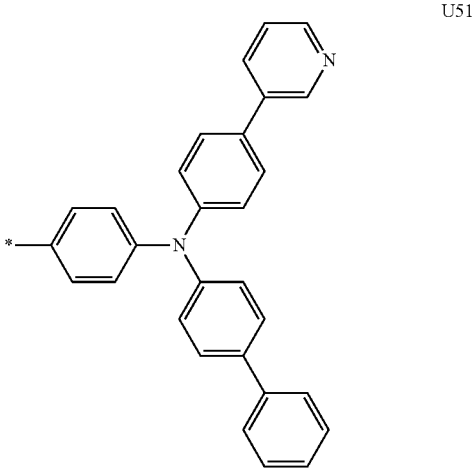

U52 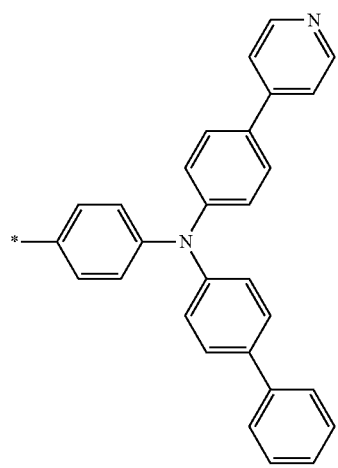
U53 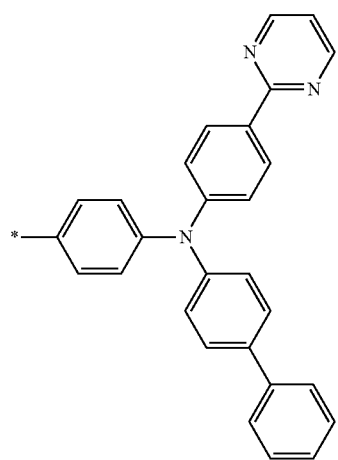
U54 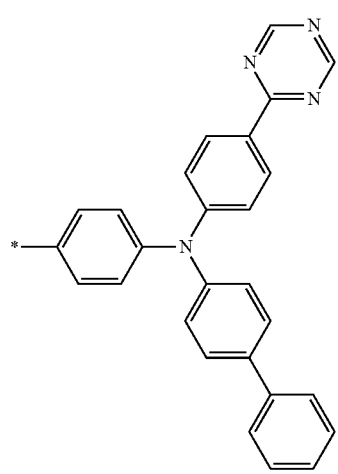
U55 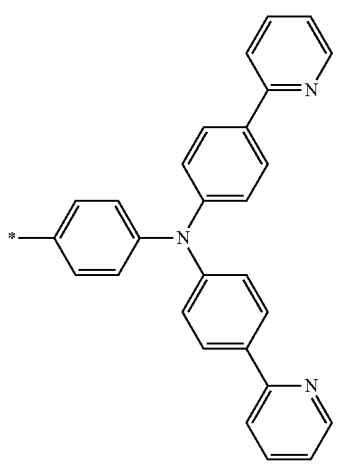
U56 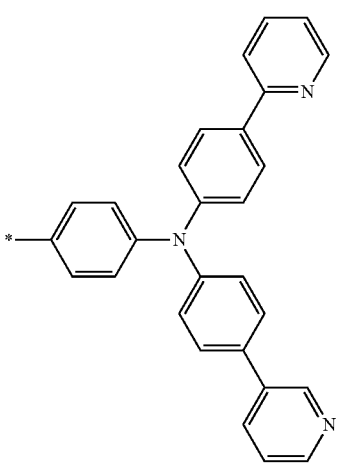
U57 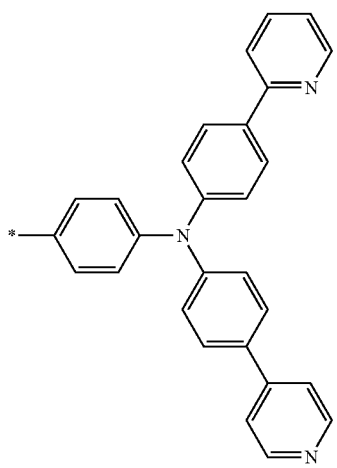

-continued
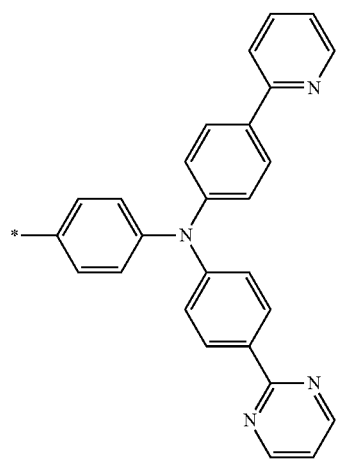
U58
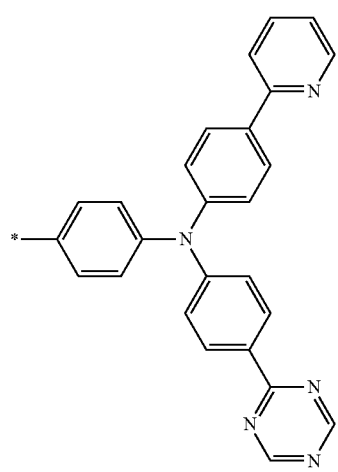
U59
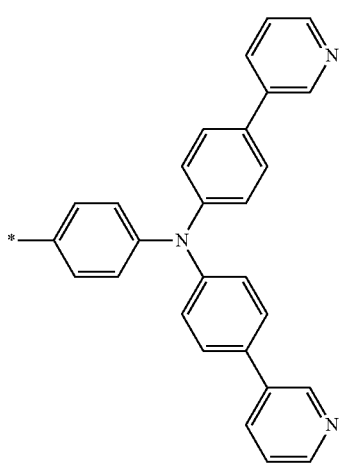
U60
-continued
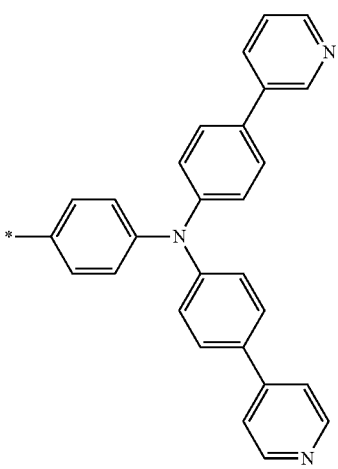
U61
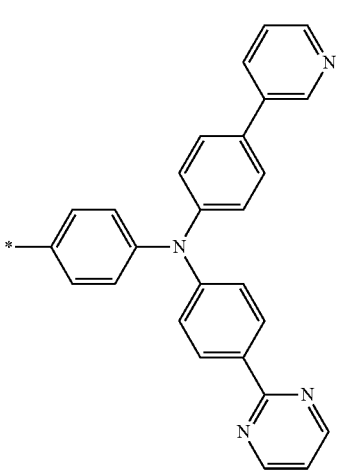
U62
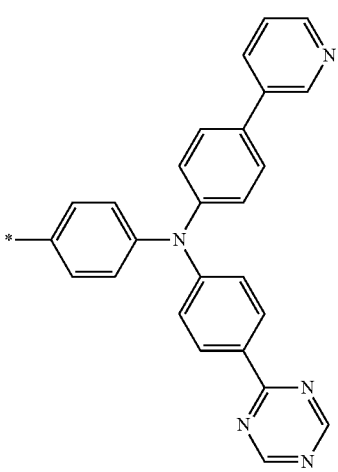
U63

U64
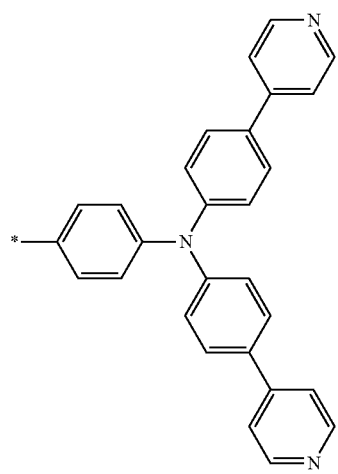
U65
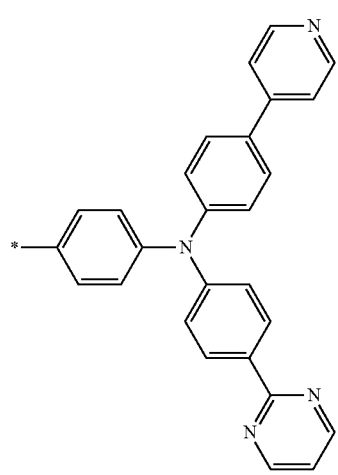
U66
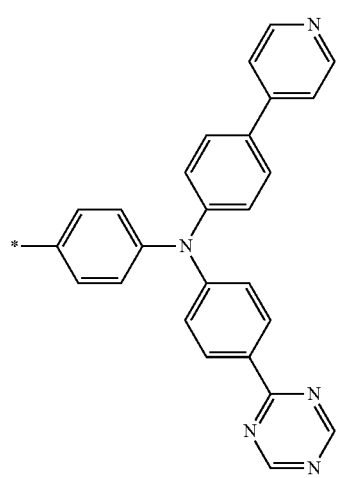
U67
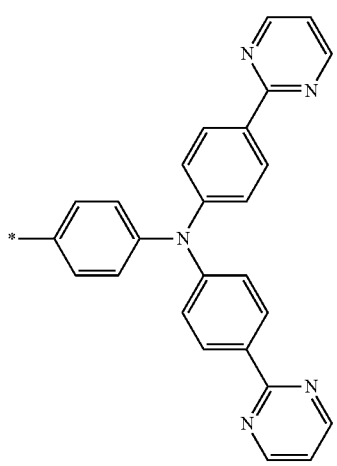
U68
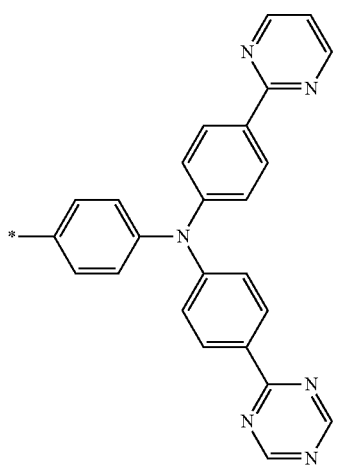
U69
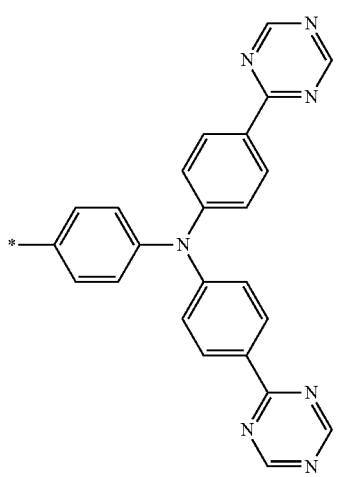

U70
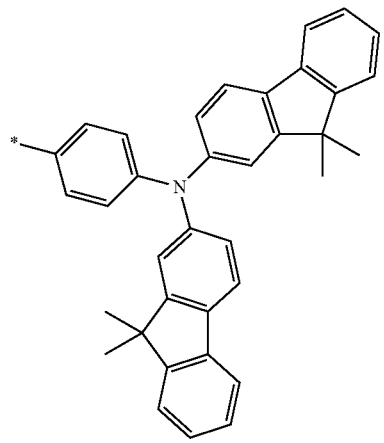
U71
U72
U73
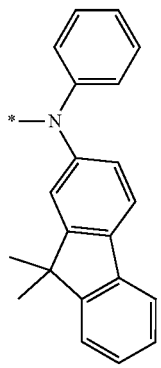
U74
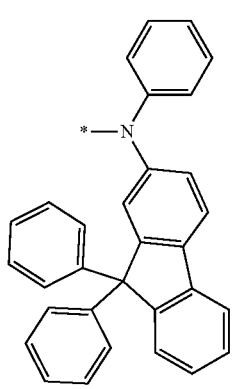
U75
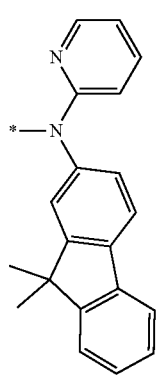
U76
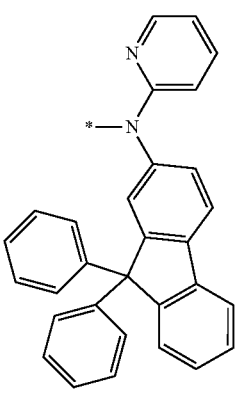

-continued
U77
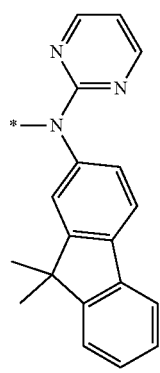
U78
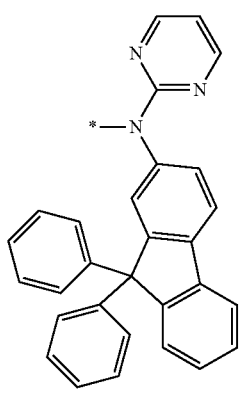
U79
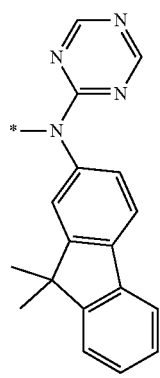
U80
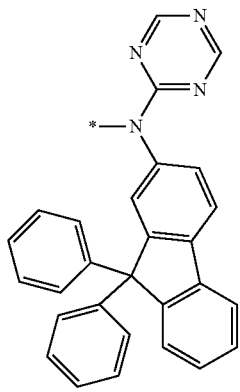
-continued
U81
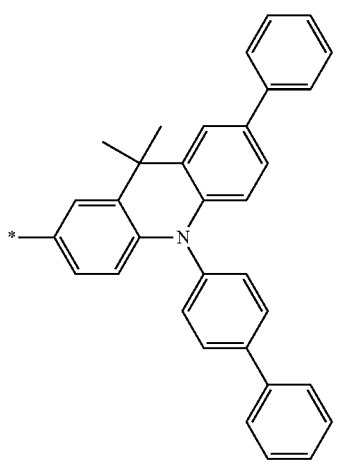
U82
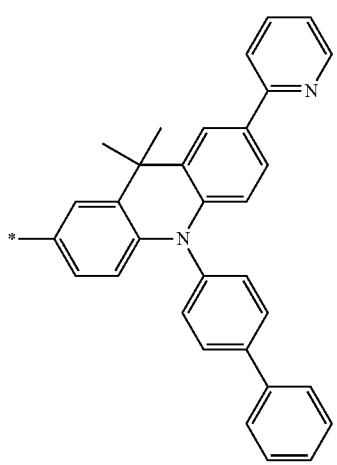
U83
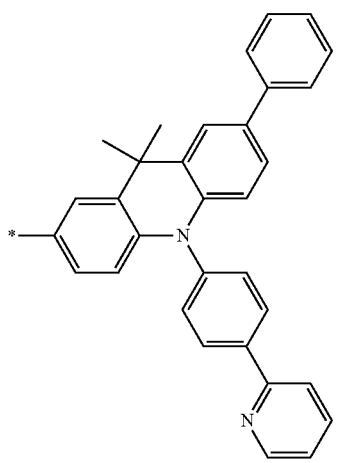

-continued

U84
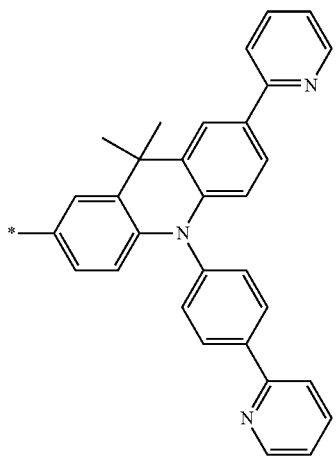

U85
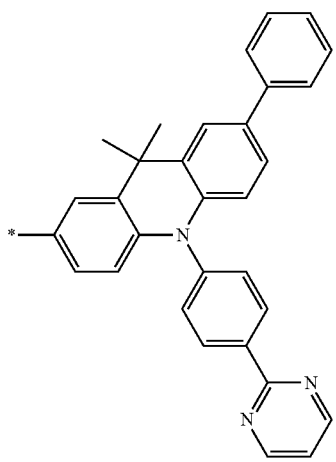

U86
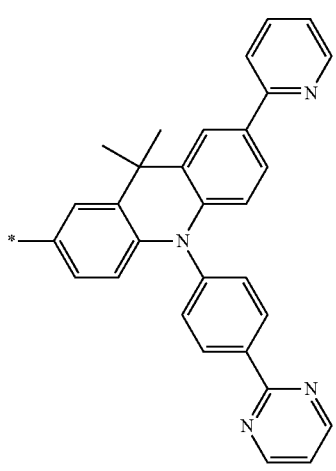

$X_1$ and $X_2$ are each $N(Ar_1)$, and are the same as or different from each other;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ to $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group; and wherein one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other.

2. A compound selected from the group consisting of the following Compounds Mat-1 to Mat-18, Mat-21, Mat-27, and Mat-31 to Mat-39:

Mat-1
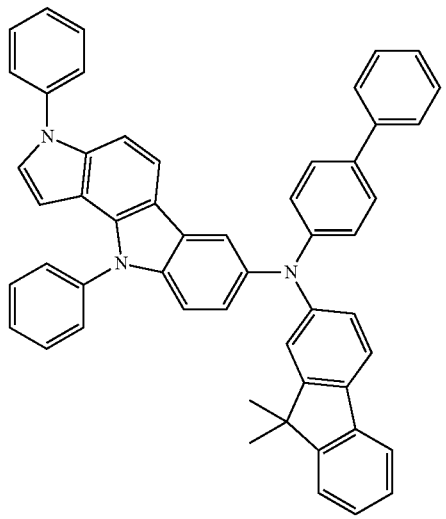
Mat-2
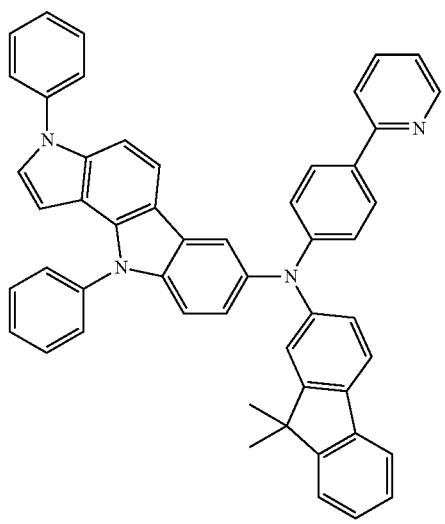
Mat-3
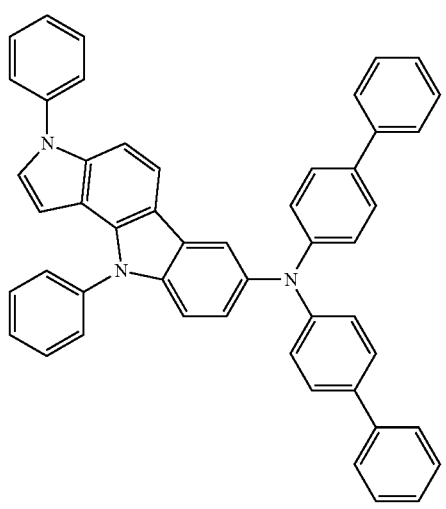
-continued
Mat-4
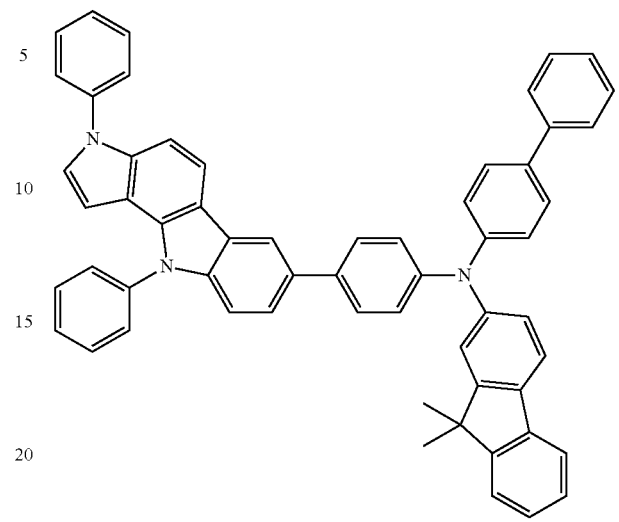
Mat-5
Mat-6

Mat-7
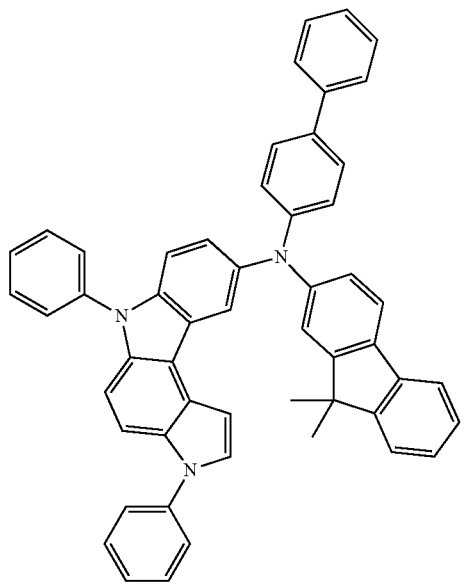
Mat-8
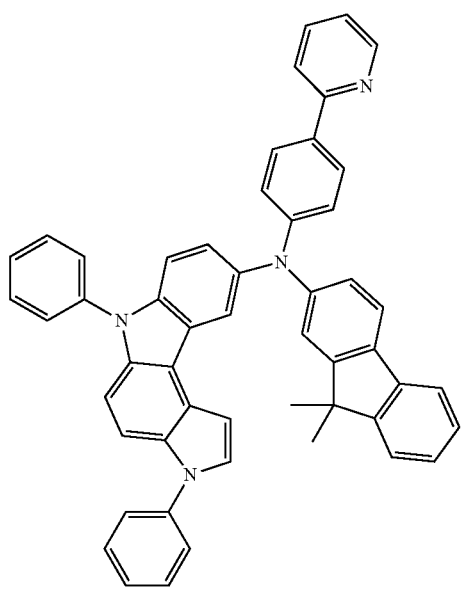
Mat-9
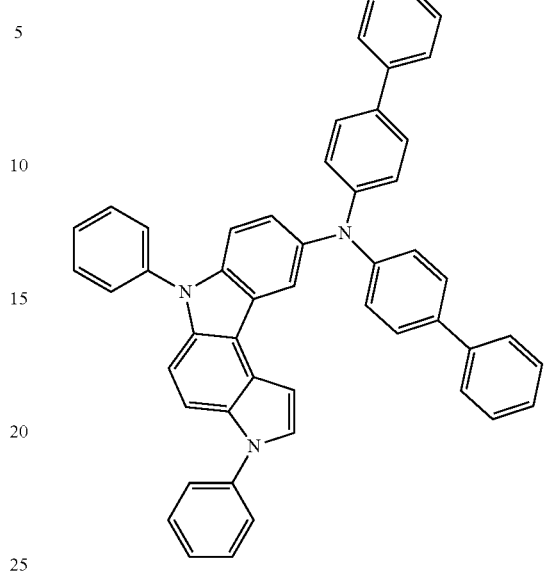
Mat-10
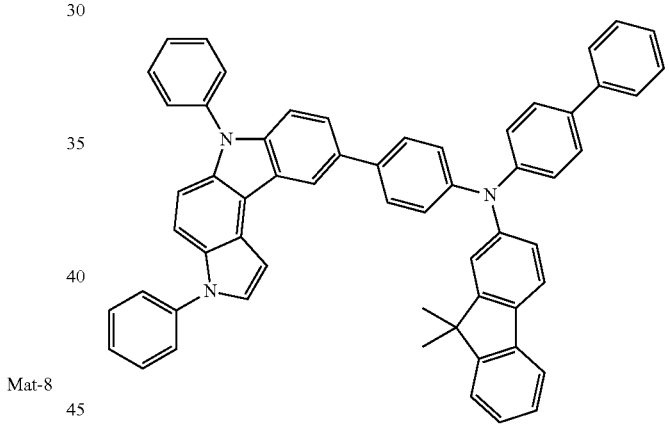
Mat-11
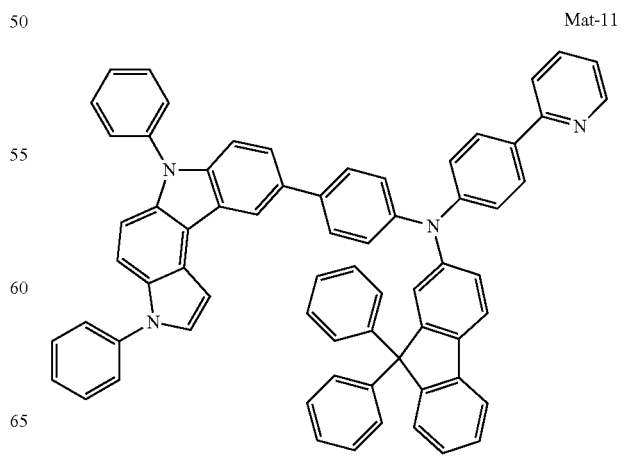

Mat-12
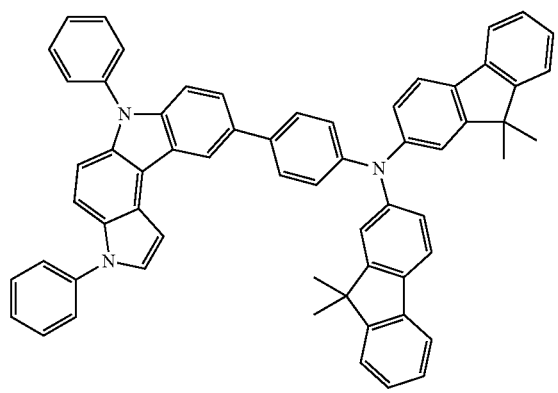
Mat-13
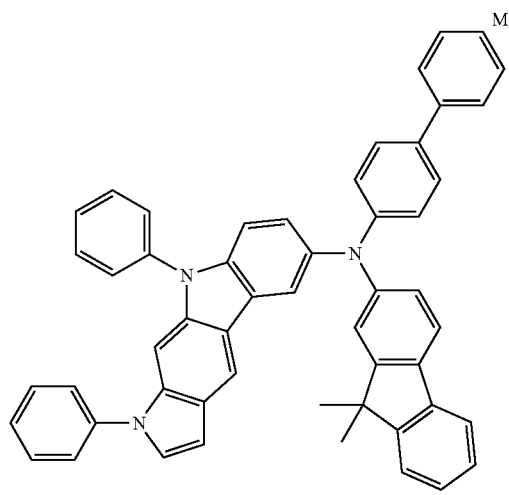
Mat-14
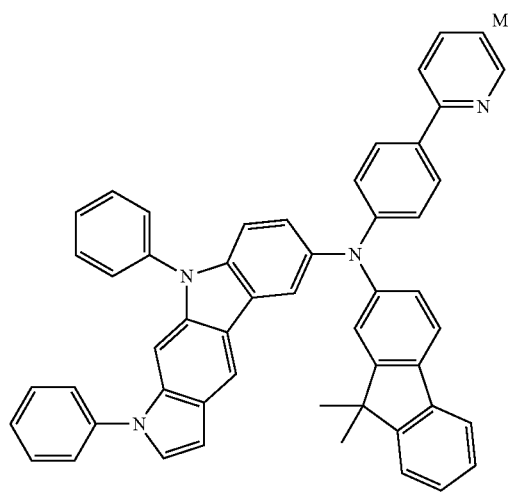
Mat-15
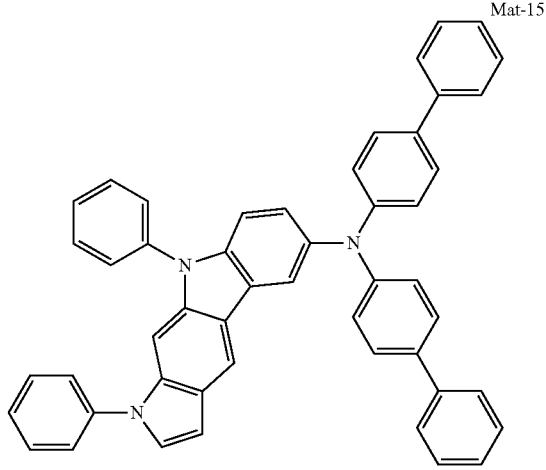
Mat-16
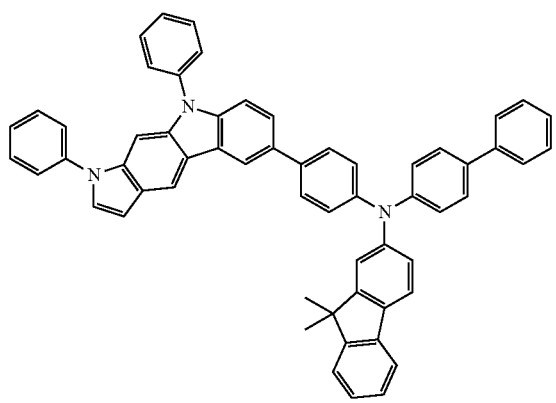
Mat-17
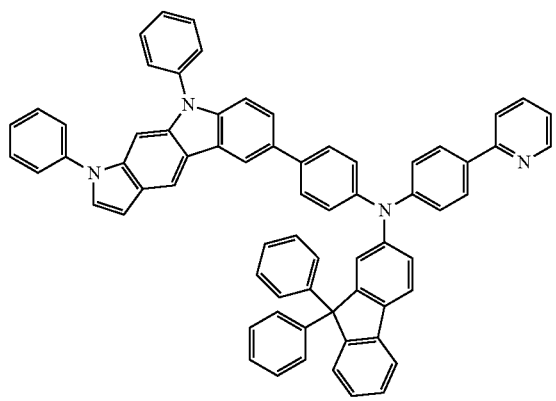

Mat-18
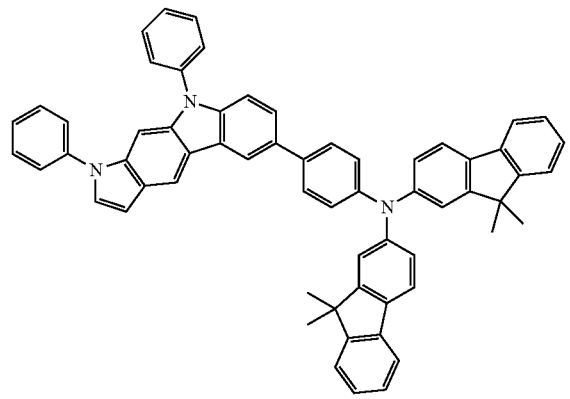
Mat-21
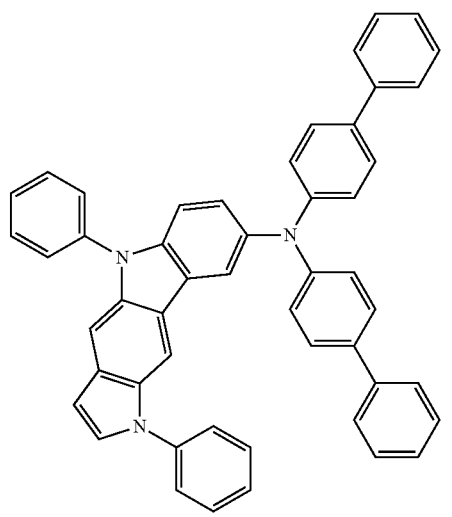
Mat-27
Mat-31
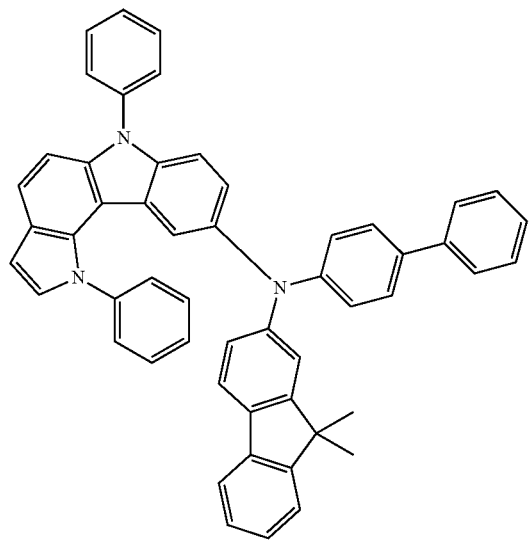
Mat-32
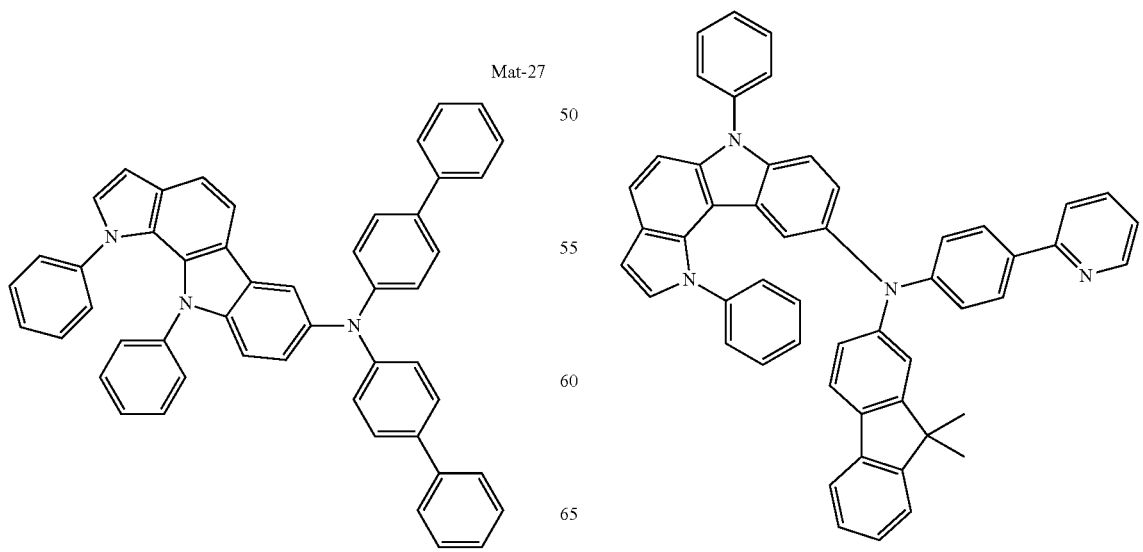

Mat-33
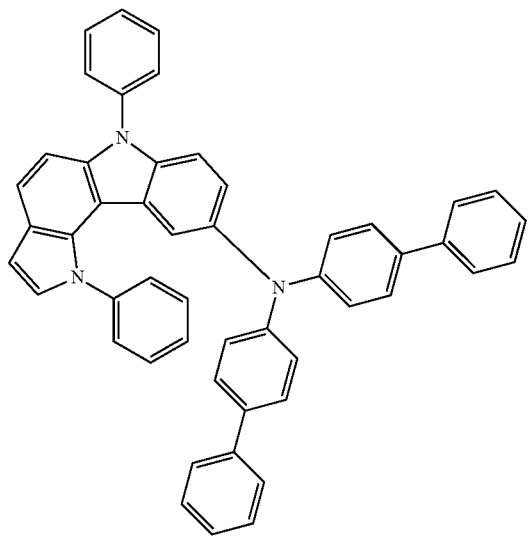
Mat-34
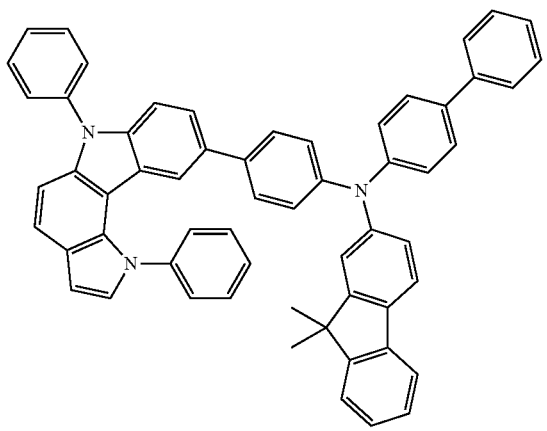
Mat-35
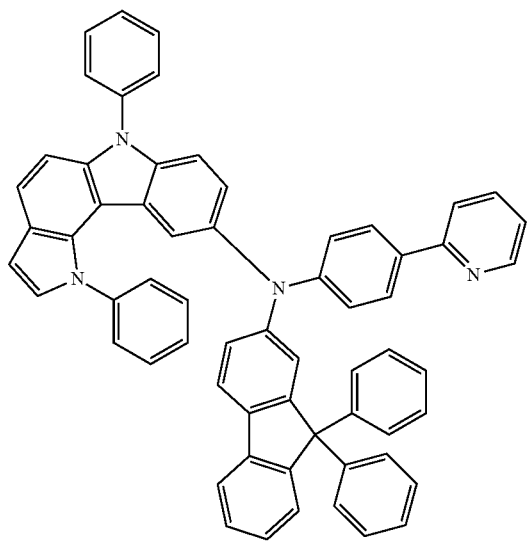
Mat-36
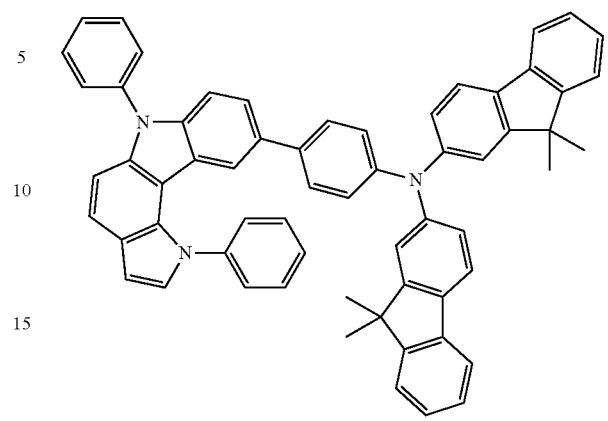
Mat-37
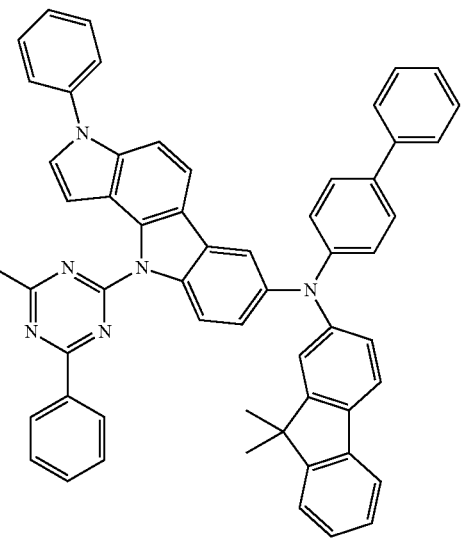
Mat-38
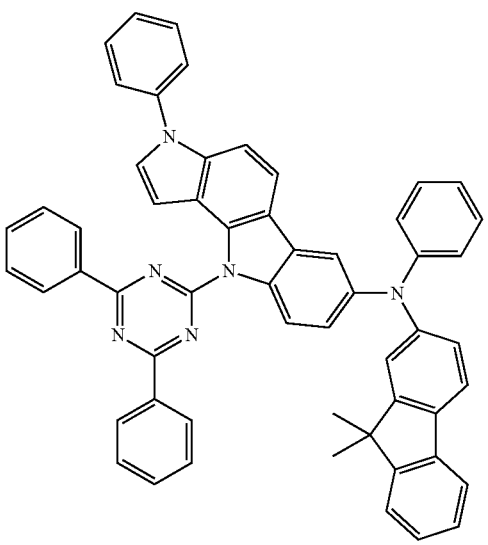

-continued

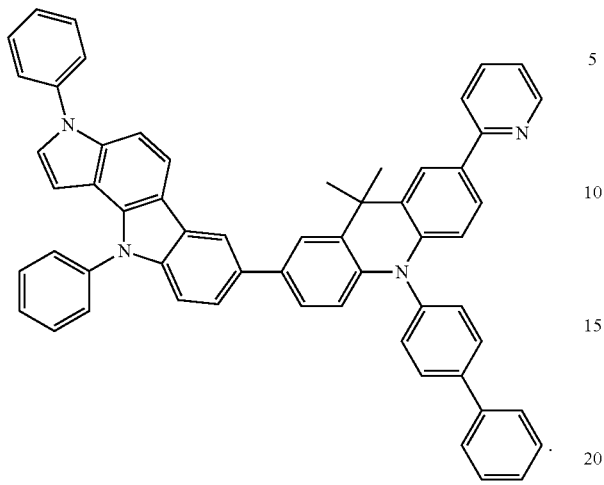
Mat-39

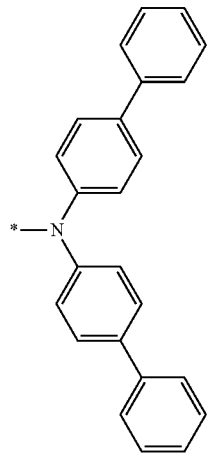
U13

3. A compound represented by the following Formula 4 or 8:

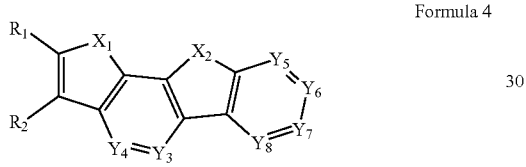
Formula 4

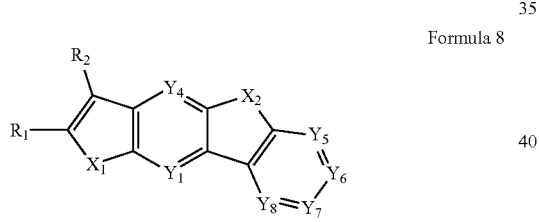
Formula 8 wherein, $Y_1$, $Y_3$ and $Y_4$ are each independently N or $CR_3$, and when $CR_3$ is present in a plural number, they are the same as or different from each other;

$Y_5$ to $Y_8$ are each independently N or $CR_4$, and when $CR_4$ is present in a plural number, they are the same as or different from each other, and provided that at least one of $Y_5$ to $Y_8$ is $CR_4$, and in this case, at least one of one or more $R_4$'s is a substituent of the following Formula 3,

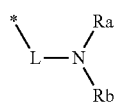
Formula 3 wherein the substituent represented by the Formula 3 is selected from the group consisting of the following substituents U13 to U33, U49 to U69, and U81 to U86;

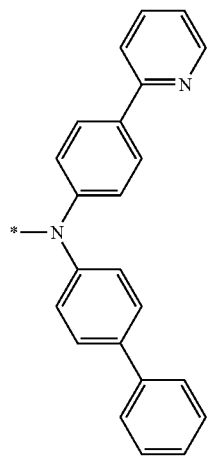
U14

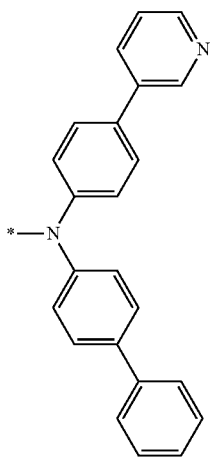
U15

U16 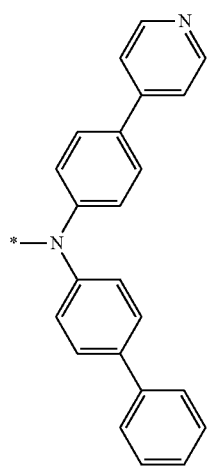
U17 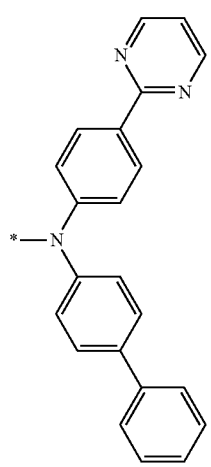
U18 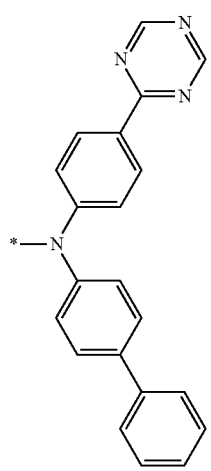
U19 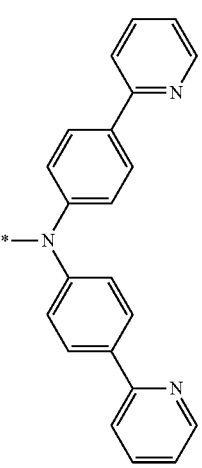
U21 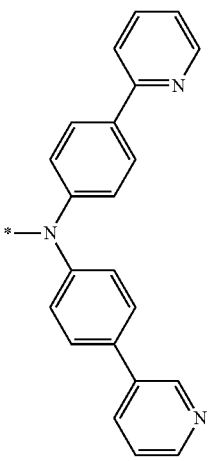
U21 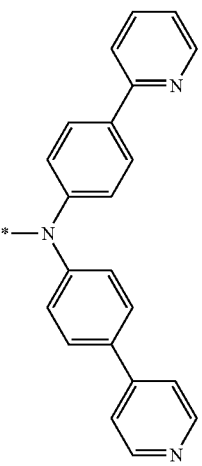

U22 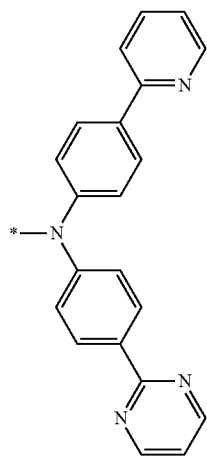
U23 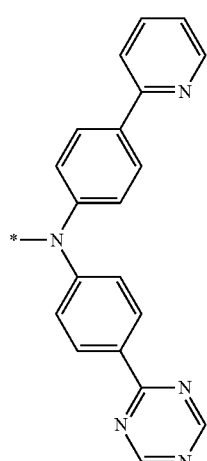
U24 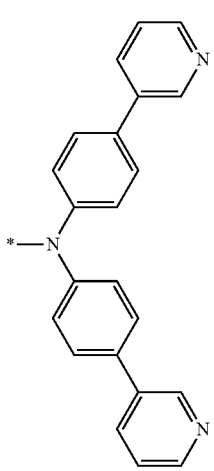
U25 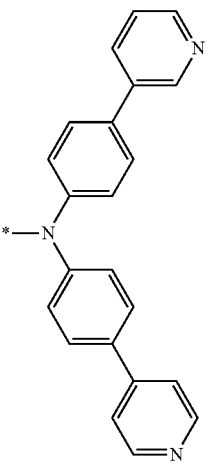
U26 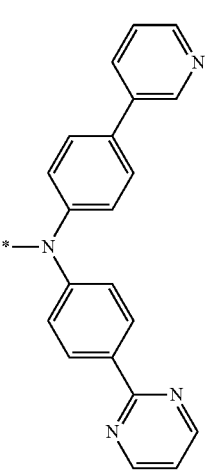
U27 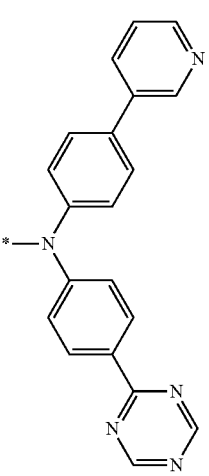

| U28 | 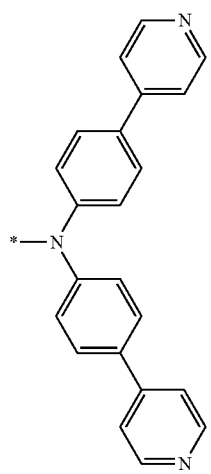 | U31 | 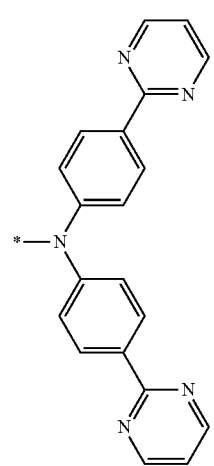 |
| U29 | 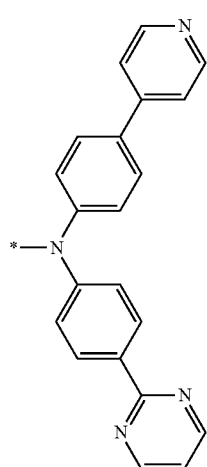 | U32 | 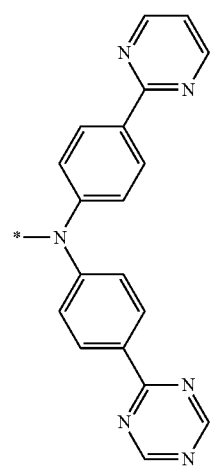 |
| U30 | 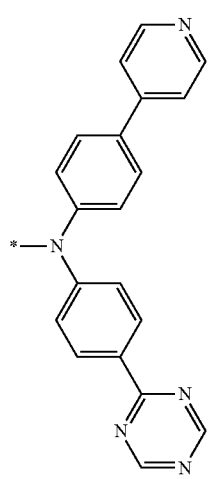 | U33 | 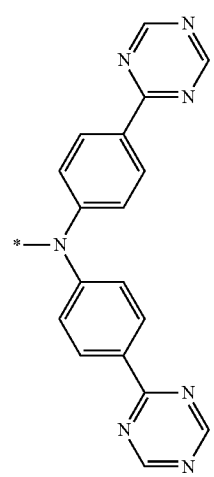 |

U49
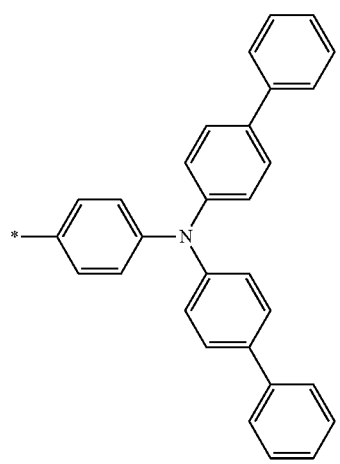
U52
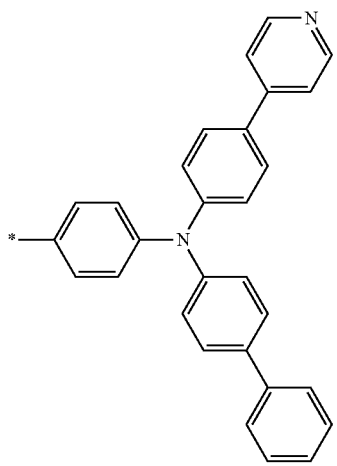
U50
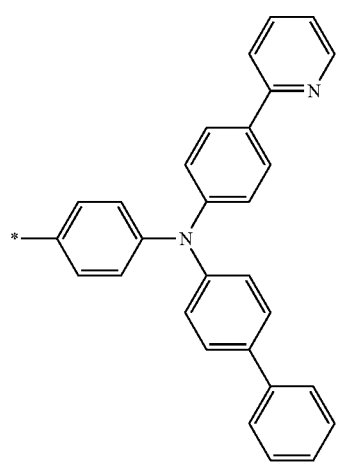
U53
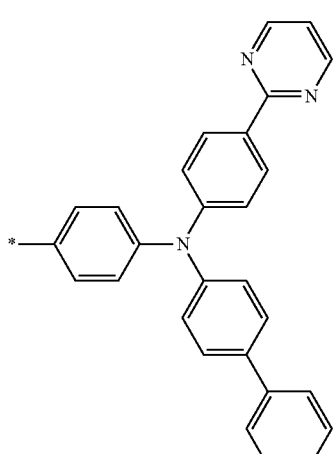
U51
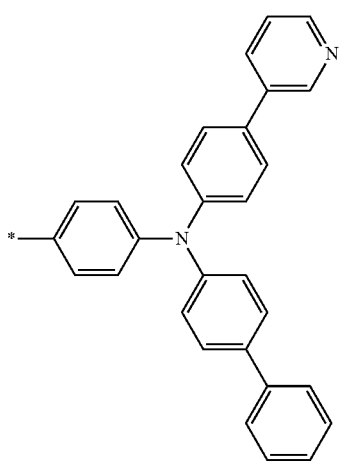
U54
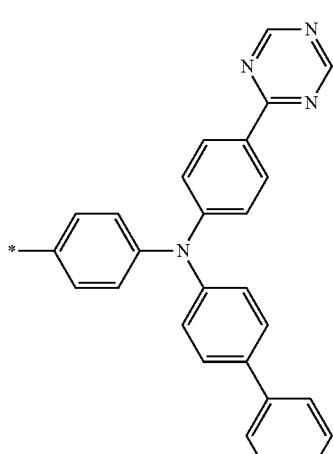

U55
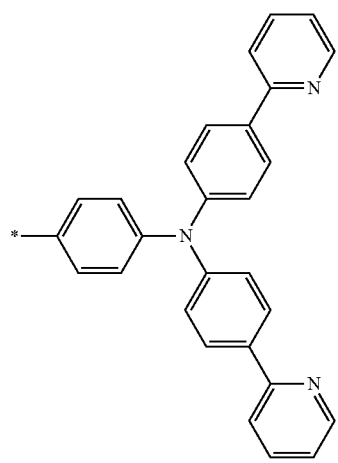
U56
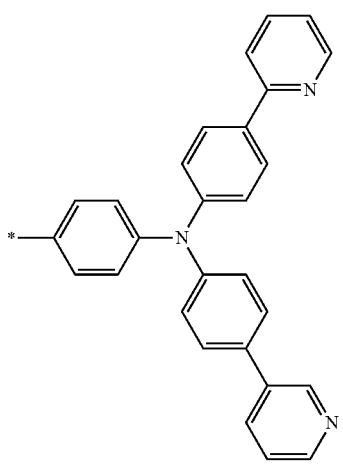
U57
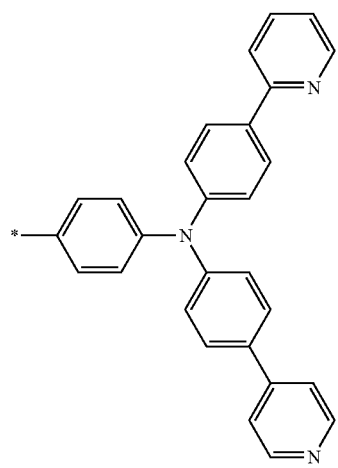
U58
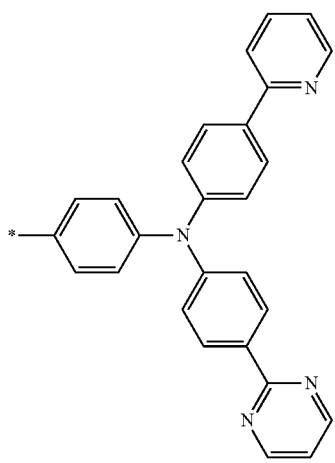
U59
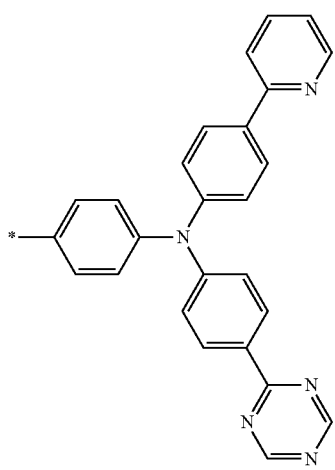
U60
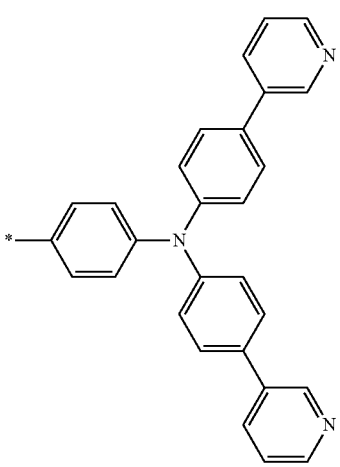

-continued
U61 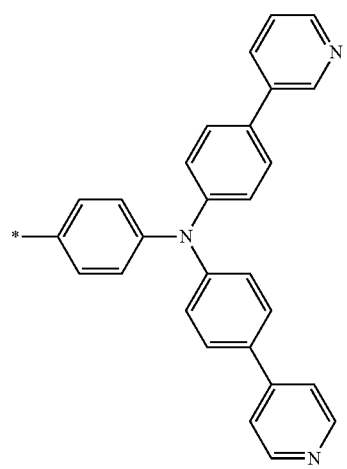
U62 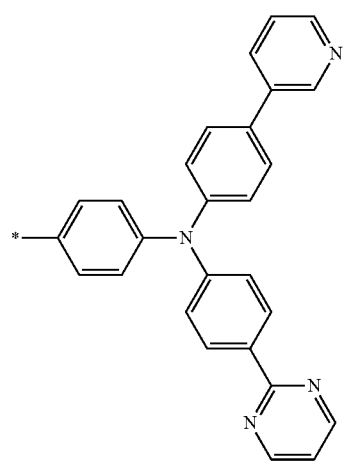
U63 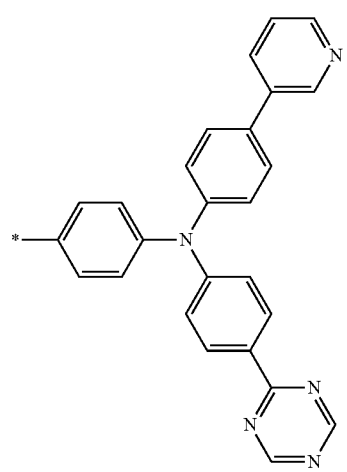
-continued
U64 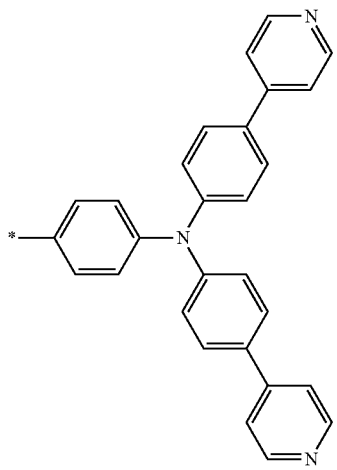
U65 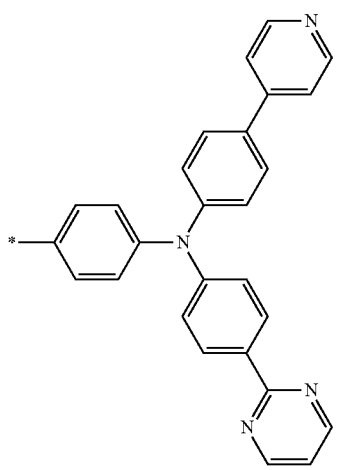
U66 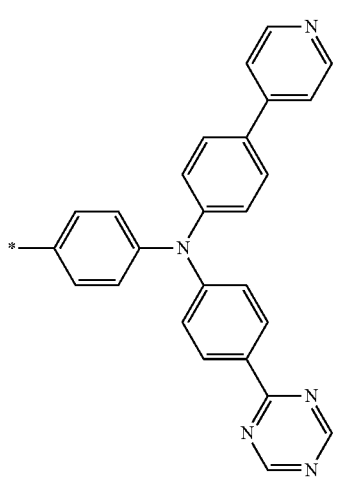

U67
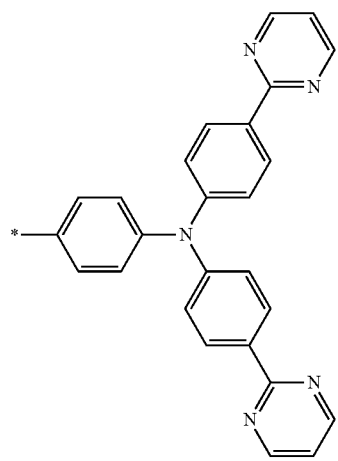
U68
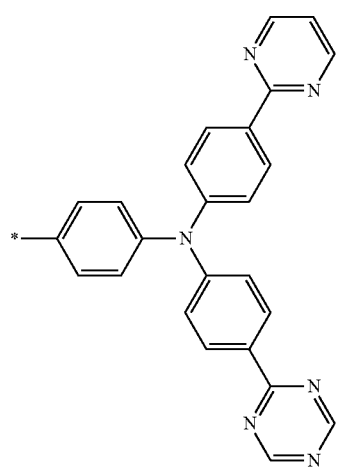
U69
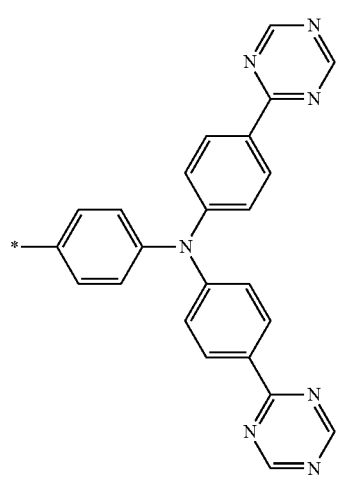
U81
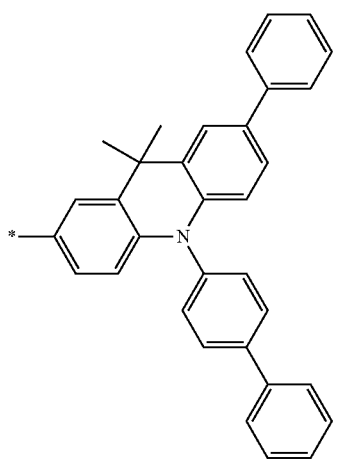
U82
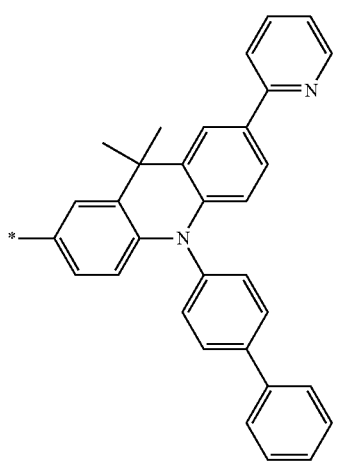
U83
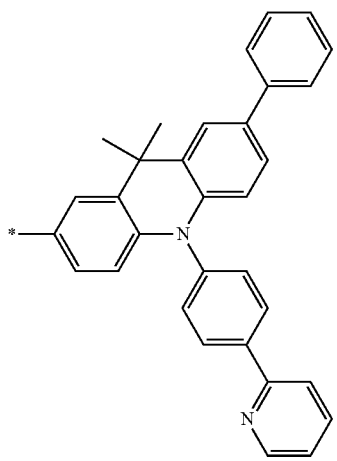

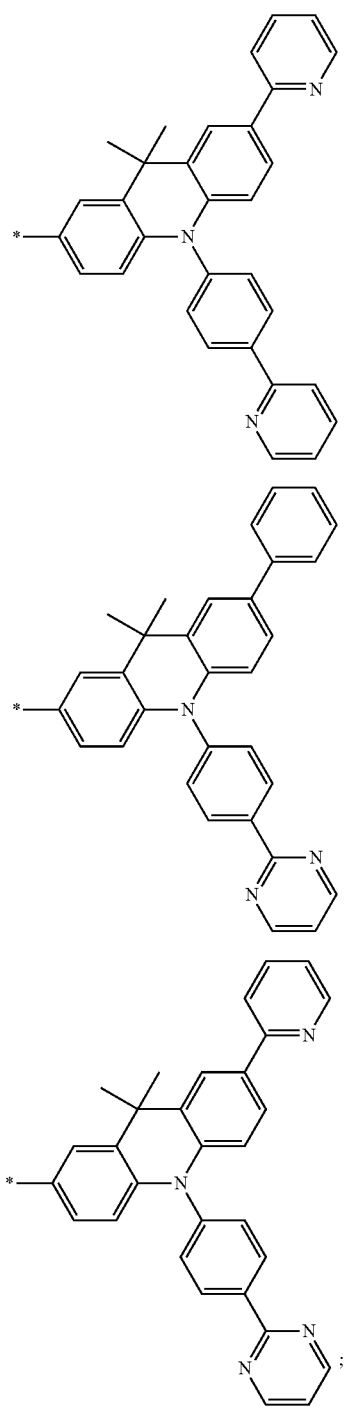

$X_1$ and $X_2$ are $N(Ar_1)$, and when $N(Ar_1)$ is present in a plural number, they are the same as or different from each other;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ and $R_2$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group;

$R_3$ and $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and they form or do not form a fused ring with an adjacent group;

wherein one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other.

4. The compound of claim 3, wherein the compound is selected from the group consisting of compounds of the following Formulae 10 and 14:

Formula 10

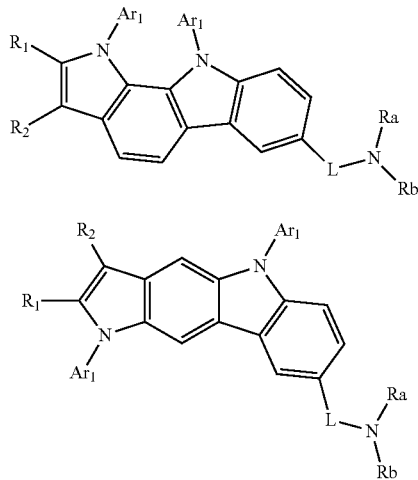

Formula 14 wherein,

R₁, R₂, Ar₁, and

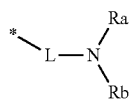

are each the same as those defined in claim 3, and when Ar₁ is present in a plural number, they are the same as or different from each other.

5. An organic electroluminescence device comprising: an anode; a cathode; and an organic material layer comprising one or more layers interposed between the anode and the cathode, wherein at least one of the one or more layers of the organic material layer comprises the compound represented by the following Formula 4 or 8:

Formula 4

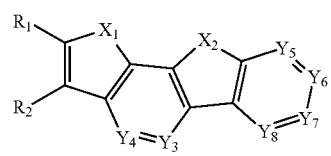

Formula 8

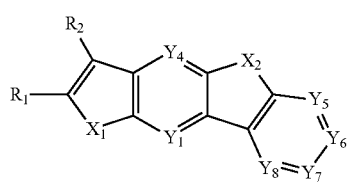

wherein, $Y_1$, $Y_3$ and $Y_4$ are each independently N or $CR_3$, and when $CR_3$ is present in a plural number, they are the same as or different from each other;

$Y_5$ to $Y_8$ are each independently N or $CR_4$, and when $CR_4$ is present in a plural number, they are the same as or different from each other, and provided that at least one of $Y_5$ to $Y_8$ is $CR_4$, and in this case, at least one $R_4$ is a substituent represented by the following Formula 3, Formula 3

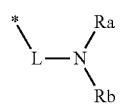

wherein the substituent represented by the Formula 3 is selected from the group consisting of the following substituents U13 to U33, U49 to U69, and U81 to U86;

U13

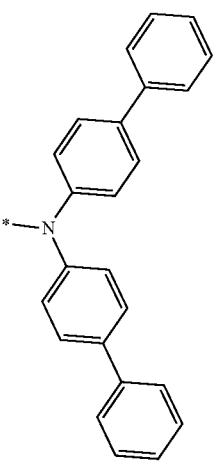

U14

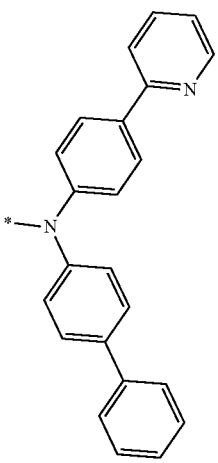

U15 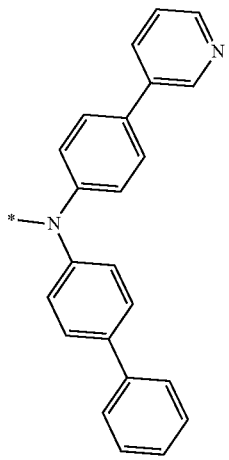
U16 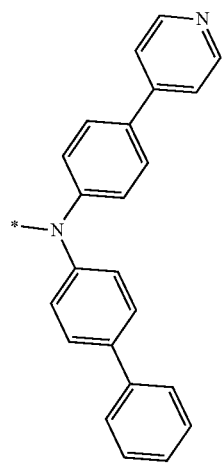
U17 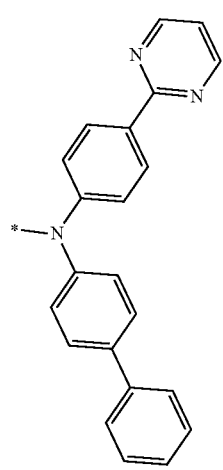
U18 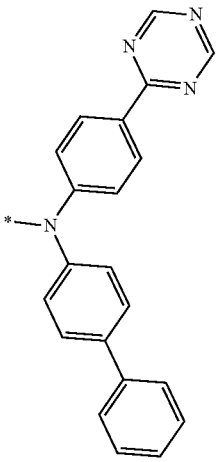
U19 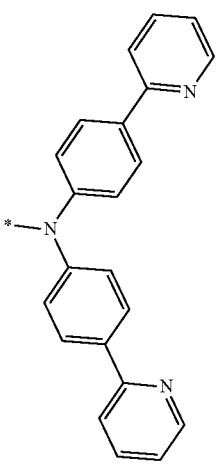
U20 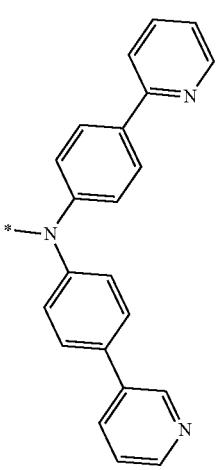

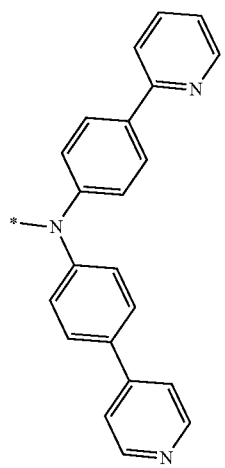
U21
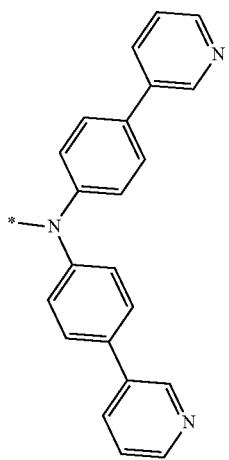
U24
U22
U25
U23
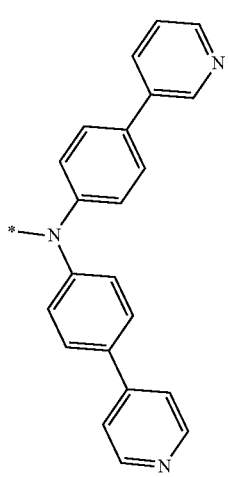
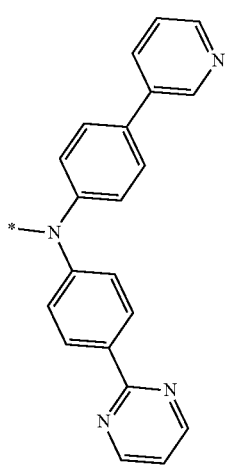
U26

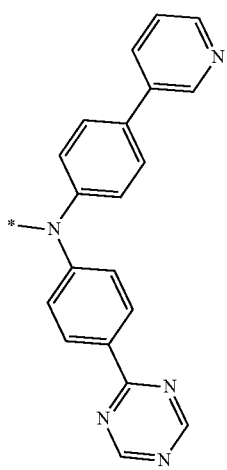 U27
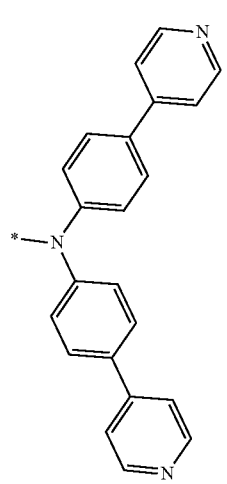 U28
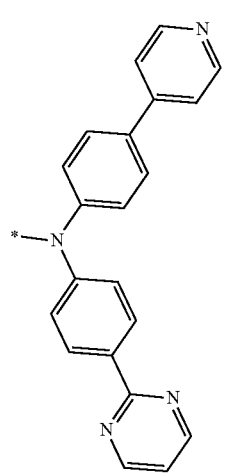 U29
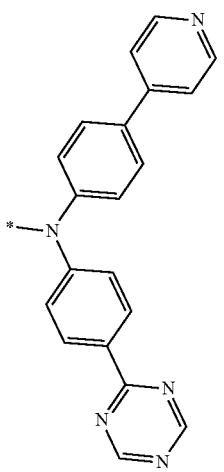 U30

-continued
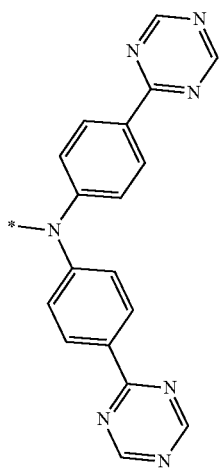
U33
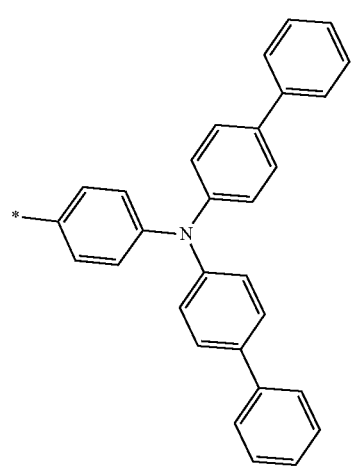
U49
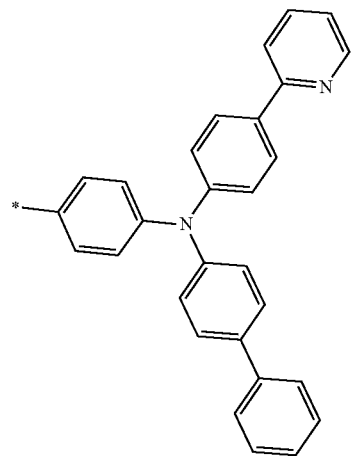
U50
-continued
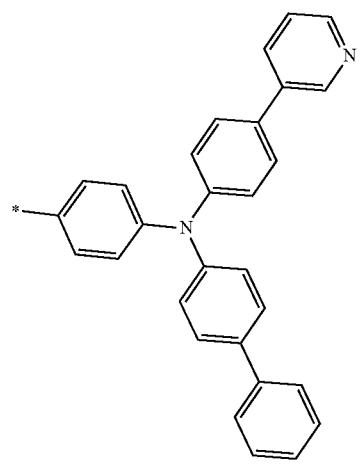
U51
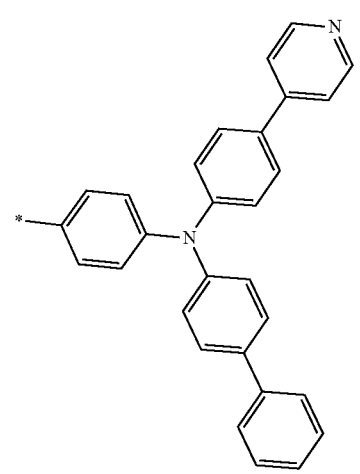
U52
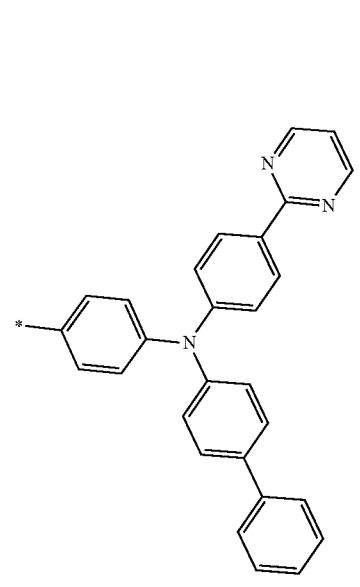
U53

U54 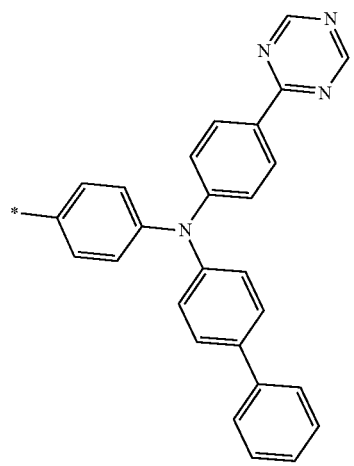
U55 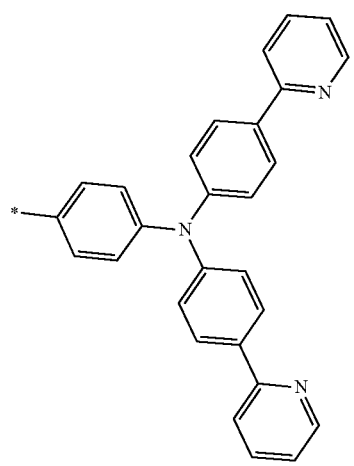
U56 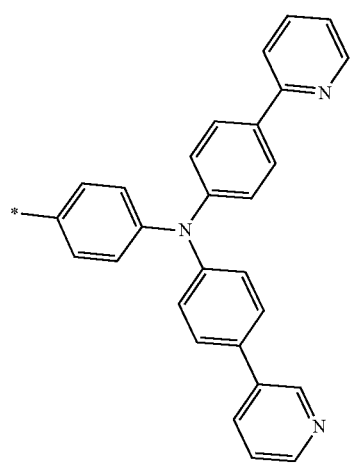
U57 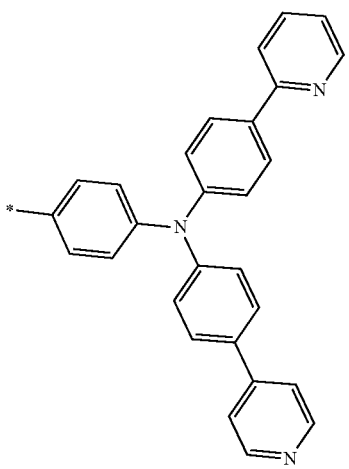
U58 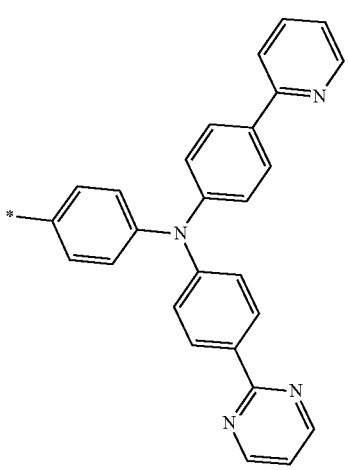
U59 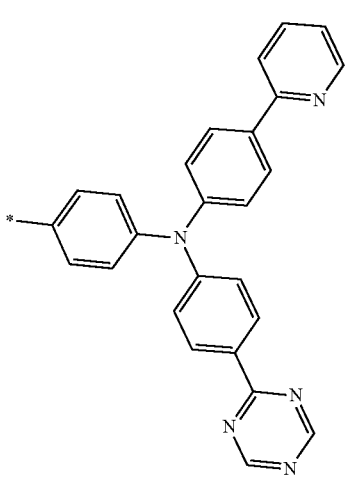

U60 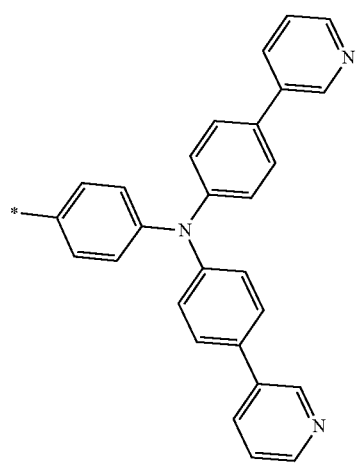
U61 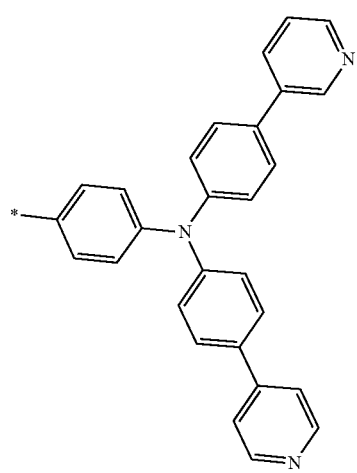
U62 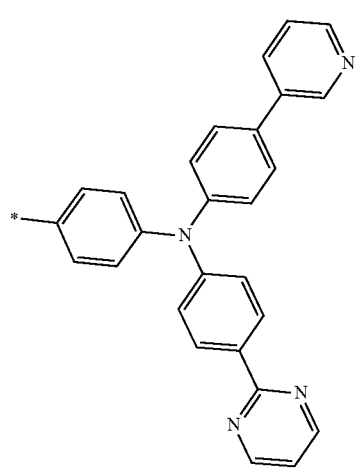
U63 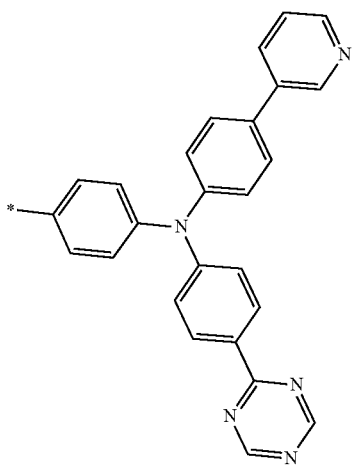
U64 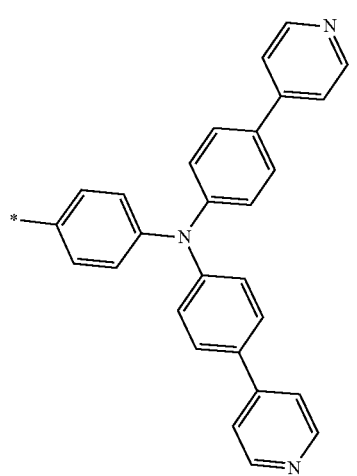
U65 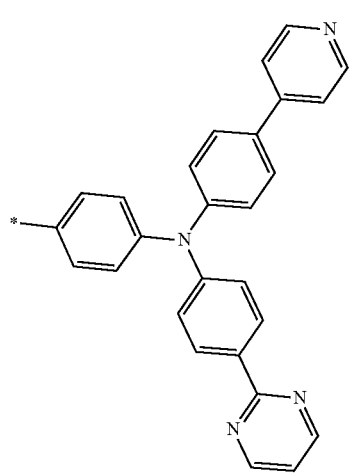

U66 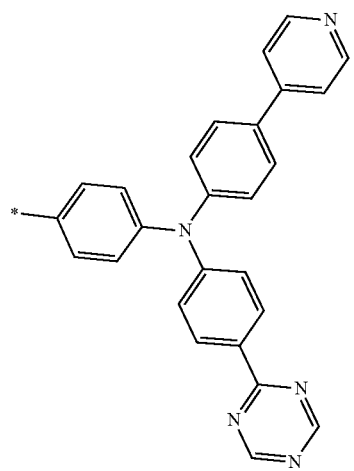
U67 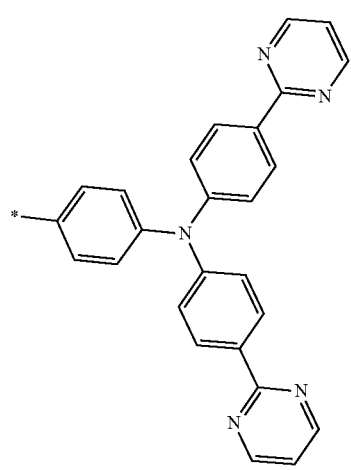
U68 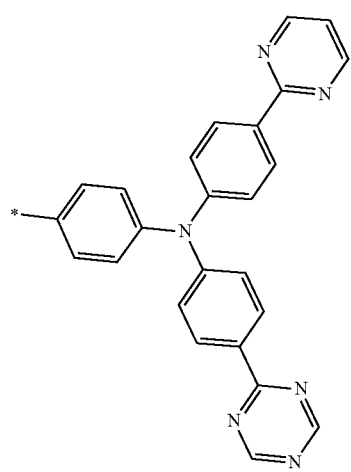
U69 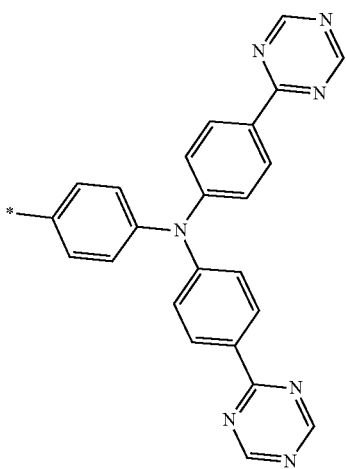
U81 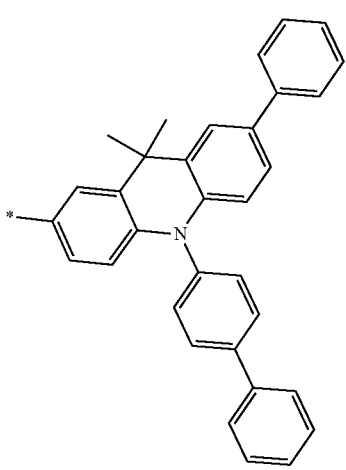
U82 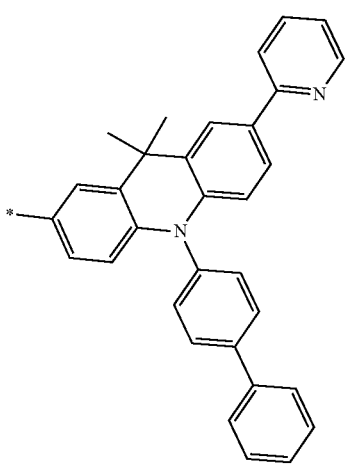

U83 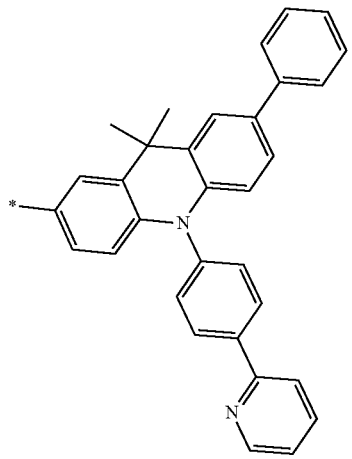

U84 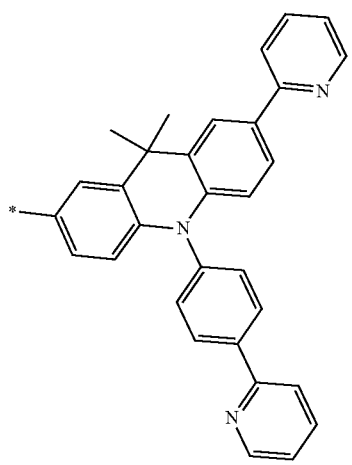

U85 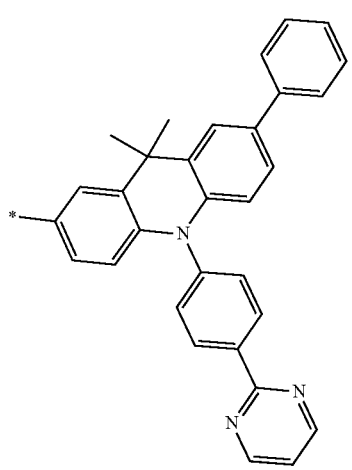

U86 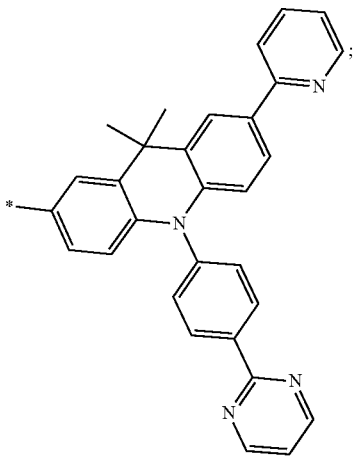

$X_1$ and $X_2$ are each $N(Ar_1)$, and are the same as or different from each other;

$Ar_1$ is independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ and $R_2$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group;

$R_3$ and $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and they form or do not form a fused ring with an adjacent group, wherein one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other.

6. The organic electroluminescent device of claim 5, wherein the compound is a compound of the following Formula 10 or 14:

Formula 10

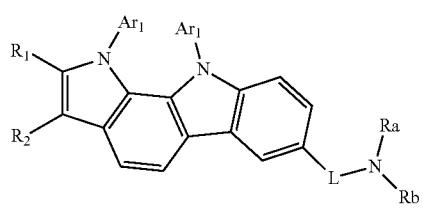

Formula 14

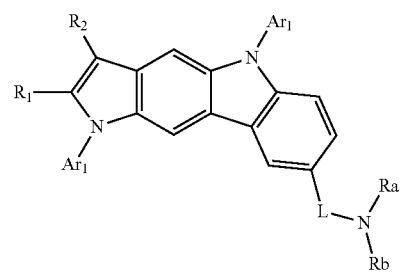

Formula 12

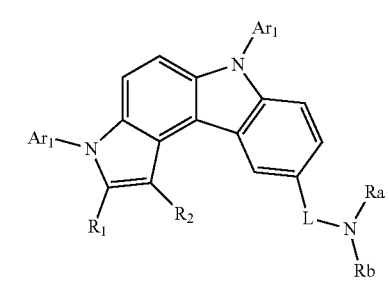

wherein the

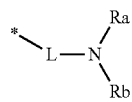

is selected from the group consisting of the following substituents U13 to U33, U49 to U69, and U81 to U86;

U13

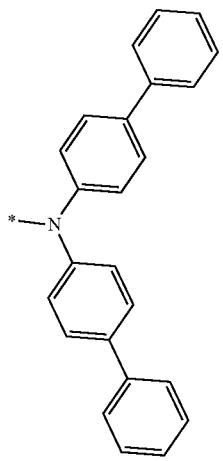

U14

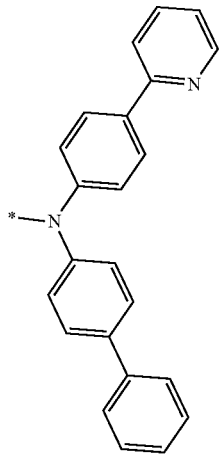

U15

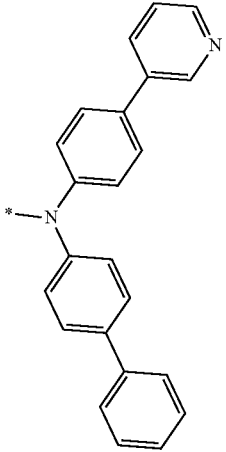

-continued
U16 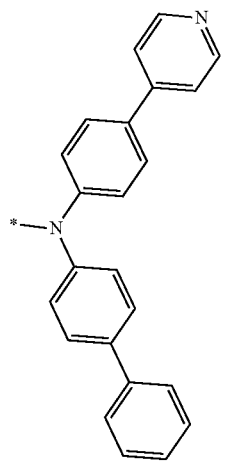
U17 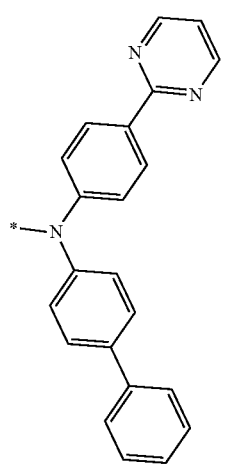
U18 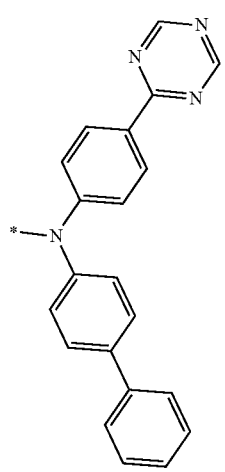
-continued
U19 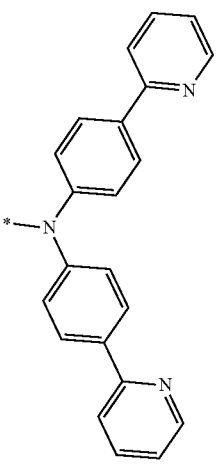
U20 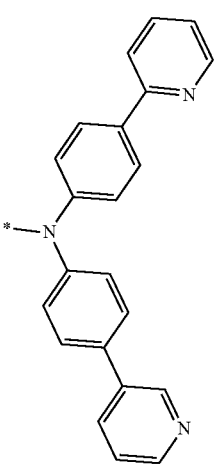
U21 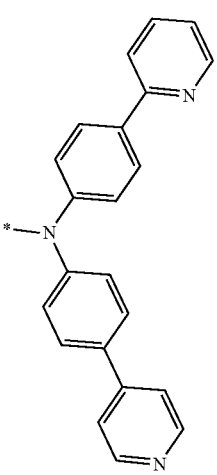

U22 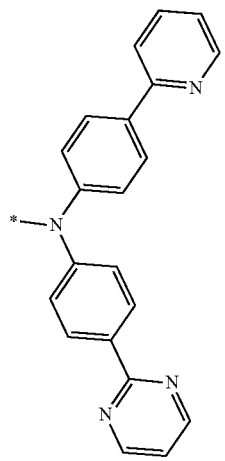
U23 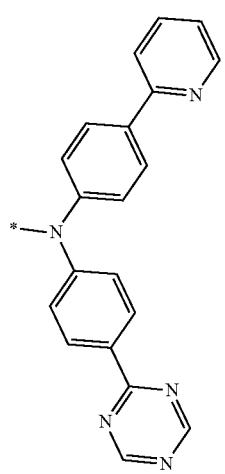
U24 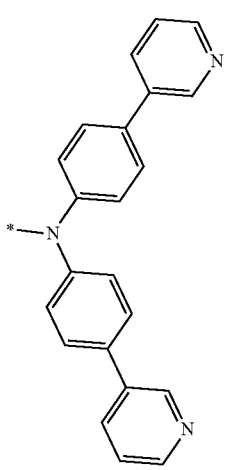
U25 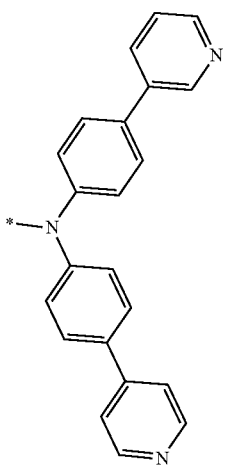
U26 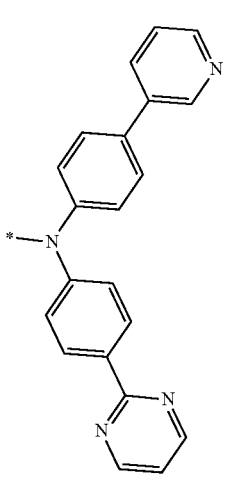
U27 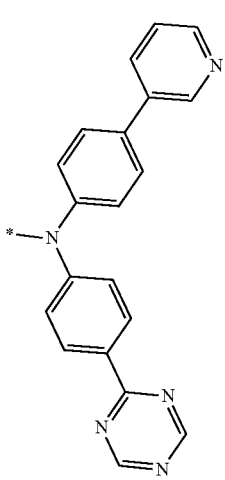

409
-continued
U28
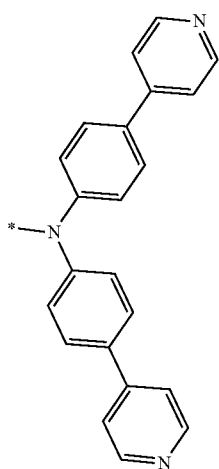
U29
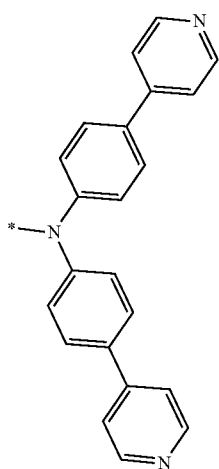
U30
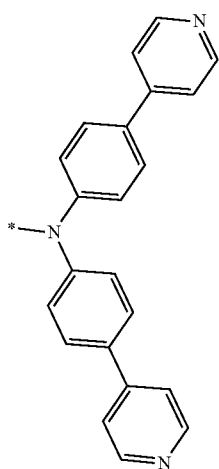
410
-continued
U31
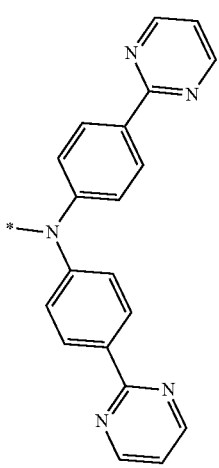
U32
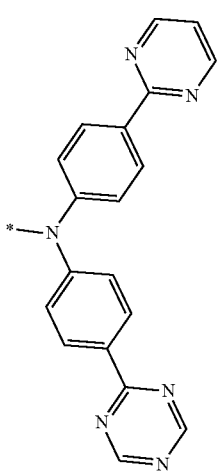
U33
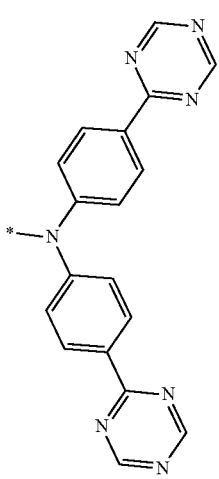

U49 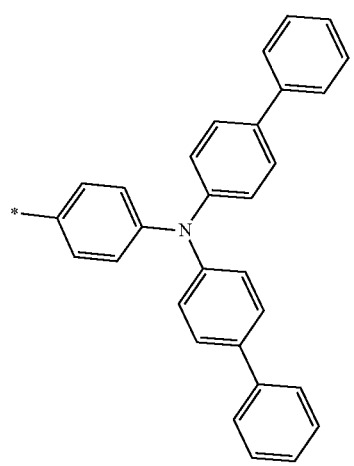
U50 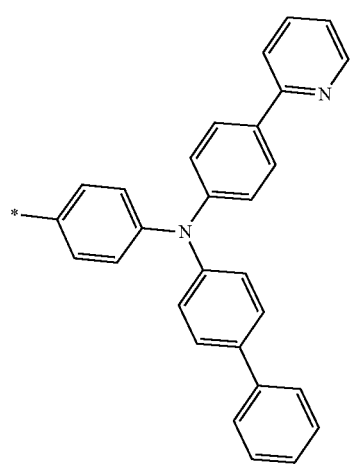
U51 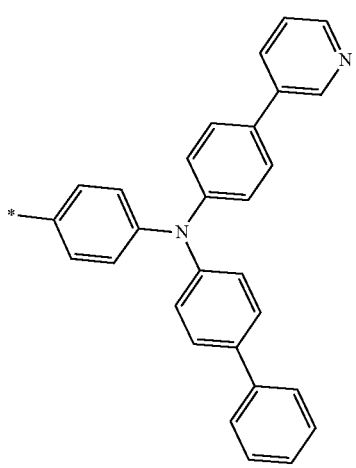
U52 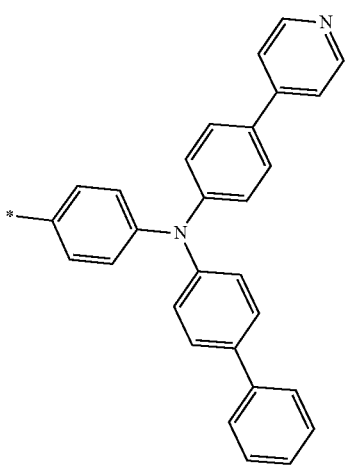
U53 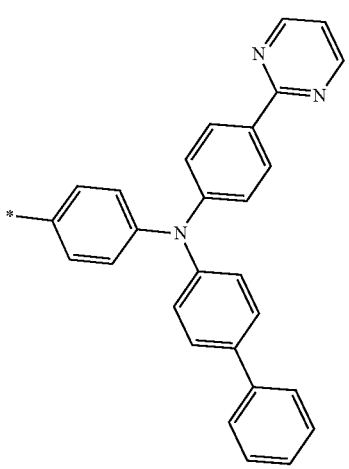
U54 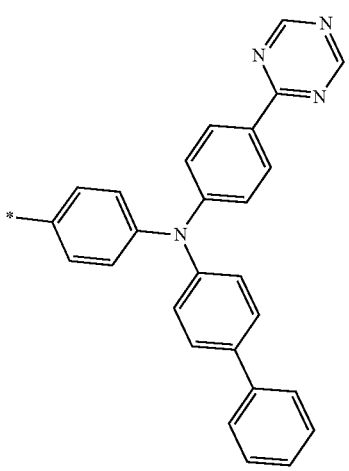

-continued
U55 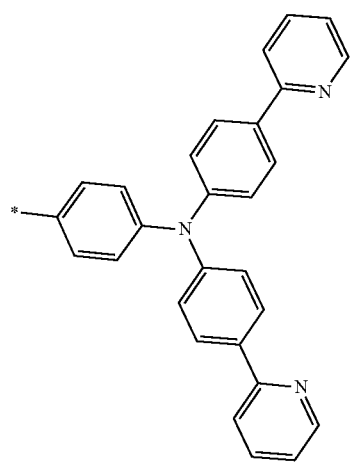
U56 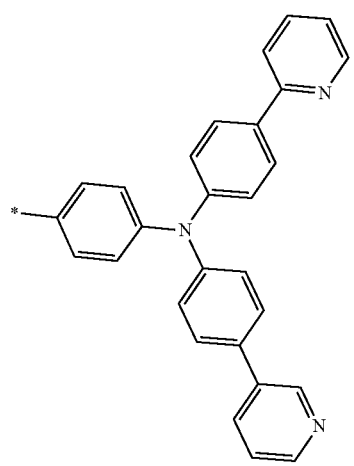
U57 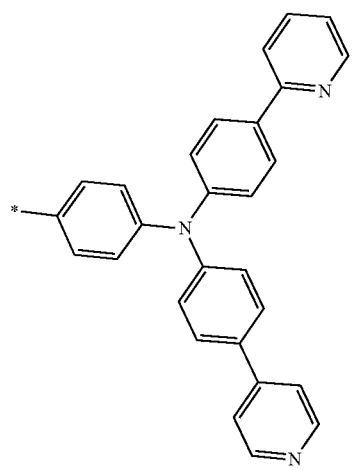
-continued
U58 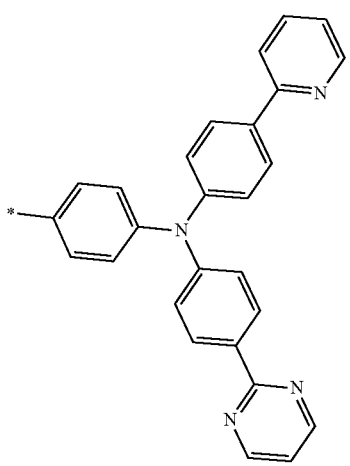
U59 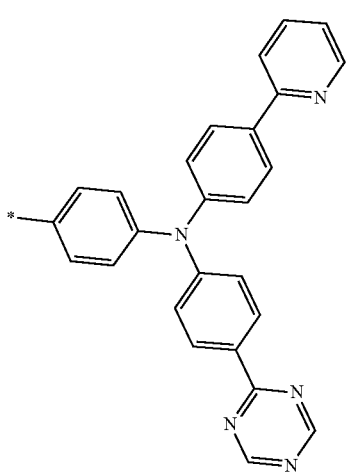
U60 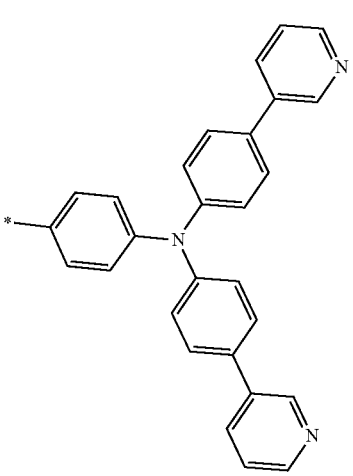

U61
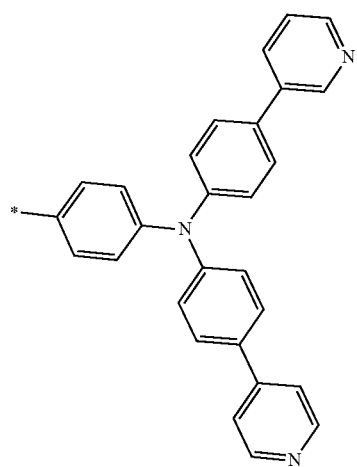
U64
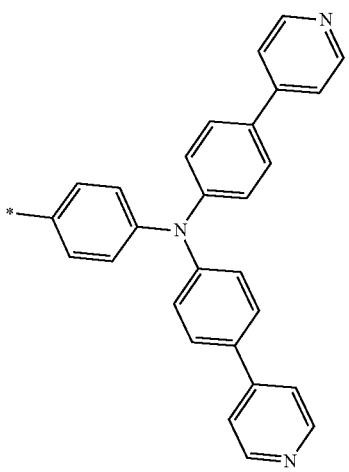
U62
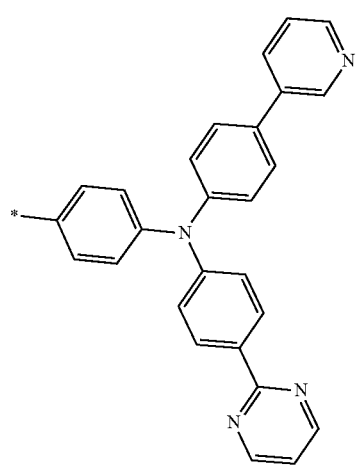
U65
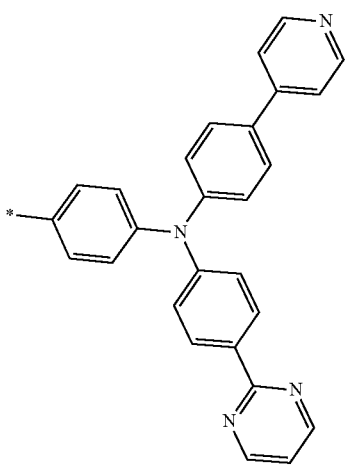
U63
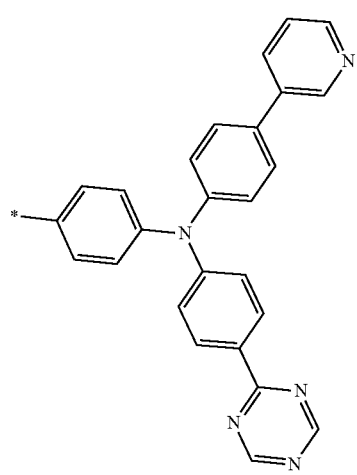
U66
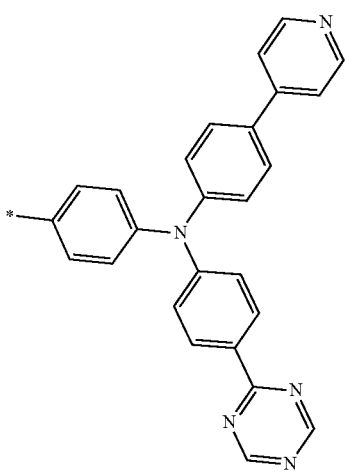

U67 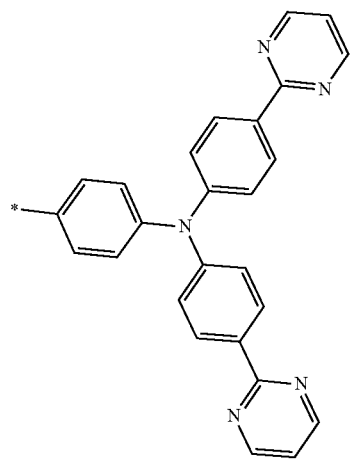
U68 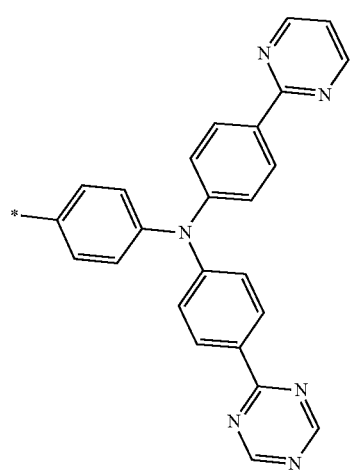
U69 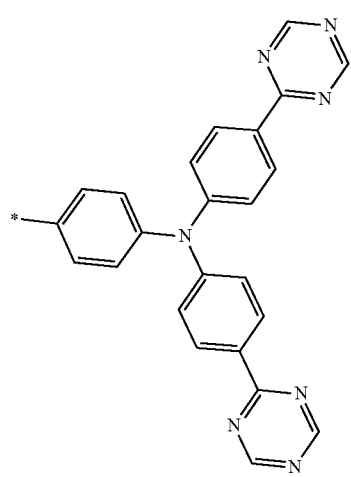
U81 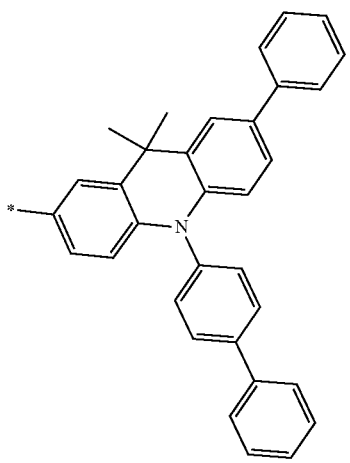
U82 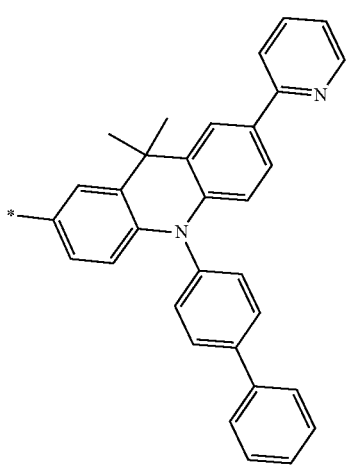
U83 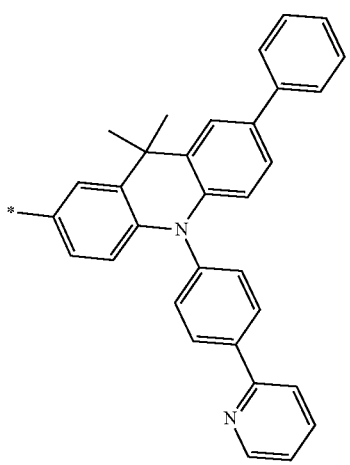

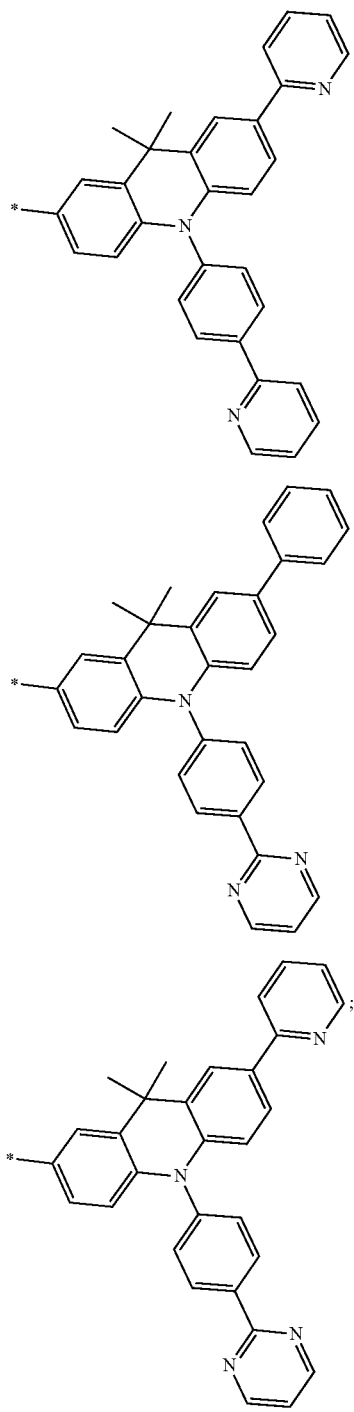

Ar₁ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

R₁ and R₂ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, wherein one or more substituents each introduced into the alkyl group, the cycloalkyl group, the heterocycloalkyl group, the aryl group, the heteroaryl group, the alkyloxy group, the aryloxy group, and the arylamine group of R₁, R₂ and Ar₁ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are optionally the same as or different from each other; and when Ar₁ is present in a plural number, they are the same as or different from each other.

7. An organic electroluminescence device comprising: an anode; a cathode; and an organic material layer comprising one or more layers interposed between the anode and the cathode, wherein at least one of the one or more layers of the organic material layer comprises the compound represented by the following 5, 6, 7, or 9:

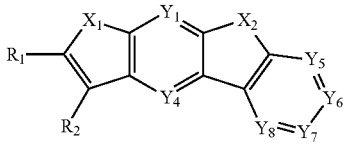

Formula 5

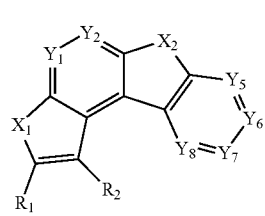

Formula 6

-continued

Formula 7

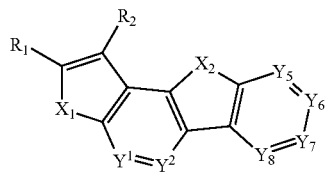

Formula 9

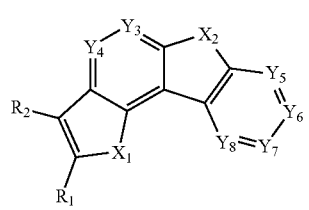

wherein, $Y_1$, $Y_3$ and $Y_4$ are each independently N or $CR_3$, and when $CR_3$ is present in a plural number, they are the same as or different from each other;

$Y_5$ to $Y_8$ are each independently N or $CR_4$, and when $CR_4$ is present in a plural number, they are the same as or different from each other, and provided that at least one of $Y_5$ to $Y_8$ is $CR_4$, and in this case, at least one $R_4$ is a substituent represented by the following Formula 3, Formula 3

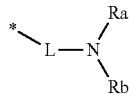

wherein the substituent represented by the Formula 3 is selected from the group consisting of the following substituents U1 to U86;

U1

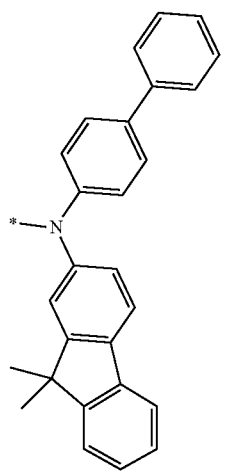

-continued

U2

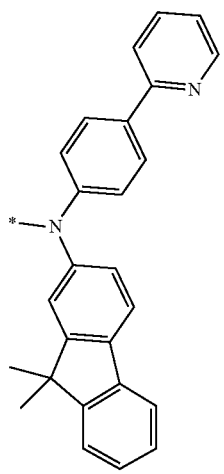

U3

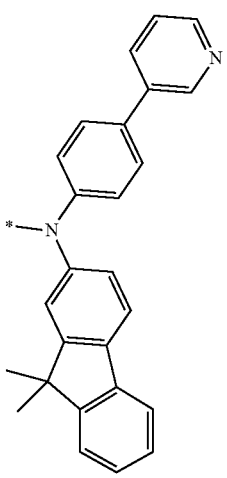

U4

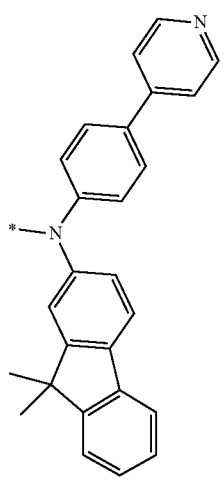

U5 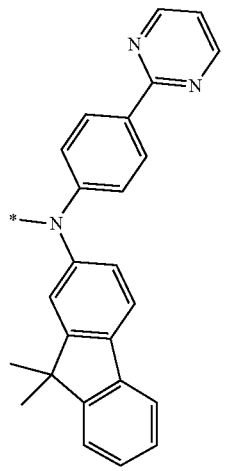
U6 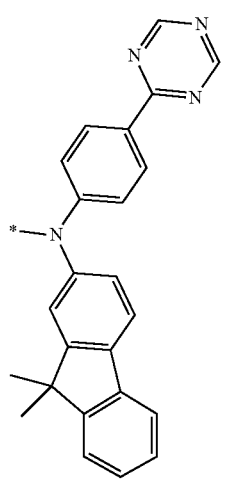
U7 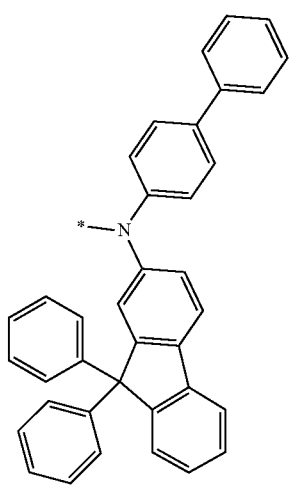
U8 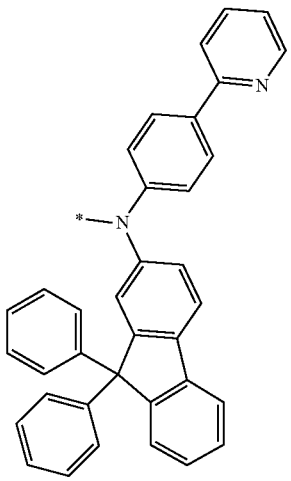
U9 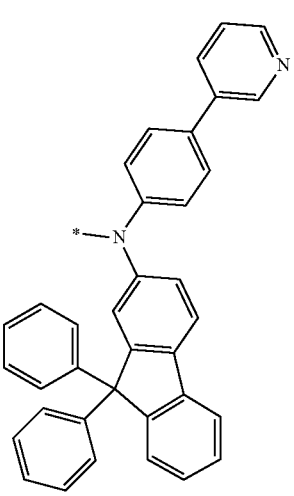
U10 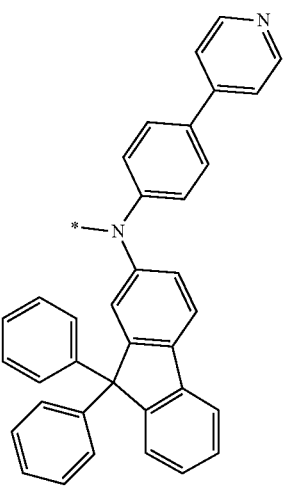

-continued
U11
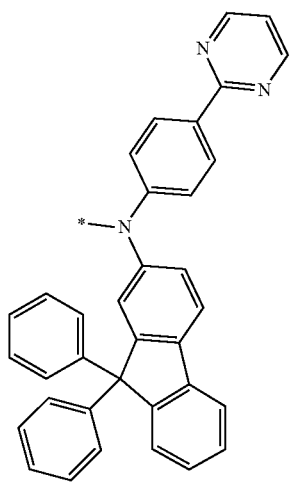
U12
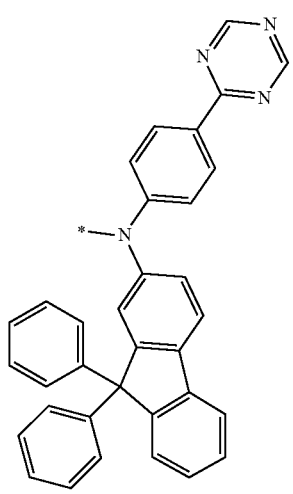
U13
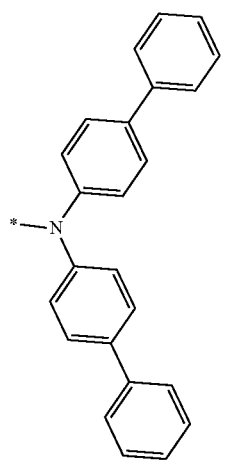
-continued
U14
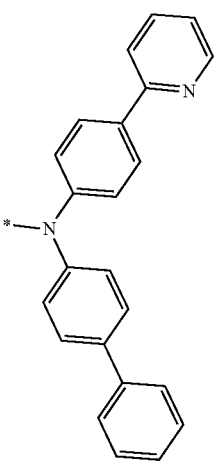
U15
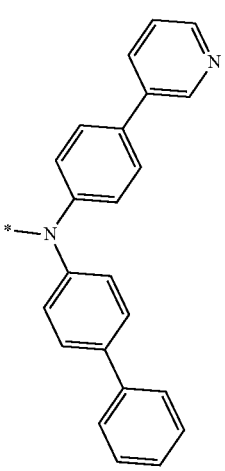
U16
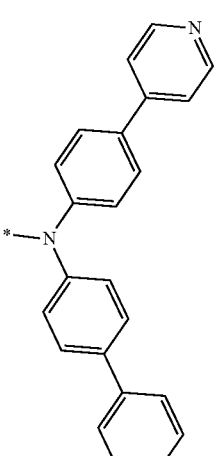

U17 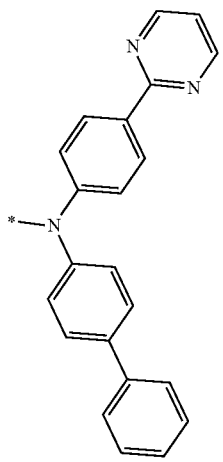
U18 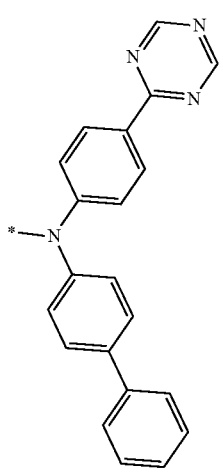
U19 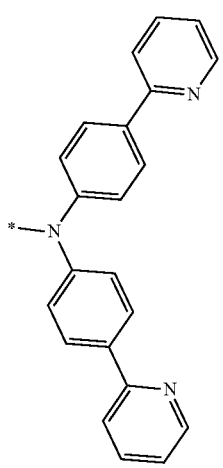
U20 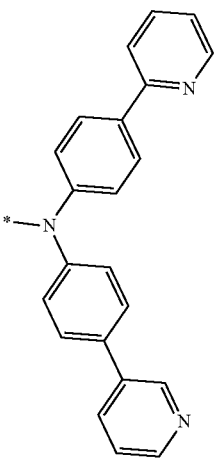
U21 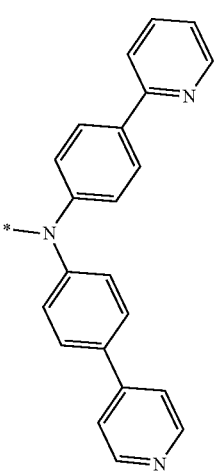
U22 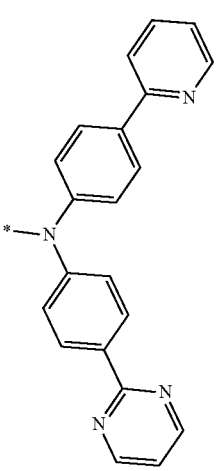

U23
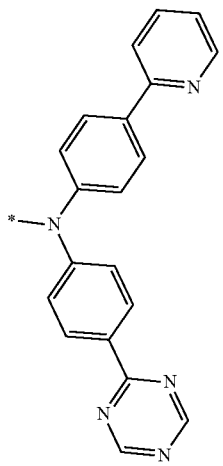
U24
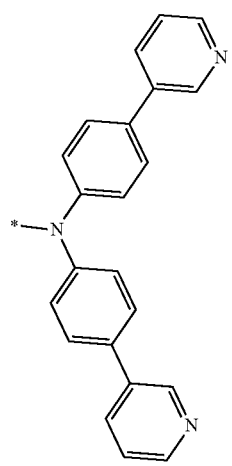
U25
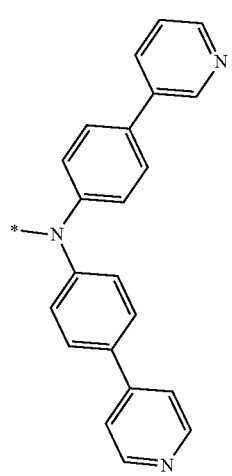
U26
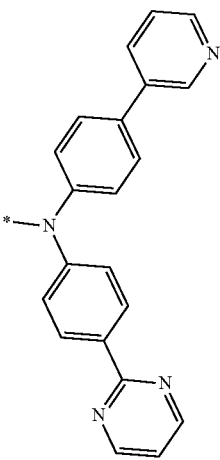
U27
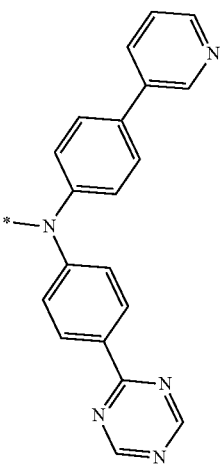
U28
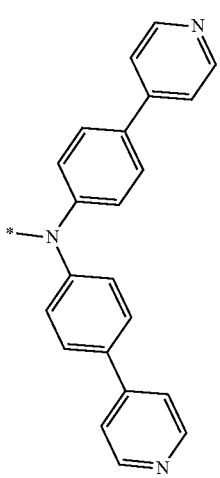

-continued
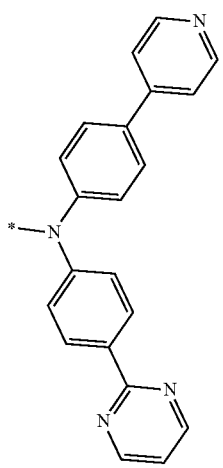
U29
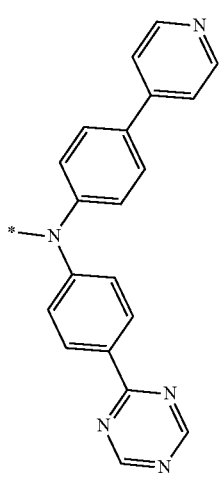
U30
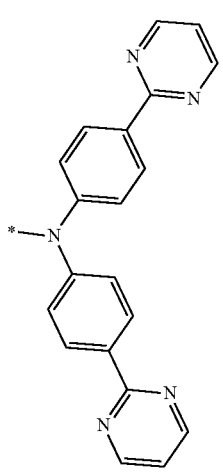
U31
-continued
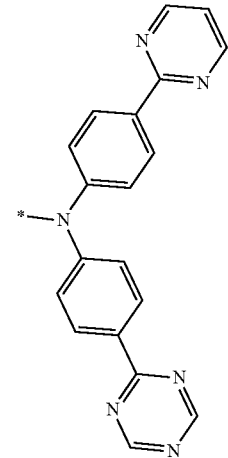
U32
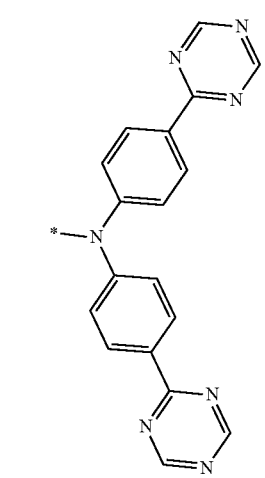
U33
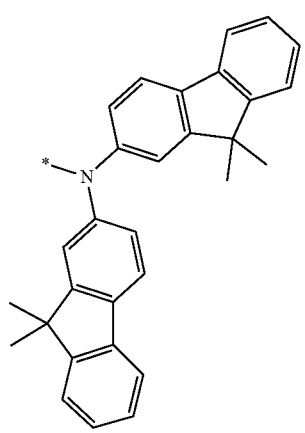
U34

U35
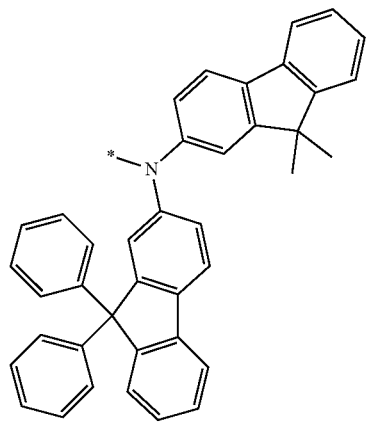
U36
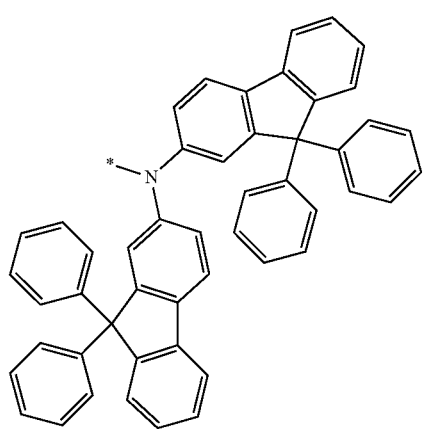
U37
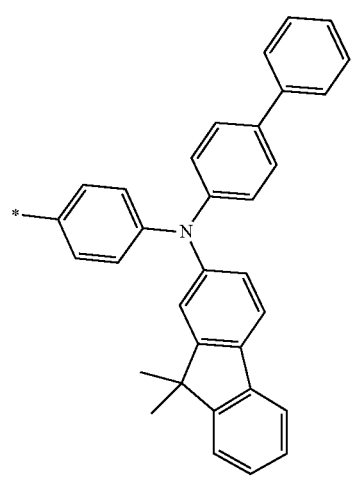
U38
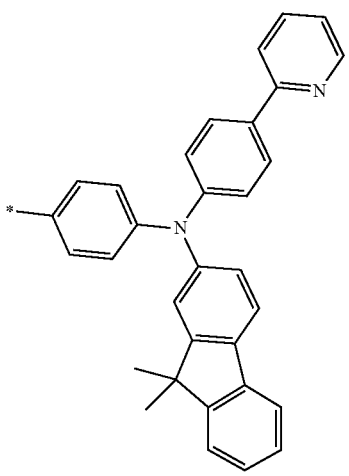
U39
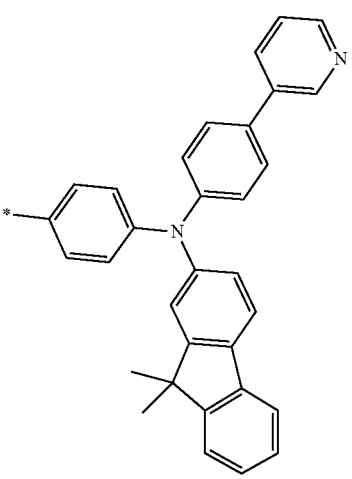
U40
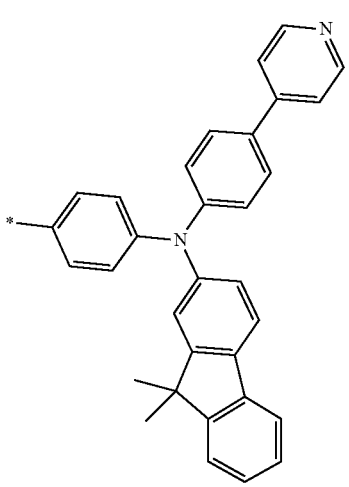

435
-continued
U41
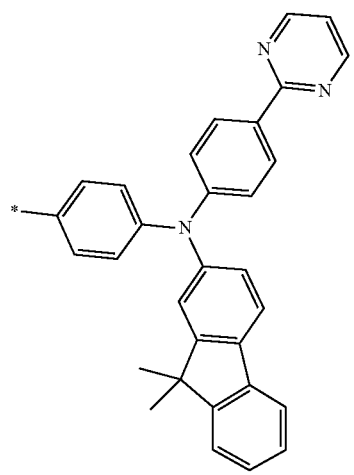
U42
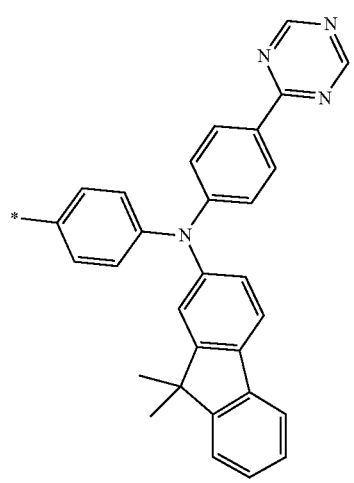
U43
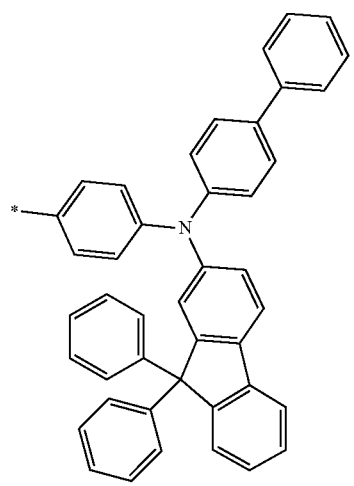
436
-continued
U44
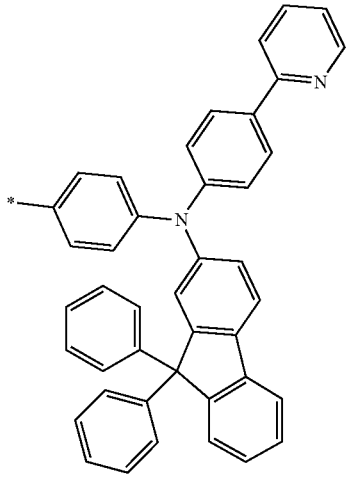
U45
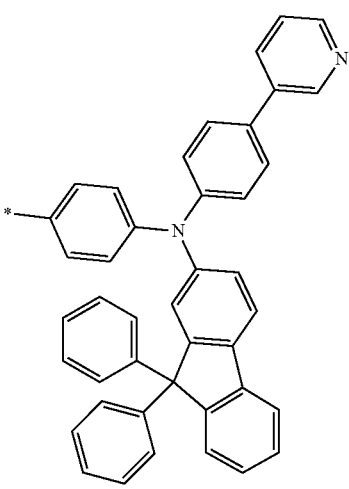
U46
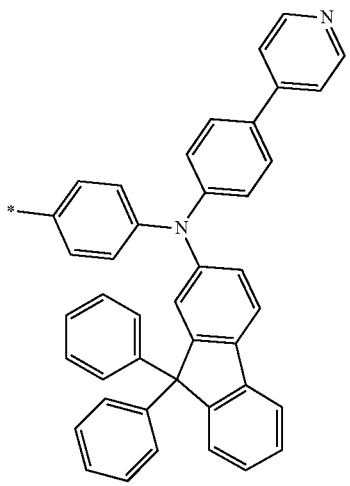

U47
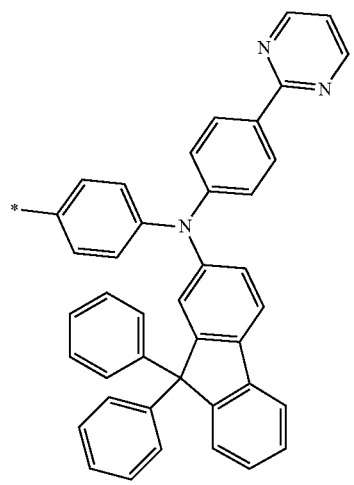
U48
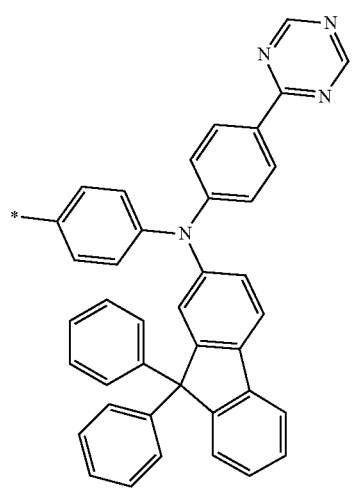
U49
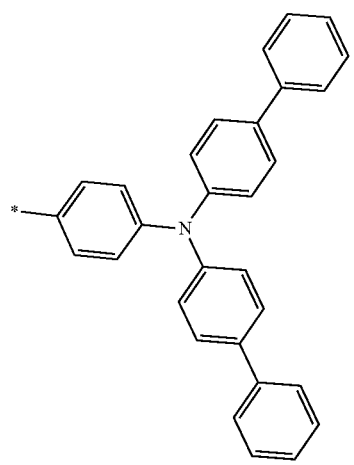
U50
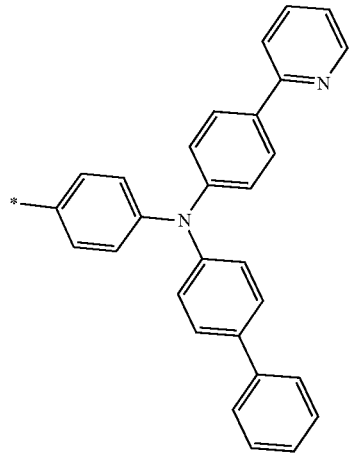
U51
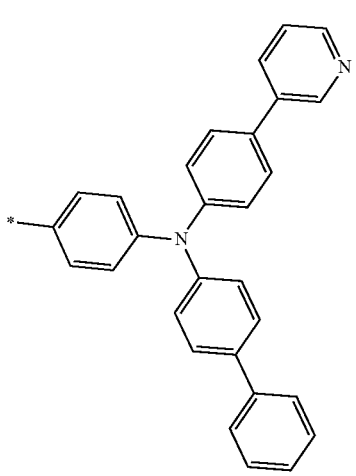
U52
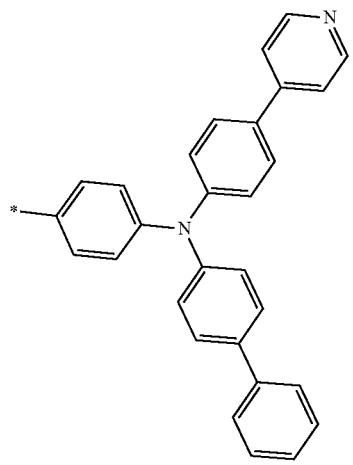

U53
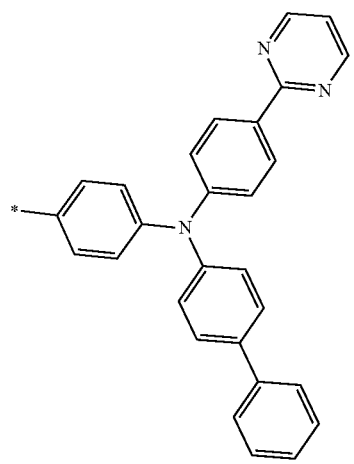
U54
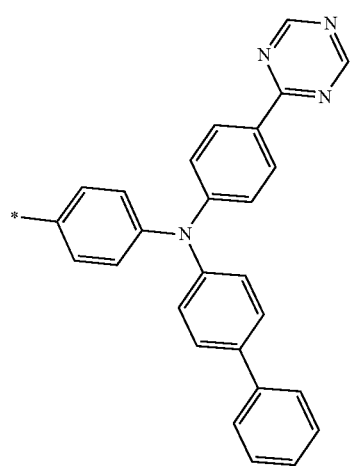
U55
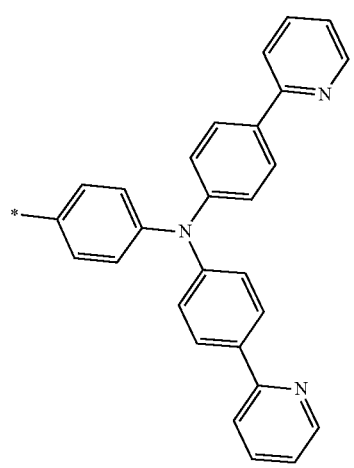
U56
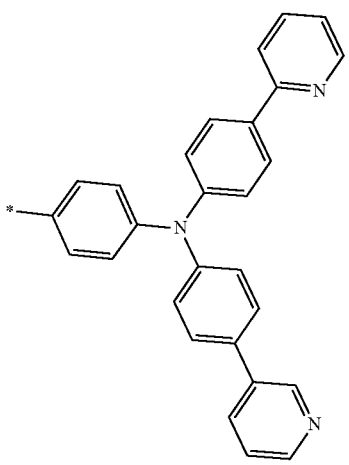
U57
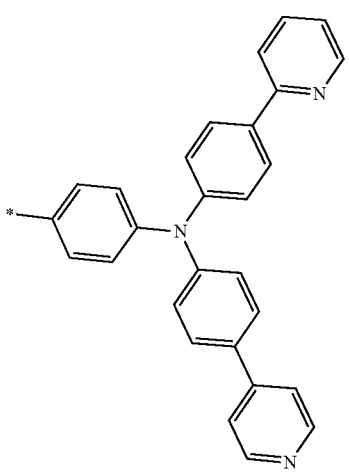
U58
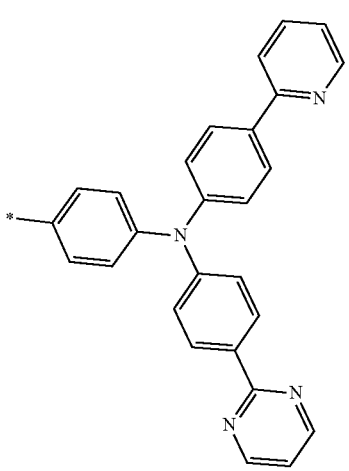

U59
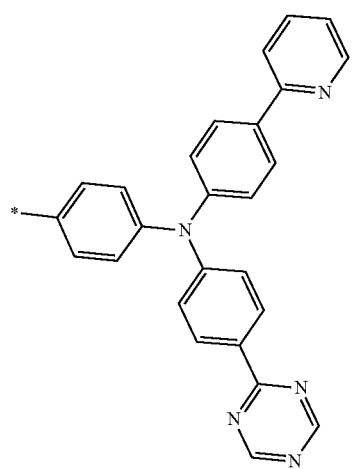
U60
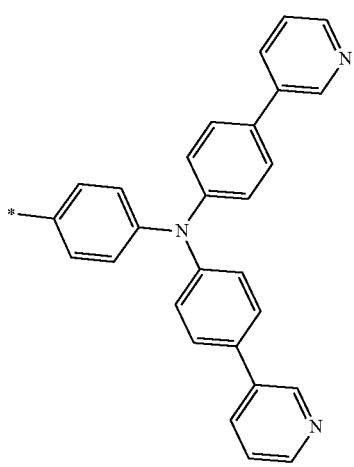
U61
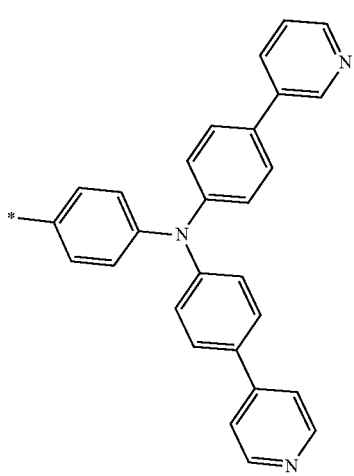
U62
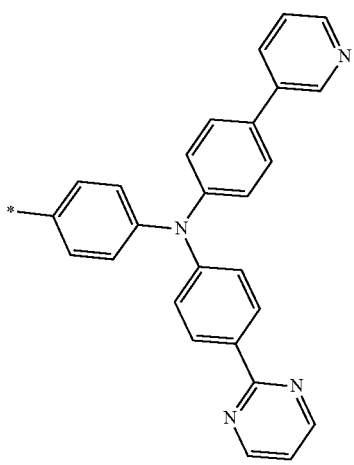
U63
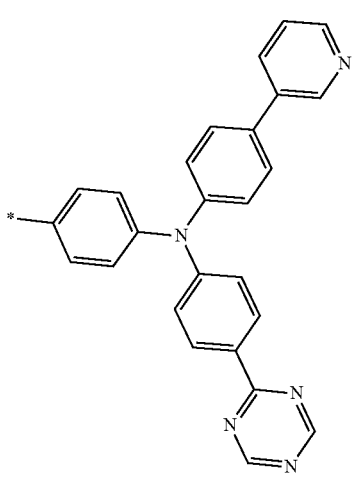
U64
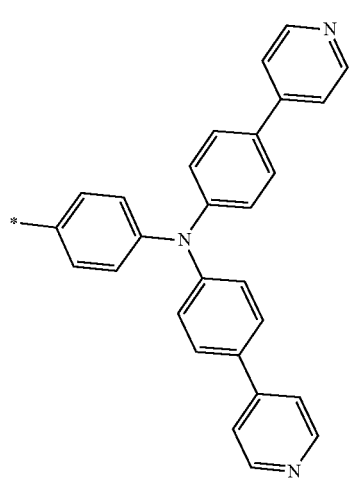

U65 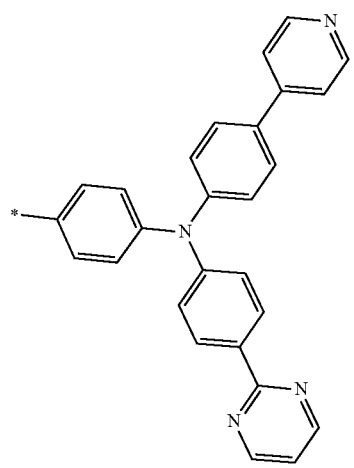
U66 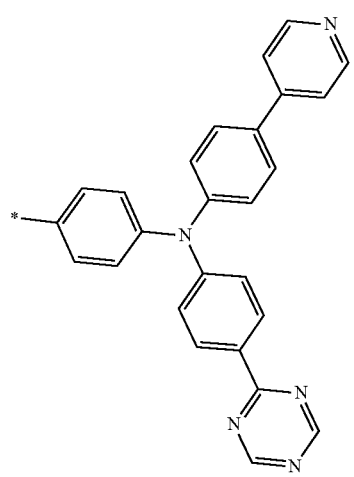
U67 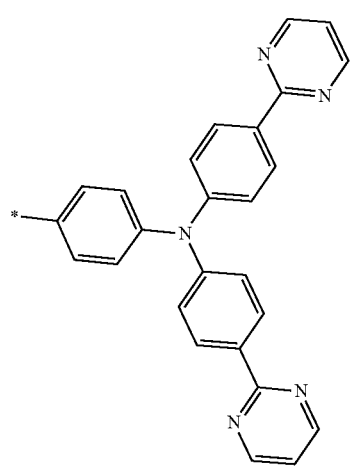
U68 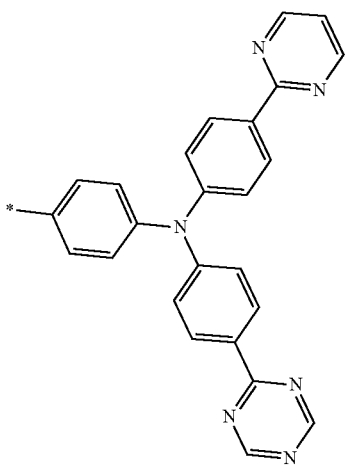
U69 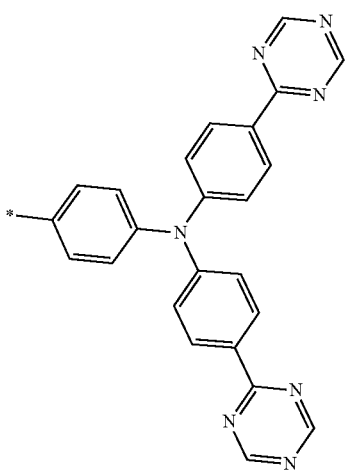
U70 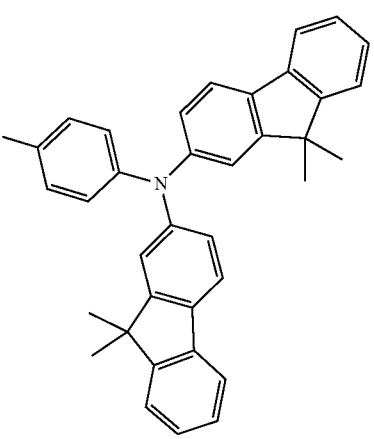

U71
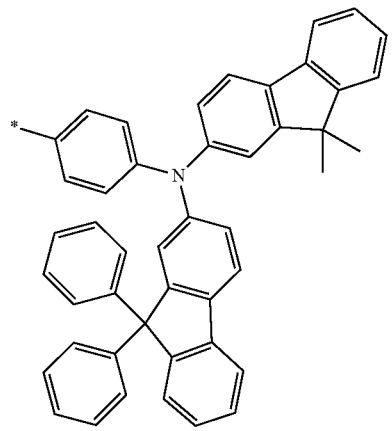
U72
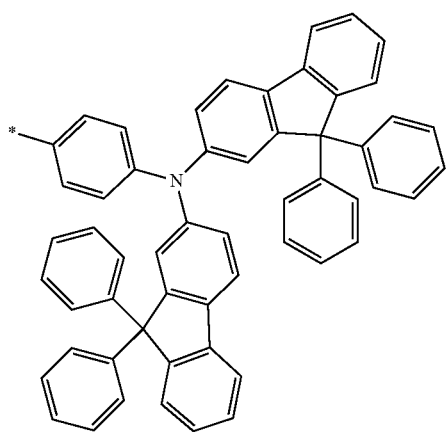
U73
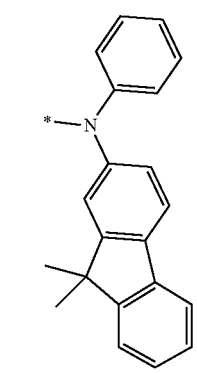
U74
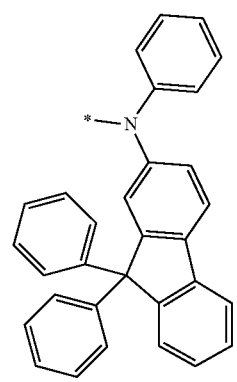
U75
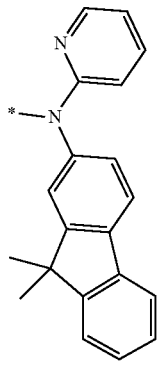
U76
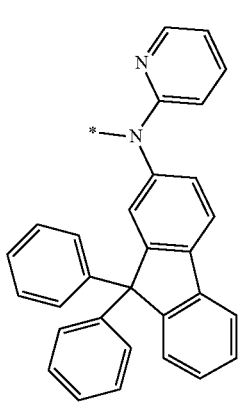
U77
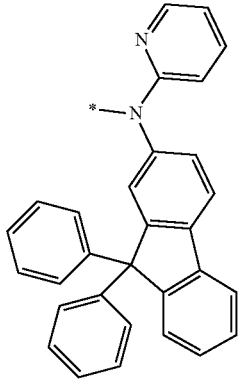
U78
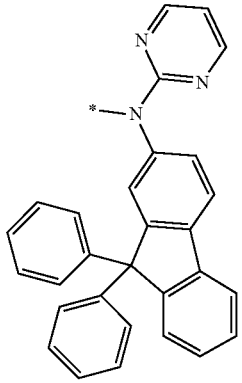

-continued
U79
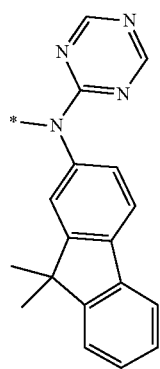
U80
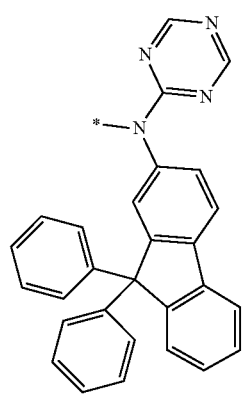
U81
-continued
U82
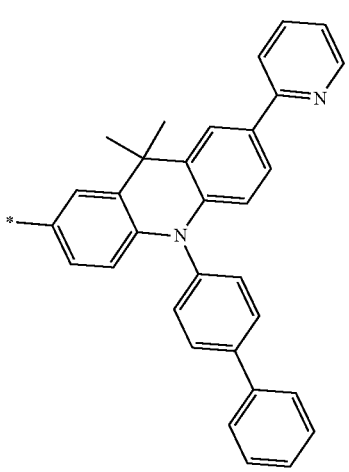
U83
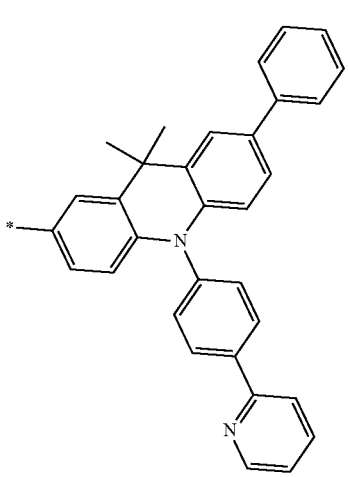
U84
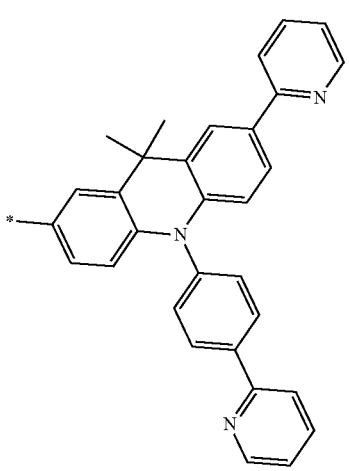

-continued

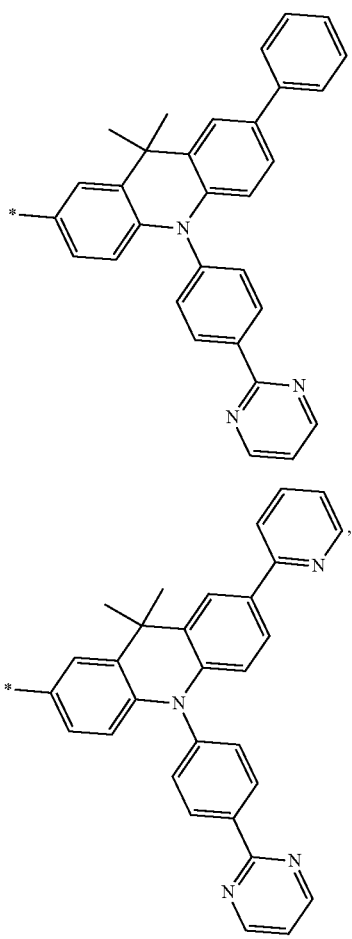

U85

U86

$X_1$ and $X_2$ are each $N(Ar_1)$, and are the same as or different from each other;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, or a substituted or unsubstituted $C_6$ to $C_{60}$ arylamine group;

$R_1$ to $R_4$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group; and wherein one or more substituents each introduced into the alkyl group, the cycloalkyl group, the heterocycloalkyl group, the aryl group, the heteroaryl group, the alkyloxy group, the aryloxy group, and the arylamine group of $R_1$ to $R_4$ and $Ar_1$ are each independently selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_{60}$ to $C_{60}$ aryloxy group, a substituted or unsubstituted $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group, and provided that when the substituent is present in a plural number, they are the same as or different from each other.

8. An organic electroluminescence device comprising: an anode; a cathode; and an organic material layer comprising one or more layers interposed between the anode and the cathode, wherein at least one of the one or more layers of the organic material layer comprises the compound selected from the group consisting of the following compounds Mat-1 to Mat-18, Mat-21, Mat-27, and Mat-31 to Mat-39:

Mat-1

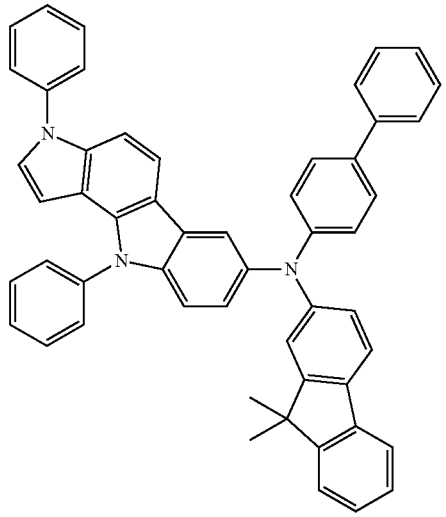

Mat-2
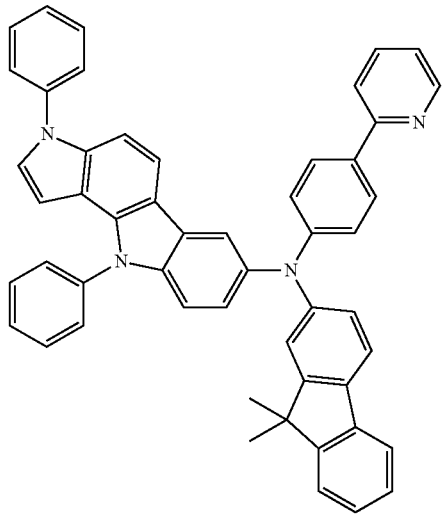
Mat-5
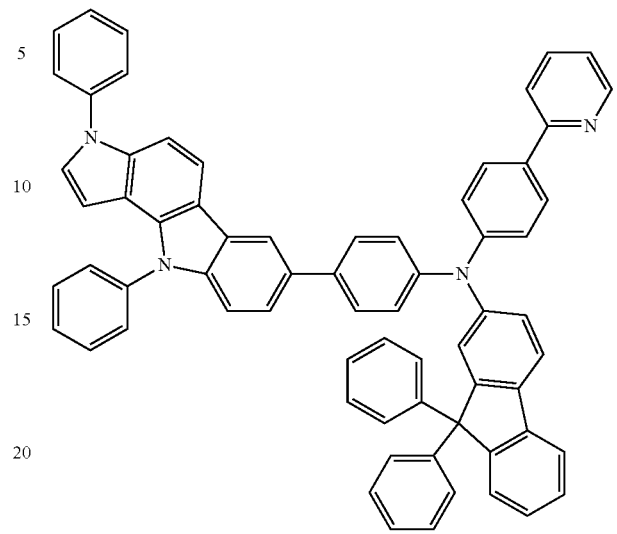
Mat-3
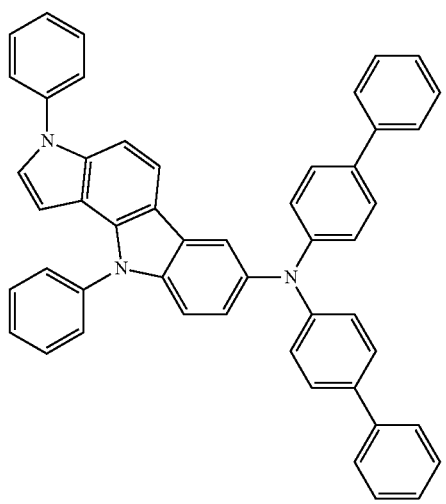
Mat-6
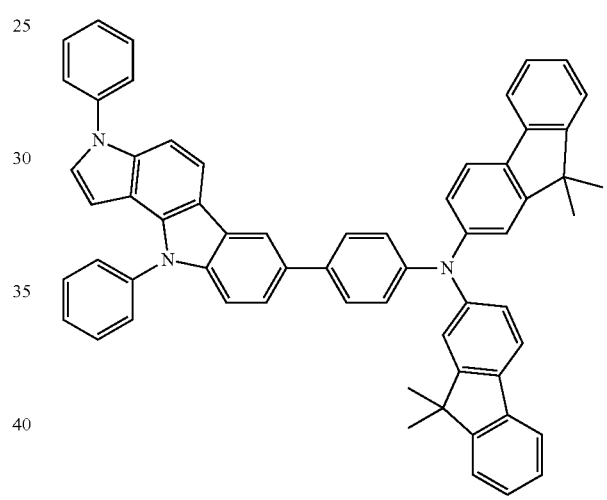
Mat-4
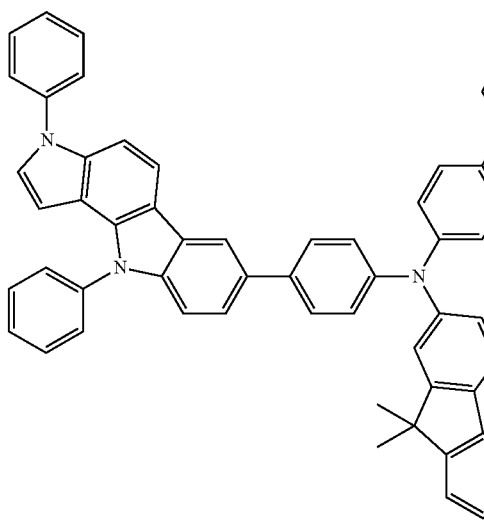
Mat-7
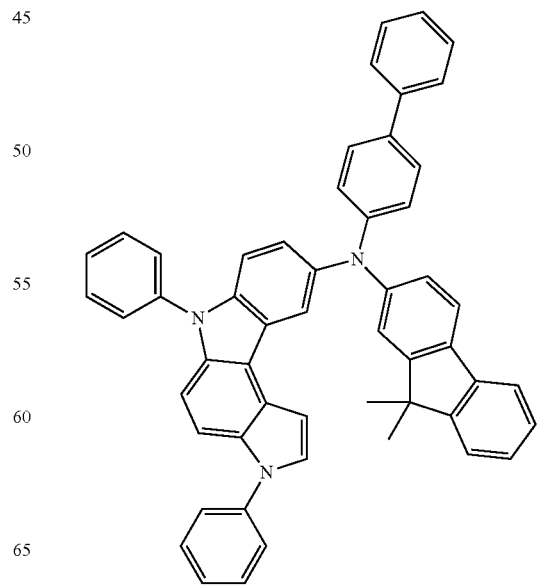

Mat-8
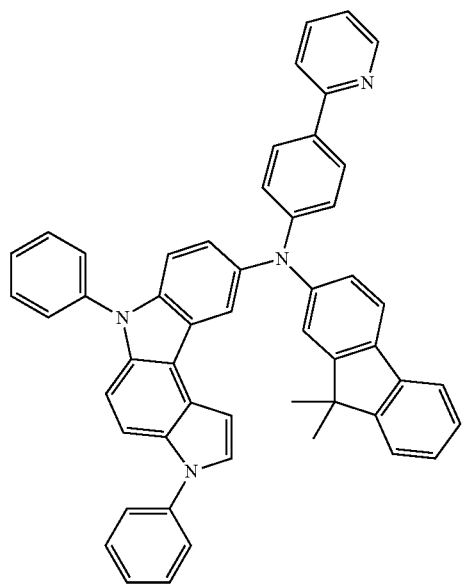
Mat-9
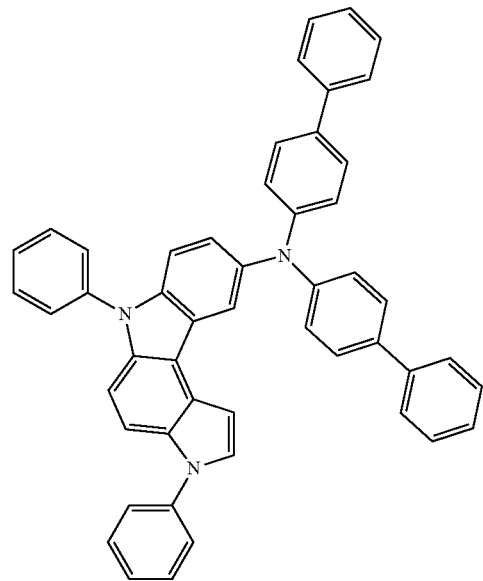
Mat-10
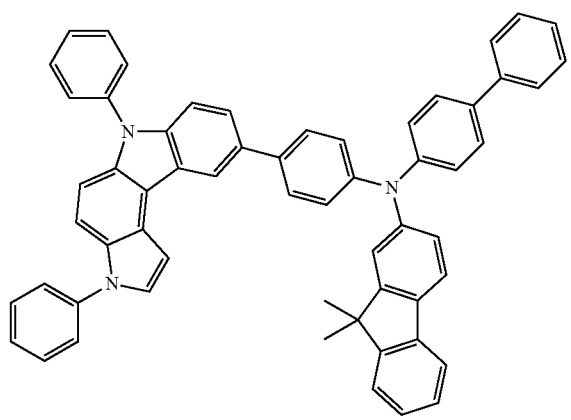
Mat-11
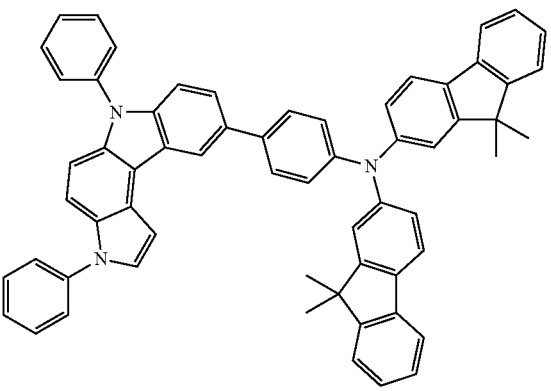
Mat-12
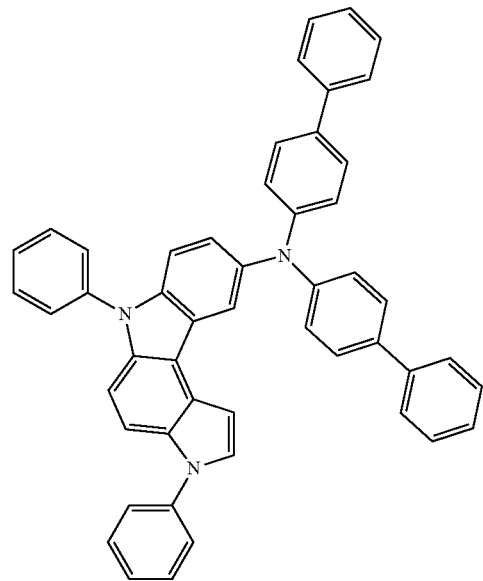
Mat-13
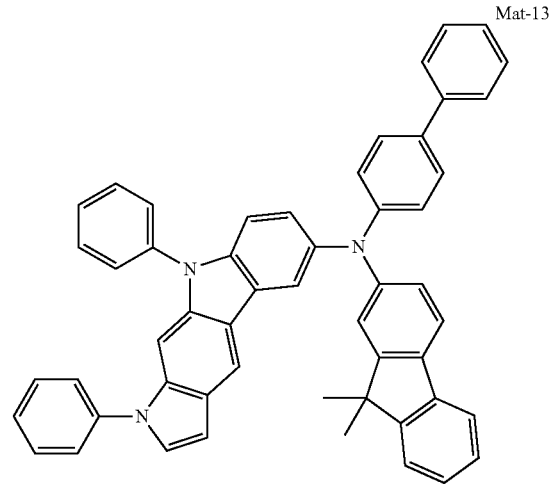

Mat-14
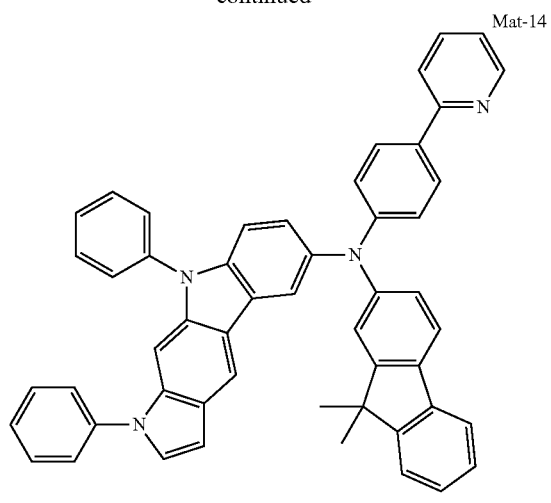
Mat-15
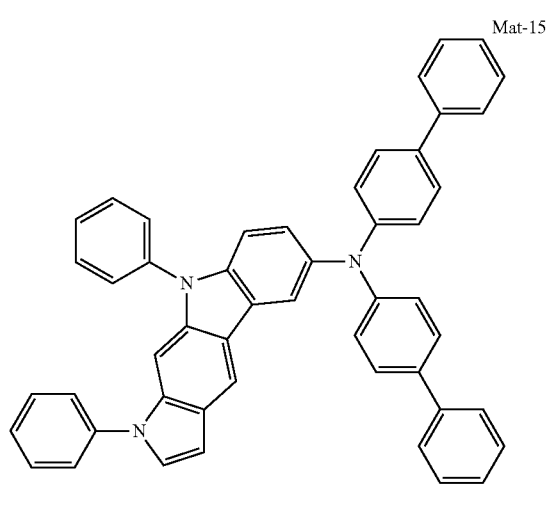
Mat-16
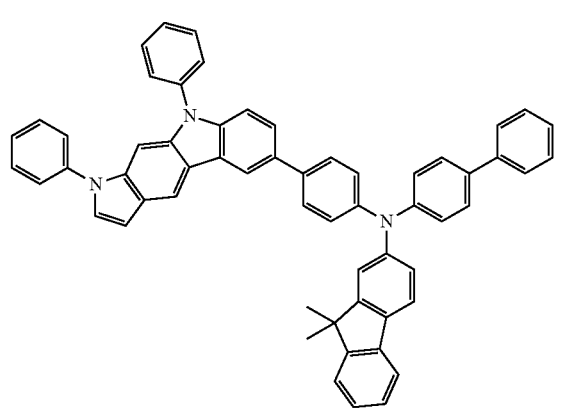
Mat-17
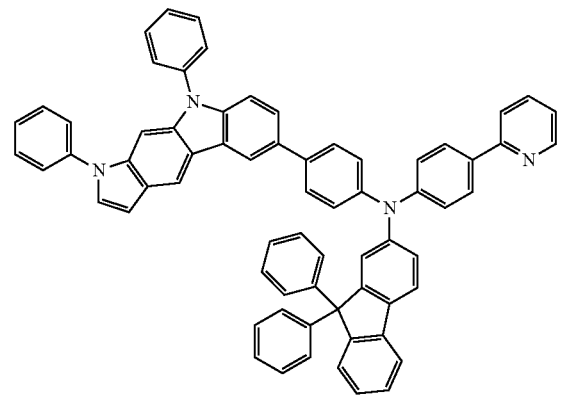
Mat-18
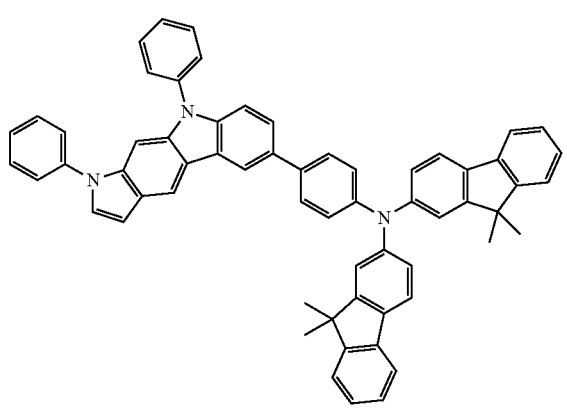
Mat-19
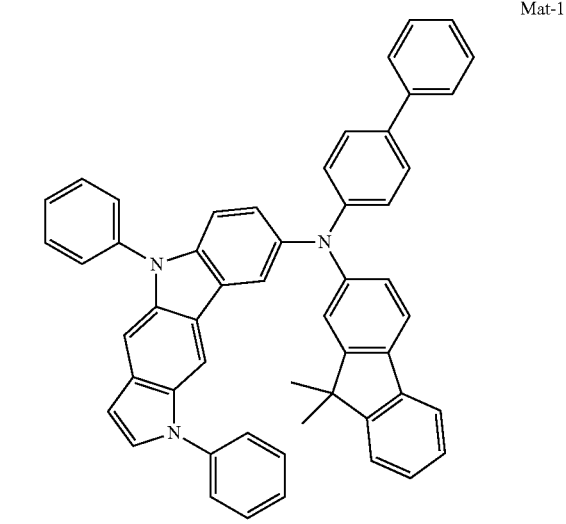

Mat-20
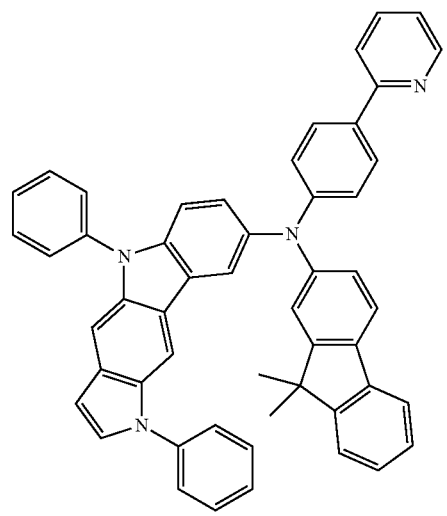
Mat-23
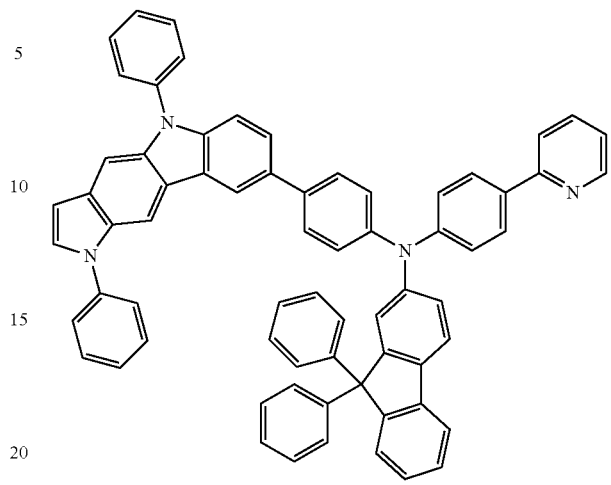
Mat-21
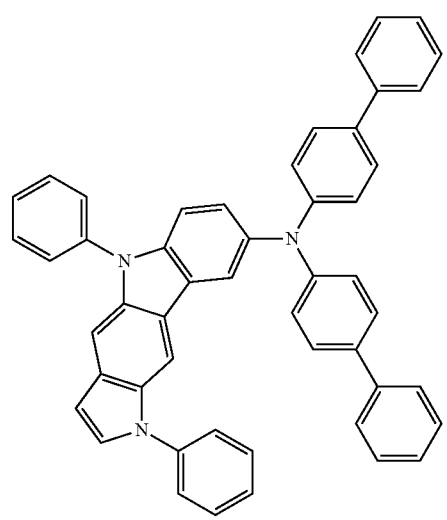
Mat-24
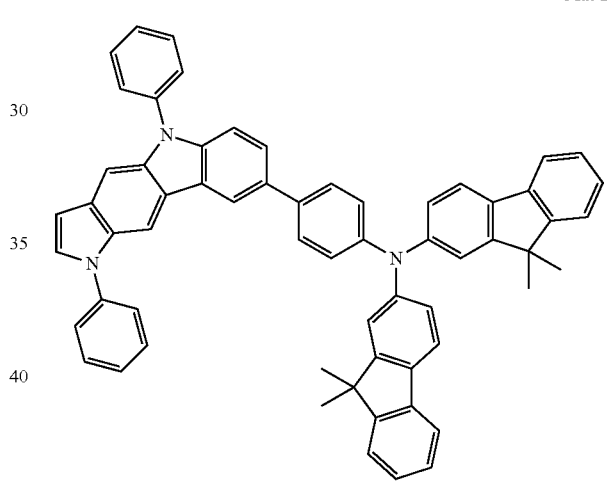
Mat-22
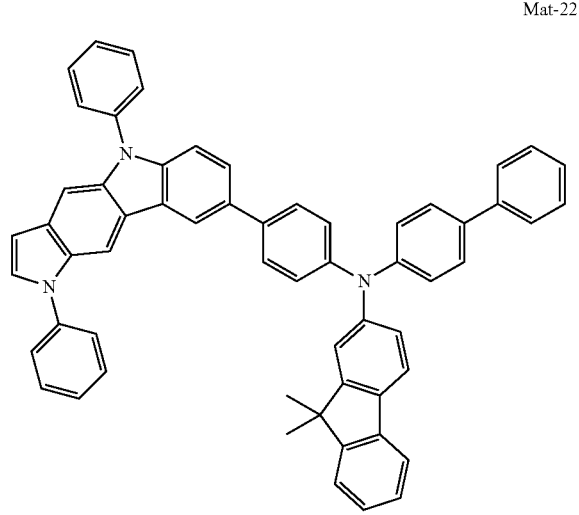
Mat-25
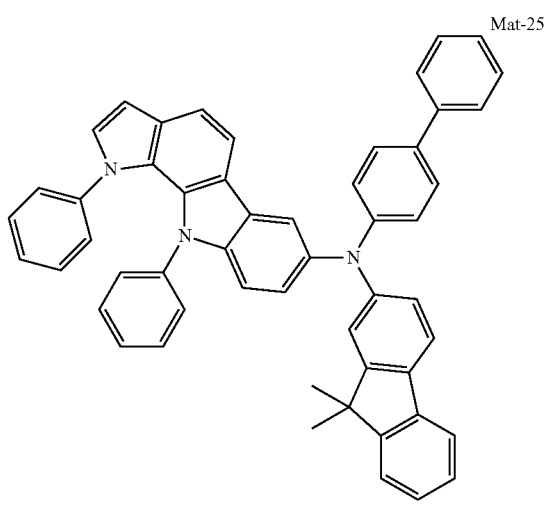

Mat-26
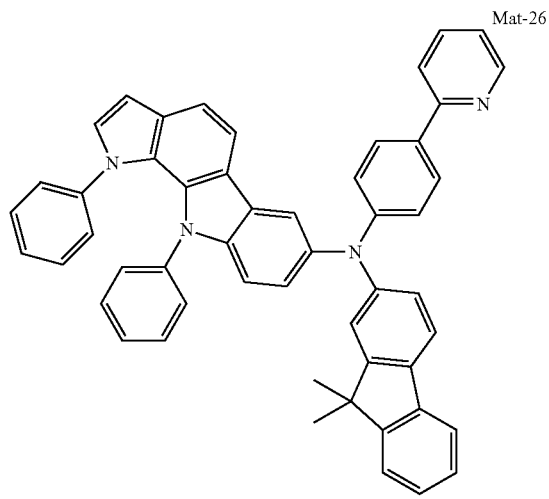
Mat-29
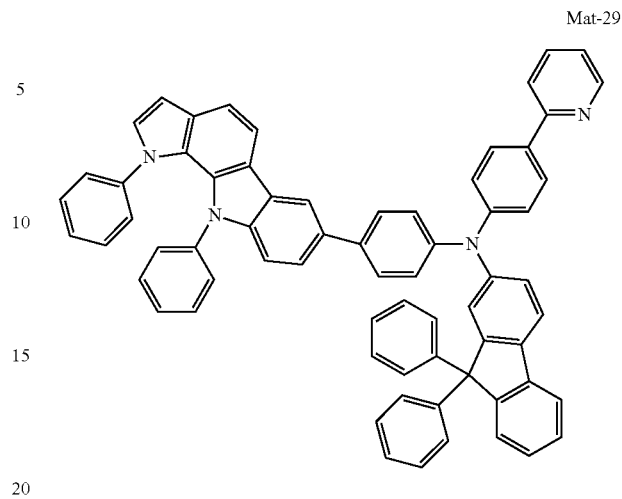
Mat-27
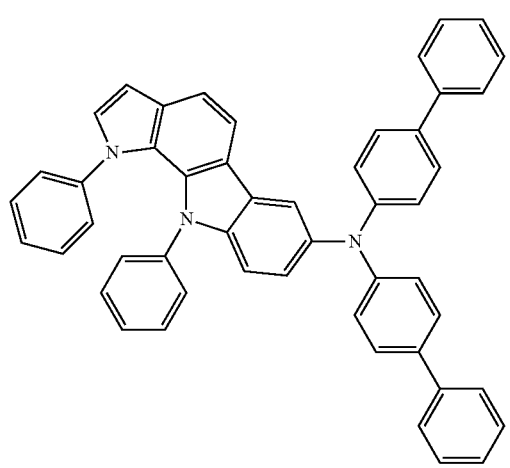
Mat-30
Mat-28
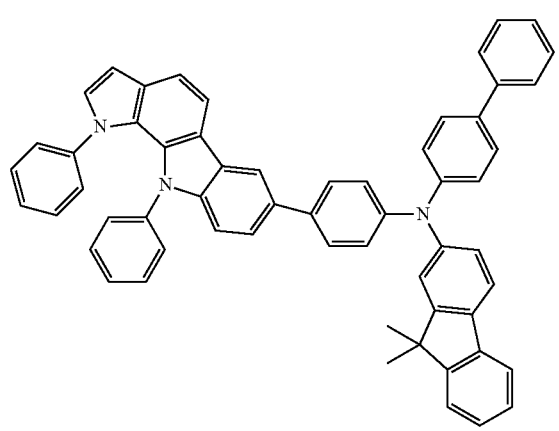
Mat-31
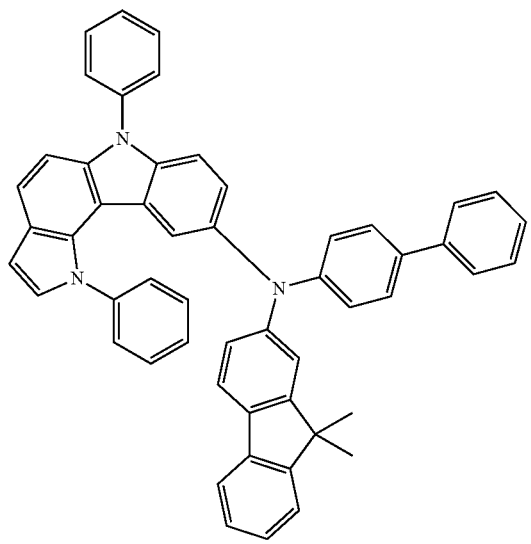

-continued
Mat-32
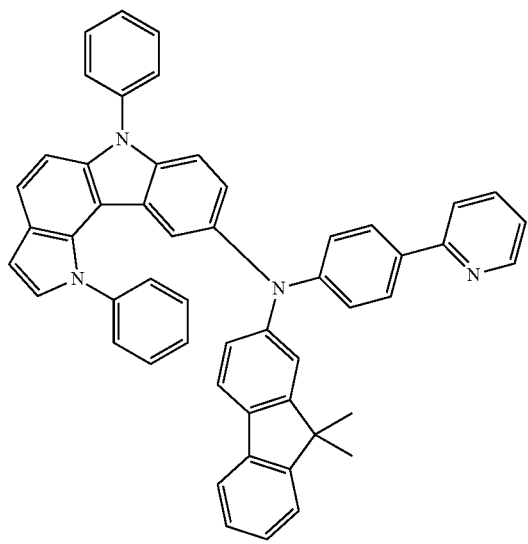
Mat-33
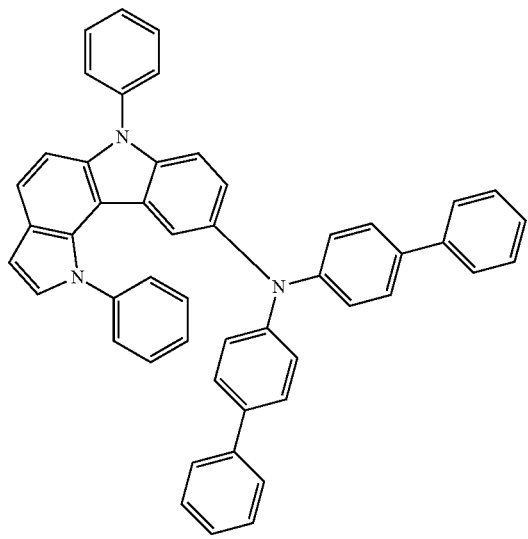
Mat-34
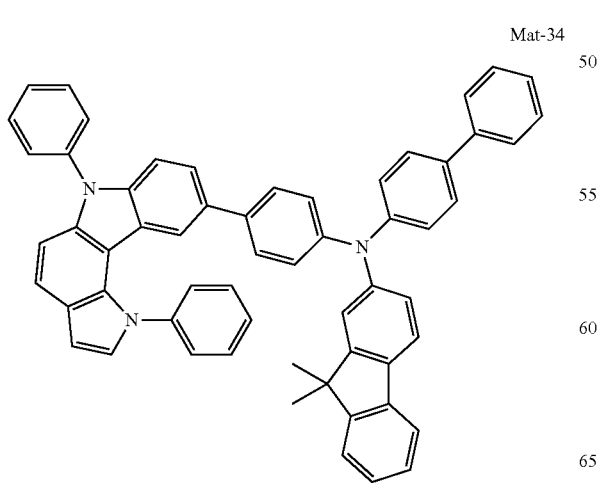
-continued
Mat-35
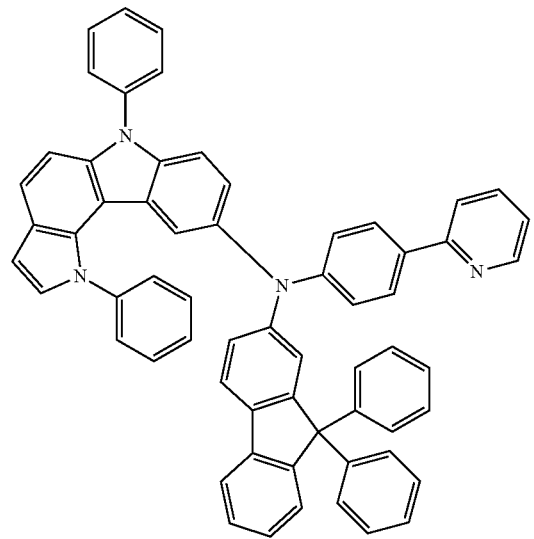
Mat-36
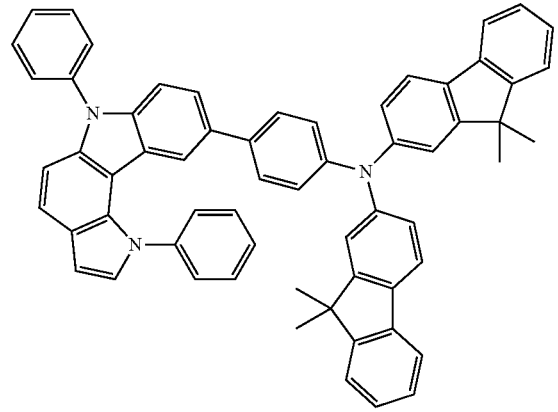
Mat-37
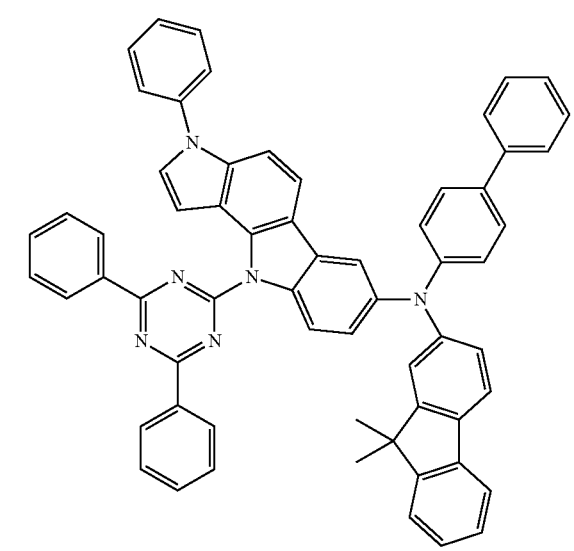

-continued
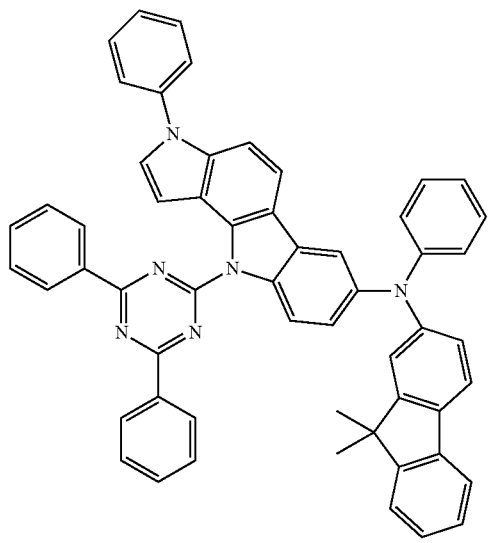
Mat-38
-continued
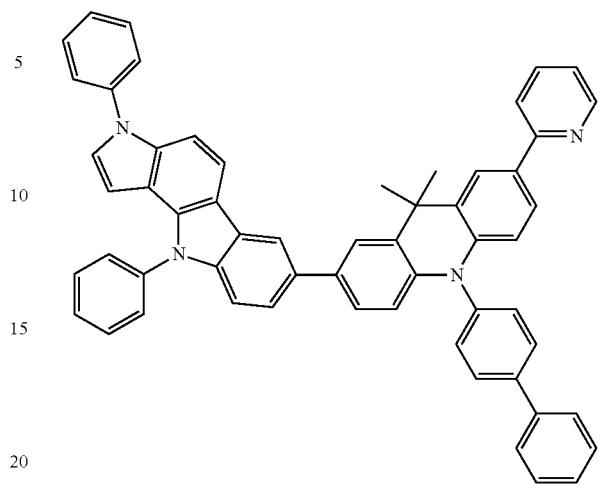
Mat-39
* * * * *